US008629147B2

(12) United States Patent
Anikin et al.

(10) Patent No.: US 8,629,147 B2
(45) Date of Patent: Jan. 14, 2014

(54) HETEROCYCLIC COMPOUNDS USEFUL IN THE TREATMENT OF NEOPLASTIC DISEASES, INFLAMMATORY DISORDERS AND IMMUNOMODULATORY DISORDERS

(75) Inventors: Alexey Vyacheslavovich Anikin, San Diego, CA (US); Vidyasagar Reddy Gantla, San Diego, CA (US); Vlad Edward Gregor, Del Mar, CA (US); Luyong Jiang, San Marcos, CA (US); Yahua Liu, San Diego, CA (US); Danny Peter Claude McGee, Vista, CA (US); Charles Chamchoumis Mikel, Escondido, CA (US); Jason Conrad Pickens, San Diego, CA (US); Thomas Roy Webb, Millington, TN (US); Zheng Yan, San Diego, CA (US); Tong Zhu, San Diego, CA (US); Aleksander Kadushkin, Zheleznodorozhnyi (RU); Sergey Sviridov, Moscow (RU); Sergey Zozulya, San Diego, CA (US); Alexander Chucholowski, San Diego, CA (US); Douglas Eric McGrath, San Marcos, CA (US)

(73) Assignee: ChemBridge Corporation, San Diego, CA (US)

( * ) Notice: Subject to any disclaimer, the term of this patent is extended or adjusted under 35 U.S.C. 154(b) by 223 days.

(21) Appl. No.: 11/593,191

(22) Filed: Nov. 2, 2006

(65) Prior Publication Data
US 2008/0207635 A1    Aug. 28, 2008

Related U.S. Application Data

(60) Provisional application No. 60/734,050, filed on Nov. 3, 2005.

(51) Int. Cl.
*A61K 31/497* (2006.01)
*A61K 31/47* (2006.01)
*A61K 31/445* (2006.01)

(52) U.S. Cl.
USPC ....... 514/253.09; 514/314; 514/318; 514/338

(58) Field of Classification Search
None
See application file for complete search history.

(56) References Cited

U.S. PATENT DOCUMENTS

| 6,696,437 B1 | 2/2004 | Lubisch et al. |
| 2004/0044203 A1 | 3/2004 | Wittman et al. |

FOREIGN PATENT DOCUMENTS

| CA | 2371645 A1 | 11/2000 | |
| JP | 09176524 | * 7/1997 | C09D 5/08 |
| WO | WO 00/35886 | * 6/2000 | C07D 235/00 |
| WO | WO 02/072090 | 9/2002 | |
| WO | WO 03/011837 | 2/2003 | |
| WO | WO 2005/028448 | 8/2004 | |
| WO | WO 2005/028448 | 3/2005 | |
| WO | WO 2005/040167 | 5/2005 | |
| WO | WO 2005/065266 | 7/2005 | |
| WO | WO 2005/065266 A2 | 7/2005 | |
| WO | WO 2005/084667 | 9/2005 | |
| WO | WO 2005-085230 | 9/2005 | |
| WO | WO 2005/085231 | 9/2005 | |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Hilliard et al (Antimicrobial Agents and Chemotherapy 43:1693-1699, 1999).*
STN Search Report (Accession No. 2000:421114).*
STN Search Report (Accession No. 1995:238098)—containing summary of Kogo et al (Nucleic Acids Symposium Series: 31(21st Symposium on Nucleic Acids Chemistry, 1994) 81-82, 1994).*
Bruckner, et al., *Science*, 275: 1640-1643 (1997).
Carmeliet, et al., *Nature*, 380: 435-439 (1996).
Davis, et al., *Cell*, 87: 1161-1169 (1996).
Dumont, et al., *Genes Dev.*, 8: 1897-1909 (1994).
Ferrara, et al., *Nature*, 380: 439-442 (1996).
Folkman, et al., *Cell*, 87: 1153-1155 (1996).
Folkman, et al., J. Biol. Chem., 267: 10931-10934 (1992).
Fong, et al., Nature, 376: 66-70 (1995).
Garner, A., "Vascular Diseases." *Pathobiology of Ocular Disease: A Dynamic Approach*. 2$^{nd}$ Edition, Marcel Dkker, NY pp. 1625-1710 (1994).
Hanahan, D., *Science*, 277:48-50 (1997).
Holland. et al., *Nature*, 383: 722-725 (1996).
Horak, et al., *Lancent*, 340: 1120-1124 (1992).
Klagsbrun, et al., Annu. Rev. Physiol.. 53: 217-239 (1991).
Macchiarini. et al., *Lancet*, 340: 145-146 (1992).
Maisonpierre, et al., *Science*, 277: 55-60 (1997).
Merenmies, et al., *Cell Groth Differ.*, 8: 3-10 (1997).
Orioli and Klein, *Trends in Genetics*, 13:354-359 (1997).
Pandey, et al., *Science*, 268: 567-569, (1995).
Pasquale, et al., *Curr. Opin. Cell Biol.*, 9: 608-615 (1997).
Powis, et al., *Anti-Cancer Drugs Design*, 9: 263-277 (1994).
Risau, W., *Nature* 386: 671-674 (1997).
Sato, et al., *Nature*, 376: 70-74 (1995).
Shalaby, et al., *Nature*, 376: 62-66, (1995).
Shawver, et al., *Drug Discovery Today*, 2: 50-63 (1997).
Stein, et al., *Genes Dev.*, 12: 667-678 (1998).
Suri, et al., *Cell*, 87: 1171-1180 (1996).
Vikkula, et al., *Cell*, 87: 1181-1190 (1996).
Wang, et al., *Cell*, 93: 741-753 (1998).
Weidner, et al., *N. Engl. J. Med.*, 324:1-6 (1991).
Yancopoulos, et al., *Cell*, 93: 661-664, (1998).
STN Search Report (Accession No. 1995:238098)—containing summary of Kogo et al (Nucleic Acids Symposium Series: 31(21$^{st}$ Symposium on Nucleic Acids Chemistry, 1994) 81-82, 1994.
Loewe H et al: "Basisch Substituierte 2, 6-Bis-Benzunudazolderivate, Eine Neue Chemotherapeutisch Aktive Koerperklasse" Arzneimittel Forschung. Drug Research, ECV Editio Cantor Verlag, Aulendorf, DE, vol. 24, No. 12, Dec. 1, 1974, pp. 1927-1933, XP000826533, ISSN: 0004-4172.

(Continued)

*Primary Examiner* — Craig Ricci
(74) *Attorney, Agent, or Firm* — Mark S. Cohen; Latzer Baratz LLP

(57) ABSTRACT

The present invention provides compounds capable of modulating tyrosine kinases, compositions comprising the compounds and methods of their use.

3 Claims, 1 Drawing Sheet

(56) References Cited

OTHER PUBLICATIONS

Hilliard J J et al: "Multiple Mechanism of Action for Inhibitors of Histidine Protein Kinases From Bacterial Two-Component Systems" Antimicrobial Agents and Chemotherapy, American Society for Microbiology, Washington, DC, US, vol. 43, No. 7, Jul. 1, 1999, pp. 1693-1699, XP002171516, ISSN: 0066-4804.
Wood E R et al.: "Discovery and In Vitro Evaluation of Potent TrkA Kinase Inhibitors: Oxindole and Aza-Oxindoles", Bioorganic and Medicinal Chemistry Letters 20040223 GB LNKD—vol. 14, No. 4, Feb. 23, 2004, pp. 953-957, XP002619093, ISSN: 0960-894X.
Weidner-Wells et al, "Amidino benzimidazole inhibitors of bacterial two-component systems", Bioorganic & Medicinal Chemistry Letters, 2001, vol. 11, 1545-1548.
CAS Registry File RN 851797-39-2, STN Entry Date Jun. 7, 2005.
CAS Registry File RN 851769-98-0, STN Entry Date Jun. 7, 2005.
Chemical Abstracts Accession No. 1997:558748 & CAS Registry File RN 193560-23-5 & Patent Abstracts of Japan, JP 09-176524 A (Tamura Kaken KK) Jul. 8, 1997.
Australian Office Action dated May 11, 2011.
Australian Office Action dated Dec. 6, 2011.
European Search Report dated Feb. 9, 2011.
European Office Action dated Nov. 22, 2011.
Manning et al. (2002) Science. 298:1912.
Blume-Jensen and Hunter (2001) Nature, 411: 355-365.
Robinson et al. (2000) Oncogene 19:5548-5557.
Bolen et al. (1992) FASEB J. 6:3403-3409 (1992).
Ullrich and Schlessinger (1990) Cell 61:203-212.
Ihle (1995) Sem. Immunol. 7:247-254.
Rao (1996) Curr. Opin. Oncol. 8:516-524.
Anderson (1997) Microbiol. Rev. 61:33.
Tibes et al (2005) Annu. Rev. Pharmacol. Toxicol.45:357.
Gschwind (2004) Nature Reviews 4:361.
Paul and Mukhopadhay (2004) Int. J. Med. Sci (2004) 1:101.
Reynolds et al., *FASEB J.*, 6: 886-892 (1992).
Risau et al., *Development*, 102: 471-478 (1988).
Davis et al., *Cell* 87:1161-1169 (1996).
Cahn et al., 1966, *Angew. Chem.* 78:413-447, *Angew. Chem., Int. Ed. Engl.* 5:385-414 (errata: *Angew. Chem., Int. Ed. Engl.* 5:511).
Prelog and Helmchen, 1982, *Angew. Chem.* 94:614-631, *Angew. Chem. Internat. Ed. Eng.* 21:567-583.
Mata and Lobo, 1993, *Tetrahedron: Asymmetry* 4:657-668.
Abdelkrim Ben Alloum et al., 2003, *Tetrahedron Letters* 44:5935-5937.
Ansel, "Introduction to Pharmaceutical Dosage Forms", 4$^{th}$ edition, pp. 49-62 and 291-320, (1985).
Cross, P.E.; Arrowsmith, J.E.; Thomas, G.N.; Gwilt, M.; Burges, R.A; Higgins, A.J.; J.Med.Chem. 1990, 33, 1151-1155.
Defacqz, N.; Tran-Trieu, V.; Cordi, A.; Marchand-Brynaert, J.;Tetrahedron Lett. 2003, 44, 9111-9114.
Bevan, C.W.L ; Journal of the Chemical Society 1968, 238-241.
Giardina, G.A.M.; Raveglia, L.F.; Grugni, M.; Sarau, H.M.; Farina, C.; J.Med.Chem. 1999, 42, 1053-1065.
Effland, R.M.; Helsley, G.C.; Tegeler, J.J.; J.Heterocycl.Chem. 1982, 19, 537-539.
Louvet, P.; Lallement, G.; Pernot-Marino, I.; Luu-Duc, C.; Blanchet, G. Eur. J.Med.Chem. 1993, 28, 71-75.
Abbott et al., 1992, *J. Biol. Chem.* 267:10759-10763.

\* cited by examiner

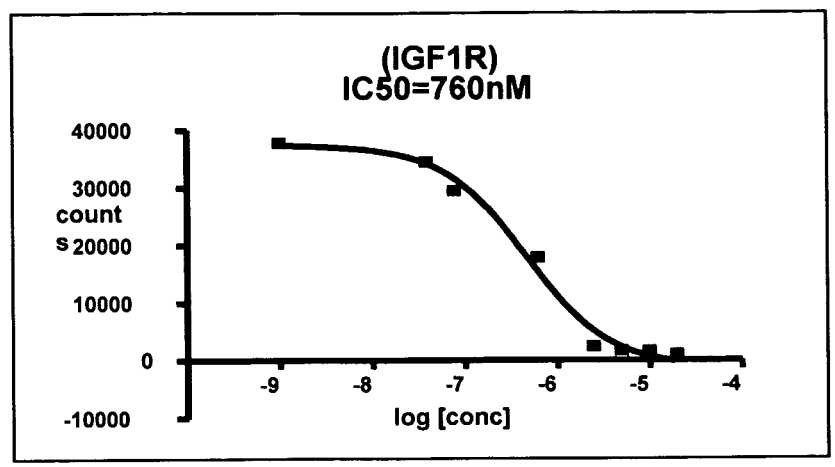

HETEROCYCLIC COMPOUNDS USEFUL IN THE TREATMENT OF NEOPLASTIC DISEASES, INFLAMMATORY DISORDERS AND IMMUNOMODULATORY DISORDERS

CROSS-REFERENCE TO RELATED APPLICATIONS

This Application claims the benefit of U.S. Provisional Application Ser. No. 60/734,050, filed on Nov. 3, 2005, which is incorporated herein by reference in its entirety.

1. FIELD OF THE INVENTION

The present invention provides compounds capable of modulating tyrosine kinases, compositions comprising the compounds and methods of their use.

2. BACKGROUND OF THE INVENTION

According to the latest American Cancer Society's annual statistical report, released in January 2005, cancer has edged out heart disease as the leading cause of death in Americans under age 85. In 2002, the most recent year for which information is available, 476,009 Americans under 85 died of cancer compared with 450,637 who died of heart disease (those under 85 comprise 98.4 percent of the US population). Protein tyrosine kinases (PTK), which historically represented the majority of first discovered oncogenes, remain today one of the most important classes of oncology drug targets.

Protein kinases are enzymes which covalently modify proteins and peptides by the attachment of a phosphate group to one or more sites on the protein or peptide (for example, PTK phosphorylate tyrosine groups). The measurement of protein kinase activity is important since studies have shown that these enzymes are key regulators of many cell functions.

Over 500 protein kinases have been identified in the human genome ("kinome") (Manning et al. (2002) *Science.* 298: 1912). Based on the recent advances in deciphering the human genome, the family of human PTK consists of approximately 90 members (Blume-Jensen and Hunter (2001) *Nature,* 411: 355-365; Robinson et al. (2000) *Oncogene* 19:5548-5557). This family can be divided in two major groups—receptor tyrosine kinases (RTK) and cytoplasmic (or non-receptor) tyrosine kinases (CTK)—and approximately 30 subfamilies based on structural similarity (see, e.g., Bolen et al. (1992) *FASEB J.* 6:3403-3409 (1992); Ullrich and Schlessinger (1990) *Cell* 61:203-212; Ihle (1995) *Sem. Immunol.* 7:247-254. PTKs are involved in regulation of many cellular processes, such as cell proliferation, survival and apoptosis. Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as LCK, or due to the homology among PTK classes, by inhibition of more than one PTK by an inhibitor.

In some forms of cancer, a PTK mutation or structural alteration can increase the ability to proliferate, and thus, provides an advantage over surrounding cells. PTK of growth factor receptors, for instance, have been shown to be involved in the transformation of normal to cancerous cells (see, e.g., Rao (1996) *Curr. Opin. Oncol.* 8:516-524). PTK also play a role in the regulation of apoptosis or programmed cell death (see, e.g., Anderson (1997) *Microbiol. Rev.* 61:33). By activation of PTK, apoptosis mechanisms can be shut off and the elimination of cancerous cells is prevented. Thus, PTK exert their oncogenic effects via a number of mechanisms such as driving proliferation and cell motility and invasion. These PTK include HER2, BCR-ABL, SRC, and IGF1R.

There are many ways that a PTK can become oncogenic. For example, mutations (such as gain-of-function mutations) or small deletions in RTK and/or CTK are known to be associated with several malignancies (e.g., KIT/SCFR, EGFR/ERBB1, CSF-1R, FGFR1, FGFR3, HGFR, RET). Additionally, overexpression of certain types of PTK resulting, for example, from gene amplification has been shown to be associated with several common cancers in humans (e.g., EGFR/ERBB1, ERBB2/HER2/NEU, ERBB3/HER3, ERBB4/HER4, CSF-1R, PDGFR, FLK2/FLT3, FLT4/VEGFR3, FGFR1, FGFR2/K-SAM, FGFR4, HGFR, RON, EPHA2, PEHB2, EPHB4, AXL, TIE/TIE1). For a review of oncogenic kinase signaling, and mutated kinase genes that may be used in the systems and methods provided herein, see Blume-Jensen and Hunter (2001) *Nature* 411:355; Tibes et al (2005) *Annu. Rev. Pharmacol. Toxicol.* 45:357; Gschwind (2004) *Nature Reviews* 4:361; Paul and Mukhopadhay (2004) *Int. J. Med. Sci* (2004) 1:101;

The majority of PTKs are believed to be important drug targets, especially for anti-cancer therapy. Indeed, a very large proportion of known PTKs have been shown to be hyperactivated in cancer cells due to overexpression or constitutively activating mutations and to directly drive tumor growth. In addition, a subset of RTKs, such as vascular endothelial growth factor receptors (VEGFR), fibroblast growth factor receptors (FGFR) and some ephrin receptor (EPH) family members, is involved in driving angiogenesis while others (e.g., Met and discoidin domain receptor (DDR)) promote cell motility and invasion (e.g., metastasis).

The formation of new blood vessels, either from differentiating endothelial cells during embryonic development (vasculogenesis) or from pre-existing vessels during adult life (angiogenesis), is an essential feature of organ development, reproduction, and wound healing in higher organisms. Folkman and Shing, *J. Biol. Chem.,* 267: 10931-10934 (1992); Reynolds et al., *FASEB J.,* 6: 886-892 (1992); Risau et al., *Development,* 102: 47'-478 (1988). Angiogenesis is implicated in the pathogenesis of a variety of disorders, including, but not limited to, solid tumors, intraocular neovascular syndromes such as proliferative retinopathies or age-related macular degeneration (AMD), rheumatoid arthritis, and psoriasis (Folkman et al., *J. Biol. Chem.* 267:10931-10934 (1992); Klagsbrun et al., *Annu. Rev. Physiol.* 53:217-239 (1991); and Garner A, "Vascular Diseases". In: Pathobiology of ocular disease. A dynamic approach. Garner A, Klintworth G K, Eds. 2nd Edition Marcel Dekker, NY, pp 1625-1710 (1994)). For example, vascularization allows tumor cells in solid tumors to acquire a growth advantage and proliferative freedom as compared to normal cells. Accordingly, a correlation has been observed between microvessel density in tumors and patient survival with various cancers and tumors (Weidner et al., *N Engl J Med* 324:1-6 (1991); Horak et al., *Lancet* 340:1120-1124 (1992); and Macchiarini et al., *Lancet* 340:145-146 (1992)).

A number of RTK have been identified that govern discrete stages of vascular development (Folkman et al., *Cell,* 87:1153-1155 (1996); Hanahan, D., *Science,* 277:48-50 (1997); Risau, W., *Nature,* 386:671-674 (1997); Yancopoulos et al., *Cell,* 93:661-664 (1998)). For example, VEGFR2 (FLK1), a receptor for vascular endothelial growth factor (VEGF), mediates endothelial and hematopoietic precursor cell differentiation (Shalaby et al., *Nature*, 376:62-66 (1995); Carrneliet et al., *Nature*, 380:435-439 (1996); Ferrara et al., *Nature* 380:439-442 (1996)). VEGF also governs later stages of angiogenesis through ligation of VEGFR1 (FLT1) (Fong et al., *Nature*, 376:66-70 (1995)). Mice that lack VEGFR1 have disorganized vascular endothelium with ectopic occurrence of endothelial cells from the earliest stages of vascular development, suggesting that VEGFR1 signaling is essential for the proper assembly of endothelial sheets (Fong et al., supra). Another tyrosine kinase receptor, TEK (TIE2) (Dumont et al., *Genes Dev.* 8:1897-1909 (1994); Sato et al., *Nature*, 376:70-74 (1995)) and its ligands ANG1 (Davis et al., *Cell* 87:1161-1169 (1996); Suri et al., *Cell* 87:1171-1180 (1996)) and ANG2 (Maisonpierre et al., *Science* 277:55-60 (1997)) are involved in assembly of non-endothelial vessel wall components. TIE (TIE1) is involved in maintaining endothelial integrity, and its inactivation results in perinatal lethality due to edema and hemorrhage (Sato, et al., *Nature* 376:70-74 (1995)). The TEK pathway seems to be involved in maturation steps and promotes interactions between the endothelium and surrounding vessel wall components (Suri et al., supra; and Vikkula et al., *Cell* 87:1181-1190 (1996)).

The EPH tyrosine kinase subfamily appears to be the largest subfamily of transmembrane RTK (Pasquale et al., *Curr. Opin. Cell Biol.* 9:608-615 (1997); and Orioli and Klein, *Trends in Genetics* 13:354-359 (1997)). Ephrins and their EPH receptors govern proper cell migration and positioning during neural development, presumably through modulating intercellular repulsion (Pasquale, supra; Orioli and Klein, supra). Bidirectional signaling has been observed for some Ephrin-B/EPHB ligand/receptor pairs (Holland et al., *Nature* 383:722-725 (1996); and Bruckner et al., *Science* 275:1640-1643 (1997)). For example, Ephrin-A1 and Ephrin-B1 have been-proposed to have angiogenic properties (Pandey et al., *Science* 268:567-569 (1995); and Stein et al., *Genes Dev.* 12:667-678 (1998)). Ephrin-B2, a ligand for EPHB4 receptor, was recently reported to mark the arterial compartment during early angiogenesis, and mice that lack Ephrin-B2 showed severe anomalies in capillary bed formation (Wang et al., *Cell* 93: 741-753 (1998)).

Thus, blocking tyrosine kinase activity represents a rational, targeted approach to cancer therapy. Additionally, because tyrosine kinases have a number of other diverse biological functions, such as regulation of metabolism, cell differentiation, inflammation, immune responses, and tissue morphogenesis, kinases are attractive for drug development outside oncology.

3. SUMMARY OF THE INVENTION

The present invention provides compounds that can modulate tyrosine kinases, compositions that comprise the compounds and methods of using the compounds for the treatment or prevention of diseases or conditions that are characterized by tyrosine kinase activity or expression including, for example, cancer, diabetes, restenosis, arteriosclerosis, psoriasis, angiogenic diseases and immunologic disorders. (see, e.g., Powis et al., 1994, *Anti-Cancer Drugs Design* 9: 263-277; Merenmies et al., 1997, *Cell Growth Differ* 8: 3-10; Shawver et al., 1997, *Drug Discovery Today* 2:50-63; the contents of each are hereby incorporated by reference in their entireties).

In one aspect, the present invention provides compounds according to formula (1), or a stereoisomer, tautomer, salt or hydrate thereof:

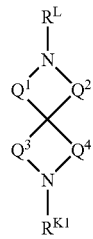

Formula (1)

In formula (1), $R^{K1}$ is selected from hydrogen, lower alkyl, lower alkenyl (such as allyl or methallyl), lower alkynyl (such as propargyl or 3-pentynyl), lower cycloalkyl (such as cyclopropyl, cyclobutyl or cyclopentyl), lower cycloalkyl-alkyl (such as cyclopropylmethyl or cyclopropylethyl), optionally substituted aryl, optionally substituted heteroaryl, optionally substituted arylalkyl or heteroarylalkyl, heteroalkyl (such as 2-methoxyethyl, 2-methoxypropyl, diethylaminoethyl or 3-dimethylaminopropyl), heterocycloalkyl (such as 3-tetrahydrofurfuryl or 3-piperidinyl), heterocycloalkyl-alkyl (such as tetrahydrofurfuryl or 2-[2-(1-methylpyrrolidino)-ethyl)]), carboxamido, primary, secondary or tertiary carboxamido-, primary, secondary or tertiary sulfamido, hydroxy-, lower alkoxy-, lower alkylsulfinyl, lower alkylsulfonyl, primary, secondary, or tertiary amino, optionally substituted arylamido, or heteroarylamido, optionally substituted alkylsulfonyl, optionally substituted arylsulfonyl, optionally substituted sulfamido.

In formula (1), each $Q^1$, $Q^2$, $Q^3$ and $Q^4$ is independently selected from:

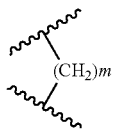

Q1

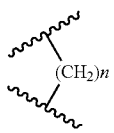

Q2

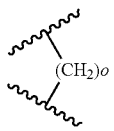

Q3

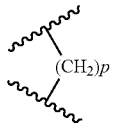

Q4 wherein m=integer from 1 to 5, in certain embodiments 1 to 3;

wherein n=integer from 1 to 5, in certain embodiments 1 to 3;

wherein o=integer from 1 to 5, in certain embodiments 1 to 3;

and wherein p=integer from 1 to 5, in certain embodiments 1 to 3.

In formula (1), $R^L$ is a selected from the following:
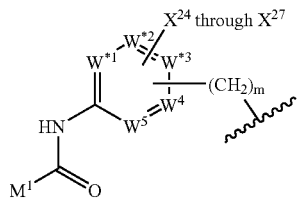
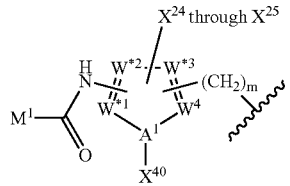
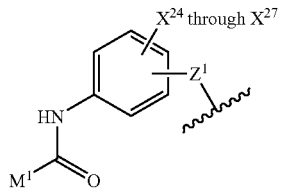
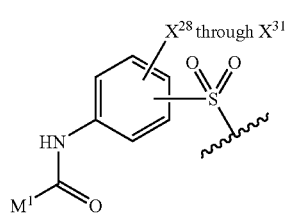
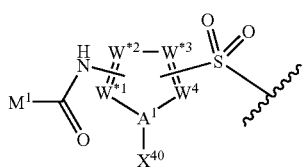
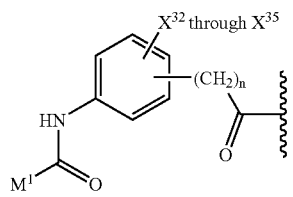
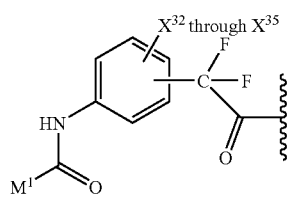
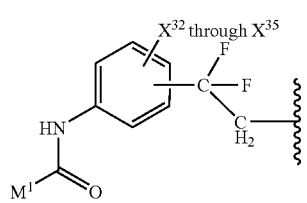
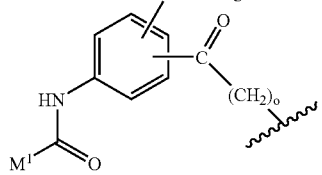
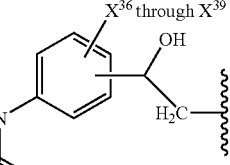
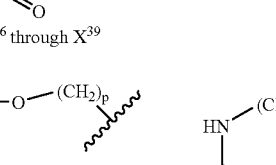
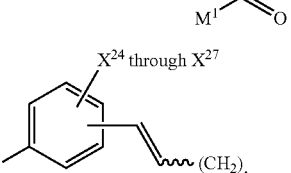
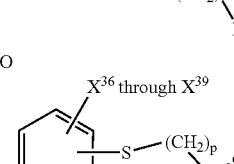
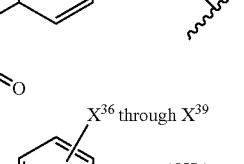
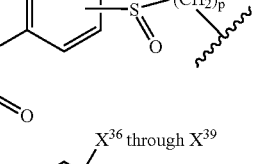
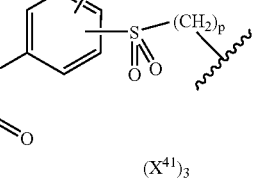
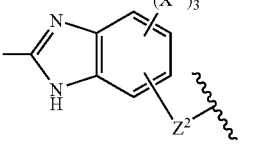
wherein the independent integers m, n, o, p, q, r, s, t, u, v etc. are from 0 to 6, in certain embodiments from 0 to 3.
In formula (1), each $W^1$ through $W^5$ is independently selected from carbon or nitrogen.
In formula (1), each $R^{10}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl and heteroarylalkyl.

In formula (1), each $A^1$ is selected from carbon, nitrogen, oxygen and sulfur. $X^{40}$ is either absent or selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (1), each $Z^1$ and $Z^2$ is independently selected from: a chemical bond or $(CH_2)_r$, wherein r is an integer from 0 to 6, or —$(CF_2)$—$(C=O)$— or —$(CF_2)$—$(CH_2)$—. In $Z^1$ and $Z^2$, any of methylene group can be optionally substituted by one or more lower alkyl group(s), including substitution, forming geminal dialkyl, such as geminal dimethyl. They can be also optionally substituted by an optionally substituted aryl or heteroaryl group or a hydroxy or lower alkoxy group. Optionally one or more of the methylene group(s) can be replaced by a heteroatom selected from —O—, —S—, —SO—, —$SO_2$— and —$N(X^{41})$—. Optionally, one or more of the methylene group(s) can be in the oxidation state of a carbonyl (keto-) group.

In formula (1), $M^1$ is selected from:

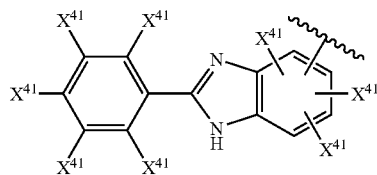

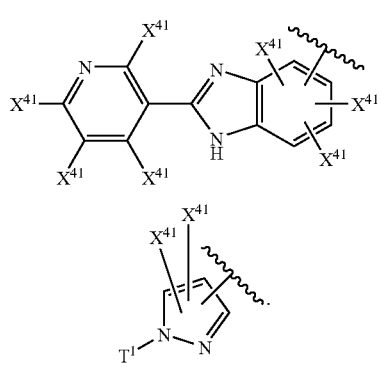

In formula (1), $M^2$ is selected from:

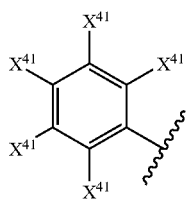 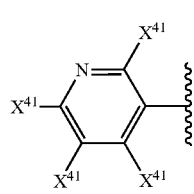

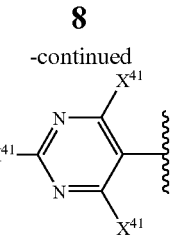

In formula (1), $T^1$ is selected from:

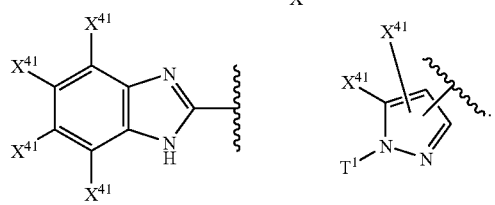

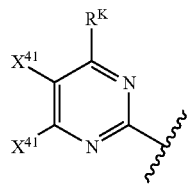 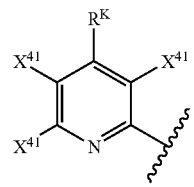

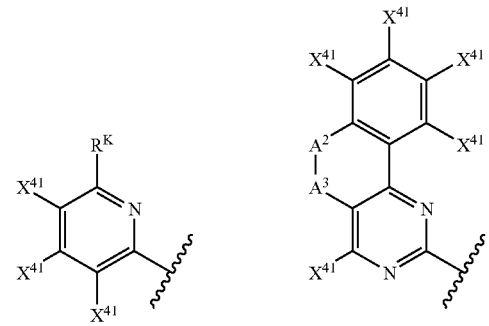

wherein $A^2$ is selected from $(CH_2)_q$, —O—, —S—, —SO—, —$SO_2$— and —$N(X^{41})$—;

and wherein $A^3$ is selected from —$CH_2$—, or C=O.

In formula (1), $R^K$ is selected from optionally substituted aryl or heteroaryl.

In formula (1), each $X^{41}$ is independently selected from the group consisting of hydrogen, hydroxy, halogen, trifluoromethyl, trifluoromethoxy, lower alkyl, lower alkoxy, optionally substituted aryl or heteroaryl, optionally substituted aryloxy or heteroaryloxy, optionally substituted arylamino and heteroarylamino. Each optionally substituted group is optionally substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl and heteroalkyl.

In formula (1), each $X^{24}$ through $X^{39}$ is independently hydrogen, halogen, trifluoromethyl, trifluoromethoxy, lower alkyl, lower alkoxy, di-lower alkylamino, hydroxy, amido such as acetamido, or carboxamido.

In another aspect, the present invention provides compounds according to formula (2), or a stereoisomer, tautomer, salt or hydrate thereof:

Formula (2)

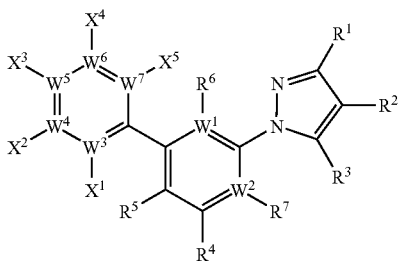

In formula (2), each $X^1$ through $X^5$ is independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclylalkyl, connected either by its nitrogen or a carbon atom (such as piperazinomethyl, piperazinoethyl, homopiperazinomethyl, morpholinomethyl, thiomorpholinomethyl, thiomorpholino-S-oxidemethyl, thiomorpholino-S,S-dioxidemethyl, pyrrolidinomethyl, piperidinoethyl, azetidinomethyl), all optionally substituted by groups selected from hydroxy, lower alkoxy, primary, secondary, or tertiary amino.

In formula (2), each $R^4$ and $R^5$ is independently selected from hydrogen, hydroxy, primary, secondary or tertiary amino, halogen, lower alkyl, lower alkoxy or lower alkylthio.

In formula (2), $W^1$ and $W^2$ are either carbon or nitrogen, but if $W^1$ is carbon, then $W^2$ is nitrogen and if $W^2$ is carbon, then $W^1$ is nitrogen. If $W^1$ is carbon, it can be optionally substituted by a substituent $R^6$ and if $W^2$ is carbon, it can be optionally substituted by a substituent $R^7$.

In formula (2), each $W^3$ through $W^7$ is independently either carbon or nitrogen and if carbon, they can be optionally substituted by a substituent $X^1$ through $X^5$.

In formula (2), each $R^6$ and $R^7$ is independently hydrogen, lower alkyl, halogen, hydroxy, primary, secondary or tertiary amino, or lower alkoxy.

In formula (2), each $R^1$ and $R^3$ is independently selected from hydrogen, hydroxy, alkoxy, amino, alkylamino, dialkylamino, acylamino, sulfonamido, and ureido. In certain embodiments, each $R^1$ and $R^3$ is independently hydrogen or —NH$_2$.

In formula (2), $R^2$ is selected from the following:

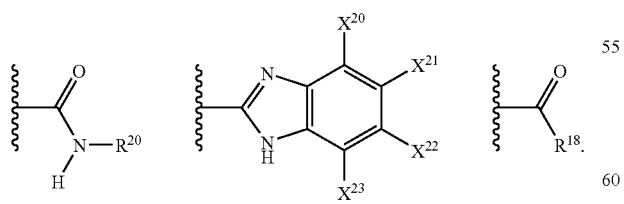

In formula (2), $R^{18}$ is —N—$(X^{42})_2$, —COOX$^{42}$ or —CON$(X^{42})$OX$^{42}$, wherein $X^{42}$ is as described below.

In formula (2), each $X^{42}$ is independently selected from hydrogen, lower alkyl, aryl, heteroaryl, all optionally substituted by, for example, hydrogen, lower alkyl, optionally substituted aryl or heteroaryl, optionally substituted arylalkyl or heteroarylalkyl, heteroalkyl or heterocycloalkyl. Where appropriate, two $X^{42}$ can be combined to form an alkyl or heteroalkyl ring with 4 to 8 members, optionally substituted by hydrogen, lower alkyl, optionally substituted aryl or heteroaryl, optionally substituted arylalkyl or heteroarylalkyl, heteroalkyl or heterocycloalkyl. The heteroalkyl ring can have from 0 to 3 heteroatoms. Exemplary heteroalkyl rings include azetidino, pyrrolidino, morpholino, piperidino, homopiperidino, piperazino and homopiperazino.

For example, $R^{18}$ can be selected from an optionally substituted nitrogen heterocyclyl, such as piperazinyl, piperidinyl, morpholinyl, homopiperazinyl, thiomorpholinyl, thiomorpholinyl-S-oxide, thiomorpholinyl-S,S-dioxide, pyrrolidinyl, piperidinyl, or azetidinyl. The optional substituent is selected from hydrogen, lower alkyl, optionally substituted aryl or heteroaryl, optionally substituted arylalkyl or heteroarylalkyl, heteroalkyl and heterocycloalkyl.

In formula (2), $R^{20}$ is selected from the following:

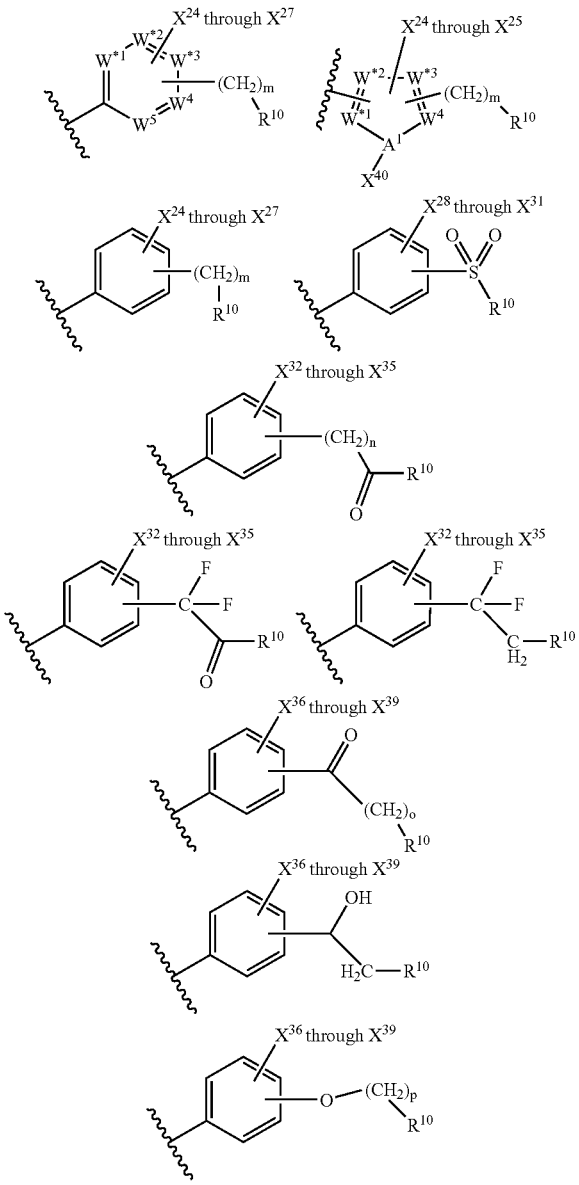

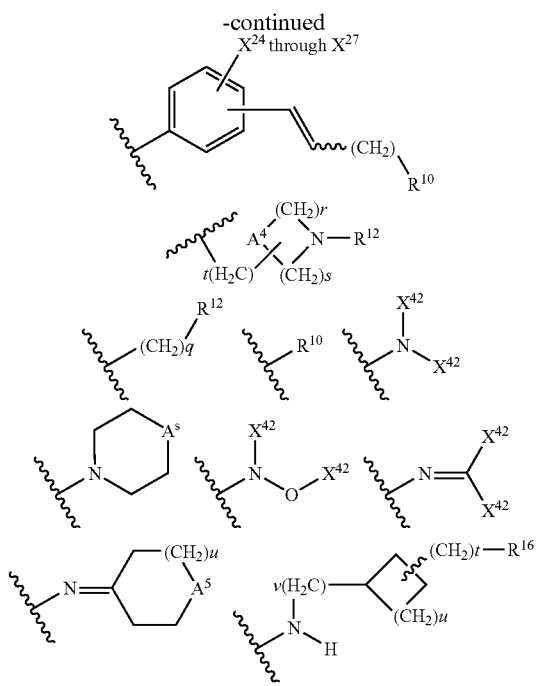

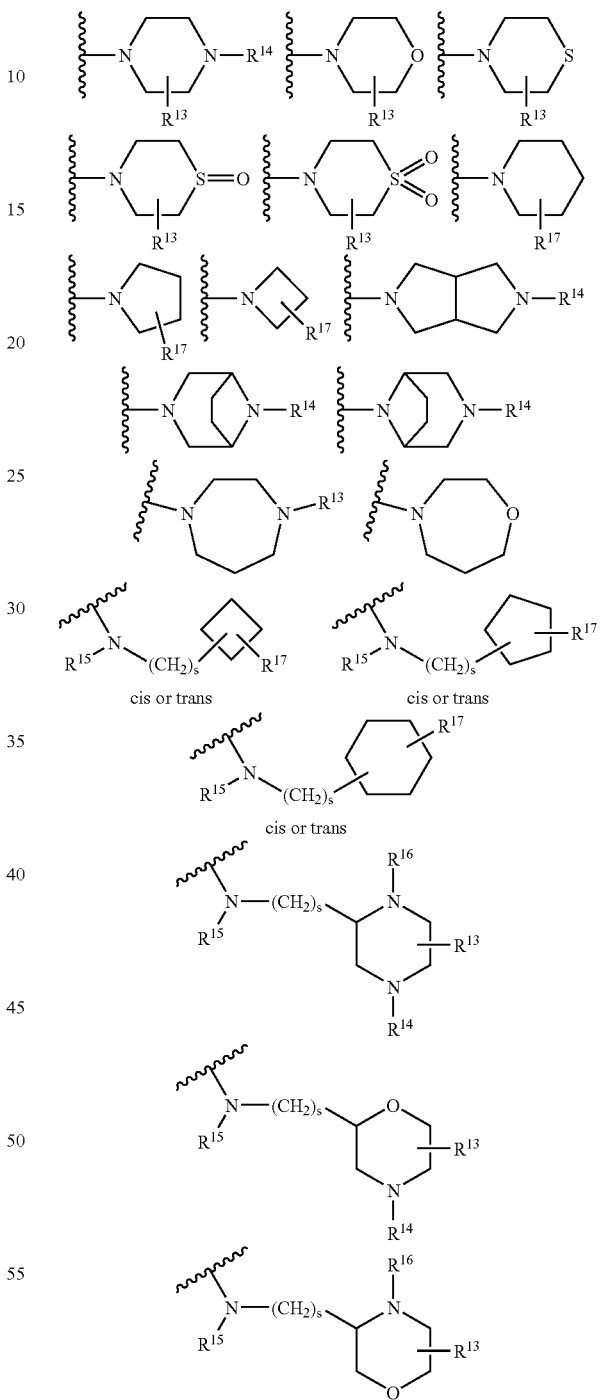

In formula (2), the independent integers m, n, o, p, q, r, s, t, u, v etc. are from 0 to 6, in certain embodiments from 0 to 3.

In formula (2), $R^{11}$ is aryl or heteroaryl, aryloxy or heteroaryloxy. In certain embodiments, $R^{11}$ is 3- or 4-pyridyl.

In formula (2), $R^{12}$ is heteroaryl or heteroarylalkyl. In certain embodiments, $R^{12}$ is 3- or 4-pyridylpropyl.

In formula (2), each $W^1$ through $W^5$ is independently selected from carbon or nitrogen.

In formula (2), each $A^1$ is selected from carbon, nitrogen, oxygen and sulfur. $X^{40}$ is either absent or selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (2), each $A^4$ is independently selected from methylene, nitrogen, oxygen and sulfur. Where appropriate, $A^4$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (2), each $A^5$ independently selected from methylene, nitrogen, oxygen and sulfur. Where appropriate, $A^5$ is optionally substituted with lower allyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (2), each $R^{10}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl and heteroarylalkyl.

In certain embodiments, exemplary $R^{10}$ include, but are not limited to, the following:

wherein the independent integers m, n, o, p, q, r, s, t, u, v etc. are from 0 to 6, in certain embodiments from 0 to 3.

In formula (2), each $R^{13}$ is independently hydrogen, lower alkyl, hydroxymethyl, methoxymethyl or may form a double bond to oxygen (C=O), thus giving the corresponding piperazinone derivative.

In formula (2), each $R^{14}$ is independently a lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (2), each $R^{15}$ is selected from hydrogen, lower alkyl, lower alkenyl, lower alkynyl, lower cycloalkyl, heterocycloalkyl, heterocycloalkyl-alkyl, heteroalkyl, optionally substituted (aryl or heteroaryl, arylalkyl or heteroarylalkyl), hydroxy-lower alkyl (such as hydroxyethyl), lower alkylaminoalkyl, lower dialkylaminoalkyl In formula (2), each $R^{16}$ is selected from hydroxy, lower alkoxy, lower alkylamino, di-lower alkylamino, N-heterocyclyl (such as azetidino, pyrrolidino, morpholino, piperidino, homopiperidino, piperazino, homopiperazino, thiomorpholino, thiomorpholino-S-oxide, thiomorpholino-S,S-dioxide and their optionally substituted derivatives, where the substituent is selected from lower alkyl, lower hydroxyalkyl or lower alkoxyalkyl).

In formula (2), each $X^{20}$ through $X^{23}$ is independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino.

In formula (2), each $X^{24}$ through $X^{39}$ is independently hydrogen, halogen, trifluoromethyl, trifluoromethoxy, lower alkyl, lower alkoxy, di-lower alkylamino, hydroxy, amido such as acetamido or carboxamido.

In formula (2), each $X^{41}$ and $R^{17}$ is independently selected from the group consisting of hydrogen, hydroxy, halogen, trifluoromethyl, trifluoromethoxy, lower alkyl, lower alkoxy, optionally substituted aryl or heteroaryl, optionally substituted aryloxy or heteroaryloxy, optionally substituted arylamino and heteroarylamino. Each optionally substituted group is optionally substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl and heteroalkyl.

In another aspect, the present invention provides compounds according to formula (3), or a stereoisomer, tautomer, salt or hydrate thereof:

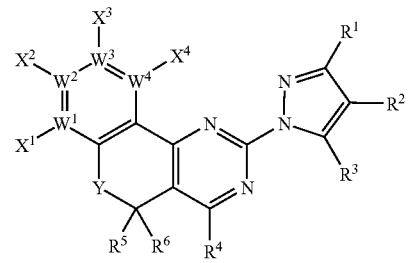

Formula 3

In formula (3), each $W^1$ through $W^4$ is independently carbon or nitrogen. When any $W^1$ through $W^4$ is nitrogen, then the corresponding substituent $X^1$ through $X^4$ is absent.

In formula (3), each $X^1$ through $X^4$ is independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxidemethyl, thiomorpholino-S,S-dioxidemethyl, pyrrolidinomethyl, piperidinoethyl, azetidinomethyl), all optionally substituted by groups selected from hydroxy, lower alkoxy, primary, secondary, or tertiary amino, any two groups taken together may form a cyclic structure.

In formula (3), $R^4$ is selected from hydrogen, hydroxy, primary, secondary or tertiary amino, halogen, lower alkyl, lower alkoxy or lower alkylthio.

In formula (3), each $R^5$ and $R^6$ is independently selected from hydrogen or methyl, or may form a double bond to oxygen thus forming an oxo-group, or may form a double bond to a nitrogen, thus forming an imino group, optionally substituted by lower alkyl, cycloalkyl, alkenyl, alkynyl, heteroalkyl, heterocyclyl, heterocyclyl-alkyl-alkyl, aryl, arylalkyl, heteroaryl and heteroarylalkyl.

In formula (3), Y is O or S or $(CH_2)_q$ or $NR^{41}$, wherein q=0 to 6, in certain embodiments 0 to 3. $R^{41}$ is independently hydrogen, lower alkyl, cycloalkyl, alkenyl, alkynyl, heteroalkyl, heterocyclyl, heterocyclyl-alkyl-alkyl, aryl, arylalkyl, heteroaryl or heteroarylalkyl. Any one of the $CH_2$ group(s) can be optionally substituted by one or two lower alkyl groups.

In formula (3), each $R^1$ and $R^3$ is independently selected from hydrogen, lower alkyl, cycloalkyl, hydroxy, alkoxy, amino, acylamino, or ureido. In certain embodiments, each $R^1$ and $R^3$ is independently hydrogen or —$NH_2$.

In formula (3), $R^2$ is selected from the following:

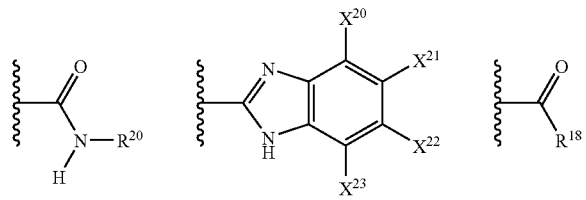

In formula (3), $R^{18}$ is $-N-(X^{42})_2$, $-COOX^{42}$ or $-CON(X)OX^{42}$, wherein $X^{42}$ is as described below.

In formula (3), each $X^{42}$ is independently selected from hydrogen, lower alkyl, aryl, heteroaryl, all optionally substituted by, for example, hydrogen, lower alkyl, optionally substituted aryl or heteroaryl, optionally substituted arylalkyl or heteroarylalkyl, heteroalkyl or heterocycloalkyl. Where appropriate, two $X^{42}$ can be combined to form an alkyl or heteroalkyl ring with 4 to 8 members, optionally substituted by hydrogen, lower alkyl, optionally substituted aryl or heteroaryl, optionally substituted arylalkyl or heteroarylalkyl, heteroalkyl or heterocycloalkyl. The heteroalkyl ring can have from 0 to 3 heteroatoms. Exemplary heteroalkyl rings include azetidino, pyrrolidino, morpholino, piperidino, homopiperidino, piperazino and homopiperazino.

For example, $R^{18}$ can be selected from an optionally substituted nitrogen heterocyclyl, such as piperazinyl, piperidinyl, morpholinyl, homopiperazinyl, thiomorpholinyl, thiomorpholinyl-S-oxide, thiomorpholinyl-S,S-dioxide, pyrrolidinyl, piperidinyl, or azetidinyl. The optional substituent is selected from hydrogen, lower alkyl, optionally substituted aryl or heteroaryl, optionally substituted arylalkyl or heteroarylalkyl, heteroalkyl and heterocycloalkyl.

In formula (3), $R^{20}$ is selected from hydrogen, $C_{1-4}$ alkyl, $C_{2-14}$ alkenyl, $C_{2-14}$ alkynyl, $C_{3-14}$ cycloalkyl, heteroalkyl, heterocycloalkyl, aryl, heteroaryl, arylalkyl, heteroarylalkyl, all groups may be optionally substituted by a substituent selected from hydroxy, lower alkyl, lower alkoxy, primary, secondary or tertiary amino, heteroalkyl, cycloalkyl, hereocycloalkyl. In formula (3), $R^{20}$ can also be selected from the following:

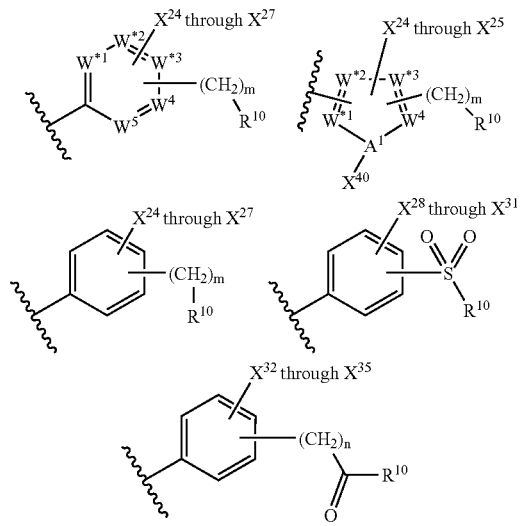

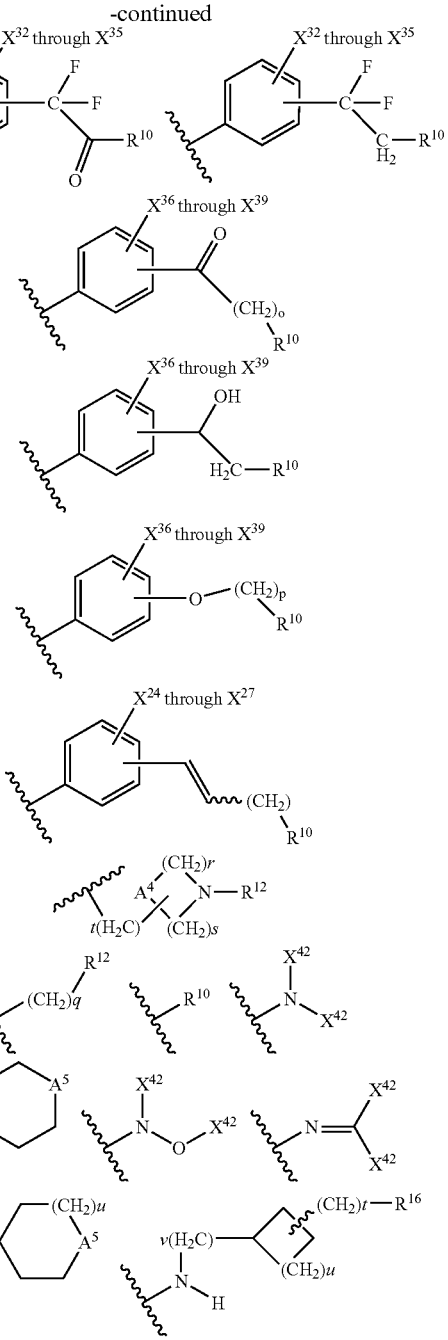

wherein the independent integers m, n, o, p, q, r, s, t, u, v etc. are from 0 to 6, in certain embodiments from 0 to 3.

In formula (3), $R^{11}$ is aryl or heteroaryl, aryloxy or heteroaryloxy. In certain embodiments, $R^{11}$ is 3- or 4-pyridyl.

In formula (3), $R^{12}$ is heteroaryl or heteroarylalkyl. In certain embodiments, $R^{12}$ is 3- or 4-pyridylpropyl.

In formula (3), each $W^1$ through $W^5$ is independently selected from carbon or nitrogen.

In formula (3), each $A^1$ is selected from carbon, nitrogen, oxygen and sulfur. $X^{40}$ is either absent or selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (3), each $A^4$ is independently selected from methylene, nitrogen, oxygen and sulfur. Where appropriate, $A^4$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (3), each $A^5$ independently selected from methylene, nitrogen, oxygen and sulfur. Where appropriate, $A^5$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (3), each $R^{10}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl, heteroarylalkyl.

Exemplary $R^{10}$ include, but are not limited to, the following:

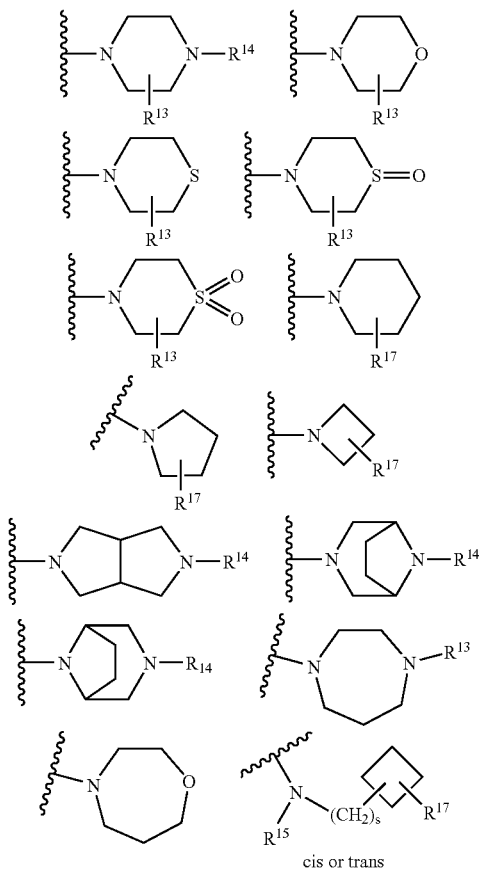

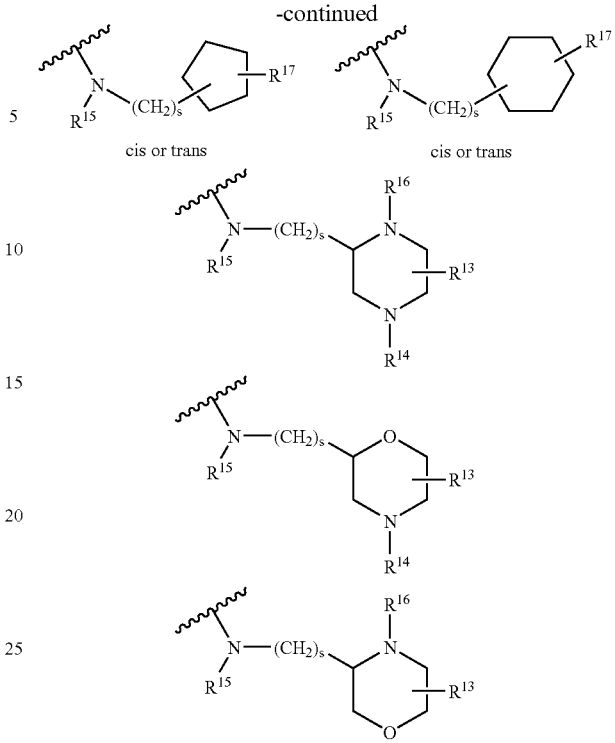

In formula (3), each $X^{24}$ through $X^{39}$ is independently hydrogen, halogen, trifluoromethyl, trifluoromethoxy, lower alkyl, lower alkoxy, di-lower alkylamino, hydroxy, amido such as acetamido, or carboxamido.

In formula (3), each $R^{13}$ is independently hydrogen, lower alkyl, hydroxymethyl, methoxymethyl or may form a double bond to oxygen (C=O), thus giving the corresponding piperazinone derivative.

In formula (3), $R^{14}$ is a lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (3), each $R^{15}$ is selected from hydrogen, lower alkyl, lower alkenyl, lower alkynyl, lower cycloalkyl, heterocycloalkyl, heterocycloalkyl-alkyl, heteroalkyl, optionally substituted (aryl or heteroaryl, arylalkyl or heteroarylalkyl), hydroxy-lower alkyl (such as hydroxyethyl), lower alkylaminoalkyl, lower dialkylaminoalkyl.

In formula (3), each $R^{16}$ is selected from hydroxy, lower alkoxy, lower alkylamino, di-lower alkylamino, N-heterocyclyl (such as azetidino, pyrrolidino, morpholino, piperidino, homopiperidino, piperazino, homopiperazino, thiomorpholino, thoimorpholino-S-oxide, thiomorpholino-S,S-dioxide and their optionally substituted derivatives, where the substituent is selected from lower alkyl, lower hydroxyalkyl or lower alkoxyalkyl).

In formula (3), each $R^{17}$ is independently selected from the group consisting of hydrogen, hydroxy, halogen, trifluoromethyl, trifluoromethoxy, lower alkyl, lower alkoxy, optionally substituted aryl or heteroaryl, optionally substituted aryloxy or heteroaryloxy, optionally substituted arylamino and heteroarylamino. Each optionally substituted group is optionally substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl and heteroalkyl.

In formula (3), each $X^{20}$ through $X^{23}$ is independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclylalkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino and also the following groups:

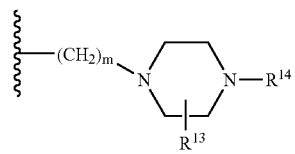
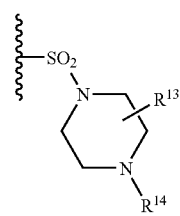
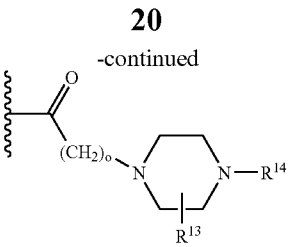

In another aspect, the present invention provides compounds according to formula (4), or a stereoisomer, tautomer, salt or hydrate thereof:

Formula 4

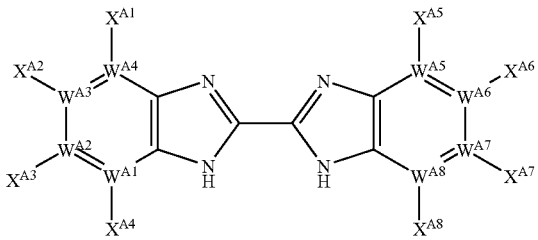

Compounds of formula (4) may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers (double bond isomers), but not limited to these, are included.

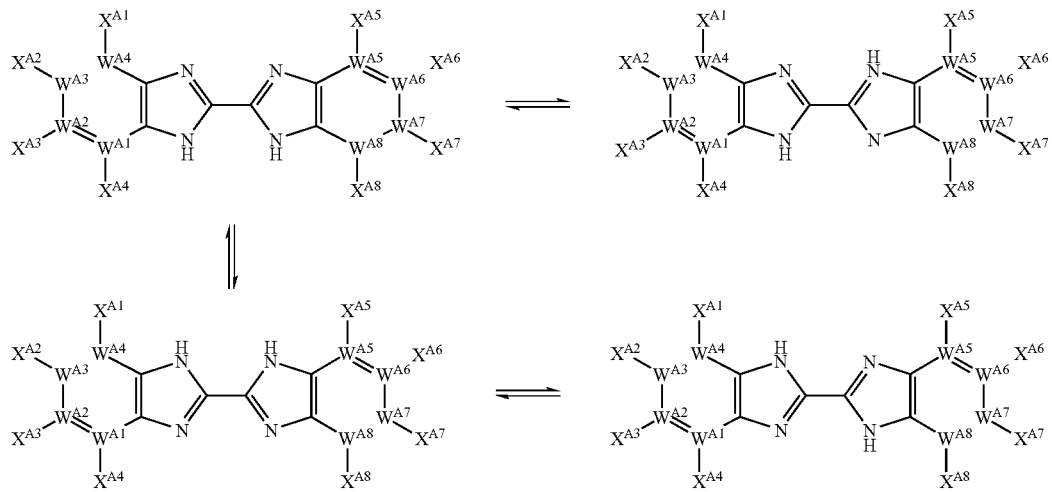

-continued

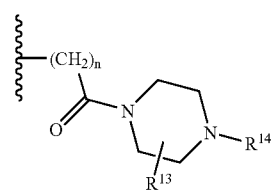

In formula (4), each $W^{A1}$ through $W^{A8}$ is independently a carbon atom or a nitrogen atom. When any of the atoms denoted $W^{A1}$ through $W^{A8}$ is N, then the corresponding substituent denoted $X^{A1}$ through $X^{A8}$ is absent.

In formula (4), each $X^{A1}$ though $X^{A4}$ is independently hydrogen, hydroxy, halogen, trifluoromethyl, trifluoromethoxy, lower alkyl, lower alkoxy, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl, heteroalkyl).

In formula (4), each $X^{45}$ through $X^{48}$ is independently selected from hydrogen, lower alkyl, trifluoromethyl, hydroxy, lower alkoxy, trifluoromethoxy, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino and also the following:

In formula (4), $R^{18}$ is —N—$(X^{42})_2$, —COO$X^{42}$ or —CON$(X^{42})$O$X^{42}$, wherein $X^{42}$ is as described below.

In formula (4), each $X^{42}$ is independently selected from hydrogen, lower alkyl, aryl, heteroaryl, all optionally substituted by, for example, hydrogen, lower alkyl, optionally substituted aryl or heteroaryl, optionally substituted arylalkyl or heteroarylalkyl, heteroalkyl or heterocycloalkyl. Where appropriate, two $X^{42}$ can be combined to form an alkyl or heteroalkyl ring with 4 to 8 members, optionally substituted by hydrogen, lower alkyl, optionally substituted aryl or heteroaryl, optionally substituted arylalkyl or heteroarylalkyl, heteroalkyl or heterocycloalkyl. The heteroalkyl ring can have from 0 to 3 heteroatoms. Exemplary heteroalkyl rings include azetidino, pyrrolidino, morpholino, piperidino, homopiperidino, piperazino and homopiperazino.

For example, $R^{18}$ can be selected from an optionally substituted nitrogen heterocyclyl, such as piperazinyl, piperidinyl, morpholinyl, homopiperazinyl, thiomorpholinyl, thiomorpholinyl-S-oxide, thiomorpholinyl-S,S-dioxide, pyrrolidinyl, piperidinyl, or azetidinyl. The optional substituent is selected from hydrogen, lower alkyl, optionally substituted aryl or heteroaryl, optionally substituted arylalkyl or heteroarylalkyl, heteroalkyl and heterocycloalkyl.

In formula (4), each $R^{20}$ is selected from:

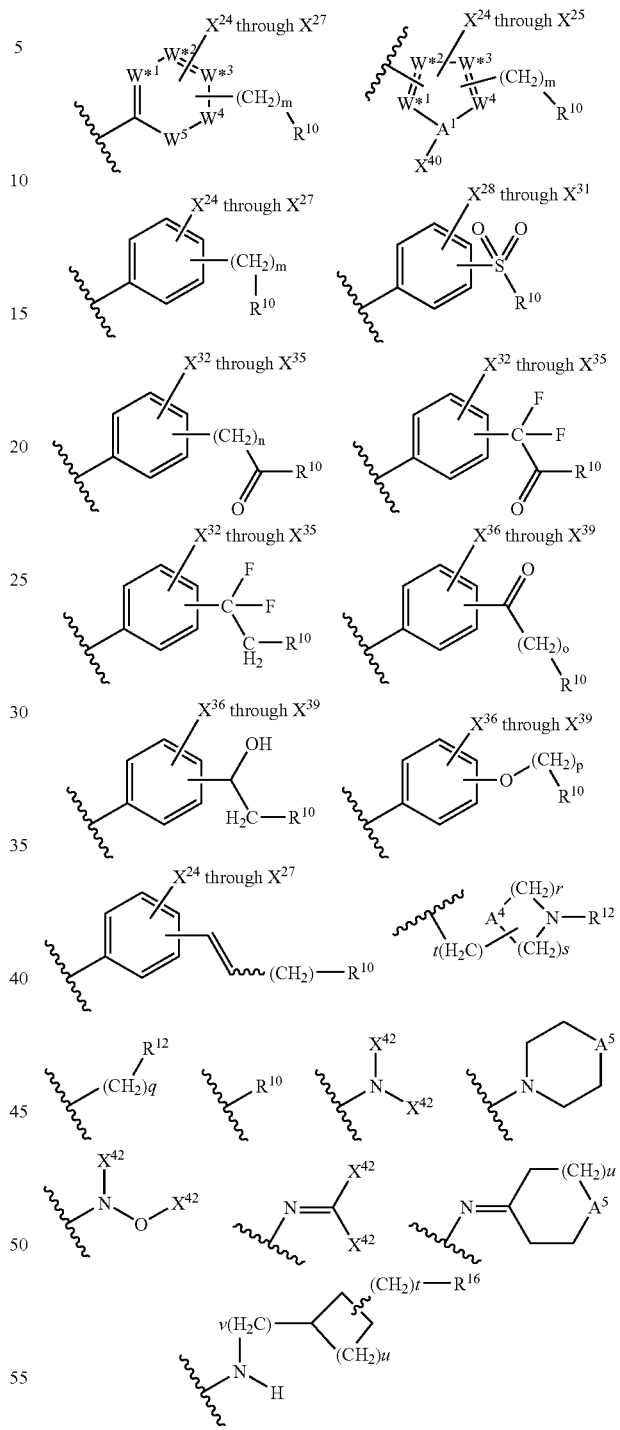

wherein the independent integers m, n, o, p, q, r, s, t, u, v etc. are from 0 to 6, in certain embodiments from 0 to 3.

In formula (4), each $W^1$ through $W^5$ is independently selected from carbon or nitrogen.

In formula (4), $R^{11}$ is aryl or heteroaryl, aryloxy or heteroaryloxy. In certain embodiments, $R^{11}$ is 3- or 4-pyridyl.

In formula (4), $R^{12}$ is heteroaryl or heteroarylalkyl. In certain embodiments, $R^{12}$ is 3- or 4-pyridylpropyl.

In formula (4), each $W^1$ through $W^5$ is independently selected from carbon or nitrogen.

In formula (4), each $A^1$ is selected from carbon, nitrogen, oxygen and sulfur. $X^{40}$ is either absent or selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (4), each $A^4$ is independently selected from methylene, nitrogen, oxygen and sulfur. Where appropriate, $A^4$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (4), each $A^5$ independently selected from methylene, nitrogen, oxygen and sulfur. Where appropriate, $A^5$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (4), each $R^{10}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl, heteroarylalkyl.

Exemplary $R^{10}$ include, but are not limited to, the following:

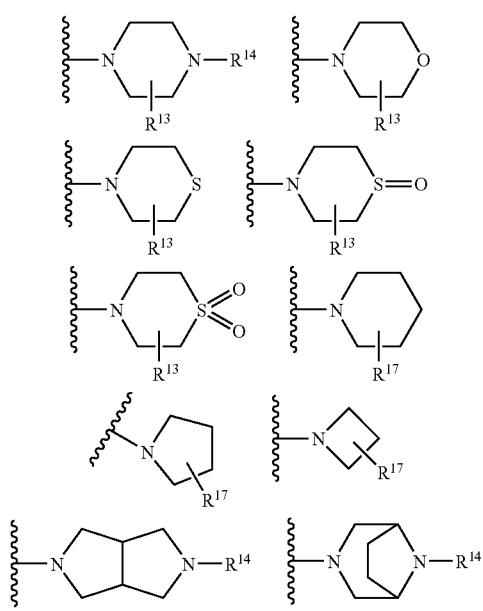

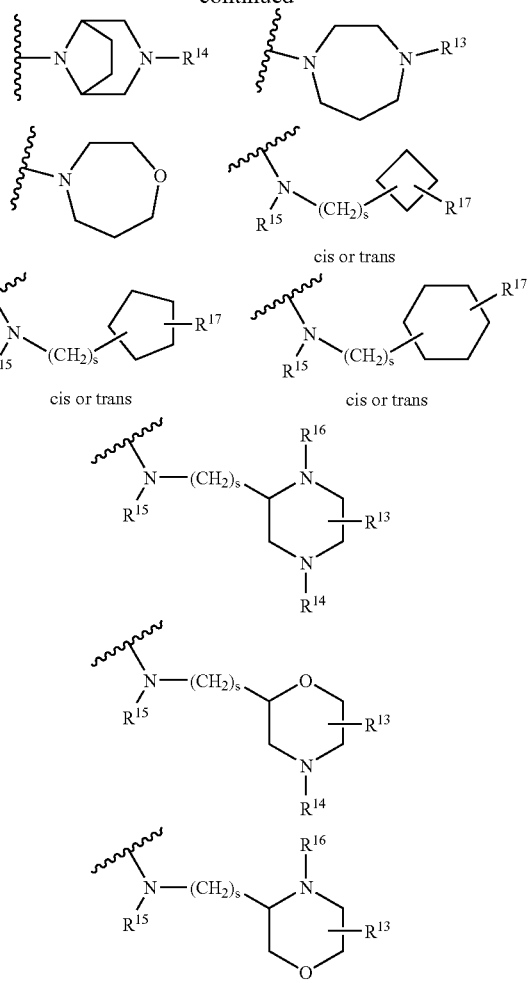

wherein the independent integers m, n, o, p, q, r, s, t, u, v etc. are from 0 to 6, in certain embodiments from 0 to 3.

In formula (4), each $X^{24}$ through $X^{39}$ is independently hydrogen, halogen, trifluoromethyl, trifluoromethoxy, lower alkyl, lower alkoxy, di-lower alkylamino, hydroxy, amido such as acetamido, or carboxamido.

In formula (4), each $R^{13}$ is independently hydrogen, lower alkyl, hydroxymethyl, methoxymethyl or may form a double bond to oxygen (C=O), thus giving the corresponding piperazinone derivative.

In formula (4), each $R^{14}$ is a lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (4), each $R^{15}$ is selected from hydrogen, lower alkyl, lower alkenyl, lower alkynyl, lower cycloalkyl, heterocycloalkyl, heterocycloalkyl-alkyl, heteroalkyl, optionally substituted (aryl or heteroaryl, arylalkyl or heteroarylalkyl), hydroxy-lower alkyl (such as hydroxyethyl), lower alkylaminoalkyl, lower dialkylaminoalkyl.

In formula (4), each $R^{16}$ is selected from hydroxy, lower alkoxy, lower alkylamino, di-lower alkylamino, N-heterocyclyl (such as azetidino, pyrrolidino, morpholino, piperidino, homopiperidino, piperazino, homopiperazino, thiomorpholino, thiomorpholino-S-oxide, thiomorpholino-S,S-dioxide and their optionally substituted derivatives, where the substituent is selected from lower alkyl, lower hydroxyalkyl or lower alkoxyalkyl).

In formula (4), each $R^{17}$ is selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (4), each $X^{20}$ through $X^{23}$ are independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclylalkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino.

In another aspect, the present invention provides compounds according to formula (5), or a stereoisomer, tautomer, salt or hydrate thereof:

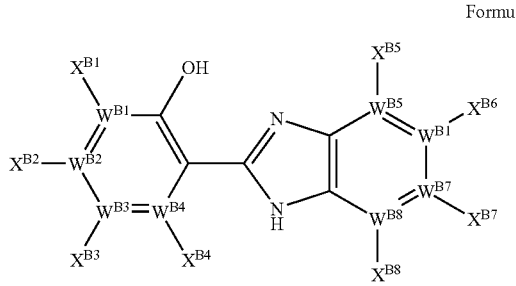

Formula 5

In formula (5), each $W^{B1}$ through $W^{B8}$ is independently a carbon atom or a nitrogen atom. When any $W^{B1}$ through $W^{B8}$ is N, then the corresponding substituent(s) $X^{B1}$ through $X^{B8}$ is absent.

Compounds according to formula (5) can also be depicted in their respective "keto" form, which under certain conditions may predominate over the corresponding "enol" form. However, all possible tautomers and stereoisomers (such as for example, but not limited to: E and Z, (trans and cis) are incorporated herein.

In formula (5), each $X^{B1}$ through $X^{B4}$ is independently selected from hydrogen, hydroxy, halogen, optionally substituted lower alkyl, optionally substituted lower alkoxy, optionally substituted acylamino, optionally substituted sulfonamido, optionally substituted ureido, trifluoromethyl, trifluoromethoxy, nitro, cyano, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, optionally substituted heterocyclyl or cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl, all optionally substituted by groups selected from hydroxyalkyl, lower alkoxyalkyl, primary, secondary, or tertiary amino-alkyl, lower alkyl cycloalkyl or heterocycloalkyl). Such aryl and heteroaryl groups can be bicyclic in certain embodiments. In the above list, lower alkyl, lower alkoxy, acyl amino, sulfonamido and ureido can be substituted, for example, with aryl, heteroaryl, cycloalkyl or cycloheteroalkyl.

In certain embodiments, any adjacent pair of $X^{B1}$ through $X^{B4}$ can be joined to form a cycloalkyl, cylcoheteroalkyl, aryl or heteroaryl ring fused to the ring comprising $W^{B1}$ through $W^{B8}$. Exemplary fused rings include naphthyl, benzodioxolyl, benzofuranyl, benzodioxinyl, dihydrobenzodioxinyl, and others that will be recognized by those of skill in the art. In further embodiments, two pairs of $X^{B1}$ through $X^{B4}$ can be joined to form a fused tricylcic ring system. Exemplary tricyclic rings include julolidinyl, tetramethyl julolidinyl and others that will be recognized by those of skill in the art.

A specific exclusion is provided that when $W^{B1}$ is nitrogen, $X^{B4}$ is not the following group:

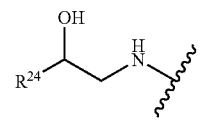

Wherein $R^{24}$ is an optionally substituted aryl.

In formula (5), each $X^{B3}$ can be selected from hydrogen, halogen, alkyl, alkenyl, alkynyl, alkoxy, cycloalkoxy, cycloalkyl, heterocycloalkyl, optionally substituted (aryl, heteroaryl, arylalkyl, heteroarylalkyl, aryloxy, heteroaryloxy, arylalkoxy, heteroarylalkoxy, arylthio, heteroarylthio, arylsulfoxy, heteroarylsulfoxy, arylsulfonyl, heteroarylsulfonyl, arylsulfonamido, heteroarylsulfonamido, arylaminosulfonyl, heteroarylaminosulfonyl), by substituents selected from halogen, hydroxy, amino, cyano, nitro, carboxamido, sulfonamido, alkoxy, lower-alkylamino, di-lower-alkylamino, cycloalkyl, cycloalkylalkyl, cycloalkoxy, cycloalkylalkoxy, trifluoromethyl, trifluoromethoxy, methylenedioxy, ethylenedioxy, methanesulfonyl, trifluoromethanesulfonyl, dialkylaminoalkyl, dialkylaminoalkoxy, heterocyclyl, heteroalkyl, heterocyclylalkyl.

In formula (5), each $X^{B5}$ through $X^{B8}$ is independently selected from hydrogen, halogen, lower alkyl, lower alkoxy, trifluoromethyl, trifluoromethoxy, nitro, cyano, optionally substituted (aryl or heteroaryl, aryloxy or heteroaryloxy, arylamino or heteroarylamino, arylthio or heteroarylthio, arylsulfinyl or heteroarylsulfinyl, arylsulfonyl or heteroarylsulfonyl), substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono- or dialkyl amido, heterocycylamido, optionally substituted heterocyclyl or cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl, all optionally substituted by groups selected from hydroxy, lower alkoxy, primary, secondary, or tertiary amino or lower alkyl).

In certain embodiments according to formula (5), one of the substituents $X^{B5}$ through $X^{B8}$ is selected from the following:

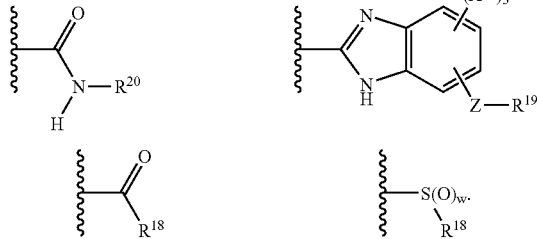

wherein each w is an integer from 0 to 2;

$R^{20}$ is selected from:

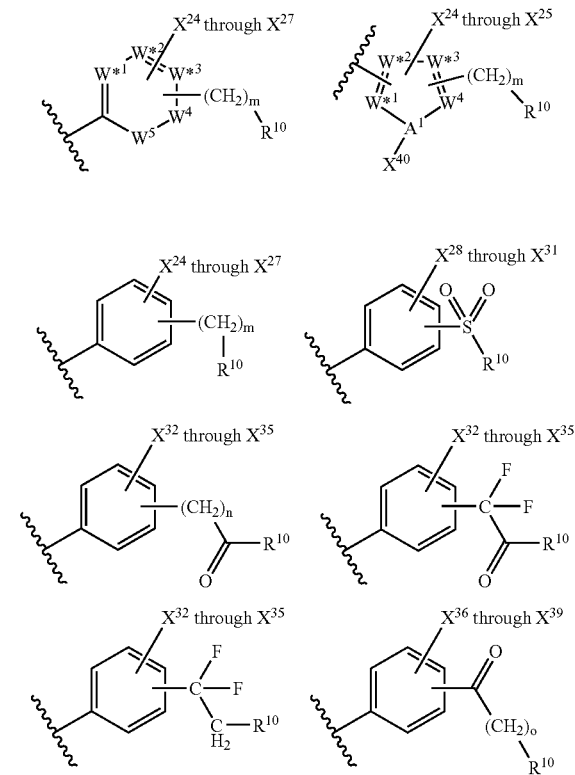

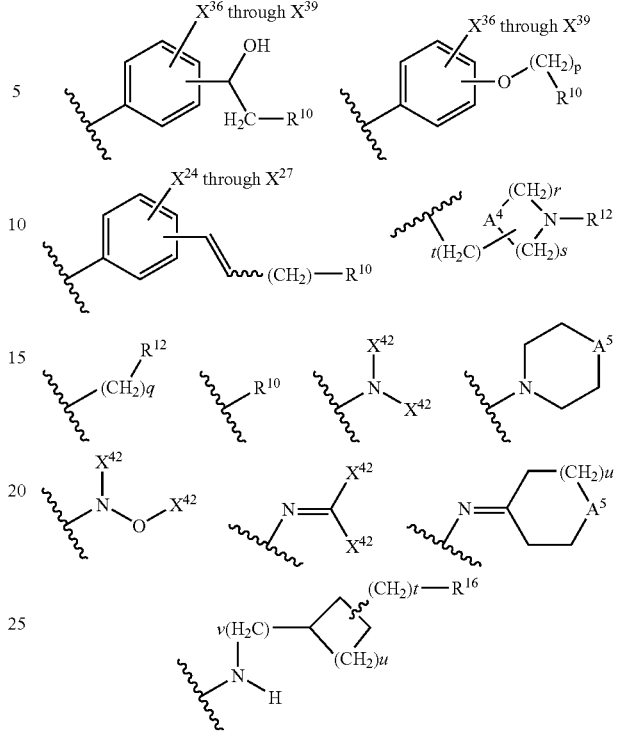

wherein the independent integers m, n, o, p, q, r, s, t, u, v etc. are from 0 to 6, in certain embodiments from 0 to 3.

In formula (5), each $W^1$ through $W^5$ is independently selected from carbon or nitrogen.

In formula (5), in certain embodiments, each $(CH_2)_q$ can be optionally substituted with one or more groups selected from hydrogen, halogen, hydroxy, optionally substituted alkoxy, optionally substituted alkyl, optionally substituted aryl and optionally substituted heteroaryl. In certain embodiments, such substituents can be joined to form a cyclic structure. In addition, in certain embodiments, one or more methylene of $(CH_2)_q$ can be replaced by a heteroatom selected from O, N and S, where appropriate according to the judgment of one of skill in the art.

In formula (5), $R^{11}$ is aryl or heteroaryl, aryloxy or heteroaryloxy. In certain embodiments, $R^{11}$ is 3- or 4-pyridyl.

In formula (5), $R^{12}$ is heteroaryl or heteroarylalkyl. In certain embodiments, $R^{12}$ is 3- or 4-pyridylpropyl.

In formula (5), each $X^{24}$ through $X^{39}$ is independently hydrogen, halogen, trifluoromethyl, trifluoromethoxy, lower alkyl, lower alkoxy, di-lower alkylamino, hydroxy, amido such as acetamido, or carboxamido.

In formula (5), each $A^1$ is selected from carbon, nitrogen, oxygen and sulfur. $X^{40}$ is either absent or selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (5), each $A^4$ is independently selected from methylene, nitrogen, oxygen and sulfur. Where appropriate, $A^4$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (5), each $A^5$ independently selected from methylene, nitrogen, oxygen and sulfur. Where appropriate, $A^5$ is optionally substituted with lower alkyl, aryl or heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (5), each $R^{10}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl, heteroarylalkyl.

Exemplary $R^{10}$ include, but are not limited to, the following:

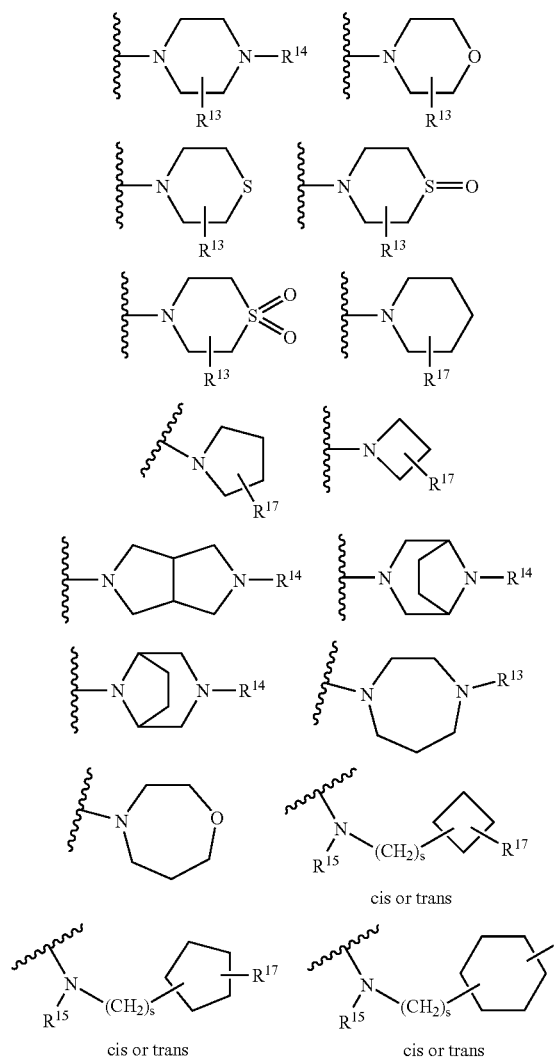

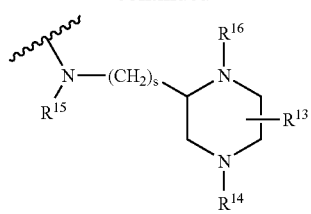

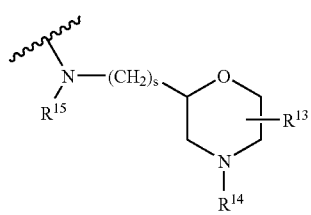

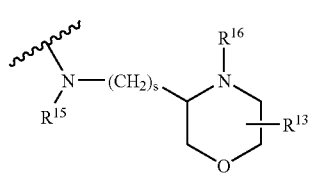

wherein the independent integers m, n, o, p, q, r, s, t, u, v etc. are from 0 to 6, embodiments from 0 to 3.

In formula (5), $R^{18}$ is $-N-(X^{42})_2$, $-COOX^{42}$ or $-CON(X^{42})OX^{42}$, wherein $X^{42}$ is as described below.

In formula (5), each $X^{42}$ is independently selected from hydrogen, lower alkyl, aryl, heteroaryl, all optionally substituted by, for example, hydrogen, lower alkyl, optionally substituted aryl or heteroaryl, optionally substituted arylalkyl or heteroarylalkyl, heteroalkyl or heterocycloalkyl. Where appropriate, two $X^{42}$ can be combined to form an alkyl or heteroalkyl ring with 4 to 8 members, optionally substituted by hydrogen, lower alkyl, optionally substituted aryl or heteroaryl, optionally substituted arylalkyl or heteroarylalkyl, heteroalkyl or heterocycloalkyl. The heteroalkyl ring can have from 0 to 3 heteroatoms. Exemplary heteroalkyl rings include azetidino, pyrrolidino, morpholino, piperidino, homopiperidino, piperazino and homopiperazino.

For example, $R^{18}$ can be selected from an optionally substituted nitrogen heterocyclclyl, such as piperazinyl, piperidinyl, morpholinyl, homopiperazinyl, thiomorpholinyl, thiomorpholinyl-S-oxide, thiomorpholinyl-S,S-dioxide, pyrrolidinyl, piperidinyl, or azetidinyl. The optional substituent is selected from hydrogen, lower alkyl, optionally substituted aryl or heteroaryl, optionally substituted arylalkyl or heteroarylalkyl, heteroalkyl and heterocycloalkyl.

In certain embodiments, each $R^{18}$ is independently selected from any of the following:

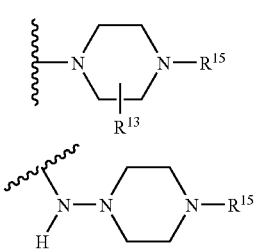

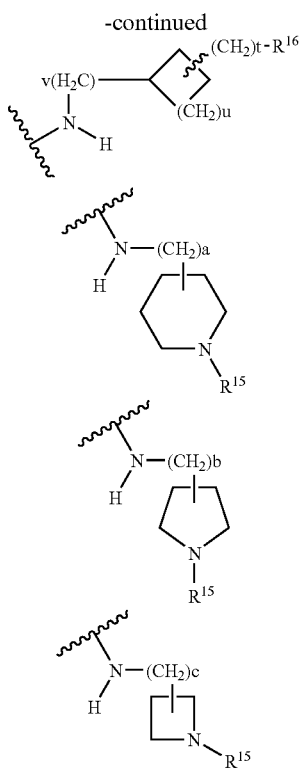

In formula (5), each b is an integer from 0 to 4.

In formula (5), each c is an integer from 0 to 4.

In formula (5), each Z is independently selected from a bond, $(CH_2)_n$—, —O—, —S—, —SO—, —SO$_2$— and —N($X^{41}$)—.

In formula (5), each $R^{19}$ is selected from: di-lower alkylamino, lower alkylamino, heterocyclyl, heterocycloalkyl, heterocycloalkylaminoalkyl, heterocycloalkoxyalkyl, heteroalkyl, di-lower alkylaminocycloalkyl, lower alkylaminocycloalkyl, heterocyclo-cycloalkyl, heterocyclo-heterocycloalkyl, heteroaryl, heteroarylalkyl.

Exemplary $R^{19}$ include, but are not limited to, the following:

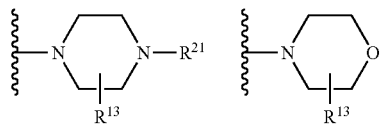

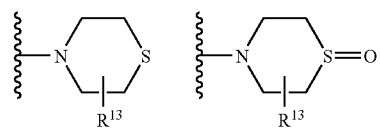

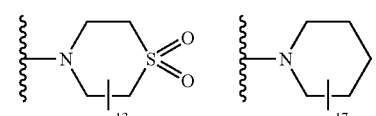

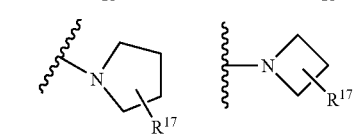

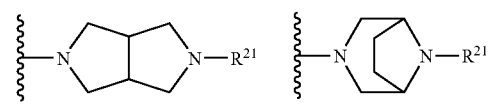

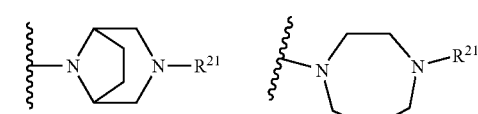

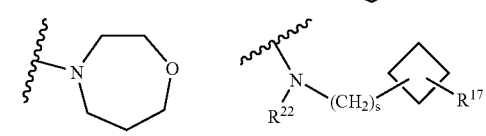

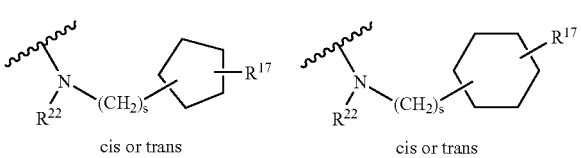

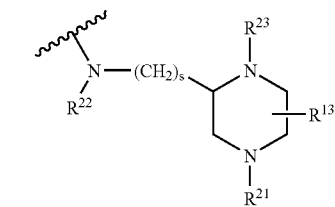

In formula (5), each $R^{13}$ is independently hydrogen, lower alkyl, hydroxymethyl, methoxymethyl or may form a double bond to oxygen (C=O), thus giving the corresponding piperazinone derivative.

In formula (5), each $R^{14}$ is a lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (5), each $R^{15}$ is selected from hydrogen, lower alkyl, lower alkenyl, lower alkynyl, lower cycloalkyl, heterocycloalkyl, heterocycloalkyl-alkyl, heteroalkyl, optionally substituted (aryl or heteroaryl, arylalkyl or heteroarylalkyl), hydroxy-lower alkyl (such as hydroxyethyl), lower alkylaminoalkyl, lower dialkylaminoalkyl In formula (5), each $R^{16}$ is selected from hydroxy, lower alkoxy, lower alkylamino, di-lower alkylamino, N-heterocyclyl (such as azetidino, pyrrolidino, morpholino, piperidino, homopiperidino, piperazino, homopiperazino, thiomorpholino, thoimorpholino-S-oxide, thiomorpholino-S,S-dioxide and their optionally substituted derivatives, where the substituent is selected from lower alkyl, lower hydroxyalkyl or lower alkoxyalkyl).

In formula (4), each $R^{17}$ is selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (5), each t is an integer from 0 to 4.

In formula (5), each u is an integer from 0 to 4.

In formula (5), each v is an integer from 0 to 4.

In formula (5), each a is an integer from 0 to 4.

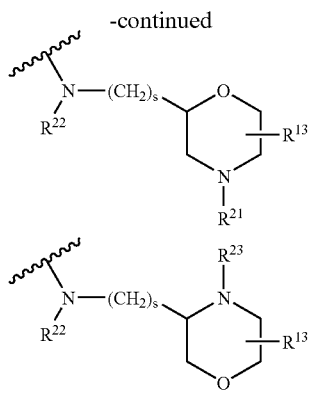

wherein the independent integers m, n, o, p, q, r, s, t, u, v etc. are from 0 to 6, in certain embodiments from 0 to 3.

In formula (5), each $R^{21}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (5), each $R^{22}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (5), each $R^{23}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In another aspect, the present invention provides compounds according to formula (6), or a stereoisomer, tautomer, salt or hydrate thereof:

Formula 6

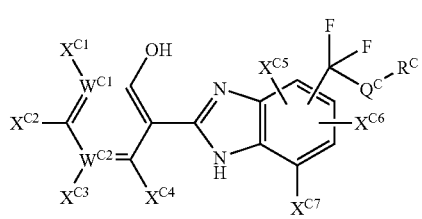

In formula (6), each $W^{C1}$ and $W^{C2}$ is independently a carbon atom or nitrogen atom. When $W^{C1}$ is N, then $X^{C1}$ is absent and when $W^{C2}$ is N then $X^{C3}$ is absent.

The compounds can also be depicted in their respective "keto" form, which under certain conditions may predominate over the corresponding "enol" form. However, all possible tautomers and stereoisomers (such as for example, but not limited to: E and Z, (trans and cis) are incorporated herein.

In formula (6), each $X^{C1}$ through $X^{C3}$ is independently selected from hydrogen, hydroxy, halogen, lower alkyl, lower alkoxy, trifluoromethyl, trifluoromethoxy, nitro, cyano, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, optionally substituted heterocyclyl or cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl, all optionally substituted by groups selected from hydroxy, lower alkoxy, primary, secondary, or tertiary amino or lower alkyl).

In formula (6), each $X^{C4}$ is selected from the following:

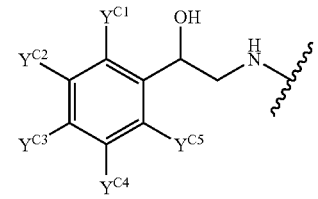

In formula (6), each $Y^{C1}$ through $Y^{C5}$ is selected from hydrogen, halogen, trifluoromethyl, trifluoromethoxy, lower alkyl, lower alkoxy, lower alkylthio, lower alkylsulfinyl, lower alkylsulfonyl, or trifluoromethanesulfonyl and can form a condensed ring such as methylenedioxy or ethylenedioxy group.

In formula (6), each $X^{C5}$ through $X^{C7}$ are independently selected from hydrogen, hydroxy, halogen, lower alkyl, lower alkoxy, trifluoromethyl, trifluoromethoxy.

In formula (6), each $Q^C$ is a carbonyl group or a methylene group.

In formula (6), each $R^C$ is selected from nitrogen-containing heterocycloalkyl groups, for example, but not limited to: optionally substituted (piperazinyl, homopiperazinyl, hexamethyleneiminyl, piperidinyl, pyrrolidinyl or azetidinyl), by a group selected from lower alkyl, hydroxy, lower alkoxy, lower alkoxyalkyl, amino, lower alkylamino, di-lower alkylamino, cycloalkyl, heterocycloalkyl, heteroalkyl, optionally substituted (aryl or heteroaryl, arylalkyl or heteroarylalkyl) by an atom or group selected from hydrogen, halogen, trifluoromethyl, trifluoromethoxy, lower alkyl, lower alkoxy, cyano, nitro, amino alkylamino or dialkylamino.

In formula (6), each $R^C$ can also be selected from a di-lower-alkylamino alkyl group, (such as dimethylaminoethylamino-), heterocyclyl-lower alkylamino (such as 1-methyl-4-piperazinoethylamino), di-lower-alkylaminoalkoxyalkylamino group (such as 2-diethylaminoethoxyamino), heteroalkylaminoalkylamino group, (such as N-(2-methoxyethyl)-N-ethylaminoethyl-), bis-heteroalkyl-aminoalkylamino group (such as bis-(2-methoxyethoxy)-amino-ethylamino-), or heterocyclylaminoalkylamino groups (such as 1-methyl-4-piperidinylaminoethylamino- or 1-methyl-4-piperazinylethylamino-). Exemplary $R^C$ include, but are not limited to, the following:

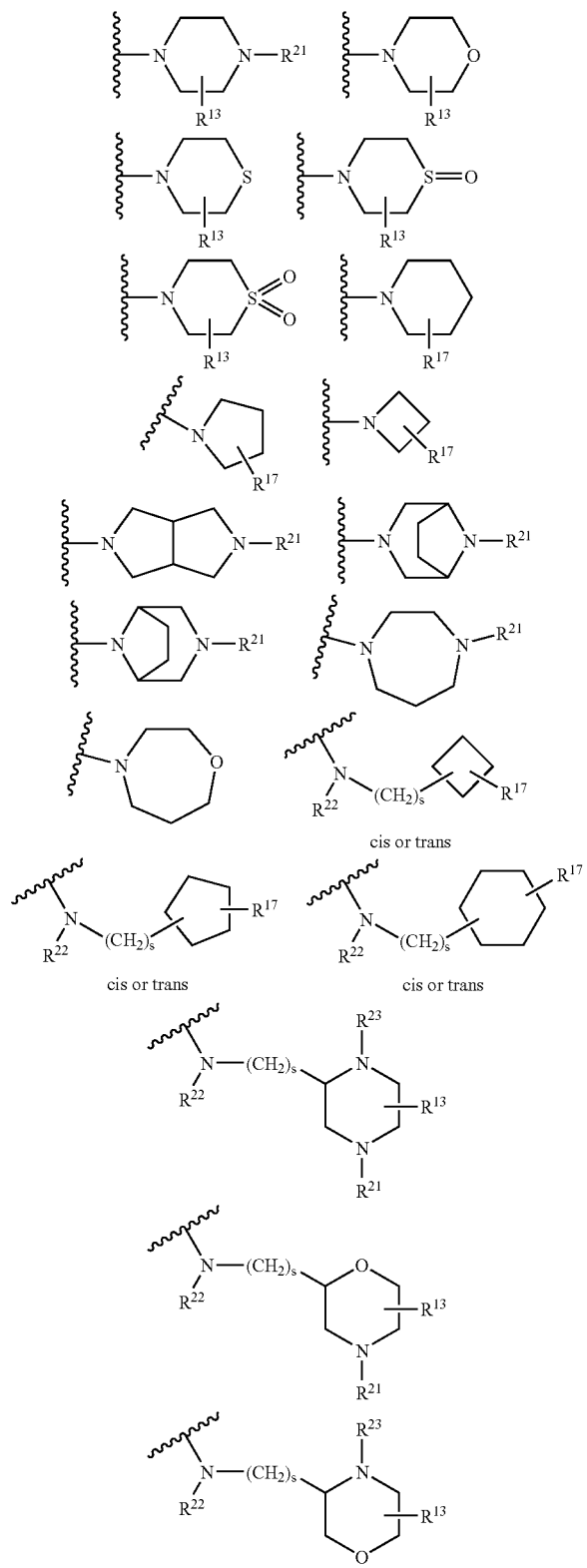

wherein the independent integers m, n, o, p, q, r, s, t, u, v etc. are from 0 to 6, in certain embodiments from 0 to 3.

In formula (6), each $R^{13}$ is independently hydrogen, lower alkyl, hydroxymethyl, methoxymethyl or may form a double bond to oxygen (C=O), (thus giving for instance the corresponding piperazinone derivative).

In formula (6), each $R^{17}$ is selected from hydrogen, lower alkyl, aryl and heteroaryl, all optionally substituted with lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl or heteroalkyl.

In formula (6), each $R^{21}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (6), each $R^{22}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In formula (6), each $R^{23}$ is a hydrogen or lower alkyl (such as methyl or ethyl), optionally substituted aryl (such as 2-methoxyphenyl) or heteroaryl, (such as 2-, 3-, or 4-pyridyl, optionally substituted arylalkyl (such as 4-methoxyphenethyl), or heteroarylalkyl (such as a 3-(4-pyridyl)-propyl), heteroalkyl, heterocycloalkyl (such as 1-methyl-4-piperidinyl).

In another aspect, the present invention provides a pharmaceutical composition comprising a compound of any of formulas (1) through (6) and a pharmaceutically acceptable carrier, excipient or diluent.

In addition to being used as single agents, it is contemplated that compounds of the invention can enhance the activity of cytotoxic or cytostatic treatments when used in combination with standard therapies known in the art.

The invention further provides a pharmaceutical composition comprising a compound of any of formulas (1) through (6) in combination with pharmaceutically acceptable carrier, excipient or diluent and at least one other anti-cancer agent.

In another aspect, the present invention provides methods of using a compound according to any of formulas (1) through (6) to modulate a tyrosine kinase. The tyrosine kinase can be any tyrosine kinase known to those of skill in the art including, but not limited to, Abl, Alk, CDK's, EGFR, EMT/Itk/Tsk, FGFR, FAK, Flk-1/KDR, HER-2, IGF-1R, 1R, Jak1, Jak2, Jak3, Tyk2, LCK, MET, PDGFR and Src. In general, the methods comprise the step of contacting the tyrosine kinase with a sufficient amount of a compound according to any of formulas (1) through (6) to modulate the tyrosine kinase.

In another aspect, the present invention provides methods of using a compound according to any of formulas (1) through (6) to treat or prevent a condition or disorder associated with tyrosine kinase activity. The condition or disorder can be any condition or disorder associated with tyrosine kinase activity including, but not limited to, cancer. psoriasis, hepatic cirrhosis, diabetes, atherosclerosis, angiogenesis, restenosis, ocular diseases, rheumatoid arthritis, inflammatory disorders, autoimmune diseases and renal disorders. In general, the methods comprise the step of administering to a subject in need thereof an amount of the compound according to any of formulas (1) through (6) effective to treat or prevent the condition or disorder.

In another aspect, the present invention provides methods of using a compound according to any of formulas (1) through (6), in combination with a second agent, to treat or prevent a condition or disorder associated with tyrosine kinase activity. The condition or disorder can be any condition or disorder associated with tyrosine kinase activity including, but not limited to, cancer. psoriasis, hepatic cirrhosis, diabetes, atherosclerosis, angiogenesis, restenosis, ocular diseases, rheumatoid arthritis, inflammatory disorders, autoimmune diseases and renal disorders. In general, the methods comprise the step of administering to a subject in need thereof an amount of the compound according to any of formulas (1) through (6), in combination with the second agent, effective to treat or prevent the condition or disorder.

4. BRIEF DESCRIPTION OF THE FIGURE

FIG. 1 provides the results of an exemplary assay for IGF1R inhibition by a compound of the invention.

5. DETAILED DESCRIPTION OF THE INVENTION

5.1 Definitions

When describing the compounds, pharmaceutical compositions containing such compounds and methods of using such compounds and compositions, the following terms have the following meanings unless otherwise indicated. When two terms referring to chemical groups are combined, the combined term refers to the to groups covalently linked in either orientation, unless specified otherwise. For instance, the term "acylamino" can refer to either "—C(O)—N(R)—" or to "—N(R)—C(O)" unless specified otherwise.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring. In certain embodiments, a bicyclic compound of the invention comprises a fused aryl.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —C=C)—.

"Ethylene" refers to substituted or unsubstituted —(C—C)—.

"Ethynyl" refers to —C≡C)—.

"Halo" or "halogen" refers to fluoro, chloro, bromo and iodo. Particular halo groups are either fluoro or chloro.

"Hydroxy" refers to the radical —OH.

"Nitro" refers to the radical —NO$_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" or "heteroaromatic" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. In certain embodiments, the heteroaryl group is between 5-20 membered heteroaryl, with 5-10 membered heteroaryl being useful in certain embodiments. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Representative examples include, but are not limited to, methylthio, ethylthio, propylthio, butylthio, and the like.

"Sulfinyl" refers to the radical —S(O)H. "Substituted sulfinyl" refers to a radical such as S(O)—R wherein R is any substituent described herein.

"Sulfonyl" refers to the divalent radical —S(O$_2$)—. "Substituted sulfonyl" refers to a radical such as —S(O$_2$)—R wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein. In particular embodiments, R is selected from H, lower alkyl, alkyl, aryl and heteroaryl.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable caution" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem., Int. Ed. Engl.* 5:385-414 (errata: *Angew. Chem., Int. Ed. Engl.* 5:511); Prelog and Helmchen, 1982, *Angew. Chem.* 94:614-631, *Angew. Chem. Internat. Ed. Eng.* 21:567-583; Mata and Lobo, 1993, *Tetrahedron: Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

In certain embodiments, the compounds of the invention are "stereochemically pure." A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

As used herein, the terms "disorder" and "disease" are used interchangeably to refer to a condition in a subject. Certain conditions may be characterized as more than one disorder. For example, certain conditions may be characterized as both non-cancerous proliferative disorders and inflammatory disorders.

As used herein, the term "effective amount" refers to the amount of a compound of the invention which is sufficient to reduce or ameliorate the severity, duration of a disorder, cause regression of a disorder, prevent the recurrence, development, or onset of one or more symptoms associated with a disorder, or enhance or improve the prophylactic or therapeutic effect(s) of another therapy.

As used herein, the term "in combination" refers to the use of more than one therapies. The use of the term "in combination" does not restrict the order in which therapies (e.g., prophylactic and/or therapeutic agents) are administered to a subject with a disorder. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound of the invention. In certain other embodiments, the term "prophylactic agent" does not refer a compound of the invention. In certain embodiments, a prophylactic agent is an agent which is known to be useful for, or has been or is currently being used to the prevent or impede the onset, development, progression and/or severity of a disorder. Prophylactic agents may be characterized as different agents based upon one or more effects that the agents have in vitro and/or in vivo. For example, an anti-angiogenic agent may also be characterized as an immunomodulatory agent.

As used herein, the terms "prevent," "preventing" and "prevention" refer to the prevention of the recurrence, onset, or development of one or more symptoms of a disorder in a subject resulting from the administration of a therapy, or the administration of a combination of therapies.

As used herein, the phrase "prophylactically effective amount" refers to the amount of a therapy which is sufficient to result in the prevention of the development, recurrence or onset of one or more symptoms associated with a disorder, or to enhance or improve the prophylactic effect(s) of another therapy.

As used herein, the terms "subject" and "patient" are used interchangeably herein. The terms "subject" and "subjects" refer to an animal, in certain embodiments a mammal including a non-primate (e.g., a cow, pig, horse, cat, dog, rat, and mouse) and a primate (e.g., a monkey such as a cynomolgous monkey, a chimpanzee and a human), and more particularly a human. In another embodiment, the subject is a farm animal (e.g., a horse, a cow, a pig, etc.) or a pet (e.g., a dog or a cat). In certain embodiments, the subject is a human.

As used herein, the term "synergistic" refers to a combination of a compound of the invention and another therapy which has been or is currently being used to prevent, manage or treat a disorder, which is more effective than the additive effects of the therapies. A synergistic effect of a combination of therapies permits the use of lower dosages of one or more of the therapies and/or less frequent administration of said therapies to a subject with a disorder. The ability to utilize lower dosages of a therapy and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies may avoid or reduce adverse or unwanted side effects associated with the use of either therapy alone.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound of the invention. In certain other embodiments, the term "therapeutic agent" refers does not refer to a compound of the invention. In certain embodiments, a therapeutic agent is an agent which is known to be useful for, or has been or is currently being used for the treatment, management, prevention, or amelioration a disorder or one or more symptoms thereof. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to that amount of a therapy sufficient to result in the amelioration of one or more symptoms of a disorder, prevent advancement of a disorder, cause regression of a disorder, or to enhance or improve the therapeutic effect(s) of another therapy. In a specific embodiment, with respect to the treatment of cancer, an effective amount refers to the amount of a therapy that inhibits or reduces the proliferation of cancerous cells, inhibits or reduces the spread of tumor cells (metastasis), inhibits or reduces the onset, development or progression of one or more symptoms associated with cancer, or reduces the size of a tumor. In certain embodiments, a therapeutically effective of a therapy reduces the proliferation of cancerous cells or the size of a tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS").

As used herein, the terms "therapies" and "therapy" can refer to any protocol(s), method(s), and/or agent(s) that can be used in the prevention, treatment, management, or amelioration of a disorder or one or more symptoms thereof. In certain embodiments, the terms "therapy" and "therapies" refer to chemotherapy, radiation therapy, hormonal therapy, biological therapy, and/or other therapies useful in the prevention, management, treatment or amelioration of a disorder or one or more symptoms thereof known to one of skill in the art (e.g., skilled medical personnel).

As used herein, the terms "treat", "treatment" and "treating" refer to the reduction or amelioration of the progression, severity and/or duration of a disorder, or the amelioration of one or more symptoms thereof resulting from the administration of one or more therapies.

5.2 Embodiments Of The Invention

5.2.1 Formula (1)

5.2.1.1 Compounds

Exemplary compounds according to formula (1) include, but are not limited to, those of formulas (1a) (1-30):

Formula (1a) 1 through 30

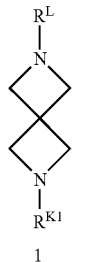 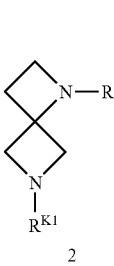 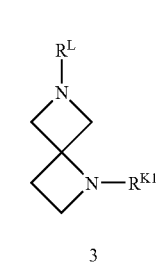 

1  2  3  4

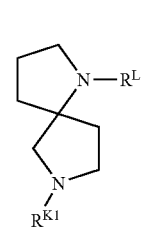 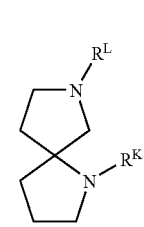 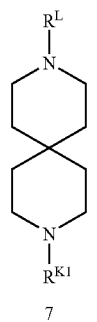

5  6  7

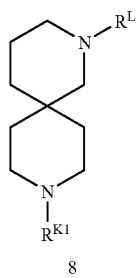 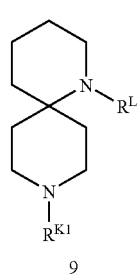 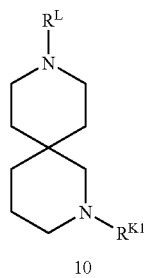

8  9  10

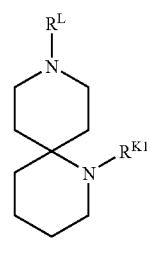 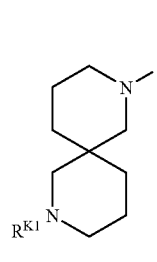 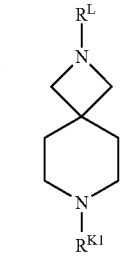

11  12  13

  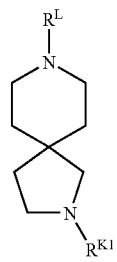

14  15  16

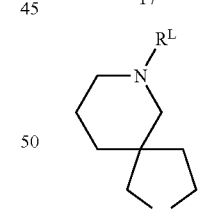 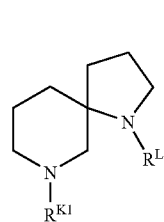 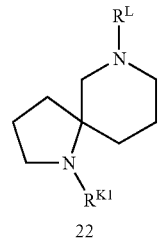

17  18  19

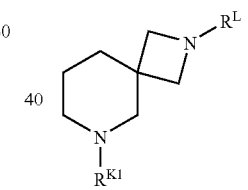 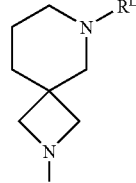 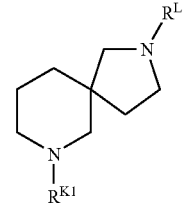

20  21  22

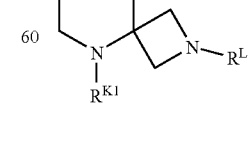 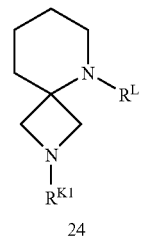 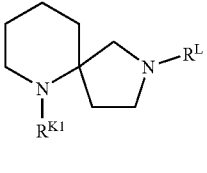

23  24  25

-continued

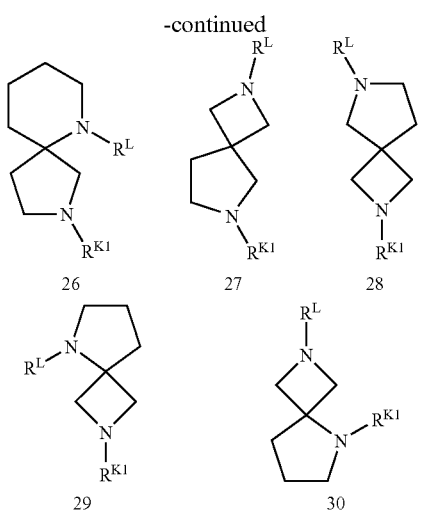

In formulas (1a) (1-30), each $R^{K1}$ is independently selected from hydrogen, lower alkyl, lower alkenyl (such as allyl or methallyl), lower alkynyl (such as propargyl or 3-pentynyl), lower cycloalkyl (such as cyclopropyl, cyclobutyl or cyclopentyl), lower cycloalkyl-alkyl (such as cyclopropylmethyl or cyclopropylethyl), optionally substituted aryl, optionally substituted heteroaryl, optionally substituted arylalkyl or heteroarylalkyl, heteroalkyl (such as 2-methoxyethyl, 2-methoxypropyl, diethylaminoethyl or 3-dimethylaminopropyl), heterocycloalkyl (such as 3-tetrahydrofurfuryl or 3-piperidinyl), heterocycloalkyl-alkyl (such as tetrahydrofurfuryl or 2-(2-(1-methylpyrrolidino)-ethyl))).

In formulas (1a) (1-30), each $R^L$ is independently selected from the following:

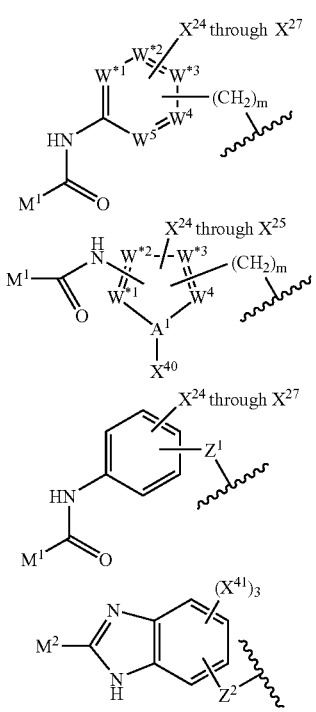

In formulas (1a) (1-30), each $Z^1$ and $Z^2$ is independently selected from: a chemical bond or $(CH_2)_r$, wherein r is an integer from 0 to 6, or $-(CF_2)-(C=O)-$ or $-(CF_2)-(CH_2)-$. Any of the methylene groups can be optionally substituted by one or more lower alkyl group(s), including substitution, forming geminal dialkyl, such as geminal dimethyl. They can be also optionally substituted by an optionally substituted aryl or heteroaryl group or a hydroxy or lower alkoxy group. Optionally one or more of the methylene group(s) can be replaced by a heteroatom selected from $-O-$, $-S-$, $-SO-$, $-SO_2-$ and $-N(X^{41})-$. Any one of the methylene group(s) can also be in the oxidation state of a carbonyl (keto-) group. $X^{41}$ is as described for formula (1) above.

In formulas (1a) (1-30), each $M^1$, $M^2$, $A^1$, $W^1$ through $W^5$, $X^{24}$ through $X^{27}$, $X^{40}$, m and $T^1$ is as described for formula (1), above.

Further exemplary compounds of formula (1) include, but are not limited to, those of formulas (1b) (1 through 9):

Formulas (1b)

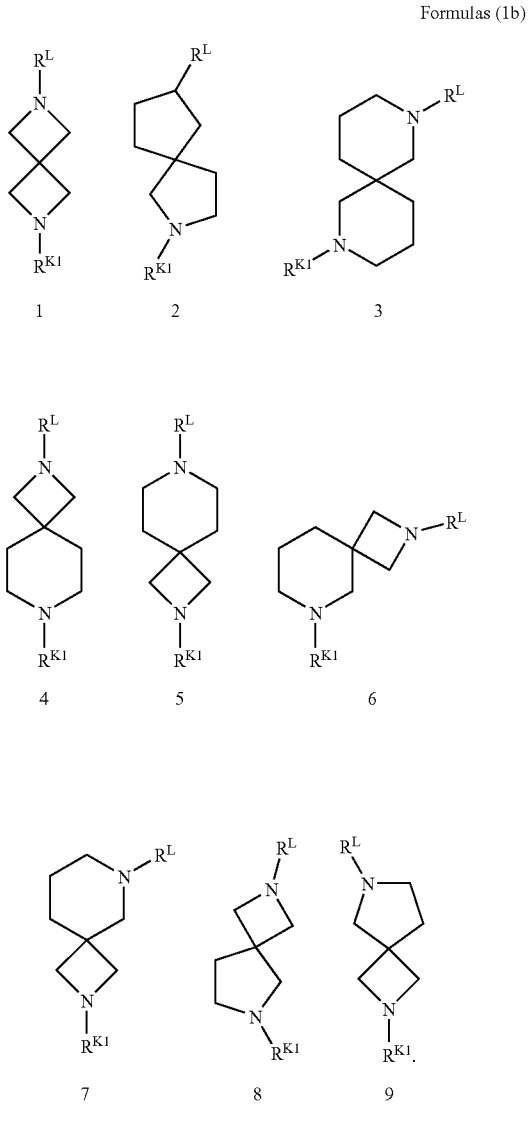

In formulas (1b) (1-30), each $R^{K1}$ is independently selected from hydrogen or lower alkyl, optionally substituted arylalkyl or heteroarylalkyl, heteroalkyl, or heterocycloalkyl.

In formulas (1a) (1-30), each $R^L$ is independently selected from the following:

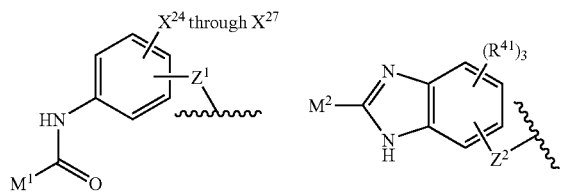

$Z^1$ and independently $Z^2$ are selected from: a chemical bond or $(CH_2)_r$, wherein r is an integer from 0 to 6, or —$(CF_2)$—$(C=O)$— or —$(CF_2)$—$(CH_2)$—. Any of the methylene groups can be optionally substituted by one or more lower alkyl group(s), including substitution, forming geminal dialkyl, such as geminal dimethyl. They can be also optionally substituted by an optionally substituted aryl or heteroaryl group or a hydroxy or lower alkoxy group. Optionally one or more of the methylene group(s) can be replaced by a heteroatom selected from —O—, —S—, —SO—, —SO$_2$— and —N($X^{41}$). Any one of the methylene group(s) can also be in the oxidation state of a carbonyl (keto-) group. $X^{41}$ is as described for formula (1) above.

In formulas (1a) (1-30), each $M^1$, $M^2$, $A^1$, $W^1$ through $W^5$, $X^{24}$ through $X^{27}$, $X^{40}$, m and $T^1$ is as described for formula (1), above.

In further embodiments, the present invention provide compounds according to the following:

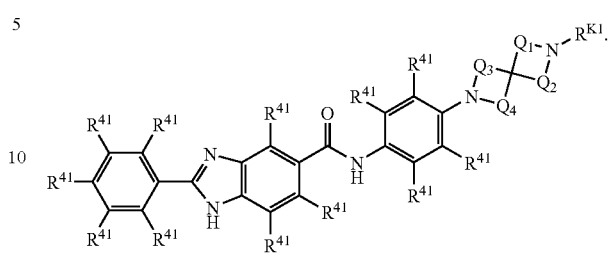

In further embodiments, the present invention provides compounds according to the following:


In further embodiments, the present invention provide compounds according to the following:

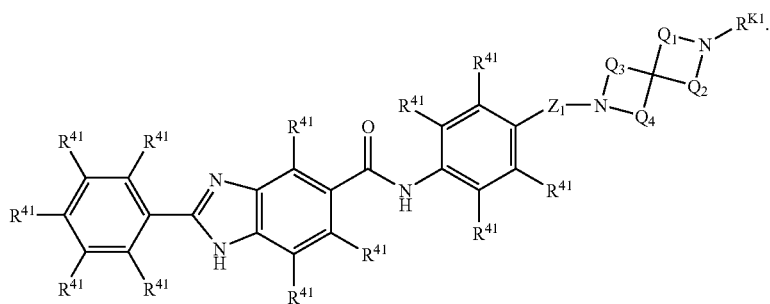

In further embodiments, the present invention provide compounds according to the following:

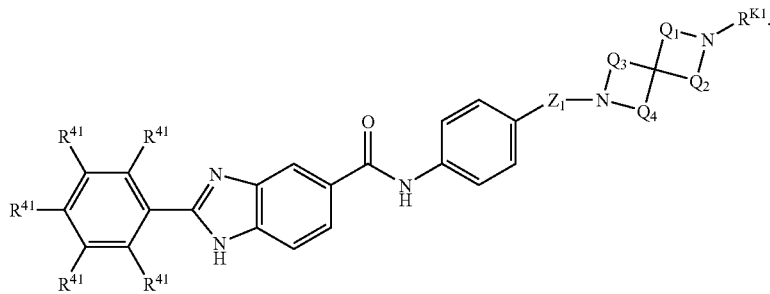

In further embodiments, the present invention provide compounds according lowing:

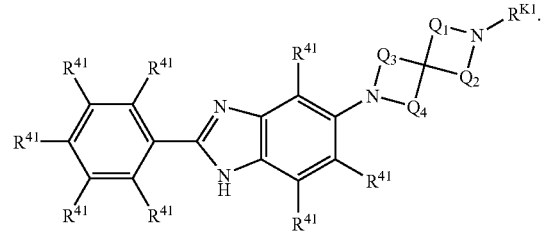

In further embodiments, the present invention provide compounds according lowing:

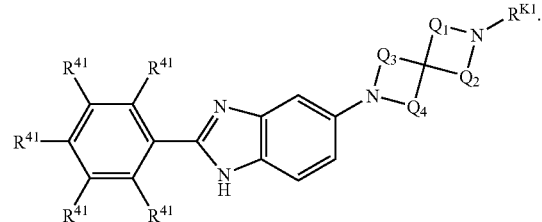

In further embodiments, the present invention provide compounds according owing:

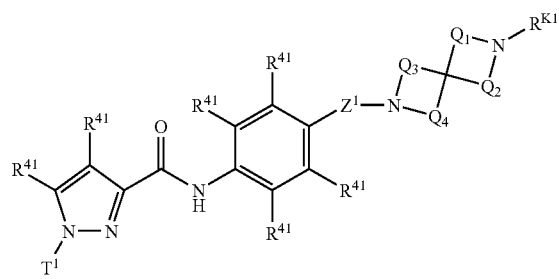

In further embodiments, the present invention provide compounds according lowing:

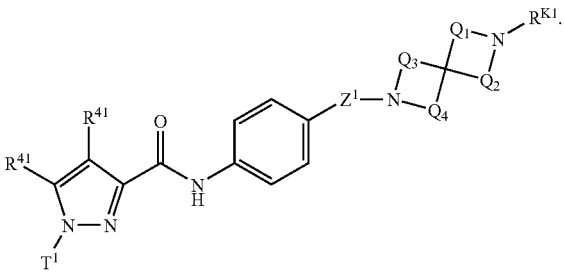

In further embodiments, the present invention provide compounds according to the following:

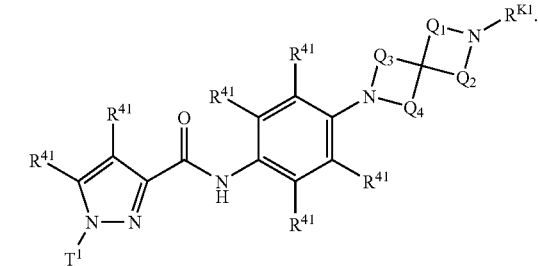

In further embodiments, the present invention provides compounds according to the following:

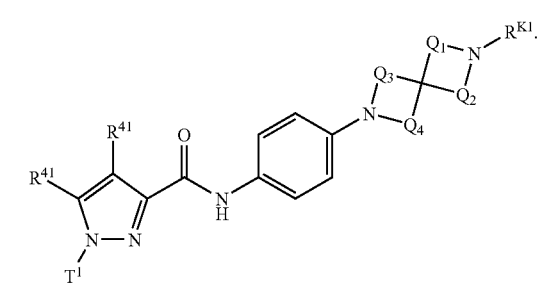

Exemplary embodiments of formulas (1), (1a) and (1b) include, but are not limited to, the specific examples shown below:

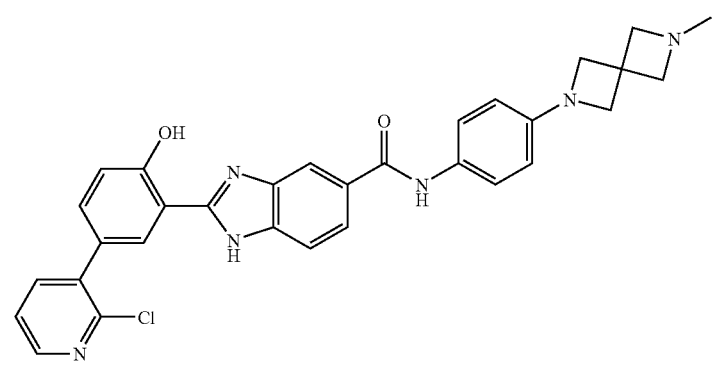

-continued
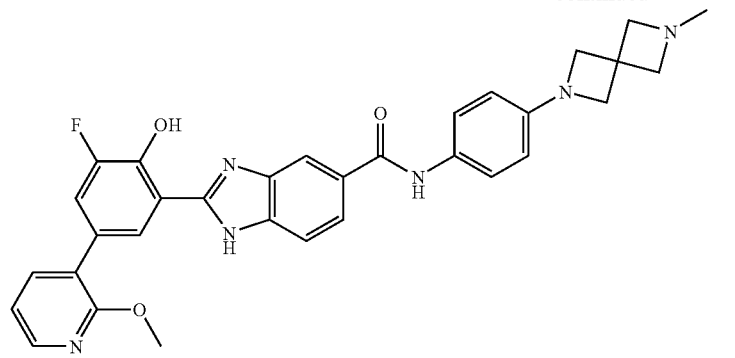
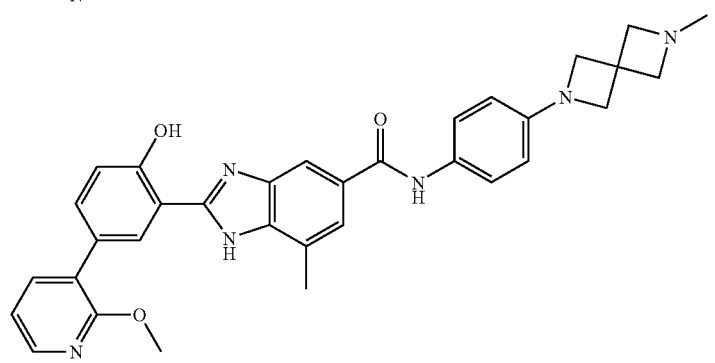
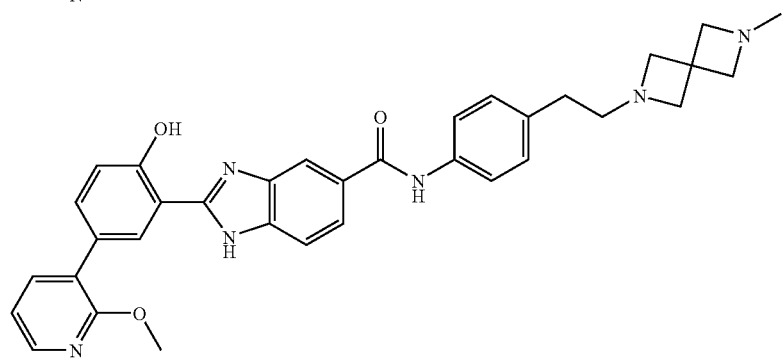
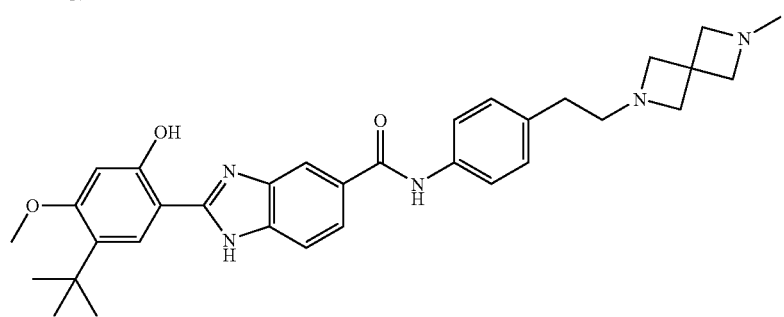
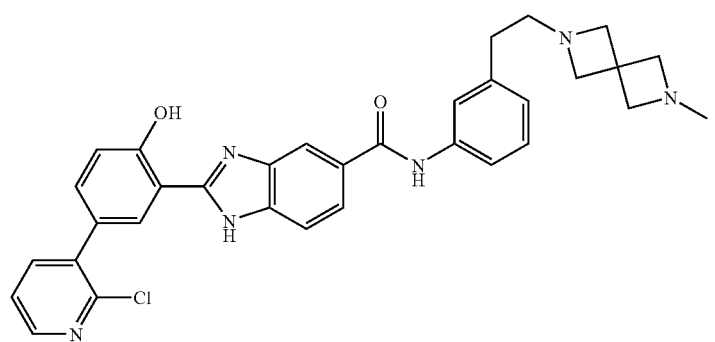

-continued
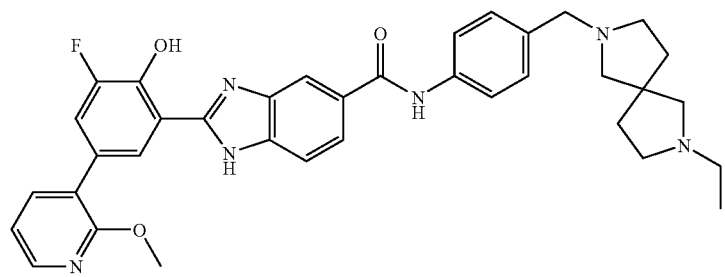
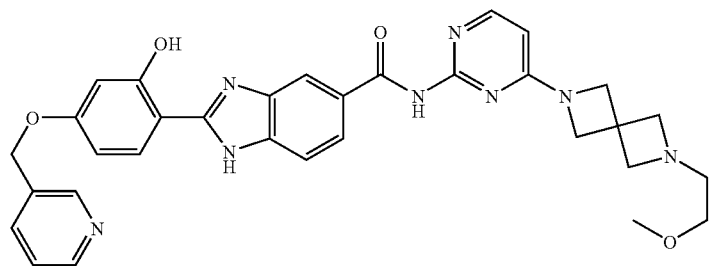
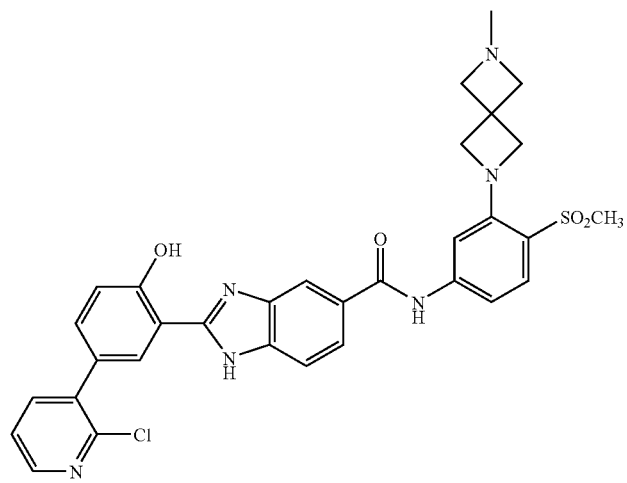
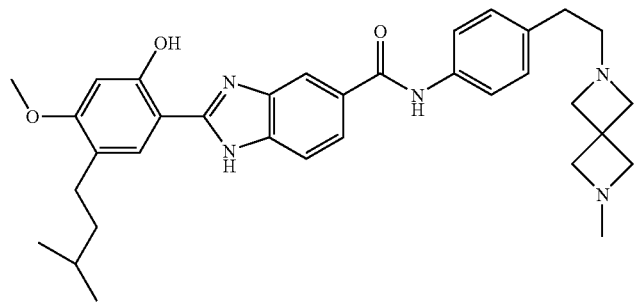
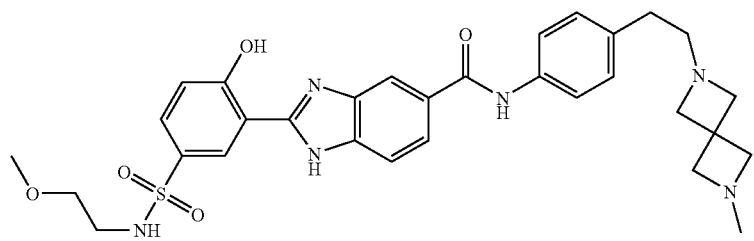

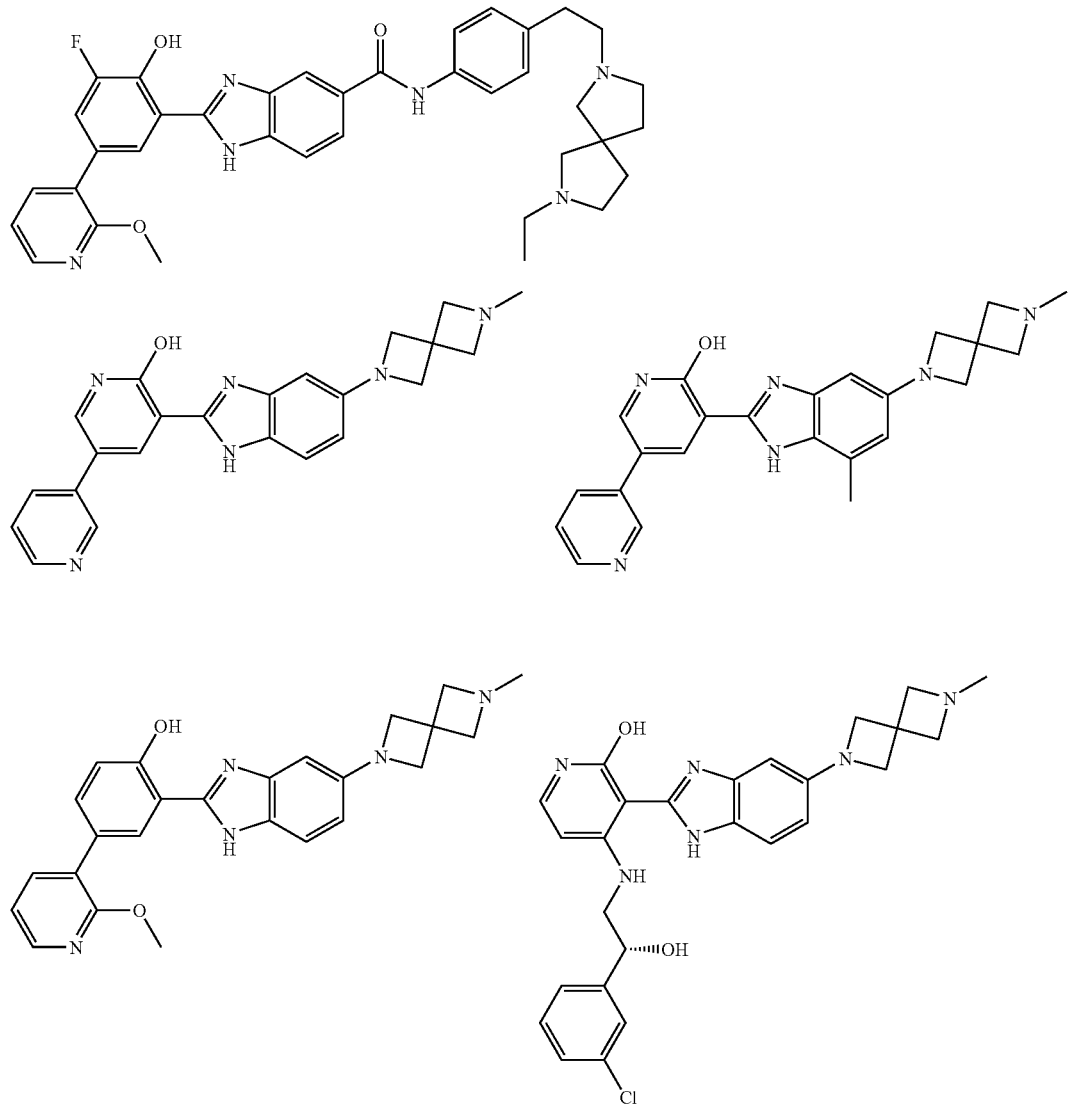
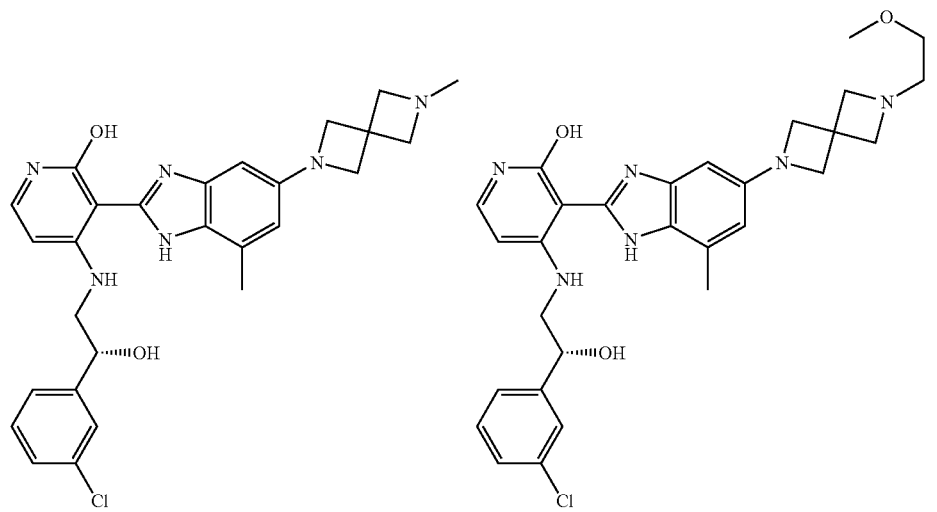

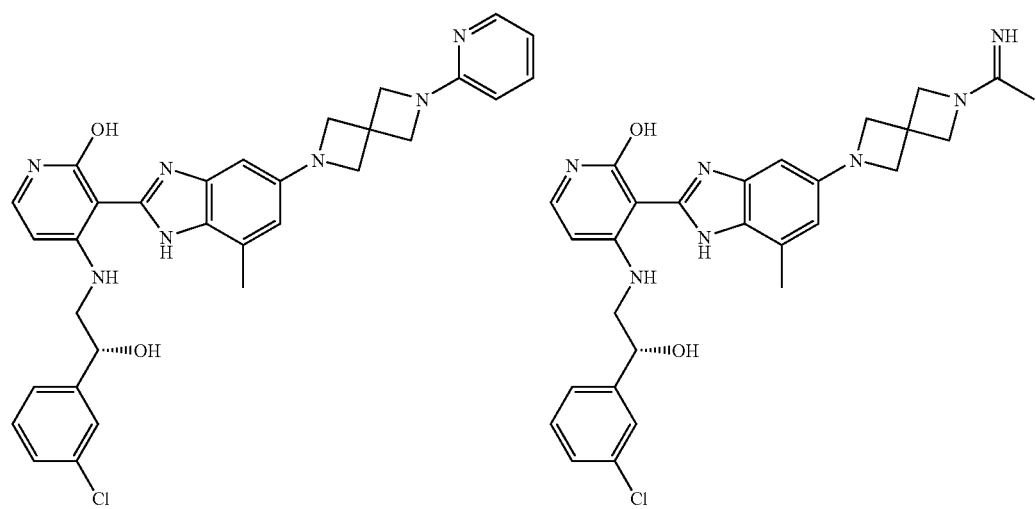
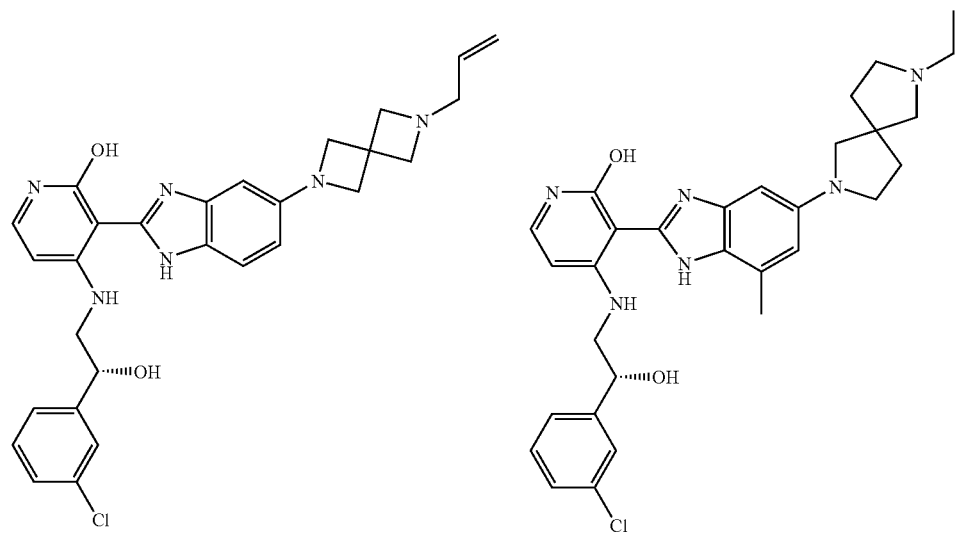
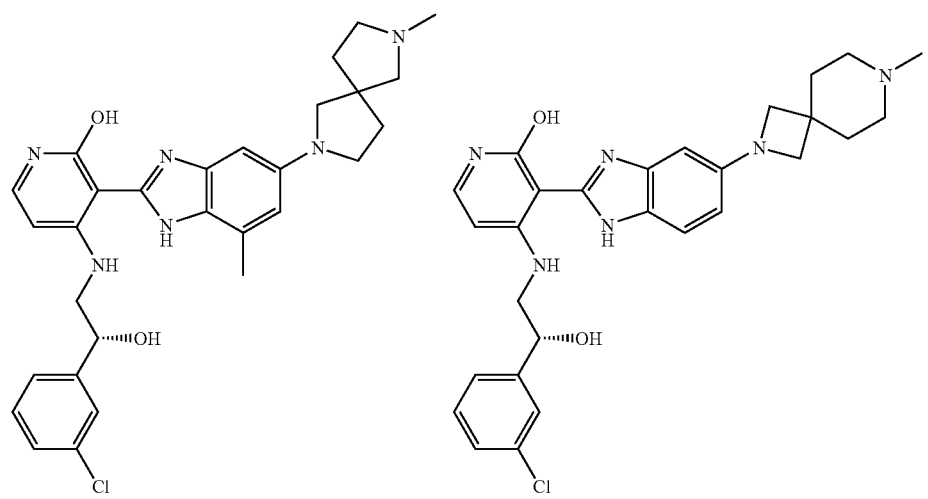

61  62
-continued
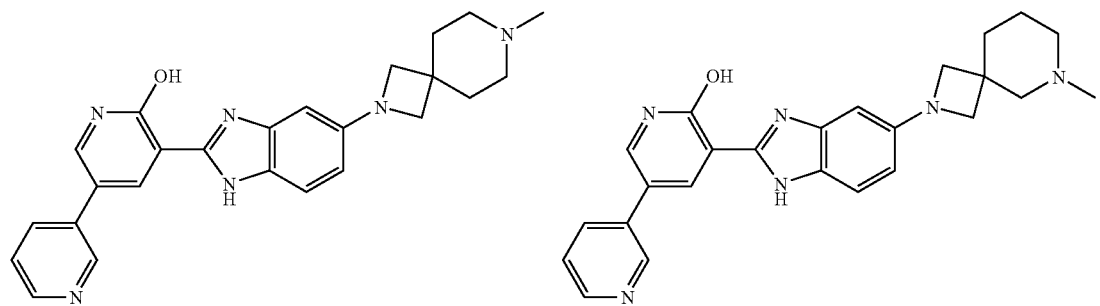
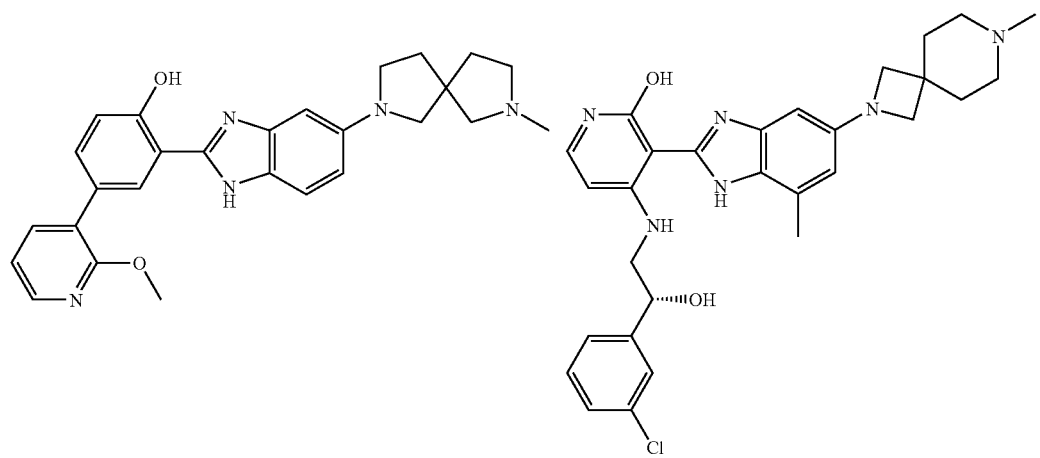
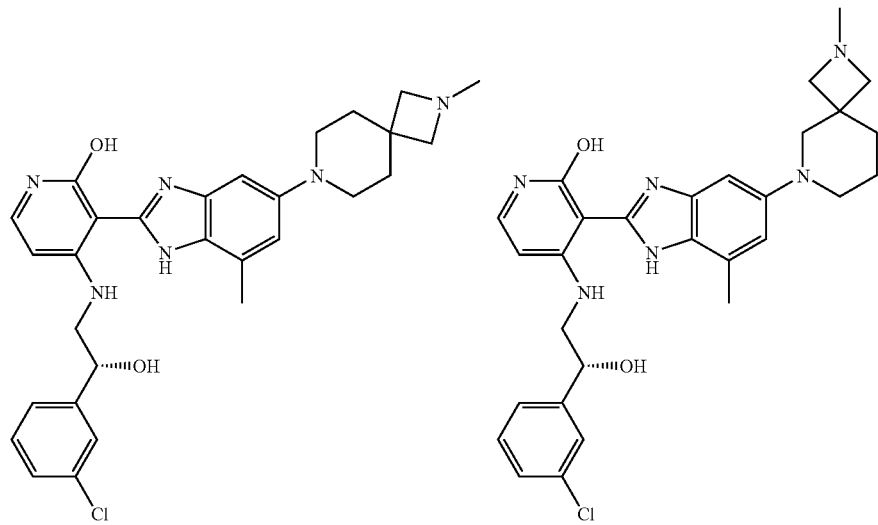

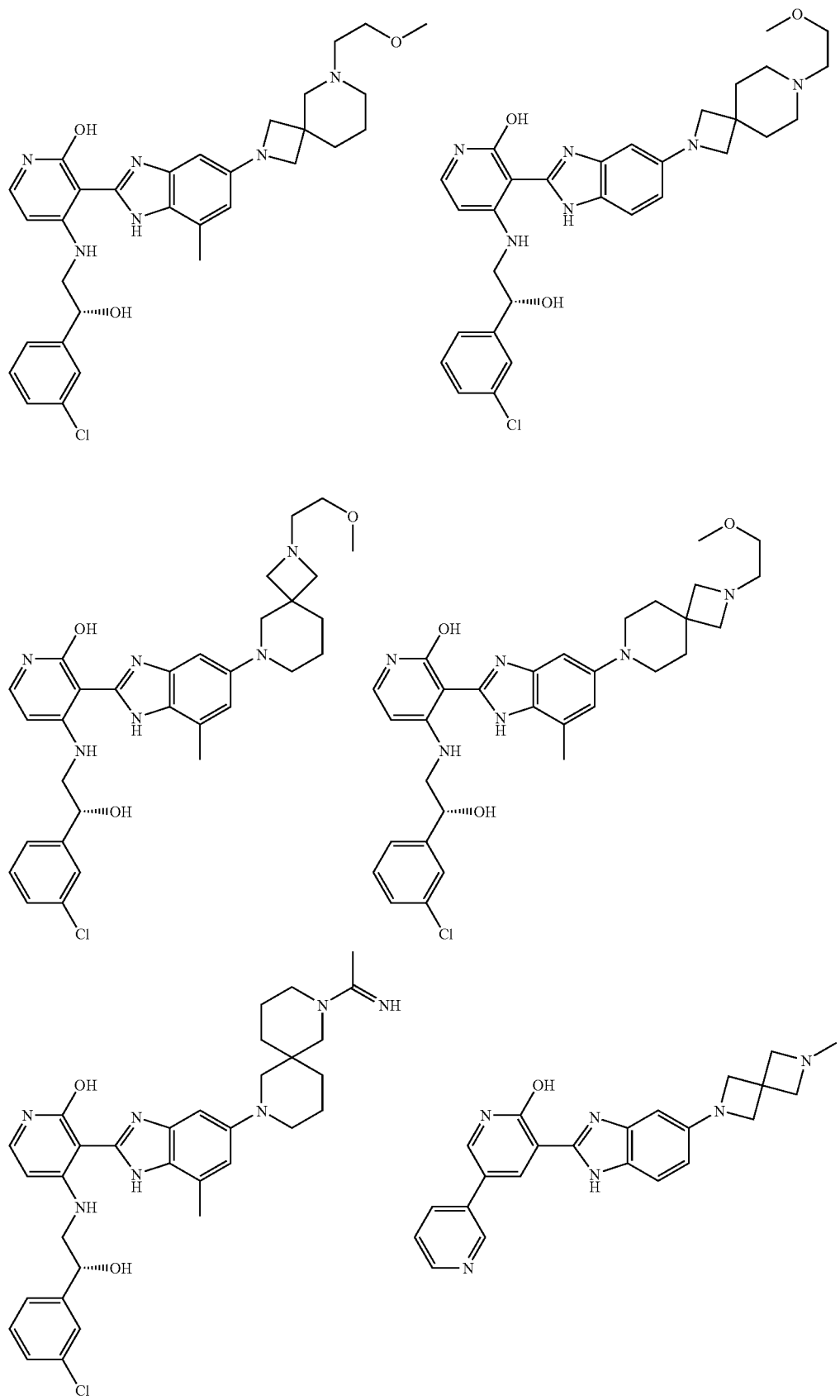

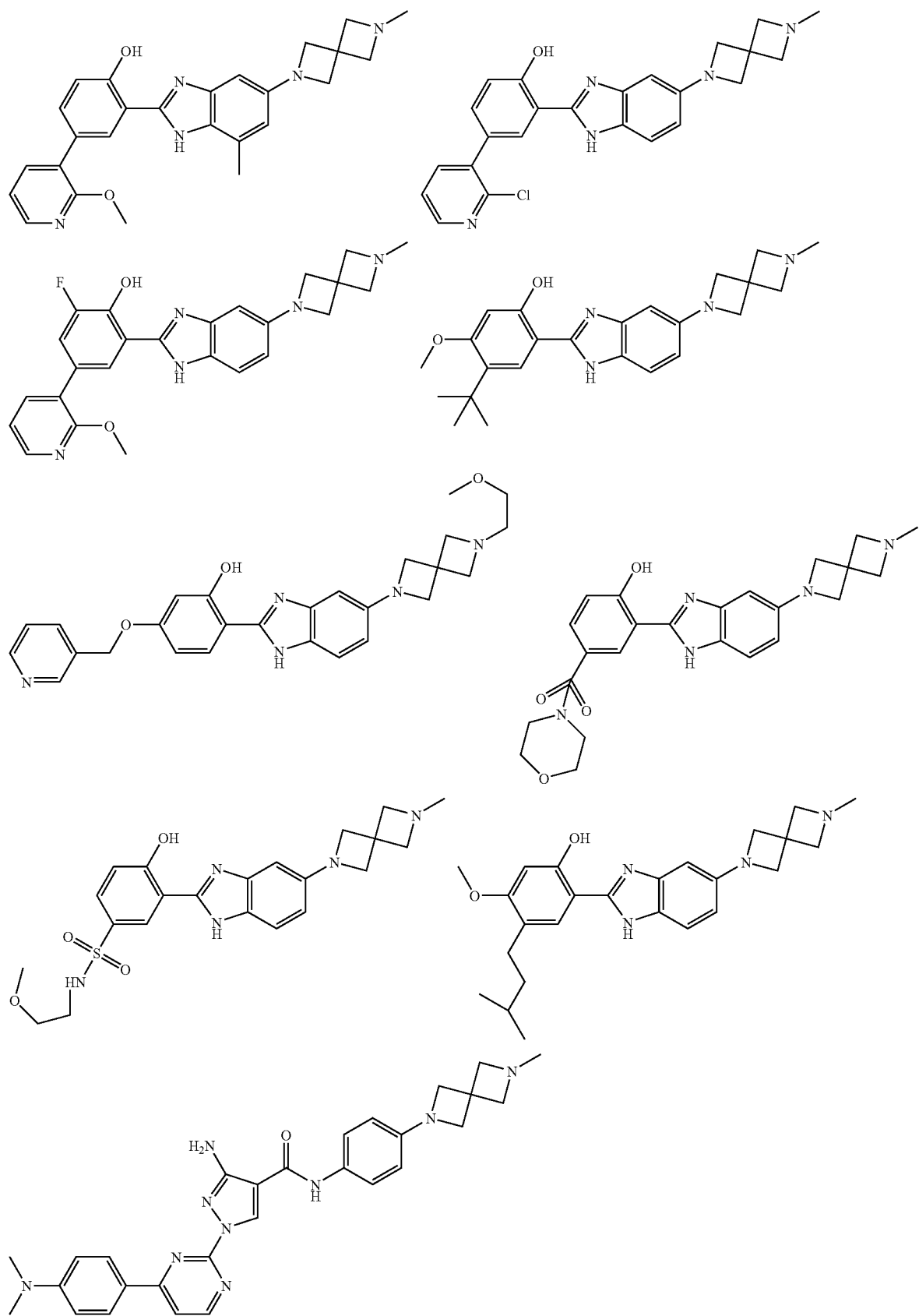

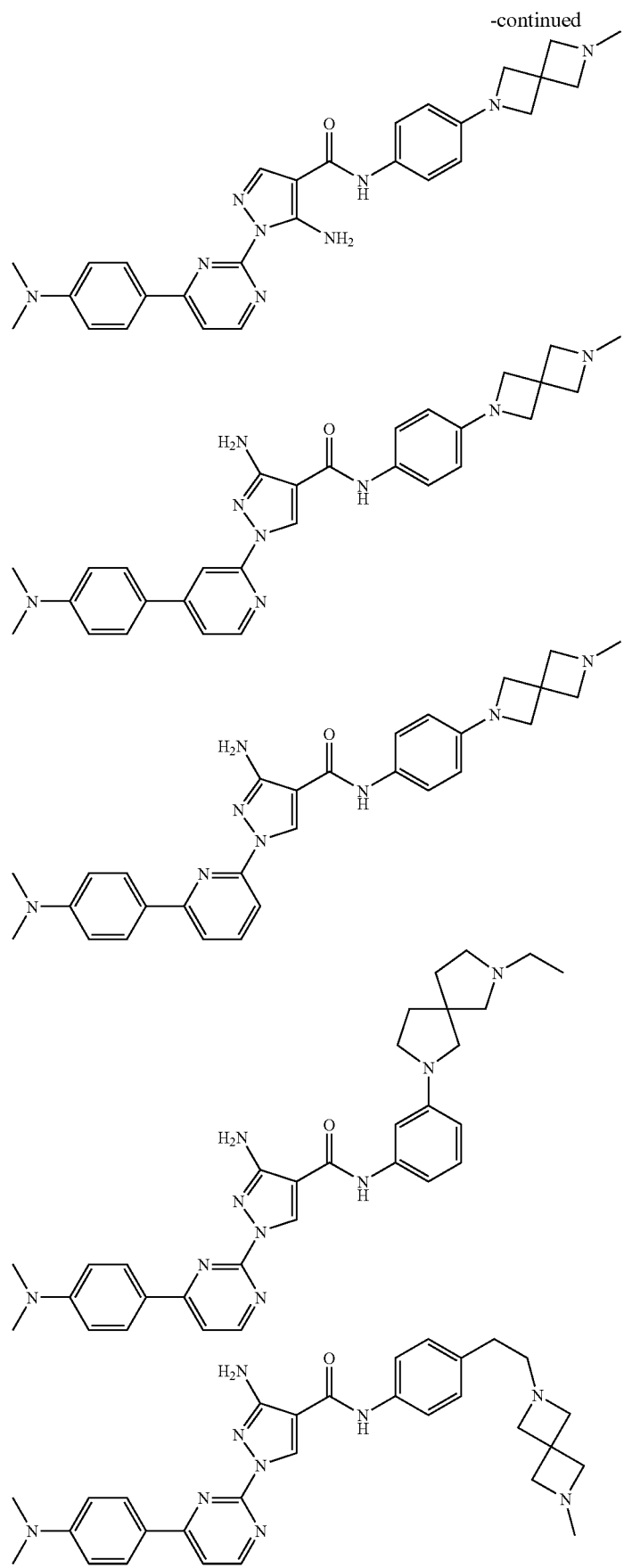

69 70
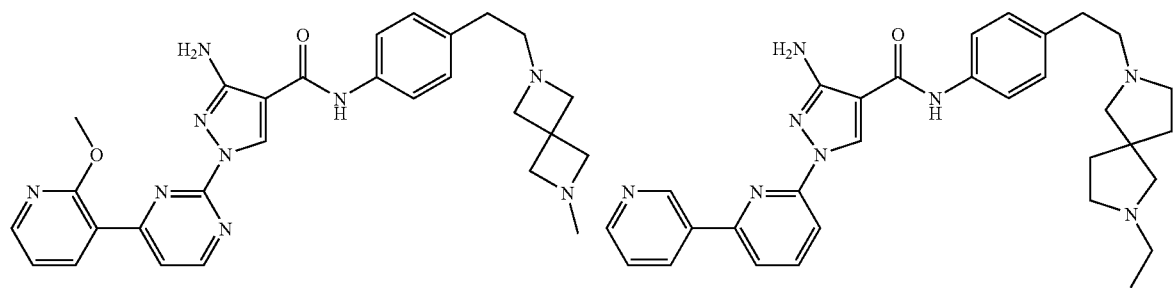
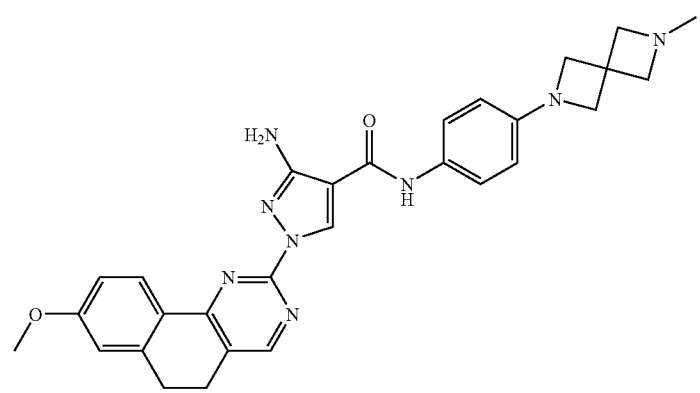
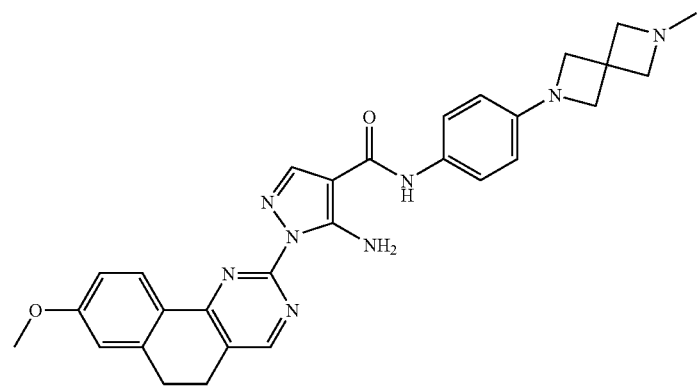
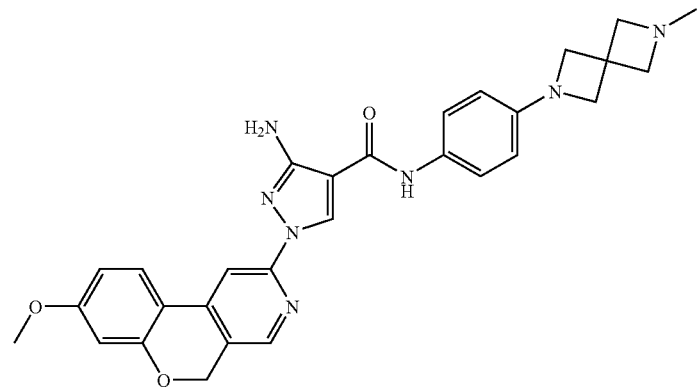

-continued
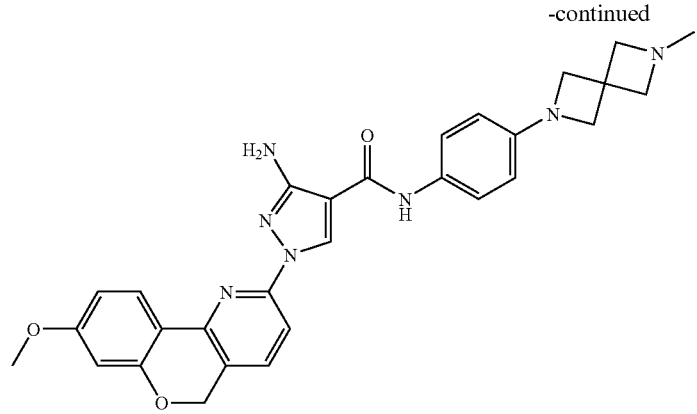
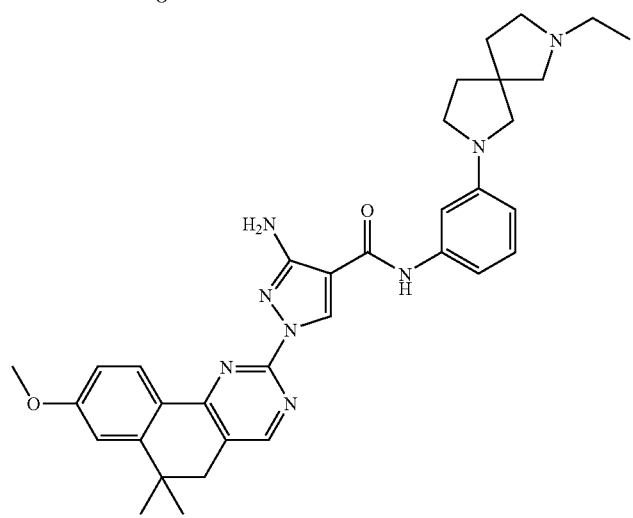
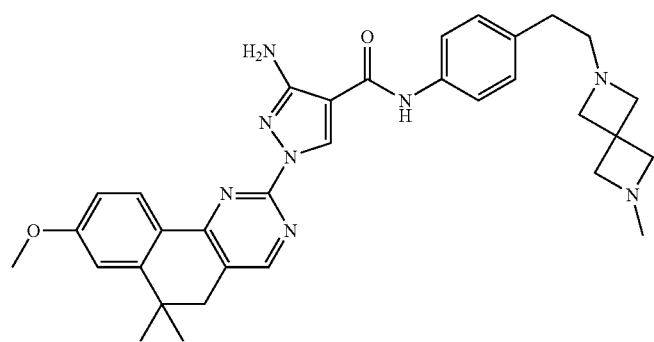
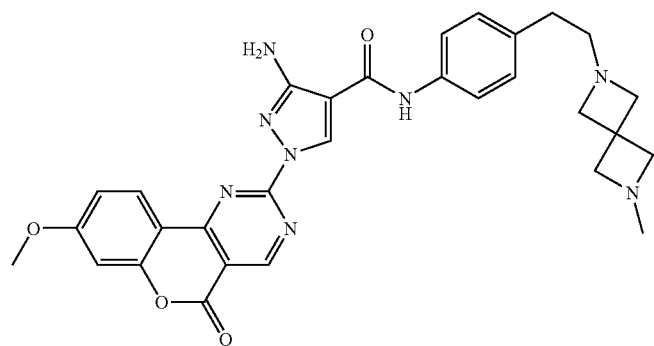

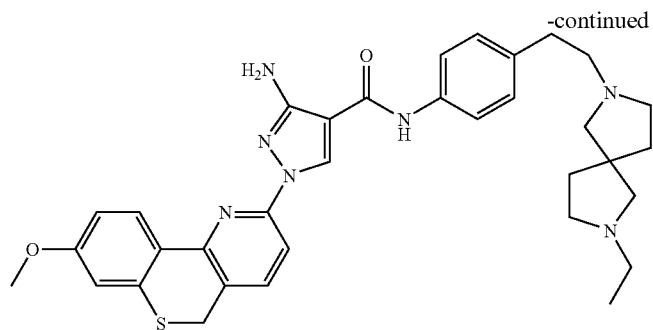

5.2.1.2 Preparation of Compounds According to Formula (1)

Compounds according to formula (1), (1a) and (1b) can be prepared according to any method apparent to those of skill in the art. The present invention provides the following exemplary methods for their preparation.

In certain embodiments, a useful reaction sequence includes treating the corresponding spiro-precursors with an alkylating or arylating (or heteroarylating) agent. The second nitrogen of the corresponding spiro-precursor is either a tertiary nirogen, or if a secondary nitrogent is desired, a protecting group can be used, such as for example, but not limited to: BOC, CBZ, trifluoroacetyl, benzyl and the like. Their removal can be performed according to procedures well-known in the art.

Certain of the starting spiro-compounds are either commercial reagents, or are prepared according to literature, or otherwise known methodologies.

Scheme 1-1 depicts the general methodology used for the synthesis of compounds of formula (1).

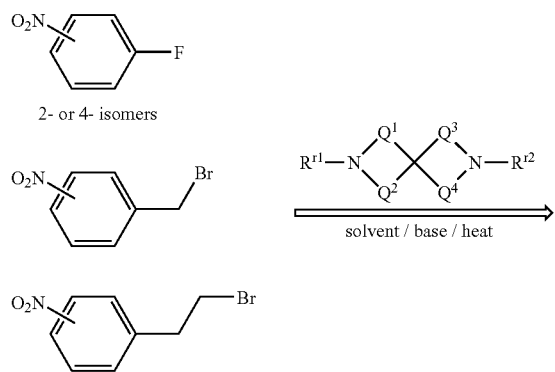

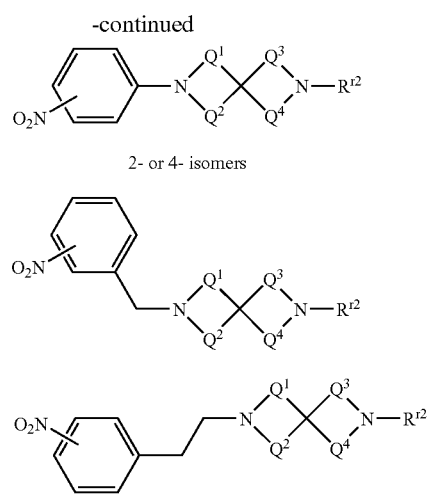

Q1-Q4 are as defined above
Rr1 is H, Rr2 is a substituent or a protecting group selected from BOC, CBZ or trifluoroacetyl The solvent is selected from DMF, DMA, THF, DME, N-methylpyrrolidone, toluene, xylene, acetonitrile, anisole, diglyme, chlorobenzene and the like, including a mixture of two or more solvents. Optionally water may be used as a co-solvent. The base is selected from diisopropylethylamine, triethylamine, potassium carbonate, potassium phosphate, cesium carbonate, DBN or DBU, NaOH, KOH, Ca(OH)2 and the like. The solution of the alkylating agent in the above solvent is treated with an equivalent amount of the optionally protected spirodiamine and excess of base and the mixture is stirred at a temperature between 20° C. to 120° C., in certain embodiments at 30-60° C. The reaction mixture is checked for progress of the reaction by LC/MS or by TLC and when substantially complete is concentrated down under vacuo and purified by further extraction and optionally column chromatography.

Alternatively, methods can be used that do not provide a limitation on the position of introduction of the spiro-moiety. Thus the iodo- or bromo-aniline derivatives can be reacted with the spiro-derivative using various palladium, or copper catalysts, such as conditions generally referred to as Buchwald reaction and others known in the art.

Scheme 2 depicts the use of a palladium, or copper-catalyzed reaction:

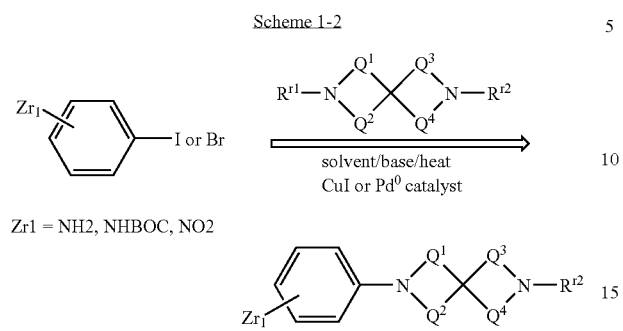

Scheme 1-2

Zr1 = NH2, NHBOC, NO2

Q1-Q4 are as defined above
Rr1 is H, Rr2 is a substituent or a protecting group selected from BOC, CBZ or trifluoroacetyl In certain embodiments, conditions include the use of the iodo-derivative, CuI, potassium phosphate as a base in isopropyl alcohol, containing catalytic amount of ethylene glycol. The reaction using palladium catalyst, which is selected from tetrakis triphenylphosphine palladium, palladium dibenzylidene acetone, palladium acetate, or palladium chloride in the optional presence of a phosphine ligand compound such as triphenylphosphine, tri-o-tolylphosphine, XANT-PHOS, bis diphenylphosphino ferrocene and the like is conducted in a solvent, such as toluene, THF, DMF, DMA, or dimethoxyethane under argon, in the presence of a base, such as cesium carbonate, potassium phosphate, KOtBu, NaOtBu and the like.

The secondary amino-group of the spiro-compounds can be reacted with reactive precursors, such as the corresponding isocyanates, acid chlorides, sulfonyl chlorides, epoxides, bromoketones and the like to provide the corresponding precursors for the compounds of formula 1, ureas, amides, sulfonamides, amino alcohols, aminoketones and the like. The methodology is generally well-known in the field.

The nitro-group is reduced by catalytic hydrogenation over palladium or Raney nickel, or is effected by any reagent suitable for this reduction, including stannous chloride, titanium III chloride solution, Zn/AcOH, Fe/AcOH and the like. The solvents for this reduction include, but are not limited to: THF, MeOH, EtOH, $H_2O$, dioxane, AcOH and the like. The workup includes concentration of the reaction mixture in vacuum and optional basification, extraction and concentration. The products can be purified by column chromatography, or converted to stable salts, such as the hydrochloride.

The so-obtained amines are used in the coupling reactions with the corresponding carboxylic acids, using any of the multitude coupling reagents known in the art. Optionally the amide coupling may be performed using the methyl ester of the corresponding acid and trimethyl aluminum, so-called Weinreb conditions.

Exemplary compounds and methods of their preparation are provided in the examples below.

5.2.2 Formula (2)

5.2.2.1 Compounds According to Formula (2)

In certain embodiments, the present invention provides compounds of formula (2) that are represented in formulas (2a) A and B:

Formulas (2a) A and B

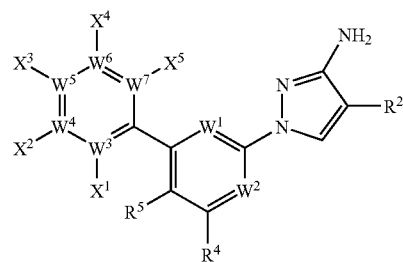

A

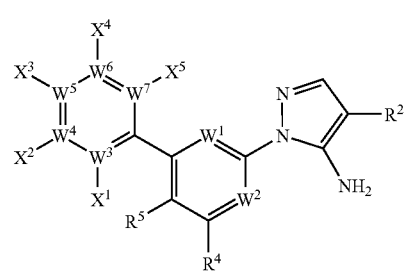

B

In formulas (2a) A and B, each $X^1$ through $X^5$, $R^1$, $R^2$, $R^3$, $R^4$, $R^5$, $R^6$, $R^7$, $W^1$ and $W^2$ is as described for formula (2), above.

In further embodiments, the present invention provides compounds according to the following:

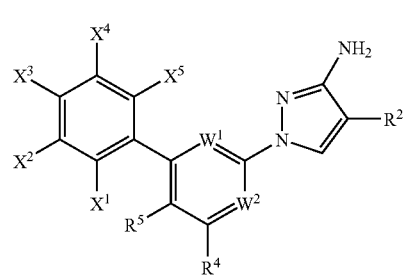

A

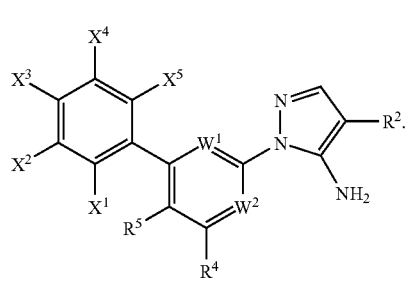

B

In further embodiments, the present invention provides compounds according to the following:

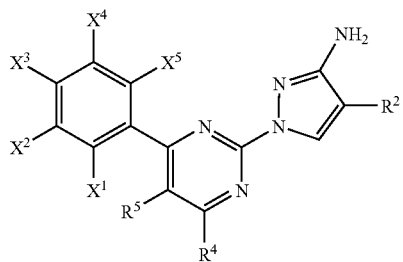

A

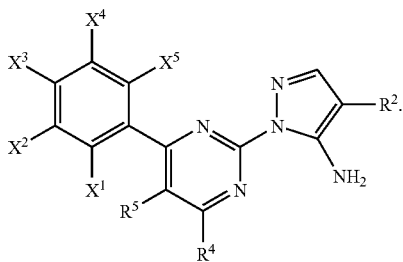

B

In further embodiments, the present invention provides compounds according to the following:

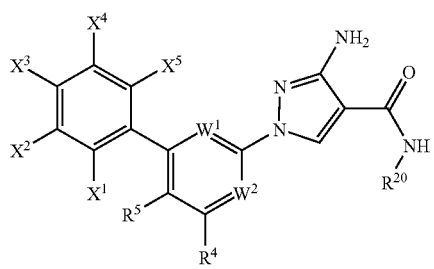

A

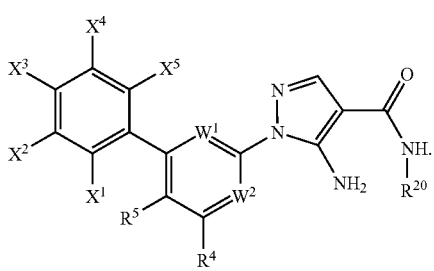

B

In further embodiments, the present invention provides compounds according to the following:

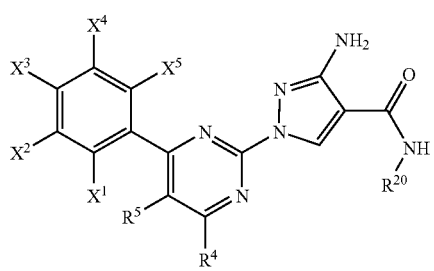

A

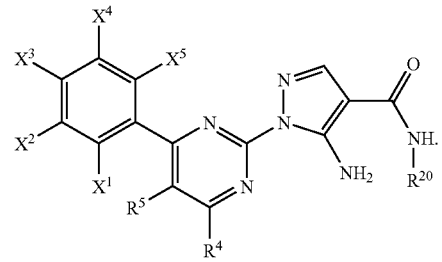

B

In further embodiments, the present invention provides compounds according to the following:

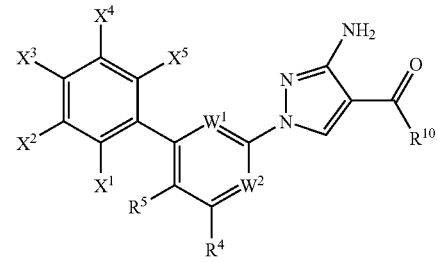

A

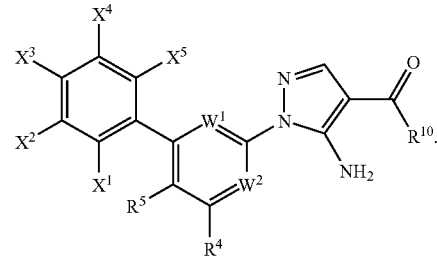

B

In further embodiments, the present invention provides compounds according following:

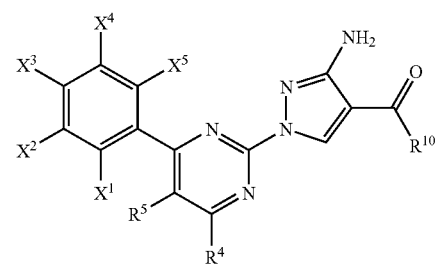

A

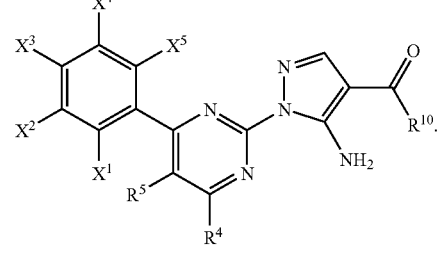

B

In further embodiments, the present invention provides compounds according following:

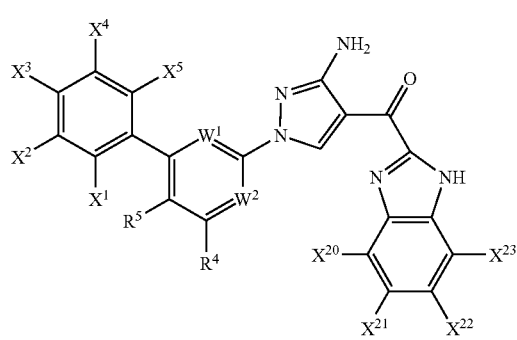

A

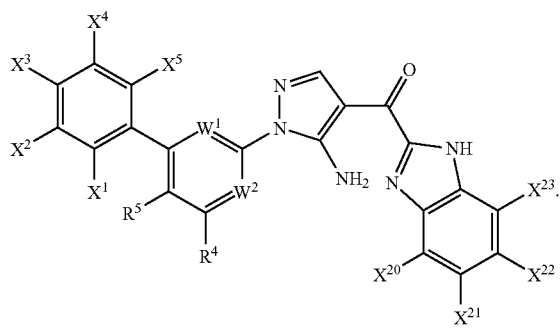

B

In further embodiments, the present invention provides compounds according to the following:

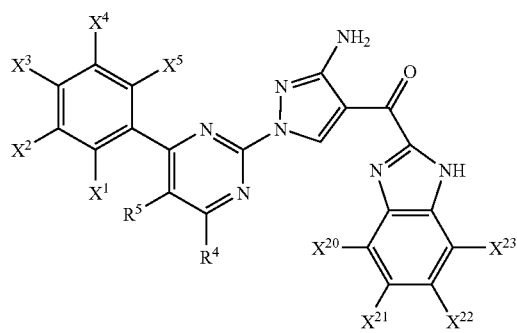

A

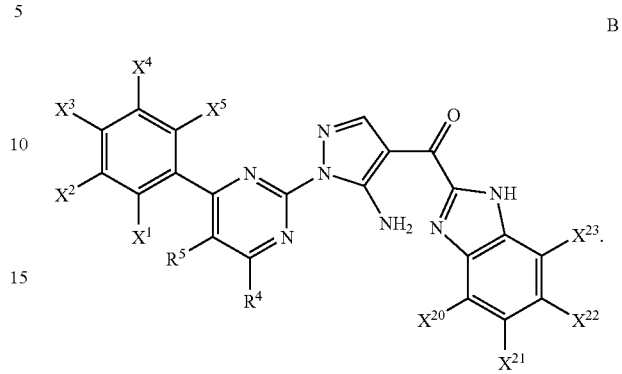

B

Exemplary compounds according to formula (2) are described in the examples below.

5.2.2.2 Preparation of Compounds According to Formula (2)

Compounds according to formula (2) and (2a) can be prepared according to any method apparent to those of skill in the art. The present invention provides the following exemplary methods for their preparation.

In certain embodiments, compounds of formula (2) are prepared according to the following procedures, according to scheme 2-1:

Scheme 2-1

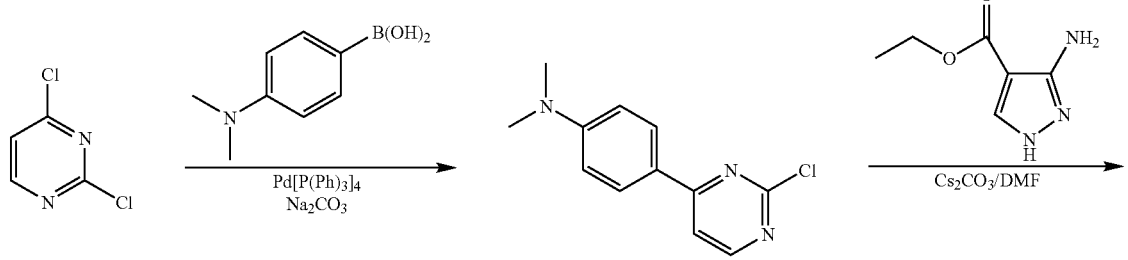

81          82
-continued
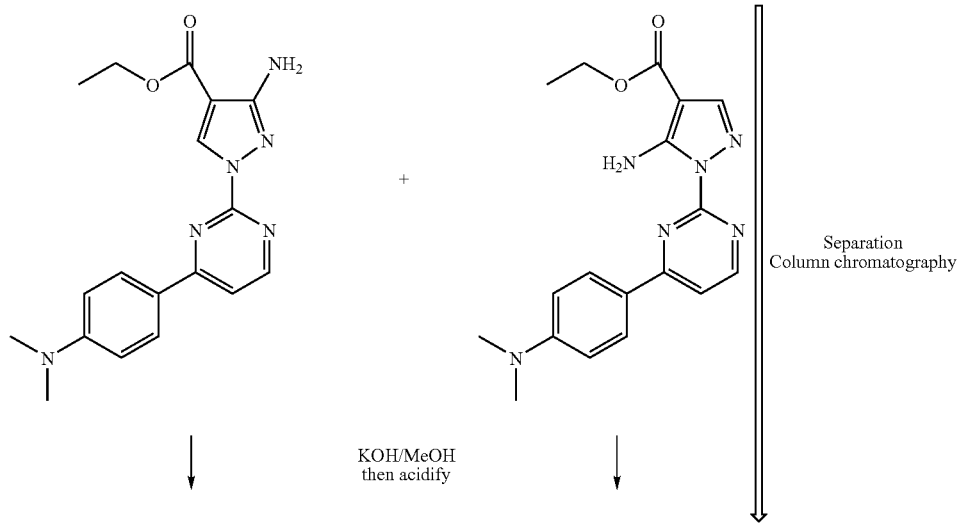
+     Separation
Column chromatography
KOH/MeOH
then acidify
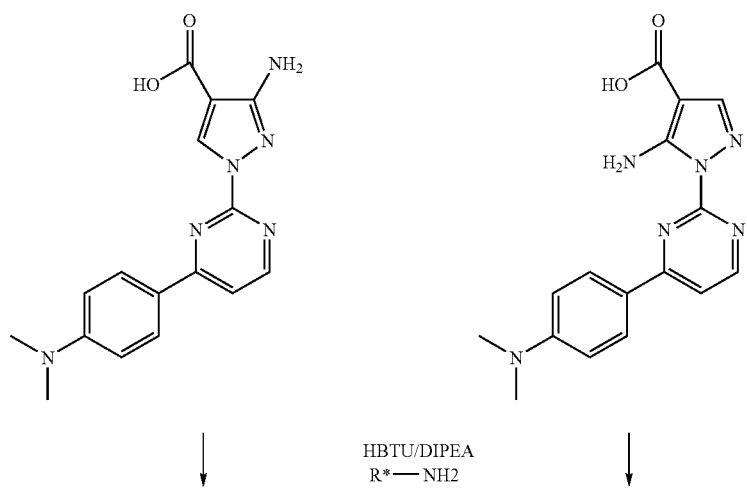
HBTU/DIPEA
R*—NH2
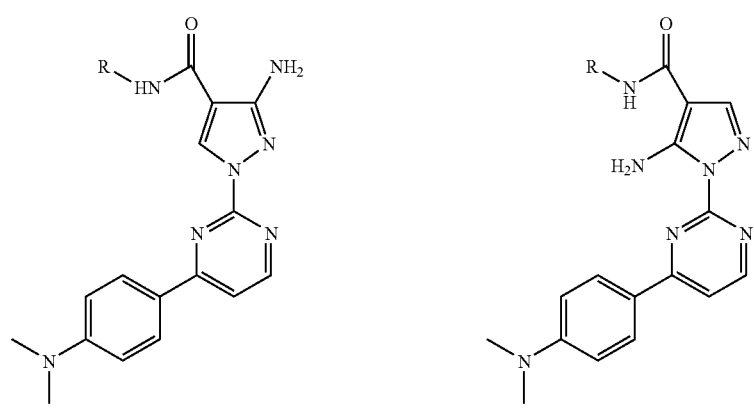

Exemplary compounds according to formula (2) and methods for their on are described in detail in the examples below.

5.2.3 Formula (3)

5.2.3.1 Compounds According to Formula (3)

In certain embodiments, the present invention provides compounds according a (3) that are represented in formulas (3a) A and B:

Formulas (3a) A and B

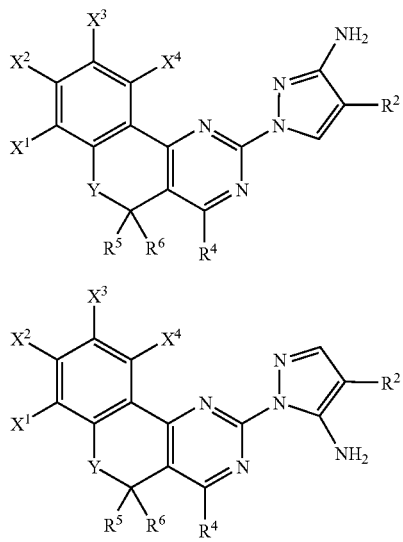

In formulas (3a) A and B, $X^1$ through $X^4$, $R^1$, $R^2$, $R^3$, $R^4$, $R^5$, $R^6$ and Y are as described for formula (3), above.

In certain embodiments, the present invention provides compounds according to formula (3) that are represented in formulas (3b) A and B Formulas (3b) A and B

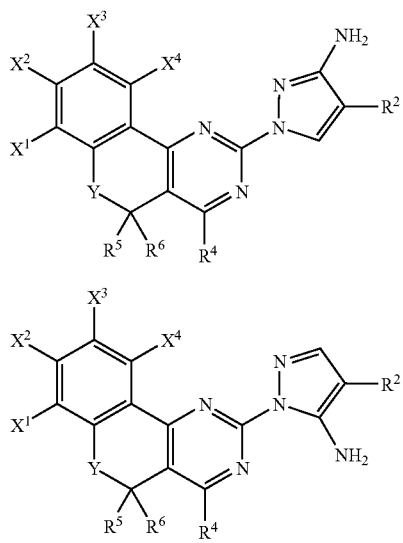

In formulas (3b) A and B, $X^1$ through $X^4$, $R^1$, $R^3$, $R^4$, $R^5$, $R^6$ and Y are as described for formula (3), above.

In formulas (3b) A and B, $R^2$ is selected from the following:

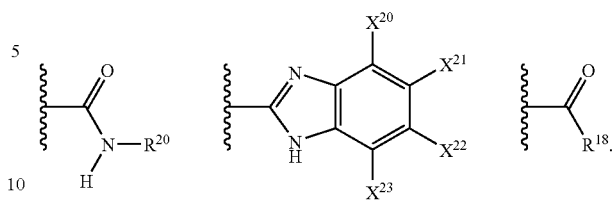

In formulas (3b) A and B, $R^{20}$ is selected from hydrogen, $C_{1-4}$ alkyl, $C_{2-14}$ alkenyl, $C_{2-14}$ alkynyl, $C_{3-14}$ cycloalkyl, heteroalkyl, heterocycloalkyl, aryl, heteroaryl, arylalkyl, heteroarylalkyl, all groups may be optionally substituted by a substituent selected from hydroxy, lower alkyl, lower alkoxy, primary, secondary or tertiary amino, heteroalkyl, cycloalkyl, hereocycloalkyl. In formulas (3b) A and B, $R^{20}$ can also be selected from the following:

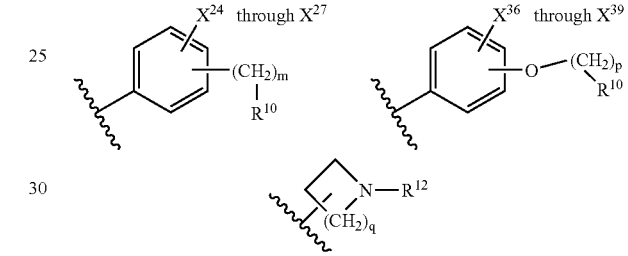

wherein the independent integers m, p and q are from 0 to 6, in certain embodiments from 0 to 3.

In formulas (3b) A and B, $X^{24}$ through $X^{39}$, $R^{10}$, $R^{12}$ and $R^{18}$ are as described for formula (3), above.

In formulas (3b) A and B, each $X^{20}$ through $X^{23}$ is independently selected from: hydrogen, halogen, trifluoromethyl, lower alkyl, lower alkoxy, lower polyfluoroalkoxy, such as trifluoromethoxy, primary, secondary or tertiary amino, hydroxy, acyloxy, such as acetoxy or isobutyryloxy, heteroalkyl, such as methoxyethyl or ethoxyethyl, nitrogen-heterocyclyl, connected either by its nitrogen or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino and also the following:

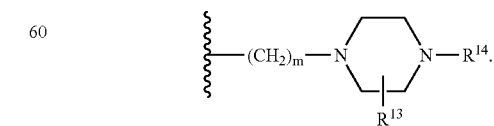

In further embodiments, the present invention provides compounds according to the following:

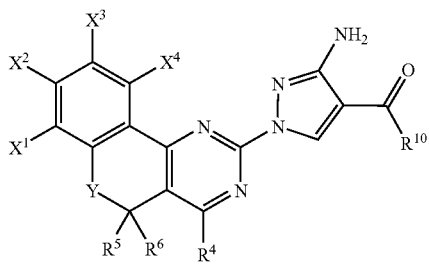

A

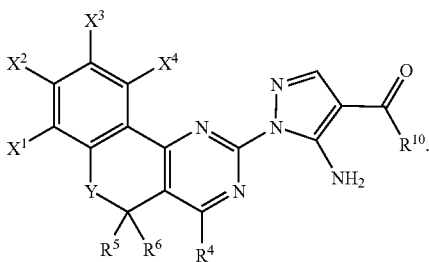

B

In further embodiments, the present invention provides compounds according to the following:

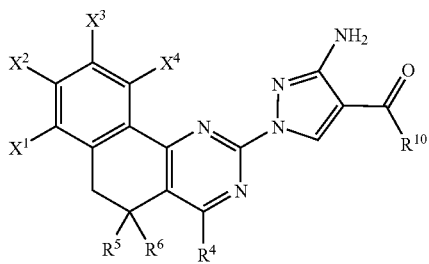

A

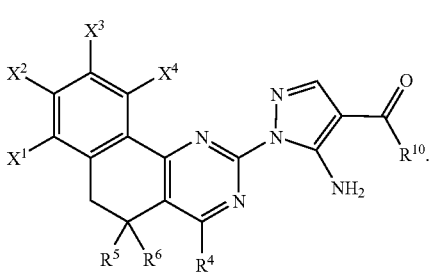

B

In further embodiments, the present invention provides compounds according to the following:

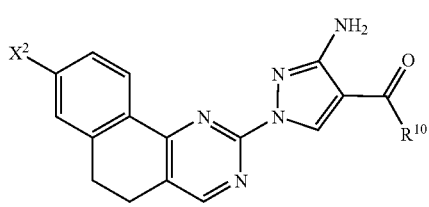

A

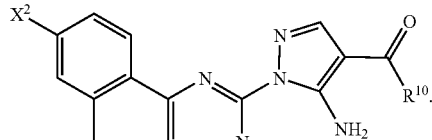

B

In further embodiments, the present invention provides compounds according to the following:

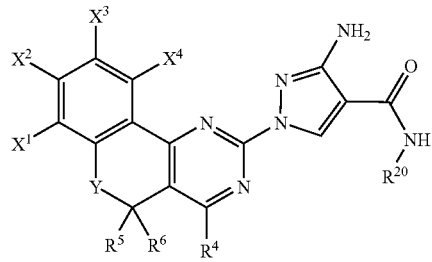

A

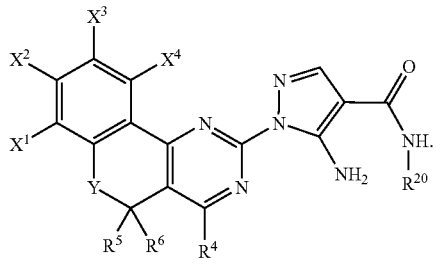

B

In further embodiments, the present invention provides compounds according to the following:

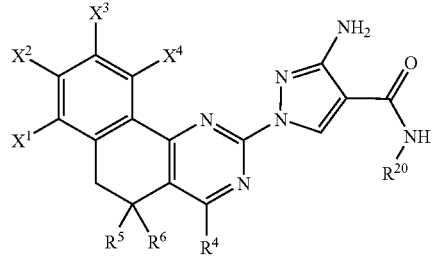

A

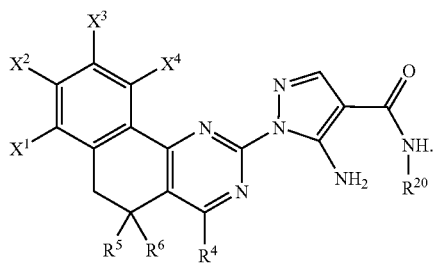

B

In further embodiments, the present invention provides compounds according to the following:

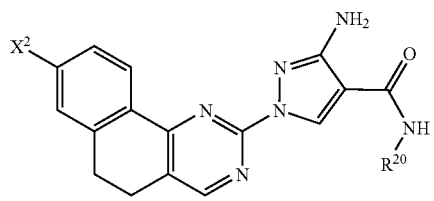

A

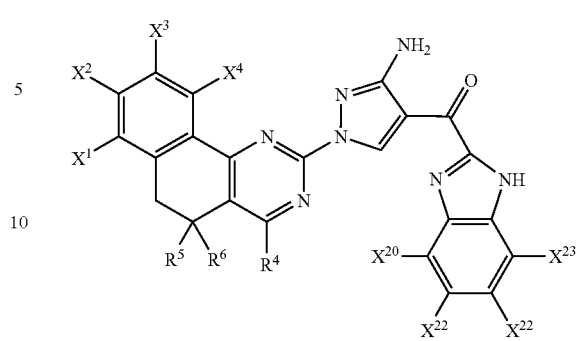

A

B

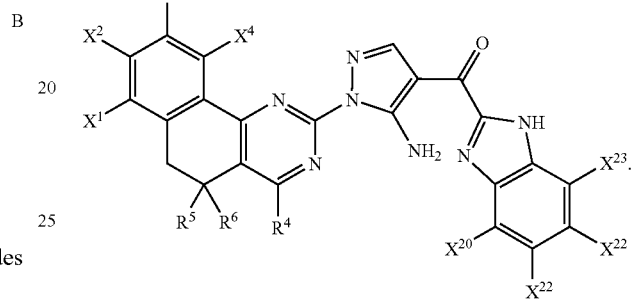

In further embodiments, the present invention provides compounds according to the following:

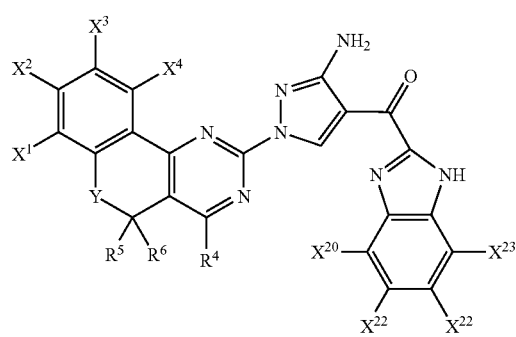

A

B

In further embodiments, the present invention provides compounds according to the following:

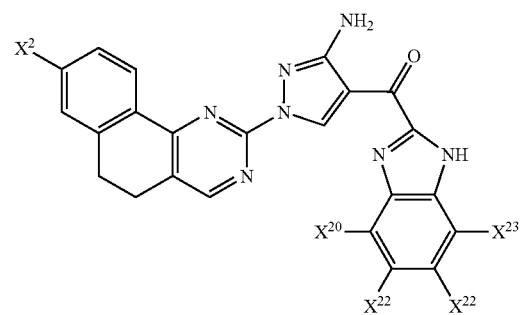

A

B

In further embodiments, the present invention provides compounds according to the following:

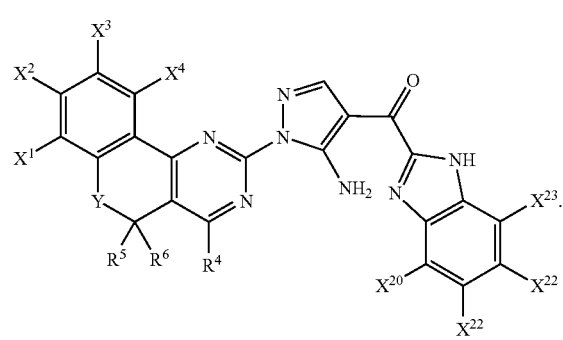

A

B

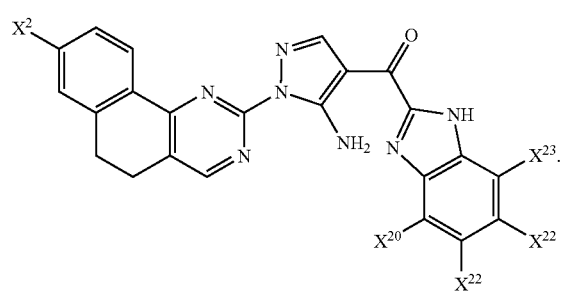

A

B

The following exemplary compounds according to formula (3) were prepared according to the methods described herein:

| MOLSTRUCTURE | MW (M + 1) |
|---|---|
| 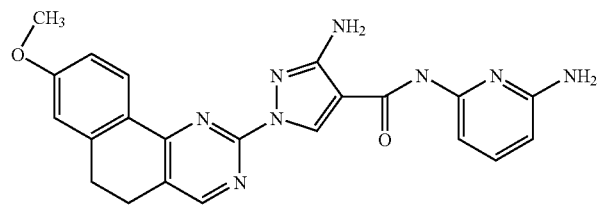 [SMILES: COc1ccc2c(c1)CCc1cnc(-n3cc(C(=O)Nc4cccc(N)n4)c(N)n3)nc1-2] | 429.5 |
| 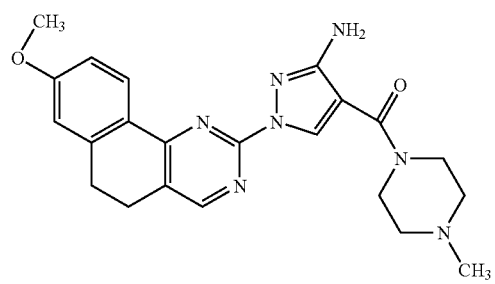 [SMILES: COc1ccc2c(c1)CCc1cnc(-n3cc(C(=O)N4CCN(C)CC4)c(N)n3)nc1-2] | 420.5 |
| 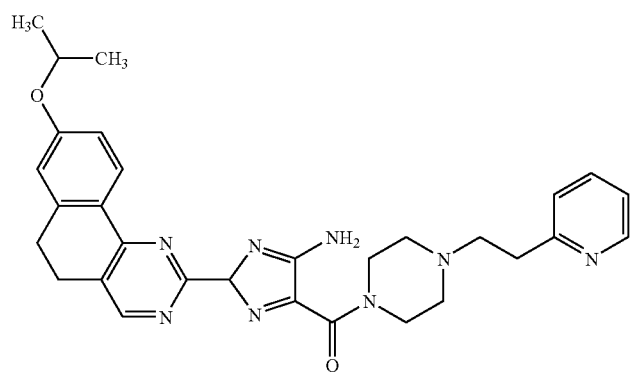 [SMILES: CC(C)Oc1ccc2c(c1)CCc1cnc(C3N=C(N)C(C(=O)N4CCN(CCc5ccccn5)CC4)=N3)nc1-2] | 539.7 |
| 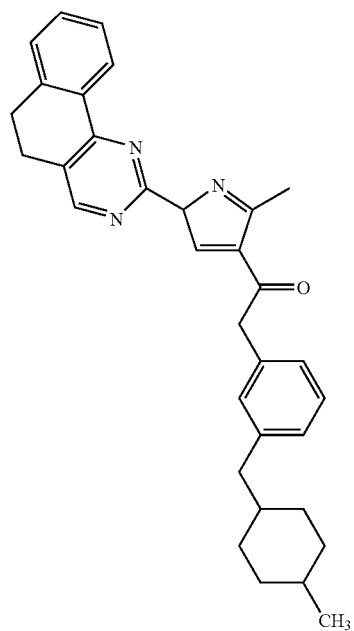 [SMILES: CC1=NC(c2ncc3c(n2)-c2ccccc2CC3)C=C1C(=O)Cc1cccc(CC2CCC(C)CC2)c1] | 497.6 |

| MOLSTRUCTURE | MW (M + 1) |
|---|---|
| 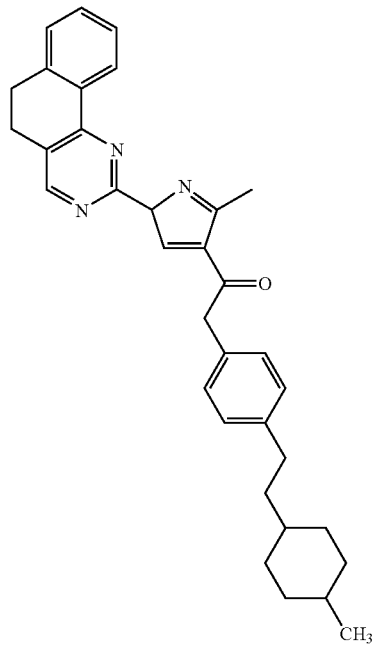 [SMILES: CC1=NC(c2ncc3c(n2)-c2ccccc2CC3)C=C1C(=O)Cc1ccc(CCC2CCC(C)CC2)cc1] | 511.6 |
| 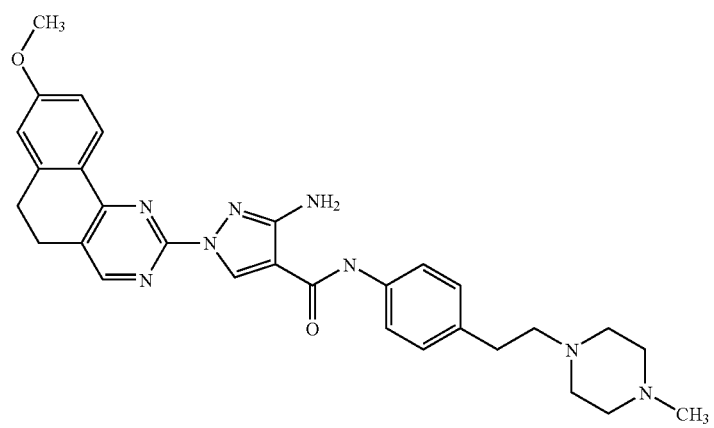 [SMILES: COc1ccc2c(c1)CCc1cnc(-n3cc(C(=O)Nc4ccc(CCN5CCN(C)CC5)cc4)c(N)n3)nc1-2] | 539.7 |
| 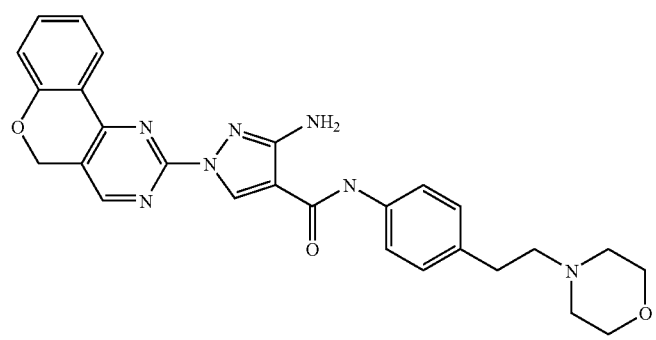 [SMILES: Nc1nn(-c2ncc3c(n2)-c2ccccc2OC3)cc1C(=O)Nc1ccc(CCN2CCOCC2)cc1] | 498.6 |

| MOLSTRUCTURE | MW (M + 1) |
|---|---|
| 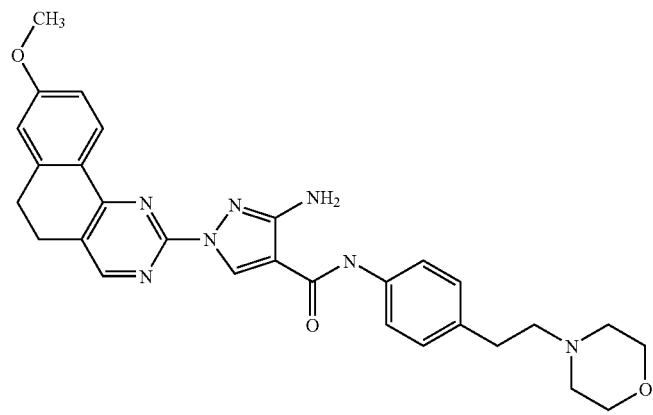 [SMILES: COc1ccc2c(c1)CCc1cnc(-n3cc(C(=O)Nc4ccc(CCN5CCOCC5)cc4)c(N)n3)nc1-2] | 526.6 |
| 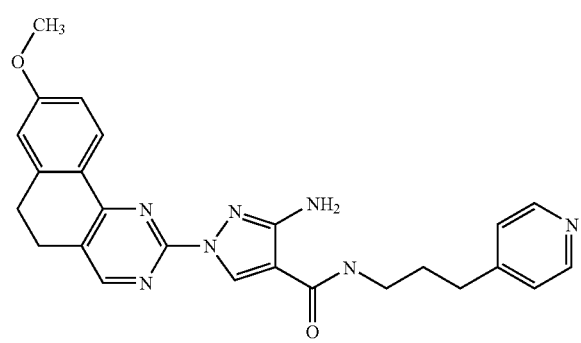 [SMILES: COc1ccc2c(c1)CCc1cnc(-n3cc(C(=O)NCCCc4ccncc4)c(N)n3)nc1-2] | 456.5 |
| 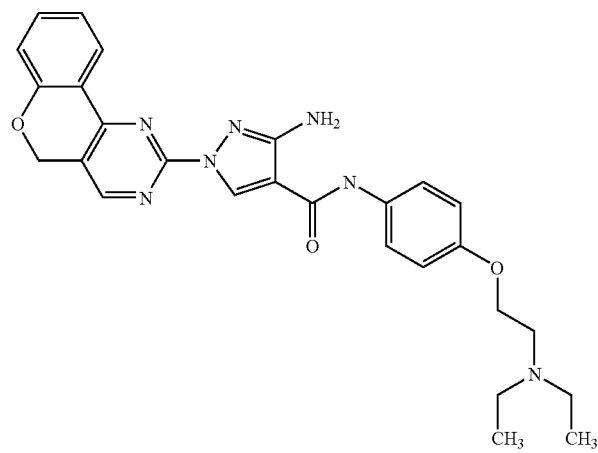 [SMILES: CCN(CC)CCOc1ccc(NC(=O)c2cn(-c3ncc4c(n3)-c3ccccc3OC4)nc2N)cc1] | 500.6 |
| 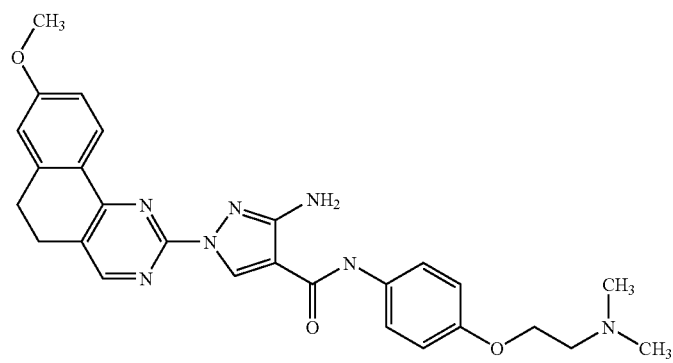 [SMILES: COc1ccc2c(c1)CCc1cnc(-n3cc(C(=O)Nc4ccc(OCCN(C)C)cc4)c(N)n3)nc1-2] | 500.6 |

| MOLSTRUCTURE | MW (M + 1) |
|---|---|
| | 514.6 |
| | 542.6 |
| | 539.7 |

| MOLSTRUCTURE | MW (M + 1) |
|---|---|
| 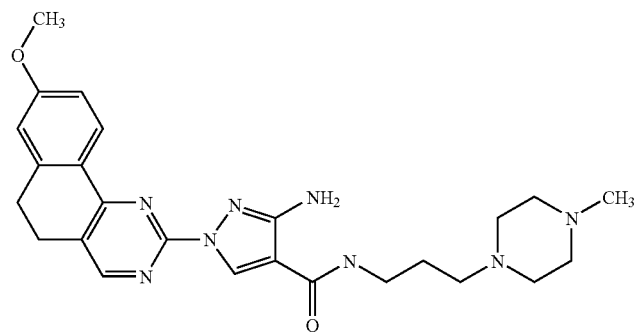 [SMILES: COc1ccc2c(c1)CCc1cnc(-n3cc(C(=O)NCCCN4CCN(C)CC4)c(N)n3)nc1-2] | 477.6 |
| 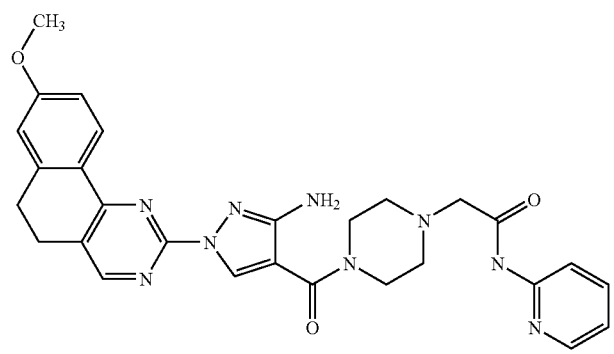 [SMILES: COc1ccc2c(c1)CCc1cnc(-n3cc(C(=O)N4CCN(CC(=O)Nc5ccccn5)CC4)c(N)n3)nc1-2] | 540.6 |
| 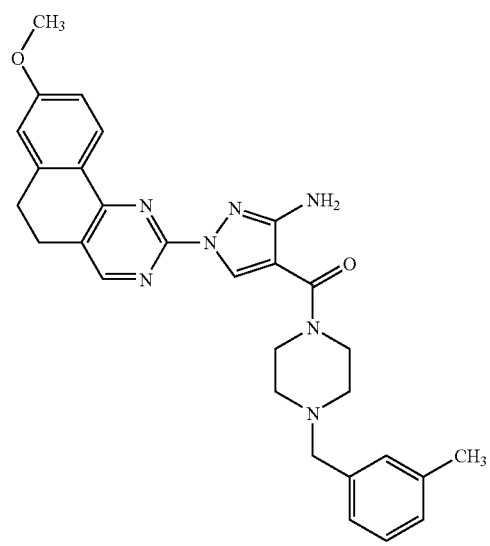 [SMILES: COc1ccc2c(c1)CCc1cnc(-n3cc(C(=O)N4CCN(Cc5cccc(C)c5)CC4)c(N)n3)nc1-2] | 541.6 |

| MOLSTRUCTURE | MW (M + 1) |
|---|---|
| 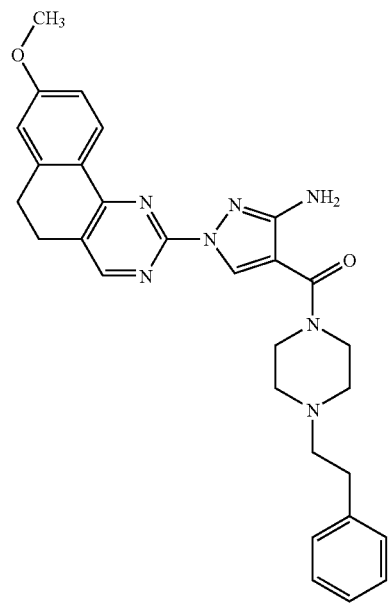 [SMILES: COc1ccc2c(c1)CCc1cnc(-n3cc(C(=O)N4CCN(CCc5ccccc5)CC4)c(N)n3)nc1-2] | 511.6 |
| 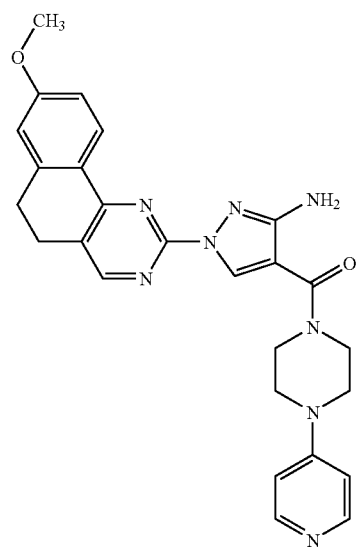 [SMILES: COc1ccc2c(c1)CCc1cnc(-n3cc(C(=O)N4CCN(c5ccncc5)CC4)c(N)n3)nc1-2] | 483.5 |

| MOLSTRUCTURE | MW (M + 1) |
|---|---|
| 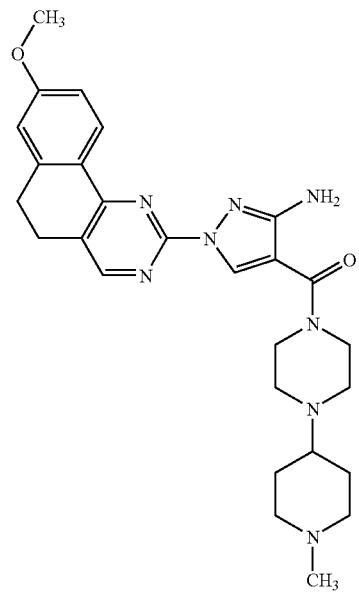 [SMILES: COc1ccc2c(c1)CCc1cnc(-n3cc(C(=O)N4CCN(C5CCN(C)CC5)CC4)c(N)n3)nc1-2] | 503.6 |
| 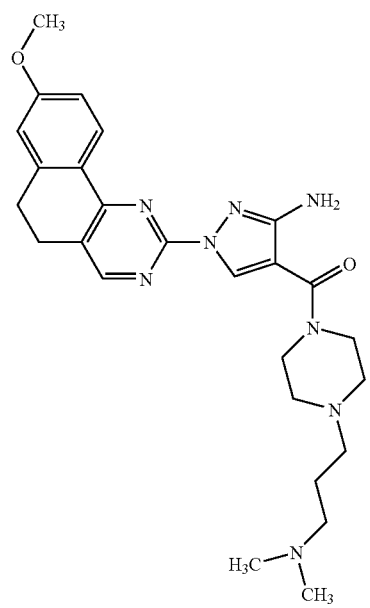 [SMILES: COc1ccc2c(c1)CCc1cnc(-n3cc(C(=O)N4CCN(CCCN(C)C)CC4)c(N)n3)nc1-2] | 491.6 |

| MOLSTRUCTURE | MW (M + 1) |
|---|---|
| 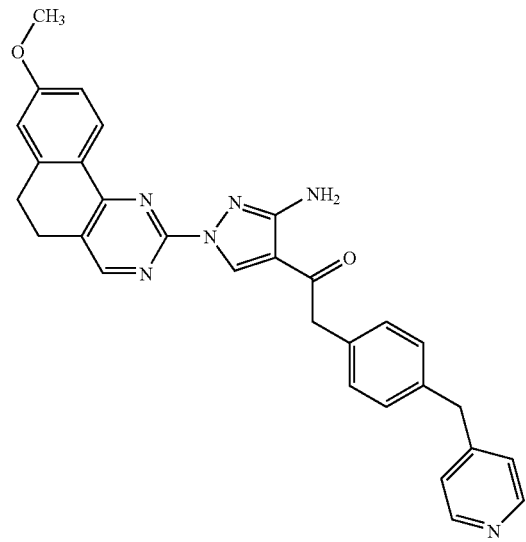 [SMILES: COc1ccc2c(c1)CCc1cnc(-n3cc(C(=O)Cc4ccc(Cc5ccncc5)cc4)c(N)n3)nc1-2] | 504.6 |
| 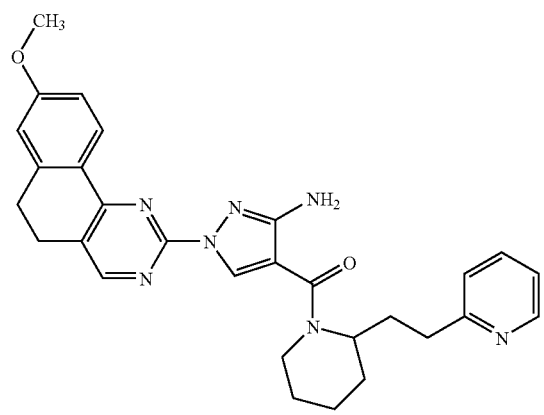 [SMILES: COc1ccc2c(c1)CCc1cnc(-n3cc(C(=O)N4CCCCC4CCc4ccccn4)c(N)n3)nc1-2] | 510.6 |
| 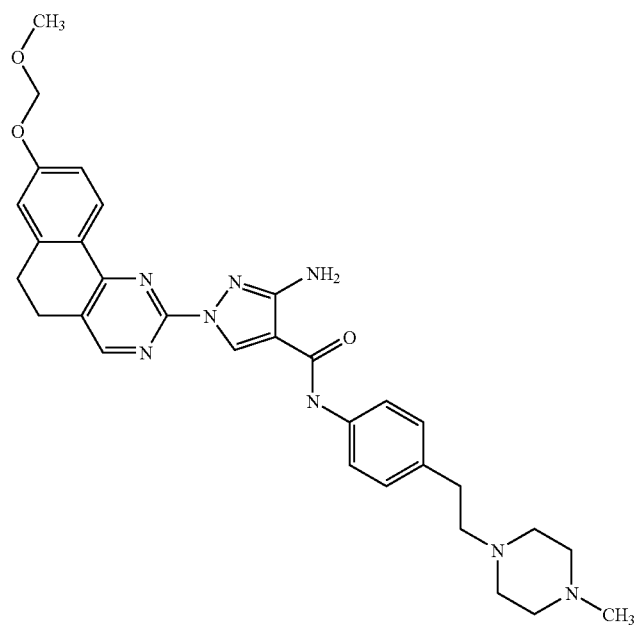 [SMILES: COCOc1ccc2c(c1)CCc1cnc(-n3cc(C(=O)Nc4ccc(CCN5CCN(C)CC5)cc4)c(N)n3)nc1-2] | 569.7 |

| MOLSTRUCTURE | MW (M + 1) |
|---|---|
| 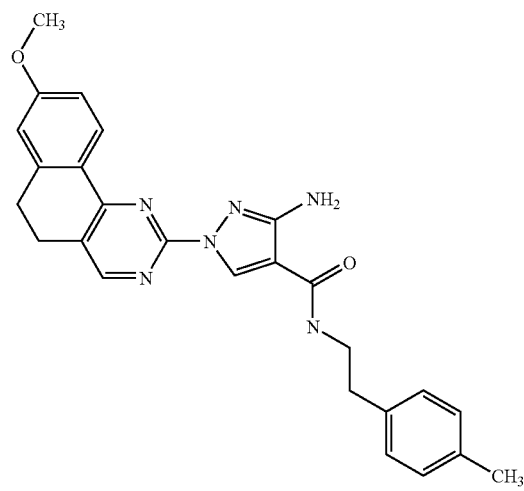 [SMILES: COc1ccc2c(c1)CCc1cnc(-n3cc(C(=O)NCCc4ccc(C)cc4)c(N)n3)nc1-2] | 456.5 |
| 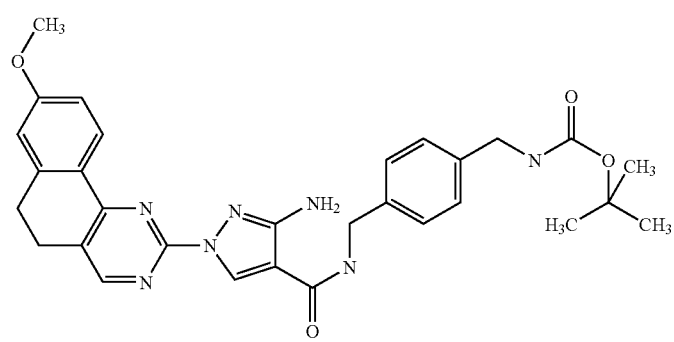 [SMILES: COc1ccc2c(c1)CCc1cnc(-n3cc(C(=O)NCc4ccc(CNC(=O)OC(C)(C)C)cc4)c(N)n3)nc1-2] | 556.6 |
| 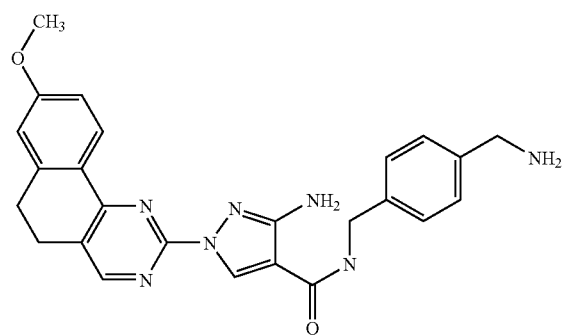 [SMILES: COc1ccc2c(c1)CCc1cnc(-n3cc(C(=O)NCc4ccc(CN)cc4)c(N)n3)nc1-2] | 456.5 |

| MOLSTRUCTURE | MW (M + 1) |
|---|---|
| 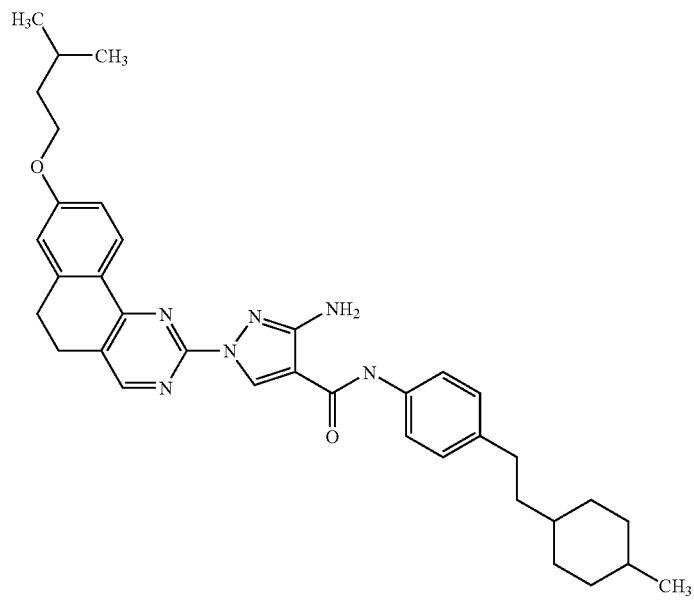 [SMILES: CC(C)CCOc1ccc2c(c1)CCc1cnc(-n3cc(C(=O)Nc4ccc(CCC5CCC(C)CC5)cc4)c(N)n3)nc1-2] | 596.8 |
| 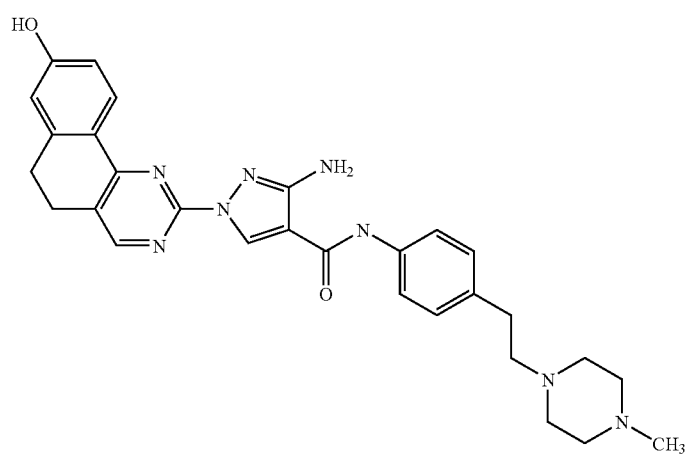 [SMILES: CN1CCN(CCc2ccc(NC(=O)c3cn(-c4ncc5c(n4)-c4ccc(O)cc4CC5)nc3N)cc2)CC1] | 525.6 |
| 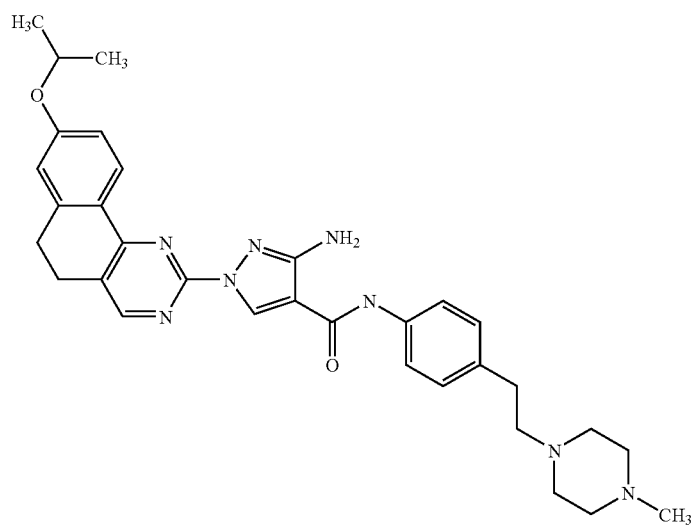 [SMILES: CC(C)Oc1ccc2c(c1)CCc1cnc(-n3cc(C(=O)Nc4ccc(CCN5CCN(C)CC5)cc4)c(N)n3)nc1-2] | 567.7 |

| MOLSTRUCTURE | MW (M + 1) |
|---|---|
| 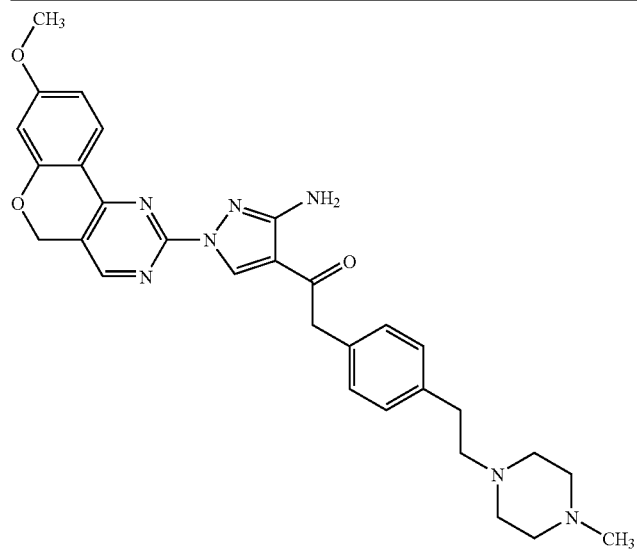 | 541.6 |
| 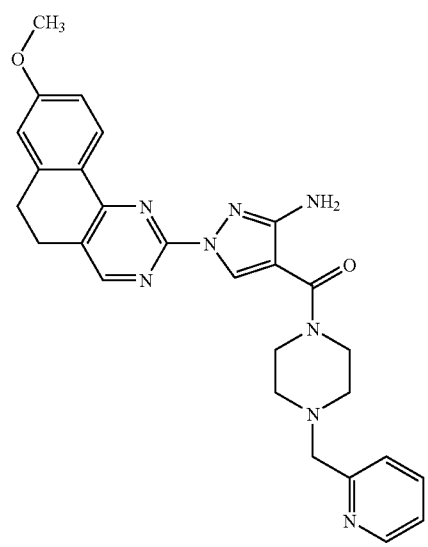 [SMILES: COc1ccc2c(c1)CCc1cnc(-n3cc(C(=O)N4CCN(Cc5ccccn5)CC4)c(N)n3)nc1-2] | 497.6 |
| 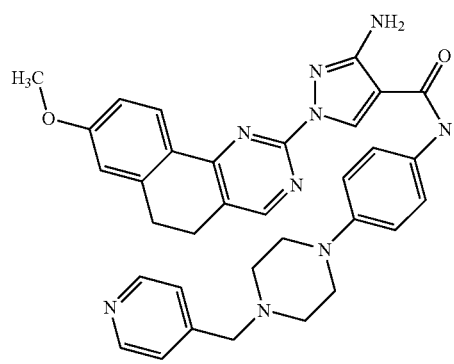 [SMILES: COc1ccc2c(c1)CCc1cnc(-n3cc(C(=O)Nc4ccc(N5CCN(Cc6ccncc6)CC5)cc4)c(N)n3)nc1-2] | 588.7 |

111 112
-continued
| MOLSTRUCTURE | MW (M + 1) |
|---|---|
| 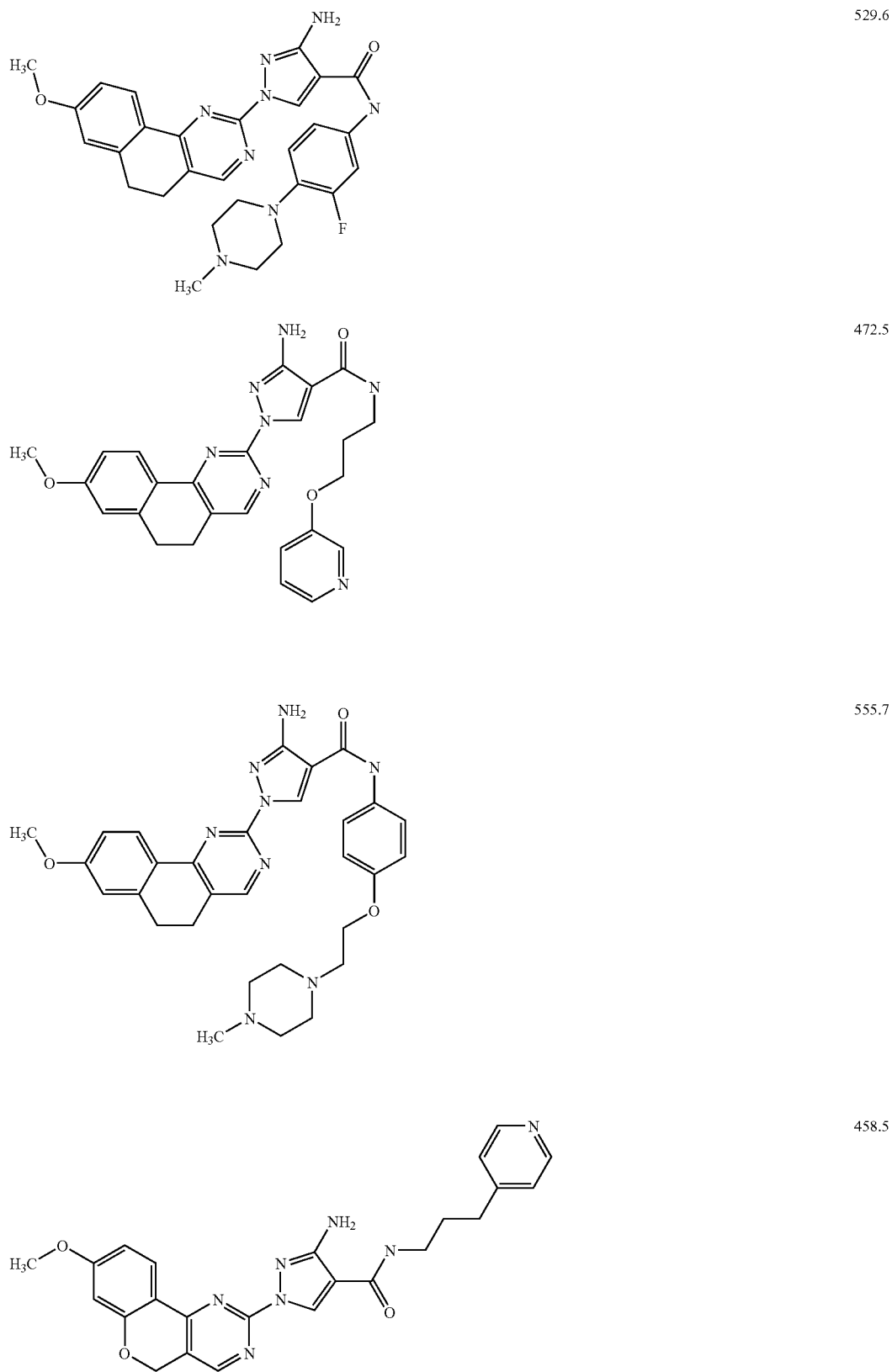 | 529.6 |
| | 472.5 |
| | 555.7 |
| | 458.5 |

| MOLSTRUCTURE | MW (M + 1) |
|---|---|
| 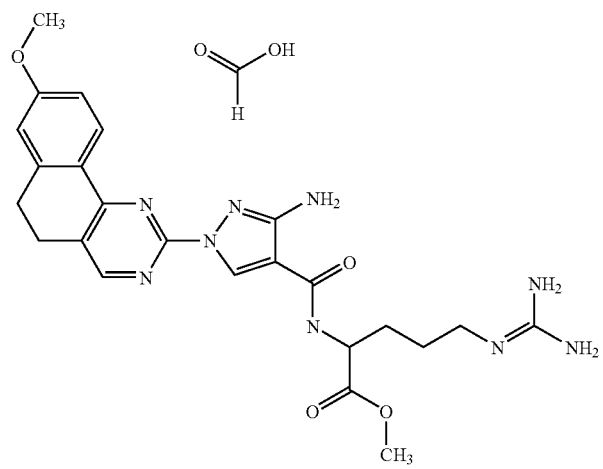 [SMILES: COC(=O)C(CCCN=C(N)N)NC(=O)c1cn(-c2ncc3c(n2)-c2ccc(OC)cc2CC3)nc1N ; O=CO] | 554.6 |
| 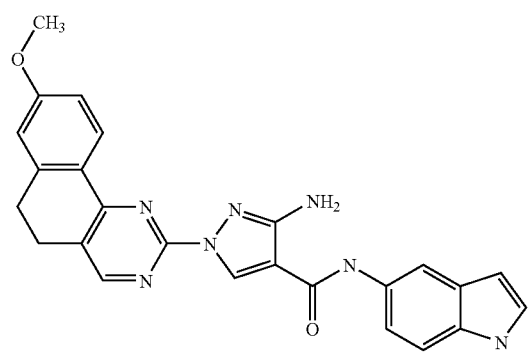 [SMILES: COc1ccc2c(c1)CCc1cnc(-n3cc(C(=O)Nc4ccc5[nH]ccc5c4)c(N)n3)nc1-2] | 452.5 |
| 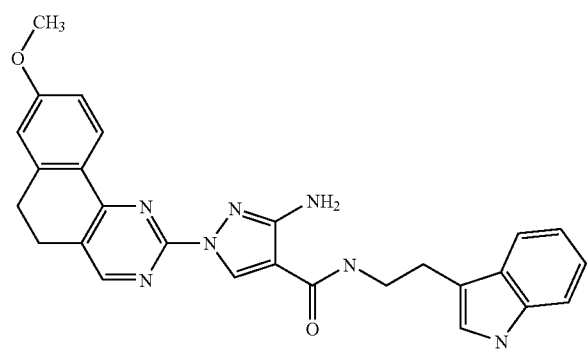 [SMILES: COc1ccc2c(c1)CCc1cnc(-n3cc(C(=O)NCCc4c[nH]c5ccccc45)c(N)n3)nc1-2] | 480.5 |
| 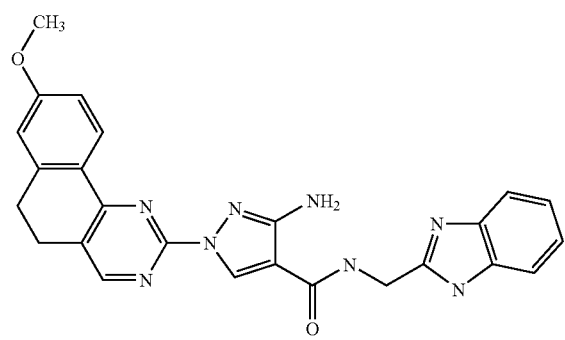 [SMILES: COc1ccc2c(c1)CCc1cnc(-n3cc(C(=O)NCc4nc5ccccc5[nH]4)c(N)n3)nc1-2] | 467.5 |

| MOLSTRUCTURE | MW (M + 1) |
|---|---|
| 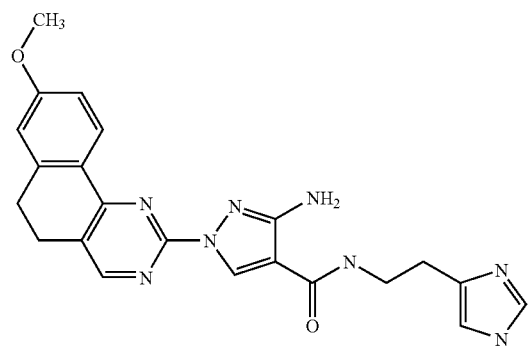 [SMILES: COc1ccc2c(c1)CCc1cnc(-n3cc(C(=O)NCCc4c[nH]cn4)c(N)n3)nc1-2] | 431.5 |
| 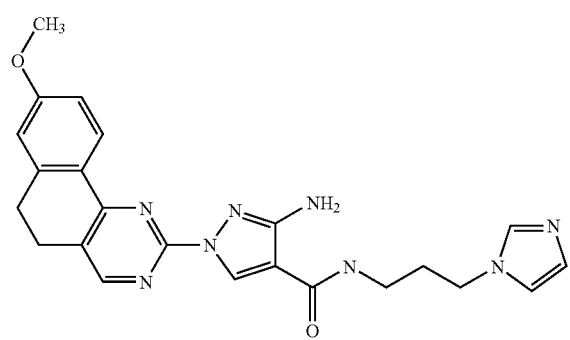 [SMILES: COc1ccc2c(c1)CCc1cnc(-n3cc(C(=O)NCCCn4ccnc4)c(N)n3)nc1-2] | 445.5 |
| 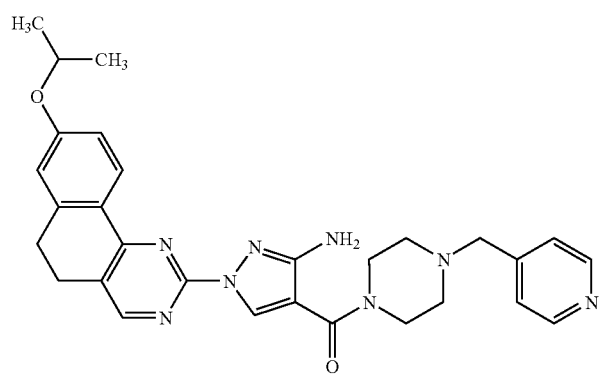 [SMILES: CC(C)Oc1ccc2c(c1)CCc1cnc(-n3cc(C(=O)N4CCN(Cc5ccncc5)CC4)c(N)n3)nc1-2] | 525.6 |
| 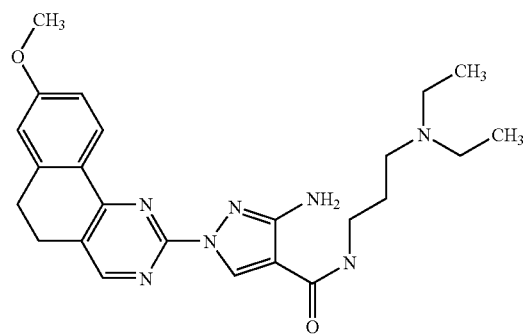 [SMILES: CCN(CC)CCCNC(=O)c1cn(-c2ncc3c(n2)-c2ccc(OC)cc2CC3)nc1N] | 450.6 |

| MOLSTRUCTURE | MW (M + 1) |
|---|---|
| 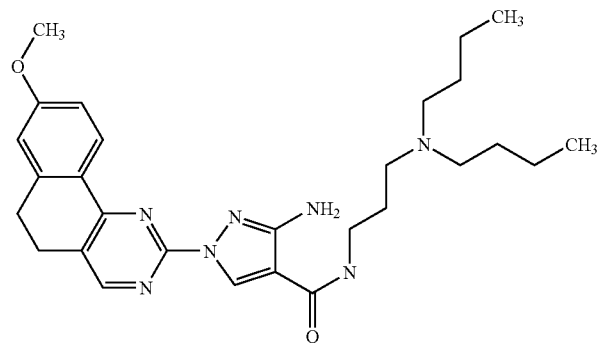 [SMILES: CCCCN(CCCC)CCCNC(=O)c1cn(-c2ncc3c(n2)-c2ccc(OC)cc2CC3)nc1N] | 506.7 |
| 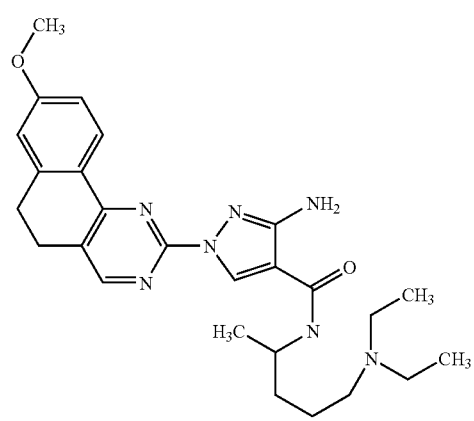 [SMILES: CCN(CC)CCCC(C)NC(=O)c1cn(-c2ncc3c(n2)-c2ccc(OC)cc2CC3)nc1N] | 478.6 |
| 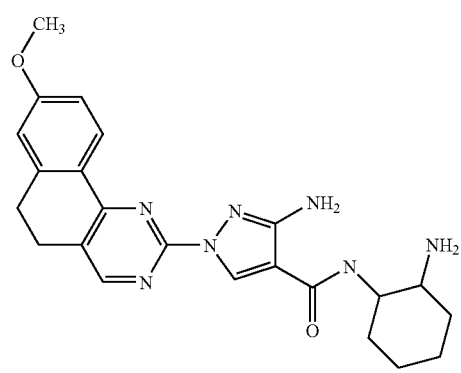 [SMILES: COc1ccc2c(c1)CCc1cnc(-n3cc(C(=O)NC4CCCCC4N)c(N)n3)nc1-2] | 434.5 |
| 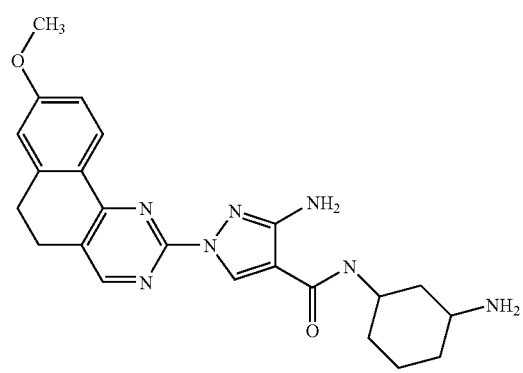 [SMILES: COc1ccc2c(c1)CCc1cnc(-n3cc(C(=O)NC4CCCC(N)C4)c(N)n3)nc1-2] | 434.5 |

| MOLSTRUCTURE | MW (M + 1) |
|---|---|
| 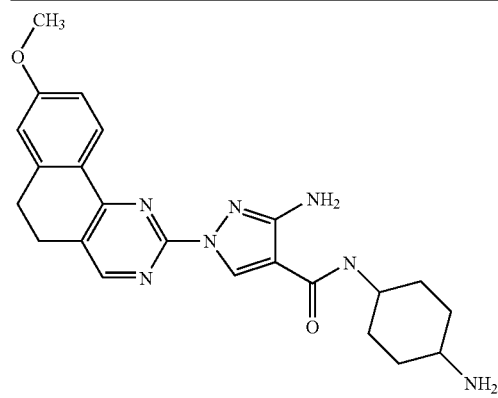 | 434.5 |
| 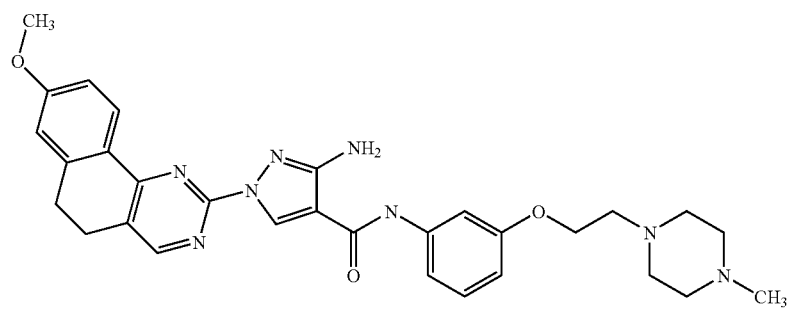 [SMILES: COc1ccc2c(c1)CCc1cnc(-n3cc(C(=O)Nc4cccc(OCCN5CCN(C)CC5)c4)c(N)n3)nc1-2] | 555.7 |
| 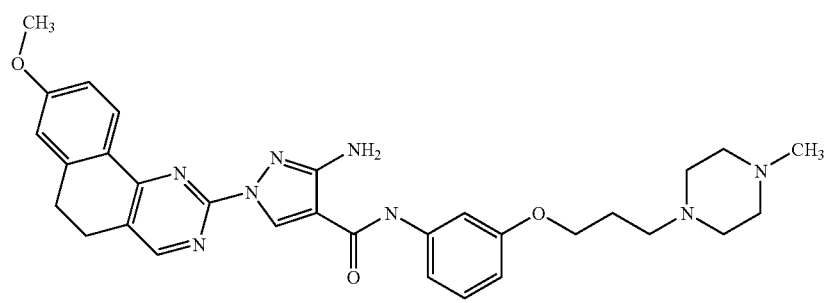 [SMILES: COc1ccc2c(c1)CCc1cnc(-n3cc(C(=O)Nc4cccc(OCCCN5CCN(C)CC5)c4)c(N)n3)nc1-2] | 569.7 |
| 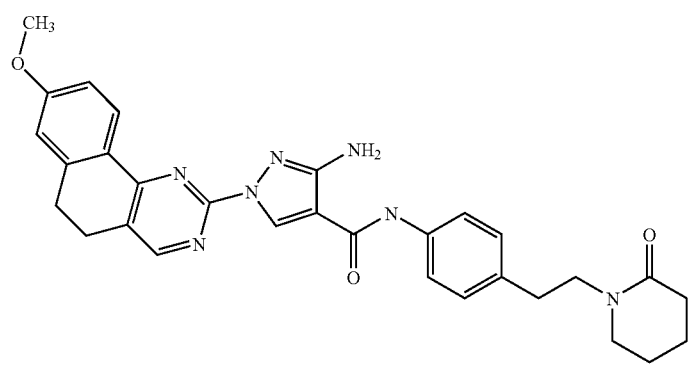 [SMILES: COc1ccc2c(c1)CCc1cnc(-n3cc(C(=O)Nc4ccc(CCN5CCCCC5=O)cc4)c(N)n3)nc1-2] | 538.6 |

| MOLSTRUCTURE | MW (M + 1) |
|---|---|
| 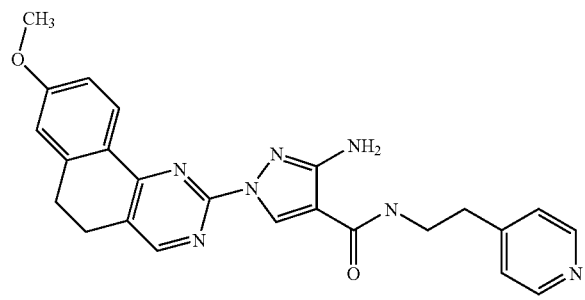 [SMILES: COc1ccc2c(c1)CCc1cnc(-n3cc(C(=O)NCCc4ccncc4)c(N)n3)nc1-2] | 442.5 |
| 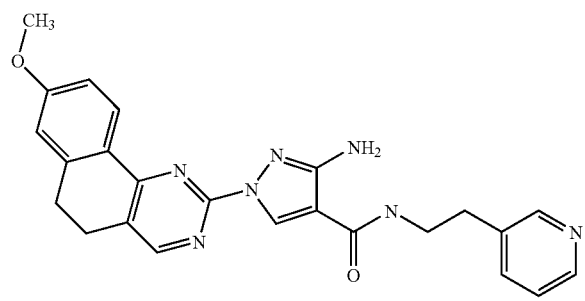 [SMILES: COc1ccc2c(c1)CCc1cnc(-n3cc(C(=O)NCCc4cccnc4)c(N)n3)nc1-2] | 442.5 |
| 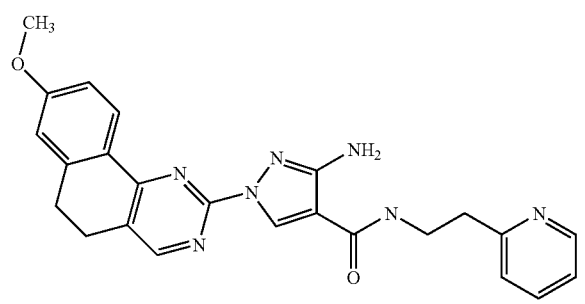 [SMILES: COc1ccc2c(c1)CCc1cnc(-n3cc(C(=O)NCCc4ccccn4)c(N)n3)nc1-2] | 442.5 |
| 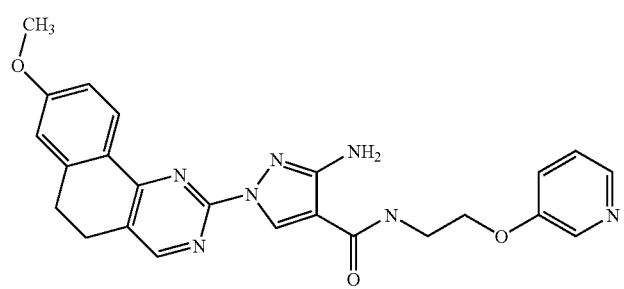 [SMILES: COc1ccc2c(c1)CCc1cnc(-n3cc(C(=O)NCCOc4cccnc4)c(N)n3)nc1-2] | 458.5 |
| 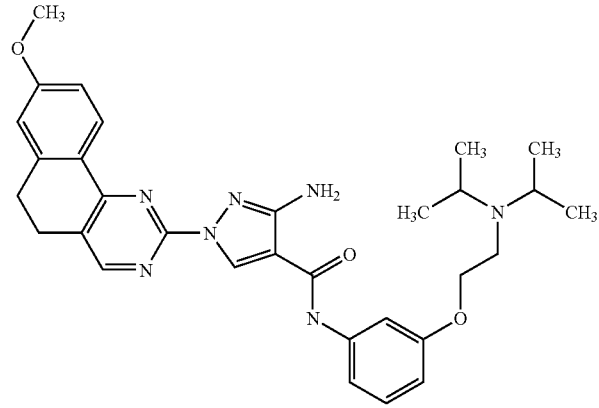 [SMILES: COc1ccc2c(c1)CCc1cnc(-n3cc(C(=O)Nc4cccc(OCCN(C(C)C)C(C)C)c4)c(N)n3)nc1-2] | 556.7 |

| MOLSTRUCTURE | MW (M + 1) |
|---|---|
| 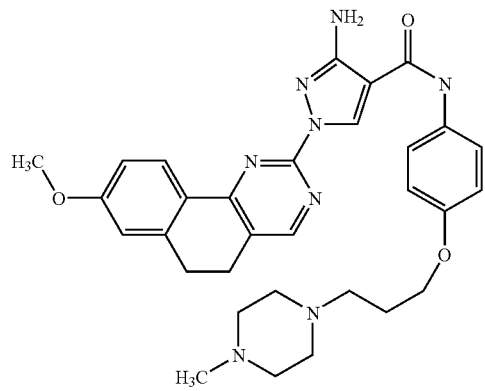 [SMILES: COc1ccc2c(c1)CCc1cnc(-n3cc(C(=O)Nc4ccc(OCCCN5CCN(C)CC5)cc4)c(N)n3)nc1-2] | 569.7 |
| 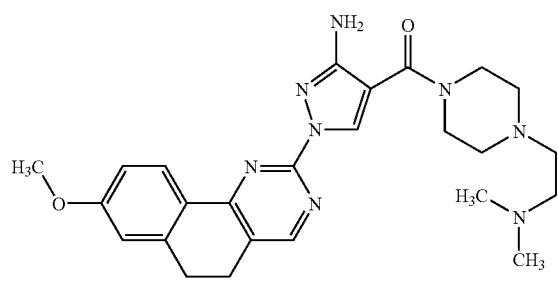 [SMILES: COc1ccc2c(c1)CCc1cnc(-n3cc(C(=O)N4CCN(CCN(C)C)CC4)c(N)n3)nc1-2] | 477.6 |
| 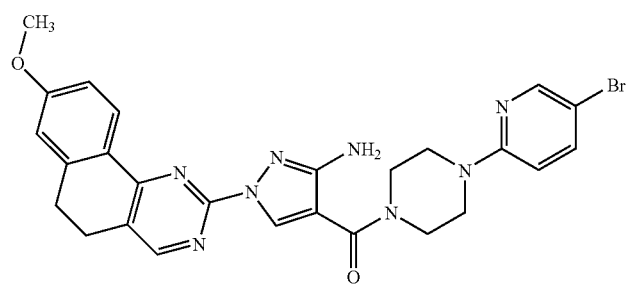 [SMILES: COc1ccc2c(c1)CCc1cnc(-n3cc(C(=O)N4CCN(c5ccc(Br)cn5)CC4)c(N)n3)nc1-2] | 562.4 |
| 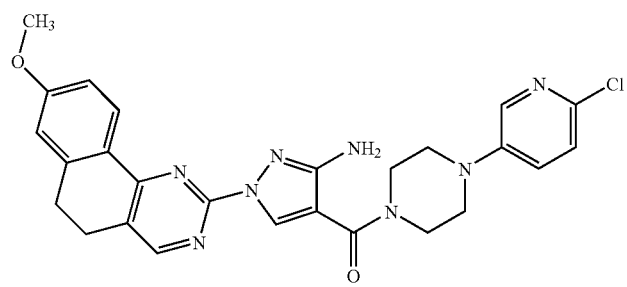 [SMILES: COc1ccc2c(c1)CCc1cnc(-n3cc(C(=O)N4CCN(c5ccc(Cl)nc5)CC4)c(N)n3)nc1-2] | 518.0 |
| 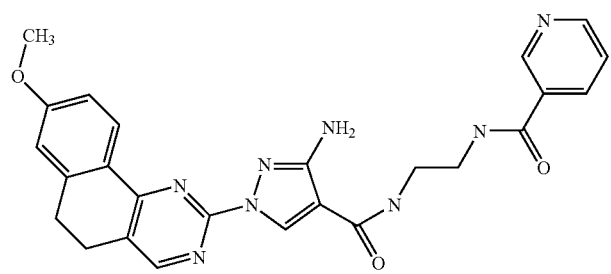 [SMILES: COc1ccc2c(c1)CCc1cnc(-n3cc(C(=O)NCCNC(=O)c4cccnc4)c(N)n3)nc1-2] | 485.5 |

| MOLSTRUCTURE | MW (M + 1) |
|---|---|
| 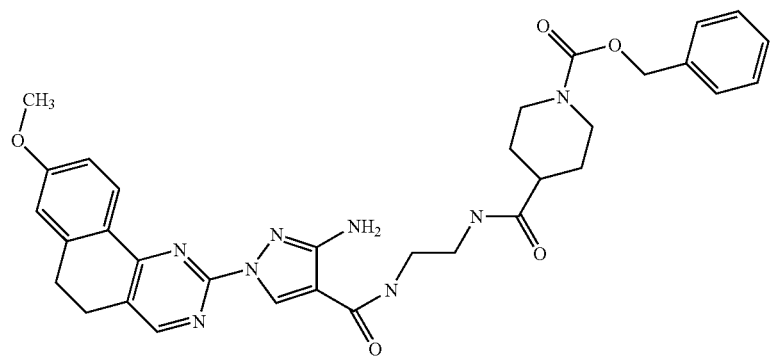 [SMILES: COc1ccc2c(c1)CCc1cnc(-n3cc(C(=O)NCCNC(=O)C4CCN(C(=O)OCc5ccccc5)CC4)c(N)n3)nc1-2] | 625.7 |
| 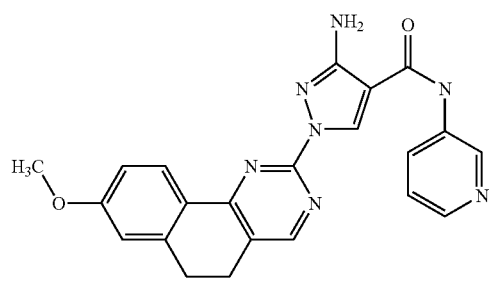 [SMILES: COc1ccc2c(c1)CCc1cnc(-n3cc(C(=O)Nc4cccnc4)c(N)n3)nc1-2] | 414.4 |
| 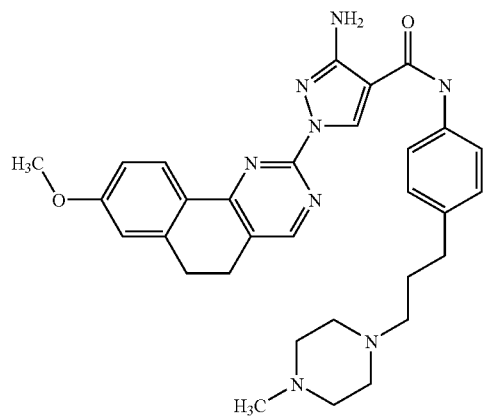 [SMILES: COc1ccc2c(c1)CCc1cnc(-n3cc(C(=O)Nc4ccc(CCCN5CCN(C)CC5)cc4)c(N)n3)nc1-2] | 553.7 |
| 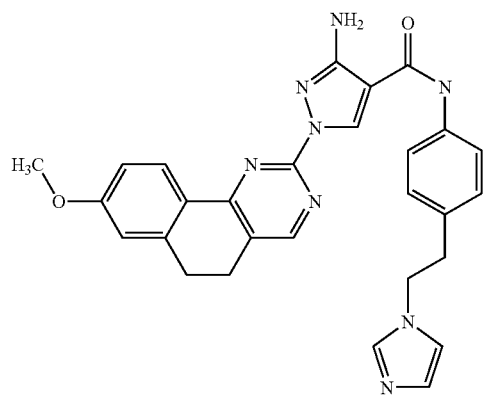 [SMILES: COc1ccc2c(c1)CCc1cnc(-n3cc(C(=O)Nc4ccc(CCn5ccnc5)cc4)c(N)n3)nc1-2] | 507.6 |

| MOLSTRUCTURE | MW (M + 1) |
|---|---|
| 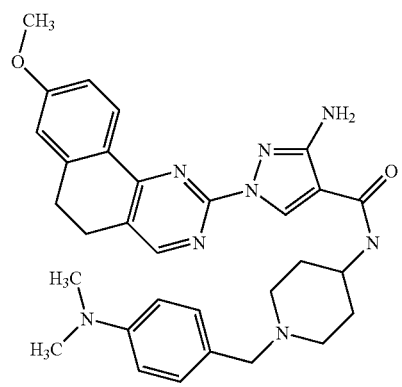 [SMILES: COc1ccc2c(c1)CCc1cnc(-n3cc(C(=O)NC4CCN(Cc5ccc(N(C)C)cc5)CC4)c(N)n3)nc1-2] | 553.7 |
| 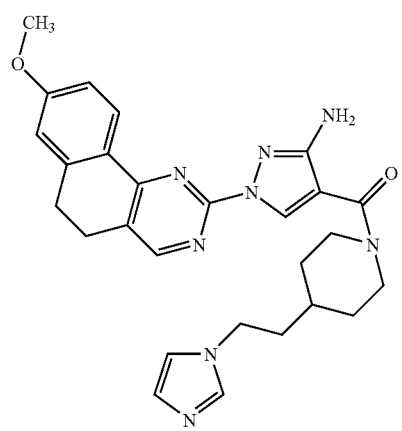 [SMILES: COc1ccc2c(c1)CCc1cnc(-n3cc(C(=O)N4CCC(CCn5ccnc5)CC4)c(N)n3)nc1-2] | 499.6 |
| 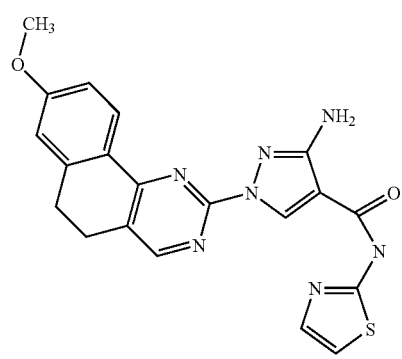 [SMILES: COc1ccc2c(c1)CCc1cnc(-n3cc(C(=O)Nc4nccs4)c(N)n3)nc1-2] | 420.5 |
| 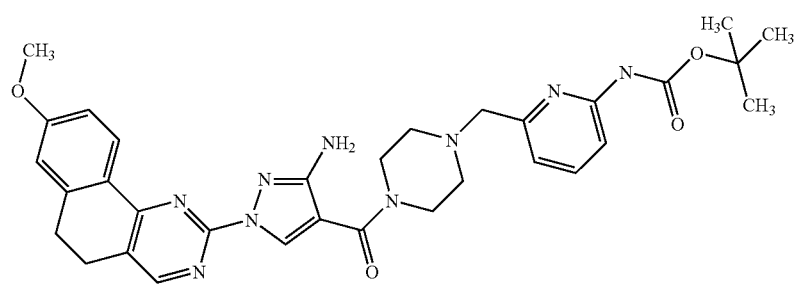 [SMILES: COc1ccc2c(c1)CCc1cnc(-n3cc(C(=O)N4CCN(Cc5cccc(NC(=O)OC(C)(C)C)n5)CC4)c(N)n3)nc1-2] | 612.7 |

-continued
| MOLSTRUCTURE | MW (M + 1) |
|---|---|
| 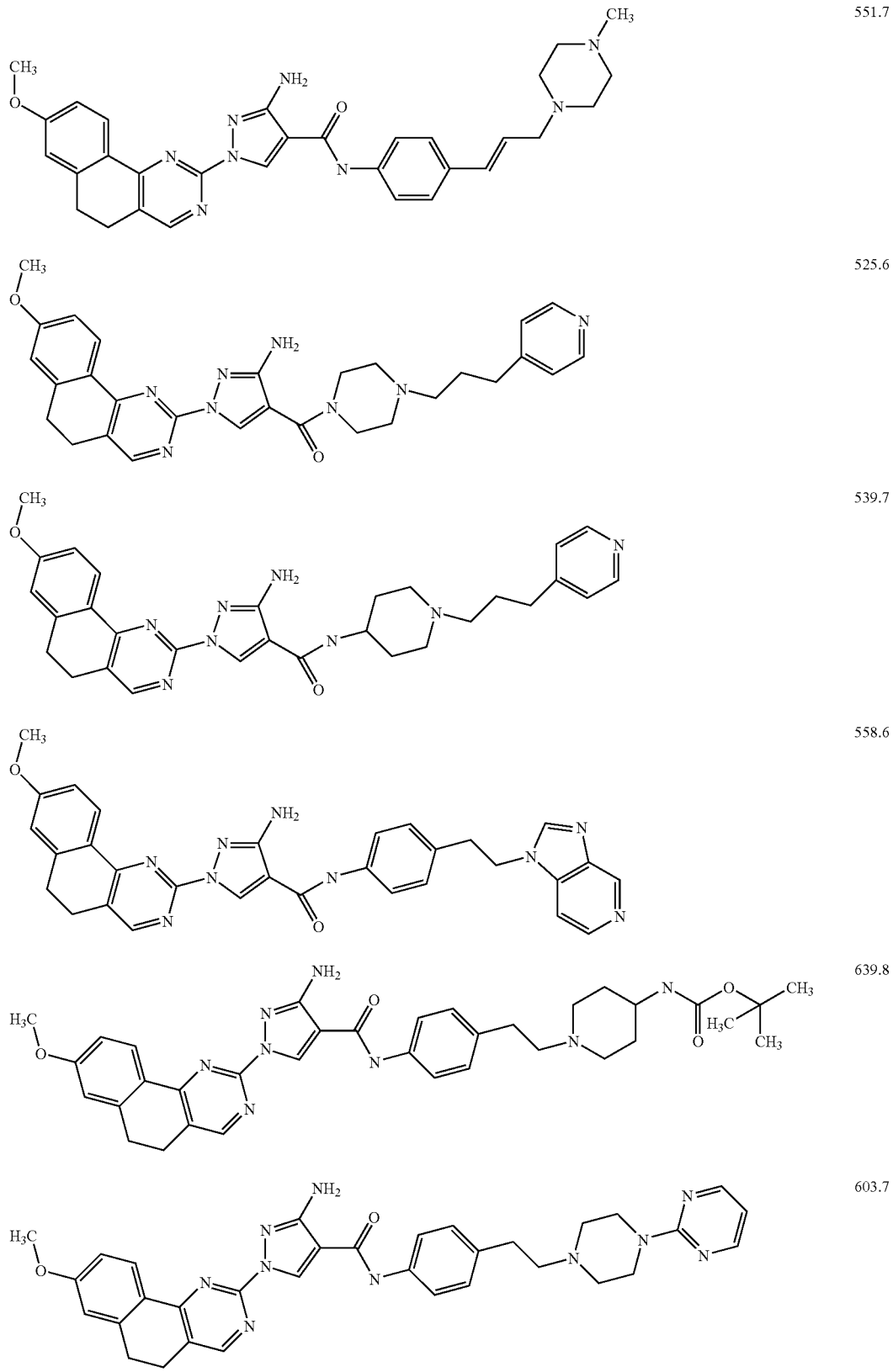 | 551.7 |
| | 525.6 |
| | 539.7 |
| | 558.6 |
| | 639.8 |
| | 603.7 |

| MOLSTRUCTURE | MW (M + 1) |
|---|---|
| 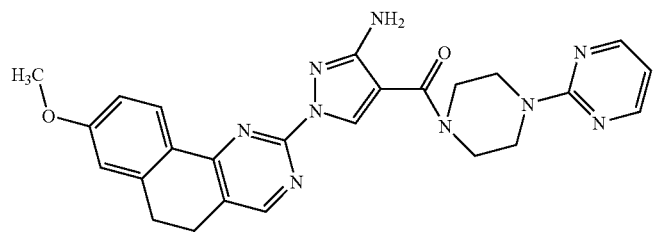 [SMILES: COc1ccc2c(c1)CCc1cnc(-n3cc(C(=O)N4CCN(c5ncccn5)CC4)c(N)n3)nc1-2] | 484.5 |
| 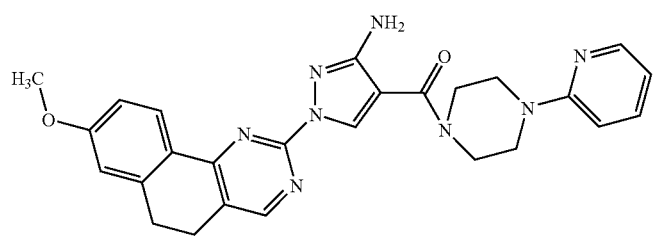 [SMILES: COc1ccc2c(c1)CCc1cnc(-n3cc(C(=O)N4CCN(c5ccccn5)CC4)c(N)n3)nc1-2] | 483.5 |
| 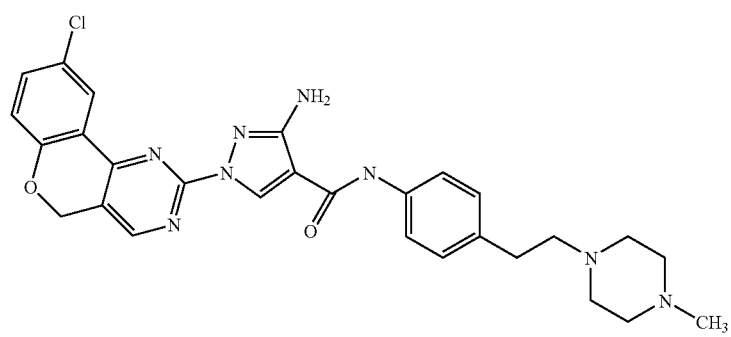 [SMILES: CN1CCN(CCc2ccc(NC(=O)c3cn(-c4ncc5c(n4)-c4cc(Cl)ccc4OC5)nc3N)cc2)CC1] | 562.1 |
| 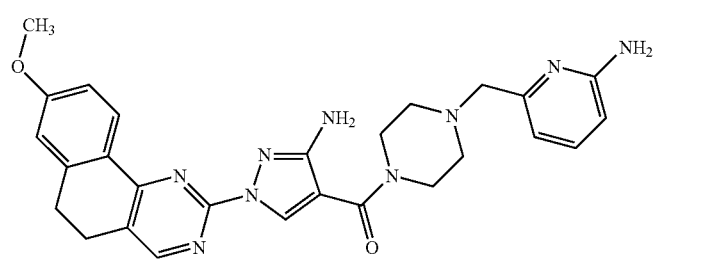 [SMILES: COc1ccc2c(c1)CCc1cnc(-n3cc(C(=O)N4CCN(Cc5cccc(N)n5)CC4)c(N)n3)nc1-2] | 512.6 |
| 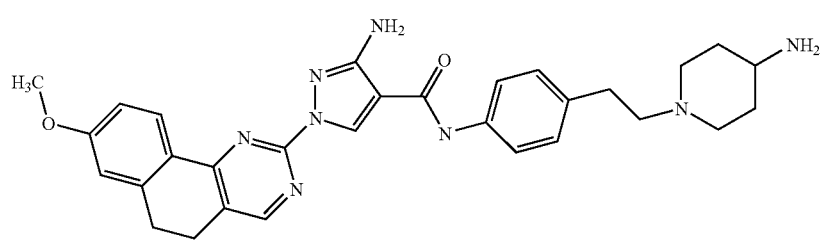 [SMILES: COc1ccc2c(c1)CCc1cnc(-n3cc(C(=O)Nc4ccc(CCN5CCC(N)CC5)cc4)c(N)n3)nc1-2] | 539.7 |
| 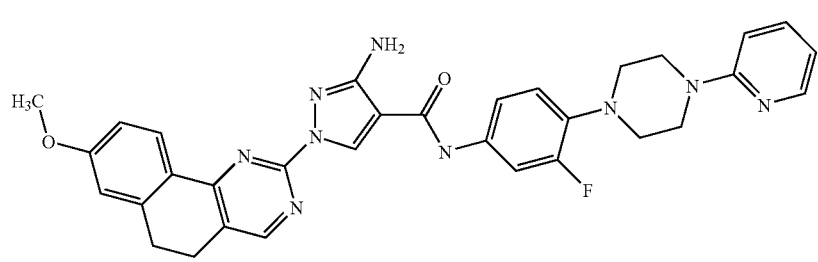 [SMILES: COc1ccc2c(c1)CCc1cnc(-n3cc(C(=O)Nc4ccc(N5CCN(c6ccccn6)CC5)c(F)c4)c(N)n3)nc1-2] | 592.7 |

| MOLSTRUCTURE | MW (M + 1) |
|---|---|
| 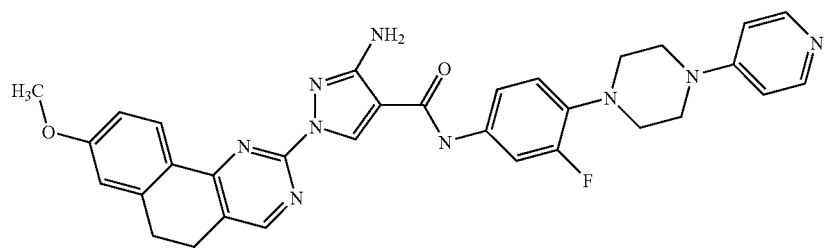 [SMILES: COc1ccc2c(c1)CCc1cnc(-n3cc(C(=O)Nc4ccc(N5CCN(c6ccncc6)CC5)c(F)c4)c(N)n3)nc1-2] | 592.7 |
| 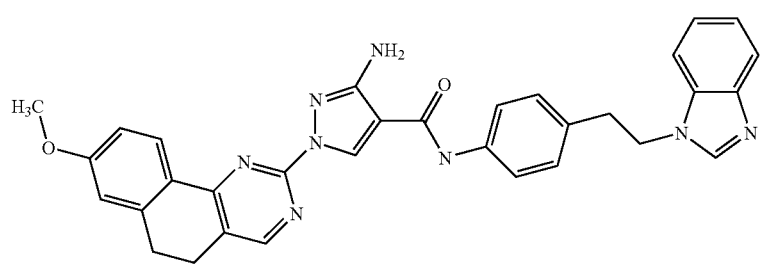 [SMILES: COc1ccc2c(c1)CCc1cnc(-n3cc(C(=O)Nc4ccc(CCn5cnc6ccccc65)cc4)c(N)n3)nc1-2] | 557.6 |
| 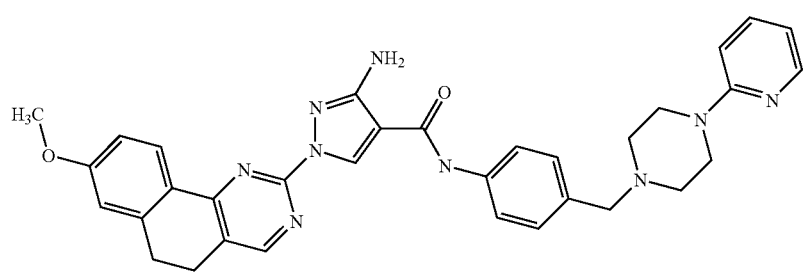 [SMILES: COc1ccc2c(c1)CCc1cnc(-n3cc(C(=O)Nc4ccc(CN5CCN(c6ccccn6)CC5)cc4)c(N)n3)nc1-2] | 588.7 |
| 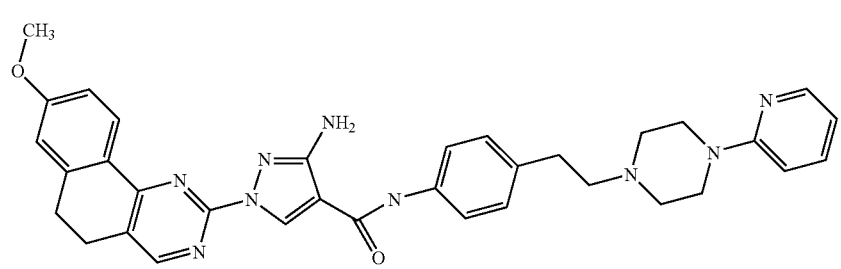 [SMILES: COc1ccc2c(c1)CCc1cnc(-n3cc(C(=O)Nc4ccc(CCN5CCN(c6ccccn6)CC5)cc4)c(N)n3)nc1-2] | 602.7 |
| 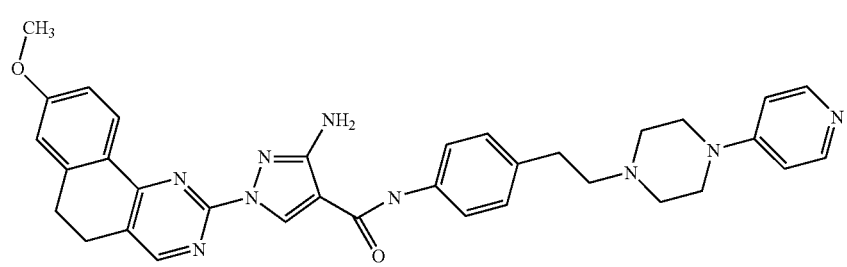 [SMILES: COc1ccc2c(c1)CCc1cnc(-n3cc(C(=O)Nc4ccc(CCN5CCN(c6ccncc6)CC5)cc4)c(N)n3)nc1-2] | 602.7 |
| 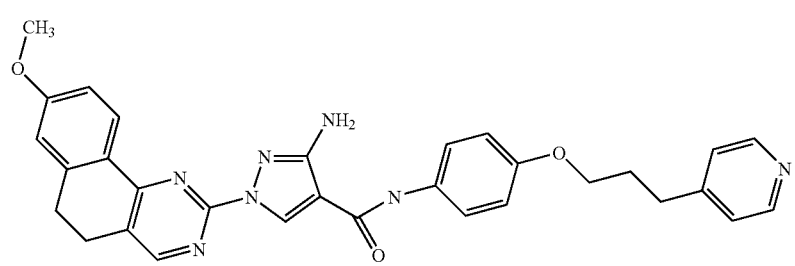 [SMILES: COc1ccc2c(c1)CCc1cnc(-n3cc(C(=O)Nc4ccc(OCCCc5ccncc5)cc4)c(N)n3)nc1-2] | 548.6 |

| MOLSTRUCTURE | MW (M + 1) |
|---|---|
| 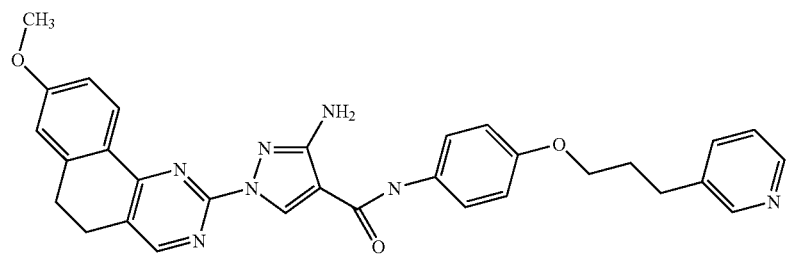 [SMILES: COc1ccc2c(c1)CCc1cnc(-n3cc(C(=O)Nc4ccc(OCCCc5cccnc5)cc4)c(N)n3)nc1-2] | 548.6 |
| 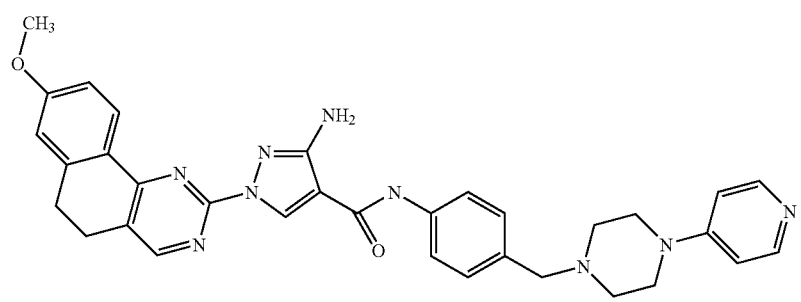 [SMILES: COc1ccc2c(c1)CCc1cnc(-n3cc(C(=O)Nc4ccc(CN5CCN(c6ccncc6)CC5)cc4)c(N)n3)nc1-2] | 588.7 |
| 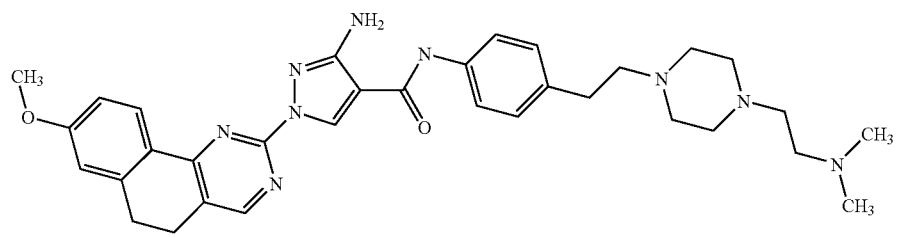 | 596.8 |
| 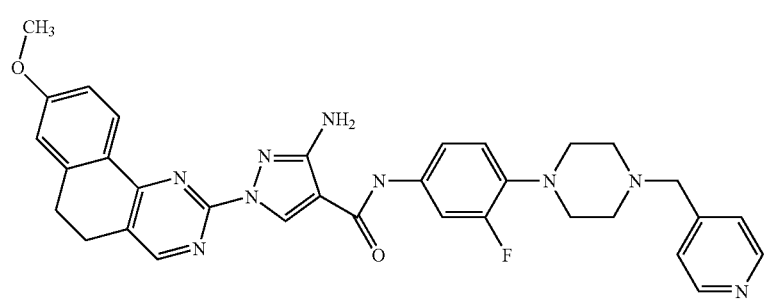 [SMILES: COc1ccc2c(c1)CCc1cnc(-n3cc(C(=O)Nc4ccc(N5CCN(Cc6ccncc6)CC5)c(F)c4)c(N)n3)nc1-2] | 606.7 |
| 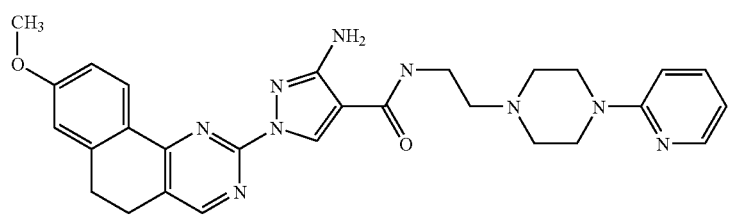 [SMILES: COc1ccc2c(c1)CCc1cnc(-n3cc(C(=O)NCCN4CCN(c5ccccn5)CC4)c(N)n3)nc1-2] | 526.6 |
| 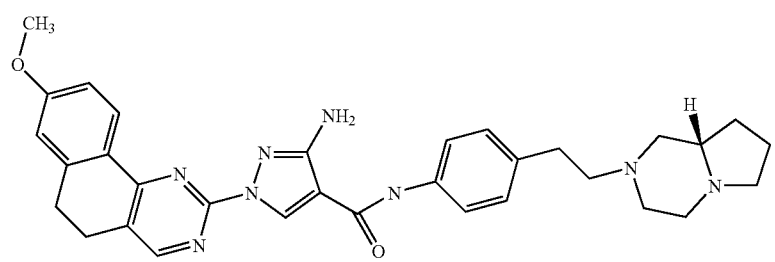 [SMILES: COc1ccc2c(c1)CCc1cnc(-n3cc(C(=O)Nc4ccc(CCN5CCN6CCC[C@H]6C5)cc4)c(N)n3)nc1-2] | 565.7 |

| MOLSTRUCTURE | MW (M + 1) |
|---|---|
| | 621.8 |
| | 582.7 |
| | 612.7 |
| | 625.7 |
| | 525.6 |
| | 553.7 |

| MOLSTRUCTURE | MW (M + 1) |
|---|---|
| 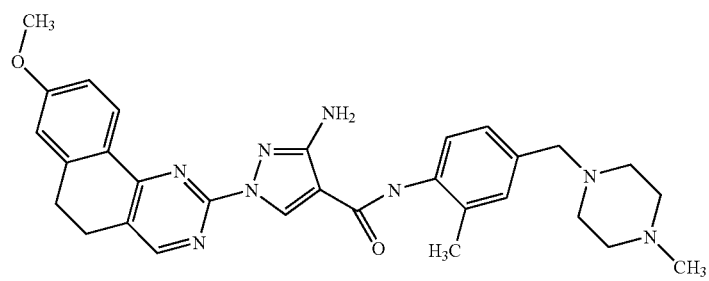 [SMILES: COc1ccc2c(c1)CCc1cnc(-n3cc(C(=O)Nc4ccc(CN5CCN(C)CC5)cc4C)c(N)n3)nc1-2] | 539.7 |
| 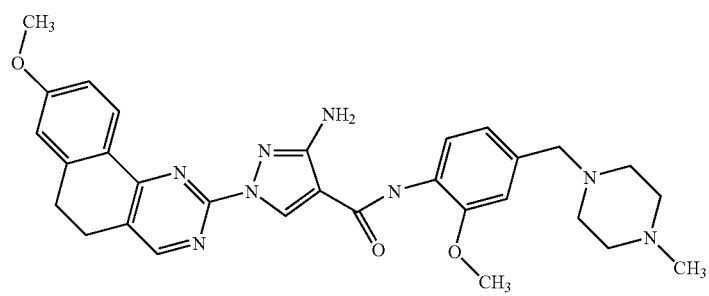 [SMILES: COc1ccc2c(c1)CCc1cnc(-n3cc(C(=O)Nc4ccc(CN5CCN(C)CC5)cc4OC)c(N)n3)nc1-2] | 555.7 |
| 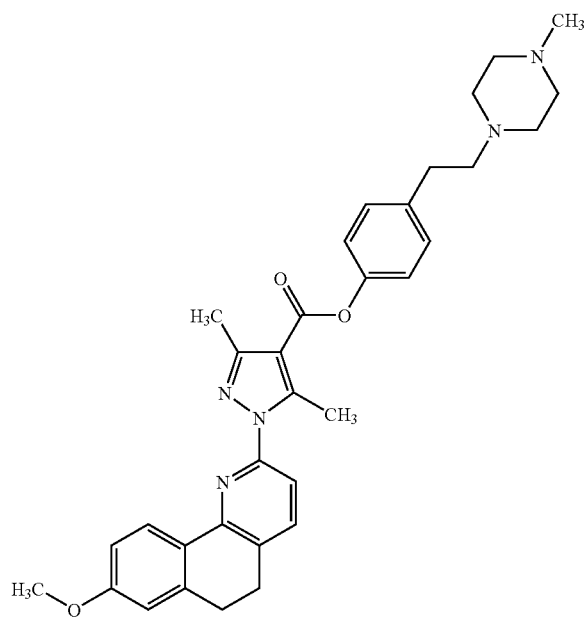 | 553.7 |
| 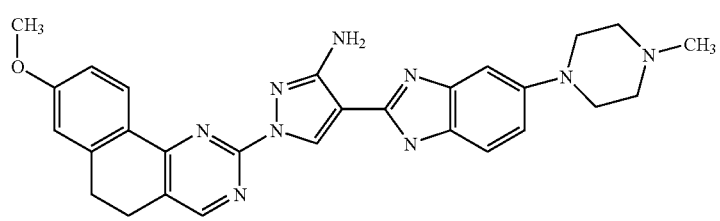 [SMILES: COc1ccc2c(c1)CCc1cnc(-n3cc(-c4nc5cc(N6CCN(C)CC6)ccc5[nH]4)c(N)n3)nc1-2] | 508.6 |

5.2.3.2 Preparation of Compounds According to Formula (3)

Compounds according to formula (3), (3a) and (3b) can be prepared according to any method apparent to those of skill in the art. The present invention provides the following exemplary methods for their preparation.

Compounds of formula (3) were prepared according to the following general schemes.

Scheme 3-1

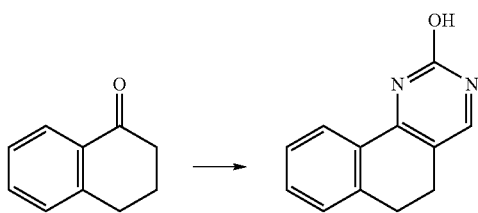

As shown in SCHEME 1 the respective ketones A can be reacted with urea, trialkylorthoformate such as trimethyl or triethylorthoformate for example to afford respective compound B. Reaction of compound B with POCl$_3$ either neat or with a cosolvent, for example toluene or dichlorobenzene, with or without the addition of PCl5 affords the respective compound C. Alternatively Compound A may be reacted with dimethylformamide dimethyl acetal for example to give intermediate D. Reaction of intermediate D with urea, sodium alkoxide for example NaOMe or NaOEt in a solvent such as ethanol affords respective compound B as the sodium salt which is neutralized with dilute acid to give B. Reaction of intermediate D with thiourea as above followed by reaction with methyl iodide affords intermediate E which is oxidized using an oxidant for example metachloro perbenzoic acid in a solvent such as dichloromethane give compound F.

Scheme 3-2

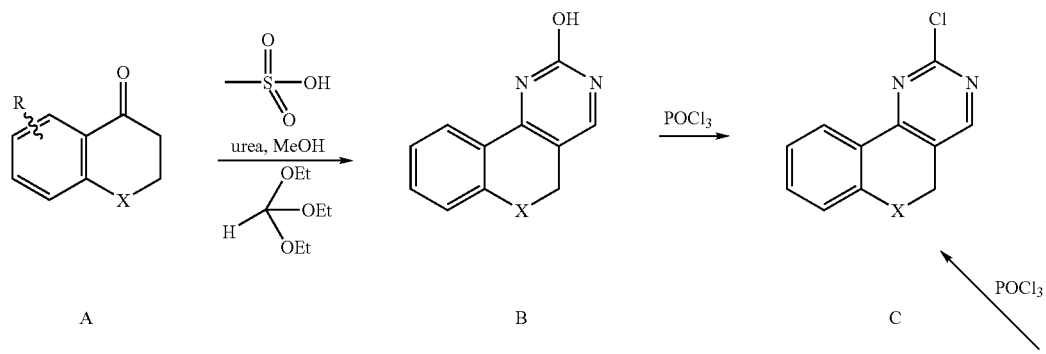

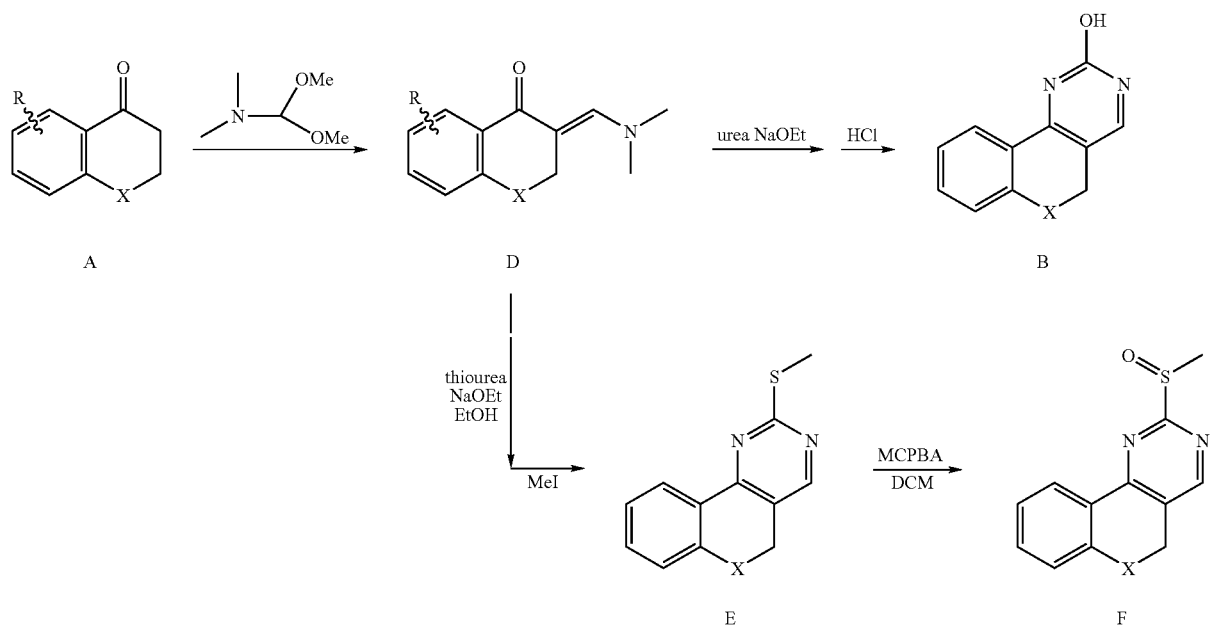

SCHEME 3-3

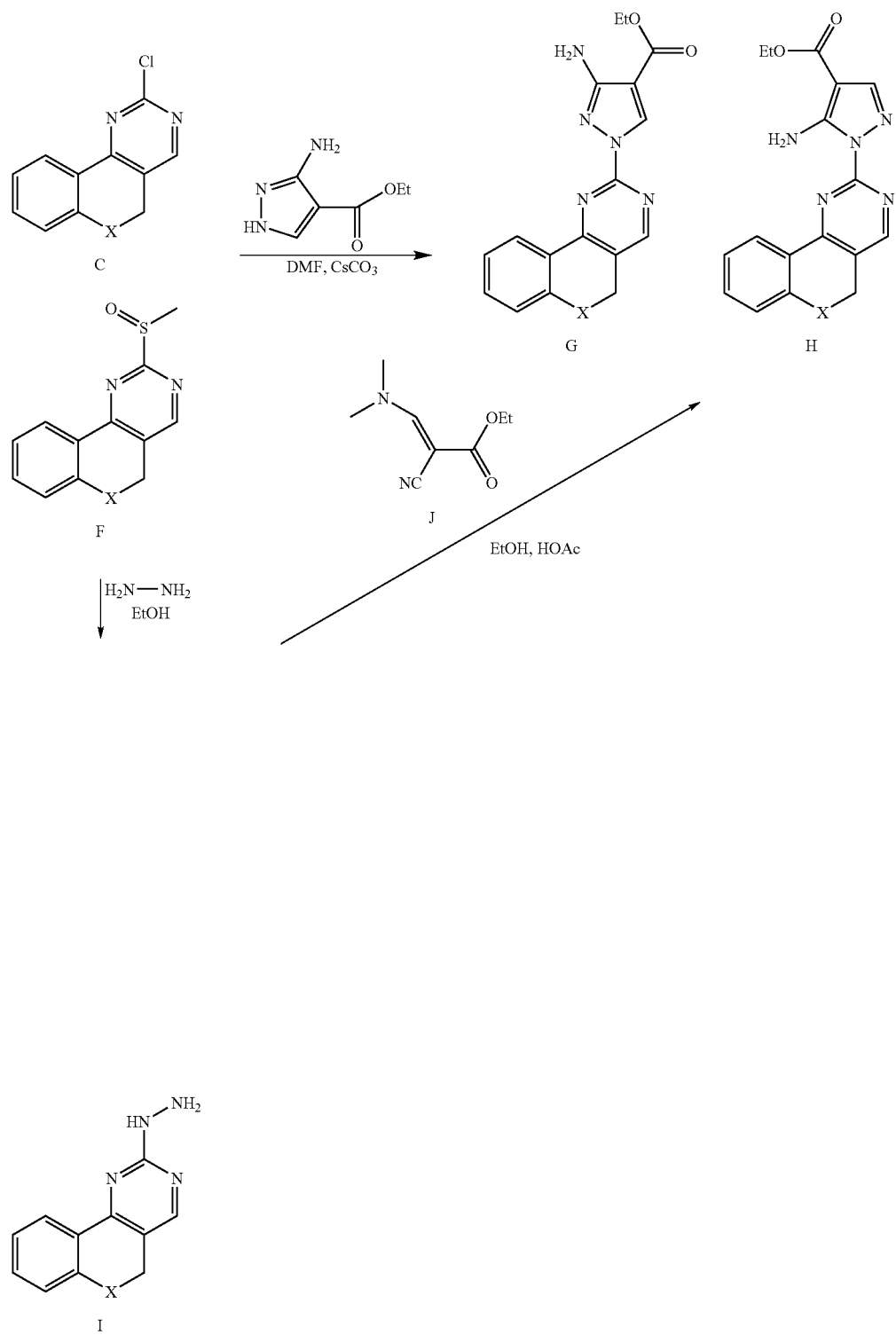

Compound C or D from SCHEME 1 may be reacted with an aminopyrazole in a solvent such as DMF with a base like cesium carbonate to afford an approximate 7:3 mixture of compounds G and H. These may be separately isolated via crystallization or chromatograpy or trituration with solvents such as ethyl acetate or ethanol. Alternatively compound H may be prepared by reaction of compound C or D with hydrazine in an alcohol to afford intermediate I which can then be reacted with compound J, prepared from reaction of the cyano acetate and DMFDMA, in a solvent like ethanol and an acid like acetic acid to give compound H.

SCHEME 3

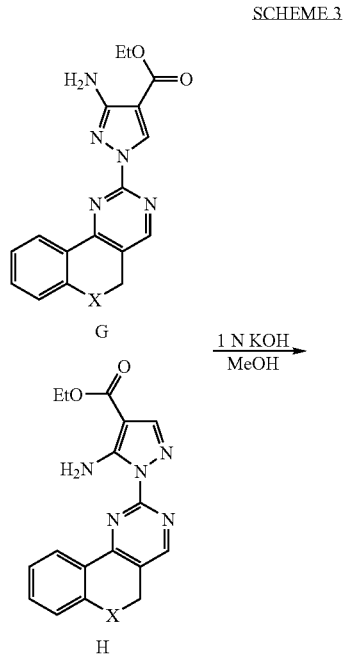

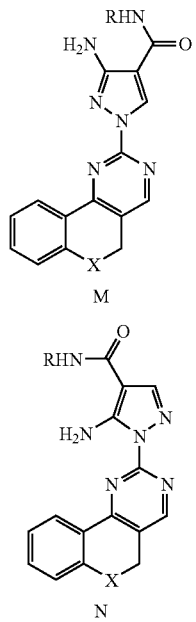

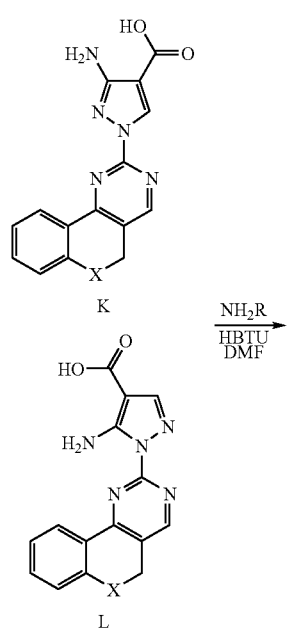

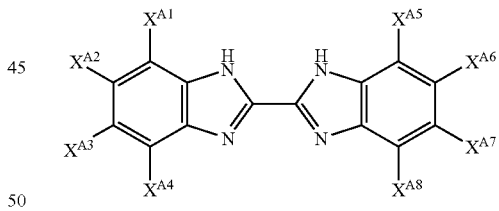

Compounds G and H may separately be treated with a hydroxide source such as aqueous potassium hydroxide and methanol to yield the respective acids K and L. Acids K and L may separately be treated in a solvent such as DMF and an organic base such as DIPEA with a coupling agent such as HBTU or BOP for example to yield amides M and N.

Exemplary compounds according to formula (3) and methods of their preparation are described in detail in the examples below.

5.2.4 Compounds According to Formula (4)

In certain embodiments, the present invention provides compounds of formula (4) that are represented in formula (4a):

Formula (4a)

The compounds can also be depicted in their respective "keto" form, which under certain conditions may predominate over the corresponding "enol" form. However, all possible tautomers and stereoisomers (such as for example, but not limited to: E and Z, (trans and cis) are incorporated herein.

In formula 4a, $X^{A1}$ though $X^{A4}$ are as described in formula (4), above.

In formula 4a, each $X^{A5}$ through $X^{A8}$ is independently selected is independently selected from hydrogen, lower alkyl, trifluoromethyl, hydroxy, lower alkoxy, trifluoromethoxy, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, heterocyclyl, cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl), all optionally substituted by groups selected from hydroxy, lower alkoxy, primary, secondary, or tertiary amino and also the following:


In formula 4a, $R^{20}$ is selected from:

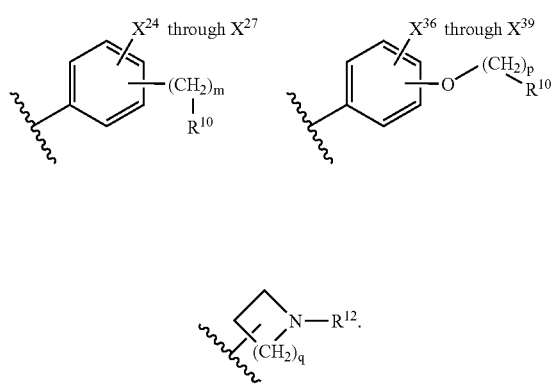

In formula 4a, $X^{24}$ through $X^{27}$, $X^{36}$ through $X^{39}$, $R^{10}$, $R^{12}$, $R^{18}$, m, p and q are as described for formula (4), above.

In certain embodiments, the present invention provides compounds of formula (4) that are represented in formula (4b):

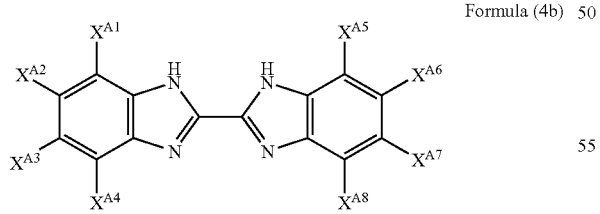

Formula (4b)

In formula (4b), $X^{A1}$ or $X^{A2}$ are independently selected from hydrogen, halogen, alkoxy, alkyl, optionally substituted aryl or heteroaryl; $X^{A3}$ and $X^{A4}$ are hydrogen; $X^{A5}$ or $X^{A6}$ are independently hydrogen or lower alkyl, halogen, alkoxy, heterocycloalkyl (such as piperazinyl or morpholinyl), —(C=O)—NH$_2$, —(C=O)—NH-(lower alkyl, or lower alkenyl, or lower alkynyl, or lower cycloalkyl, or heterocyclyl, or heterocycloalkyl), or the groups:


In formula (4b), $R^{20}$ is selected from the following:

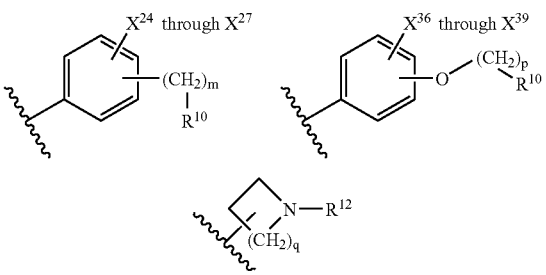

In formula (4b), $X^{24}$ through $X^{27}$, $X^{36}$ through $X^{39}$, $R^{10}$, $R^{12}$, $R^{18}$, m, p and q are as described for formula (4), above.

Exemplary compounds according to formula 4 include, but are not limited to, the following:

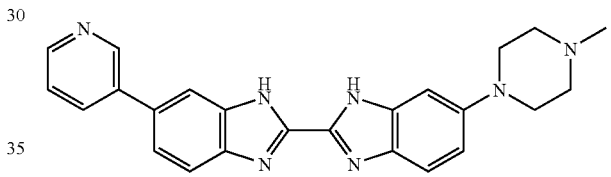

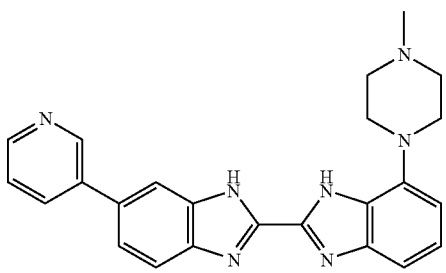

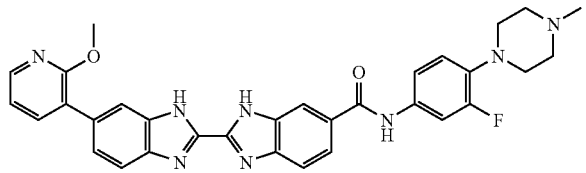

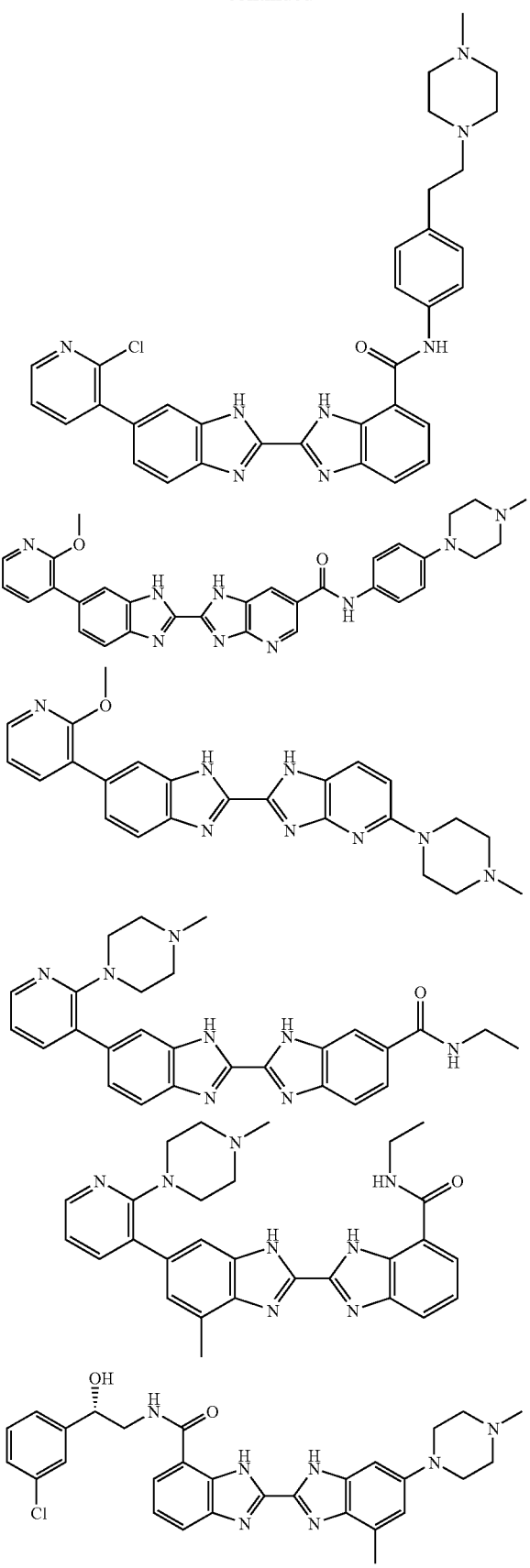


Further exemplary compounds according to formula (4) are described in the below.

5.2.4.1 Preparation of Compounds According to Formula (4)

Compounds according to formula (4), (4a) and (4b) can be prepared according to any method apparent to those of skill in the art. The present invention provides the following exemplary methods for their preparation.

Compounds of formula 4 can be prepared by several routes, such as those outlined in scheme 4-1.

Scheme 4-1

Method 1

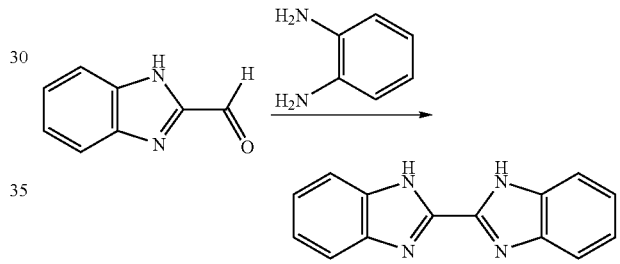

Method 2

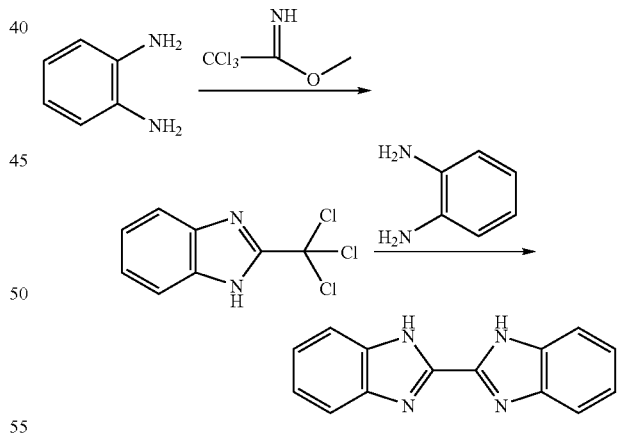

Method 1.

Treatment of an aromatic, or heterocyclic o-diamine (such as an o-phenylenediamine derivative or analog) with the corresponding 2-benzimidazolecarboxaldehyde affords the benzimidazolyl-benzimidazole. The reaction is generally performed in an organic solvent, such as acetonitrile, DMF, DMA, or methanol, ethanol, isopropyl alcohol and the like at temperatures between 0° C. to 120° C., in certain embodiments at 20 to 80° C. The reaction is performed under aerobic conditions, or in the presence of sodium bisulfite or benzoquinone. The product is then isolated by concentration of the reaction mixture in vacuo. The product may be purified if desired by column chromatography or recrystallization. This is a general reaction and many modification of this procedure are known. The benzimidazole carboxaldehydes are either commercial products, or are prepared according to literature procedures, or other procedures commonly known in the art.

Method 2.

Treatment of an aromatic, or heterocyclic o-diamine (such as an o-phenylenediamine derivative or analog) with methyl trichloroacetimidate in a suitable solvent, such as dichloromethane, 1,2-dichloroethane, glacial acetic acid, chloroform, or their mixture at minus 78° C. to 100° C., in certain embodiments minus 10 to 60° C. produces the desired 2-trichloromethyl benzimidazole intermediate. When the reaction is complete, it is worked up by evaporation, or in the case of acetic acid solvent by precipitation of the product by pouring to water and filtration, or extraction of the product by an organic solvent, such as chloroform. The desired 2-trichloromethyl benzimidazole product can optionally be purified by recrystallization or column chromatography.

The 2-trichloromethylbenzimidazole intermediates (or their heterocyclic analogs) react with aromatic, or heterocyclic o-diamines, (such as o-phenylenediamine derivatives or analogs), providing the desired benzimidazolyl-benzimidazole derivatives or analogs.

Exemplary compounds according to formula (4) and methods of their preparation are described in detail in the examples below.

5.2.5 Formula (5)

5.2.5.1 Compounds According to Formula 5

In certain embodiments, the present invention provides compounds of formula (5) that are represented in formula (5a):

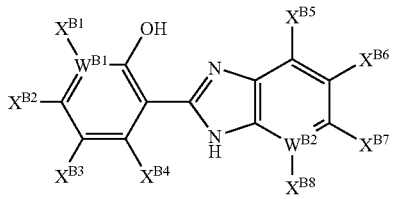

Formula (5a)

The compounds can also be depicted in their respective "keto" form, which under certain conditions may predominate over the corresponding "enol" form. However, all possible tautomers and stereoisomers (such as for example, but not limited to: E and Z, (trans and cis) are incorporated herein.

In formula (5a), $W^{B1}$, $W^{B2}$, $X^{B1}$, $X^{B2}$, $X^{B3}$, $X^{B4}$, $X^{B5}$, $X^{B6}$, $X^{B7}$ ad $X^{B8}$ as described for formula (5), above, with the following exceptions.

In formula (5a), one of the substituents $X^{B5}$ through $X^{B8}$ can be the following group:

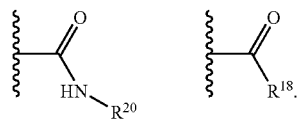

In formula (5a), each $W^1$, $W^2$, $W^3$, $X^{24}$ through $X^{39}$, $R^{18}$, $R^{19}$, $R^{20}$, m, n, o, p, q, r, s, t, u, v, is as described for formula (5), above.

In certain embodiments, the present invention provides compounds of formula (5) that are represented in formula (5b):

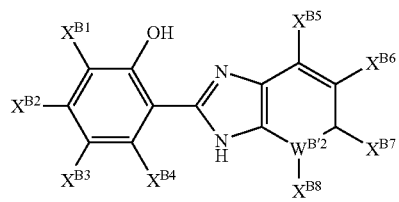

Formula (5b)

In formula (5b), $W^{B2}$ is a carbon atom or a nitrogen atom. If $W^{B2}$ is a nitrogen atom, $X^{B8}$ is absent.

In formula (5b), each $X^{B1}$, $X^{B2}$ and $X^{B4}$ is independently selected from hydrogen, hydroxy, halogen, lower alkyl, lower alkoxy, trifluoromethyl, trifluoromethoxy, nitro, cyano, optionally substituted aryl or heteroaryl, aryloxy or heteroaryloxy, arylamino or heteroarylamino (substituted by one or more groups selected from lower alkyl, hydroxy, halogen, lower alkoxy, trifluoromethyl, trifluoromethoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, optionally substituted heterocyclyl or cycloalkyl, optionally substituted heterocyclylalkyl, heteroalkyl).

In formula (5b), $X^{B3}$ is selected from hydrogen, halogen, alkyl, alkenyl, alkynyl, alkoxy, cycloalkoxy, cycloalkyl, heterocycloalkyl, optionally substituted (aryl, heteroaryl, arylalkyl, heteroarylalkyl, aryloxy, heteroaryloxy, arylalkoxy, heteroarylalkoxy, arylthio, heteroarylthio, arylsulfoxy, heteroarylsulfoxy, arylsulfonyl, heteroarylsulfonyl, arylsulfonamido, heteroarylsulfonamido, arylaminosulfonyl, heteroarylaminosulfonyl), by substituents selected from halogen, hydroxy, amino, cyano, nitro, carboxamido, sulfonamido, alkoxy, lower-alkylamino, di-lower-alkylamino, cycloalkyl, cycloalkylalkyl, cycloalkoxy, cycloalkylalkoxy, trifluoromethyl, trifluoromethoxy, methylenedioxy, ethylenedioxy, methanesulfonyl, trifluoromethanesulfonyl, dialkylaminoalkyl, di-lower-alkylaminoalkyl, dialkylaminoalkoxy, heterocyclyl, heteroalkyl, heterocyclylalkyl.

In formula (5b), each $X^{B5}$, $X^{B7}$ and $X^{B8}$ is independently selected from hydrogen, halogen, lower alkyl, lower alkoxy, hydroxy, nitro, cyano, carboxamido, sulfonamido, azido, trifluoromethyl or trifluoromethoxy.

In formula (5b), $X^{B6}$ is selected from nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-S-oxide-methyl, thiomorpholino-S,S-dioxide-methyl, pyrrolidinomethyl, piperidinoethyl, azetidinomethyl, all optionally substituted by groups selected from hydroxy, lower alkoxy, primary, secondary, or tertiary amino or lower alkyl) and the following:

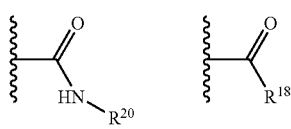
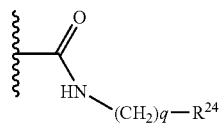

In formula (5a), each $W^1$, $W^2$, $W^3$, $X^{24}$ through $X^{39}$, $R^{18}$, $R^{19}$, $R^{20}$, m, n, o, p, q, r, s, t, u, v, is as described for formula (5), above.

In particular embodiments according to formula (5), (5a) or (5b), $X^{B6}$ is according to the following:

wherein $R^{24}$ is selected from optionally substituted alkyl amino, optionally substituted dialkylamino, and optionally substituted heteroaryl, for example, optionally substituted triazole, optionally substituted imidazole, and optionally substituted pyrazole. In certain embodiments, $R^{24}$ is selected from dimethylamine, diethylamine, optionally substituted, triazole, imidazole and pyrazole. In certain embodiments, $R^{24}$ is selected from diethylamine, 5-pyrid-3-yl-triazole, 4-imidazole and 4-pyrazole.

Specific embodiments of compounds of formulas (5), (5a) and (5b) include, but are not limited to the following compounds that were prepared according to the methods described herein:

| MOLSTRUCTURE | MW (M + 1) |
|---|---|
| | 361.4 |
| | 457.5 |
| | 562.6 |

-continued
| MOLSTRUCTURE | MW (M + 1) |
|---|---|
| 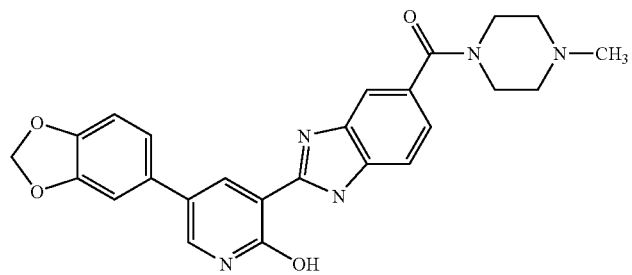 [SMILES: CN1CCN(C(=O)c2ccc3[nH]c(-c4cc(-c5ccc6c(c5)OCO6)cnc4O)nc3c2)CC1] | 458.5 |
| 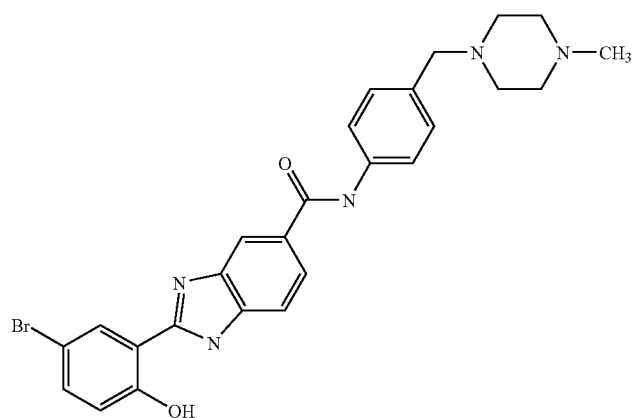 [SMILES: CN1CCN(Cc2ccc(NC(=O)c3ccc4[nH]c(-c5cc(Br)ccc5O)nc4c3)cc2)CC1] | 521.4 |
| 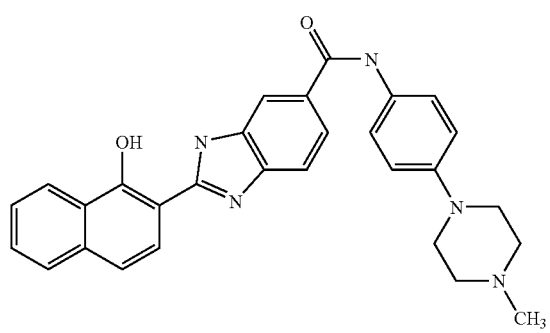 [SMILES: CN1CCN(c2ccc(NC(=O)c3ccc4nc(-c5ccc6ccccc6c5O)[nH]c4c3)cc2)CC1] | 478.6 |
| 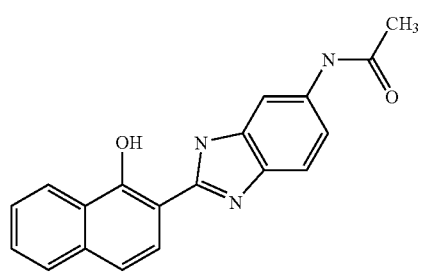 [SMILES: CC(=O)Nc1ccc2nc(-c3ccc4ccccc4c3O)[nH]c2c1] | 318.4 |

| MOLSTRUCTURE | MW (M + 1) |
|---|---|
| 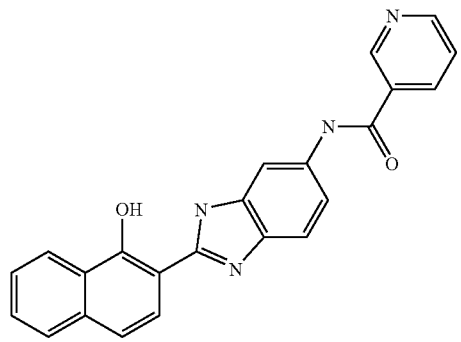 [SMILES: O=C(Nc1ccc2nc(-c3ccc4ccccc4c3O)[nH]c2c1)c1cccnc1] | 381.4 |
| 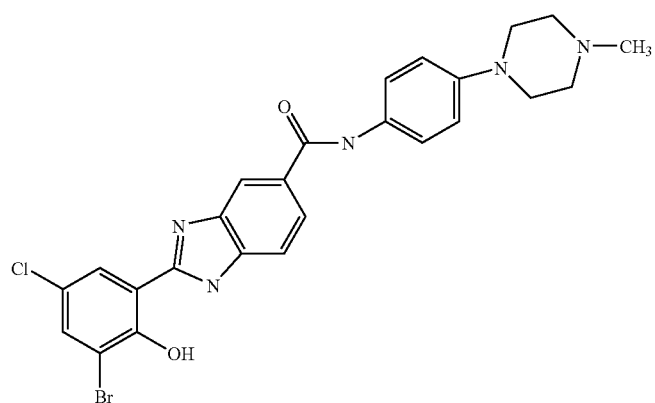 [SMILES: CN1CCN(c2ccc(NC(=O)c3ccc4[nH]c(-c5cc(Cl)cc(Br)c5O)nc4c3)cc2)CC1] | 541.9 |
| 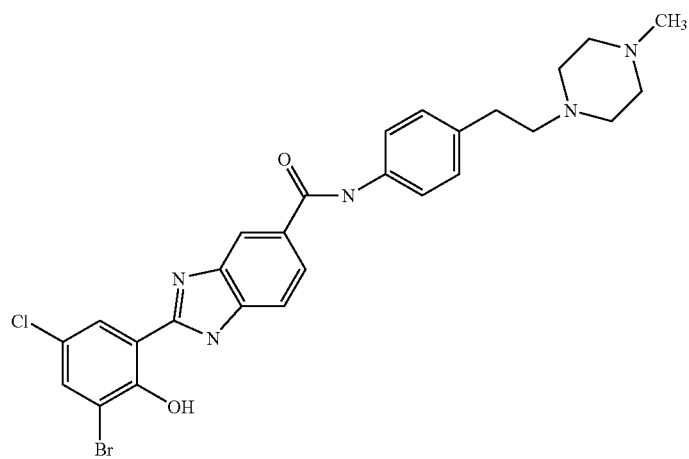 [SMILES: CN1CCN(CCc2ccc(NC(=O)c3ccc4[nH]c(-c5cc(Cl)cc(Br)c5O)nc4c3)cc2)CC1] | 569.9 |
| 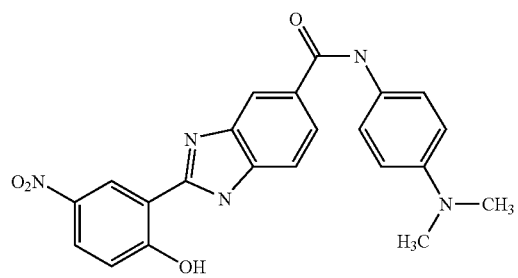 [SMILES: CN(C)c1ccc(NC(=O)c2ccc3[nH]c(-c4cc([N+](=O)[O-])ccc4O)nc3c2)cc1] | 418.4 |

| MOLSTRUCTURE | MW (M + 1) |
|---|---|
| 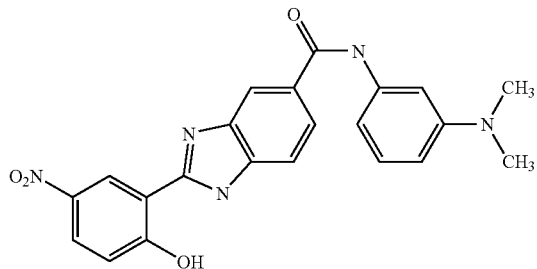 [SMILES: CN(C)c1cccc(NC(=O)c2ccc3[nH]c(-c4cc([N+](=O)[O-])ccc4O)nc3c2)c1] | 418.4 |
| 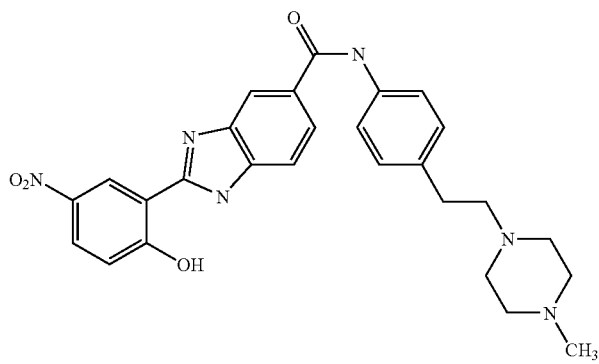 [SMILES: CN1CCN(CCc2ccc(NC(=O)c3ccc4[nH]c(-c5cc([N+](=O)[O-])ccc5O)nc4c3)cc2)CC1] | 501.6 |
| 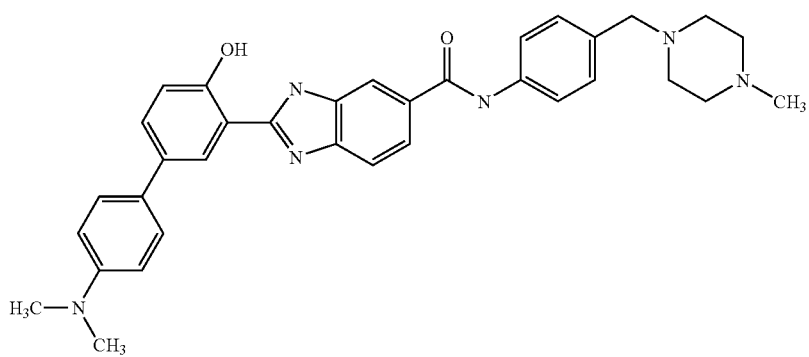 | 561.7 |
| 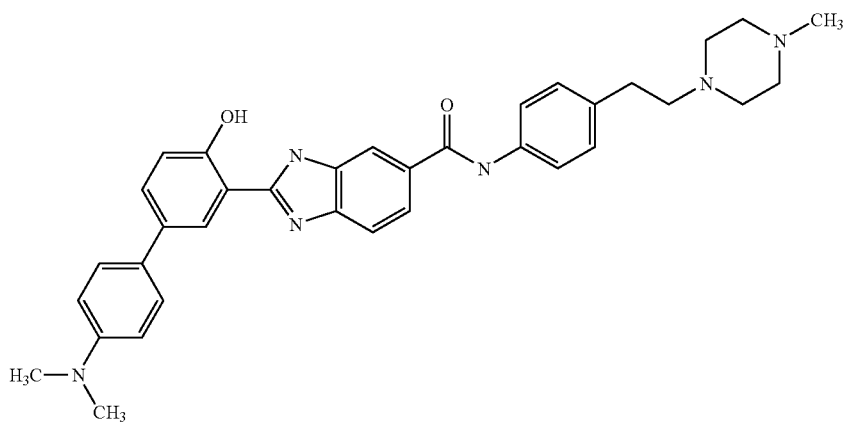 | 575.7 |

| MOLSTRUCTURE | MW (M + 1) |
|---|---|
| 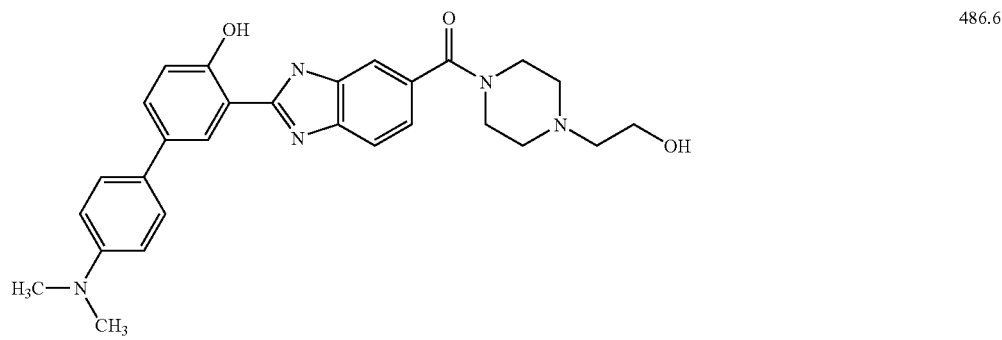 | 486.6 |
| 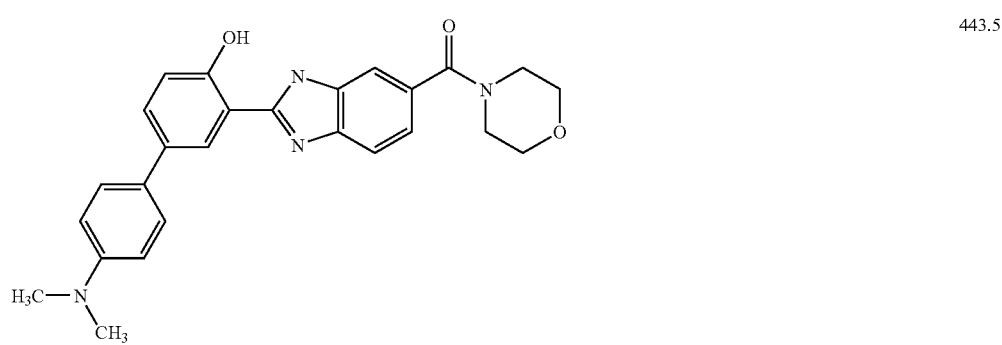 | 443.5 |
| 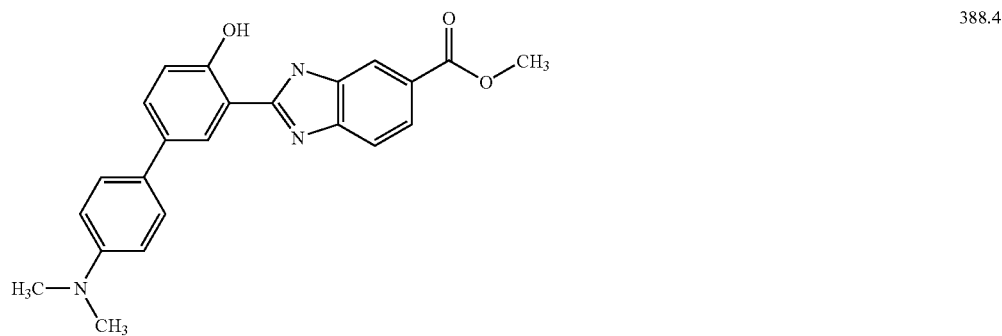 | 388.4 |
| 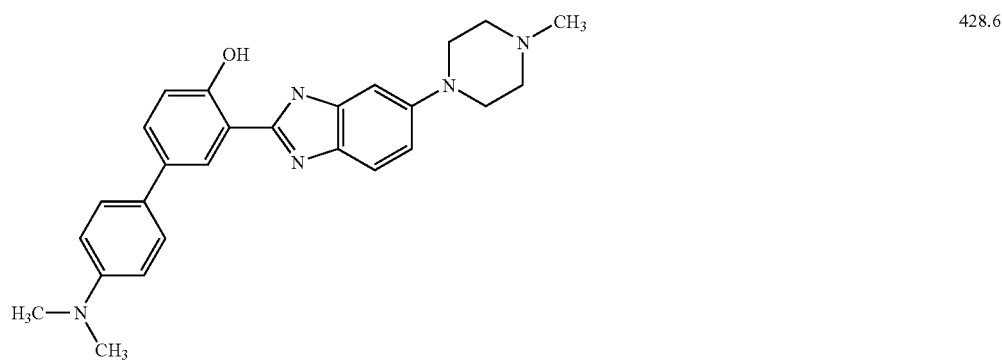 | 428.6 |

-continued
| MOLSTRUCTURE | MW (M + 1) |
|---|---|
| 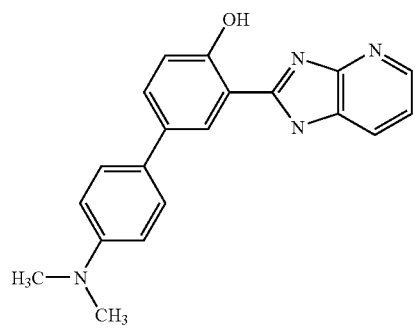 [SMILES: CN(C)c1ccc(-c2ccc(O)c(-c3nc4ncccc4[nH]3)c2)cc1] | 331.4 |
| 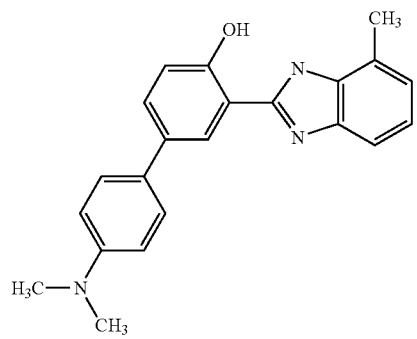 [SMILES: Cc1cccc2nc(-c3cc(-c4ccc(N(C)C)cc4)ccc3O)[nH]c12] | 344.4 |
| 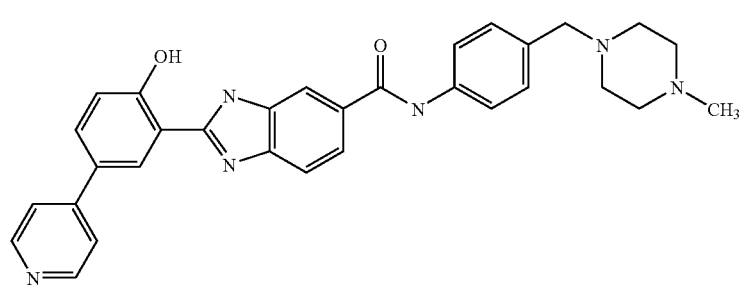 [SMILES: CN1CCN(Cc2ccc(NC(=O)c3ccc4nc(-c5cc(-c6ccncc6)ccc5O)[nH]c4c3)cc2)CC1] | 519.6 |
| 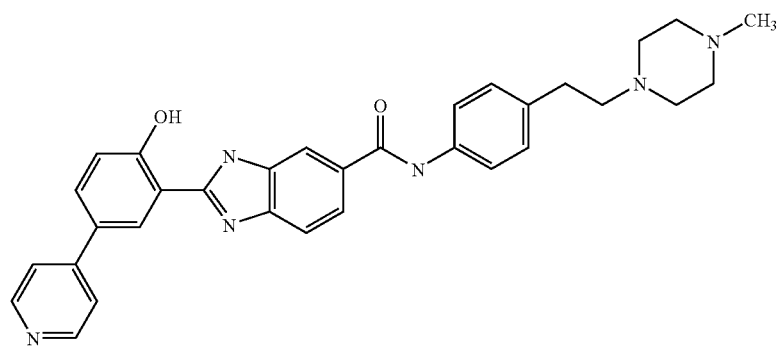 [SMILES: CN1CCN(CCc2ccc(NC(=O)c3ccc4nc(-c5cc(-c6ccncc6)ccc5O)[nH]c4c3)cc2)CC1] | 533.7 |
| 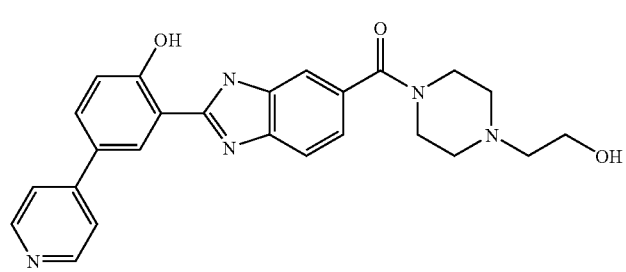 [SMILES: O=C(c1ccc2nc(-c3cc(-c4ccncc4)ccc3O)[nH]c2c1)N1CCN(CCO)CC1] | 444.5 |

-continued
| MOLSTRUCTURE | MW (M + 1) |
|---|---|
| 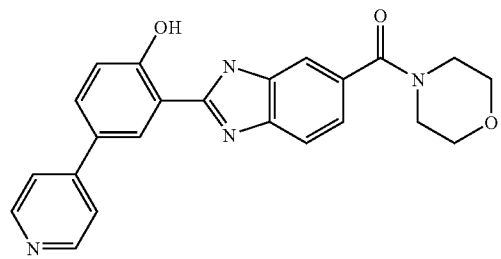 [SMILES: O=C(c1ccc2nc(-c3cc(-c4ccncc4)ccc3O)[nH]c2c1)N1CCOCC1] | 401.4 |
| 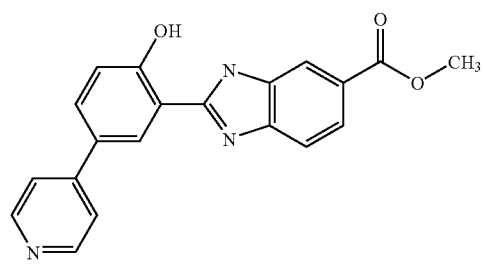 [SMILES: COC(=O)c1ccc2nc(-c3cc(-c4ccncc4)ccc3O)[nH]c2c1] | 346.4 |
| 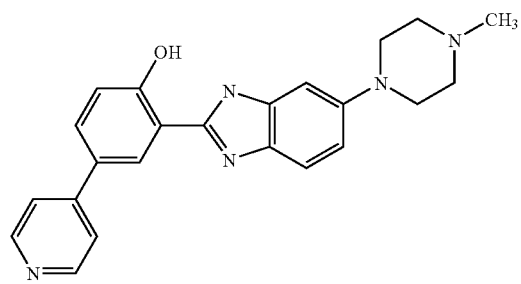 [SMILES: CN1CCN(c2ccc3nc(-c4cc(-c5ccncc5)ccc4O)[nH]c3c2)CC1] | 386.5 |
| 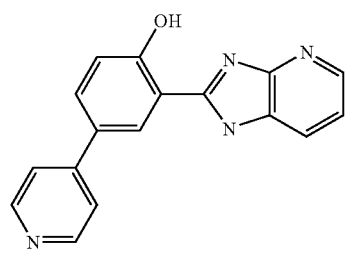 [SMILES: Oc1ccc(-c2ccncc2)cc1-c1nc2ncccc2[nH]1] | 289.3 |
| 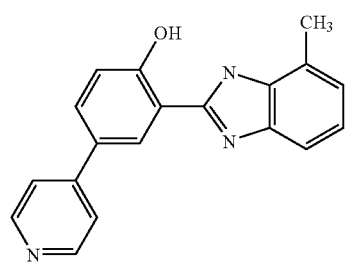 [SMILES: Cc1cccc2nc(-c3cc(-c4ccncc4)ccc3O)[nH]c12] | 302.4 |

-continued

| MOLSTRUCTURE | MW (M + 1) |
|---|---|
| | 553.1 |
| | 567.1 |
| | 478.0 |
| | 434.9 |
| | 379.8 |

-continued
| MOLSTRUCTURE | MW (M + 1) |
|---|---|
| 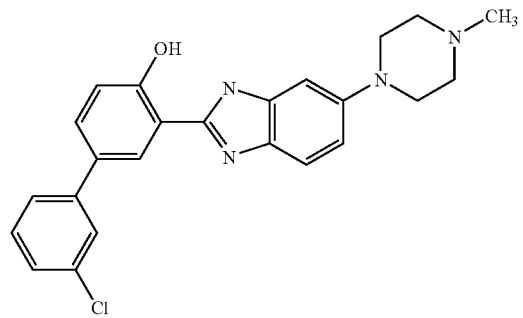 [SMILES: CN1CCN(c2ccc3nc(-c4cc(-c5cccc(Cl)c5)ccc4O)[nH]c3c2)CC1] | 419.9 |
| 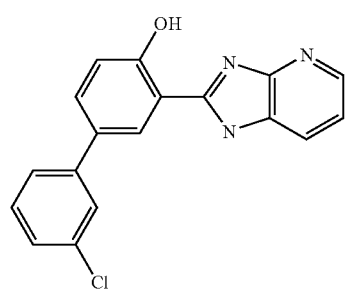 [SMILES: Oc1ccc(-c2cccc(Cl)c2)cc1-c1nc2ncccc2[nH]1] | 322.8 |
| 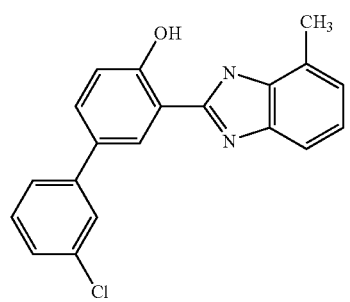 [SMILES: Cc1cccc2nc(-c3cc(-c4cccc(Cl)c4)ccc3O)[nH]c12] | 335.8 |
| 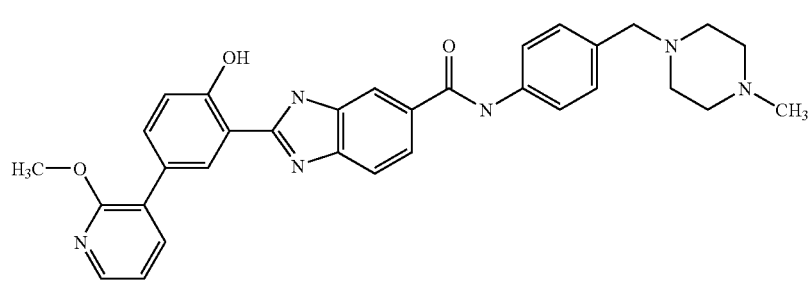 | 549.7 |
| 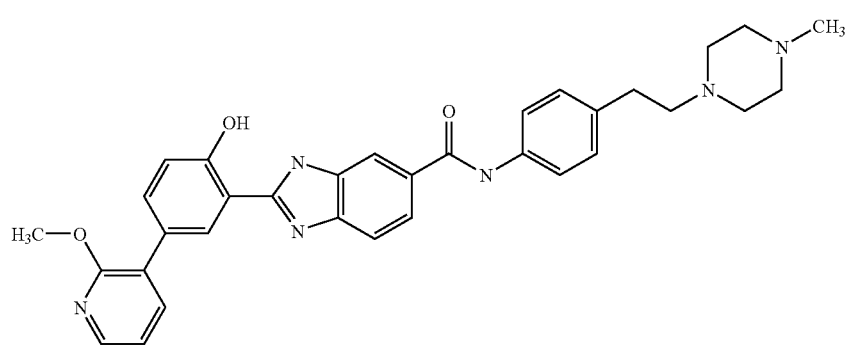 | 563.7 |

-continued

| MOLSTRUCTURE | MW (M + 1) |
|---|---|
| | 474.5 |
| | 431.5 |
| | 376.4 |
| | 416.5 |
| | 319.3 |
| | 332.4 |

| MOLSTRUCTURE | MW (M + 1) |
|---|---|
| 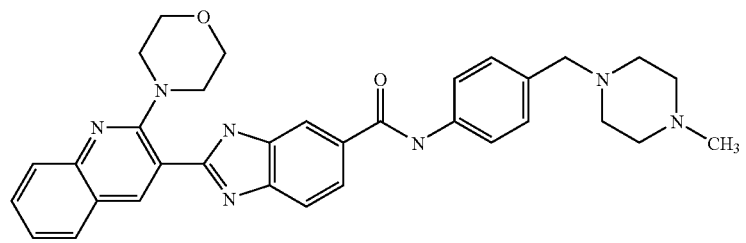 [SMILES: CN1CCN(Cc2ccc(NC(=O)c3ccc4nc(-c5cc6ccccc6nc5N5CCOCC5)[nH]c4c3)cc2)CC1] | 1.0 |
| 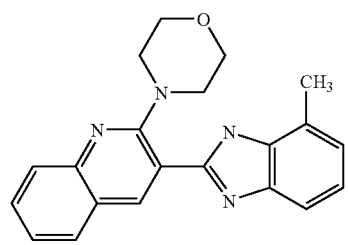 [SMILES: Cc1cccc2nc(-c3cc4ccccc4nc3N3CCOCC3)[nH]c12] | 345.4 |
| 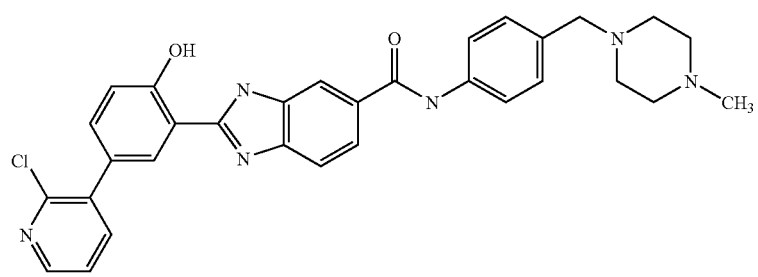 [SMILES: CN1CCN(Cc2ccc(NC(=O)c3ccc4nc(-c5cc(-c6cccnc6Cl)ccc5O)[nH]c4c3)cc2)CC1] | 554.1 |
| 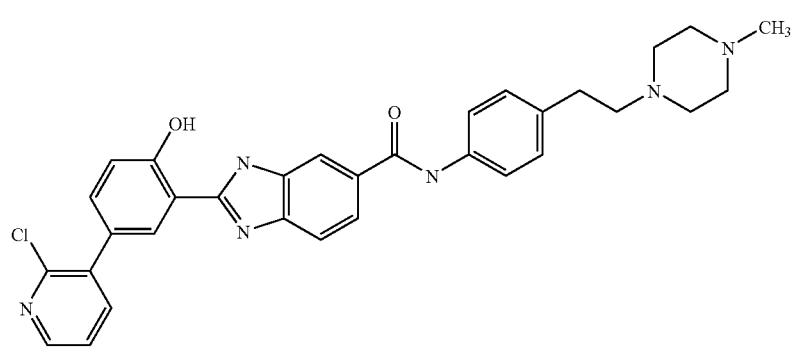 [SMILES: CN1CCN(CCc2ccc(NC(=O)c3ccc4nc(-c5cc(-c6cccnc6Cl)ccc5O)[nH]c4c3)cc2)CC1] | 568.1 |
| 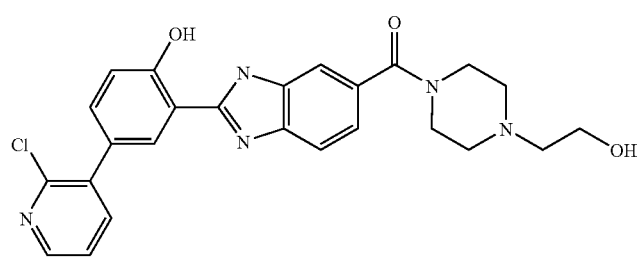 [SMILES: O=C(c1ccc2nc(-c3cc(-c4cccnc4Cl)ccc3O)[nH]c2c1)N1CCN(CCO)CC1] | 479.0 |

-continued
| MOLSTRUCTURE | MW (M + 1) |
|---|---|
| 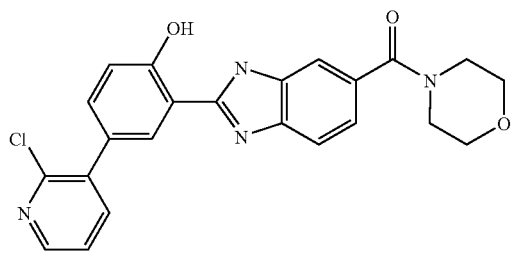 [SMILES: O=C(c1ccc2nc(-c3cc(-c4cccnc4Cl)ccc3O)[nH]c2c1)N1CCOCC1] | 435.9 |
| 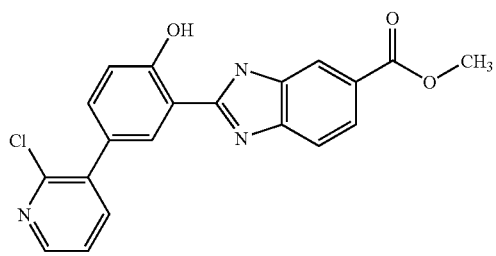 [SMILES: COC(=O)c1ccc2nc(-c3cc(-c4cccnc4Cl)ccc3O)[nH]c2c1] | 380.8 |
| 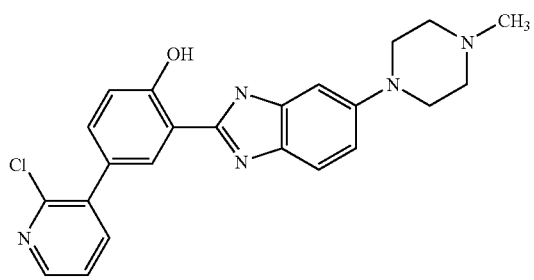 [SMILES: CN1CCN(c2ccc3nc(-c4cc(-c5cccnc5Cl)ccc4O)[nH]c3c2)CC1] | 420.9 |
| 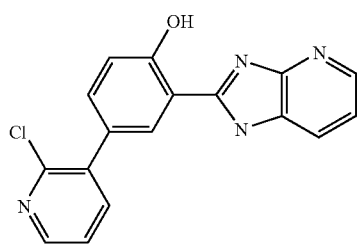 [SMILES: Oc1ccc(-c2cccnc2Cl)cc1-c1nc2ncccc2[nH]1] | 323.8 |
| 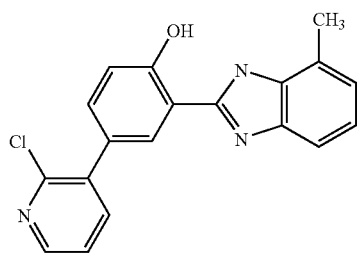 [SMILES: Cc1cccc2nc(-c3cc(-c4cccnc4Cl)ccc3O)[nH]c12] | 336.8 |
| 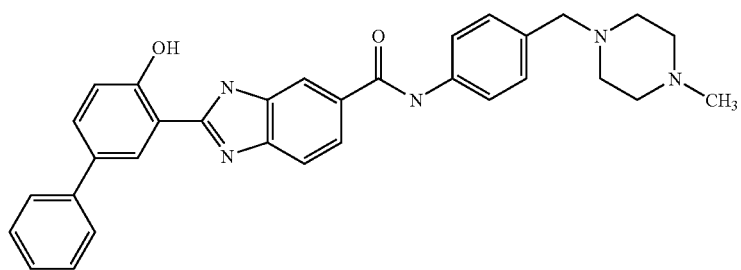 [SMILES: CN1CCN(Cc2ccc(NC(=O)c3ccc4nc(-c5cc(-c6ccccc6)ccc5O)[nH]c4c3)cc2)CC1] | 518.6 |

| MOLSTRUCTURE | MW (M + 1) |
|---|---|
| 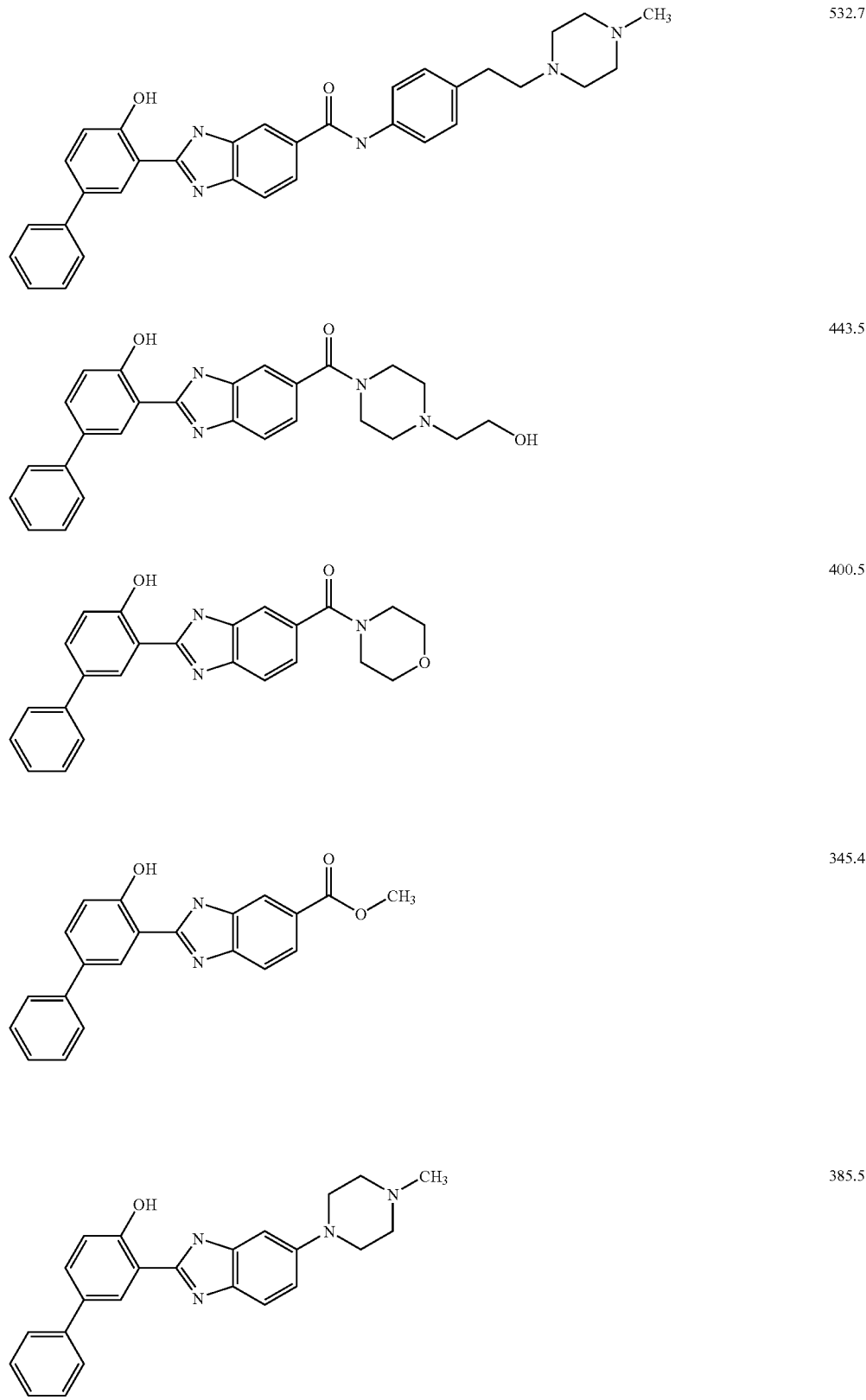 | 532.7 |
| | 443.5 |
| | 400.5 |
| | 345.4 |
| | 385.5 |

-continued
| MOLSTRUCTURE | MW (M + 1) |
|---|---|
| 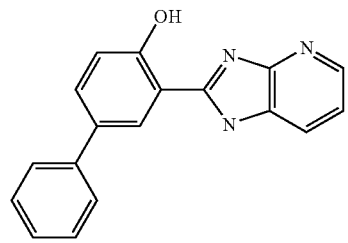 [SMILES: Oc1ccc(-c2ccccc2)cc1-c1nc2ncccc2[nH]1] | 288.3 |
| 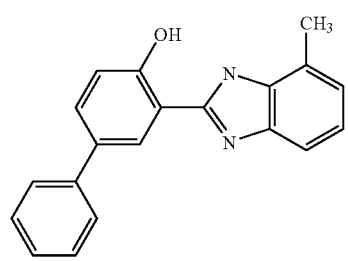 [SMILES: Cc1cccc2nc(-c3cc(-c4ccccc4)ccc3O)[nH]c12] | 301.4 |
| 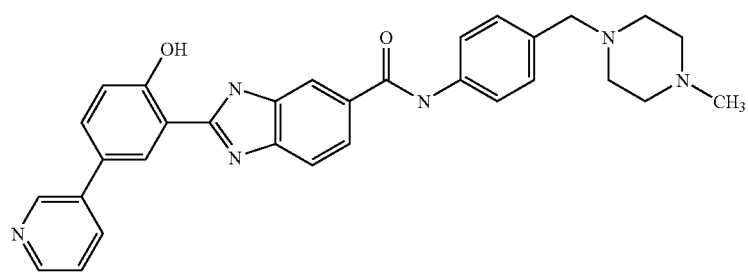 [SMILES: CN1CCN(Cc2ccc(NC(=O)c3ccc4nc(-c5cc(-c6cccnc6)ccc5O)[nH]c4c3)cc2)CC1] | 519.6 |
| 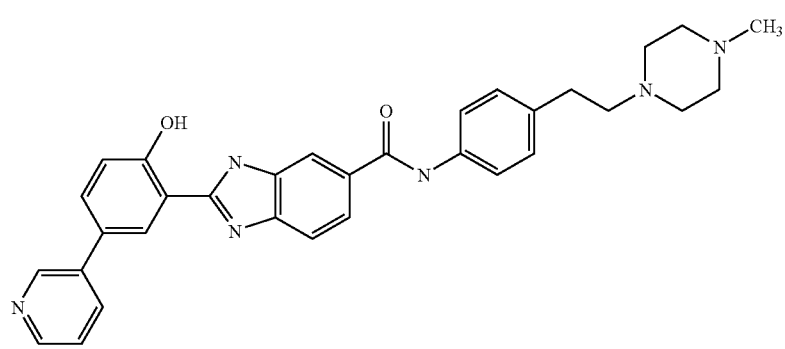 [SMILES: CN1CCN(CCc2ccc(NC(=O)c3ccc4nc(-c5cc(-c6cccnc6)ccc5O)[nH]c4c3)cc2)CC1] | 533.7 |
| 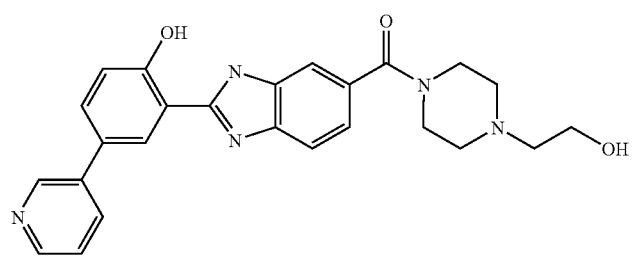 [SMILES: O=C(c1ccc2nc(-c3cc(-c4cccnc4)ccc3O)[nH]c2c1)N1CCN(CCO)CC1] | 444.5 |

| MOLSTRUCTURE | MW (M + 1) |
|---|---|
| 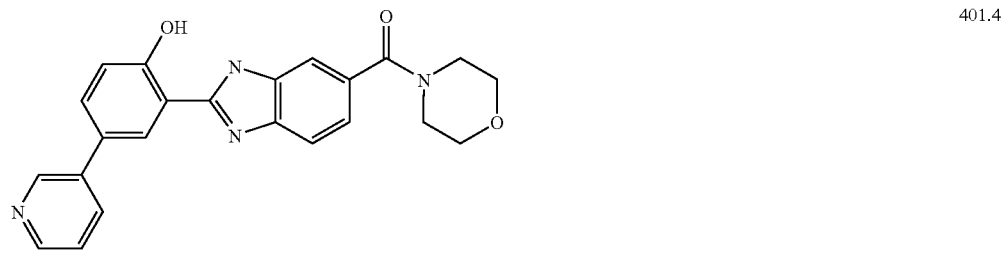 | 401.4 |
| 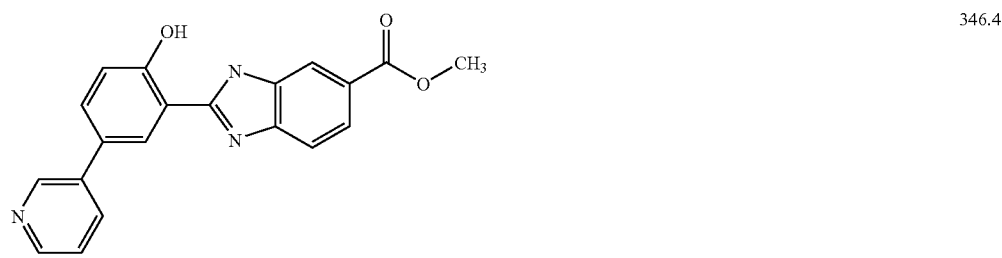 | 346.4 |
| 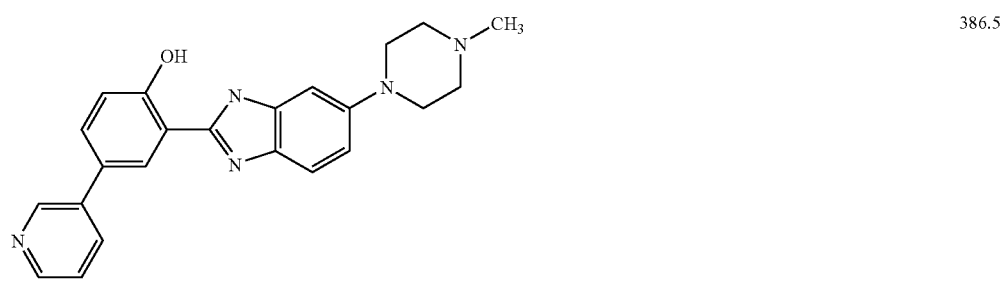 | 386.5 |
|  | 289.3 |
| 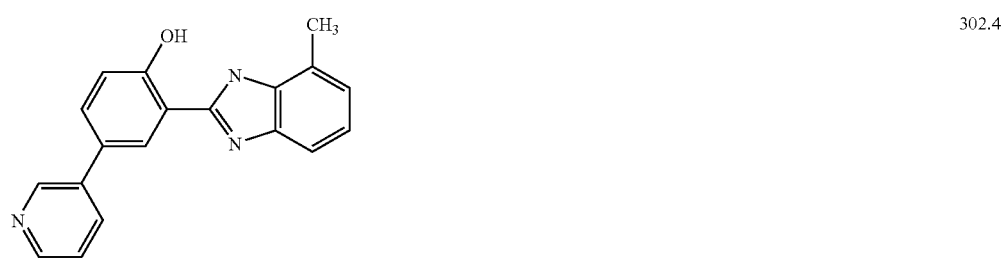 | 302.4 |

-continued
| MOLSTRUCTURE | MW (M + 1) |
|---|---|
| 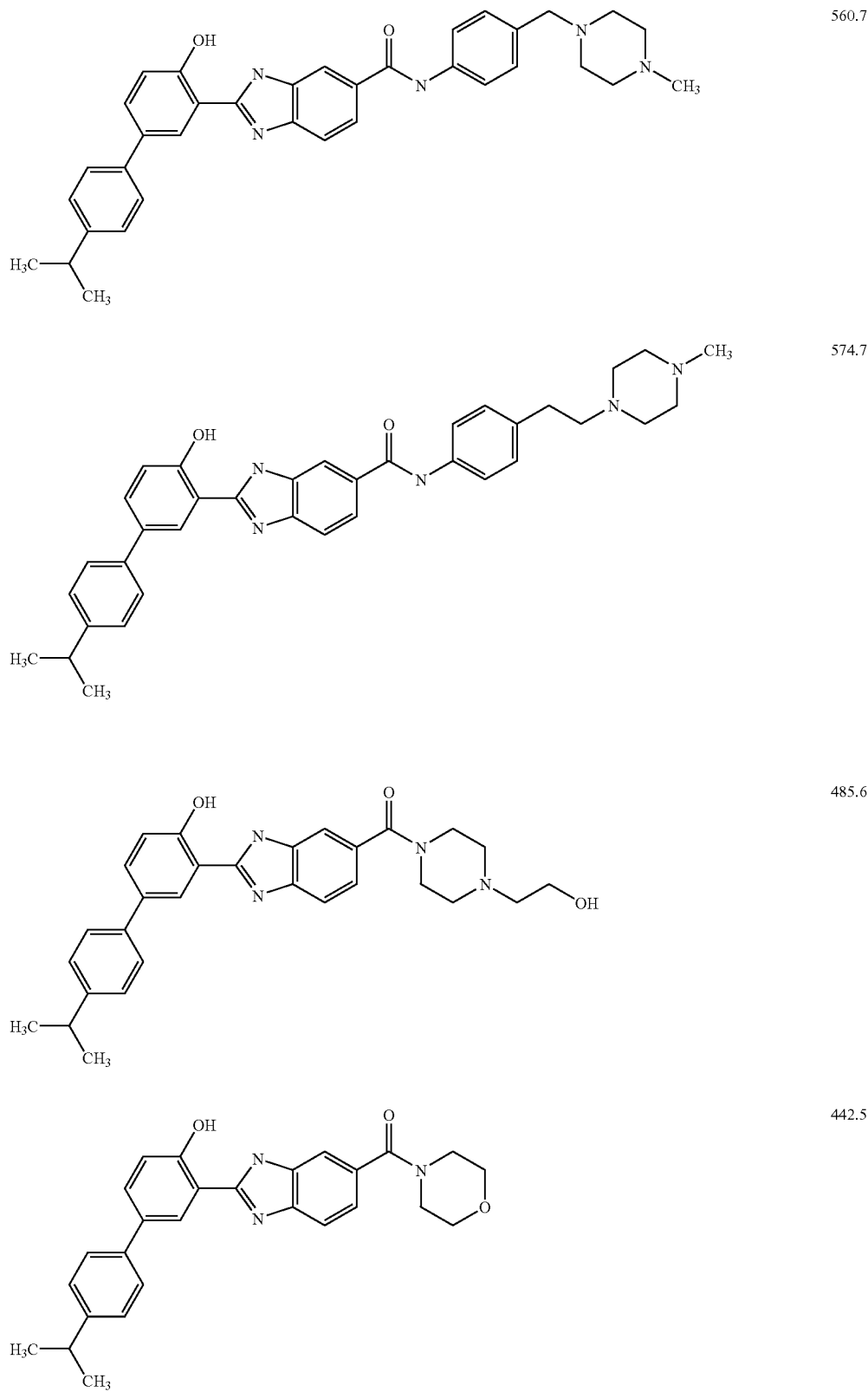 | 560.7 |
| | 574.7 |
| | 485.6 |
| | 442.5 |

-continued
| MOLSTRUCTURE | MW (M + 1) |
|---|---|
| 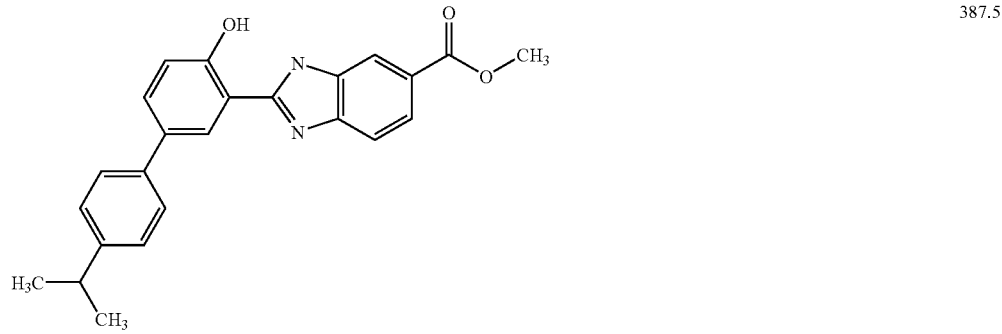 | 387.5 |
| 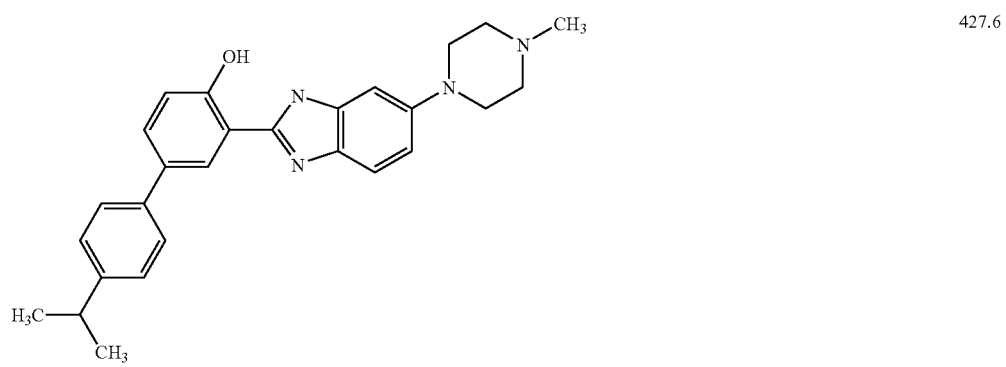 | 427.6 |
| 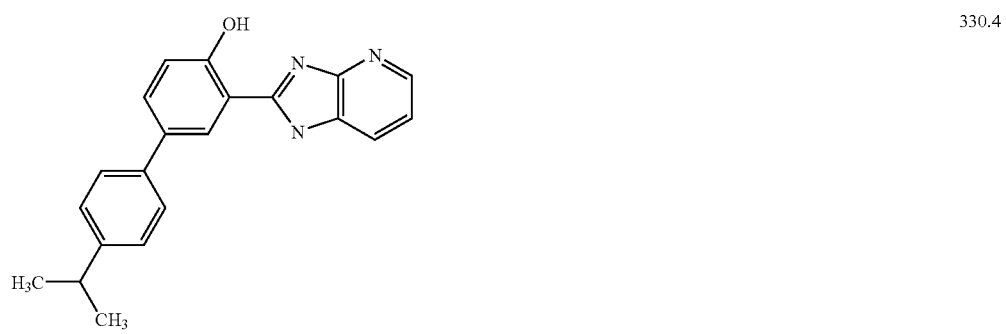 | 330.4 |
| 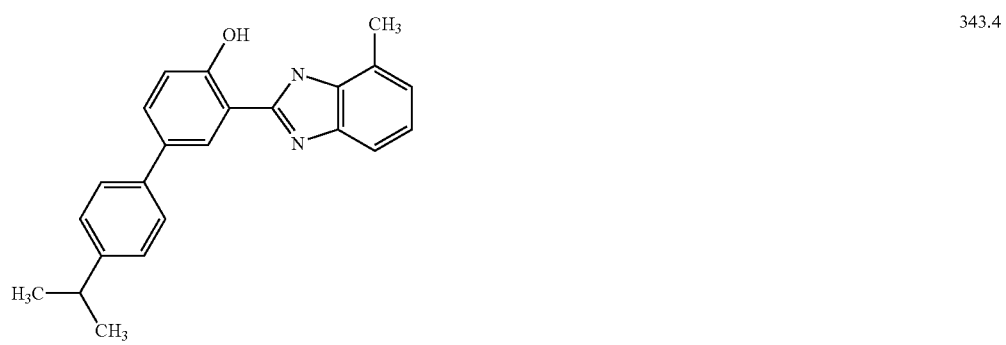 | 343.4 |

| MOLSTRUCTURE | MW (M + 1) |
|---|---|
| *(structure)* | 554.8 |
| *(structure)* | 568.8 |
| *(structure)* | 479.6 |
| *(structure)* | 436.6 |
| *(structure)* | 381.5 |
| *(structure)* | 421.6 |

-continued
| MOLSTRUCTURE | MW (M + 1) |
|---|---|
| 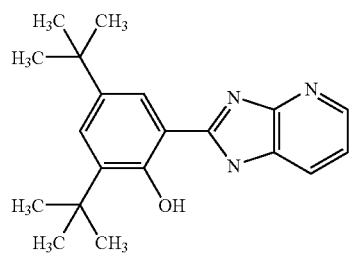 | 324.4 |
| 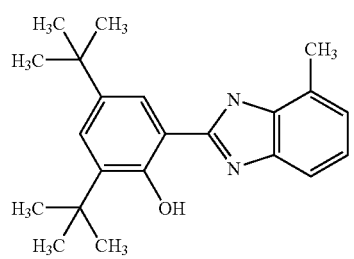 | 337.5 |
| 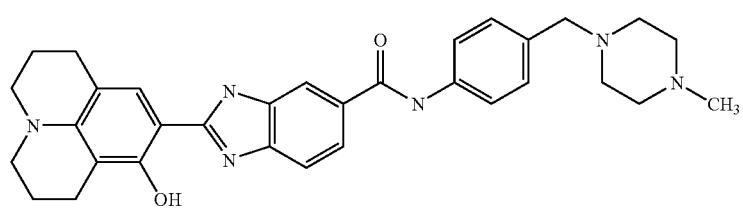 [SMILES: CN1CCN(Cc2ccc(NC(=O)c3ccc4nc(-c5cc6c7c(c5O)CCCN7CCC6)[nH]c4c3)cc2)CC1] | 537.7 |
| 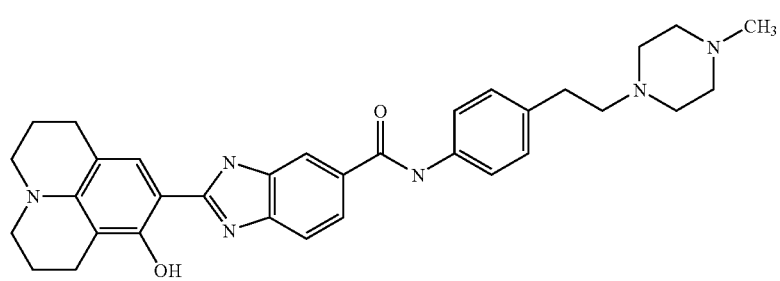 | 551.7 |
| 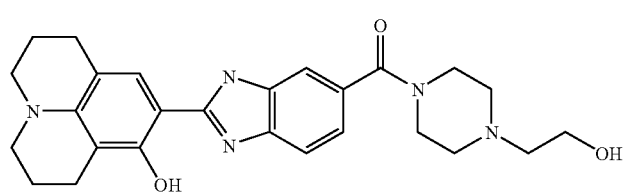 [SMILES: O=C(c1ccc2nc(-c3cc4c5c(c3O)CCCN5CCC4)[nH]c2c1)N1CCN(CCO)CC1] | 462.6 |
| 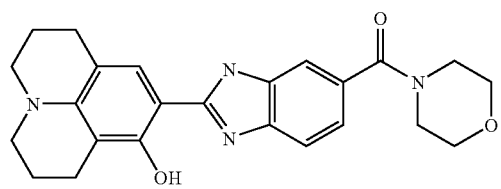 [SMILES: O=C(c1ccc2nc(-c3cc4c5c(c3O)CCCN5CCC4)[nH]c2c1)N1CCOCC1] | 419.5 |
| 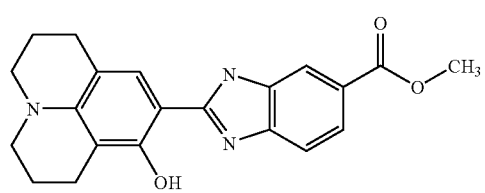 [SMILES: COC(=O)c1ccc2nc(-c3cc4c5c(c3O)CCCN5CCC4)[nH]c2c1] | 364.4 |

| MOLSTRUCTURE | MW (M + 1) |
|---|---|
| 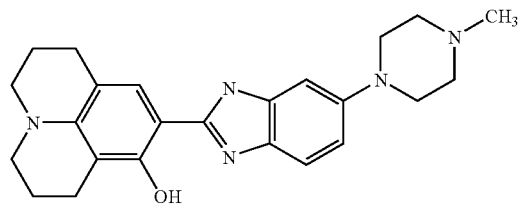 [SMILES: CN1CCN(c2ccc3nc(-c4cc5c6c(c4O)CCCN6CCC5)[nH]c3c2)CC1] | 404.5 |
| 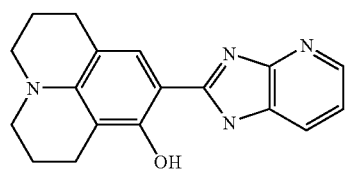 [SMILES: Oc1c(-c2nc3ncccc3[nH]2)cc2c3c1CCCN3CCC2] | 307.4 |
| 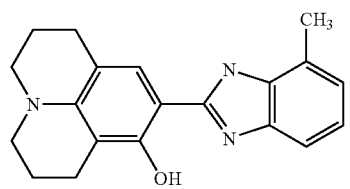 [SMILES: Cc1cccc2nc(-c3cc4c5c(c3O)CCCN5CCC4)[nH]c12] | 320.4 |
| 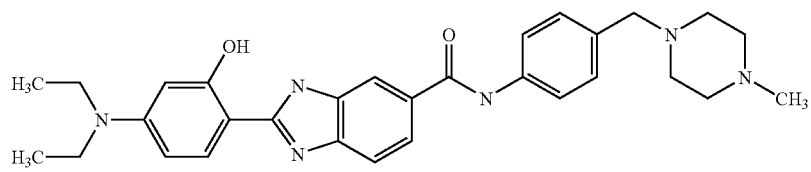 [SMILES: CCN(CC)c1ccc(-c2nc3ccc(C(=O)Nc4ccc(CN5CCN(C)CC5)cc4)cc3[nH]2)c(O)c1] | 513.7 |
| 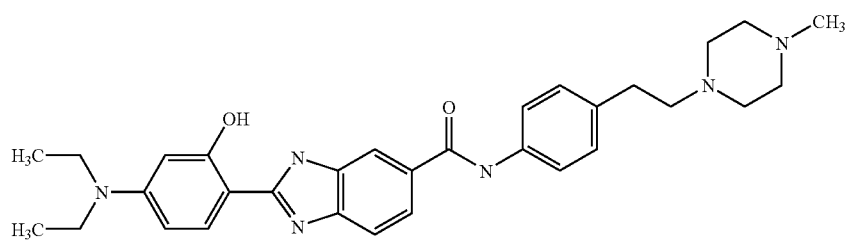 | 527.7 |
| 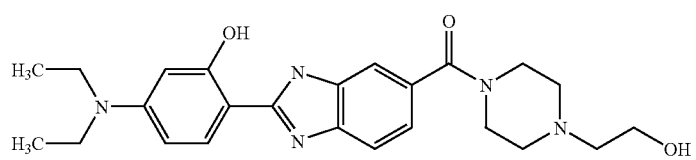 [SMILES: CCN(CC)c1ccc(-c2nc3ccc(C(=O)N4CCN(CCO)CC4)cc3[nH]2)c(O)c1] | 438.5 |
| 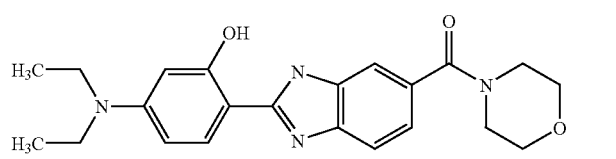 | 395.5 |
| 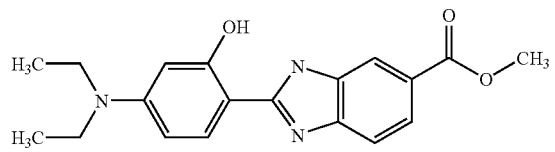 | 340.4 |

-continued

| MOLSTRUCTURE | MW (M + 1) |
|---|---|
| (diethylamino-hydroxyphenyl)-(methylpiperazinyl)benzimidazole | 380.5 |
| (diethylamino-hydroxyphenyl)-imidazopyridine | 283.3 |
| (diethylamino-hydroxyphenyl)-(methyl)benzimidazole | 296.4 |
| (tert-butyl-hydroxyphenyl)-benzimidazole-carboxamide-N-(phenyl-methyl-methylpiperazine) | 498.6 |
| (tert-butyl-hydroxyphenyl)-benzimidazole-carboxamide-N-(phenyl-ethyl-methylpiperazine) | 512.7 |
| (tert-butyl-hydroxyphenyl)-benzimidazole-carbonyl-(hydroxyethyl-piperazine) | 423.5 |
| (tert-butyl-hydroxyphenyl)-benzimidazole-carbonyl-morpholine | 380.5 |

-continued
| MOLSTRUCTURE | MW (M + 1) |
|---|---|
| 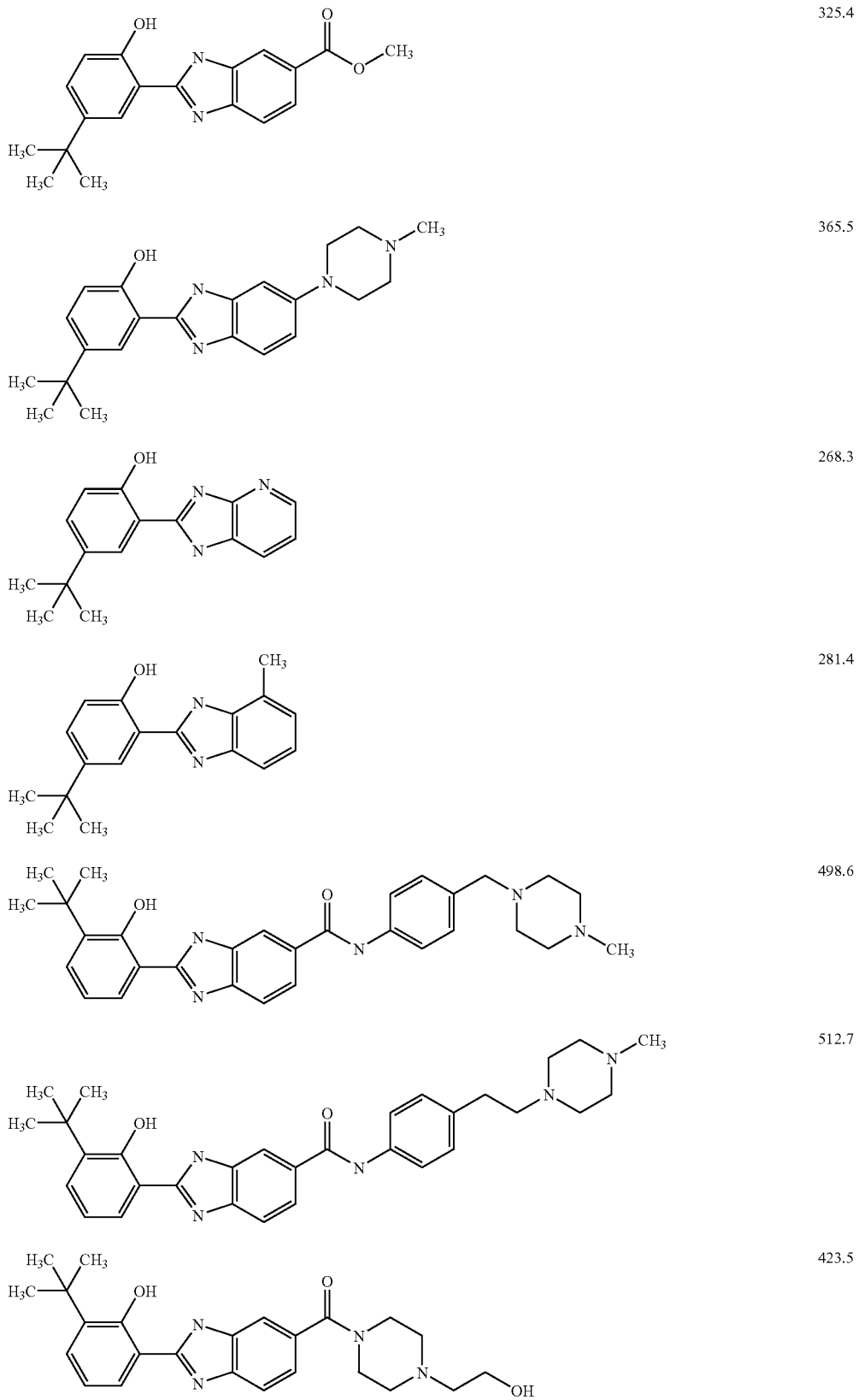 | 325.4 |
| | 365.5 |
| | 268.3 |
| | 281.4 |
| | 498.6 |
| | 512.7 |
| | 423.5 |

| MOLSTRUCTURE | MW (M + 1) |
|---|---|
| (tert-butyl, OH-phenyl)-benzimidazole-morpholine amide | 380.5 |
| (tert-butyl, OH-phenyl)-benzimidazole-methyl ester | 325.4 |
| (tert-butyl, OH-phenyl)-benzimidazole-(4-methylpiperazinyl) | 365.5 |
| (tert-butyl, OH-phenyl)-imidazopyridine | 268.3 |
| (tert-butyl, OH-phenyl)-4-methylbenzimidazole | 281.4 |
| (benzyloxy, OH-phenyl)-benzimidazole-C(O)NH-phenyl-CH2-(4-methylpiperazine) | 548.7 |
| (benzyloxy, OH-phenyl)-benzimidazole-C(O)NH-phenyl-CH2CH2-(4-methylpiperazine) | 562.7 |
| (benzyloxy, OH-phenyl)-benzimidazole-C(O)-piperazine-CH2CH2OH | 473.5 |

| MOLSTRUCTURE | MW (M + 1) |
| --- | --- |
| | 430.5 |
| | 375.4 |
| | 415.5 |
| | 318.4 |
| | 331.4 |
| | 474.5 |
| | 488.6 |

-continued

| MOLSTRUCTURE | MW (M + 1) |
|---|---|
| | 399.4 |
| | 356.4 |
| | 301.3 |
| | 341.4 |
| | 244.2 |
| | 257.3 |
| | 593.8 |

-continued

| MOLSTRUCTURE | MW (M + 1) |
|---|---|
| | 607.8 |
| | 518.7 |
| | 475.6 |
| | 420.5 |
| | 460.6 |

-continued

| MOLSTRUCTURE | MW (M + 1) |
|---|---|
| | 363.5 |
| | 376.5 |
| | 492.6 |
| | 506.6 |
| | 417.5 |
| | 374.4 |
| | 319.3 |

-continued

| MOLSTRUCTURE | MW (M + 1) |
|---|---|
| (structure) | 359.4 |
| (structure) | 262.3 |
| (structure) | 275.3 |
| (structure) | 535.6 |
| (structure) | 549.7 |
| (structure) | 460.5 |

| MOLSTRUCTURE | MW (M + 1) |
|---|---|
| 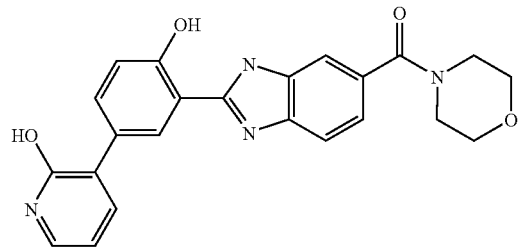 [SMILES: O=C(c1ccc2nc(-c3cc(-c4cccnc4O)ccc3O)[nH]c2c1)N1CCOCC1] | 417.4 |
| 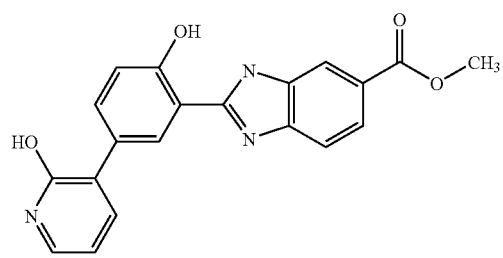 [SMILES: COC(=O)c1ccc2nc(-c3cc(-c4cccnc4O)ccc3O)[nH]c2c1] | 362.4 |
| 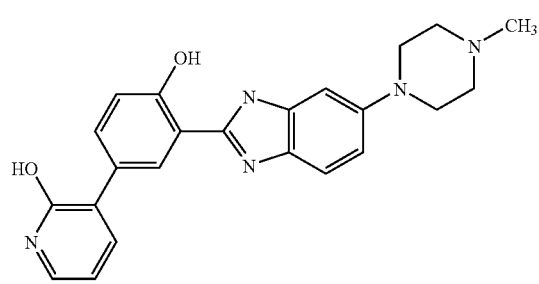 [SMILES: CN1CCN(c2ccc3nc(-c4cc(-c5cccnc5O)ccc4O)[nH]c3c2)CC1] | 402.5 |
| 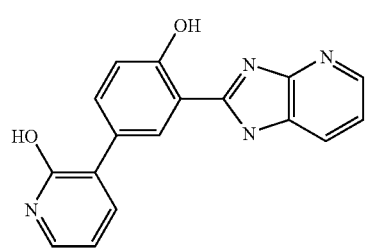 [SMILES: Oc1ccc(-c2cccnc2O)cc1-c1nc2ncccc2[nH]1] | 305.3 |
| 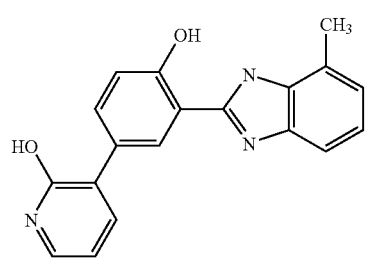 [SMILES: Cc1cccc2nc(-c3cc(-c4cccnc4O)ccc3O)[nH]c12] | 318.4 |

| MOLSTRUCTURE | MW (M + 1) |
|---|---|
| 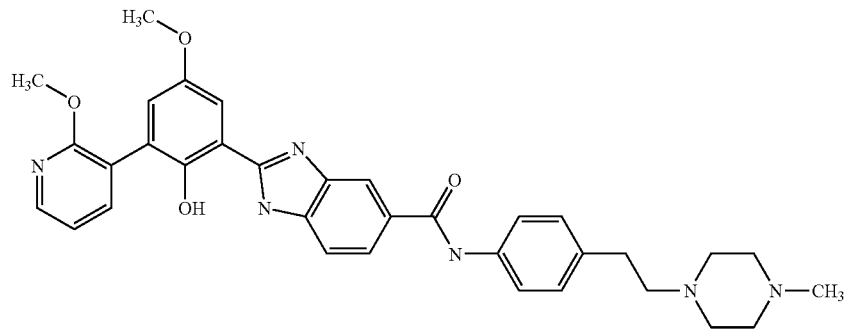 [SMILES: COc1cc(-c2nc3cc(C(=O)Nc4ccc(CCN5CCN(C)CC5)cc4)ccc3[nH]2)c(O)c(-c2cccnc2OC)c1] | 593.7 |
| 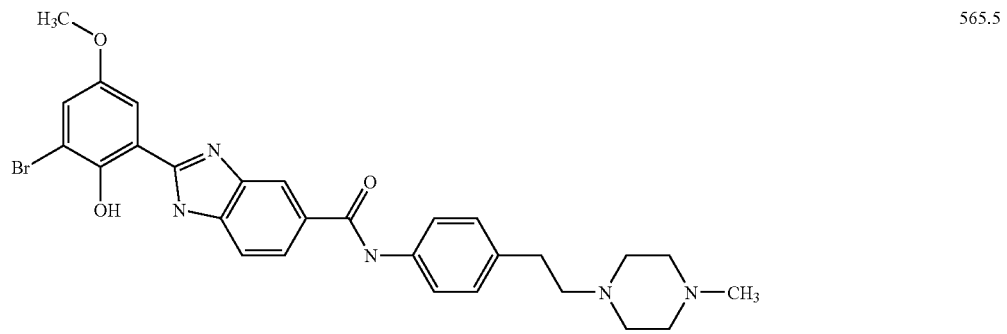 | 565.5 |
| 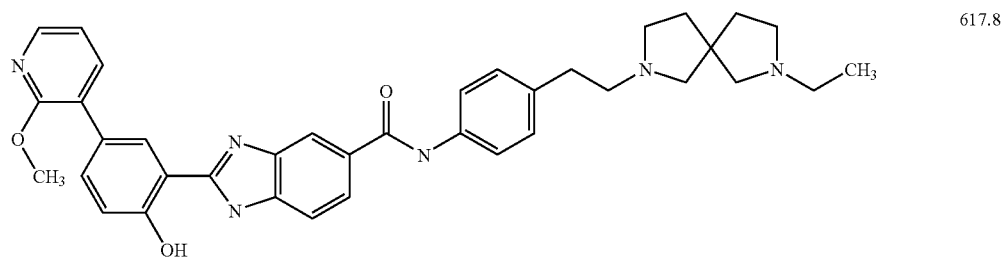 | 617.8 |
| 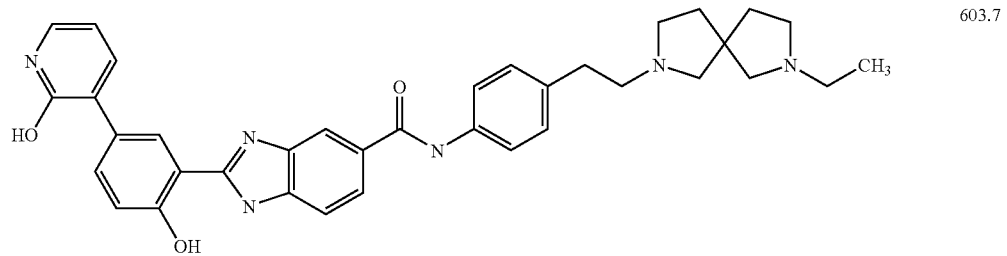 | 603.7 |

| MOLSTRUCTURE | MW (M + 1) |
|---|---|
| 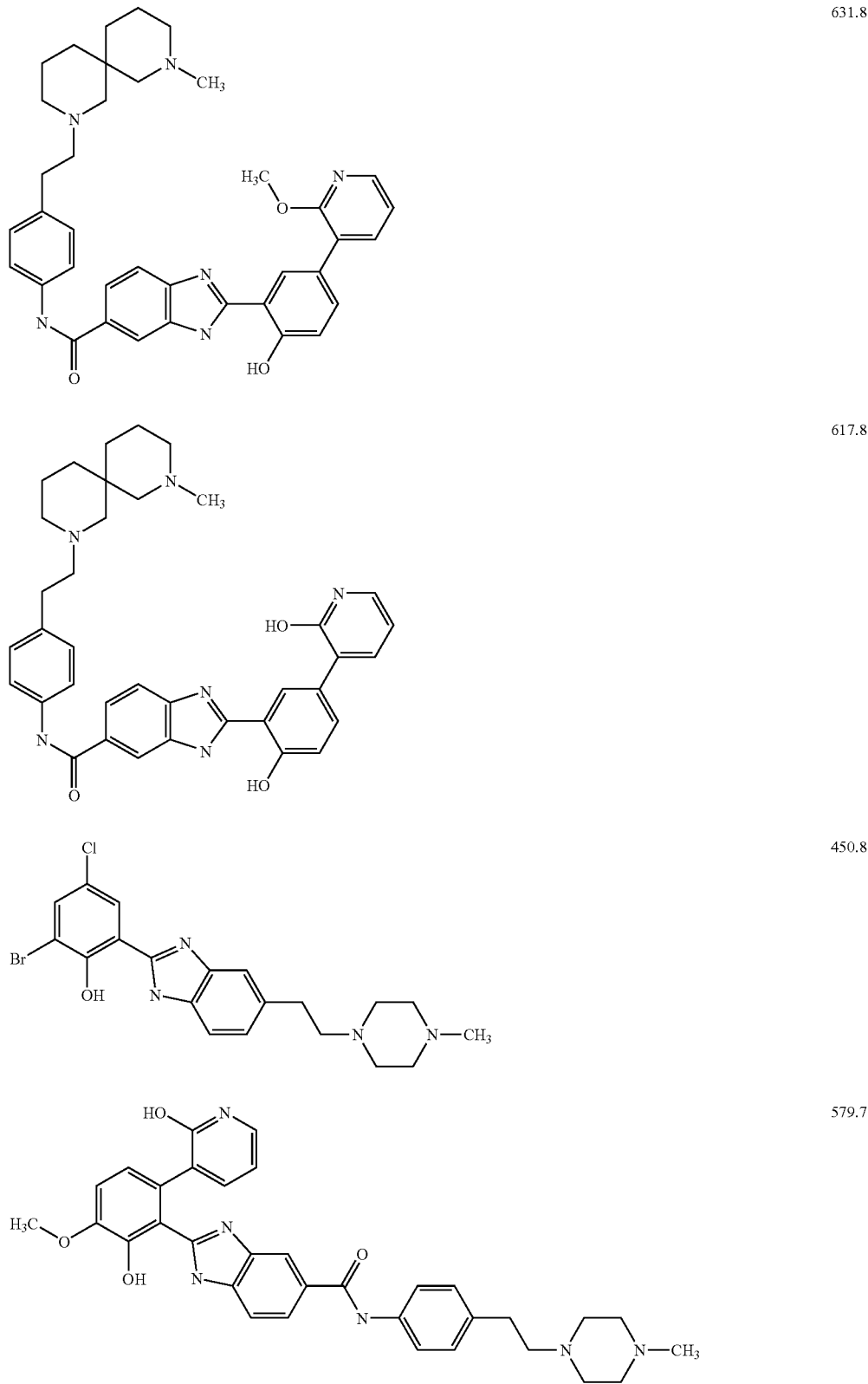 | 631.8 |
| | 617.8 |
| | 450.8 |
| | 579.7 |

-continued
| MOLSTRUCTURE | MW (M + 1) |
|---|---|
| 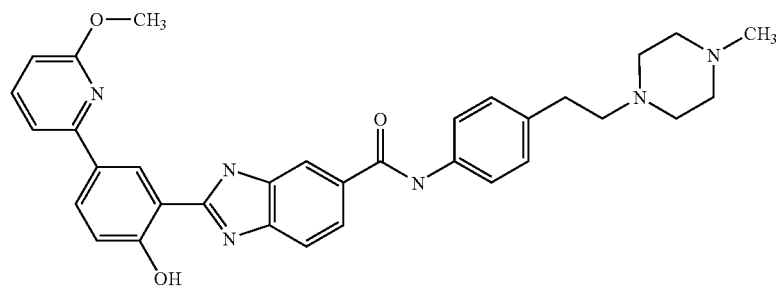 [SMILES: COc1cccc(-c2ccc(O)c(-c3nc4ccc(C(=O)Nc5ccc(CCN6CCN(C)CC6)cc5)cc4[nH]3)c2)n1] | 563.7 |
| 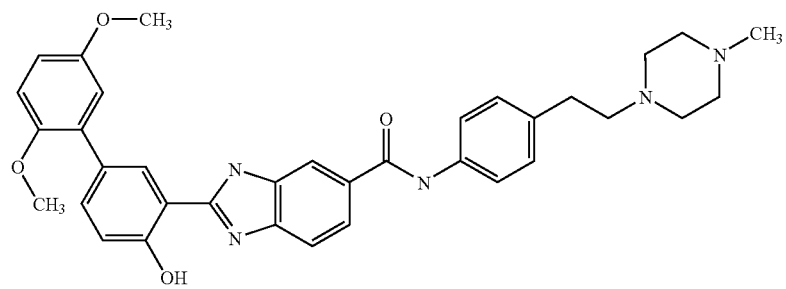 [SMILES: COc1ccc(OC)c(-c2ccc(O)c(-c3nc4ccc(C(=O)Nc5ccc(CCN6CCN(C)CC6)cc5)cc4[nH]3)c2)c1] | 592.7 |
| 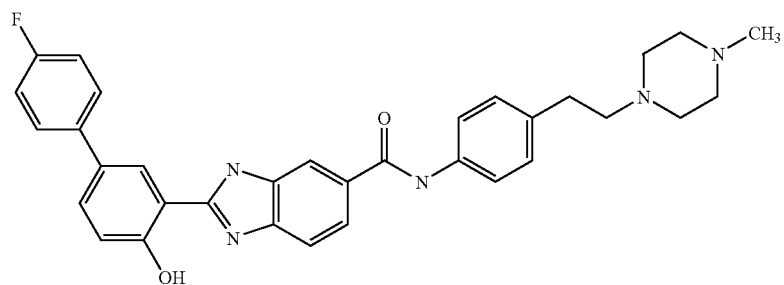 [SMILES: CN1CCN(CCc2ccc(NC(=O)c3ccc4nc(-c5cc(-c6ccc(F)cc6)ccc5O)[nH]c4c3)cc2)CC1] | 550.7 |
| 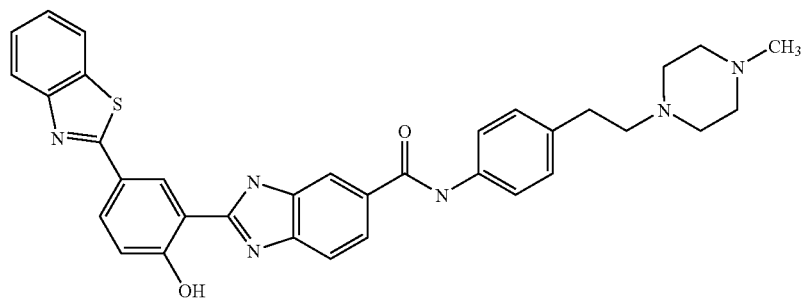 [SMILES: CN1CCN(CCc2ccc(NC(=O)c3ccc4nc(-c5cc(-c6nc7ccccc7s6)ccc5O)[nH]c4c3)cc2)CC1] | 589.7 |
| 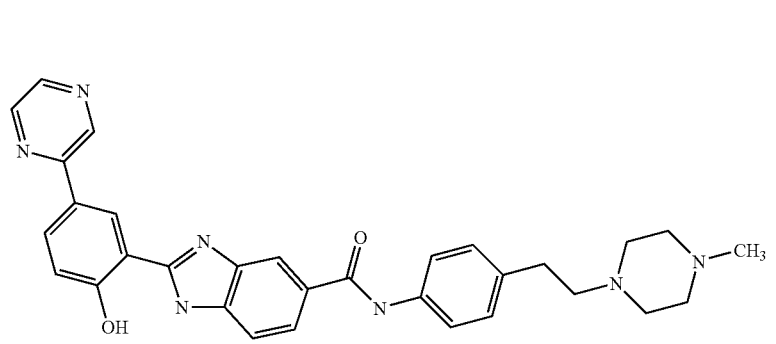 [SMILES: CN1CCN(CCc2ccc(NC(=O)c3ccc4[nH]c(-c5cc(-c6cnccn6)ccc5O)nc4c3)cc2)CC1] | 534.6 |

-continued
| MOLSTRUCTURE | MW (M + 1) |
|---|---|
| 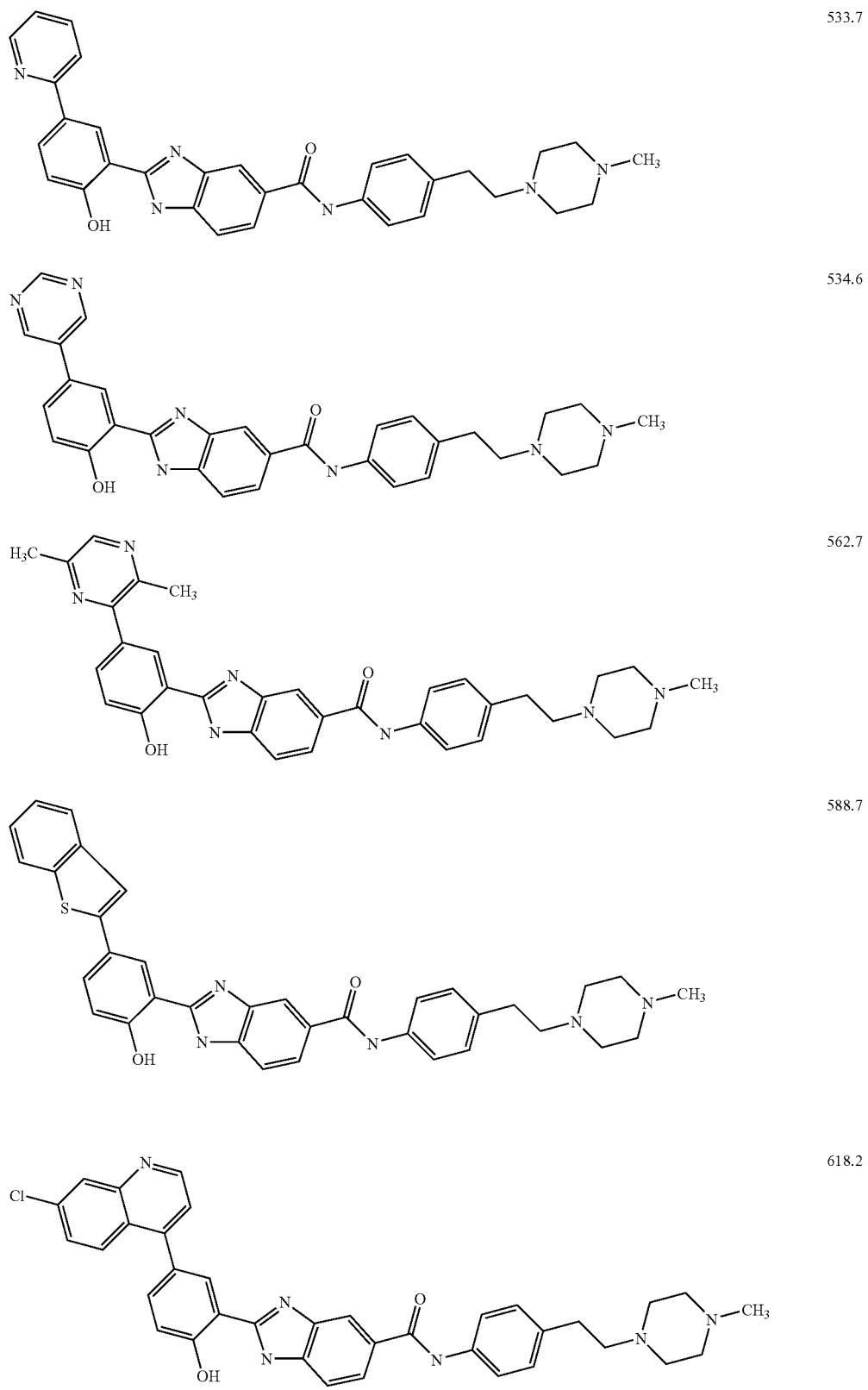 | 533.7 |
| | 534.6 |
| | 562.7 |
| | 588.7 |
| | 618.2 |

| MOLSTRUCTURE | MW (M + 1) |
|---|---|
| 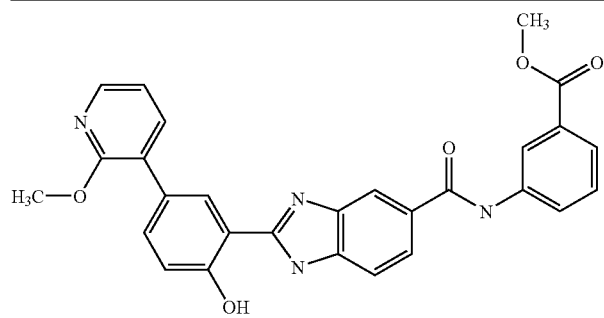 | 495.5 |
| 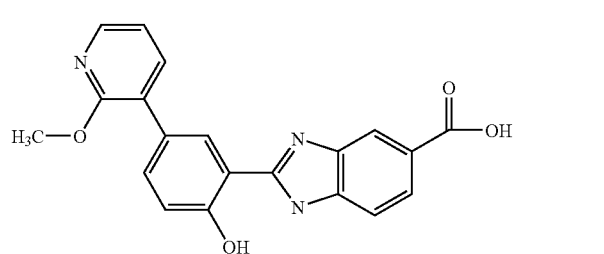 [SMILES: COc1ncccc1-c1ccc(O)c(-c2nc3cc(C(=O)O)ccc3[nH]2)c1] | 362.4 |
| 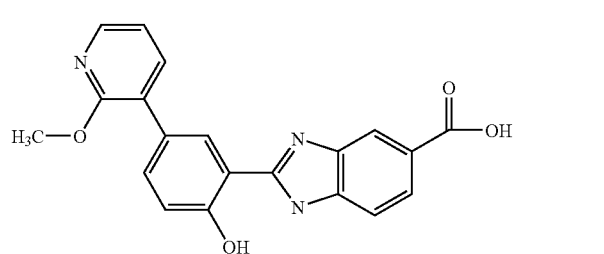 [SMILES: COc1ncccc1-c1ccc(O)c(-c2nc3cc(C(=O)O)ccc3[nH]2)c1] | 524.6 |
| 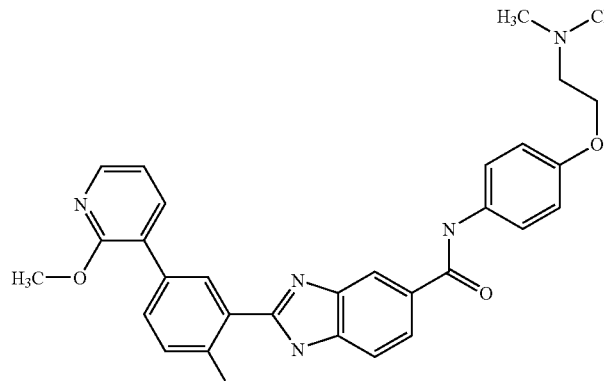 | 538.6 |

-continued
| MOLSTRUCTURE | MW (M + 1) |
|---|---|
| 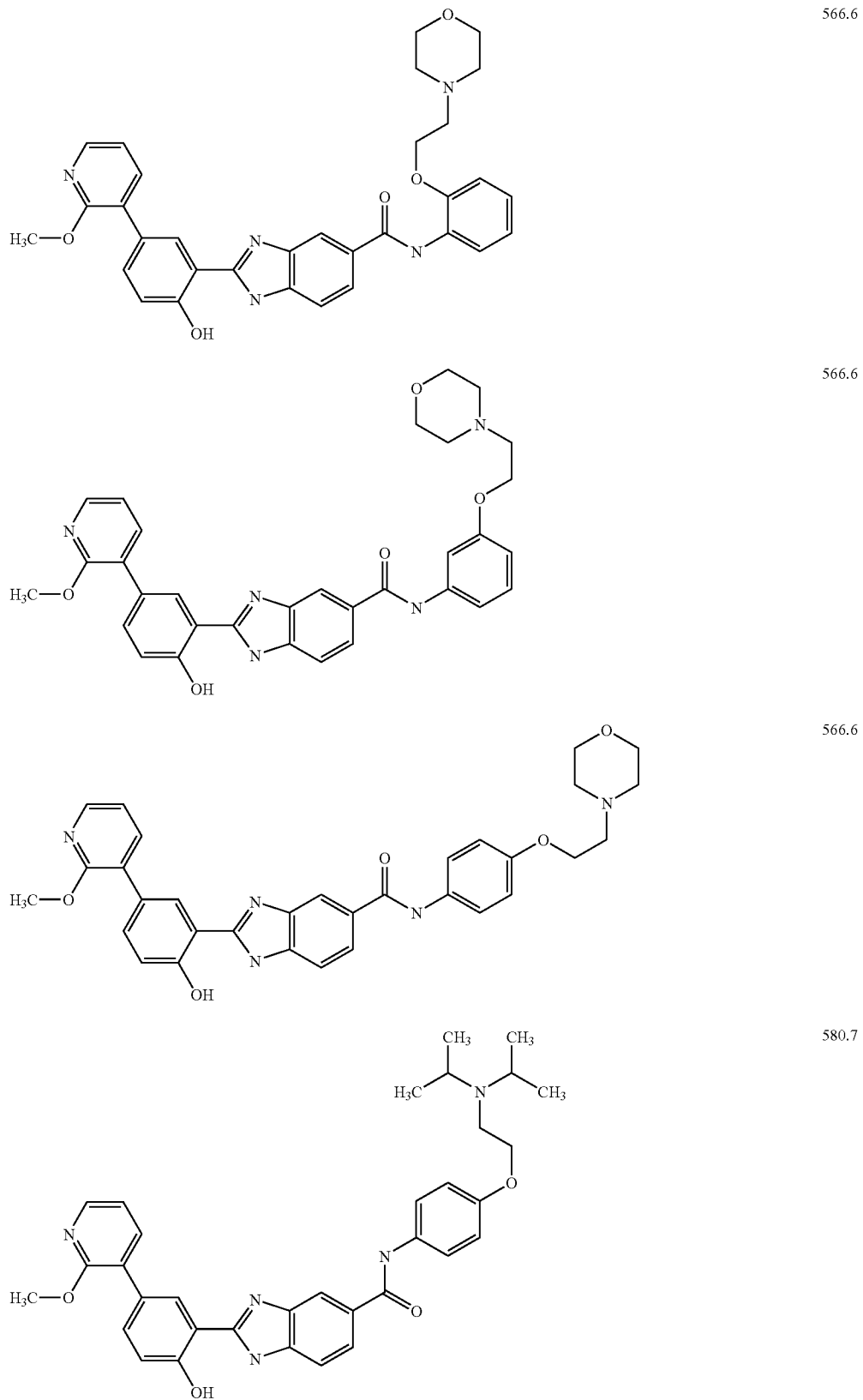 | 566.6 |
| | 566.6 |
| | 566.6 |
| | 580.7 |

-continued
| MOLSTRUCTURE | MW (M + 1) |
|---|---|
| 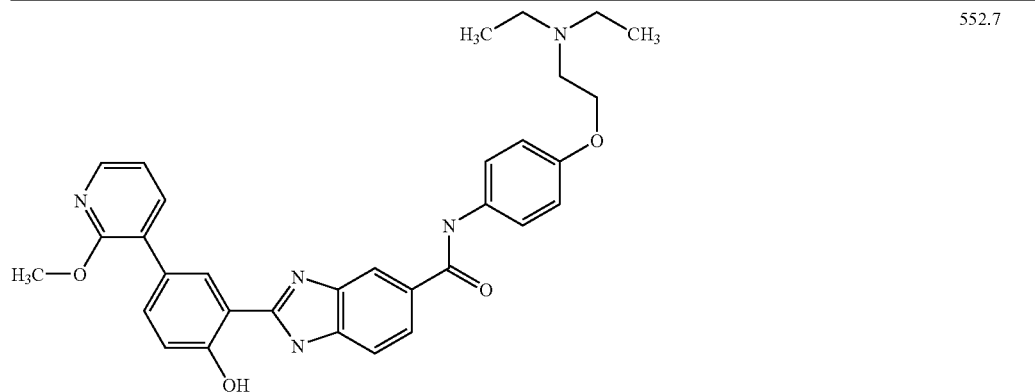 | 552.7 |
| 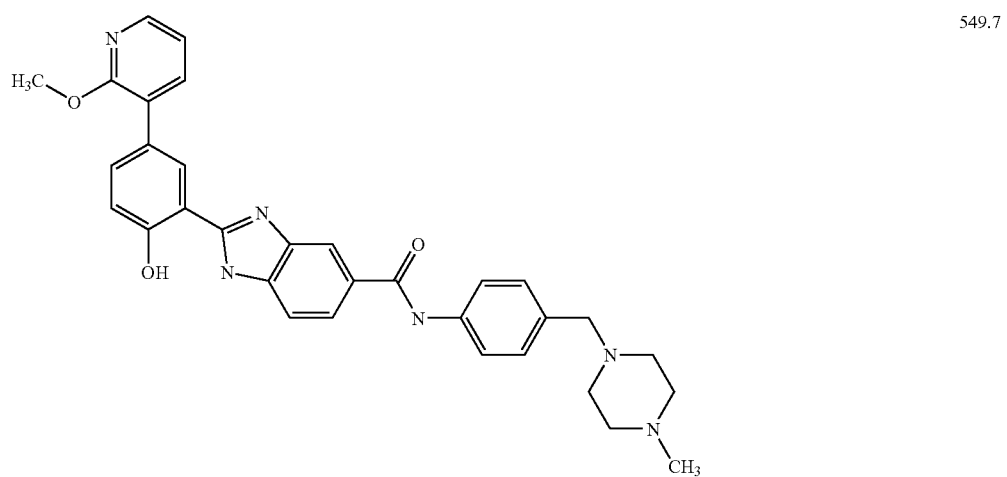 | 549.7 |
| 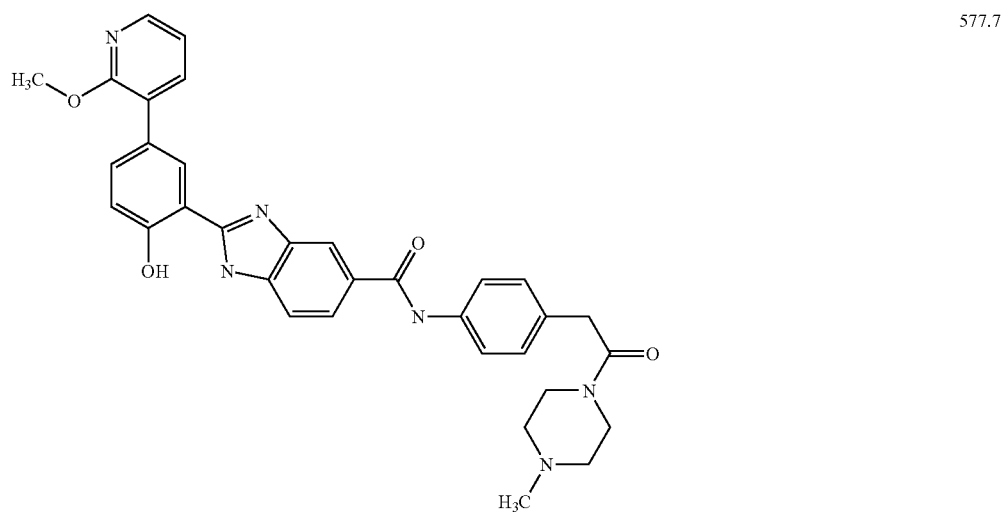 | 577.7 |

| MOLSTRUCTURE | MW (M + 1) |
|---|---|
| 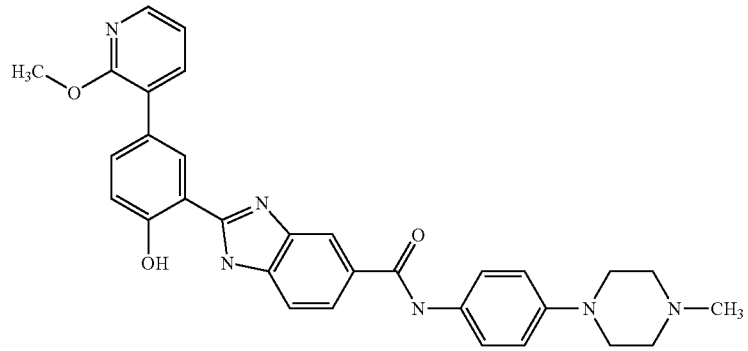 | 535.6 |
| 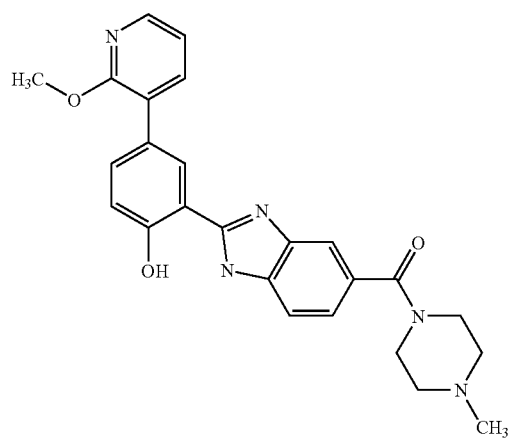 | 444.5 |
| 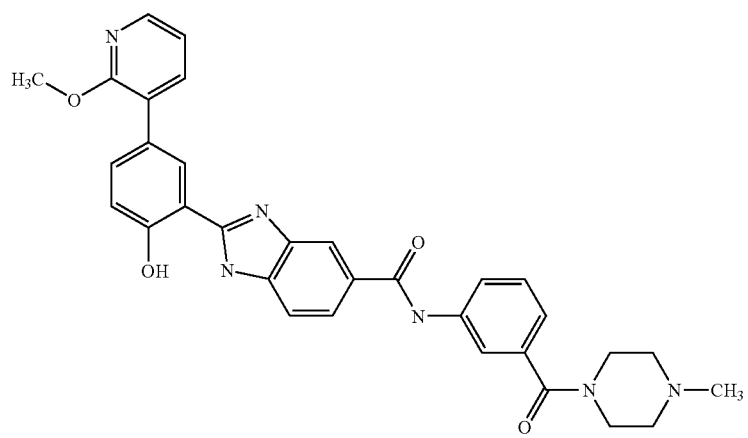 | 563.6 |
| 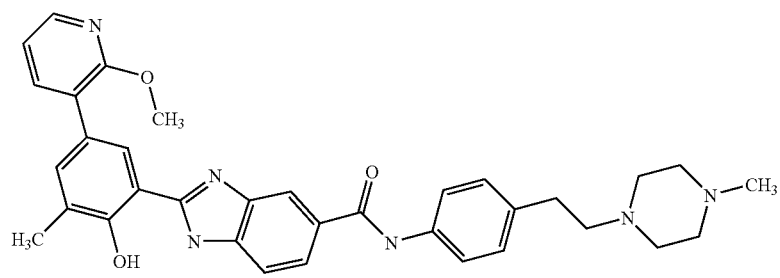 [SMILES: COc1ncccc1-c1cc(C)c(O)c(-c2nc3cc(C(=O)Nc4ccc(CCN5CCN(C)CC5)cc4)ccc3[nH]2)c1] | 577.7 |

| MOLSTRUCTURE | MW (M + 1) |
|---|---|
| 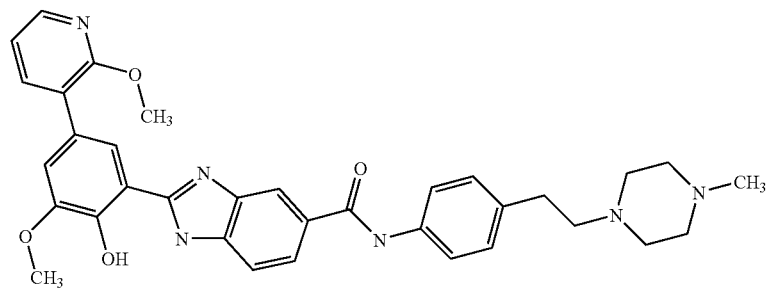 [SMILES: COc1cc(-c2cccnc2OC)cc(-c2nc3cc(C(=O)Nc4ccc(CCN5CCN(C)CC5)cc4)ccc3[nH]2)c1O] | 593.7 |
| 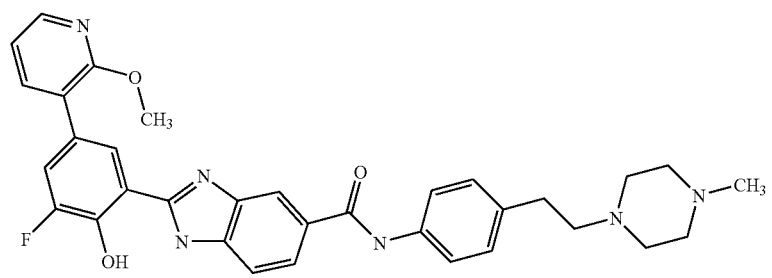 [SMILES: COc1ncccc1-c1cc(F)c(O)c(-c2nc3cc(C(=O)Nc4ccc(CCN5CCN(C)CC5)cc4)ccc3[nH]2)c1] | 581.7 |
| 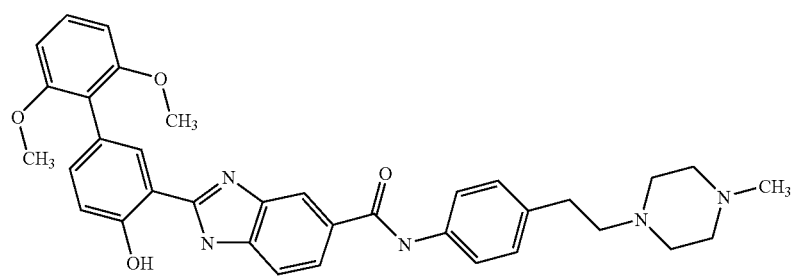 [SMILES: COc1cccc(OC)c1-c1ccc(O)c(-c2nc3cc(C(=O)Nc4ccc(CCN5CCN(C)CC5)cc4)ccc3[nH]2)c1] | 592.7 |
| 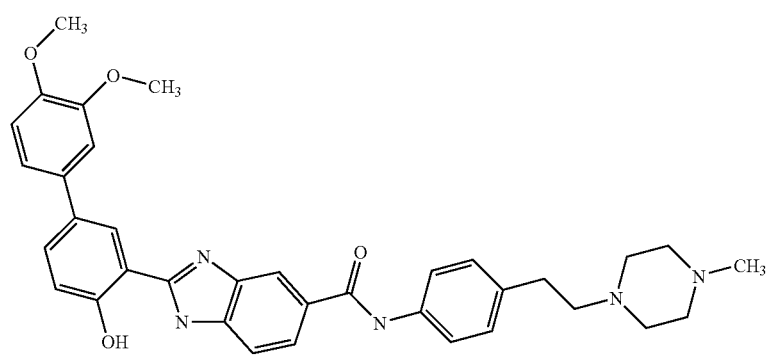 [SMILES: COc1ccc(-c2ccc(O)c(-c3nc4cc(C(=O)Nc5ccc(CCN6CCN(C)CC6)cc5)ccc4[nH]3)c2)cc1OC] | 592.7 |
| 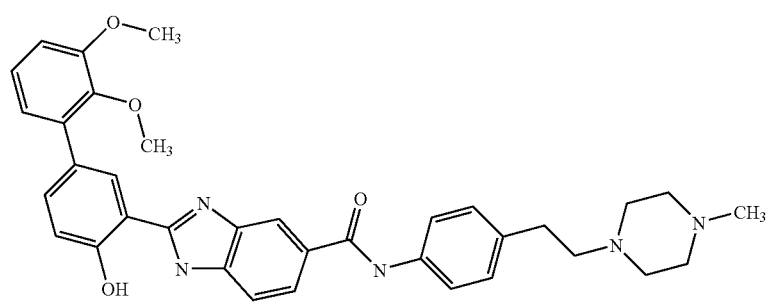 [SMILES: COc1cccc(-c2ccc(O)c(-c3nc4cc(C(=O)Nc5ccc(CCN6CCN(C)CC6)cc5)ccc4[nH]3)c2)c1OC] | 592.7 |

| MOLSTRUCTURE | MW (M + 1) |
|---|---|
| (structure) | 562.7 |
| (structure) | 580.7 |
| (structure) | 567.1 |
| (structure) | 634.8 |
| (structure) | 376.4 |

| MOLSTRUCTURE | MW (M + 1) |
|---|---|
| 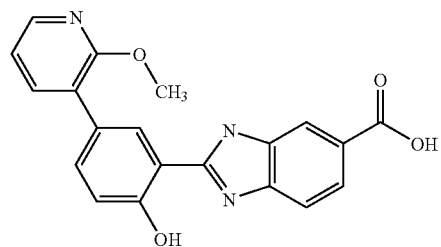 [SMILES: COc1ncccc1-c1ccc(O)c(-c2nc3ccc(C(=O)O)cc3[nH]2)c1] | 362.4 |
| 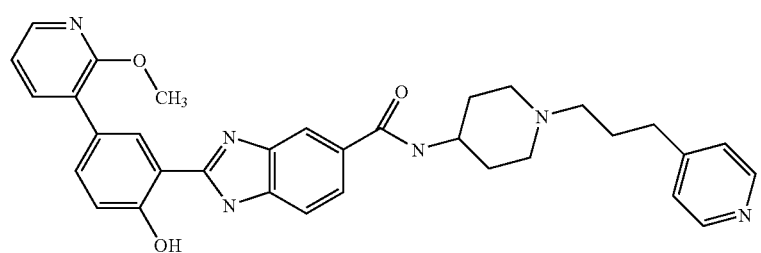 [SMILES: COc1ncccc1-c1ccc(O)c(-c2nc3cc(C(=O)NC4CCN(CCCc5ccncc5)CC4)ccc3[nH]2)c1] | 563.7 |
| 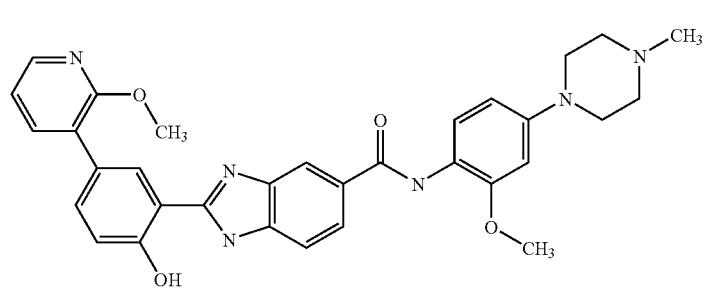 [SMILES: COc1cc(N2CCN(C)CC2)ccc1NC(=O)c1ccc2[nH]c(-c3cc(-c4cccnc4OC)ccc3O)nc2c1] | 565.6 |
| 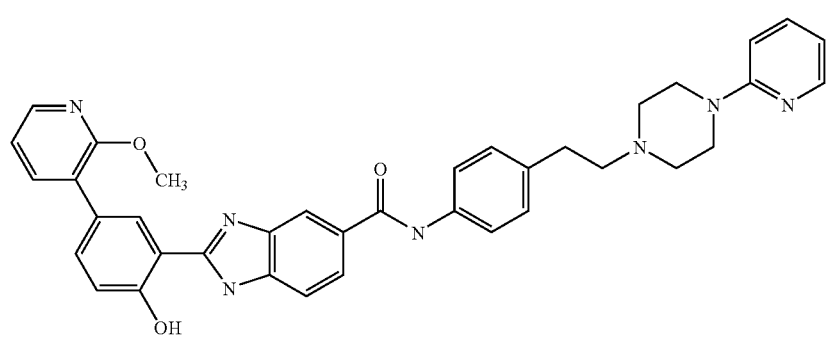 [SMILES: COc1ncccc1-c1ccc(O)c(-c2nc3cc(C(=O)Nc4ccc(CCN5CCN(c6ccccn6)CC5)cc4)ccc3[nH]2)c1] | 626.7 |
| 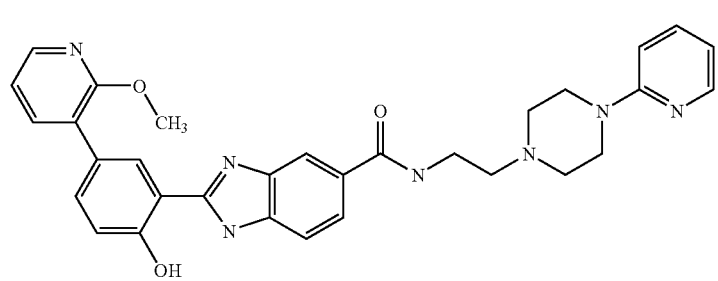 [SMILES: COc1ncccc1-c1ccc(O)c(-c2nc3cc(C(=O)NCCN4CCN(c5ccccn5)CC4)ccc3[nH]2)c1] | 550.6 |

-continued
| MOLSTRUCTURE | MW (M + 1) |
|---|---|
| 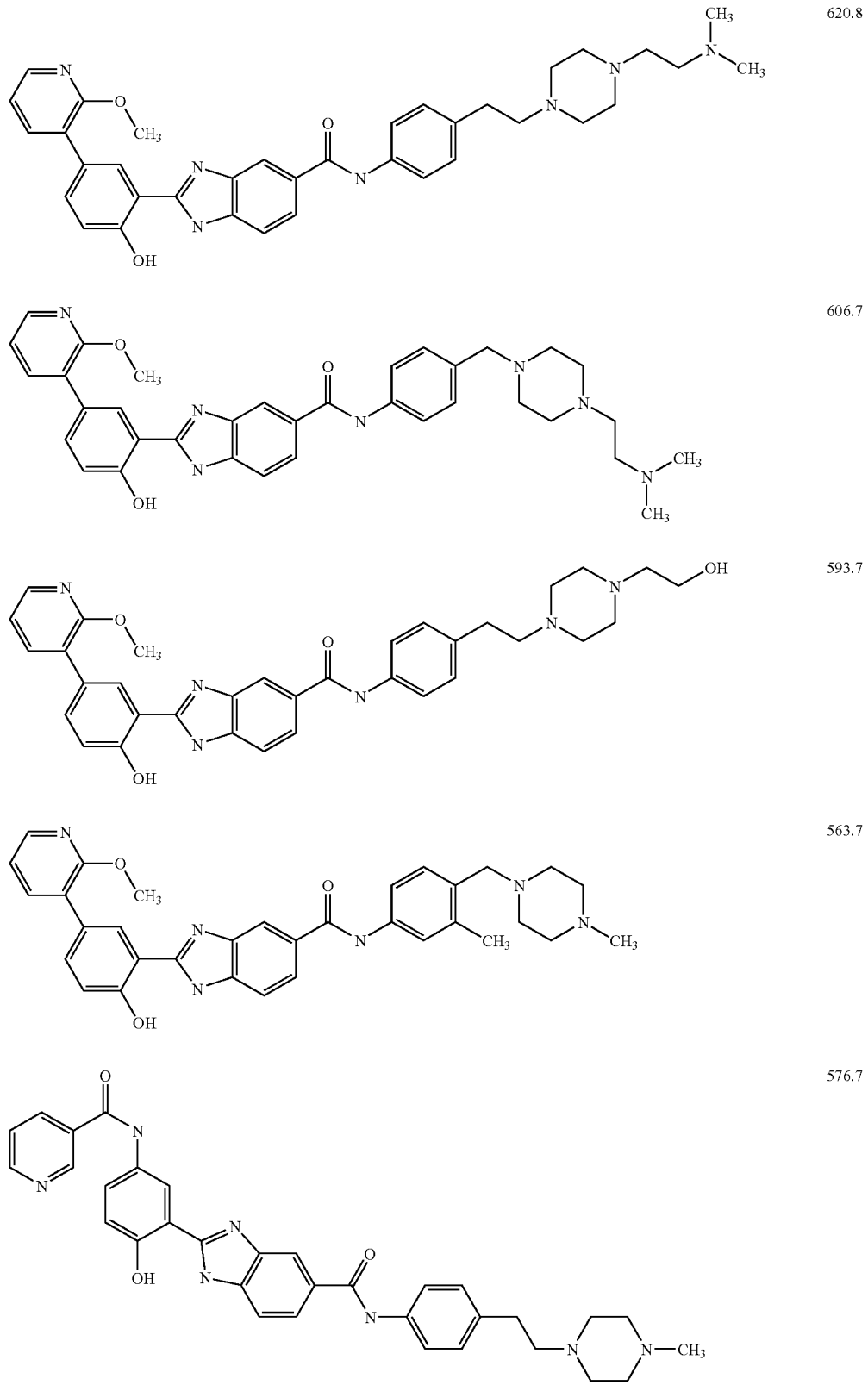 | 620.8 |
| | 606.7 |
| | 593.7 |
| | 563.7 |
| | 576.7 |

| MOLSTRUCTURE | MW (M + 1) |
|---|---|
| 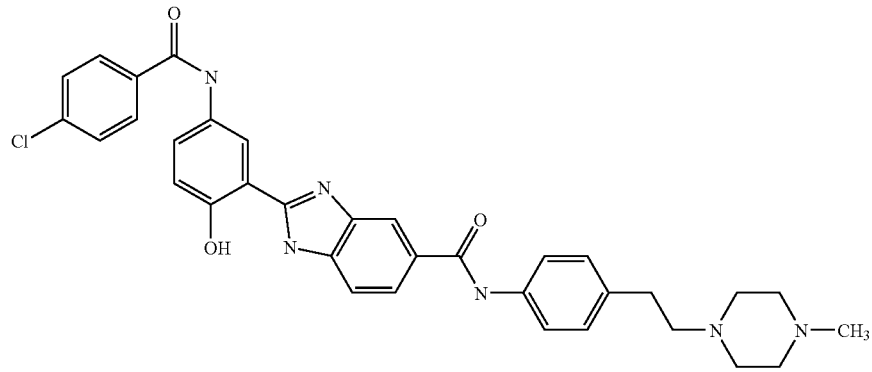 [SMILES: CN1CCN(CCc2ccc(NC(=O)c3ccc4[nH]c(-c5cc(NC(=O)c6ccc(Cl)cc6)ccc5O)nc4c3)cc2)CC1] | 610.1 |
| 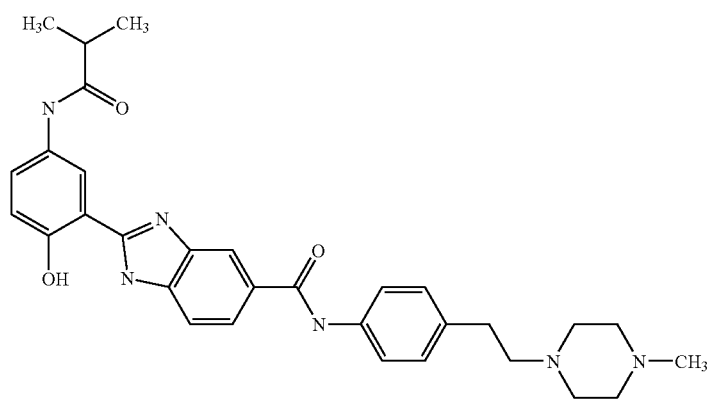 [SMILES: CC(C)C(=O)Nc1ccc(O)c(-c2nc3cc(C(=O)Nc4ccc(CCN5CCN(C)CC5)cc4)ccc3[nH]2)c1] | 541.7 |
| 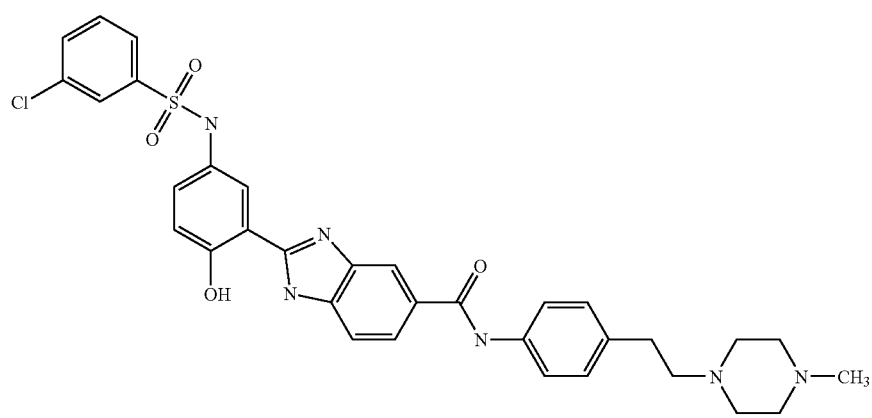 [SMILES: CN1CCN(CCc2ccc(NC(=O)c3ccc4[nH]c(-c5cc(NS(=O)(=O)c6cccc(Cl)c6)ccc5O)nc4c3)cc2)CC1] | 646.2 |

-continued
| MOLSTRUCTURE | MW (M + 1) |
|---|---|
| 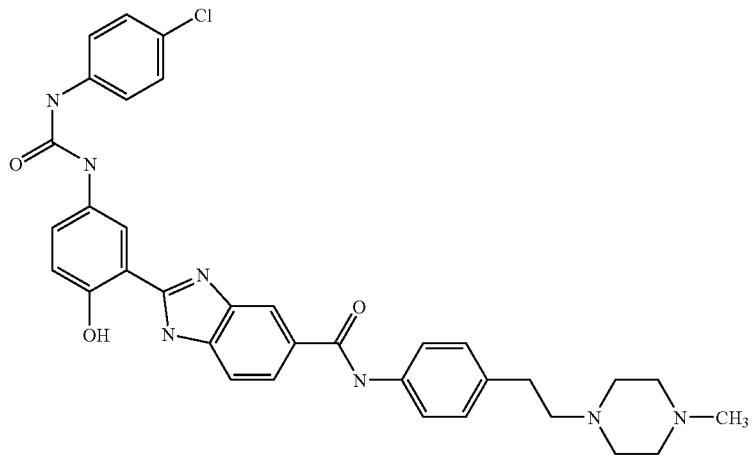 [SMILES: CN1CCN(CCc2ccc(NC(=O)c3ccc4[nH]c(-c5cc(NC(=O)Nc6ccc(Cl)cc6)ccc5O)nc4c3)cc2)CC1] | 625.1 |
| 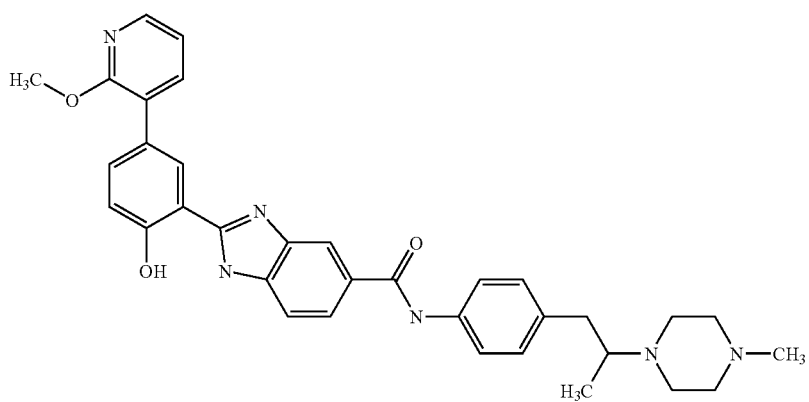 | 577.7 |
| 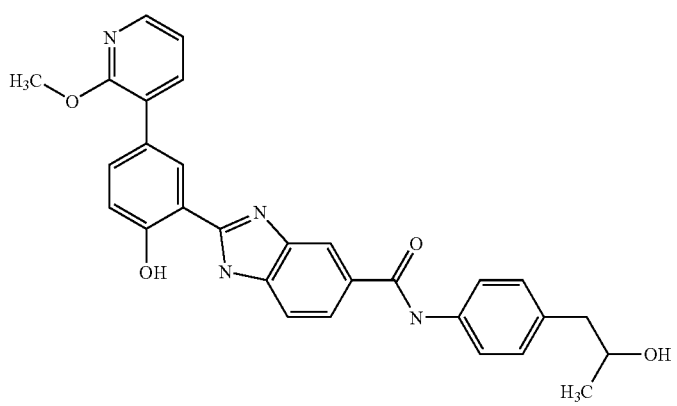 [SMILES: COc1ncccc1-c1ccc(O)c(-c2nc3cc(C(=O)Nc4ccc(CC(C)O)cc4)ccc3[nH]2)c1] | 495.6 |

| MOLSTRUCTURE | MW (M + 1) |
|---|---|
| 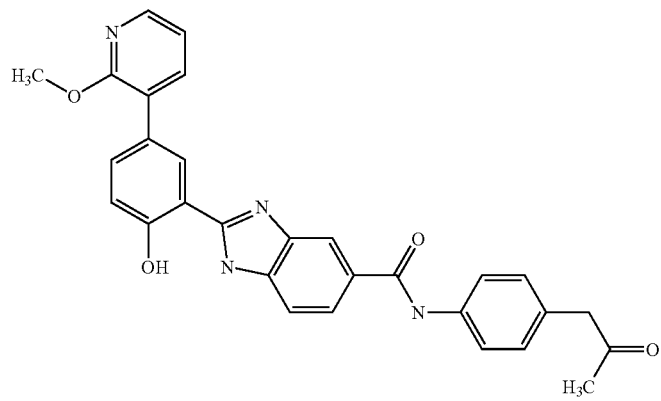 [SMILES: COc1ncccc1-c1ccc(O)c(-c2nc3cc(C(=O)Nc4ccc(CC(C)=O)cc4)ccc3[nH]2)c1] | 493.5 |
| 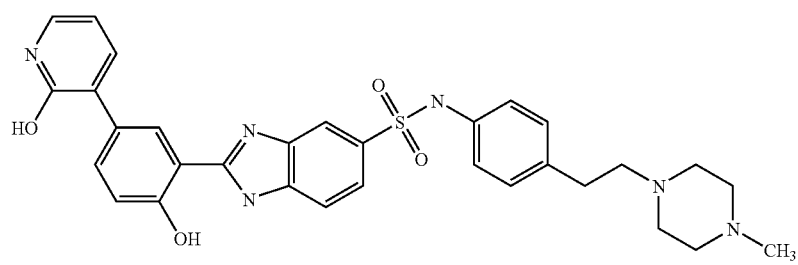 [SMILES: CN1CCN(CCc2ccc(NS(=O)(=O)c3ccc4[nH]c(-c5cc(-c6cccnc6O)ccc5O)nc4c3)cc2)CC1] | 585.7 |
| 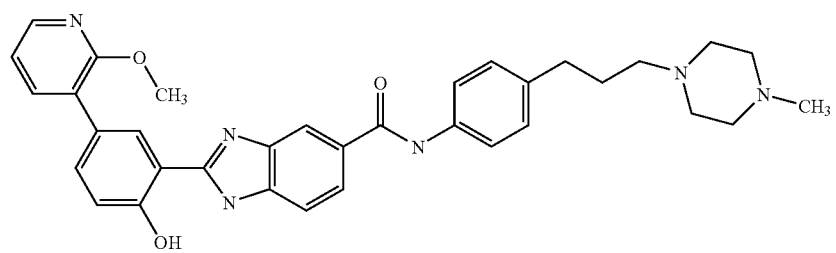 [SMILES: COc1ncccc1-c1ccc(O)c(-c2nc3cc(C(=O)Nc4ccc(CCCN5CCN(C)CC5)cc4)ccc3[nH]2)c1] | 577.7 |
| 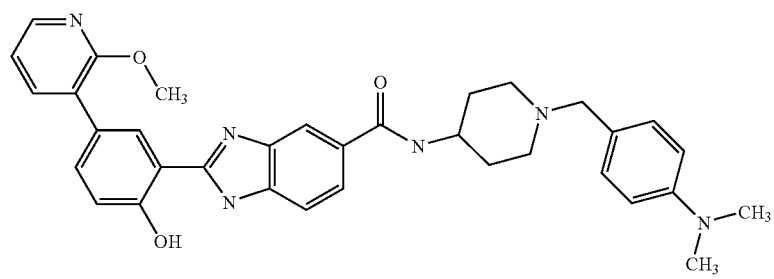 [SMILES: COc1ncccc1-c1ccc(O)c(-c2nc3cc(C(=O)NC4CCN(Cc5ccc(N(C)C)cc5)CC4)ccc3[nH]2)c1] | 577.7 |
| 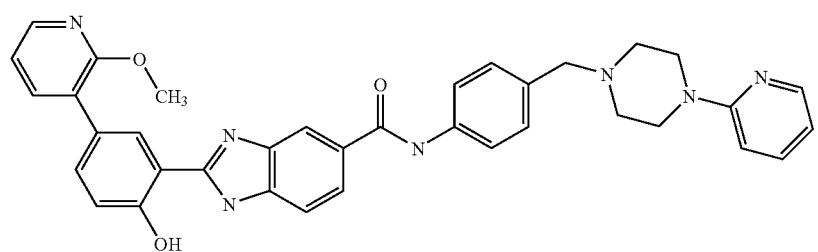 [SMILES: COc1ncccc1-c1ccc(O)c(-c2nc3cc(C(=O)Nc4ccc(CN5CCN(c6ccccn6)CC5)cc4)ccc3[nH]2)c1] | 612.7 |

| MOLSTRUCTURE | MW (M + 1) |
|---|---|
| (structure) | 612.7 |
| (structure) | 627.7 |

Further specific embodiments of compounds of formulas (5), (5a) and 5b include, the following compounds that were prepared according to the methods described herein:

| MOLSTRUCTURE | MW (M + 1) |
|---|---|
| (structure) | 452.5 |
| (structure) | 520.6 |
| (structure) | 419.5 |

| MOLSTRUCTURE | MW (M + 1) |
| --- | --- |
| | 446.5 |
| | 474.5 |
| | 458.5 |
| | 502.6 |
| | 521.6 |

| MOLSTRUCTURE | MW (M + 1) |
|---|---|
| 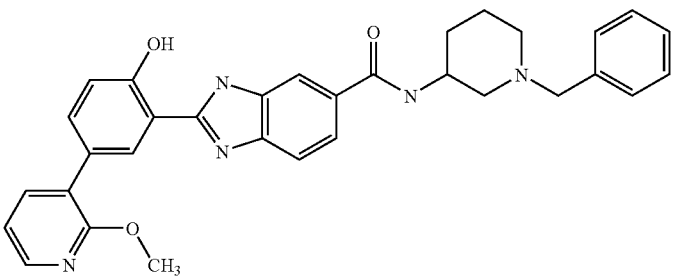 [SMILES: COc1ncccc1-c1ccc(O)c(-c2nc3ccc(C(=O)NC4CCCN(Cc5ccccc5)C4)cc3[nH]2)c1] | 534.6 |
| 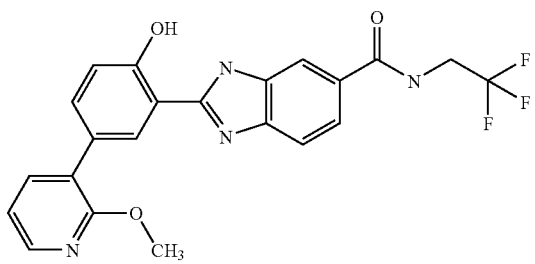 [SMILES: COc1ncccc1-c1ccc(O)c(-c2nc3ccc(C(=O)NCC(F)(F)F)cc3[nH]2)c1] | 443.4 |
| 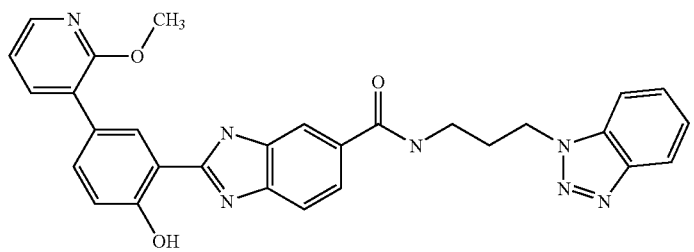 [SMILES: COc1ncccc1-c1ccc(O)c(-c2nc3ccc(C(=O)NCCCn4nnc5ccccc54)cc3[nH]2)c1] | 520.6 |
| 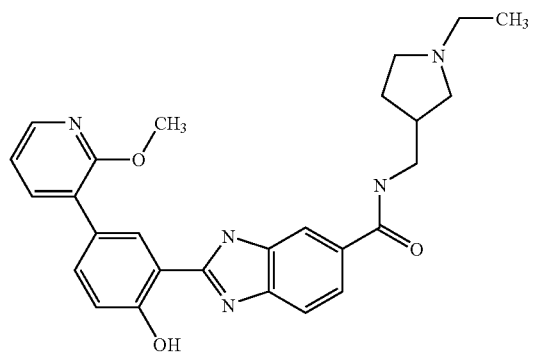 [SMILES: CCN1CCC(CNC(=O)c2ccc3nc(-c4cc(-c5cccnc5OC)ccc4O)[nH]c3c2)C1] | 472.6 |
| 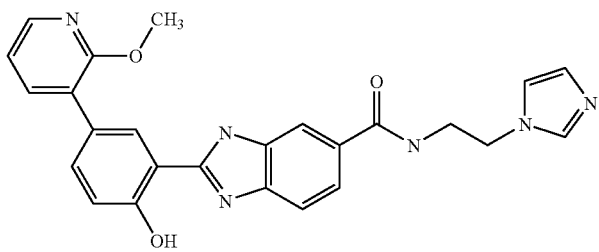 [SMILES: COc1ncccc1-c1ccc(O)c(-c2nc3ccc(C(=O)NCCn4ccnc4)cc3[nH]2)c1] | 455.5 |

| MOLSTRUCTURE | MW (M + 1) |
|---|---|
| 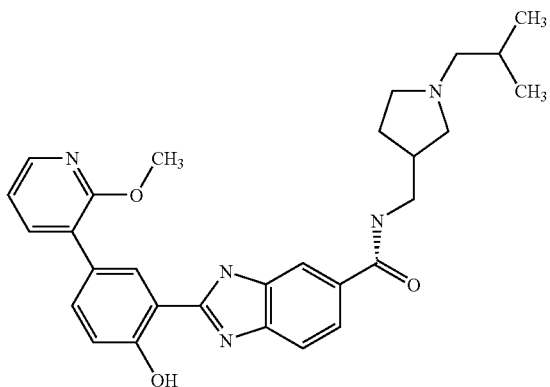 | 500.6 |
| 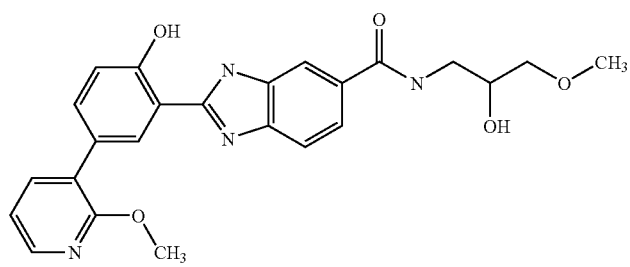 [SMILES: COCC(O)CNC(=O)c1ccc2nc(-c3cc(-c4cccnc4OC)ccc3O)[nH]c2c1] | 449.5 |
| 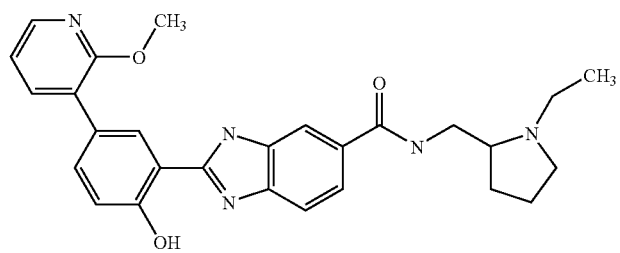 [SMILES: CCN1CCCC1CNC(=O)c1ccc2nc(-c3cc(-c4cccnc4OC)ccc3O)[nH]c2c1] | 472.6 |
| 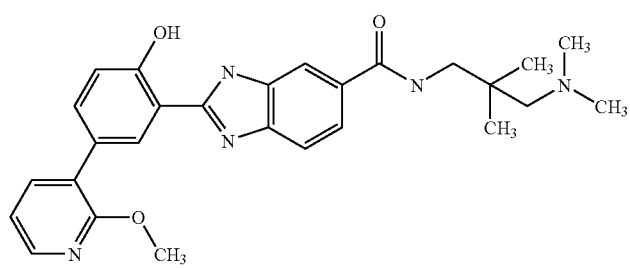 [SMILES: COc1ncccc1-c1ccc(O)c(-c2nc3ccc(C(=O)NCC(C)(C)CN(C)C)cc3[nH]2)c1] | 474.6 |
| 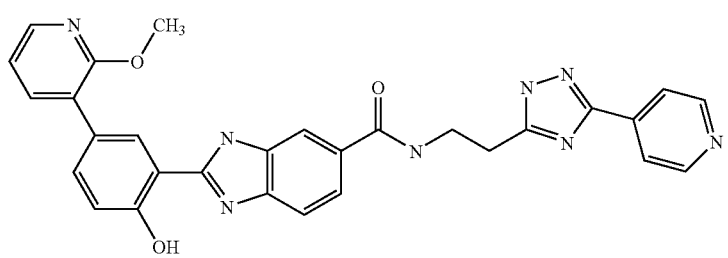 [SMILES: COc1ncccc1-c1ccc(O)c(-c2nc3ccc(C(=O)NCCc4nc(-c5ccncc5)n[nH]4)cc3[nH]2)c1] | 533.6 |

| MOLSTRUCTURE | MW (M + 1) |
|---|---|
| 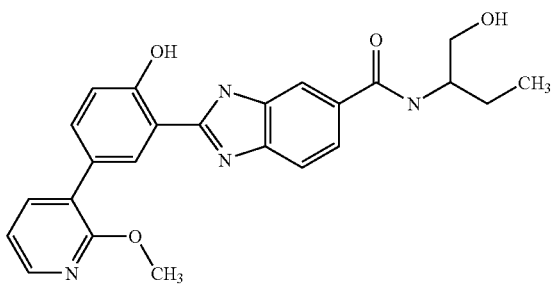 [SMILES: CCC(CO)NC(=O)c1ccc2nc(-c3cc(-c4cccnc4OC)ccc3O)[nH]c2c1] | 433.5 |
| 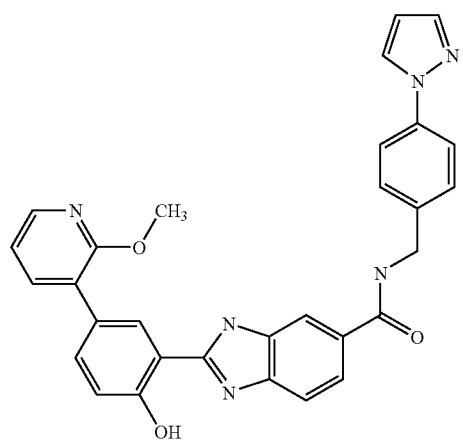 [SMILES: COc1ncccc1-c1ccc(O)c(-c2nc3ccc(C(=O)NCc4ccc(-n5cccn5)cc4)cc3[nH]2)c1] | 517.6 |
| 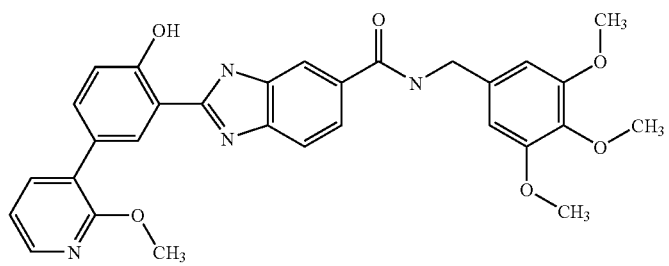 [SMILES: COc1cc(CNC(=O)c2ccc3nc(-c4cc(-c5cccnc5OC)ccc4O)[nH]c3c2)cc(OC)c1OC] | 541.6 |
| 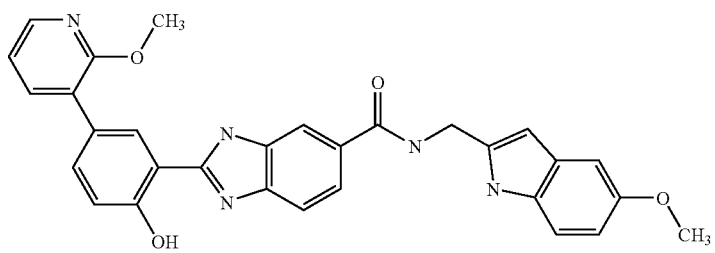 [SMILES: COc1ccc2[nH]c(CNC(=O)c3ccc4nc(-c5cc(-c6cccnc6OC)ccc5O)[nH]c4c3)cc2c1] | 520.6 |
| 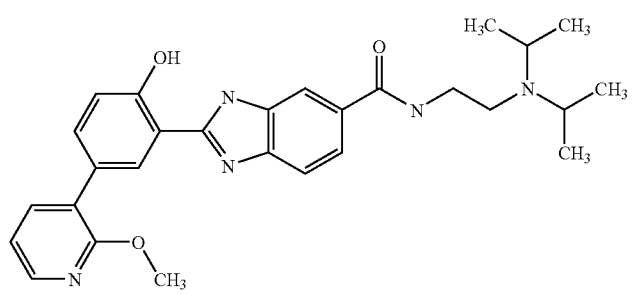 [SMILES: COc1ncccc1-c1ccc(O)c(-c2nc3ccc(C(=O)NCCN(C(C)C)C(C)C)cc3[nH]2)c1] | 488.6 |

| MOLSTRUCTURE | MW (M + 1) |
|---|---|
| 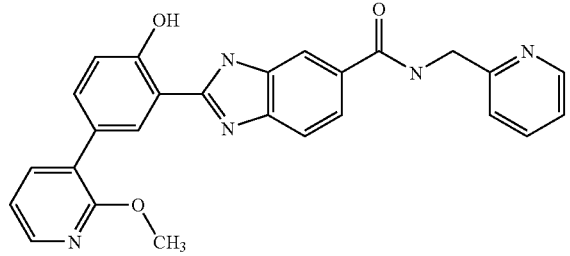 [SMILES: COc1ncccc1-c1ccc(O)c(-c2nc3ccc(C(=O)NCc4ccccn4)cc3[nH]2)c1] | 452.5 |
| 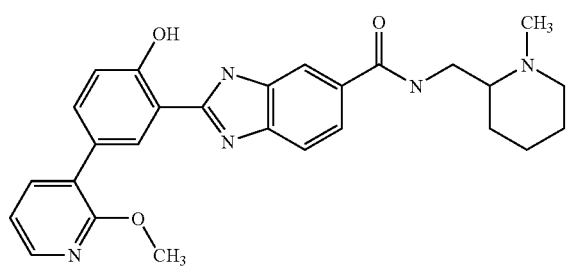 [SMILES: COc1ncccc1-c1ccc(O)c(-c2nc3ccc(C(=O)NCC4CCCCN4C)cc3[nH]2)c1] | 472.6 |
| 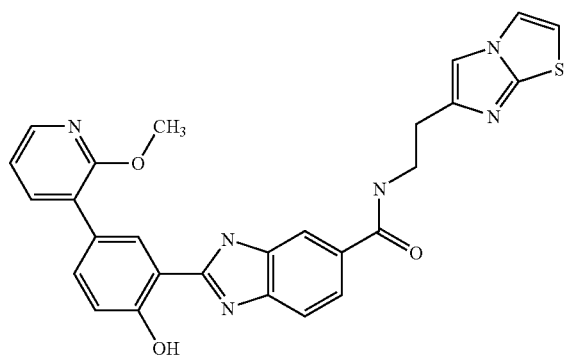 [SMILES: COc1ncccc1-c1ccc(O)c(-c2nc3ccc(C(=O)NCCc4cn5ccsc5n4)cc3[nH]2)c1] | 511.6 |
| 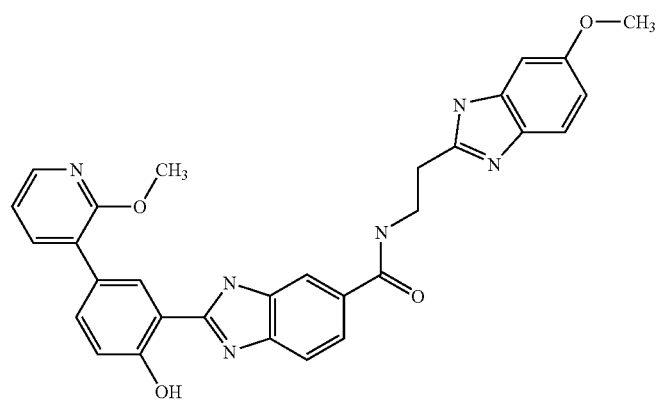 [SMILES: COc1ccc2nc(CCNC(=O)c3ccc4nc(-c5cc(-c6cccnc6OC)ccc5O)[nH]c4c3)[nH]c2c1] | 535.6 |

| MOLSTRUCTURE | MW (M + 1) |
|---|---|
| 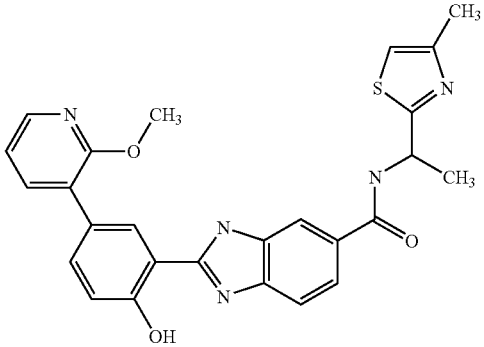 [SMILES: COc1ncccc1-c1ccc(O)c(-c2nc3ccc(C(=O)NC(C)c4nc(C)cs4)cc3[nH]2)c1] | 486.6 |
| 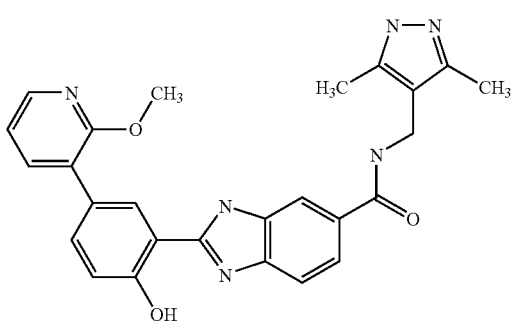 [SMILES: COc1ncccc1-c1ccc(O)c(-c2nc3ccc(C(=O)NCc4c(C)n[nH]c4C)cc3[nH]2)c1] | 469.5 |
| 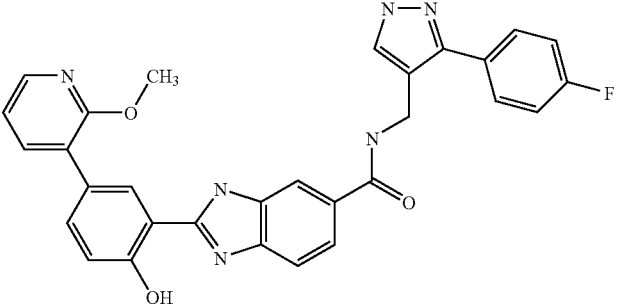 [SMILES: COc1ncccc1-c1ccc(O)c(-c2nc3ccc(C(=O)NCc4c[nH]nc4-c4ccc(F)cc4)cc3[nH]2)c1] | 535.6 |
| 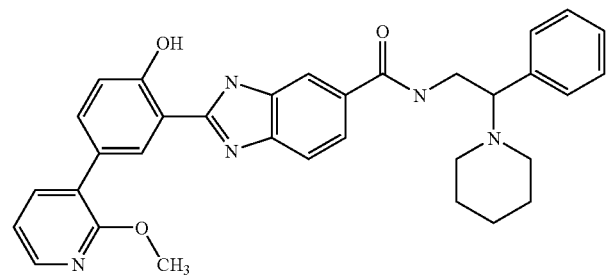 [SMILES: COc1ncccc1-c1ccc(O)c(-c2nc3ccc(C(=O)NCC(c4ccccc4)N4CCCCC4)cc3[nH]2)c1] | 548.7 |
| 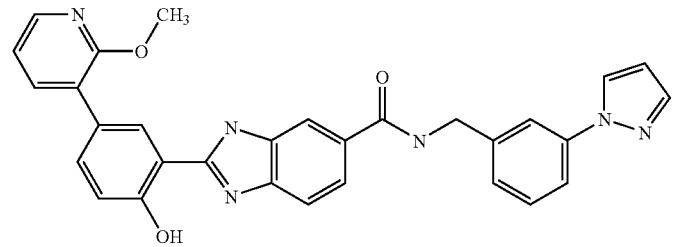 [SMILES: COc1ncccc1-c1ccc(O)c(-c2nc3ccc(C(=O)NCc4cccc(-n5cccn5)c4)cc3[nH]2)c1] | 517.6 |

| MOLSTRUCTURE | MW (M + 1) |
|---|---|
| 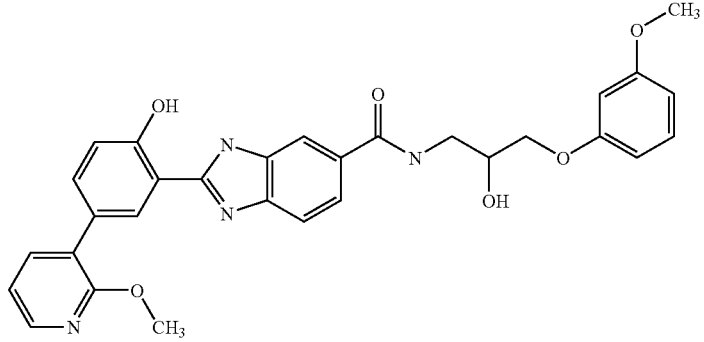 [SMILES: COc1cccc(OCC(O)CNC(=O)c2ccc3nc(-c4cc(-c5cccnc5OC)ccc4O)[nH]c3c2)c1] | 541.6 |
| 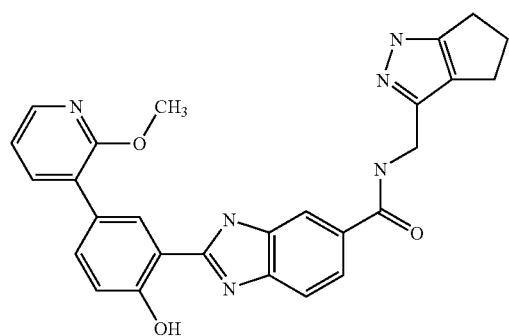 [SMILES: COc1ncccc1-c1ccc(O)c(-c2nc3ccc(C(=O)NCc4n[nH]c5c4CCC5)cc3[nH]2)c1] | 481.5 |
| 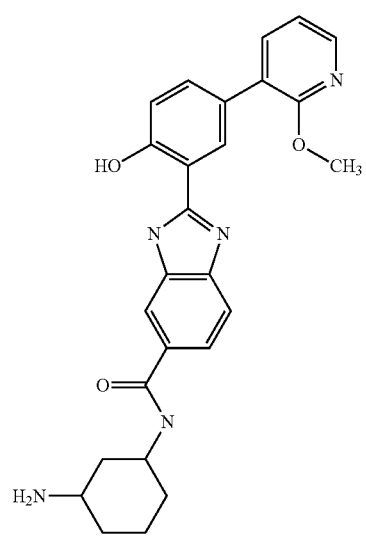 [SMILES: COc1ncccc1-c1ccc(O)c(-c2nc3ccc(C(=O)NC4CCCC(N)C4)cc3[nH]2)c1] | 458.5 |

| MOLSTRUCTURE | MW (M + 1) |
|---|---|
| 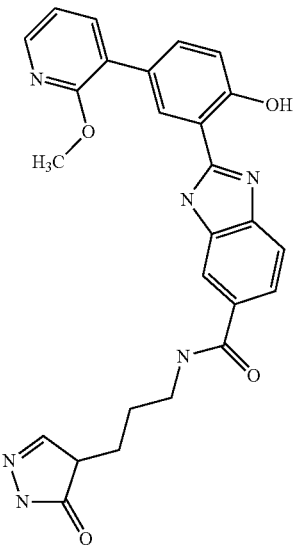 [SMILES: COc1ncccc1-c1ccc(O)c(-c2nc3ccc(C(=O)NCCCC4C=NNC4=O)cc3[nH]2)c1] | 485.5 |
| 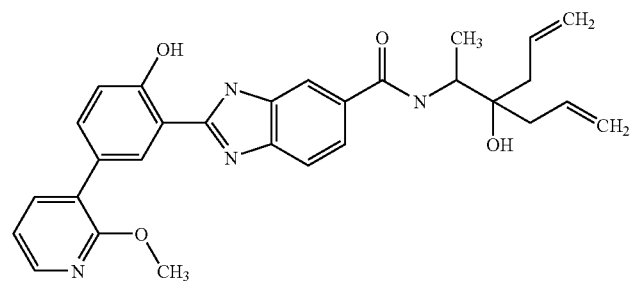 [SMILES: C=CCC(O)(CC=C)C(C)NC(=O)c1ccc2nc(-c3cc(-c4cccnc4OC)ccc3O)[nH]c2c1] | 499.6 |
| 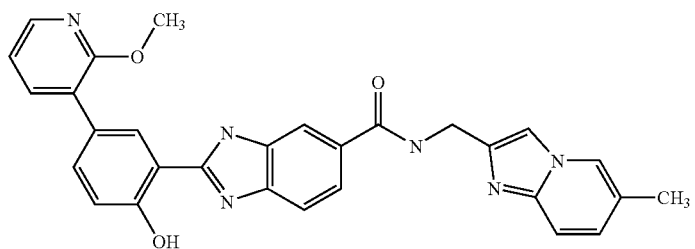 [SMILES: COc1ncccc1-c1ccc(O)c(-c2nc3ccc(C(=O)NCc4cn5cc(C)ccc5n4)cc3[nH]2)c1] | 505.6 |
| 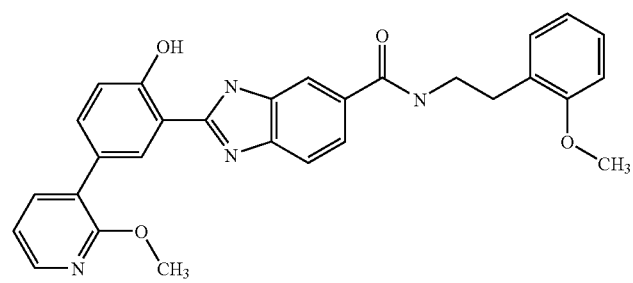 [SMILES: COc1ccccc1CCNC(=O)c1ccc2nc(-c3cc(-c4cccnc4OC)ccc3O)[nH]c2c1] | 495.6 |

-continued

| MOLSTRUCTURE | MW (M + 1) |
|---|---|
| | 481.5 |
| | 520.5 |
| | 469.5 |
| | 486.5 |
| | 516.6 |

| MOLSTRUCTURE | MW (M + 1) |
|---|---|
| 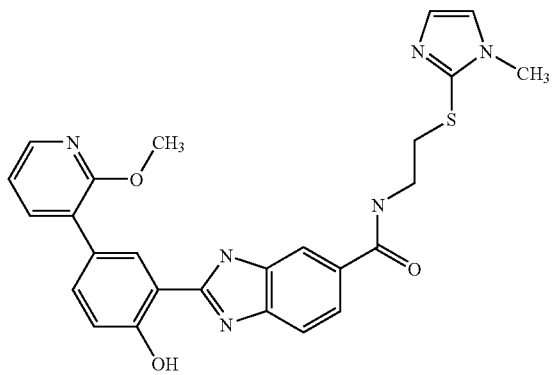 [SMILES: COc1ncccc1-c1ccc(O)c(-c2nc3ccc(C(=O)NCCSc4nccn4C)cc3[nH]2)c1] | 501.6 |
| 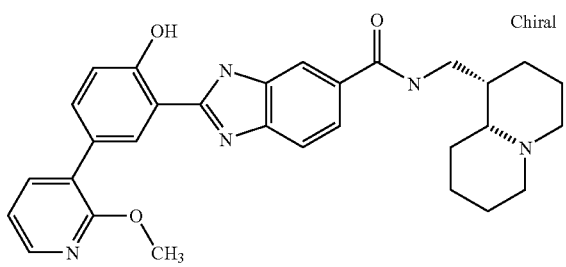 [SMILES: COc1ncccc1-c1ccc(O)c(-c2nc3ccc(C(=O)NC[C@@H]4CCCN5CCCC[C@H]45)cc3[nH]2)c1] | 512.6 |
| 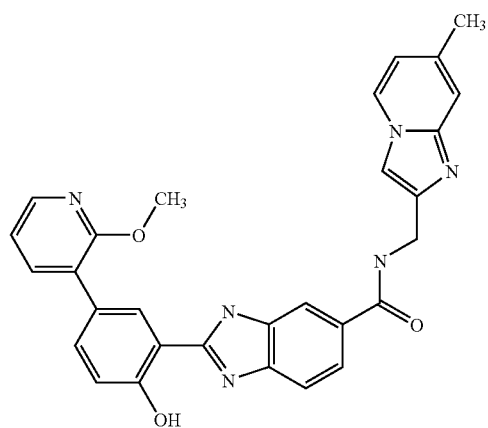 [SMILES: COc1ncccc1-c1ccc(O)c(-c2nc3ccc(C(=O)NCc4cn5ccc(C)cc5n4)cc3[nH]2)c1] | 505.6 |
| 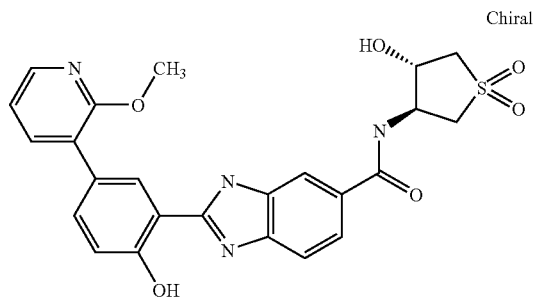 [SMILES: COc1ncccc1-c1ccc(O)c(-c2nc3ccc(C(=O)N[C@@H]4CS(=O)(=O)C[C@H]4O)cc3[nH]2)c1] | 495.5 |

-continued
| MOLSTRUCTURE | MW (M + 1) |
|---|---|
| 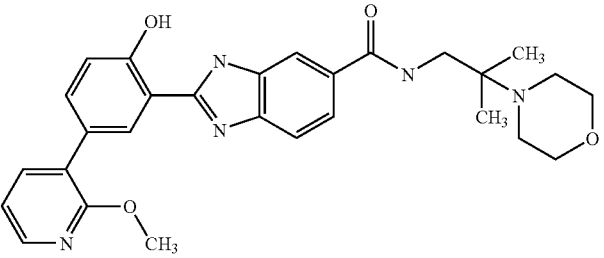 [SMILES: COc1ncccc1-c1ccc(O)c(-c2nc3ccc(C(=O)NCC(C)(C)N4CCOCC4)cc3[nH]2)c1] | 502.6 |
| 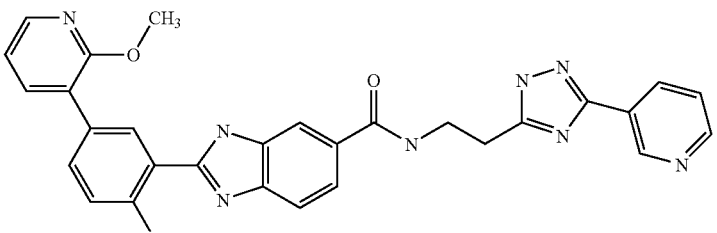 | 533.6 |
| 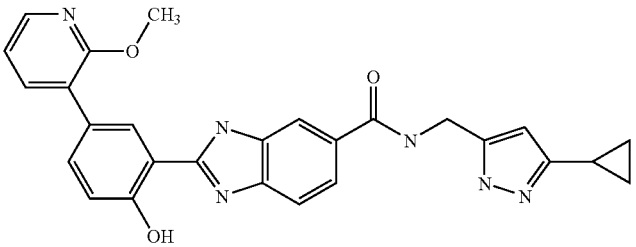 [SMILES: COc1ncccc1-c1ccc(O)c(-c2nc3ccc(C(=O)NCc4cc(C5CC5)n[nH]4)cc3[nH]2)c1] | 481.5 |
| 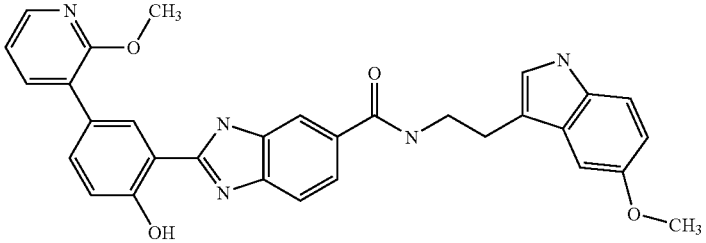 [SMILES: COc1ccc2[nH]cc(CCNC(=O)c3ccc4nc(-c5cc(-c6cccnc6OC)ccc5O)[nH]c4c3)c2c1] | 534.6 |
| 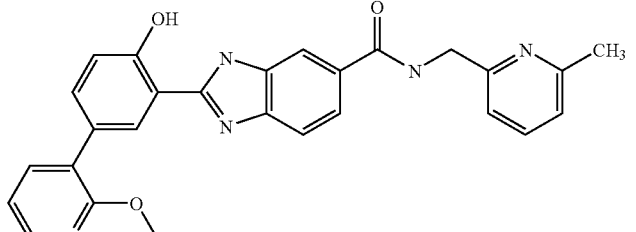 | 466.5 |
| 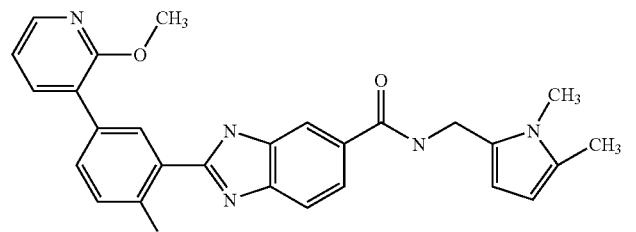 | 468.5 |

| MOLSTRUCTURE | MW (M + 1) |
|---|---|
| 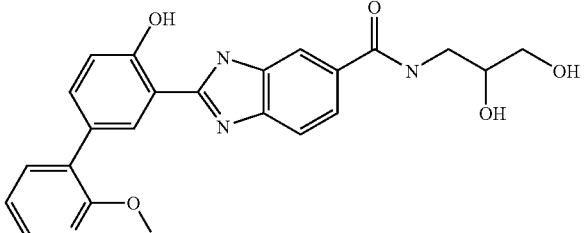 | 435.5 |
| 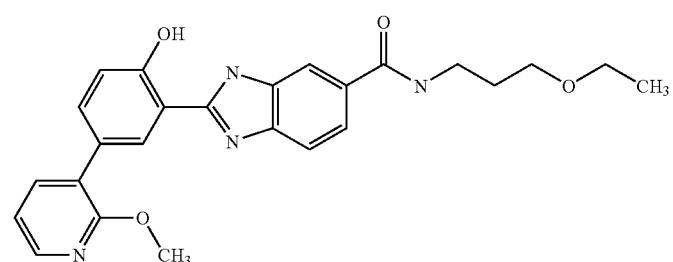 | 447.5 |
| 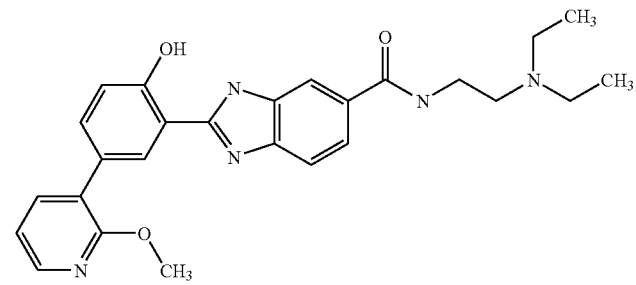 [SMILES: CCN(CC)CCNC(=O)c1ccc2nc(-c3cc(-c4cccnc4OC)ccc3O)[nH]c2c1] | 460.6 |
| 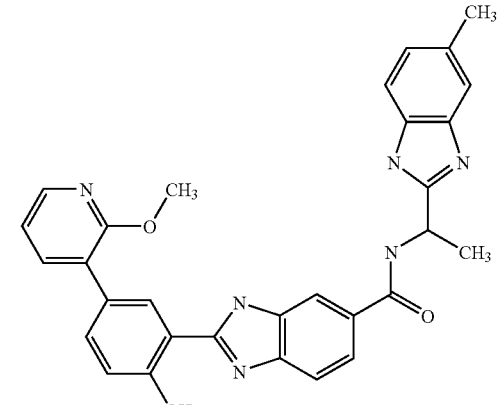 | 519.6 |
| 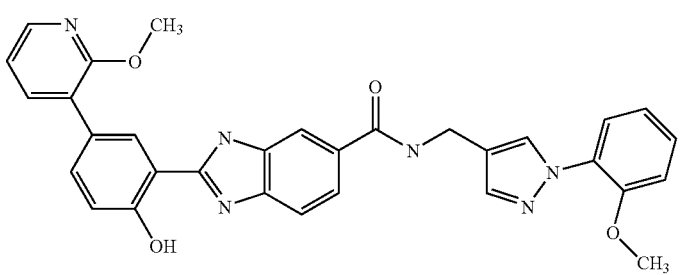 [SMILES: COc1ccccc1-n1cc(CNC(=O)c2ccc3nc(-c4cc(-c5cccnc5OC)ccc4O)[nH]c3c2)cn1] | 547.6 |

| MOLSTRUCTURE | MW (M + 1) |
|---|---|
| 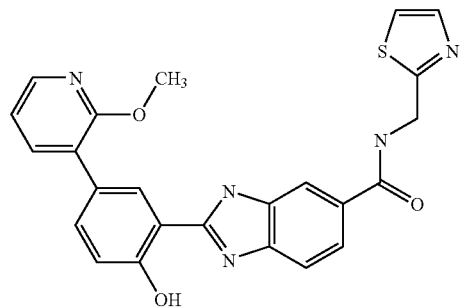 [SMILES: COc1ncccc1-c1ccc(O)c(-c2nc3ccc(C(=O)NCc4nccs4)cc3[nH]2)c1] | 458.5 |
| 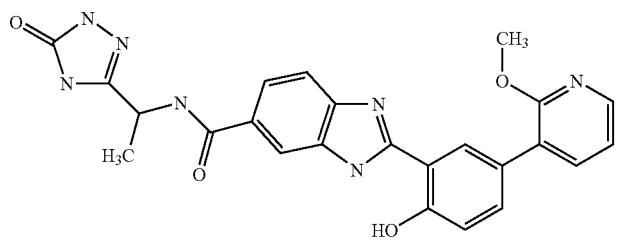 [SMILES: COc1ncccc1-c1ccc(O)c(-c2nc3ccc(C(=O)NC(C)c4n[nH]c(=O)[nH]4)cc3[nH]2)c1] | 472.5 |
| 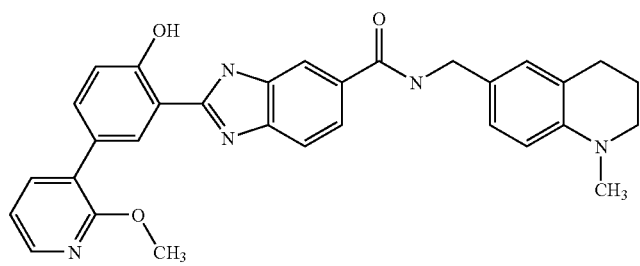 [SMILES: COc1ncccc1-c1ccc(O)c(-c2nc3ccc(C(=O)NCc4ccc5c(c4)CCCN5C)cc3[nH]2)c1] | 520.6 |
| 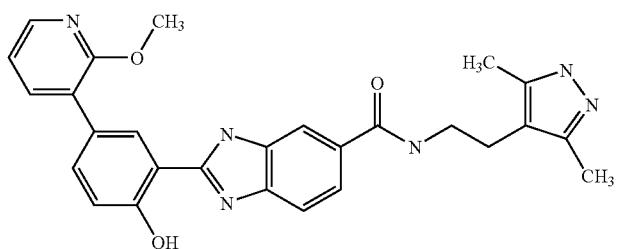 [SMILES: COc1ncccc1-c1ccc(O)c(-c2nc3ccc(C(=O)NCCc4c(C)n[nH]c4C)cc3[nH]2)c1] | 483.5 |
| 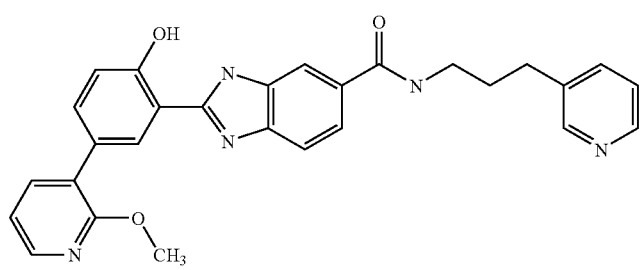 [SMILES: COc1ncccc1-c1ccc(O)c(-c2nc3ccc(C(=O)NCCCc4cccnc4)cc3[nH]2)c1] | 480.5 |

| MOLSTRUCTURE | MW (M + 1) |
|---|---|
| 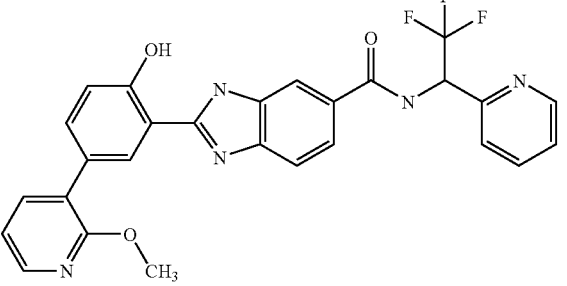 | 520.5 |
| 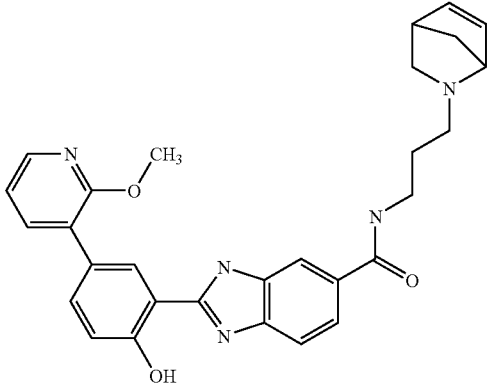 [SMILES: COc1ncccc1-c1ccc(O)c(-c2nc3ccc(C(=O)NCCCN4CC5C=CC4C5)cc3[nH]2)c1] | 496.6 |
| 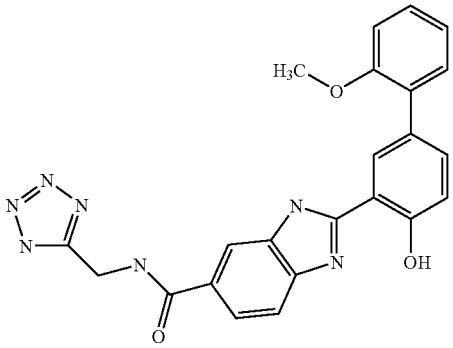 [SMILES: COc1ccccc1-c1ccc(O)c(-c2nc3ccc(C(=O)NCc4nnn[nH]4)cc3[nH]2)c1] | 443.4 |
| 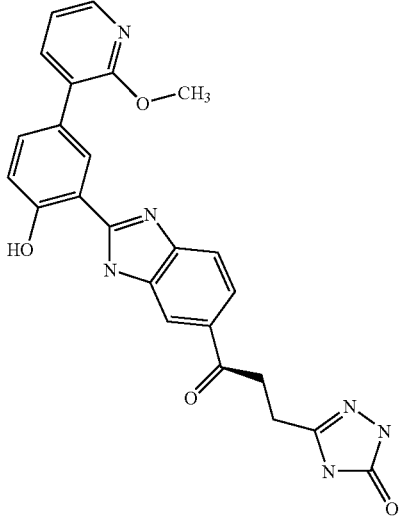 | 458.5 |

-continued
| MOLSTRUCTURE | MW (M + 1) |
|---|---|
| 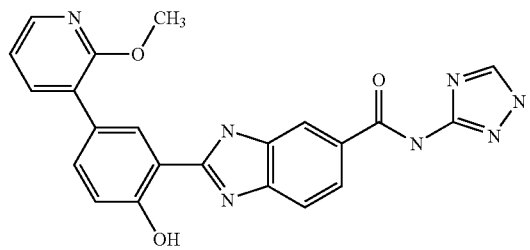 [SMILES: COc1ncccc1-c1ccc(O)c(-c2nc3ccc(C(=O)Nc4nc[nH]n4)cc3[nH]2)c1] | 428.4 |
| 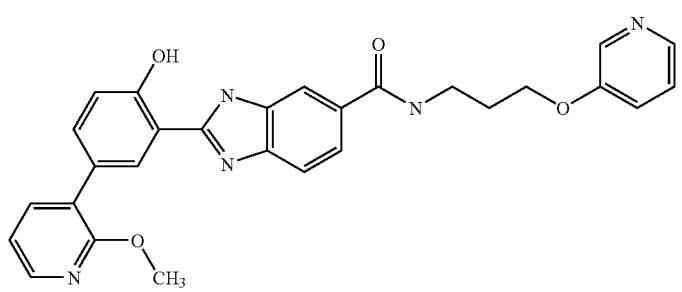 [SMILES: COc1ncccc1-c1ccc(O)c(-c2nc3ccc(C(=O)NCCCOc4cccnc4)cc3[nH]2)c1] | 496.5 |
| 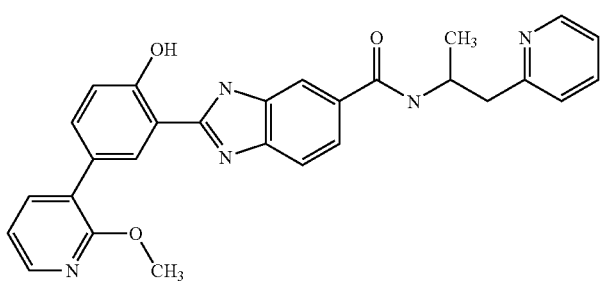 [SMILES: COc1ncccc1-c1ccc(O)c(-c2nc3ccc(C(=O)NC(C)Cc4ccccn4)cc3[nH]2)c1] | 480.5 |
| 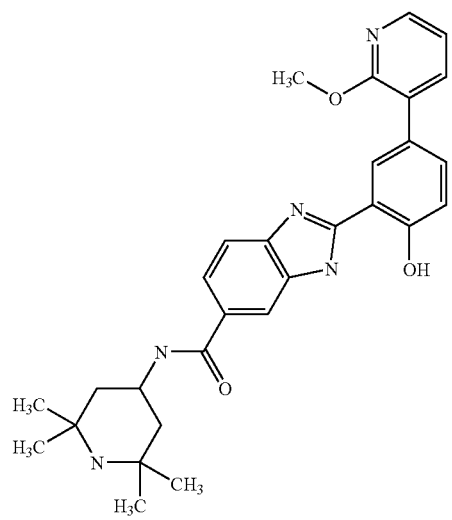 [SMILES: COc1ncccc1-c1ccc(O)c(-c2nc3ccc(C(=O)NC4CC(C)(C)NC(C)(C)C4)cc3[nH]2)c1] | 500.6 |

-continued

| MOLSTRUCTURE | MW (M + 1) |
|---|---|
| | 466.5 |
| | 472.6 |
| | 534.6 |
| | 499.6 |
| | 472.5 |

| MOLSTRUCTURE | MW (M + 1) |
| --- | --- |
| 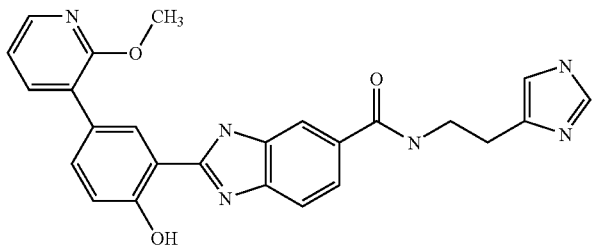 [SMILES: COc1ncccc1-c1ccc(O)c(-c2nc3ccc(C(=O)NCCc4c[nH]cn4)cc3[nH]2)c1] | 455.5 |
| 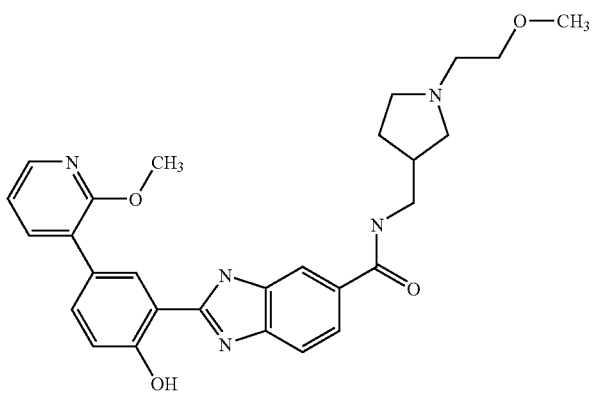 [SMILES: COCCN1CCC(CNC(=O)c2ccc3nc(-c4cc(-c5cccnc5OC)ccc4O)[nH]c3c2)C1] | 502.6 |
| 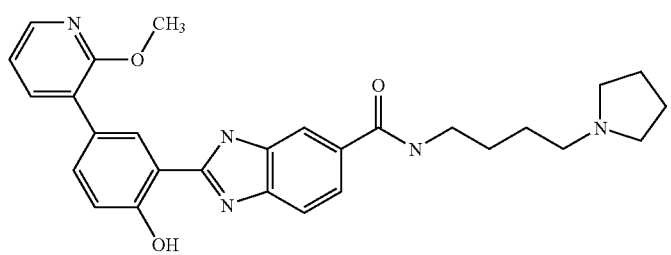 [SMILES: COc1ncccc1-c1ccc(O)c(-c2nc3ccc(C(=O)NCCCCN4CCCC4)cc3[nH]2)c1] | 486.6 |
| 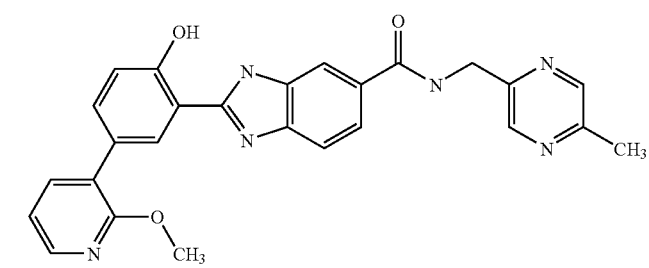 [SMILES: COc1ncccc1-c1ccc(O)c(-c2nc3ccc(C(=O)NCc4cnc(C)cn4)cc3[nH]2)c1] | 467.5 |
| 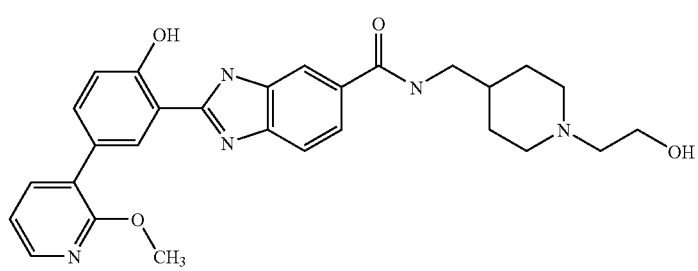 [SMILES: COc1ncccc1-c1ccc(O)c(-c2nc3ccc(C(=O)NCC4CCN(CCO)CC4)cc3[nH]2)c1] | 502.6 |

| MOLSTRUCTURE | MW (M + 1) |
|---|---|
| 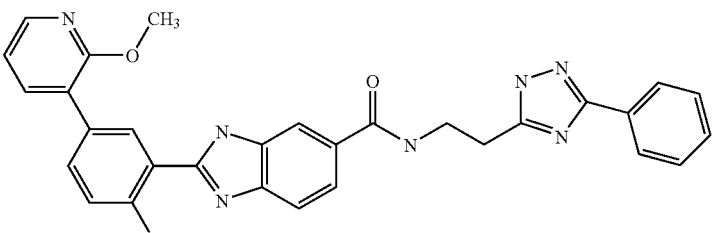 | 532.6 |
| 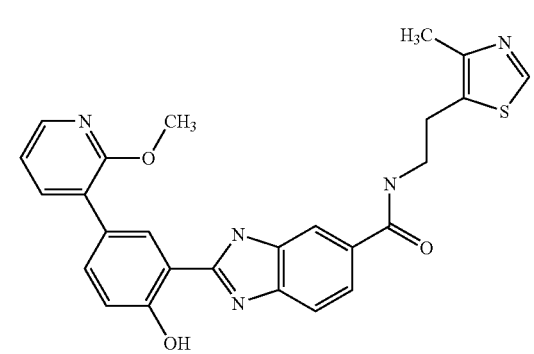 [SMILES: COc1ncccc1-c1ccc(O)c(-c2nc3ccc(C(=O)NCCc4scnc4C)cc3[nH]2)c1] | 486.6 |
| 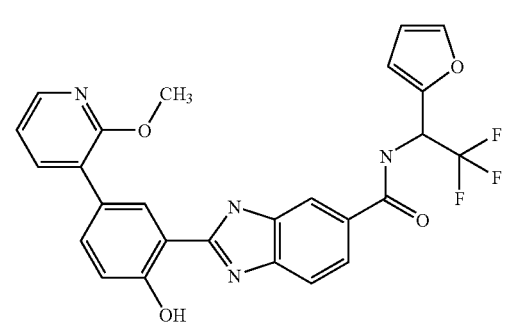 [SMILES: COc1ncccc1-c1ccc(O)c(-c2nc3ccc(C(=O)NC(c4ccco4)C(F)(F)F)cc3[nH]2)c1] | 509.5 |
| 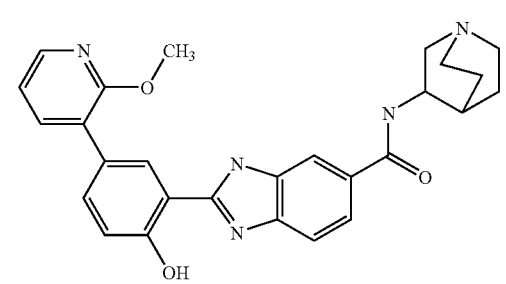 [SMILES: COc1ncccc1-c1ccc(O)c(-c2nc3ccc(C(=O)NC4CN5CCC4CC5)cc3[nH]2)c1] | 470.5 |
| 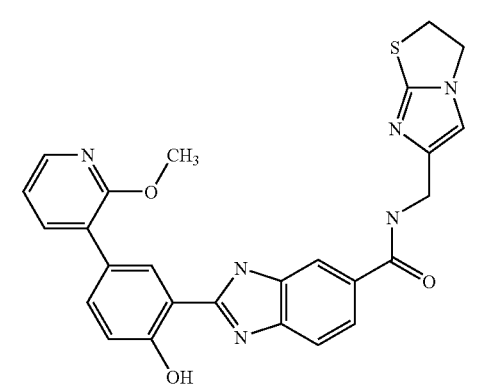 [SMILES: COc1ncccc1-c1ccc(O)c(-c2nc3ccc(C(=O)NCc4cn5c(n4)SCC5)cc3[nH]2)c1] | 499.6 |

| MOLSTRUCTURE | MW (M + 1) |
|---|---|
| 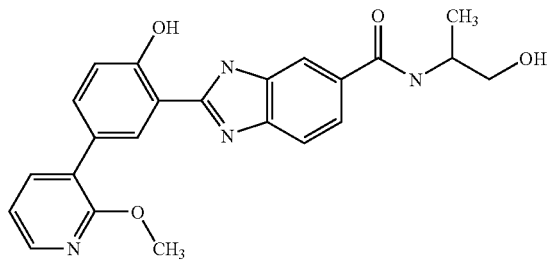 [SMILES: COc1ncccc1-c1ccc(O)c(-c2nc3ccc(C(=O)NC(C)CO)cc3[nH]2)c1] | 419.5 |
| 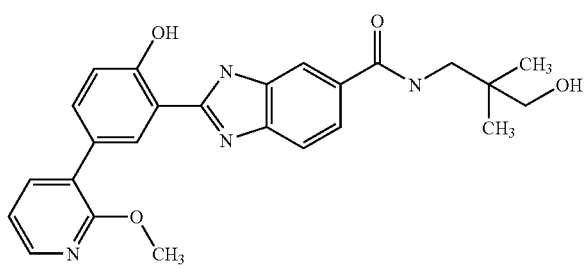 [SMILES: COc1ncccc1-c1ccc(O)c(-c2nc3ccc(C(=O)NCC(C)(C)CO)cc3[nH]2)c1] | 447.5 |
| 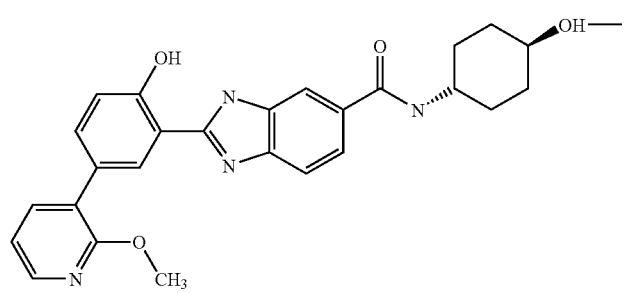 | 459.5 |
| 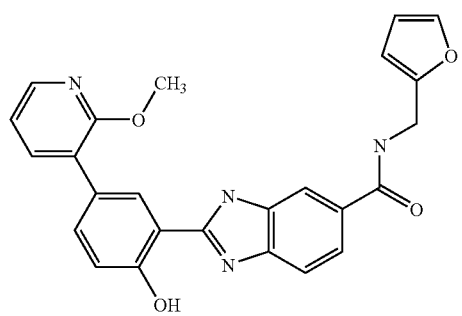 [SMILES: COc1ncccc1-c1ccc(O)c(-c2nc3ccc(C(=O)NCc4ccco4)cc3[nH]2)c1] | 441.5 |
| 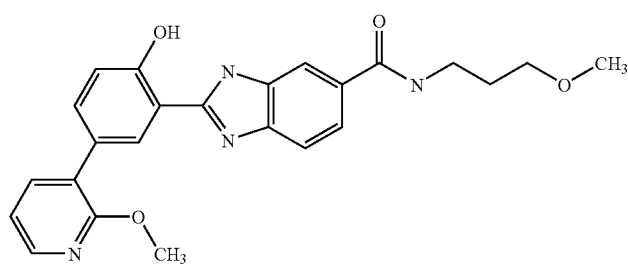 [SMILES: COCCCNC(=O)c1ccc2nc(-c3cc(-c4cccnc4OC)ccc3O)[nH]c2c1] | 433.5 |

-continued

| MOLSTRUCTURE | MW (M + 1) |
| --- | --- |
| | 431.5 |
| | 473.6 |
| | 445.5 |
| | 500.6 |

-continued

| MOLSTRUCTURE | MW (M + 1) |
| --- | --- |
|  | 472.6 |
|  | 484.6 |
|  | 500.6 |
|  | 447.5 |
|  | 544.6 |

| MOLSTRUCTURE | MW (M + 1) |
|---|---|
| 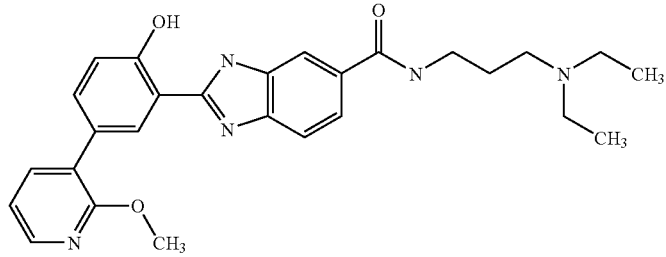 | 474.6 |
| 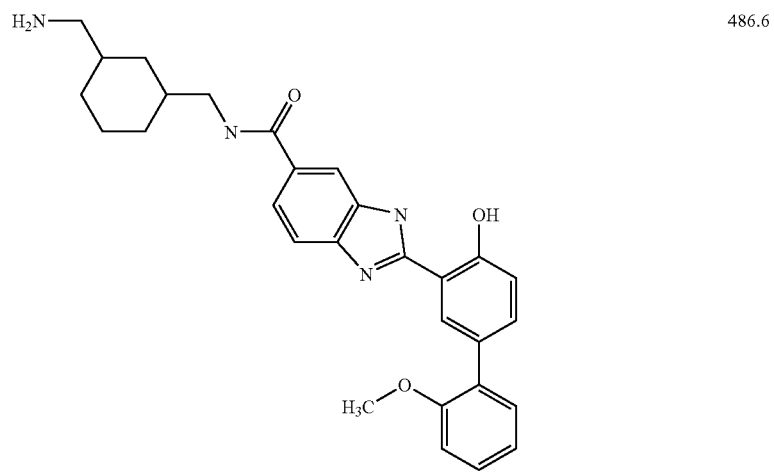 | 486.6 |
| 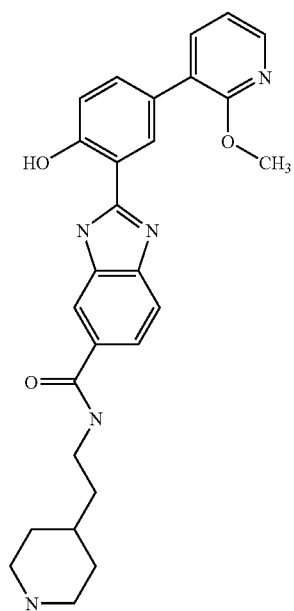 [SMILES: COc1ncccc1-c1ccc(O)c(-c2nc3ccc(C(=O)NCCN4CCNCC4)cc3[nH]2)c1] | 473.6 |

| MOLSTRUCTURE | MW (M + 1) |
|---|---|
| 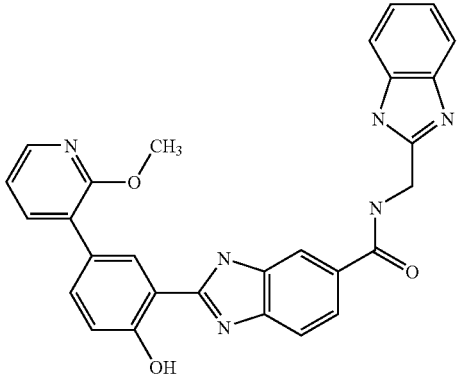 [SMILES: COc1ncccc1-c1ccc(O)c(-c2nc3ccc(C(=O)NCc4nc5ccccc5[nH]4)cc3[nH]2)c1] | 491.5 |
| 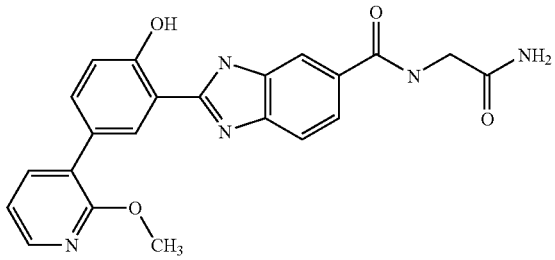 [SMILES: COc1ncccc1-c1ccc(O)c(-c2nc3ccc(C(=O)NCC(N)=O)cc3[nH]2)c1] | 418.4 |
| 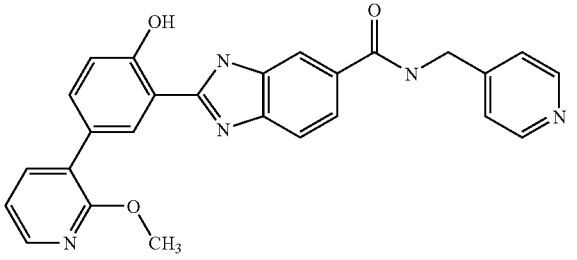 [SMILES: COc1ncccc1-c1ccc(O)c(-c2nc3ccc(C(=O)NCc4ccncc4)cc3[nH]2)c1] | 452.5 |
| 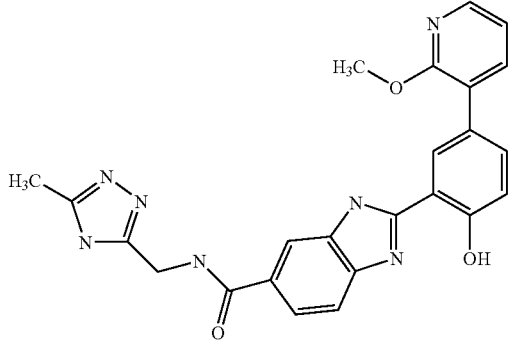 [SMILES: COc1ncccc1-c1ccc(O)c(-c2nc3ccc(C(=O)NCc4nnc(C)[nH]4)cc3[nH]2)c1] | 456.5 |
| 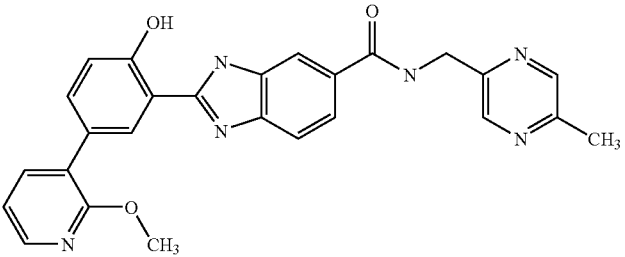 [SMILES: COc1ncccc1-c1ccc(O)c(-c2nc3ccc(C(=O)NCc4cnc(C)cn4)cc3[nH]2)c1] | 467.5 |

| MOLSTRUCTURE | MW (M + 1) |
| --- | --- |
| | 455.5 |
| | 473.5 |
| | 454.5 |
| | 458.5 |
| | 458.5 |

| MOLSTRUCTURE | MW (M + 1) |
|---|---|
| 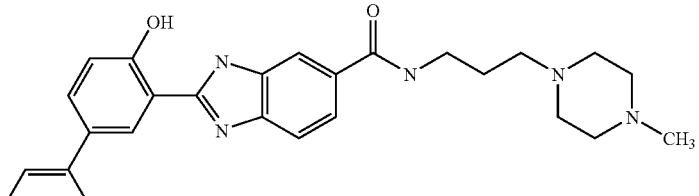 | 501.6 |
| 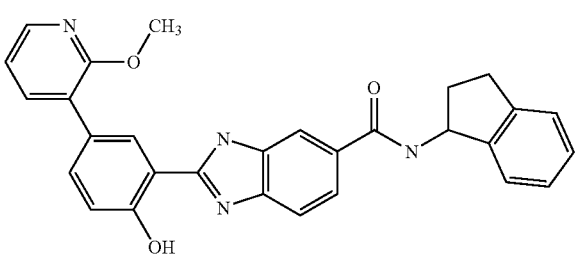 [SMILES: COc1ncccc1-c1ccc(O)c(-c2nc3ccc(C(=O)NC4CCc5ccccc54)cc3[nH]2)c1] | 477.5 |
| 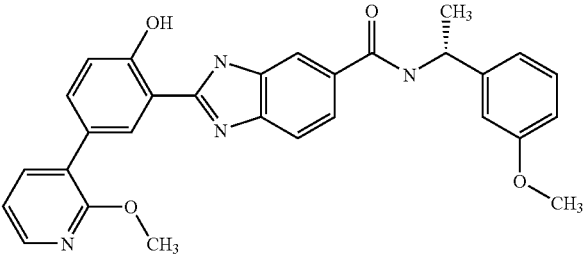 Chiral | 495.6 |
| 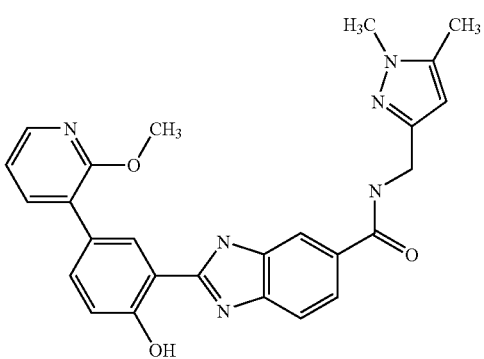 [SMILES: COc1ncccc1-c1ccc(O)c(-c2nc3ccc(C(=O)NCc4cc(C)n(C)n4)cc3[nH]2)c1] | 469.5 |
| 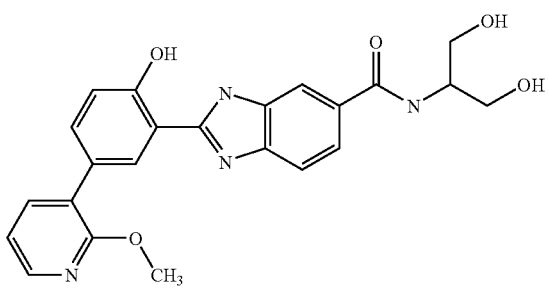 [SMILES: COc1ncccc1-c1ccc(O)c(-c2nc3ccc(C(=O)NC(CO)CO)cc3[nH]2)c1] | 435.5 |

-continued

| MOLSTRUCTURE | MW (M + 1) |
|---|---|
| | 466.5 |
| | 447.5 |
| | 445.5 |
| Chiral | 472.5 |
| | 486.6 |

| MOLSTRUCTURE | MW (M + 1) |
|---|---|
| 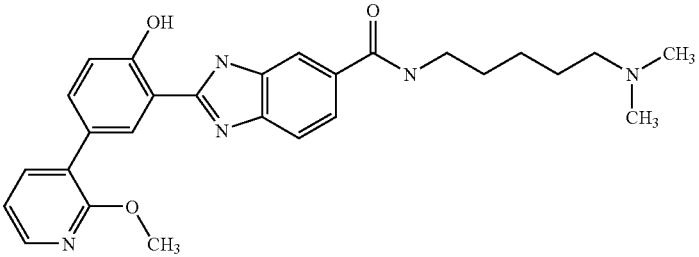 [SMILES: COc1ncccc1-c1ccc(O)c(-c2nc3ccc(C(=O)NCCCCCN(C)C)cc3[nH]2)c1] | 474.6 |
| 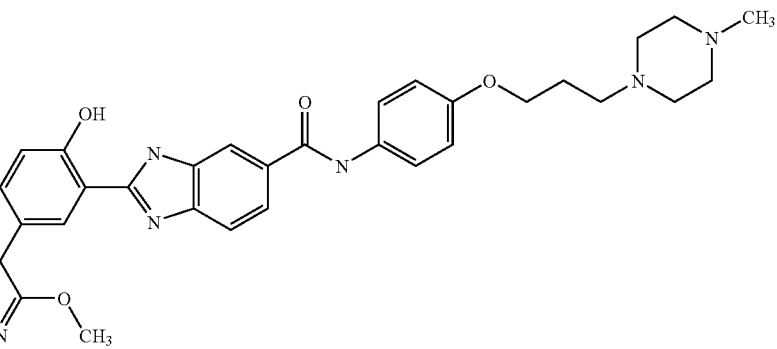 | 593.7 |
| 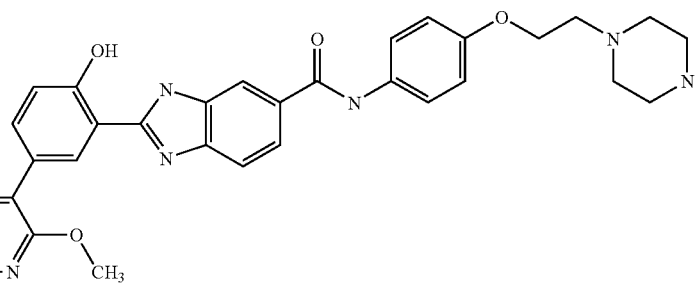 | 579.7 |
| 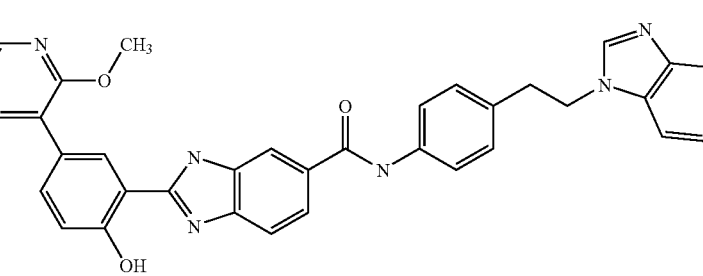 | 581.7 |
| 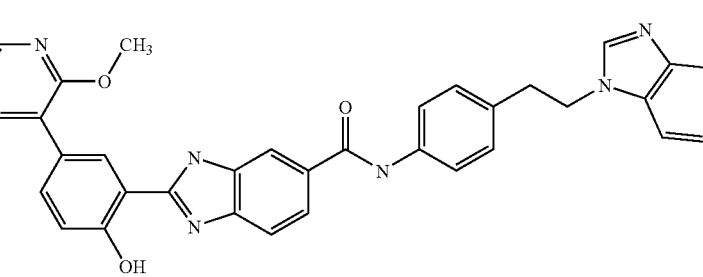 | 582.6 |

-continued

| MOLSTRUCTURE | MW (M + 1) |
|---|---|
| | 505.6 |
| | 593.7 |
| | 531.6 |
| | 496.5 |

| MOLSTRUCTURE | MW (M + 1) |
|---|---|
| 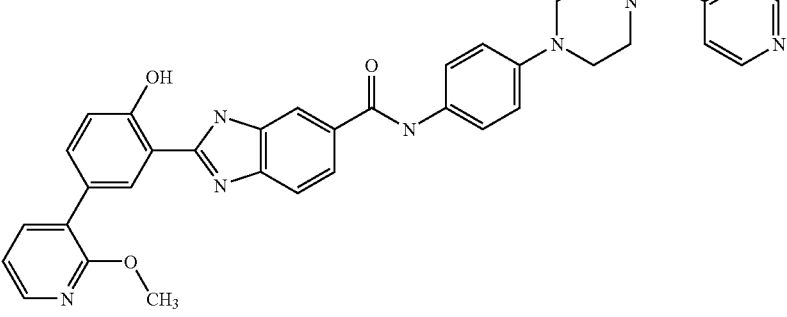 | 612.7 |
| 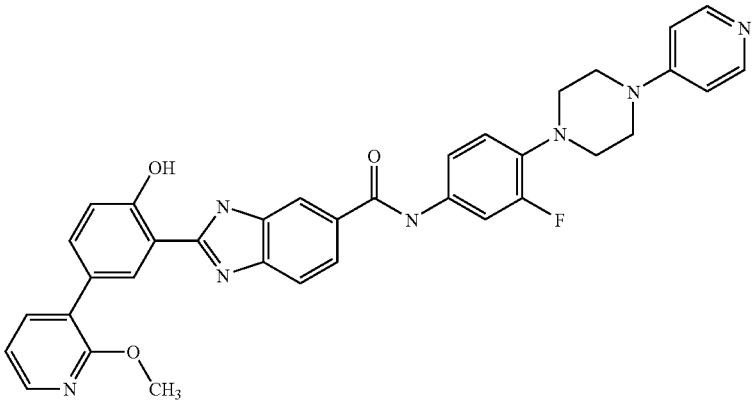 [SMILES: COc1ncccc1-c1ccc(O)c(-c2nc3ccc(C(=O)Nc4ccc(N5CCN(c6ccncc6)CC5)c(F)c4)cc3[nH]2)c1] | 616.7 |
| 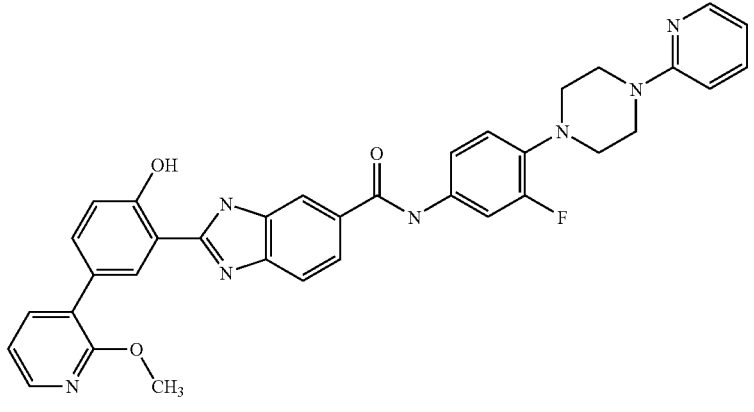 [SMILES: COc1ncccc1-c1ccc(O)c(-c2nc3ccc(C(=O)Nc4ccc(N5CCN(c6ccccn6)CC5)c(F)c4)cc3[nH]2)c1] | 616.7 |
| 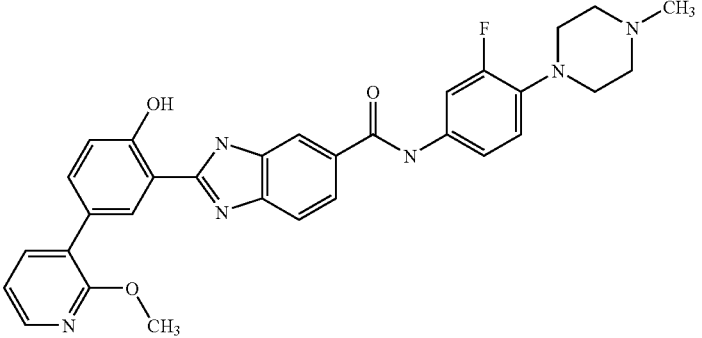 [SMILES: COc1ncccc1-c1ccc(O)c(-c2nc3ccc(C(=O)Nc4ccc(N5CCN(C)CC5)c(F)c4)cc3[nH]2)c1] | 553.6 |

| MOLSTRUCTURE | MW (M + 1) |
|---|---|
| 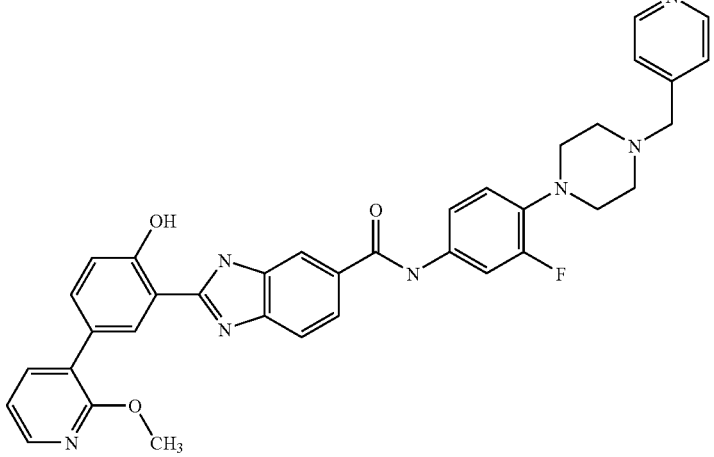 | 630.7 |
| 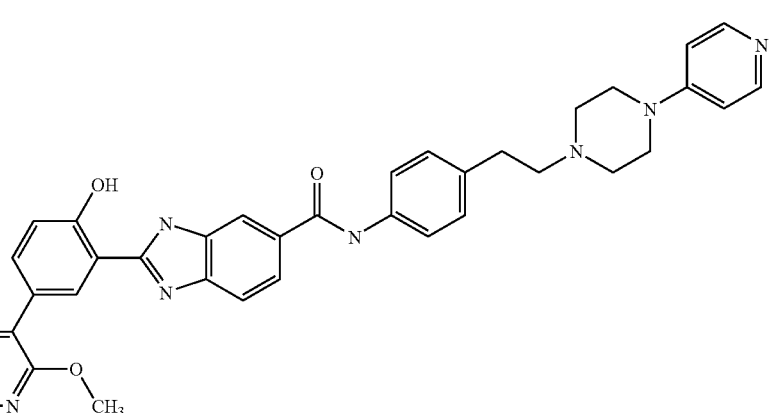 | 626.7 |
| 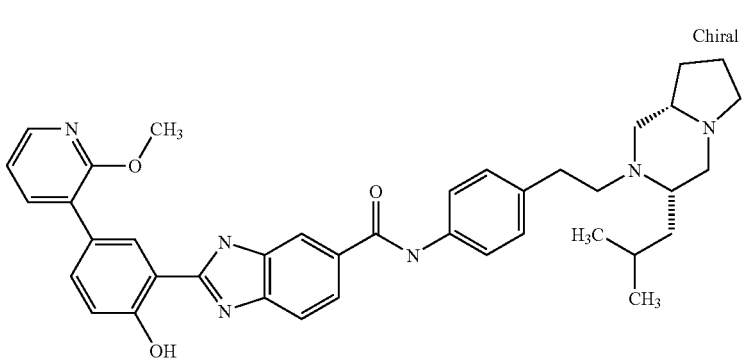 [SMILES: COc1ncccc1-c1ccc(O)c(-c2nc3ccc(C(=O)Nc4ccc(CCN5C[C@@H]6CCCN6C[C@@H]5CC(C)C)cc4)cc3[nH]2)c1] | 645.8 |
| 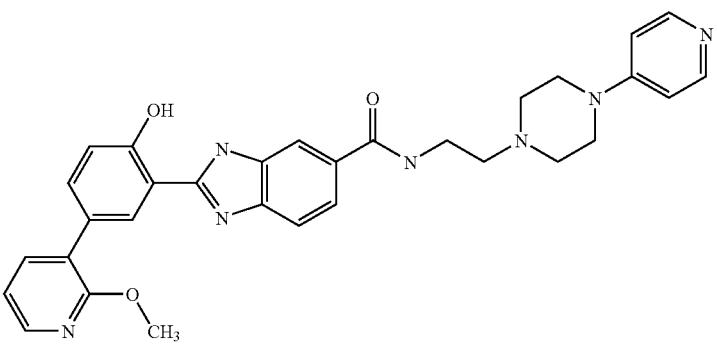 [SMILES: COc1ncccc1-c1ccc(O)c(-c2nc3ccc(C(=O)NCCN4CCN(c5ccncc5)CC4)cc3[nH]2)c1] | 550.6 |

-continued

| MOLSTRUCTURE | MW (M + 1) |
|---|---|
| | 564.6 |
| | 535.5 |
| | 577.7 |
| | 536.6 |
| | 375.4 |

| MOLSTRUCTURE | MW (M + 1) |
|---|---|
| | 389.4 |
| | 458.5 |
| | 416.5 |
| | 563.7 |

5.2.5.2 Procedure for the Production of Amines in the Following Table

In this section, the term Int refers to acid and the term BB refers to amines.

Procedure 1 (For Primary and Secondary Amines)

Each of a set of glass-tubes (6 mL) was charged with 100 µmol (500 µL) of Int, 110 µmol (500 µL) of HBTU, 125 µmol (350 µL) of amines (BB), and 75 µL of TEA. All the solutions were in DMF. The reaction mixtures were stirred on a Vortex shaker at 45° C. for 24 h. The reaction mixtures were purified by preparative LCMS.

Procedure 2 (For Anilines and Low Basicity Amines)

Each of a set of glass-tubes (6 mL) was charged with 100 µmol (500 µL) of Int, 110 µmol (500 µL) of HATU, 125 µmol (350 µL) of amines (BB), and 100 µL of DIPEA. All the solutions were in DMF. The reaction mixtures were stirred on a Vortex shaker at 65° C. for 2 h. Then 50 µmol of HATU in DMF was added. The reaction mixtures were shaken again on a Vortex shaker at 65° C. for 24 h. The reaction mixtures were purified by preparative LCMS.

In either procedure 1 or procedure 2, along with the target product, a by-product of a reaction with the OH group formed (By). In order to hydrolyze the byproduct, a mixture of TFA (100 uL) and water (100 uL) was added to the reaction mixture 24 h before purification.

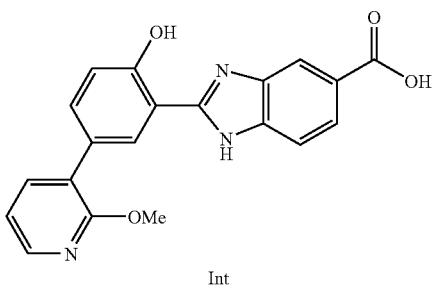

Int

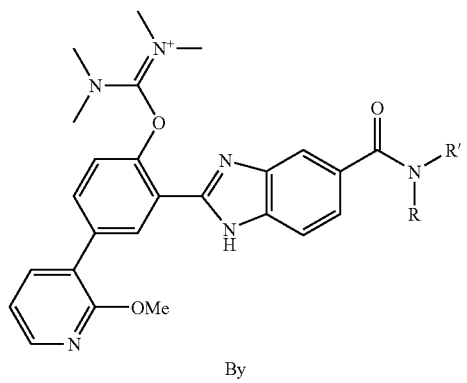
By
By application of the above methodologies the compounds in the following table were prepared:
| Structure | M + 1 |
| --- | --- |
| 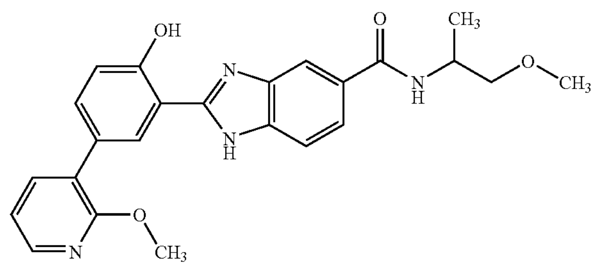 [SMILES: COCC(C)NC(=O)c1ccc2[nH]c(-c3cc(-c4cccnc4OC)ccc3O)nc2c1] | 433.48 |
| 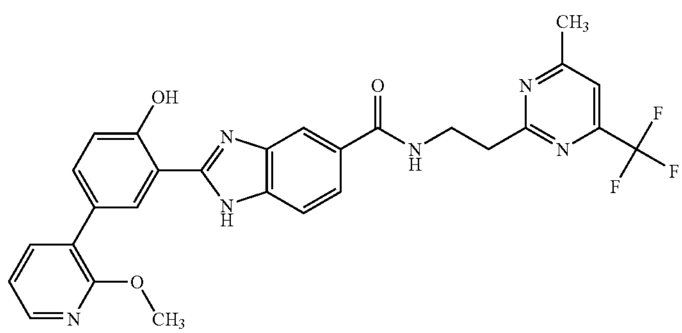 [SMILES: COc1ncccc1-c1ccc(O)c(-c2nc3cc(C(=O)NCCc4nc(C)cc(C(F)(F)F)n4)ccc3[nH]2)c1] | 549.53 |
| 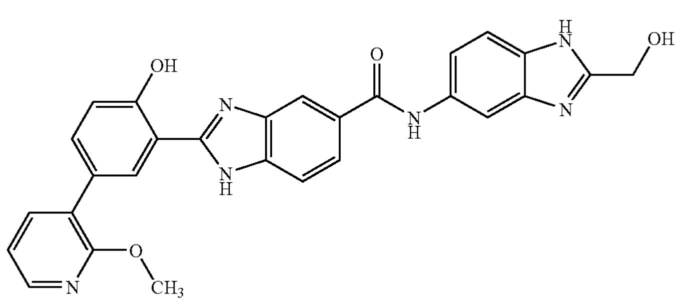 [SMILES: COc1ncccc1-c1ccc(O)c(-c2nc3cc(C(=O)Nc4ccc5[nH]c(CO)nc5c4)ccc3[nH]2)c1] | 507.53 |

-continued
| Structure | M + 1 |
|---|---|
| 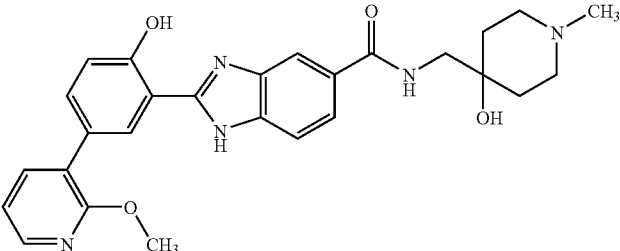 | 488.56 |
| 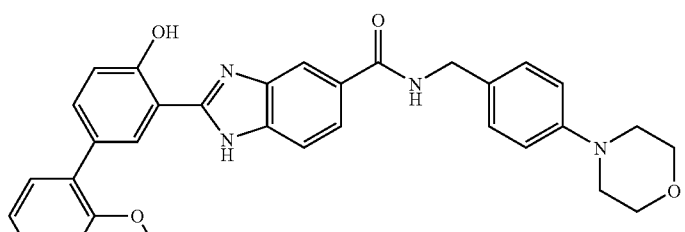 | 536.61 |
| 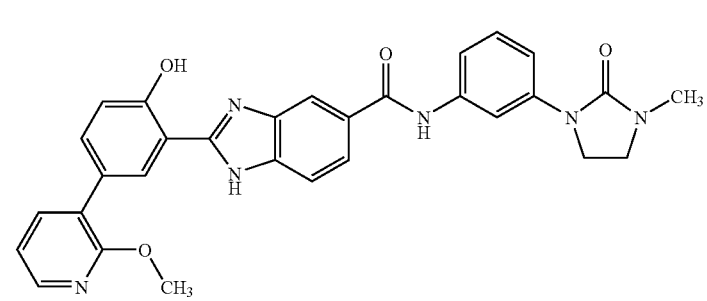 [SMILES: COc1ncccc1-c1ccc(O)c(-c2nc3cc(C(=O)Nc4cccc(N5CCN(C)C5=O)c4)ccc3[nH]2)c1] | 535.58 |
| 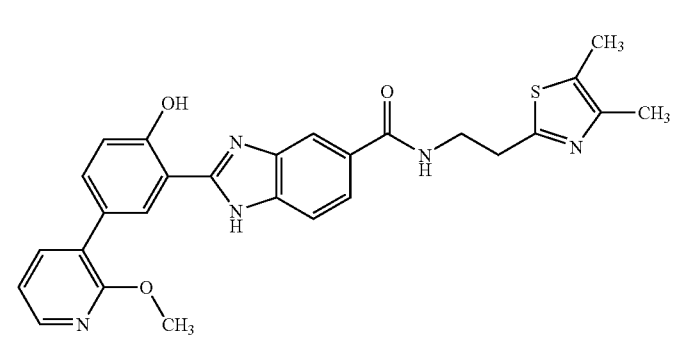 [SMILES: COc1ncccc1-c1ccc(O)c(-c2nc3cc(C(=O)NCCc4nc(C)c(C)s4)ccc3[nH]2)c1] | 500.60 |
| 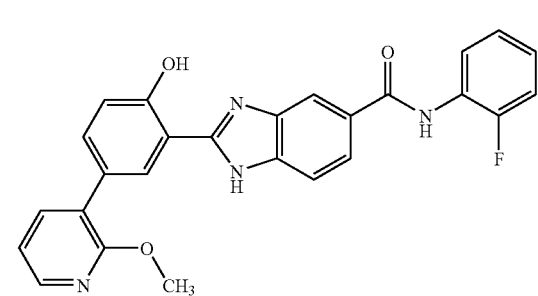 | 455.46 |

| Structure | M + 1 |
|---|---|
| 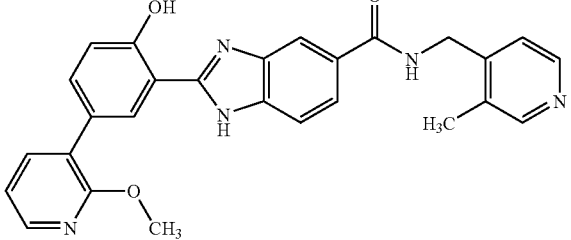 | 466.52 |
| 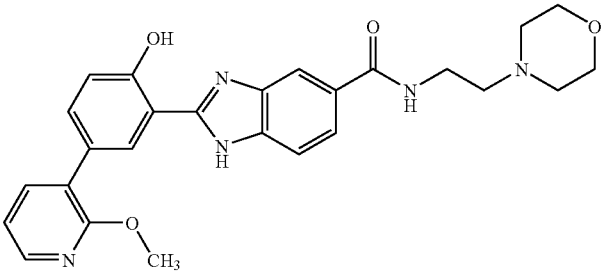 [SMILES: COc1ncccc1-c1ccc(O)c(-c2nc3cc(C(=O)NCCN4CCOCC4)ccc3[nH]2)c1] | 474.54 |
| 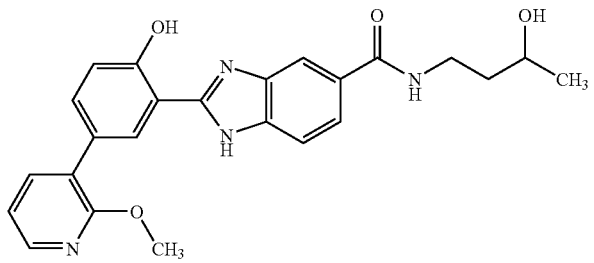 | 433.48 |
| 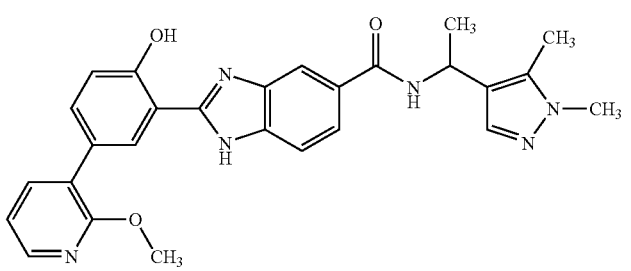 | 483.55 |
| 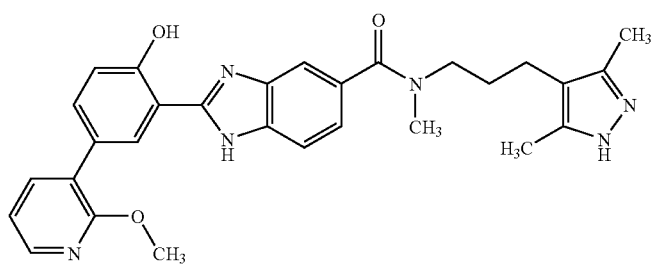 [SMILES: COc1ncccc1-c1ccc(O)c(-c2nc3cc(C(=O)N(C)CCCc4c(C)n[nH]c4C)ccc3[nH]2)c1] | 511.60 |

-continued

| Structure | M + 1 |
|---|---|
| Chiral | 489.55 |
| 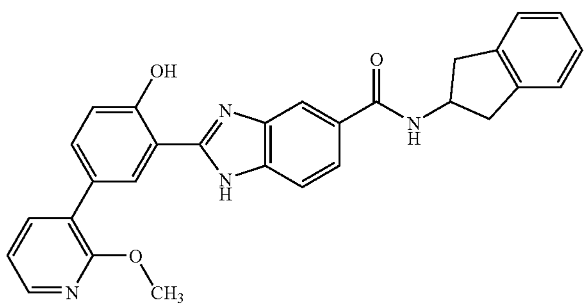 [SMILES: COc1ncccc1-c1ccc(O)c(-c2nc3cc(C(=O)NC4Cc5ccccc5C4)ccc3[nH]2)c1] | 477.54 |
| Chiral | 526.66 |
| | 455.49 |
| | 455.49 |

| Structure | M + 1 |
|---|---|
| 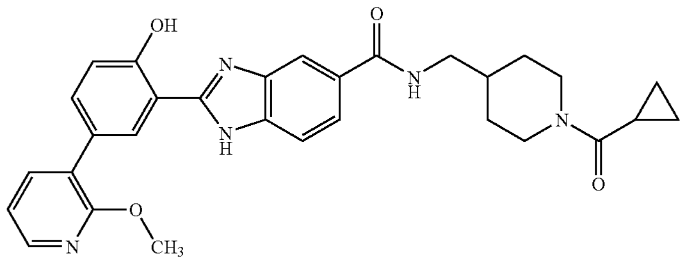 [SMILES: COc1ncccc1-c1ccc(O)c(-c2nc3cc(C(=O)NCC4CCN(C(=O)C5CC5)CC4)ccc3[nH]2)c1] | 526.61 |
| 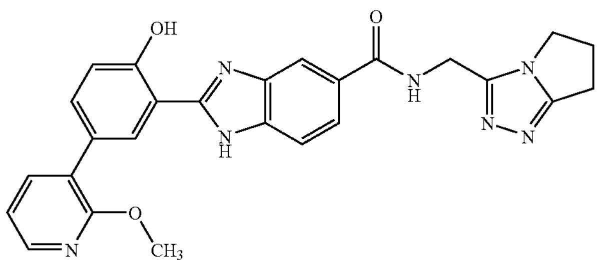 [SMILES: COc1ncccc1-c1ccc(O)c(-c2nc3cc(C(=O)NCc4nnc5n4CCC5)ccc3[nH]2)c1] | 482.52 |
| 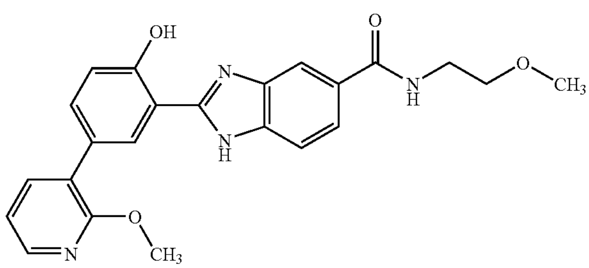 [SMILES: COCCNC(=O)c1ccc2[nH]c(-c3cc(-c4cccnc4OC)ccc3O)nc2c1] | 419.46 |
| 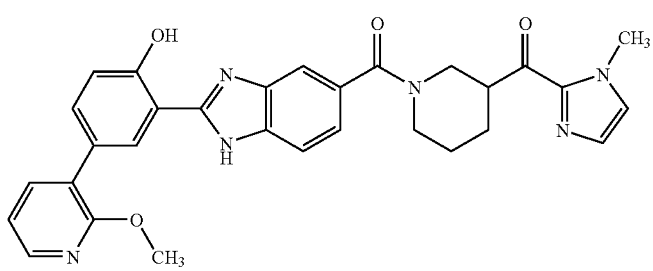 [SMILES: COc1ncccc1-c1ccc(O)c(-c2nc3cc(C(=O)N4CCCC(C(=O)c5nccn5C)C4)ccc3[nH]2)c1] | 537.60 |
| 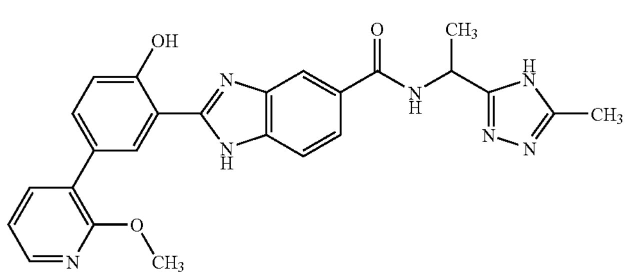 [SMILES: COc1ncccc1-c1ccc(O)c(-c2nc3cc(C(=O)NC(C)c4nnc(C)[nH]4)ccc3[nH]2)c1] | 470.51 |

-continued
| Structure | M + 1 |
|---|---|
| 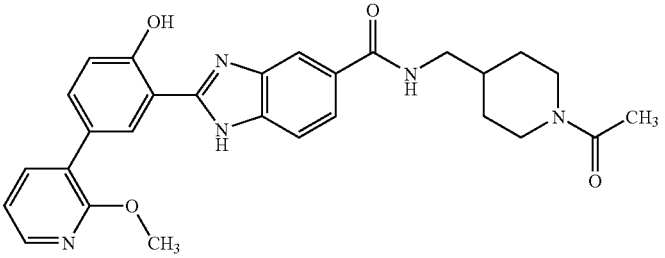 [SMILES: COc1ncccc1-c1ccc(O)c(-c2nc3cc(C(=O)NCC4CCN(C(C)=O)CC4)ccc3[nH]2)c1] | 500.57 |
| 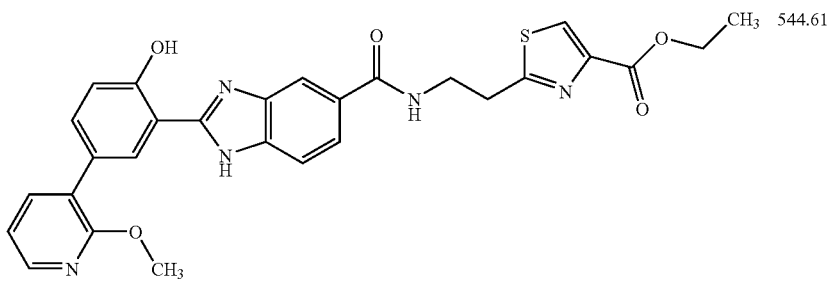 | 544.61 |
| 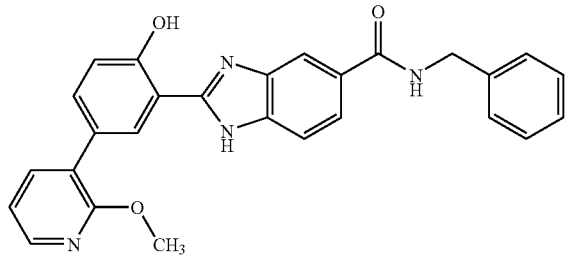 [SMILES: COc1ncccc1-c1ccc(O)c(-c2nc3cc(C(=O)NCc4ccccc4)ccc3[nH]2)c1] | 451.50 |
| 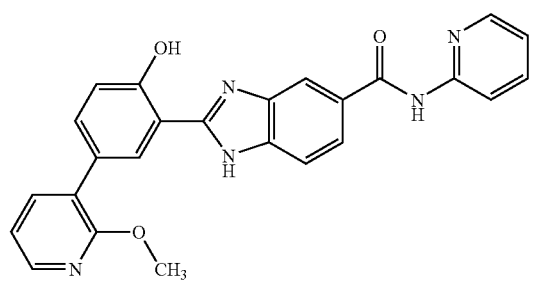 | 438.46 |
| 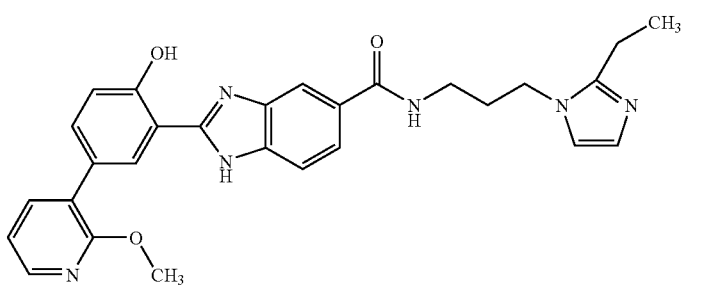 [SMILES: CCc1nccn1CCCNC(=O)c1ccc2[nH]c(-c3cc(-c4cccnc4OC)ccc3O)nc2c1] | 497.57 |

| Structure | M + 1 |
|---|---|
| (structure) | 523.57 |
| (structure) | 509.58 |
| (structure) | 520.52 |
| (structure) | 518.55 |
| (structure) | 516.62 |

-continued

| Structure | M + 1 |
|---|---|
| 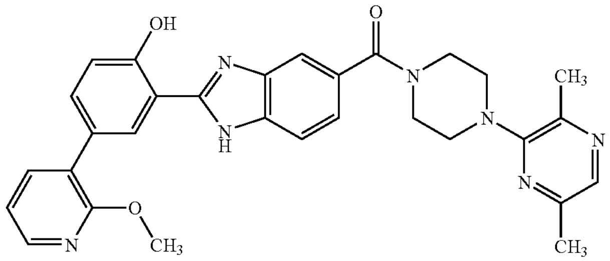 [SMILES: COc1ncccc1-c1ccc(O)c(-c2nc3cc(C(=O)N4CCN(c5nc(C)cnc5C)CC4)ccc3[nH]2)c1] | 536.61 |
| 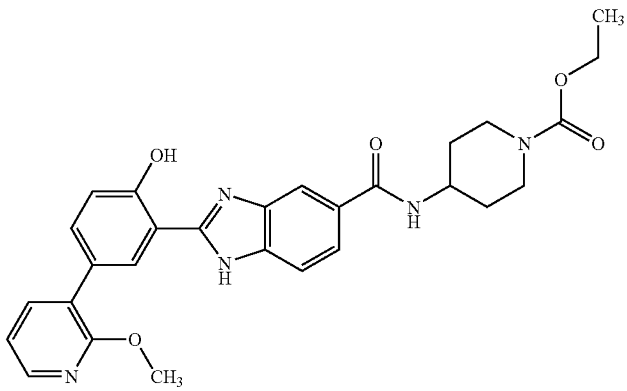 [SMILES: CCOC(=O)N1CCC(NC(=O)c2ccc3[nH]c(-c4cc(-c5cccnc5OC)ccc4O)nc3c2)CC1] | 516.57 |
| 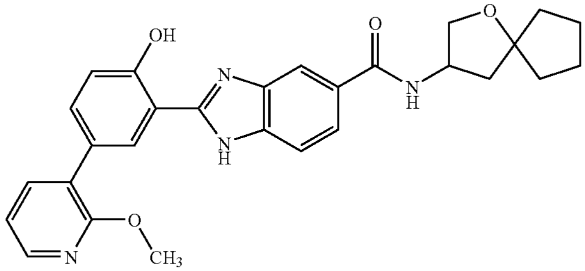 [SMILES: COc1ncccc1-c1ccc(O)c(-c2nc3cc(C(=O)NC4COC5(CCCC5)C4)ccc3[nH]2)c1] | 485.56 |
| 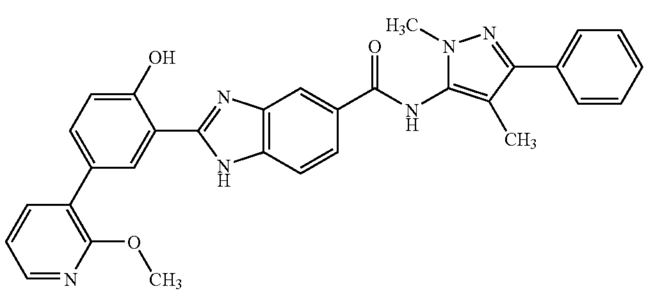 [SMILES: COc1ncccc1-c1ccc(O)c(-c2nc3cc(C(=O)Nc4c(C)c(-c5ccccc5)nn4C)ccc3[nH]2)c1] | 531.59 |
| 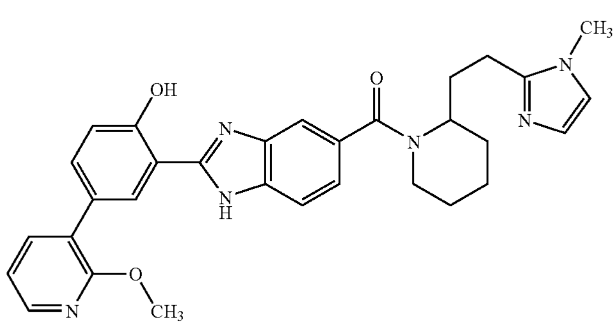 [SMILES: COc1ncccc1-c1ccc(O)c(-c2nc3cc(C(=O)N4CCCCC4CCc4nccn4C)ccc3[nH]2)c1] | 537.64 |

-continued
| Structure | M + 1 |
|---|---|
| 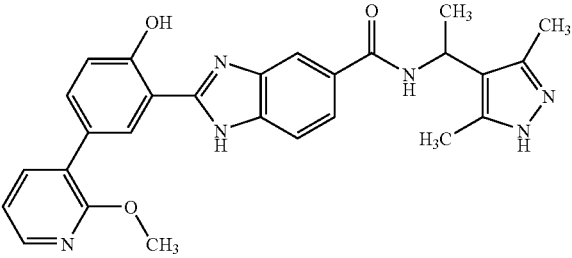 [SMILES: COc1ncccc1-c1ccc(O)c(-c2nc3cc(C(=O)NC(C)c4c(C)n[nH]c4C)ccc3[nH]2)c1] | 483.55 |
| 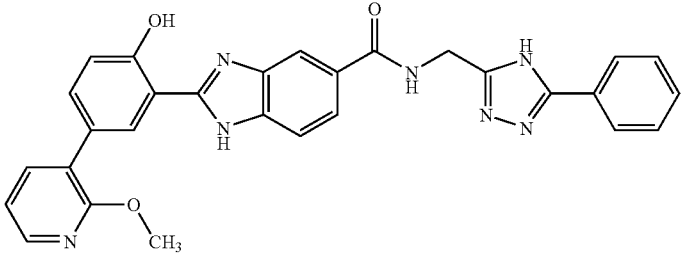 | 518.55 |
| 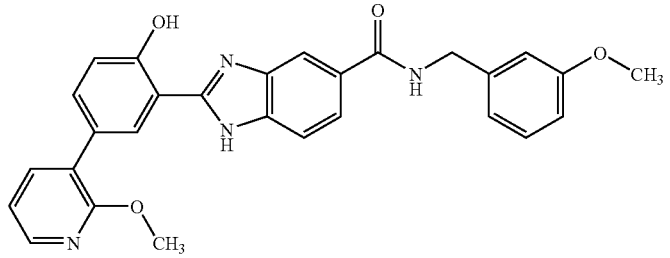 [SMILES: COc1cccc(CNC(=O)c2ccc3[nH]c(-c4cc(-c5cccnc5OC)ccc4O)nc3c2)c1] | 481.53 |
| 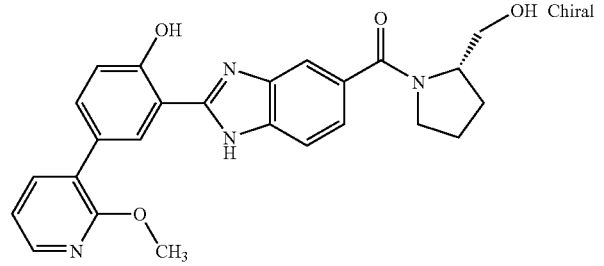 [SMILES: COc1ncccc1-c1ccc(O)c(-c2nc3cc(C(=O)N4CCC[C@H]4CO)ccc3[nH]2)c1] | 445.49 |
| 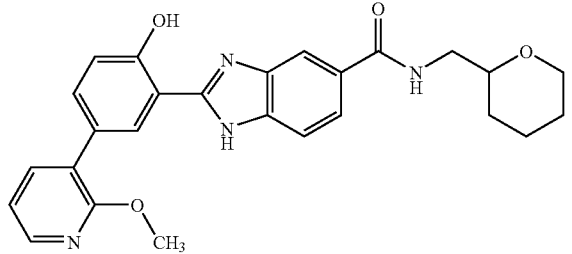 | 459.52 |

-continued

| Structure | M + 1 |
|---|---|
| Chiral | 431.51 |
| 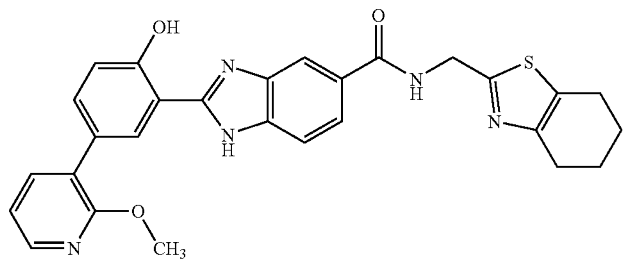 [SMILES: COc1ncccc1-c1ccc(O)c(-c2nc3cc(C(=O)NCc4nc5c(s4)CCCC5)ccc3[nH]2)c1] | 512.61 |
| 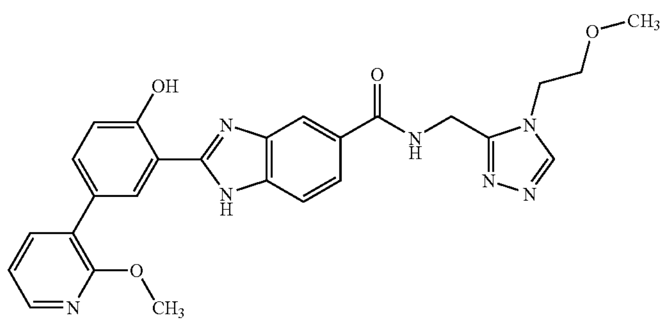 [SMILES: COCCn1cnnc1CNC(=O)c1ccc2[nH]c(-c3cc(-c4cccnc4OC)ccc3O)nc2c1] | 500.53 |
| Chiral | 433.48 |
| 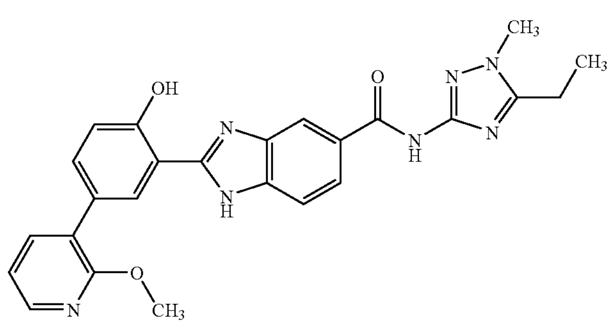 [SMILES: CCc1nc(NC(=O)c2ccc3[nH]c(-c4cc(-c5cccnc5OC)ccc4O)nc3c2)nn1C] | 470.51 |

| Structure | M + 1 |
|---|---|
| 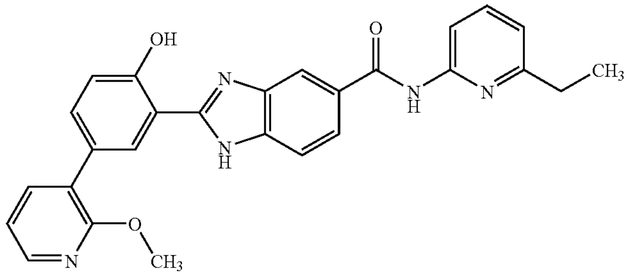 [SMILES: CCc1cccc(NC(=O)c2ccc3[nH]c(-c4cc(-c5cccnc5OC)ccc4O)nc3c2)n1] | 466.52 |
| 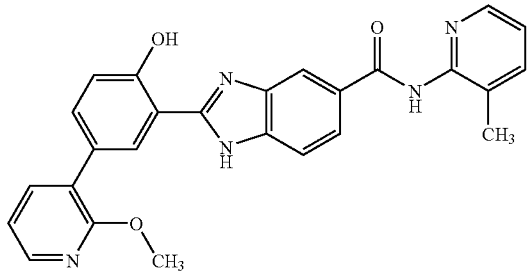 | 452.49 |
| 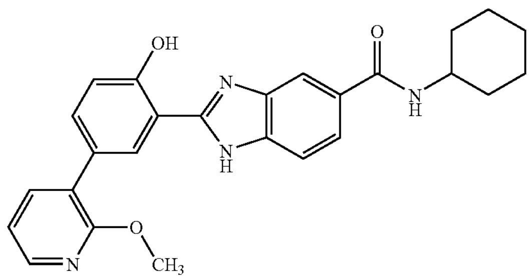 [SMILES: COc1ncccc1-c1ccc(O)c(-c2nc3cc(C(=O)NC4CCCCC4)ccc3[nH]2)c1] | 443.52 |
| 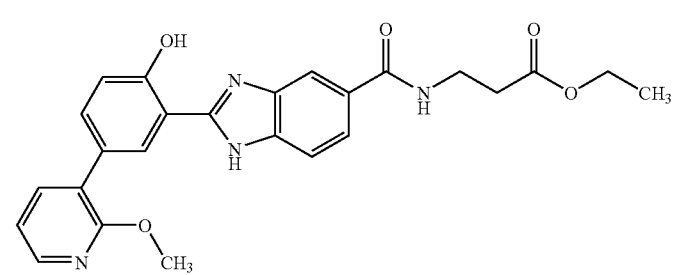 [SMILES: CCOC(=O)CCNC(=O)c1ccc2[nH]c(-c3cc(-c4cccnc4OC)ccc3O)nc2c1] | 461.49 |
| 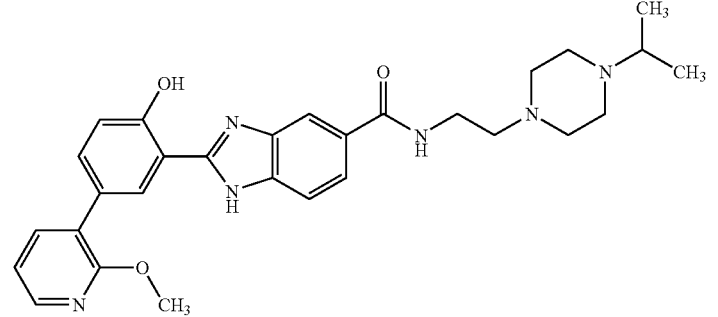 [SMILES: COc1ncccc1-c1ccc(O)c(-c2nc3cc(C(=O)NCCN4CCN(C(C)C)CC4)ccc3[nH]2)c1] | 515.63 |

-continued
| Structure | M + 1 |
|---|---|
| 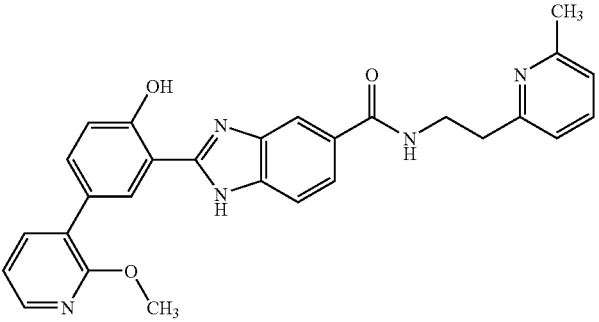 [SMILES: COc1ncccc1-c1ccc(O)c(-c2nc3cc(C(=O)NCCc4cccc(C)n4)ccc3[nH]2)c1] | 480.54 |
| 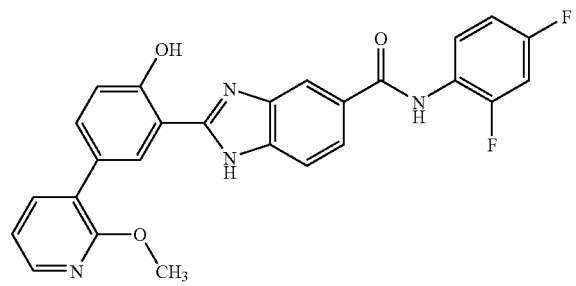 [SMILES: COc1ncccc1-c1ccc(O)c(-c2nc3cc(C(=O)Nc4ccc(F)cc4F)ccc3[nH]2)c1] | 473.46 |
| 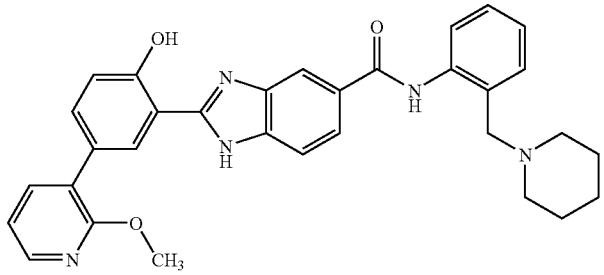 [SMILES: COc1ncccc1-c1ccc(O)c(-c2nc3cc(C(=O)Nc4ccccc4CN4CCCCC4)ccc3[nH]2)c1] | 534.64 |
| 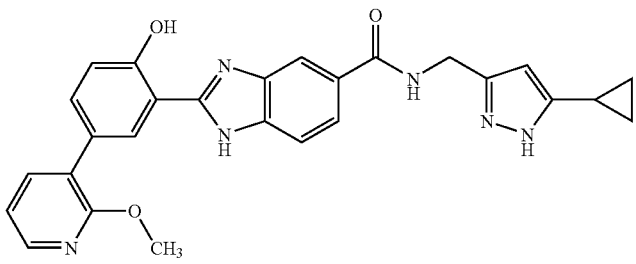 [SMILES: COc1ncccc1-c1ccc(O)c(-c2nc3cc(C(=O)NCc4cc(C5CC5)[nH]n4)ccc3[nH]2)c1] | 481.53 |
| 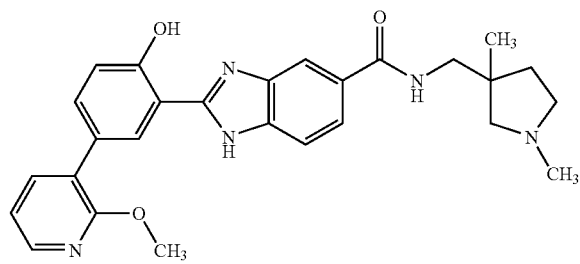 [SMILES: COc1ncccc1-c1ccc(O)c(-c2nc3cc(C(=O)NCC4(C)CCN(C)C4)ccc3[nH]2)c1] | 472.56 |

| Structure | M + 1 |
|---|---|
| 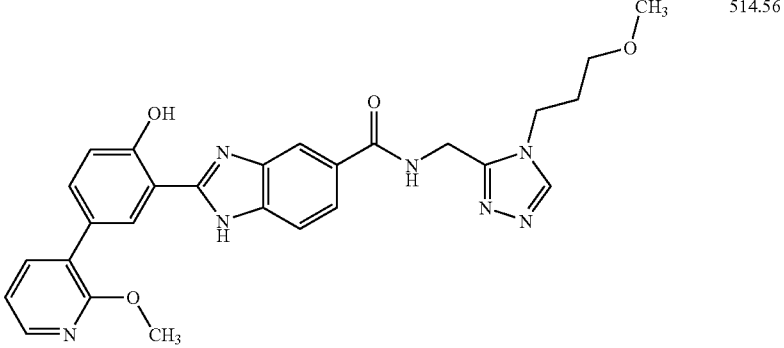 | 514.56 |
| 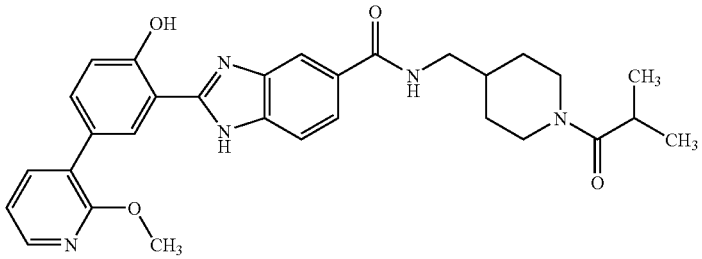 [SMILES: COc1ncccc1-c1ccc(O)c(-c2nc3cc(C(=O)NCC4CCN(C(=O)C(C)C)CC4)ccc3[nH]2)c1] | 528.63 |
| 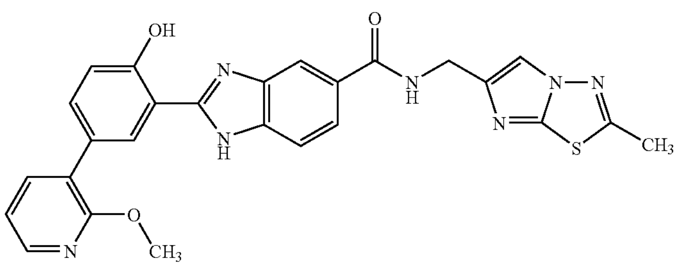 [SMILES: COc1ncccc1-c1ccc(O)c(-c2nc3cc(C(=O)NCc4cn5nc(C)sc5n4)ccc3[nH]2)c1] | 512.57 |
| 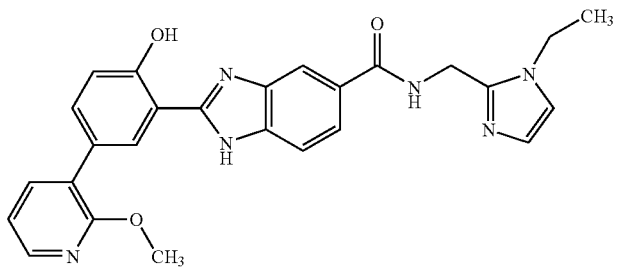 [SMILES: CCn1ccnc1CNC(=O)c1ccc2[nH]c(-c3cc(-c4cccnc4OC)ccc3O)nc2c1] | 469.52 |
| 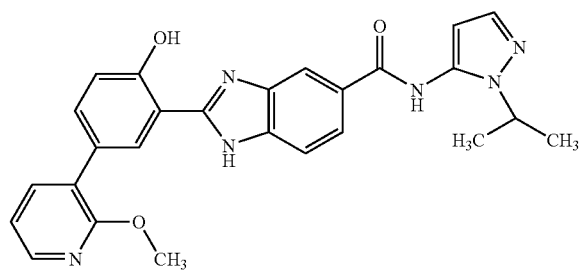 [SMILES: COc1ncccc1-c1ccc(O)c(-c2nc3cc(C(=O)Nc4ccnn4C(C)C)ccc3[nH]2)c1] | 469.52 |

-continued

| Structure | M + 1 |
|---|---|
| 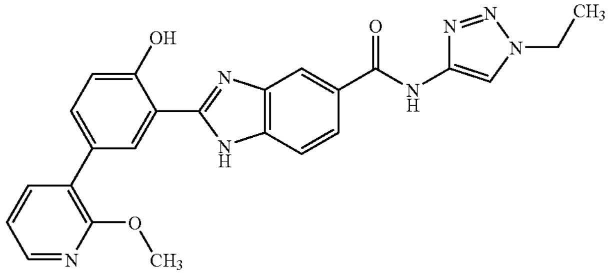 [SMILES: CCn1cc(NC(=O)c2ccc3[nH]c(-c4cc(-c5cccnc5OC)ccc4O)nc3c2)nn1] | 456.48 |
| 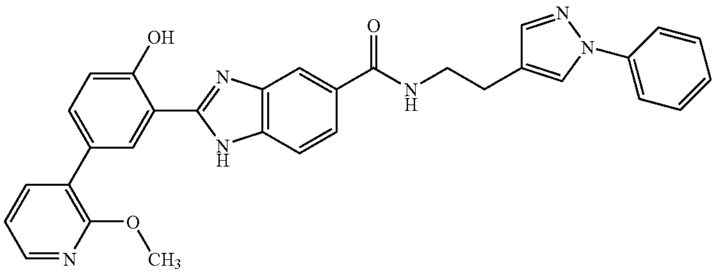 [SMILES: COc1ncccc1-c1ccc(O)c(-c2nc3cc(C(=O)NCCc4cnn(-c5ccccc5)c4)ccc3[nH]2)c1] | 531.59 |
| 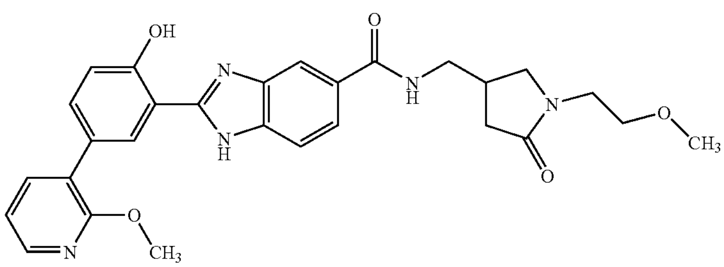 [SMILES: COCCN1CC(CNC(=O)c2ccc3[nH]c(-c4cc(-c5cccnc5OC)ccc4O)nc3c2)CC1=O] | 516.57 |
| 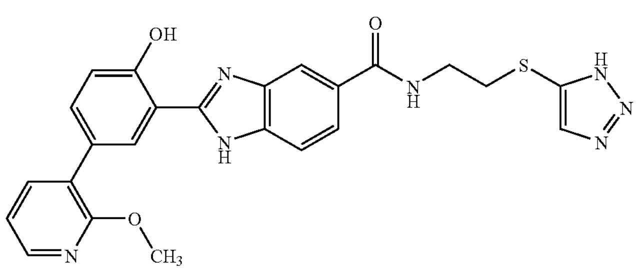 [SMILES: COc1ncccc1-c1ccc(O)c(-c2nc3cc(C(=O)NCCSc4cnn[nH]4)ccc3[nH]2)c1] | 488.54 |
| 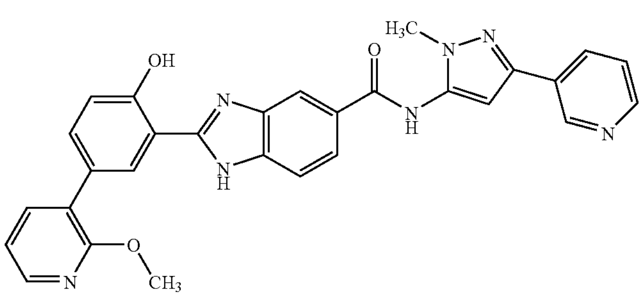 | 518.55 |

| Structure | M + 1 |
|---|---|
| (structure) | 480.54 |
| (structure) | 497.57 |
| (structure) | 530.67 |
| (structure) | 534.59 |
| (structure) | 470.55 |

-continued

| Structure | M + 1 |
|---|---|
| 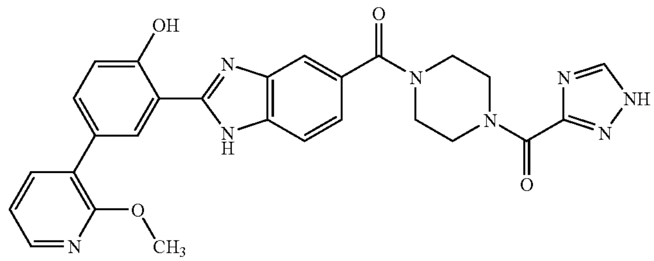 [SMILES: COc1ncccc1-c1ccc(O)c(-c2nc3cc(C(=O)N4CCN(C(=O)c5nc[nH]n5)CC4)ccc3[nH]2)c1] | 525.54 |
| 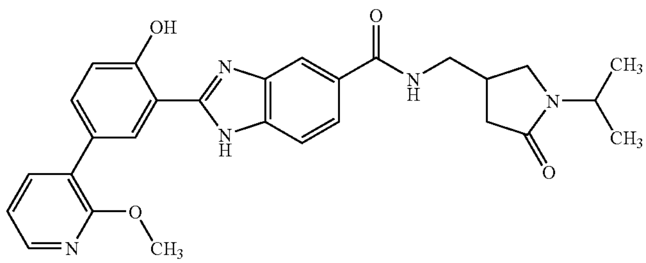 [SMILES: COc1ncccc1-c1ccc(O)c(-c2nc3cc(C(=O)NCC4CC(=O)N(C(C)C)C4)ccc3[nH]2)c1] | 500.57 |
| 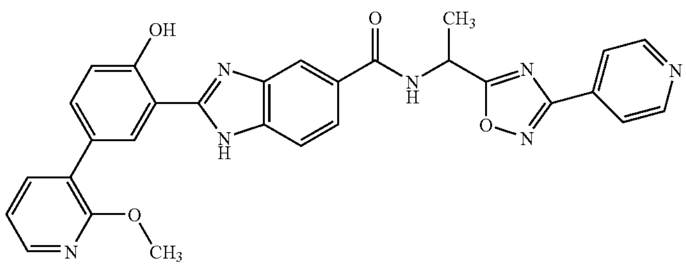 [SMILES: COc1ncccc1-c1ccc(O)c(-c2nc3cc(C(=O)NC(C)c4nc(-c5ccncc5)no4)ccc3[nH]2)c1] | 534.55 |
| 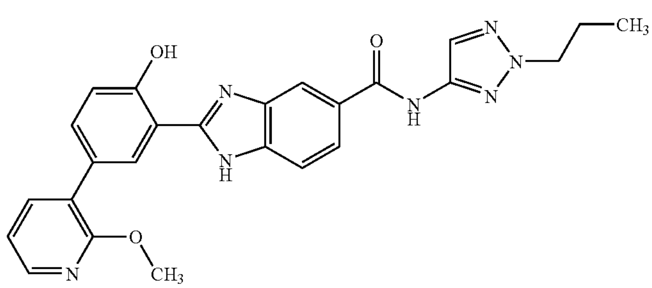 [SMILES: CCCn1ncc(NC(=O)c2ccc3[nH]c(-c4cc(-c5cccnc5OC)ccc4O)nc3c2)n1] | 470.51 |
| 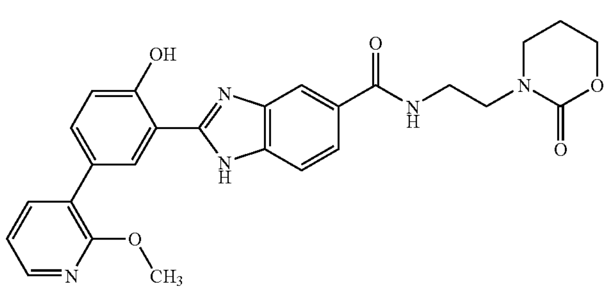 [SMILES: COc1ncccc1-c1ccc(O)c(-c2nc3cc(C(=O)NCCN4CCCOC4=O)ccc3[nH]2)c1] | 488.52 |

-continued

| Structure | M + 1 |
|---|---|
| 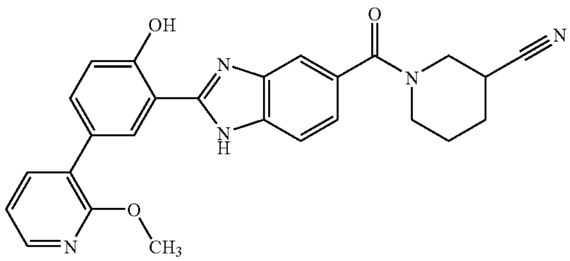 [SMILES: COc1ncccc1-c1ccc(O)c(-c2nc3cc(C(=O)N4CCCC(C#N)C4)ccc3[nH]2)c1] | 454.50 |
| 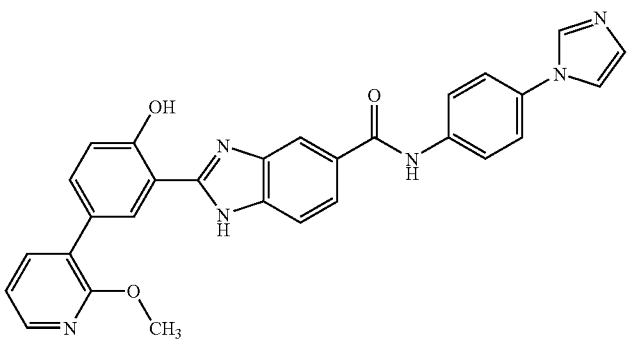 | 503.54 |
| 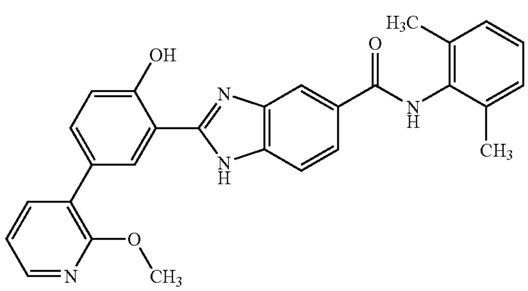 [SMILES: COc1ncccc1-c1ccc(O)c(-c2nc3cc(C(=O)Nc4c(C)cccc4C)ccc3[nH]2)c1] | 465.53 |
| 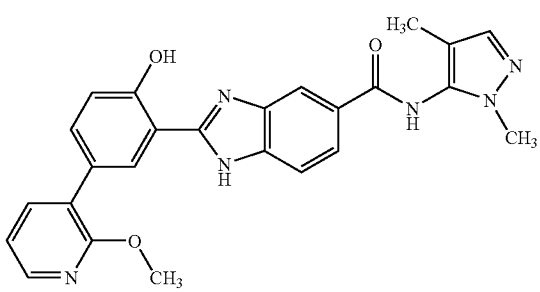 [SMILES: COc1ncccc1-c1ccc(O)c(-c2nc3cc(C(=O)Nc4c(C)cnn4C)ccc3[nH]2)c1] | 455.49 |
| 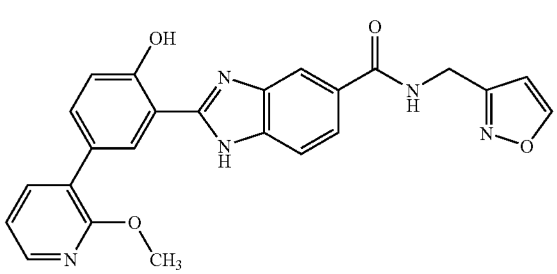 [SMILES: COc1ncccc1-c1ccc(O)c(-c2nc3cc(C(=O)NCc4ccon4)ccc3[nH]2)c1] | 442.45 |

| Structure | M + 1 |
|---|---|
| 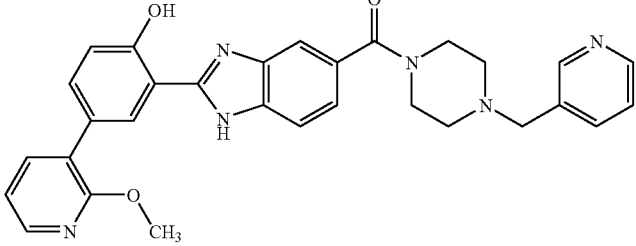 | 521.60 |
| 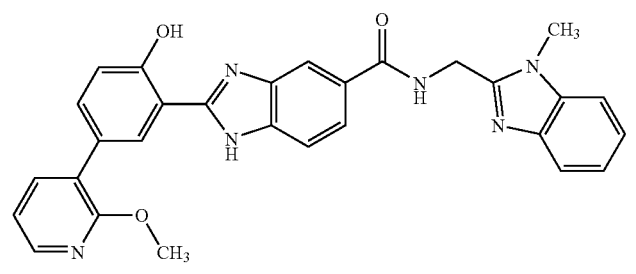 [SMILES: COc1ncccc1-c1ccc(O)c(-c2nc3cc(C(=O)NCc4nc5ccccc5n4C)ccc3[nH]2)c1] | 505.55 |
| 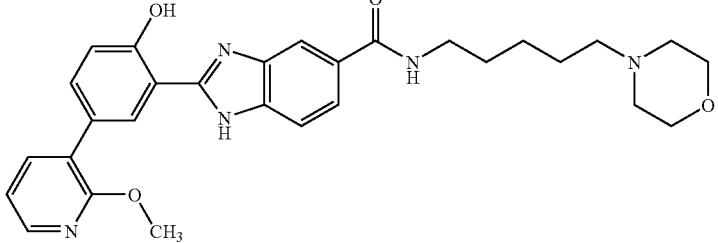 | 516.62 |
| 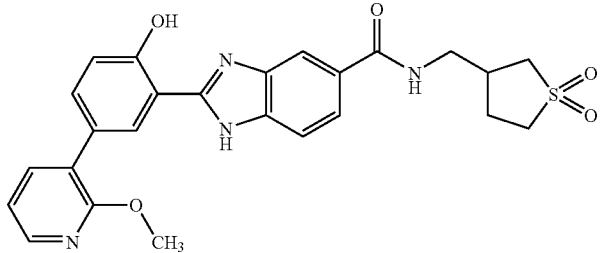 [SMILES: COc1ncccc1-c1ccc(O)c(-c2nc3cc(C(=O)NCC4CCS(=O)(=O)C4)ccc3[nH]2)c1] | 493.56 |
| 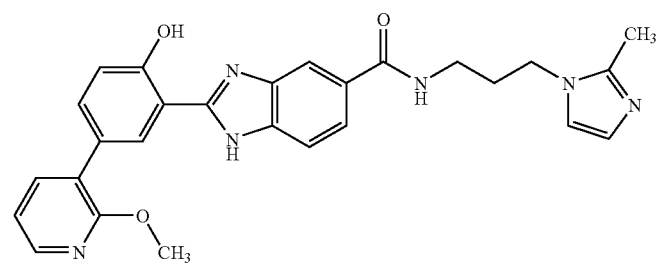 [SMILES: COc1ncccc1-c1ccc(O)c(-c2nc3cc(C(=O)NCCCn4ccnc4C)ccc3[nH]2)c1] | 483.55 |

| Structure | M + 1 |
|---|---|
| (structure) | 470.51 |
| (structure) | 549.56 |
| (structure) | 469.52 |
| (structure) | 517.56 |
| (structure) | 483.55 |

-continued

| Structure | M + 1 |
|-----------|-------|
| (structure) | 509.54 |
| (structure) | 401.44 |
| (structure) | 522.58 |
| (structure) | 456.48 |
| (structure) | 481.53 |

-continued

| Structure | M + 1 |
|---|---|
| 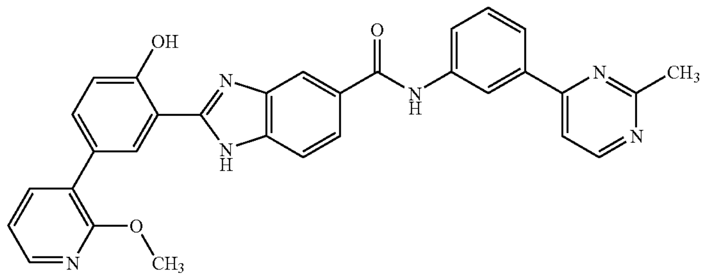 [SMILES: COc1ncccc1-c1ccc(O)c(-c2nc3cc(C(=O)Nc4cccc(-c5ccnc(C)n5)c4)ccc3[nH]2)c1] | 529.58 |
| 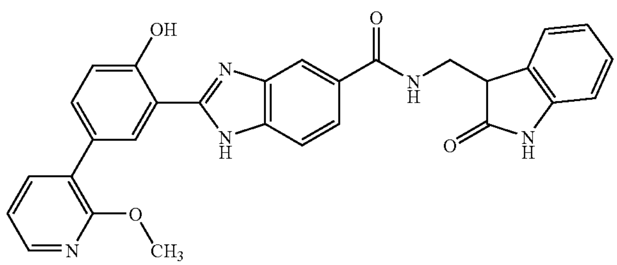 [SMILES: COc1ncccc1-c1ccc(O)c(-c2nc3cc(C(=O)NCC4C(=O)Nc5ccccc54)ccc3[nH]2)c1] | 506.54 |
| 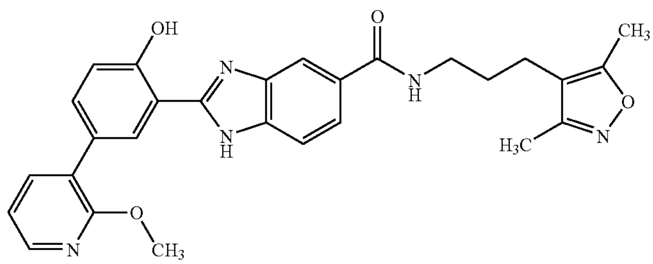 [SMILES: COc1ncccc1-c1ccc(O)c(-c2nc3cc(C(=O)NCCCc4c(C)noc4C)ccc3[nH]2)c1] | 498.56 |
| 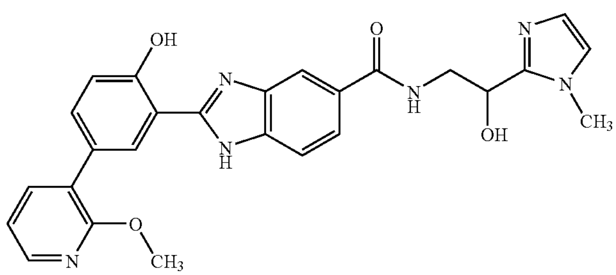 [SMILES: COc1ncccc1-c1ccc(O)c(-c2nc3cc(C(=O)NCC(O)c4nccn4C)ccc3[nH]2)c1] | 485.52 |
| 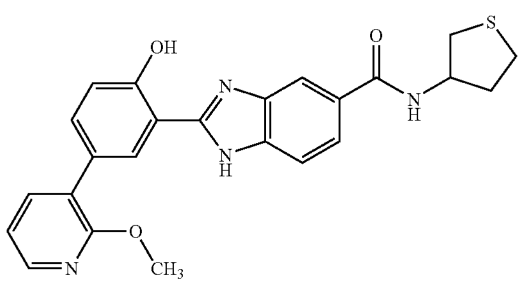 [SMILES: COc1ncccc1-c1ccc(O)c(-c2nc3cc(C(=O)NC4CCSC4)ccc3[nH]2)c1] | 447.53 |

-continued
| Structure | M + 1 |
|---|---|
| 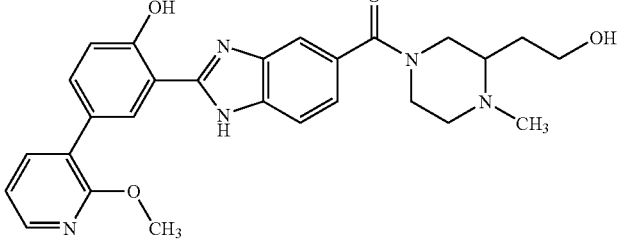 | 488.56 |
| 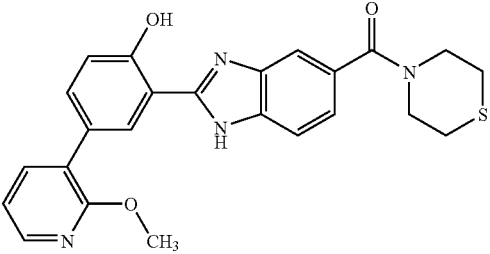 [SMILES: COc1ncccc1-c1ccc(O)c(-c2nc3cc(C(=O)N4CCSCC4)ccc3[nH]2)c1] | 447.53 |
| 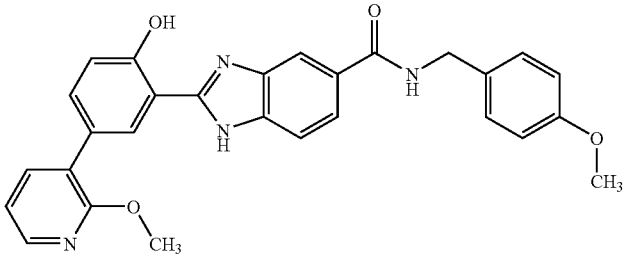 [SMILES: COc1ccc(CNC(=O)c2ccc3[nH]c(-c4cc(-c5cccnc5OC)ccc4O)nc3c2)cc1] | 481.53 |
| 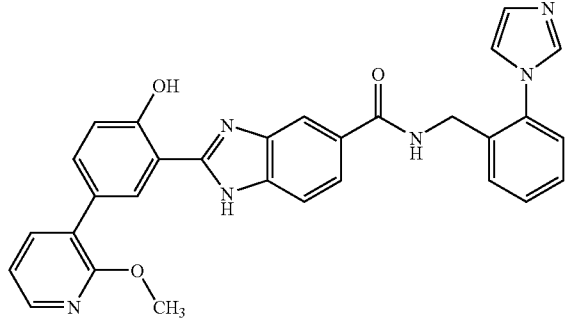 [SMILES: COc1ncccc1-c1ccc(O)c(-c2nc3cc(C(=O)NCc4ccccc4-n4ccnc4)ccc3[nH]2)c1] | 517.56 |
| 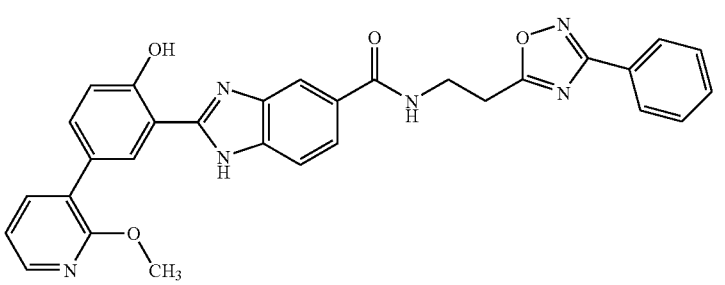 [SMILES: COc1ncccc1-c1ccc(O)c(-c2nc3cc(C(=O)NCCc4nc(-c5ccccc5)no4)ccc3[nH]2)c1] | 533.56 |

| Structure | M + 1 |
|---|---|
| 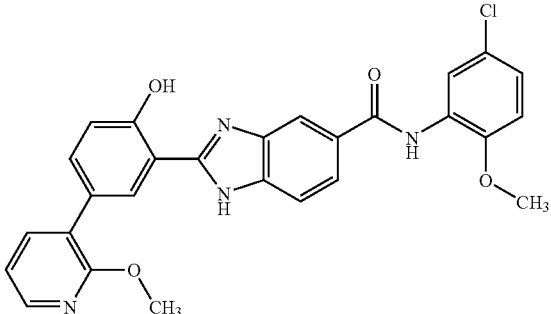 [SMILES: COc1ccc(Cl)cc1NC(=O)c1ccc2[nH]c(-c3cc(-c4cccnc4OC)ccc3O)nc2c1] | 501.95 |
| 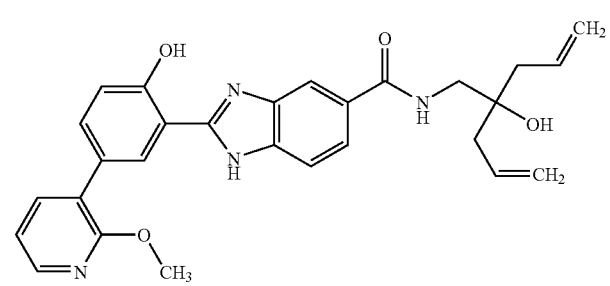 [SMILES: C=CCC(O)(CC=C)CNC(=O)c1ccc2[nH]c(-c3cc(-c4cccnc4OC)ccc3O)nc2c1] | 485.56 |
| 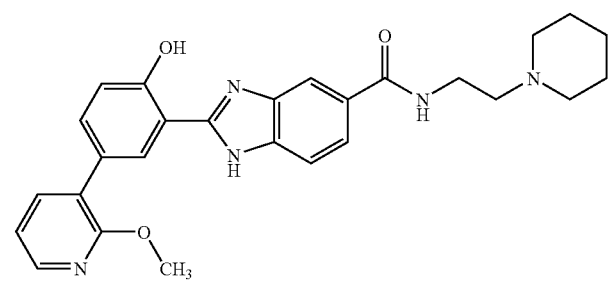 | 472.56 |
| 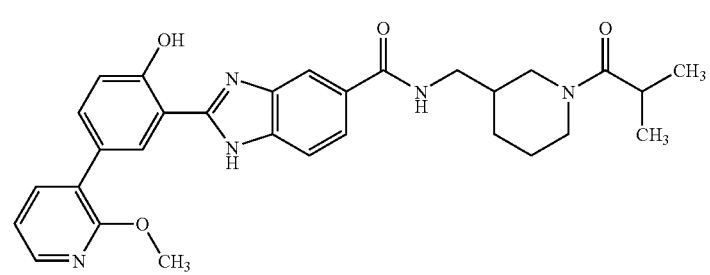 [SMILES: COc1ncccc1-c1ccc(O)c(-c2nc3cc(C(=O)NCC4CCCN(C(=O)C(C)C)C4)ccc3[nH]2)c1] | 528.63 |
| 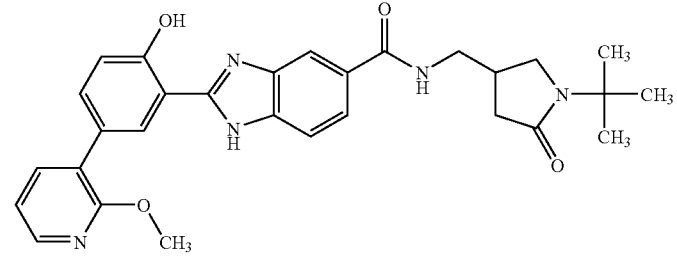 [SMILES: COc1ncccc1-c1ccc(O)c(-c2nc3cc(C(=O)NCC4CC(=O)N(C(C)(C)C)C4)ccc3[nH]2)c1] | 514.60 |

-continued
| Structure | M + 1 |
|---|---|
| 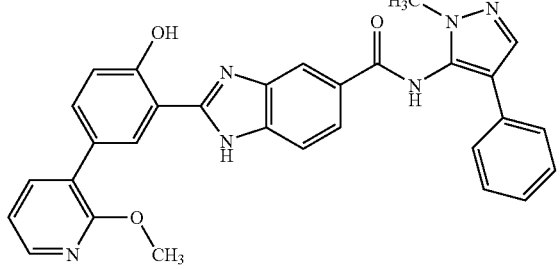 | 517.56 |
| 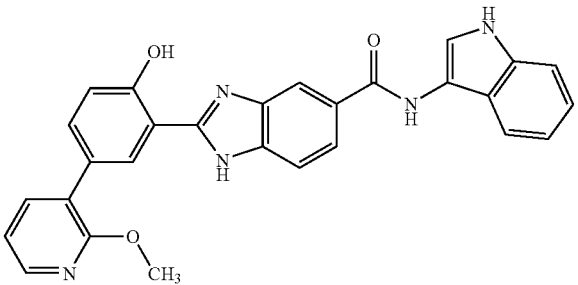 [SMILES: COc1ncccc1-c1ccc(O)c(-c2nc3cc(C(=O)Nc4c[nH]c5ccccc45)ccc3[nH]2)c1] | 476.51 |
| 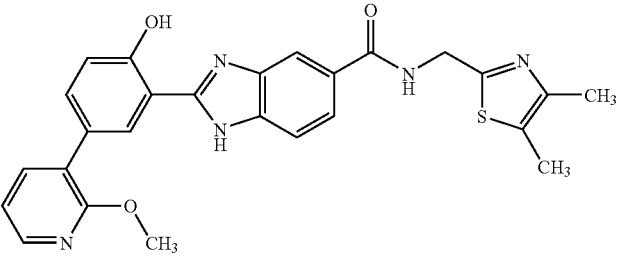 [SMILES: COc1ncccc1-c1ccc(O)c(-c2nc3cc(C(=O)NCc4nc(C)c(C)s4)ccc3[nH]2)c1] | 486.57 |
| 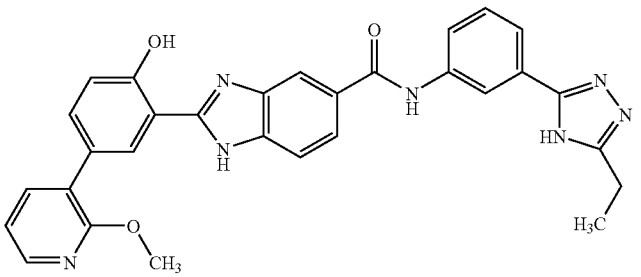 [SMILES: CCc1nnc(-c2cccc(NC(=O)c3ccc4[nH]c(-c5cc(-c6cccnc6OC)ccc5O)nc4c3)c2)[nH]1] | 532.58 |
| 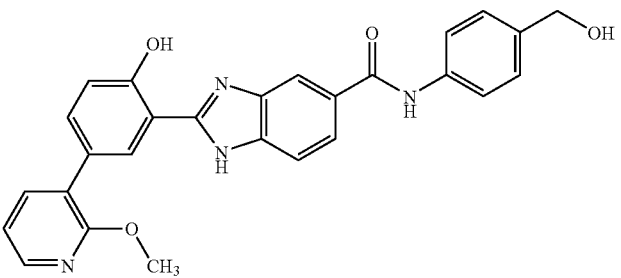 [SMILES: COc1ncccc1-c1ccc(O)c(-c2nc3cc(C(=O)Nc4ccc(CO)cc4)ccc3[nH]2)c1] | 467.50 |

-continued
| Structure | M + 1 |
|---|---|
| 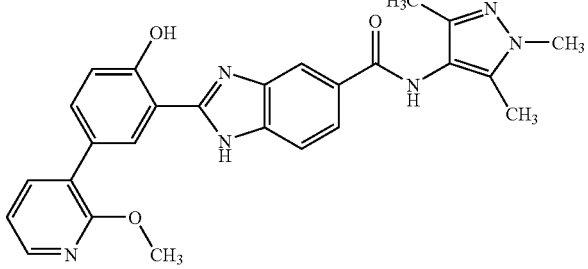 | 469.52 |
| 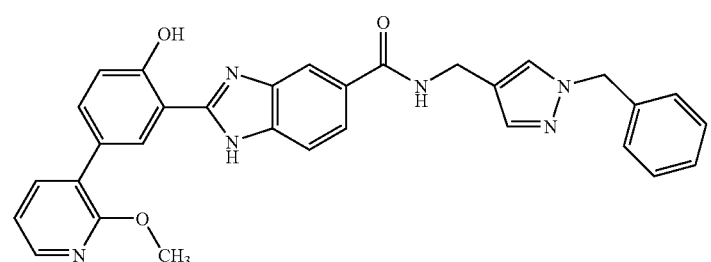 | 531.59 |
| 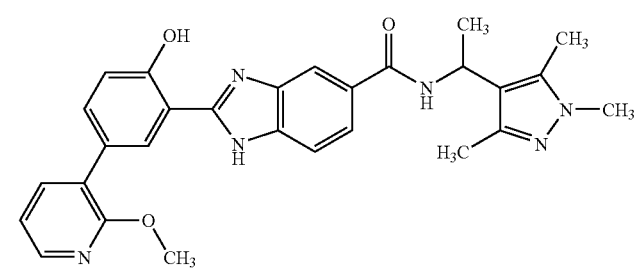 [SMILES: COc1ncccc1-c1ccc(O)c(-c2nc3cc(C(=O)NC(C)c4c(C)nn(C)c4C)ccc3[nH]2)c1] | 497.57 |
| 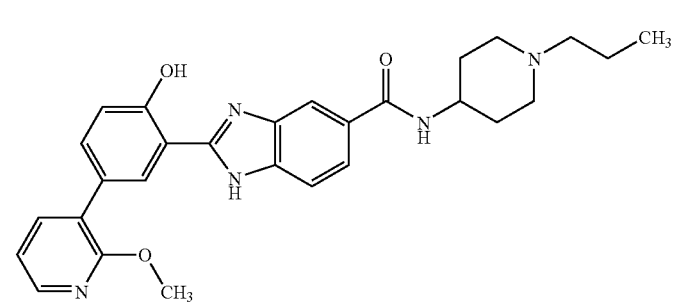 [SMILES: CCCN1CCC(NC(=O)c2ccc3[nH]c(-c4cc(-c5cccnc5OC)ccc4O)nc3c2)CC1] | 486.59 |
| 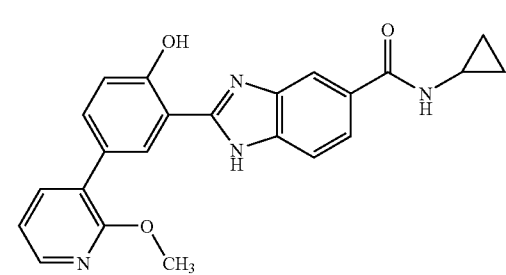 [SMILES: COc1ncccc1-c1ccc(O)c(-c2nc3cc(C(=O)NC4CC4)ccc3[nH]2)c1] | 401.44 |

| Structure | M + 1 |
|---|---|
| 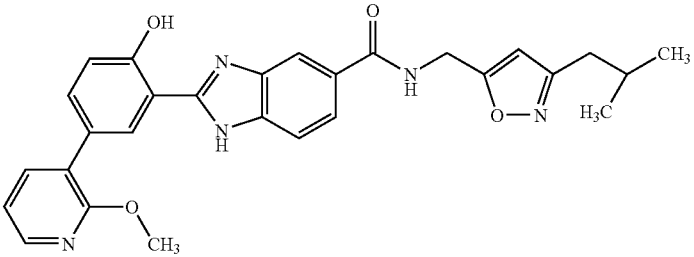 [SMILES: COc1ncccc1-c1ccc(O)c(-c2nc3cc(C(=O)NCc4cc(CC(C)C)no4)ccc3[nH]2)c1] | 498.56 |
| 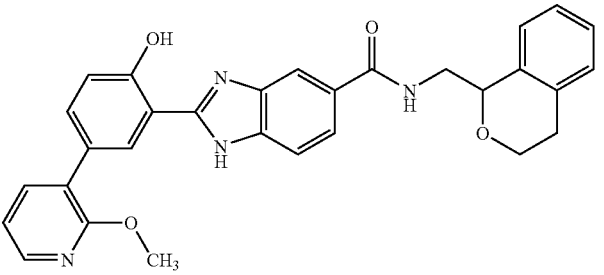 [SMILES: COc1ncccc1-c1ccc(O)c(-c2nc3cc(C(=O)NCC4OCCc5ccccc54)ccc3[nH]2)c1] | 507.57 |
| 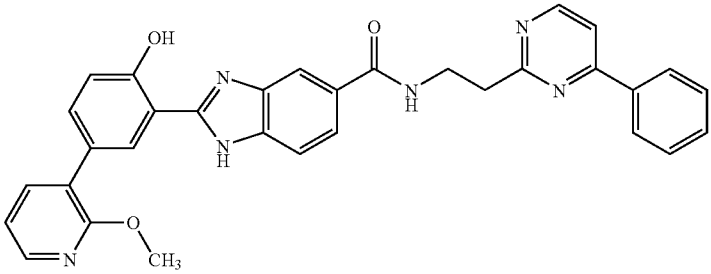 [SMILES: COc1ncccc1-c1ccc(O)c(-c2nc3cc(C(=O)NCCc4nccc(-c5ccccc5)n4)ccc3[nH]2)c1] | 543.60 |
| 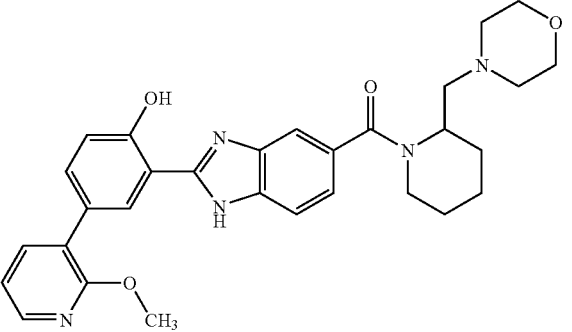 [SMILES: COc1ncccc1-c1ccc(O)c(-c2nc3cc(C(=O)N4CCCCC4CN4CCOCC4)ccc3[nH]2)c1] | 528.63 |
| 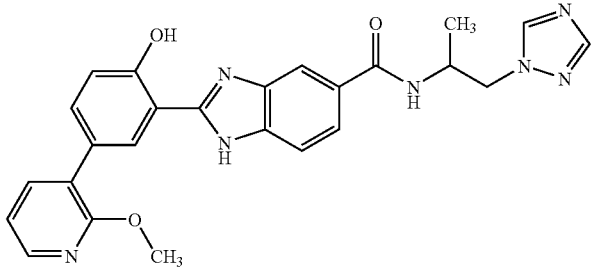 [SMILES: COc1ncccc1-c1ccc(O)c(-c2nc3cc(C(=O)NC(C)Cn4cncn4)ccc3[nH]2)c1] | 470.51 |

-continued
| Structure | M + 1 |
|---|---|
| 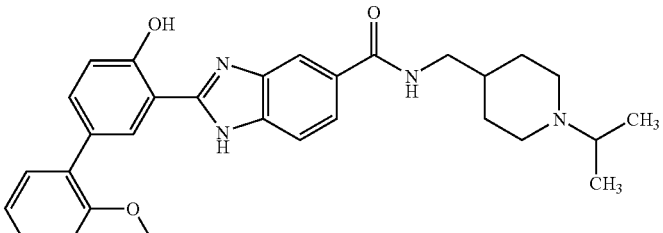 | 500.62 |
| 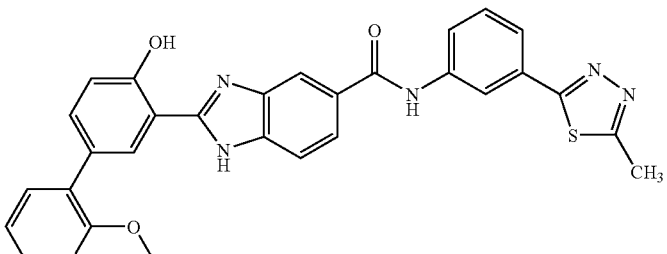 | 535.60 |
| 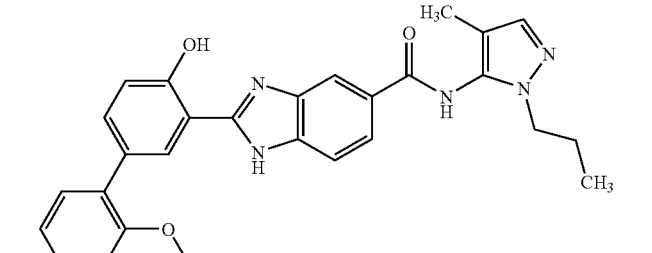 | 483.55 |
| 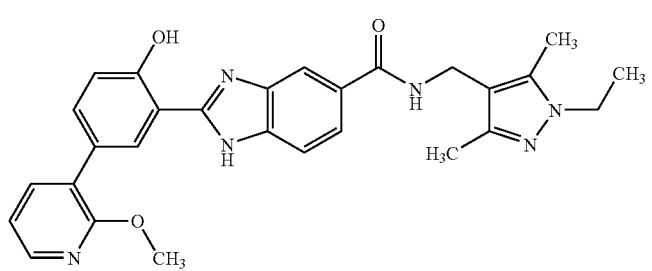 [SMILES: CCn1nc(C)c(CNC(=O)c2ccc3[nH]c(-c4cc(-c5cccnc5OC)ccc4O)nc3c2)c1C] | 497.57 |
| 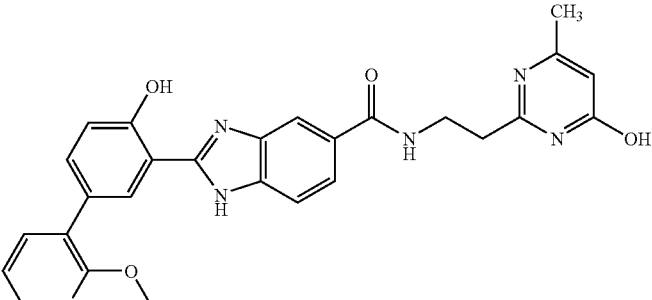 | 497.53 |

| Structure | M + 1 |
|---|---|
| 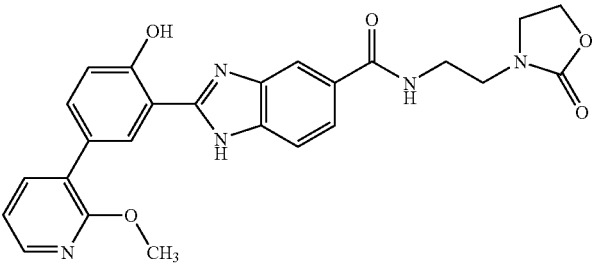 | 474.49 |
| 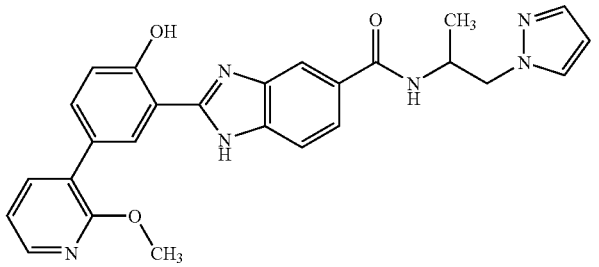 [SMILES: COc1ncccc1-c1ccc(O)c(-c2nc3cc(C(=O)NC(C)Cn4cccn4)ccc3[nH]2)c1] | 469.52 |
| 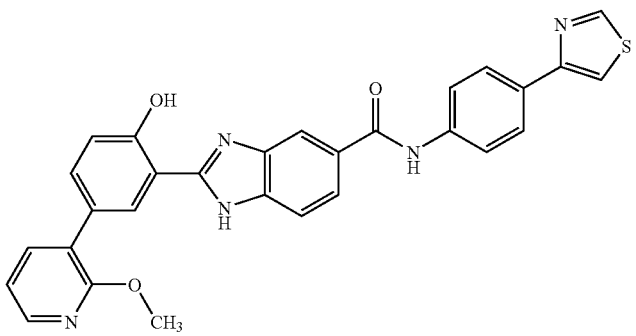 [SMILES: COc1ncccc1-c1ccc(O)c(-c2nc3cc(C(=O)Nc4ccc(-c5cscn5)cc4)ccc3[nH]2)c1] | 520.59 |
| 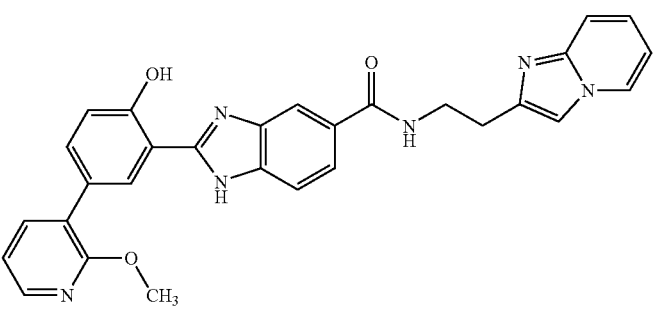 [SMILES: COc1ncccc1-c1ccc(O)c(-c2nc3cc(C(=O)NCCc4cn5ccccc5n4)ccc3[nH]2)c1] | 505.55 |
| 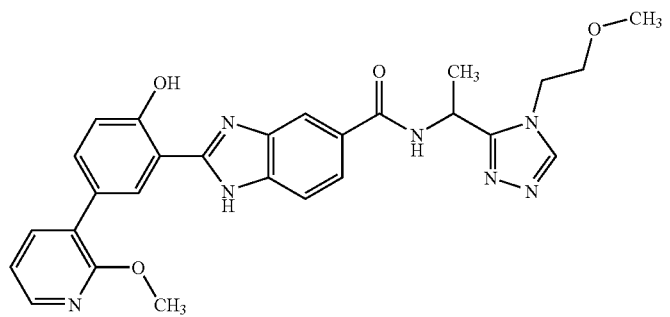 [SMILES: COCCn1cnnc1C(C)NC(=O)c1ccc2[nH]c(-c3cc(-c4cccnc4OC)ccc3O)nc2c1] | 514.56 |

-continued
| Structure | M + 1 |
|---|---|
| 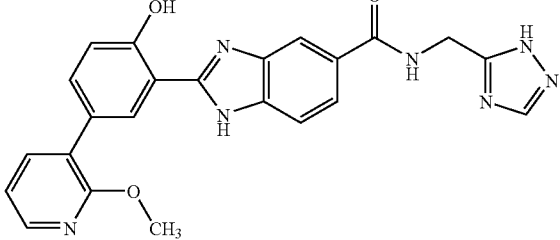 | 442.45 |
| 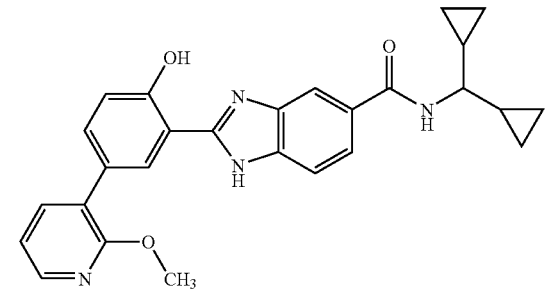 [SMILES: COc1ncccc1-c1ccc(O)c(-c2nc3cc(C(=O)NC(C4CC4)C4CC4)ccc3[nH]2)c1] | 455.53 |
| 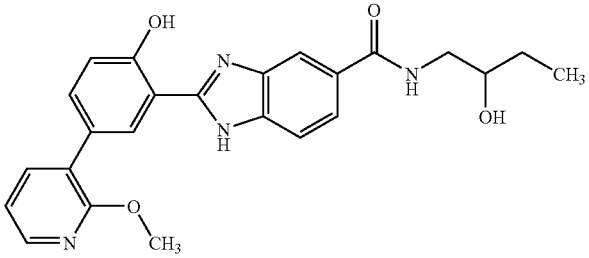 [SMILES: CCC(O)CNC(=O)c1ccc2[nH]c(-c3cc(-c4cccnc4OC)ccc3O)nc2c1] | 433.48 |
| 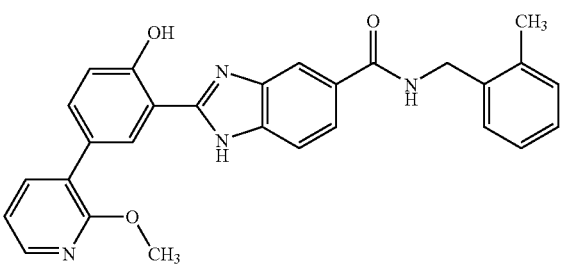 | 466.52 |
| 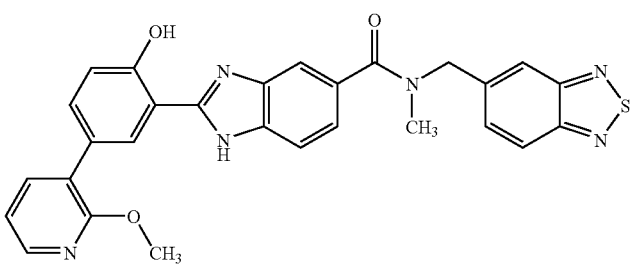 [SMILES: COc1ncccc1-c1ccc(O)c(-c2nc3cc(C(=O)N(C)Cc4ccc5nsnc5c4)ccc3[nH]2)c1] | 523.59 |

| Structure | M + 1 |
|---|---|
| (structure) | 512.61 |
| (structure) | 487.53 |
| (structure) | 519.58 |
| (structure) | 473.51 |
| (structure) | 509.58 |

-continued

| Structure | M + 1 |
|---|---|
| 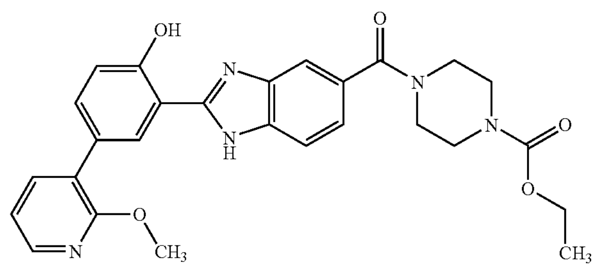 [SMILES: CCOC(=O)N1CCN(C(=O)c2ccc3[nH]c(-c4cc(-c5cccnc5OC)ccc4O)nc3c2)CC1] | 502.55 |
| 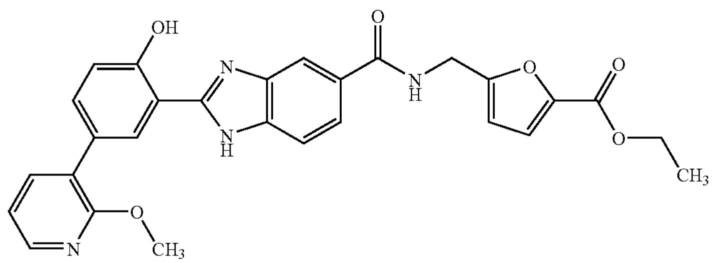 [SMILES: CCOC(=O)c1ccc(CNC(=O)c2ccc3[nH]c(-c4cc(-c5cccnc5OC)ccc4O)nc3c2)o1] | 513.53 |
| 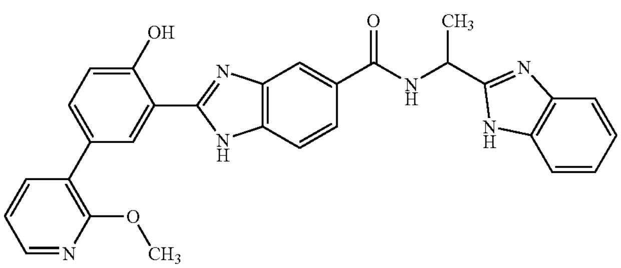 [SMILES: COc1ncccc1-c1ccc(O)c(-c2nc3cc(C(=O)NC(C)c4nc5ccccc5[nH]4)ccc3[nH]2)c1] | 505.55 |
| 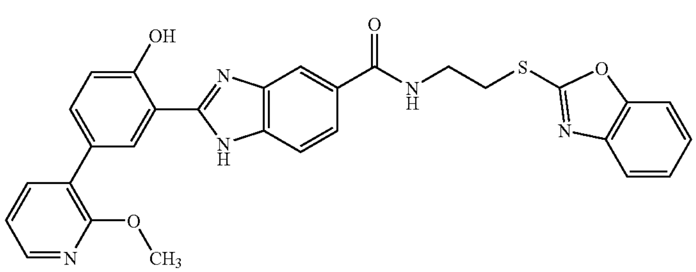 [SMILES: COc1ncccc1-c1ccc(O)c(-c2nc3cc(C(=O)NCCSc4nc5ccccc5o4)ccc3[nH]2)c1] | 538.60 |
| 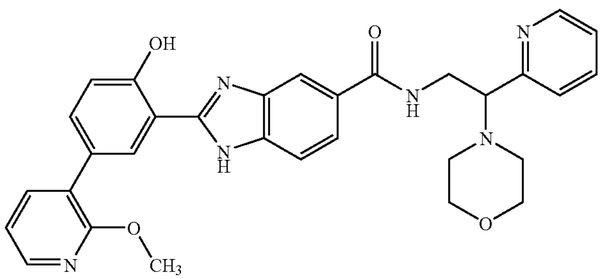 [SMILES: COc1ncccc1-c1ccc(O)c(-c2nc3cc(C(=O)NCC(c4ccccn4)N4CCOCC4)ccc3[nH]2)c1] | 551.62 |

-continued
| Structure | M + 1 |
|---|---|
| 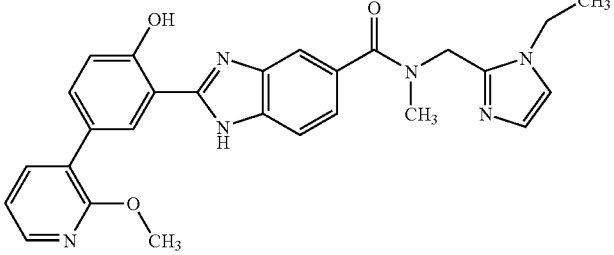 | 483.55 |
| 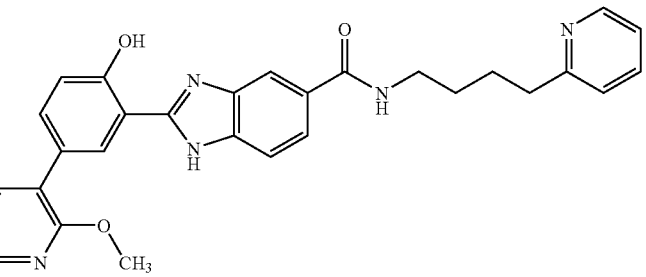 | 494.57 |
| 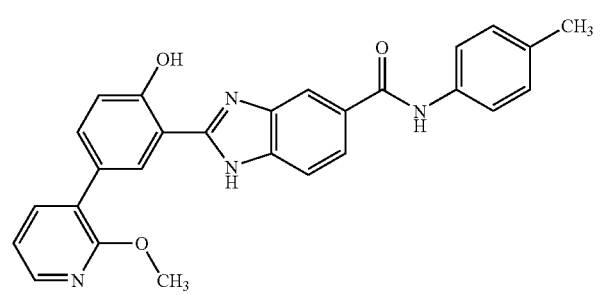 | 451.50 |
| 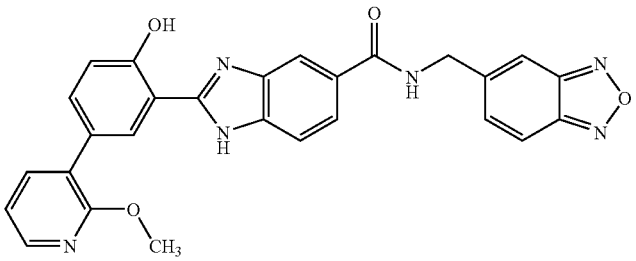 [SMILES: COc1ncccc1-c1ccc(O)c(-c2nc3cc(C(=O)NCc4ccc5nonc5c4)ccc3[nH]2)c1] | 493.50 |
| 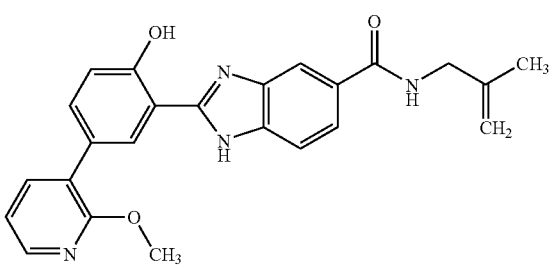 [SMILES: C=C(C)CNC(=O)c1ccc2[nH]c(-c3cc(-c4cccnc4OC)ccc3O)nc2c1] | 415.47 |

-continued
| Structure | M + 1 |
|---|---|
| 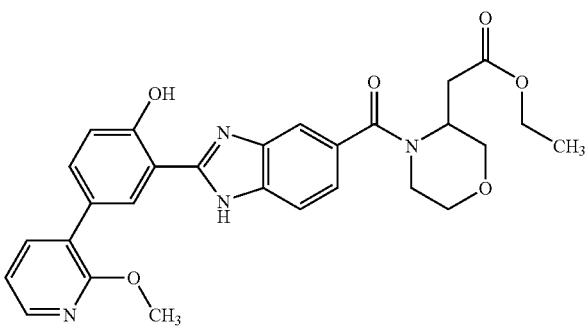 [SMILES: CCOC(=O)CC1COCCN1C(=O)c1ccc2[nH]c(-c3cc(-c4cccnc4OC)ccc3O)nc2c1] | 517.56 |
| 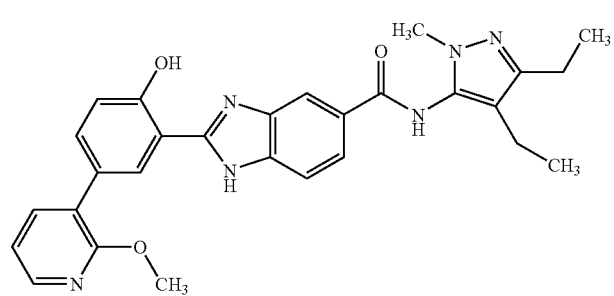 [SMILES: CCc1nn(C)c(NC(=O)c2ccc3[nH]c(-c4cc(-c5cccnc5OC)ccc4O)nc3c2)c1CC] | 497.57 |
| 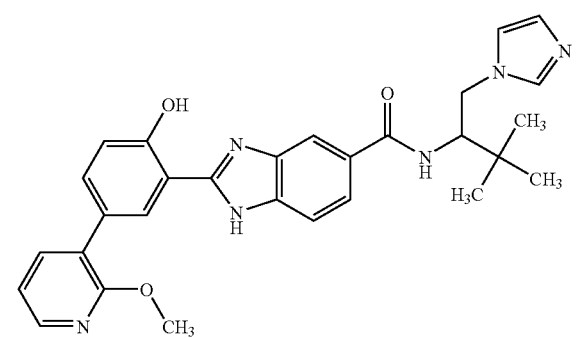 [SMILES: COc1ncccc1-c1ccc(O)c(-c2nc3cc(C(=O)NC(Cn4ccnc4)C(C)(C)C)ccc3[nH]2)c1] | 511.60 |
| 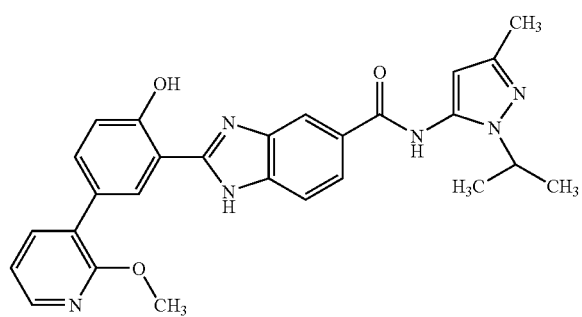 [SMILES: COc1ncccc1-c1ccc(O)c(-c2nc3cc(C(=O)Nc4cc(C)nn4C(C)C)ccc3[nH]2)c1] | 483.55 |
| 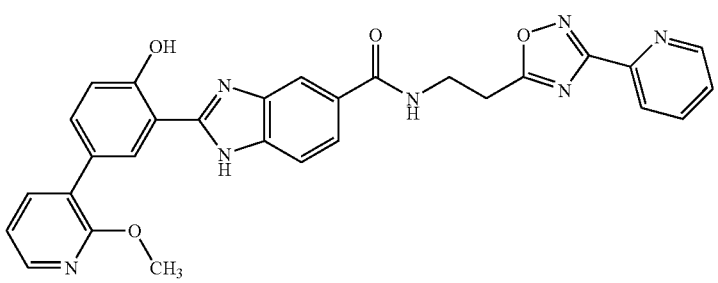 | 534.55 |

-continued
| Structure | M + 1 |
|---|---|
| 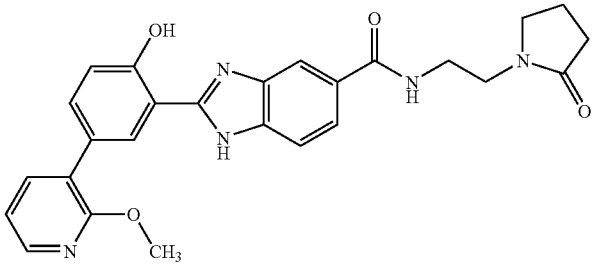 [SMILES: COc1ncccc1-c1ccc(O)c(-c2nc3cc(C(=O)NCCN4CCCC4=O)ccc3[nH]2)c1] | 472.52 |
| 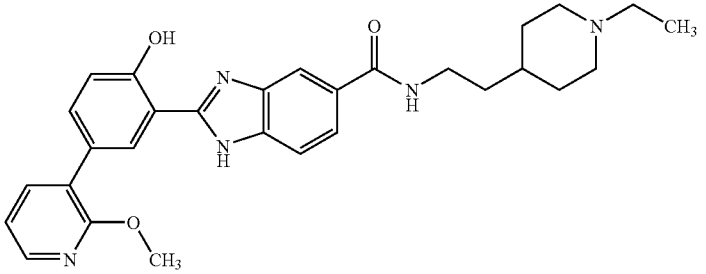 [SMILES: CCN1CCC(CCNC(=O)c2ccc3[nH]c(-c4cc(-c5cccnc5OC)ccc4O)nc3c2)CC1] | 500.62 |
| 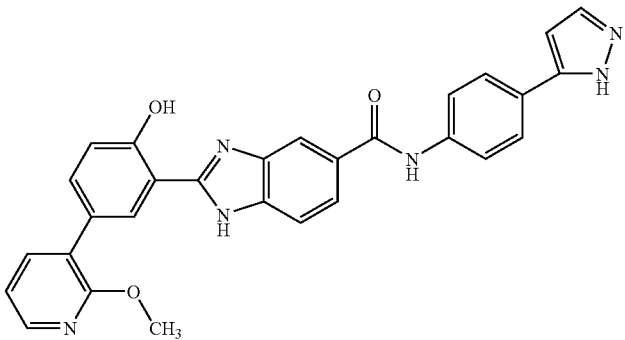 [SMILES: COc1ncccc1-c1ccc(O)c(-c2nc3cc(C(=O)Nc4ccc(-c5ccn[nH]5)cc4)ccc3[nH]2)c1] | 503.54 |
| 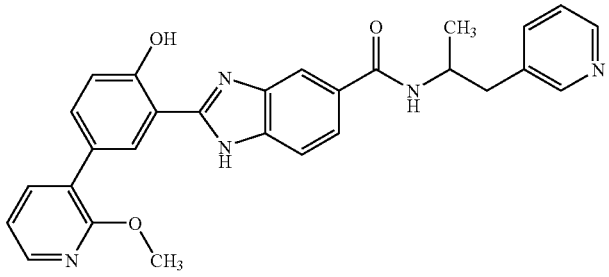 [SMILES: COc1ncccc1-c1ccc(O)c(-c2nc3cc(C(=O)NC(C)Cc4cccnc4)ccc3[nH]2)c1] | 480.54 |
| 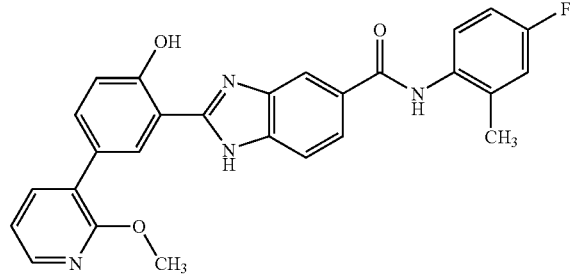 [SMILES: COc1ncccc1-c1ccc(O)c(-c2nc3cc(C(=O)Nc4ccc(F)cc4C)ccc3[nH]2)c1] | 469.49 |

| Structure | M + 1 |
|---|---|
| 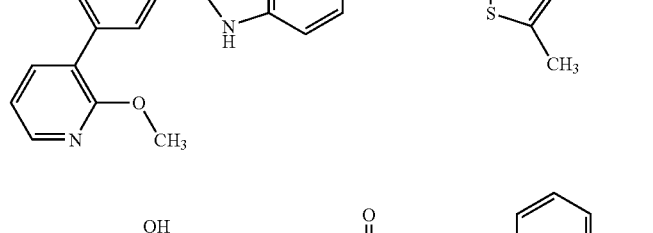 | 471.55 |
| 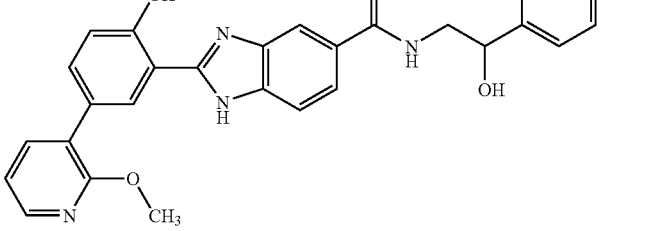 | 481.53 |
| 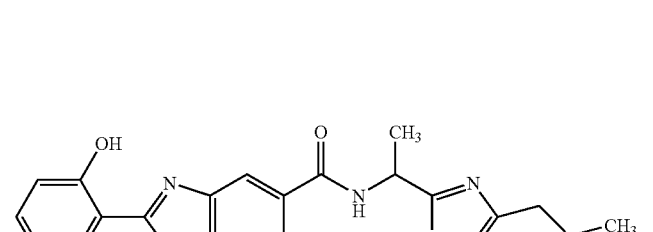 | 499.55 |
| 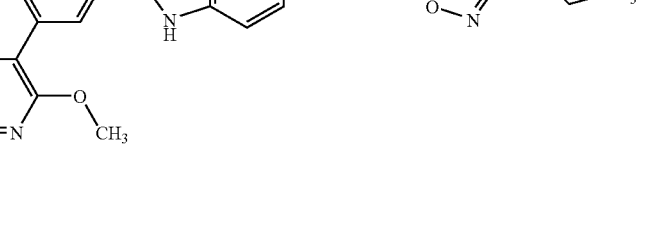 | 495.51 |
| 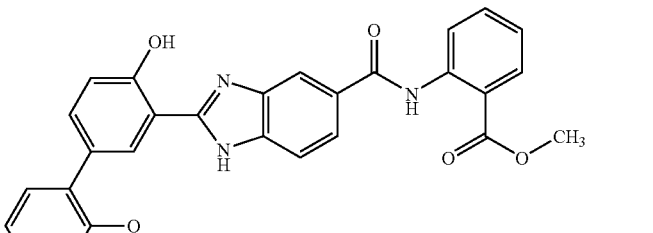 | 535.62 |

-continued
| Structure | M + 1 |
|---|---|
| 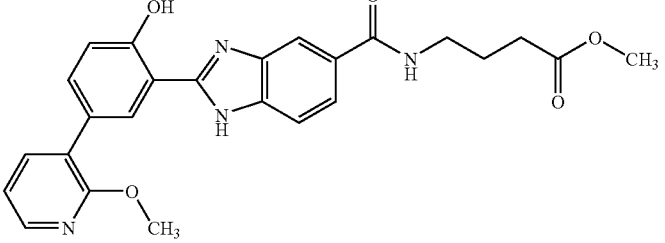 | 461.49 |
| 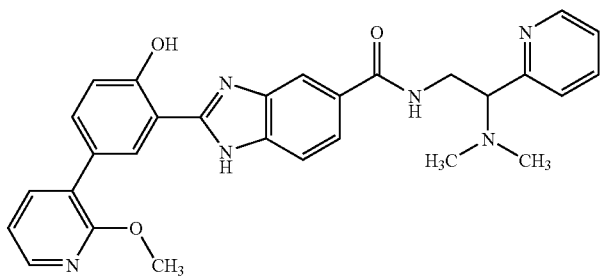 [SMILES: COc1ncccc1-c1ccc(O)c(-c2nc3cc(C(=O)NCC(c4ccccn4)N(C)C)ccc3[nH]2)c1] | 509.58 |
| 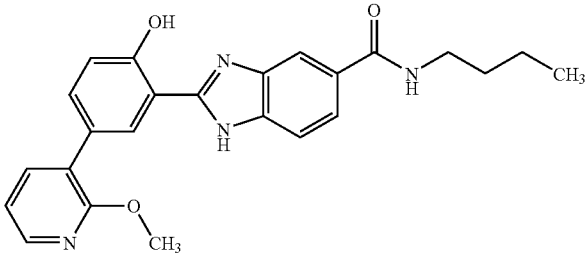 | 417.48 |
| 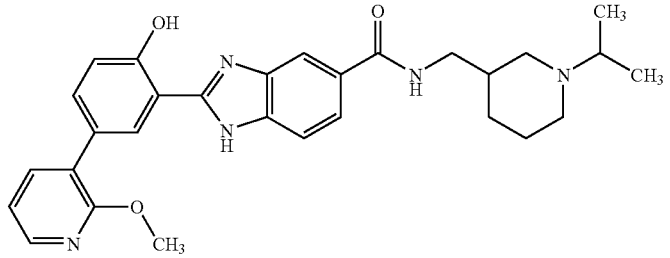 [SMILES: COc1ncccc1-c1ccc(O)c(-c2nc3cc(C(=O)NCC4CCCN(C(C)C)C4)ccc3[nH]2)c1] | 500.62 |
| 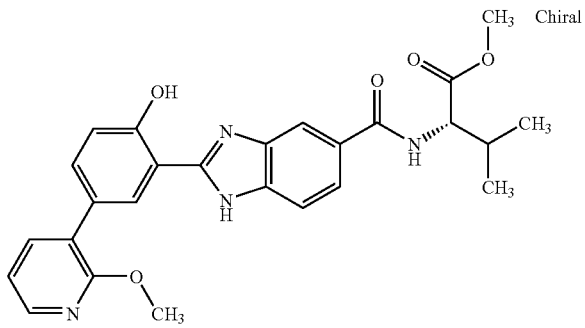 [SMILES: COC(=O)[C@@H](NC(=O)c1ccc2[nH]c(-c3cc(-c4cccnc4OC)ccc3O)nc2c1)C(C)C] | 475.52 |

-continued
| Structure | M + 1 |
| --- | --- |
| 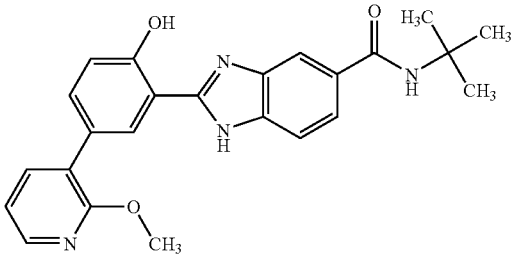 [SMILES: COc1ncccc1-c1ccc(O)c(-c2nc3cc(C(=O)NC(C)(C)C)ccc3[nH]2)c1] | 417.48 |
| 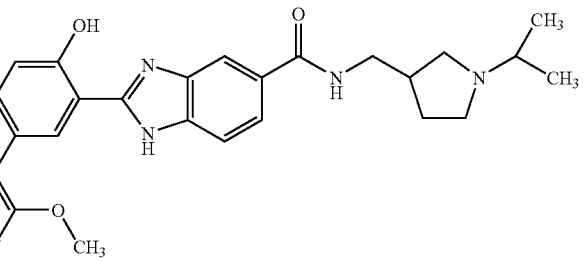 | 486.59 |
| 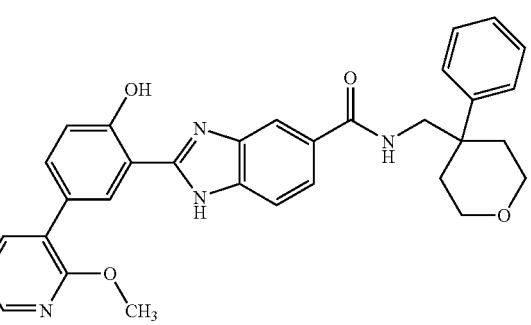 | 535.62 |
| 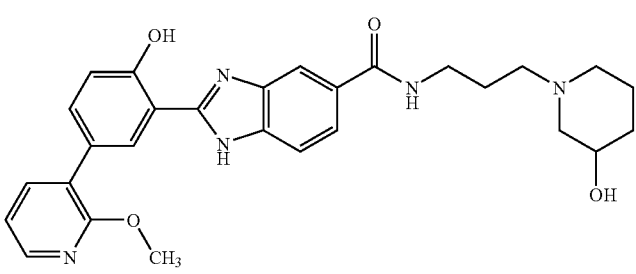 [SMILES: COc1ncccc1-c1ccc(O)c(-c2nc3cc(C(=O)NCCCN4CCCC(O)C4)ccc3[nH]2)c1] | 502.59 |
| 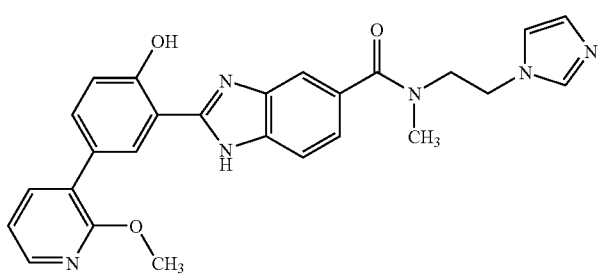 [SMILES: COc1ncccc1-c1ccc(O)c(-c2nc3cc(C(=O)N(C)CCn4ccnc4)ccc3[nH]2)c1] | 469.52 |

| Structure | M + 1 |
|---|---|
| 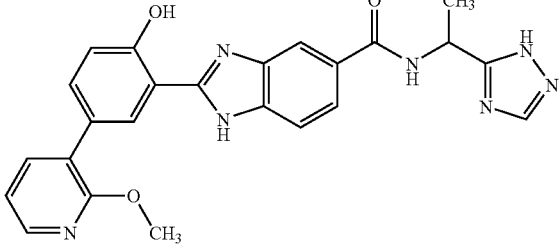 | 456.48 |
| 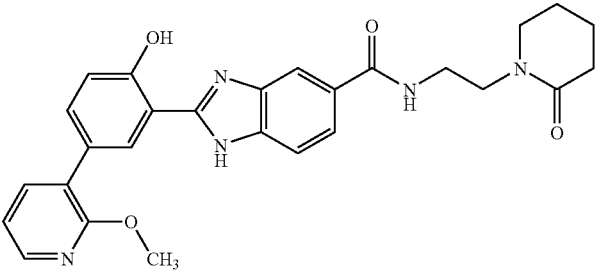 [SMILES: COc1ncccc1-c1ccc(O)c(-c2nc3cc(C(=O)NCCN4CCCCC4=O)ccc3[nH]2)c1] | 486.55 |
| 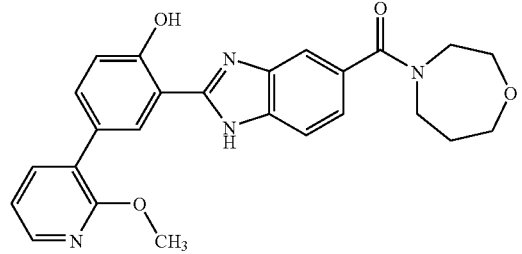 [SMILES: COc1ncccc1-c1ccc(O)c(-c2nc3cc(C(=O)N4CCCOCC4)ccc3[nH]2)c1] | 445.49 |
| 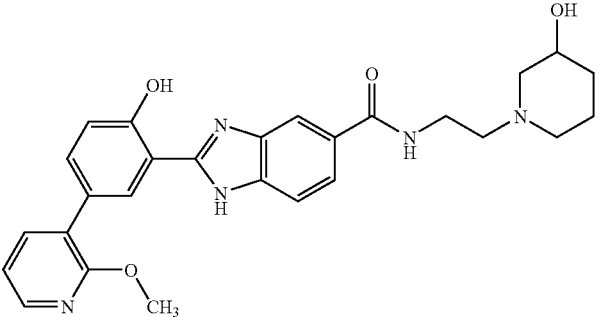 [SMILES: COc1ncccc1-c1ccc(O)c(-c2nc3cc(C(=O)NCCN4CCCC(O)C4)ccc3[nH]2)c1] | 488.56 |
| 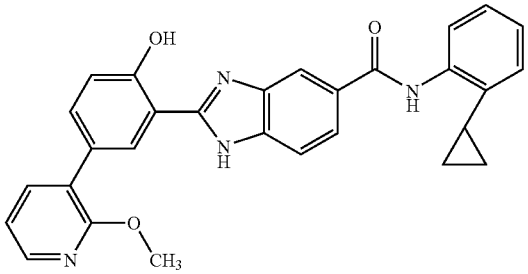 [SMILES: COc1ncccc1-c1ccc(O)c(-c2nc3cc(C(=O)Nc4ccccc4C4CC4)ccc3[nH]2)c1] | 477.54 |

-continued
| Structure | M + 1 |
|---|---|
| 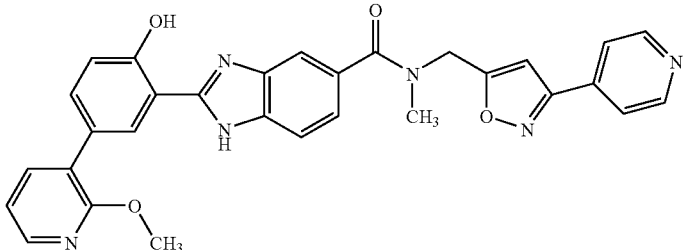 | 533.56 |
| 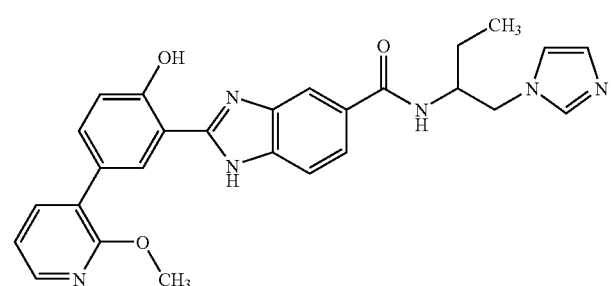 | 483.55 |
| 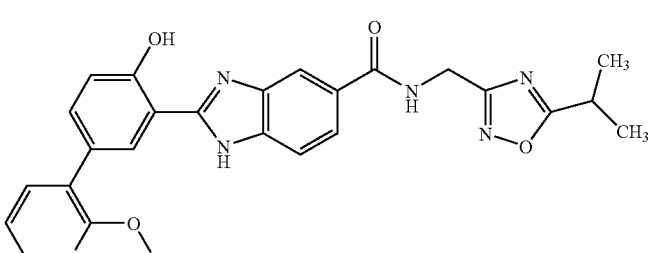 | 485.52 |
| 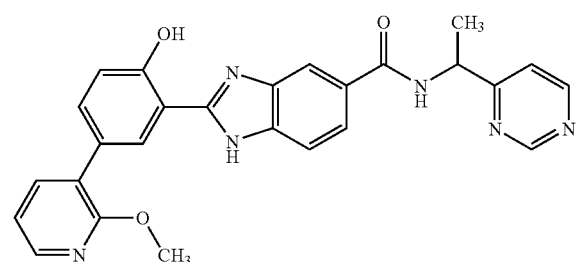 | 467.50 |
| 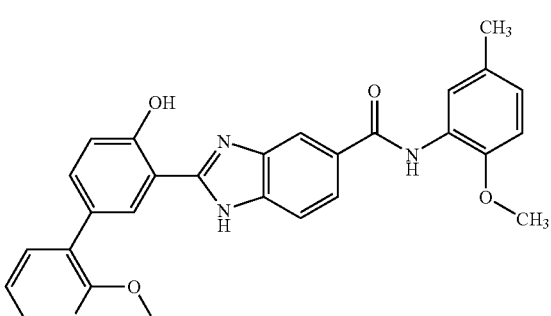 | 481.53 |

| Structure | M + 1 |
|---|---|
| 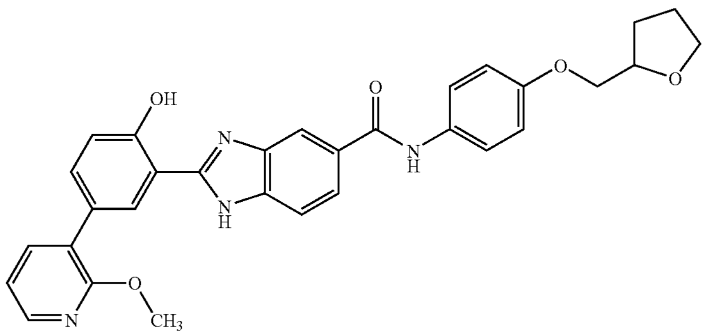 [SMILES: COc1ncccc1-c1ccc(O)c(-c2nc3cc(C(=O)Nc4ccc(OCC5CCCO5)cc4)ccc3[nH]2)c1] | 537.59 |
| 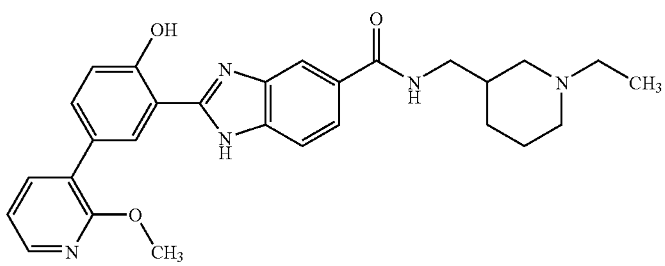 [SMILES: CCN1CCCC(CNC(=O)c2ccc3[nH]c(-c4cc(-c5cccnc5OC)ccc4O)nc3c2)C1] | 486.59 |
| 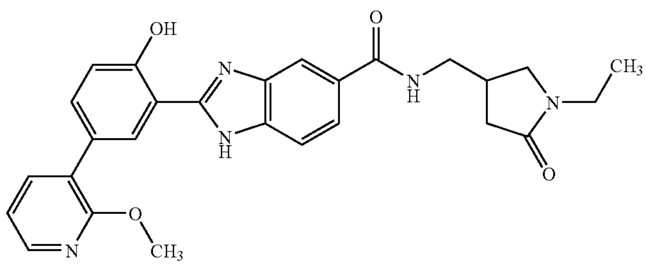 [SMILES: CCN1CC(CNC(=O)c2ccc3[nH]c(-c4cc(-c5cccnc5OC)ccc4O)nc3c2)CC1=O] | 486.55 |
| 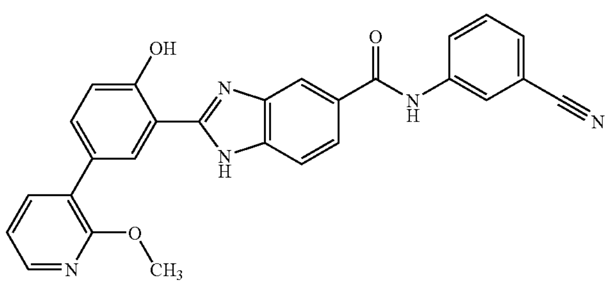 [SMILES: COc1ncccc1-c1ccc(O)c(-c2nc3cc(C(=O)Nc4cccc(C#N)c4)ccc3[nH]2)c1] | 462.48 |
| 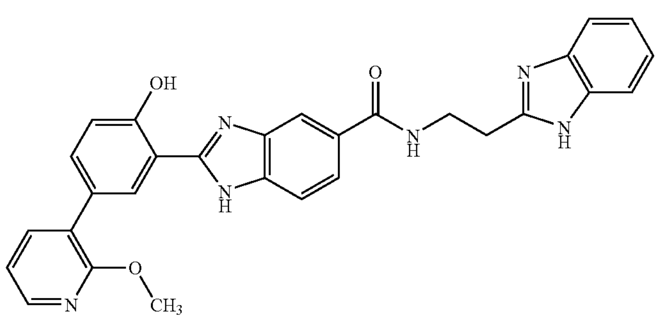 [SMILES: COc1ncccc1-c1ccc(O)c(-c2nc3cc(C(=O)NCCc4nc5ccccc5[nH]4)ccc3[nH]2)c1] | 505.55 |

| Structure | M + 1 |
|---|---|
| 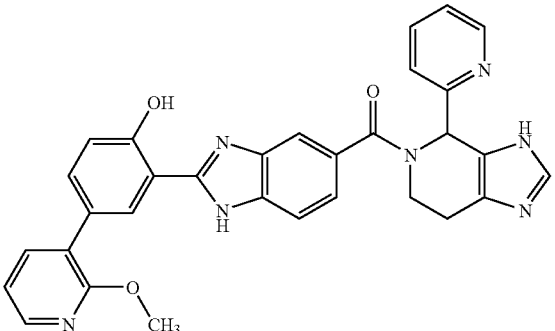 | 544.59 |
| 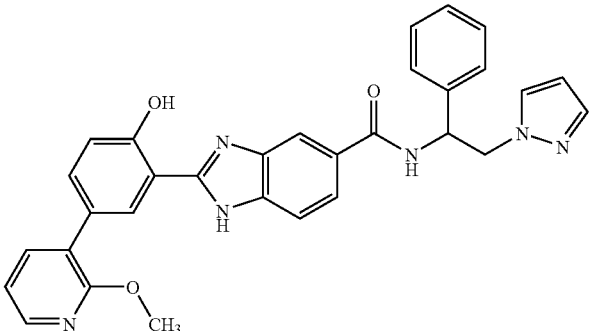 | 531.59 |
| 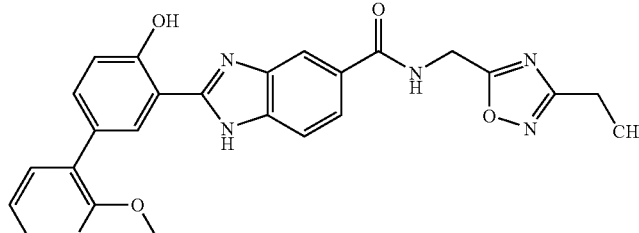 | 471.49 |
| 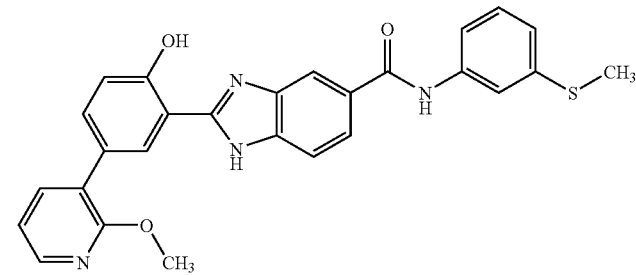 [SMILES: COc1ncccc1-c1ccc(O)c(-c2nc3cc(C(=O)Nc4cccc(SC)c4)ccc3[nH]2)c1] | 483.57 |
| 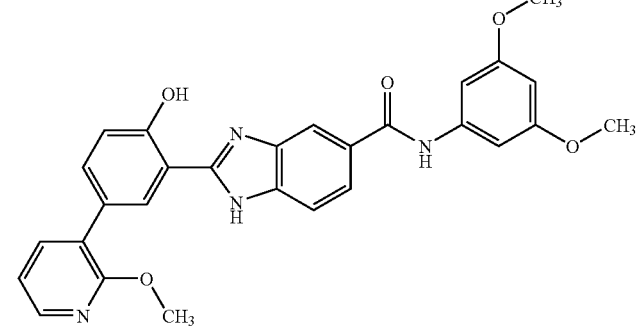 | 497.53 |

| Structure | M + 1 |
|---|---|
| 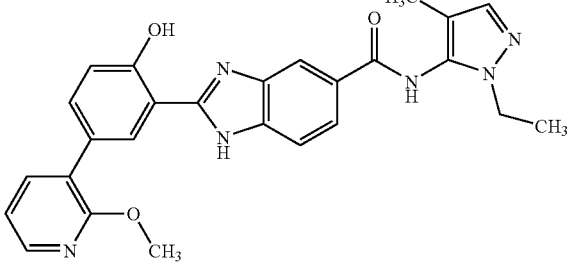 | 469.52 |
| 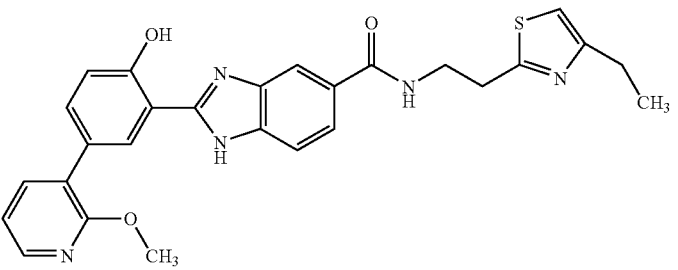 [SMILES: CCc1csc(CCNC(=O)c2ccc3[nH]c(-c4cc(-c5cccnc5OC)ccc4O)nc3c2)n1] | 500.60 |
| 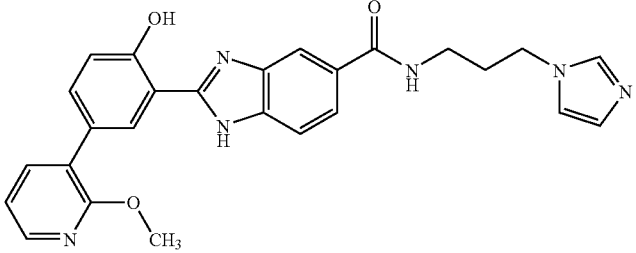 [SMILES: COc1ncccc1-c1ccc(O)c(-c2nc3cc(C(=O)NCCCn4ccnc4)ccc3[nH]2)c1] | 469.52 |
| 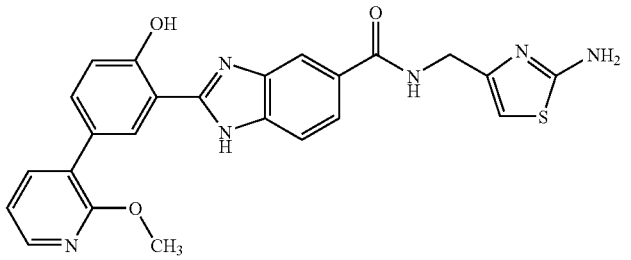 [SMILES: COc1ncccc1-c1ccc(O)c(-c2nc3cc(C(=O)NCc4csc(N)n4)ccc3[nH]2)c1] | 473.53 |
| 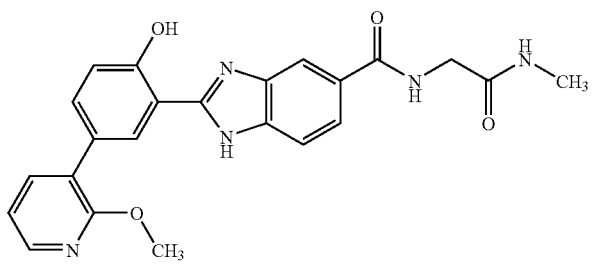 [SMILES: CNC(=O)CNC(=O)c1ccc2[nH]c(-c3cc(-c4cccnc4OC)ccc3O)nc2c1] | 432.45 |

| Structure | M + 1 |
|---|---|
| 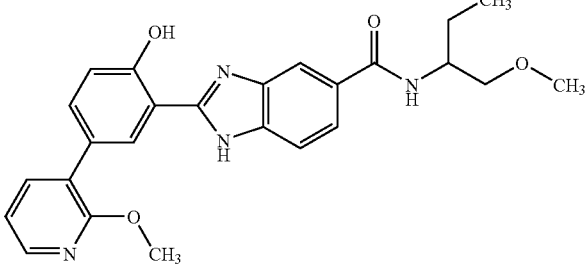 | 447.51 |
| 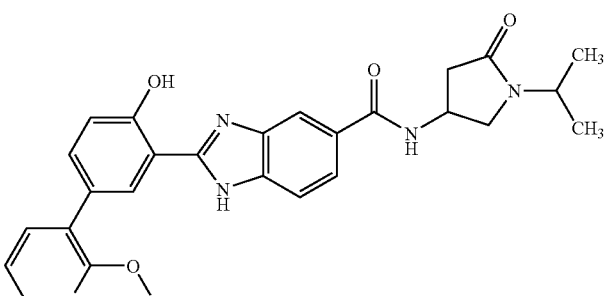 | 486.55 |
| 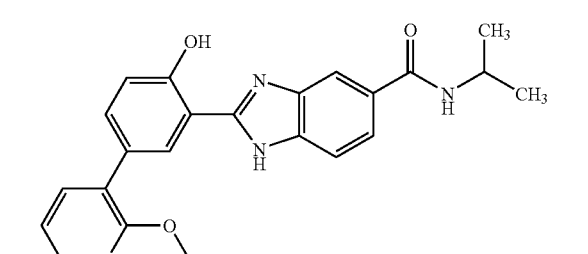 | 403.46 |
| 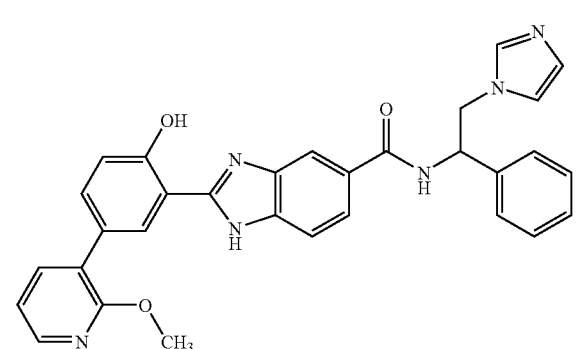 | 531.59 |
| 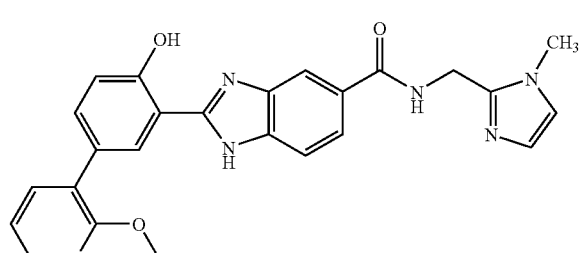 | 455.49 |

| Structure | M + 1 |
|---|---|
| 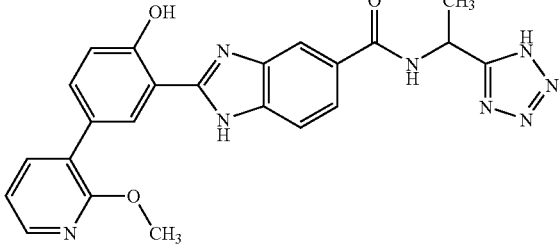 | 457.47 |
| 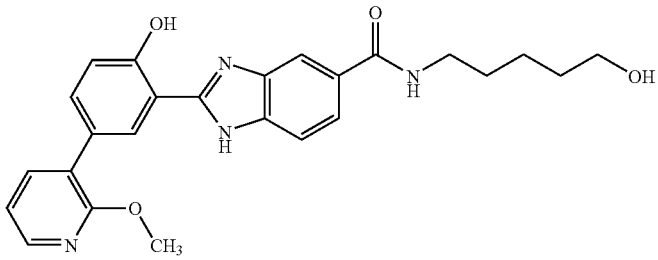 [SMILES: COc1ncccc1-c1ccc(O)c(-c2nc3cc(C(=O)NCCCCCO)ccc3[nH]2)c1] | 447.51 |
| 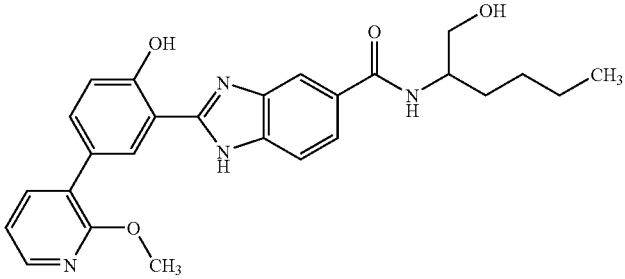 [SMILES: CCCCC(CO)NC(=O)c1ccc2[nH]c(-c3cc(-c4cccnc4OC)ccc3O)nc2c1] | 461.54 |
| 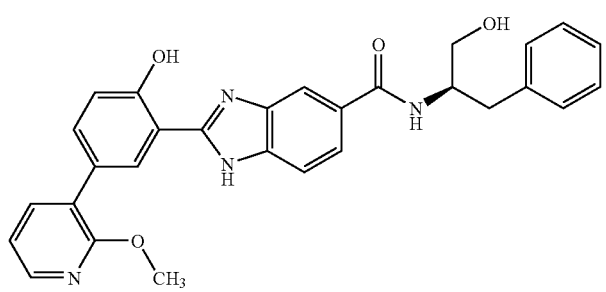 Chiral | 495.55 |
| 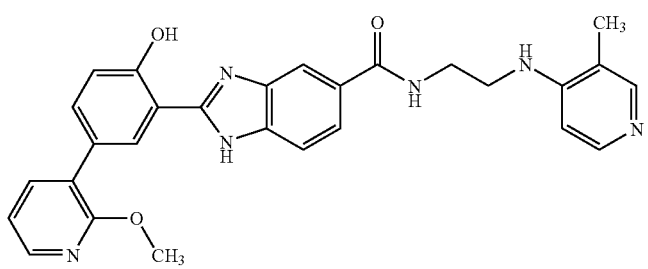 [SMILES: COc1ncccc1-c1ccc(O)c(-c2nc3cc(C(=O)NCCNc4ccncc4C)ccc3[nH]2)c1] | 495.56 |

-continued
| Structure | M + 1 |
|---|---|
| 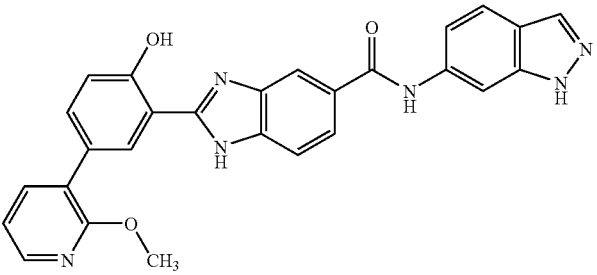 [SMILES: COc1ncccc1-c1ccc(O)c(-c2nc3cc(C(=O)Nc4ccc5cn[nH]c5c4)ccc3[nH]2)c1] | 477.50 |
| 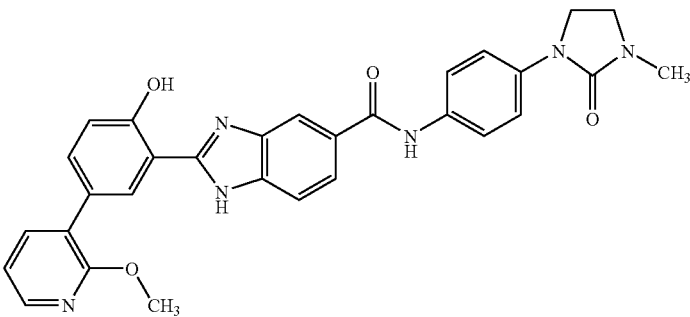 [SMILES: COc1ncccc1-c1ccc(O)c(-c2nc3cc(C(=O)Nc4ccc(N5CCN(C)C5=O)cc4)ccc3[nH]2)c1] | 535.58 |
| 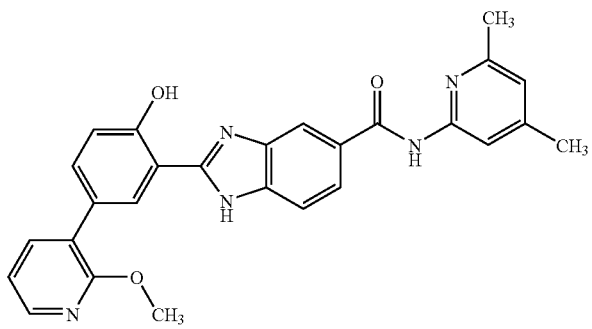 [SMILES: COc1ncccc1-c1ccc(O)c(-c2nc3cc(C(=O)Nc4cc(C)cc(C)n4)ccc3[nH]2)c1] | 466.52 |
| 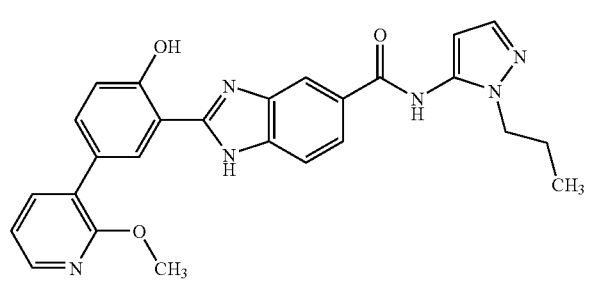 [SMILES: CCCn1nccc1NC(=O)c1ccc2[nH]c(-c3cc(-c4cccnc4OC)ccc3O)nc2c1] | 469.52 |
| 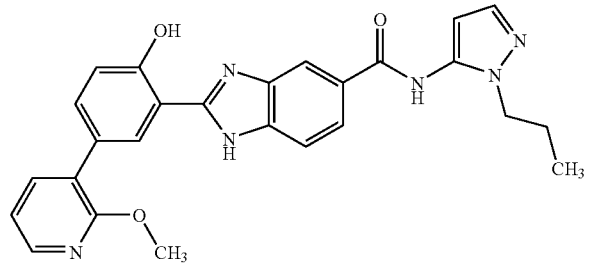 [SMILES: CCCn1nccc1NC(=O)c1ccc2[nH]c(-c3cc(-c4cccnc4OC)ccc3O)nc2c1] | 469.52 |

| Structure | M + 1 |
|---|---|
| 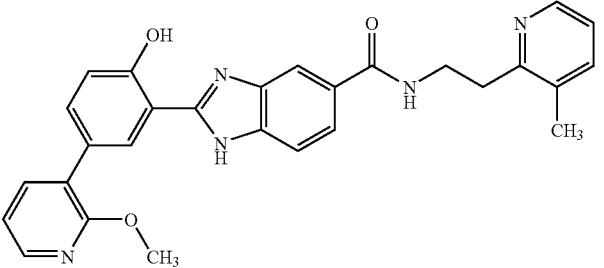 [SMILES: COc1ncccc1-c1ccc(O)c(-c2nc3cc(C(=O)NCCc4ncccc4C)ccc3[nH]2)c1] | 480.54 |
| 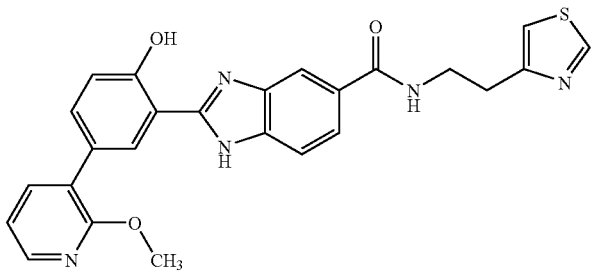 [SMILES: COc1ncccc1-c1ccc(O)c(-c2nc3cc(C(=O)NCCc4cscn4)ccc3[nH]2)c1] | 472.54 |
| 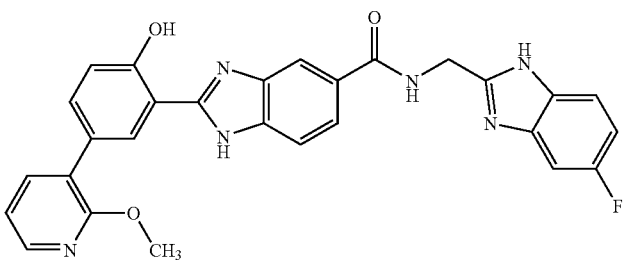 [SMILES: COc1ncccc1-c1ccc(O)c(-c2nc3cc(C(=O)NCc4nc5cc(F)ccc5[nH]4)ccc3[nH]2)c1] | 509.52 |
| 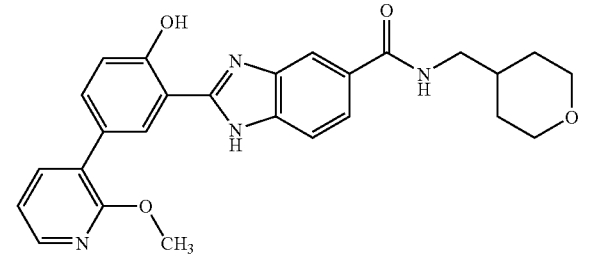 | 459.52 |
| 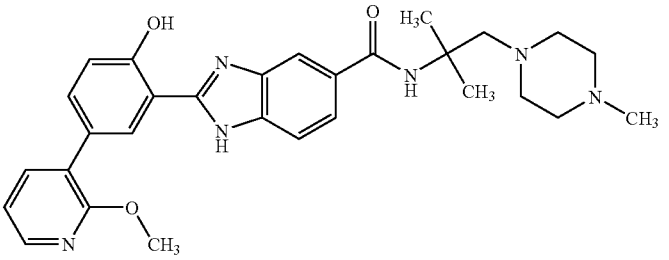 [SMILES: COc1ncccc1-c1ccc(O)c(-c2nc3cc(C(=O)NC(C)(C)CN4CCN(C)CC4)ccc3[nH]2)c1] | 515.63 |

| Structure | M + 1 |
|---|---|
| (structure) | 490.54 |
| (structure) | 429.50 |
| (structure) | 484.53 |
| (structure) | 531.59 |
| (structure) | 415.47 |

US 8,629,147 B2
401                                                                                                                         402
-continued
| Structure | M + 1 |
|-----------|-------|
| 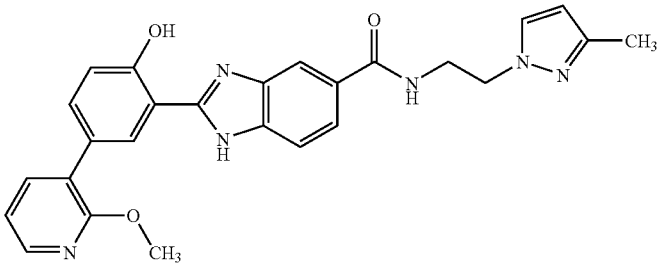 [SMILES: COc1ncccc1-c1ccc(O)c(-c2nc3cc(C(=O)NCCn4ccc(C)n4)ccc3[nH]2)c1] | 469.52 |
| 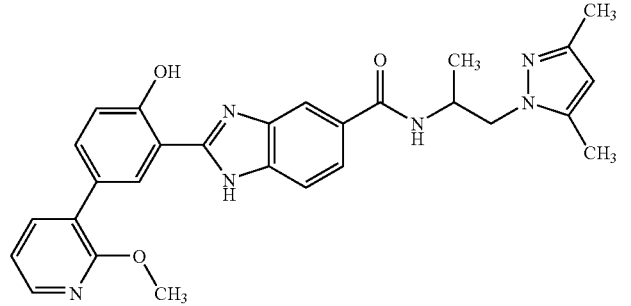 [SMILES: COc1ncccc1-c1ccc(O)c(-c2nc3cc(C(=O)NC(C)Cn4nc(C)cc4C)ccc3[nH]2)c1] | 497.57 |
| 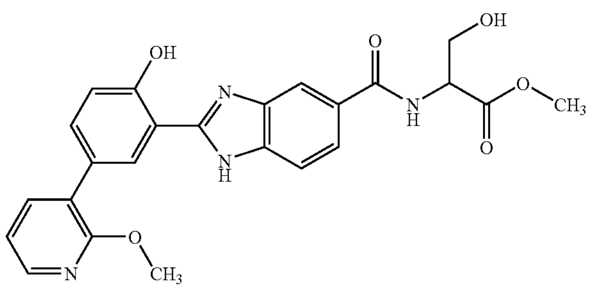 [SMILES: COC(=O)C(CO)NC(=O)c1ccc2[nH]c(-c3cc(-c4cccnc4OC)ccc3O)nc2c1] | 463.47 |
| 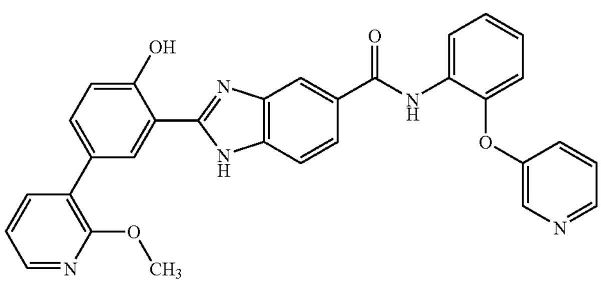 [SMILES: COc1ncccc1-c1ccc(O)c(-c2nc3cc(C(=O)Nc4ccccc4Oc4cccnc4)ccc3[nH]2)c1] | 530.56 |
| 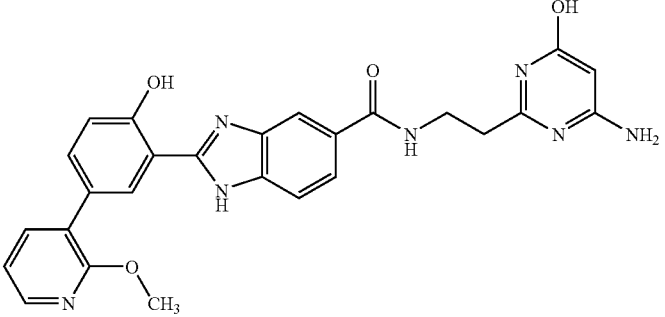 [SMILES: COc1ncccc1-c1ccc(O)c(-c2nc3cc(C(=O)NCCc4nc(N)cc(O)n4)ccc3[nH]2)c1] | 498.52 |

-continued
| Structure | M + 1 |
|---|---|
| 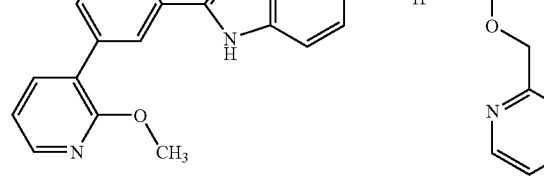 | 544.59 |
| 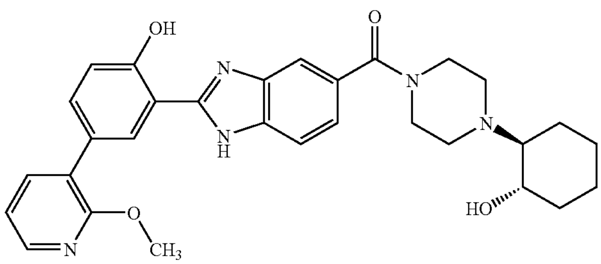 [SMILES: COc1ncccc1-c1ccc(O)c(-c2nc3cc(C(=O)N4CCN([C@H]5CCCC[C@@H]5O)CC4)ccc3[nH]2)c1] | 528.63 |
| 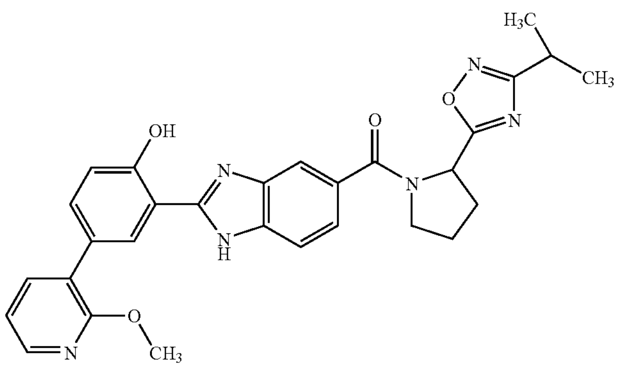 [SMILES: COc1ncccc1-c1ccc(O)c(-c2nc3cc(C(=O)N4CCCC4c4nc(C(C)C)no4)ccc3[nH]2)c1] | 525.58 |
| 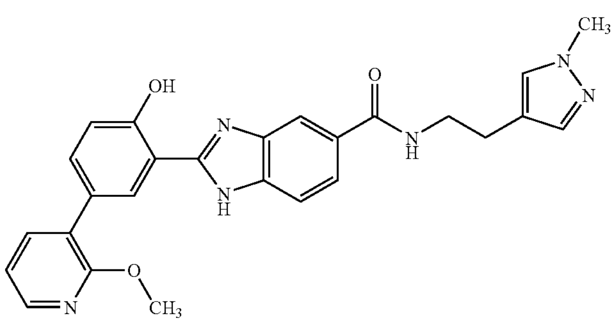 [SMILES: COc1ncccc1-c1ccc(O)c(-c2nc3cc(C(=O)NCCc4cnn(C)c4)ccc3[nH]2)c1] | 469.52 |
| 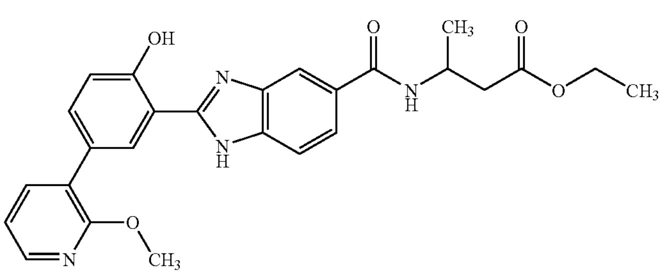 [SMILES: CCOC(=O)CC(C)NC(=O)c1ccc2[nH]c(-c3cc(-c4cccnc4OC)ccc3O)nc2c1] | 475.52 |

-continued
| Structure | M + 1 |
|---|---|
| 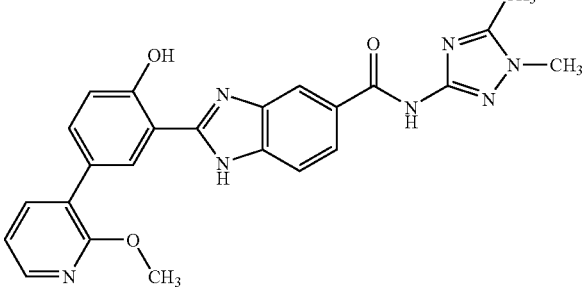 | 456.48 |
| 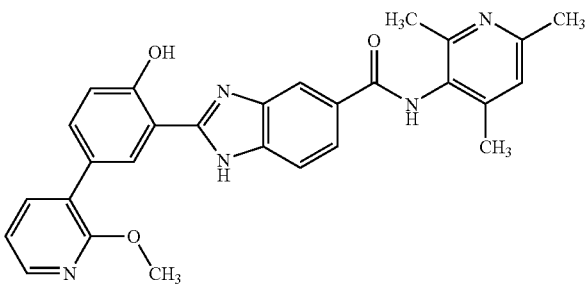 [SMILES: COc1ncccc1-c1ccc(O)c(-c2nc3cc(C(=O)Nc4c(C)cc(C)nc4C)ccc3[nH]2)c1] | 480.54 |
| 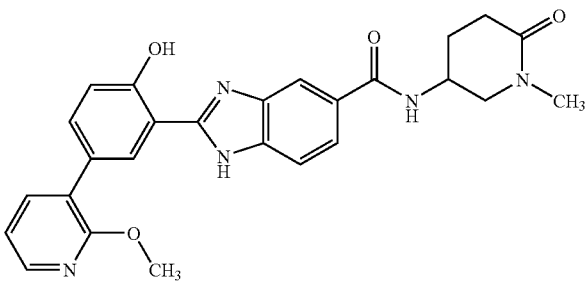 [SMILES: COc1ncccc1-c1ccc(O)c(-c2nc3cc(C(=O)NC4CCC(=O)N(C)C4)ccc3[nH]2)c1] | 472.52 |
| 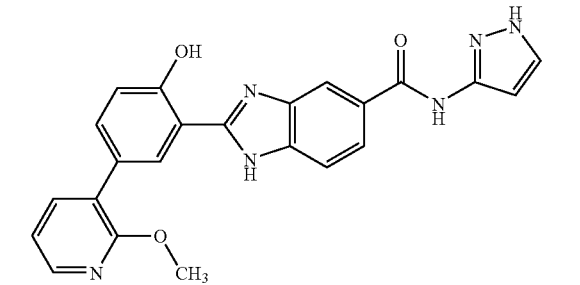 [SMILES: COc1ncccc1-c1ccc(O)c(-c2nc3cc(C(=O)Nc4cc[nH]n4)ccc3[nH]2)c1] | 427.44 |
| 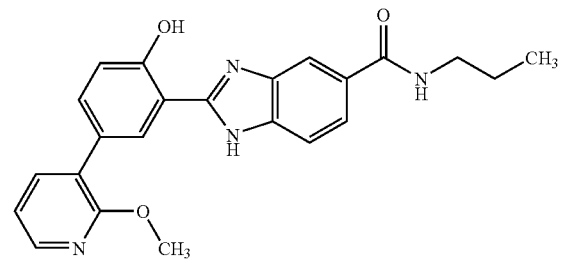 | 403.46 |

-continued
| Structure | M + 1 |
|---|---|
| 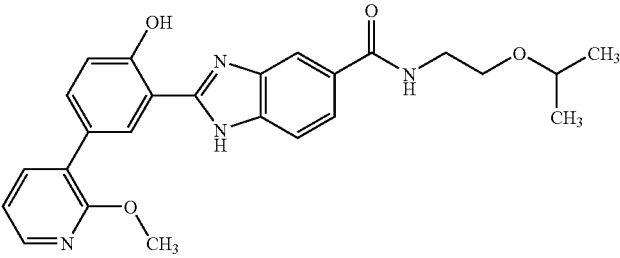 [SMILES: COc1ncccc1-c1ccc(O)c(-c2nc3cc(C(=O)NCCOC(C)C)ccc3[nH]2)c1] | 447.51 |
| 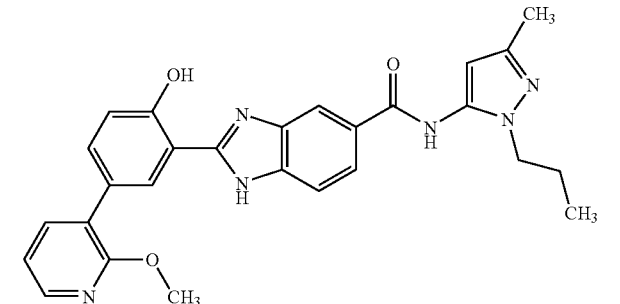 | 483.55 |
| 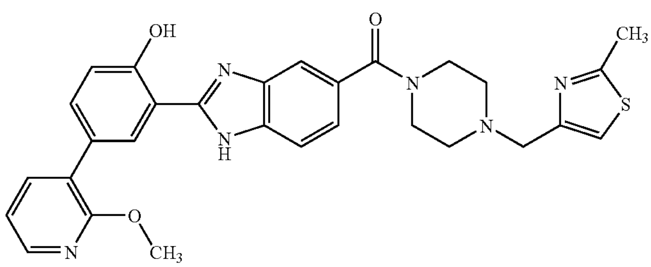 [SMILES: COc1ncccc1-c1ccc(O)c(-c2nc3cc(C(=O)N4CCN(Cc5csc(C)n5)CC4)ccc3[nH]2)c1] | 541.65 |
| 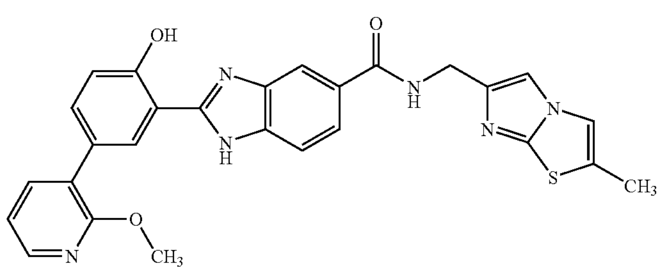 [SMILES: COc1ncccc1-c1ccc(O)c(-c2nc3cc(C(=O)NCc4cn5cc(C)sc5n4)ccc3[nH]2)c1] | 511.58 |
| 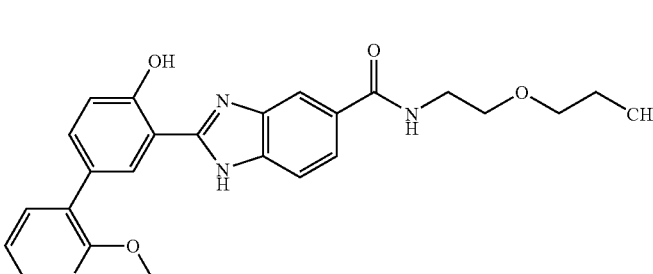 | 447.51 |

-continued
| Structure | M + 1 |
|---|---|
| 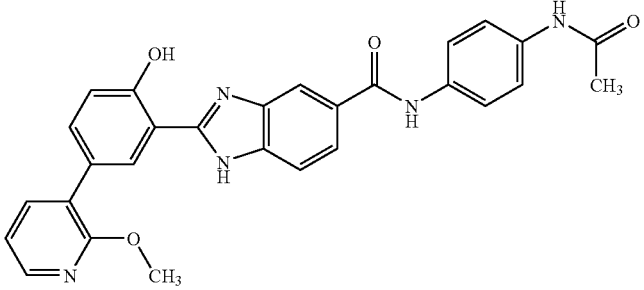 [SMILES: COc1ncccc1-c1ccc(O)c(-c2nc3cc(C(=O)Nc4ccc(NC(C)=O)cc4)ccc3[nH]2)c1] | 494.53 |
| 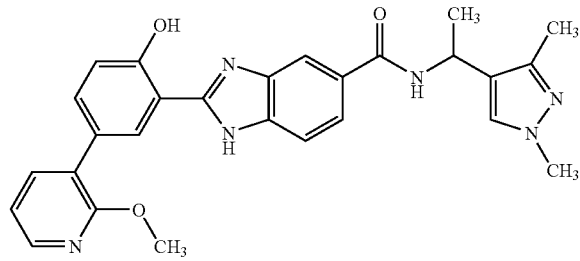 | 483.55 |
| 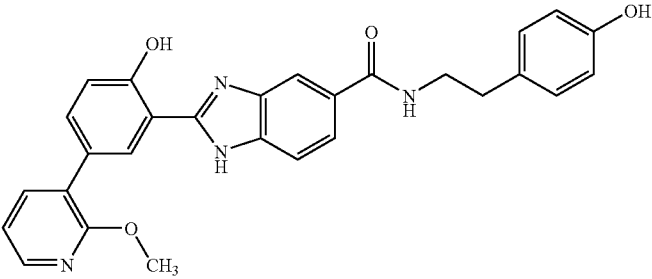 [SMILES: COc1ncccc1-c1ccc(O)c(-c2nc3cc(C(=O)NCCc4ccc(O)cc4)ccc3[nH]2)c1] | 481.53 |
| 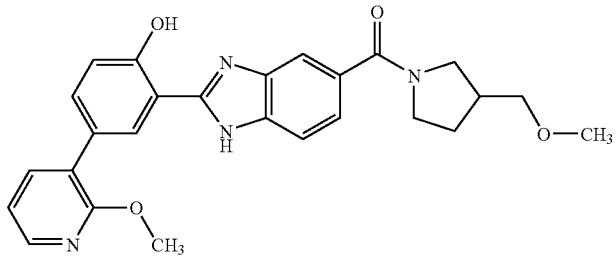 [SMILES: COCC1CCN(C(=O)c2ccc3[nH]c(-c4cc(-c5cccnc5OC)ccc4O)nc3c2)C1] | 459.52 |
| 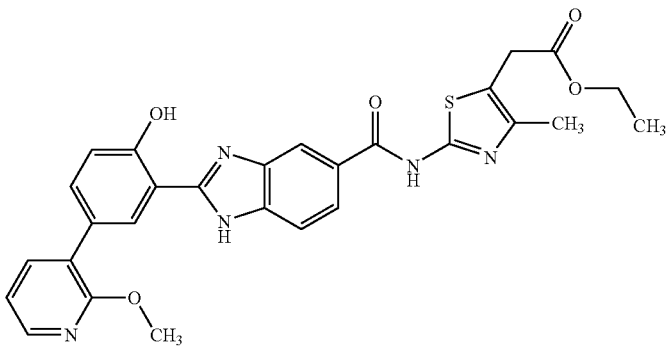 [SMILES: CCOC(=O)Cc1sc(NC(=O)c2ccc3[nH]c(-c4cc(-c5cccnc5OC)ccc4O)nc3c2)nc1C] | 544.61 |

-continued
| Structure | M + 1 |
|---|---|
| 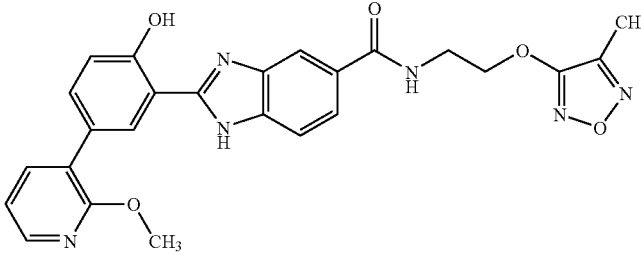 | 487.49 |
| 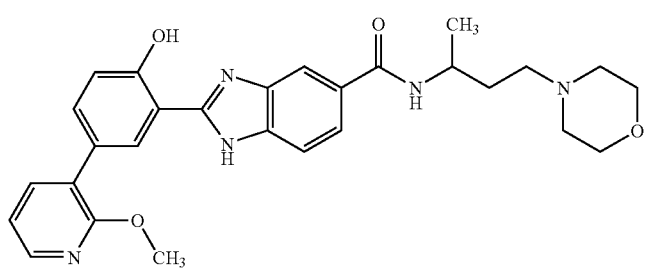 [SMILES: COc1ncccc1-c1ccc(O)c(-c2nc3cc(C(=O)NC(C)CCN4CCOCC4)ccc3[nH]2)c1] | 502.59 |
| 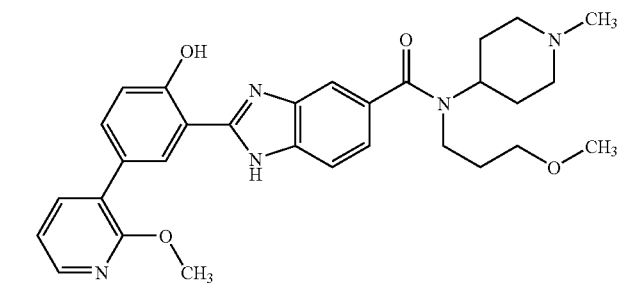 [SMILES: COCCCN(C(=O)c1ccc2[nH]c(-c3cc(-c4cccnc4OC)ccc3O)nc2c1)C1CCN(C)CC1] | 530.64 |
| 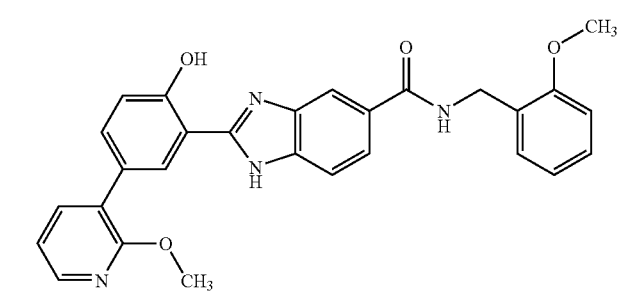 [SMILES: COc1ccccc1CNC(=O)c1ccc2[nH]c(-c3cc(-c4cccnc4OC)ccc3O)nc2c1] | 481.53 |
| 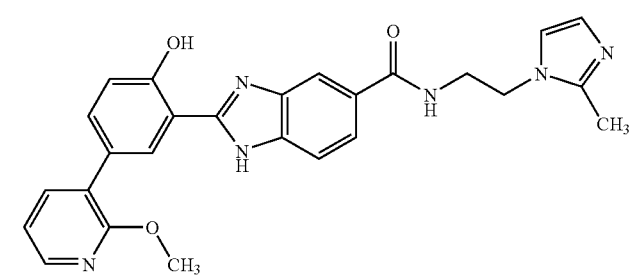 [SMILES: COc1ncccc1-c1ccc(O)c(-c2nc3cc(C(=O)NCCn4ccnc4C)ccc3[nH]2)c1] | 469.52 |

-continued
| Structure | M + 1 |
|---|---|
| 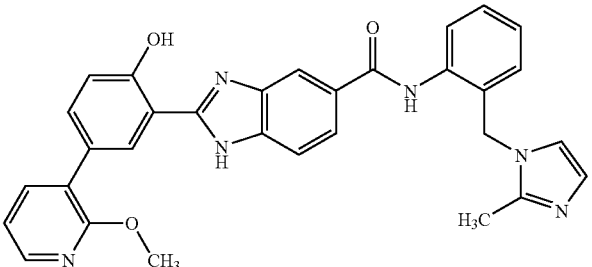 | 531.59 |
| 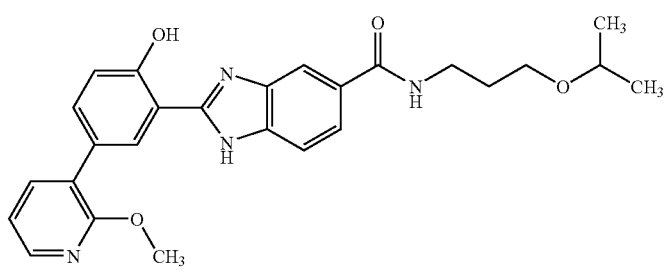 [SMILES: COc1ncccc1-c1ccc(O)c(-c2nc3cc(C(=O)NCCCOC(C)C)ccc3[nH]2)c1] | 461.54 |
| 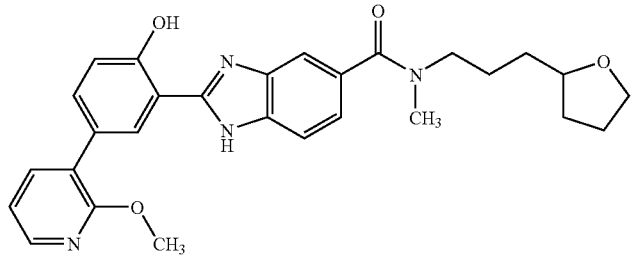 [SMILES: COc1ncccc1-c1ccc(O)c(-c2nc3cc(C(=O)N(C)CCCC4CCCO4)ccc3[nH]2)c1] | 487.58 |
| 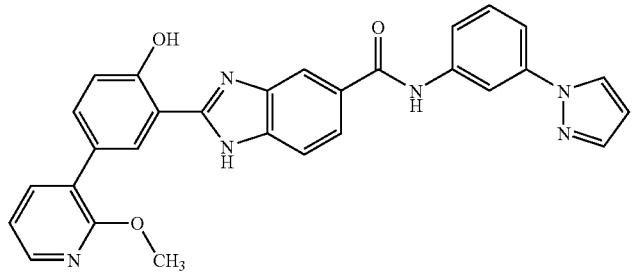 [SMILES: COc1ncccc1-c1ccc(O)c(-c2nc3cc(C(=O)Nc4cccc(-n5cccn5)c4)ccc3[nH]2)c1] | 503.54 |
| 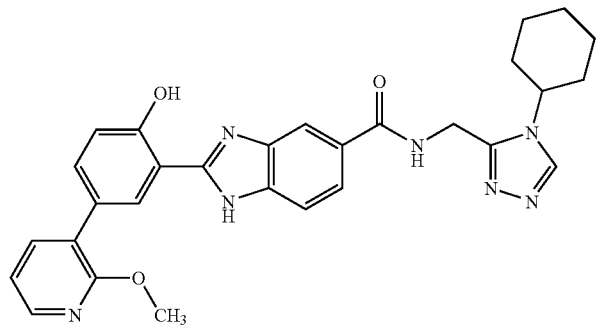 [SMILES: COc1ncccc1-c1ccc(O)c(-c2nc3cc(C(=O)NCc4nncn4C4CCCCC4)ccc3[nH]2)c1] | 524.60 |

-continued

| Structure | M + 1 |
|---|---|
| 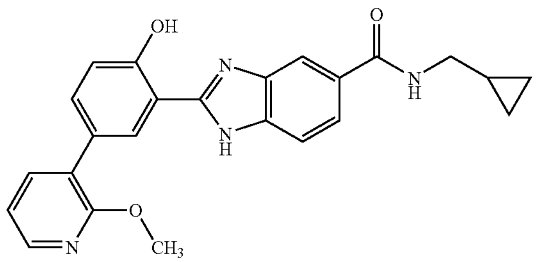 [SMILES: COc1ncccc1-c1ccc(O)c(-c2nc3cc(C(=O)NCC4CC4)ccc3[nH]2)c1] | 415.47 |
| 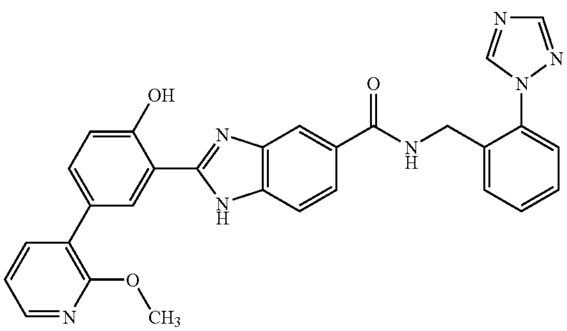 [SMILES: COc1ncccc1-c1ccc(O)c(-c2nc3cc(C(=O)NCc4ccccc4-n4cncn4)ccc3[nH]2)c1] | 518.55 |
| 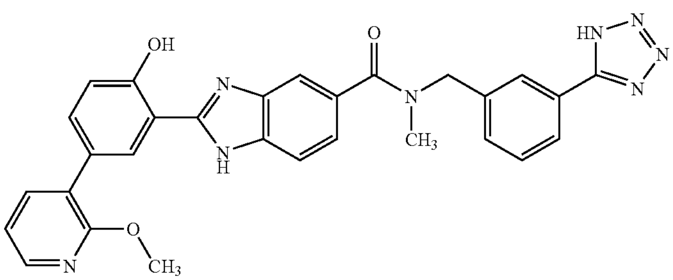 [SMILES: COc1ncccc1-c1ccc(O)c(-c2nc3cc(C(=O)N(C)Cc4cccc(-c5nnn[nH]5)c4)ccc3[nH]2)c1] | 533.57 |
| 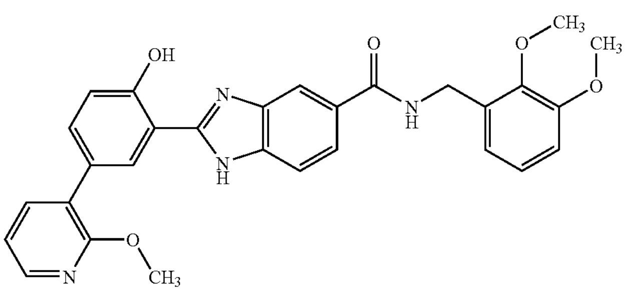 [SMILES: COc1cccc(CNC(=O)c2ccc3[nH]c(-c4cc(-c5cccnc5OC)ccc4O)nc3c2)c1OC] | 511.55 |
| 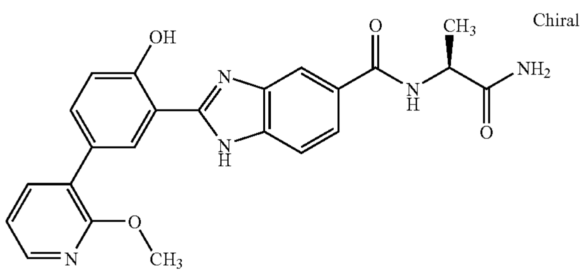 [SMILES: COc1ncccc1-c1ccc(O)c(-c2nc3cc(C(=O)N[C@@H](C)C(N)=O)ccc3[nH]2)c1] | 432.45 |

| Structure | M + 1 |
|---|---|
| 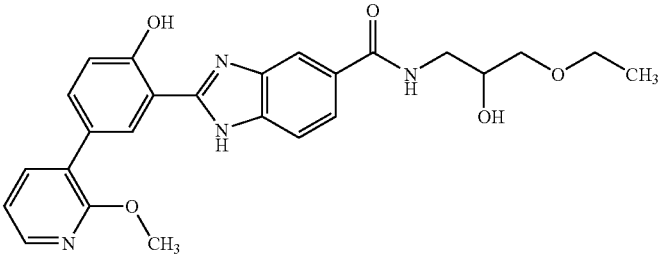 [SMILES: CCOCC(O)CNC(=O)c1ccc2[nH]c(-c3cc(-c4cccnc4OC)ccc3O)nc2c1] | 463.51 |
| 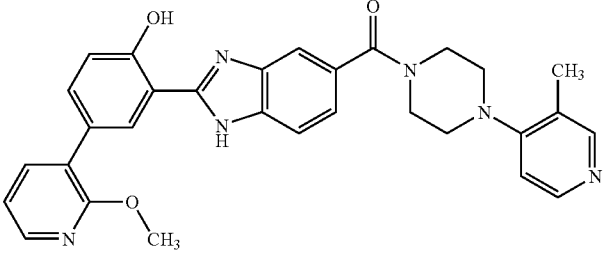 [SMILES: COc1ncccc1-c1ccc(O)c(-c2nc3cc(C(=O)N4CCN(c5ccncc5C)CC4)ccc3[nH]2)c1] | 521.60 |
| 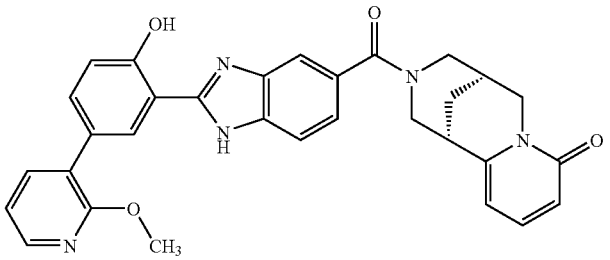 Chiral | 534.59 |
| 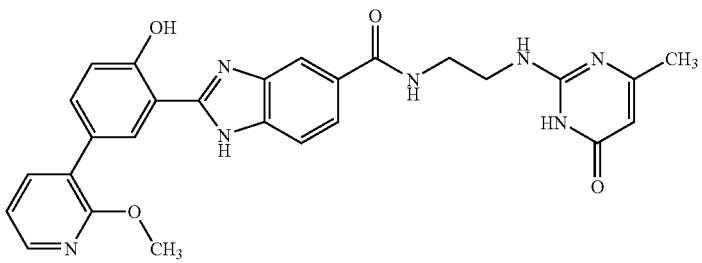 [SMILES: COc1ncccc1-c1ccc(O)c(-c2nc3cc(C(=O)NCCNc4nc(C)cc(=O)[nH]4)ccc3[nH]2)c1] | 512.54 |
| 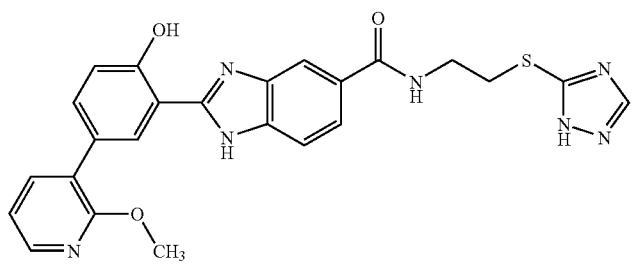 [SMILES: COc1ncccc1-c1ccc(O)c(-c2nc3cc(C(=O)NCCSc4ncn[nH]4)ccc3[nH]2)c1] | 488.54 |

-continued

| Structure | M + 1 |
|---|---|
| 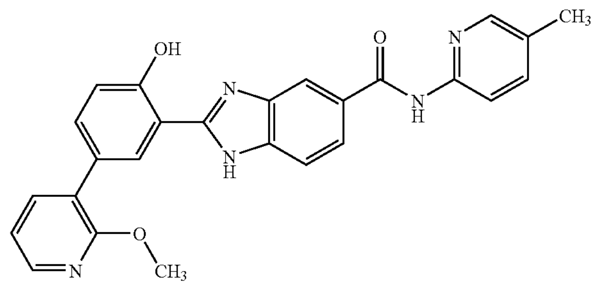 [SMILES: COc1ncccc1-c1ccc(O)c(-c2nc3cc(C(=O)Nc4ccc(C)cn4)ccc3[nH]2)c1] | 452.49 |
| 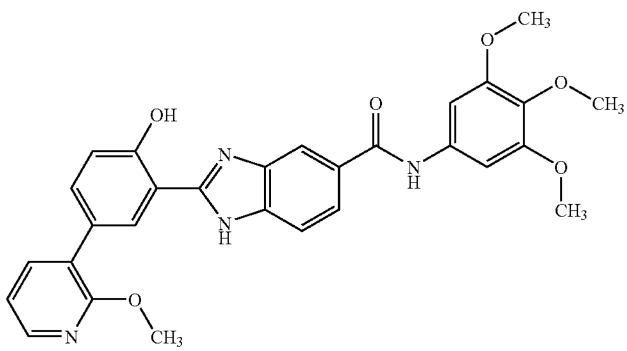 [SMILES: COc1cc(NC(=O)c2ccc3[nH]c(-c4cc(-c5cccnc5OC)ccc4O)nc3c2)cc(OC)c1OC] | 527.55 |
| 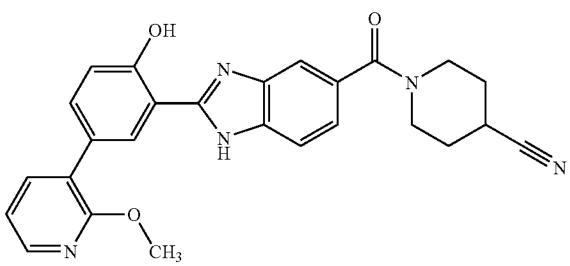 [SMILES: COc1ncccc1-c1ccc(O)c(-c2nc3cc(C(=O)N4CCC(C#N)CC4)ccc3[nH]2)c1] | 454.50 |
| 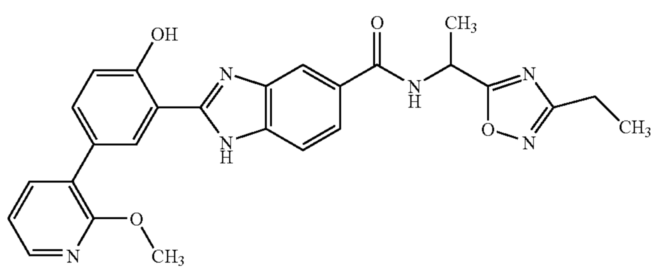 [SMILES: CCc1noc(C(C)NC(=O)c2ccc3[nH]c(-c4cc(-c5cccnc5OC)ccc4O)nc3c2)n1] | 485.52 |
| 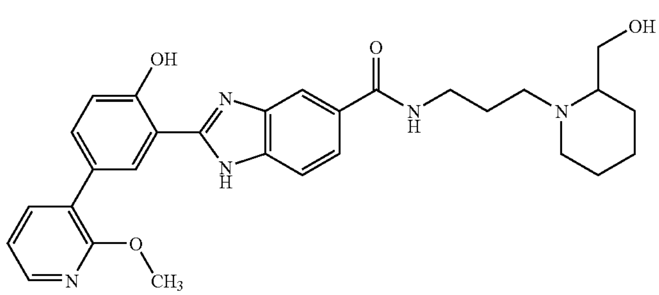 [SMILES: COc1ncccc1-c1ccc(O)c(-c2nc3cc(C(=O)NCCCN4CCCCC4CO)ccc3[nH]2)c1] | 516.62 |

-continued

| Structure | M + 1 |
|---|---|
| 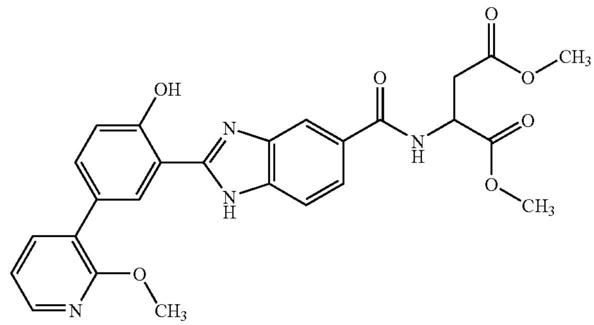 [SMILES: COC(=O)CC(NC(=O)c1ccc2[nH]c(-c3cc(-c4cccnc4OC)ccc3O)nc2c1)C(=O)OC] | 505.50 |
| 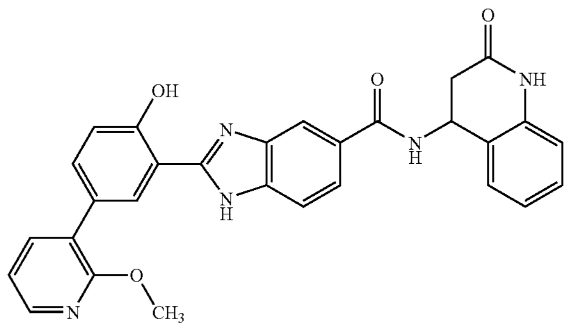 [SMILES: COc1ncccc1-c1ccc(O)c(-c2nc3cc(C(=O)NC4CC(=O)Nc5ccccc54)ccc3[nH]2)c1] | 506.54 |
| 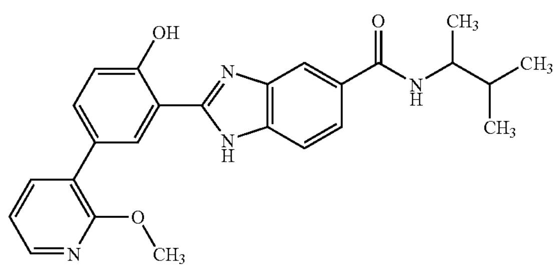 [SMILES: COc1ncccc1-c1ccc(O)c(-c2nc3cc(C(=O)NC(C)C(C)C)ccc3[nH]2)c1] | 431.51 |
| 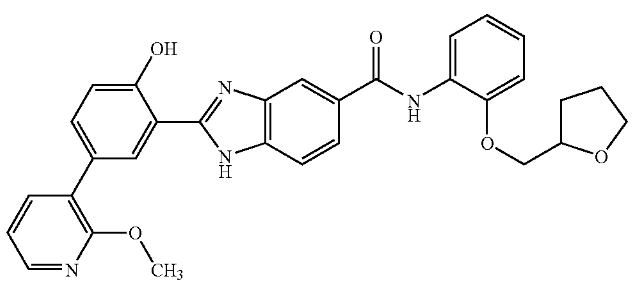 [SMILES: COc1ncccc1-c1ccc(O)c(-c2nc3cc(C(=O)Nc4ccccc4OCC4CCCO4)ccc3[nH]2)c1] | 537.59 |
| 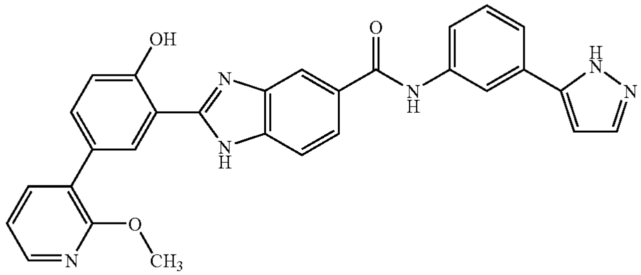 [SMILES: COc1ncccc1-c1ccc(O)c(-c2nc3cc(C(=O)Nc4cccc(-c5ccn[nH]5)c4)ccc3[nH]2)c1] | 503.54 |

-continued
| Structure | M + 1 |
|---|---|
| 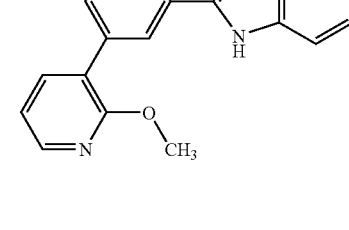 | 489.91 |
| 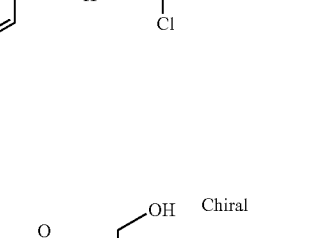 Chiral | 461.54 |
| 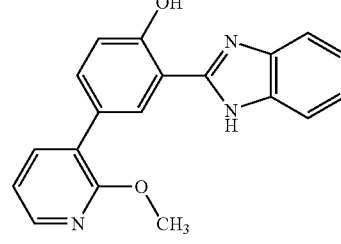 | 444.49 |
| 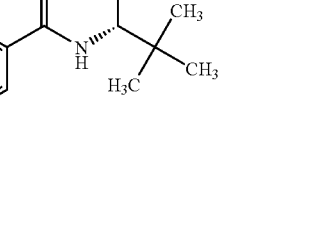 | 494.57 |
| 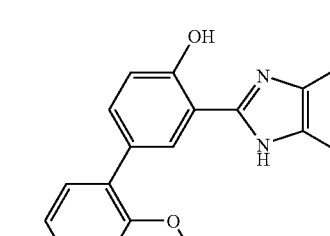 | 457.47 |

-continued
| Structure | M + 1 |
|---|---|
| 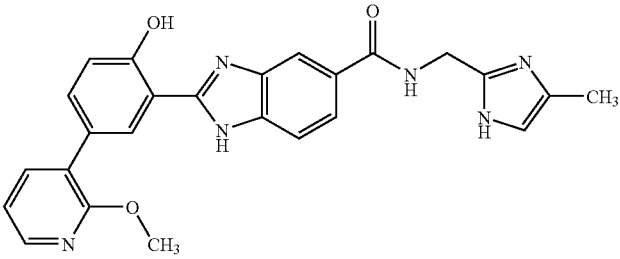 | 455.49 |
| 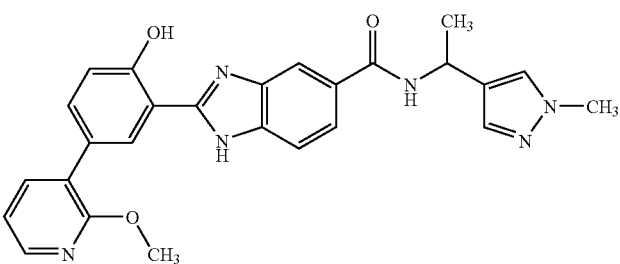 [SMILES: COc1ncccc1-c1ccc(O)c(-c2nc3cc(C(=O)NC(C)c4cnn(C)c4)ccc3[nH]2)c1] | 469.52 |
| 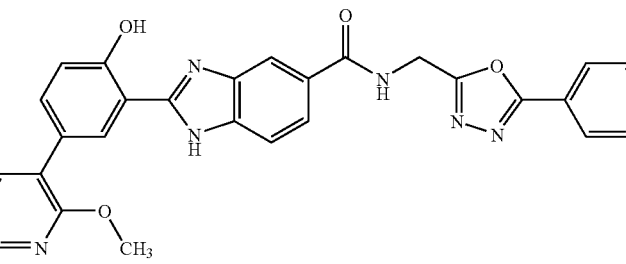 | 519.54 |
| 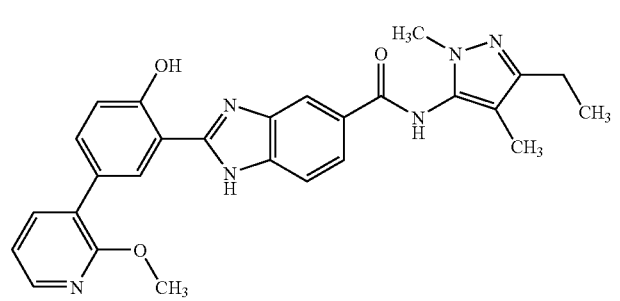 [SMILES: CCc1nn(C)c(NC(=O)c2ccc3[nH]c(-c4cc(-c5cccnc5OC)ccc4O)nc3c2)c1C] | 483.55 |
| 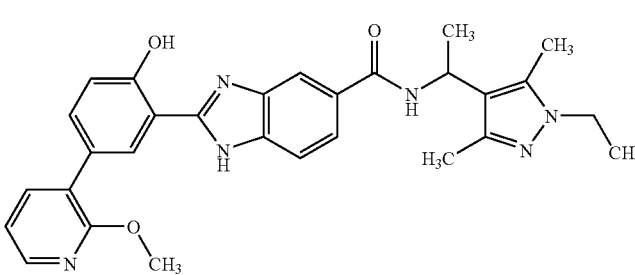 | 511.60 |

-continued
| Structure | M + 1 |
|---|---|
| 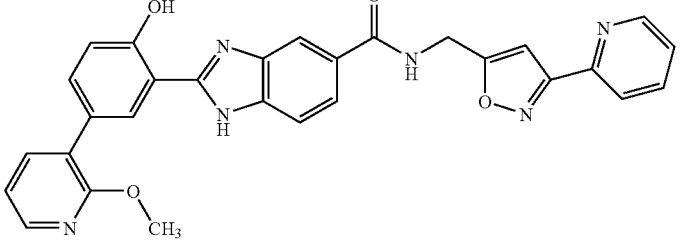 | 519.54 |
| 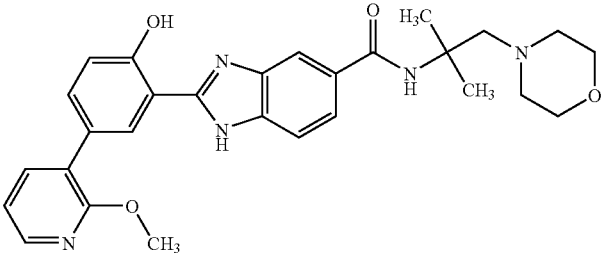 [SMILES: COc1ncccc1-c1ccc(O)c(-c2nc3cc(C(=O)NC(C)(C)CN4CCOCC4)ccc3[nH]2)c1] | 502.59 |
| 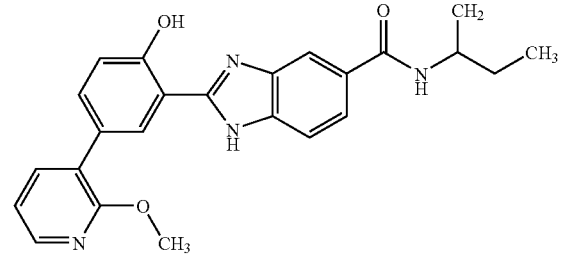 [SMILES: CCC(C)NC(=O)c1ccc2[nH]c(-c3cc(-c4cccnc4OC)ccc3O)nc2c1] | 417.48 |
| 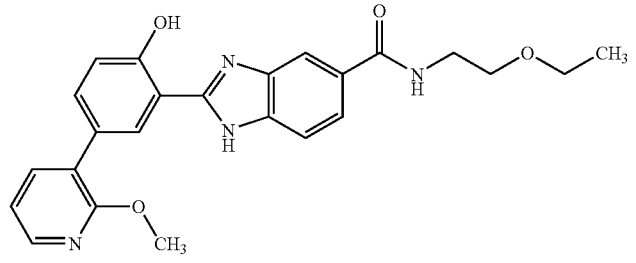 [SMILES: CCOCCNC(=O)c1ccc2[nH]c(-c3cc(-c4cccnc4OC)ccc3O)nc2c1] | 433.48 |
| 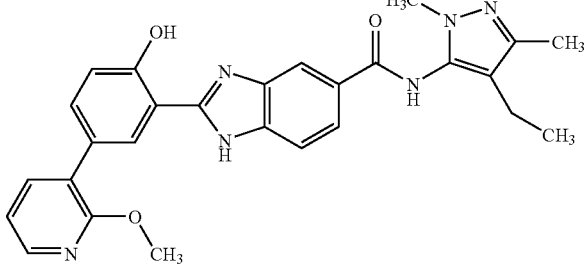 | 483.55 |

-continued

| Structure | M + 1 |
|---|---|
| (structure) | 488.56 |
| (structure) | 482.52 |
| (structure) | 486.59 |
| (structure) | 534.61 |
| (structure) | 480.50 |

| Structure | M + 1 |
|---|---|
| 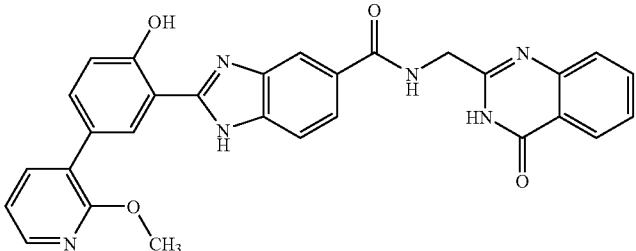 | 519.54 |
| 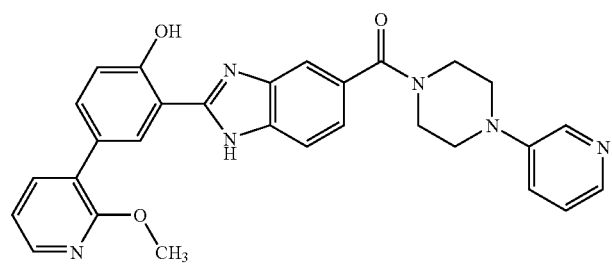 [SMILES: COc1ncccc1-c1ccc(O)c(-c2nc3cc(C(=O)N4CCN(c5cccnc5)CC4)ccc3[nH]2)c1] | 507.57 |
| 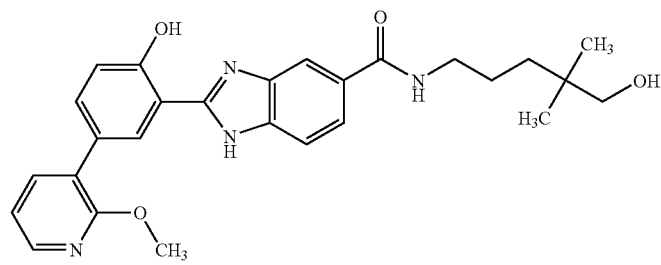 [SMILES: COc1ncccc1-c1ccc(O)c(-c2nc3cc(C(=O)NCCCC(C)(C)CO)ccc3[nH]2)c1] | 475.56 |
| 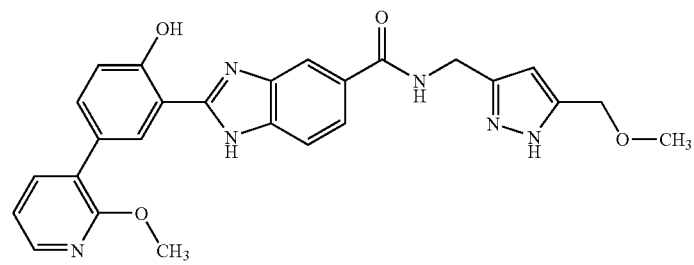 [SMILES: COCc1cc(CNC(=O)c2ccc3[nH]c(-c4cc(-c5cccnc5OC)ccc4O)nc3c2)n[nH]1] | 485.52 |
| 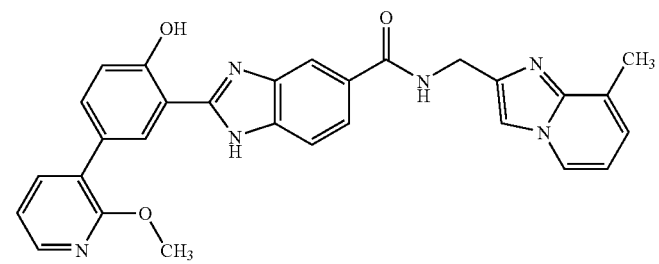 [SMILES: COc1ncccc1-c1ccc(O)c(-c2nc3cc(C(=O)NCc4cn5cccc(C)c5n4)ccc3[nH]2)c1] | 505.55 |

433
434
-continued
| Structure | M + 1 |
|---|---|
| 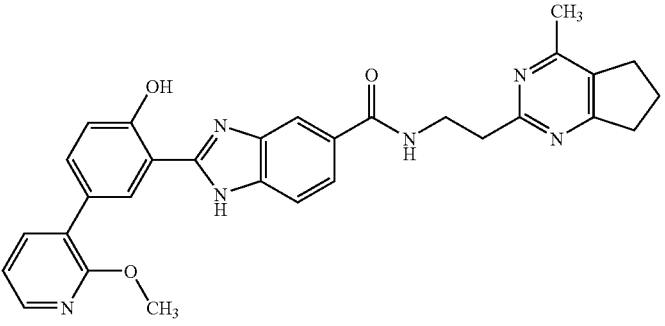 [SMILES: COc1ncccc1-c1ccc(O)c(-c2nc3cc(C(=O)NCCc4nc(C)c5c(n4)CCC5)ccc3[nH]2)c1] | 521.60 |
| 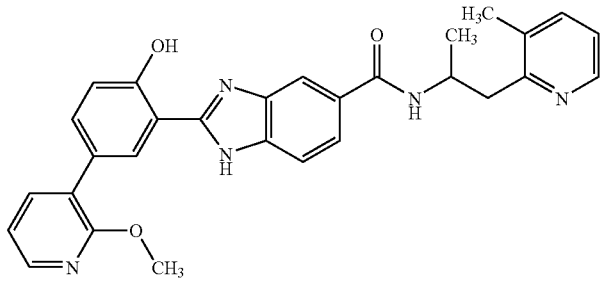 [SMILES: COc1ncccc1-c1ccc(O)c(-c2nc3cc(C(=O)NC(C)Cc4ncccc4C)ccc3[nH]2)c1] | 494.57 |
| 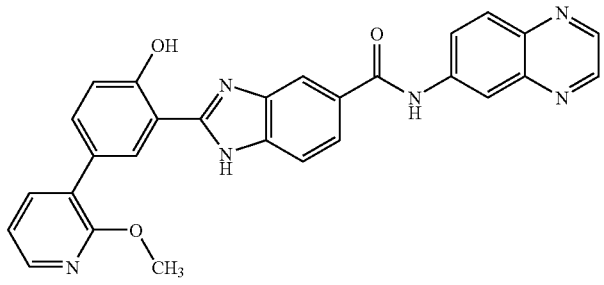 [SMILES: COc1ncccc1-c1ccc(O)c(-c2nc3cc(C(=O)Nc4ccc5nccnc5c4)ccc3[nH]2)c1] | 489.51 |
| 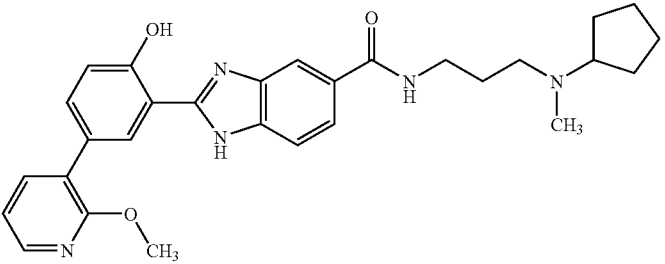 [SMILES: COc1ncccc1-c1ccc(O)c(-c2nc3cc(C(=O)NCCCN(C)C4CCCC4)ccc3[nH]2)c1] | 500.62 |
| 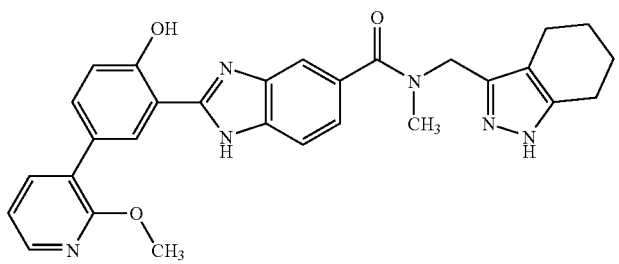 [SMILES: COc1ncccc1-c1ccc(O)c(-c2nc3cc(C(=O)N(C)Cc4n[nH]c5c4CCCC5)ccc3[nH]2)c1] | 509.58 |

| Structure | M + 1 |
|---|---|
| 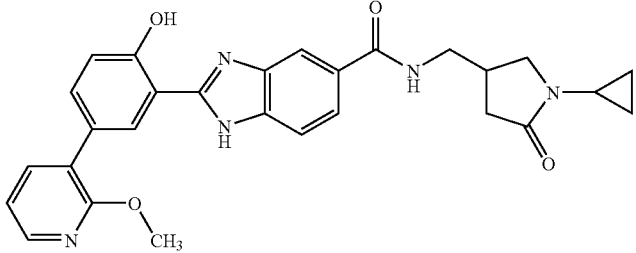 [SMILES: COc1ncccc1-c1ccc(O)c(-c2nc3cc(C(=O)NCC4CC(=O)N(C5CC5)C4)ccc3[nH]2)c1] | 498.56 |
| 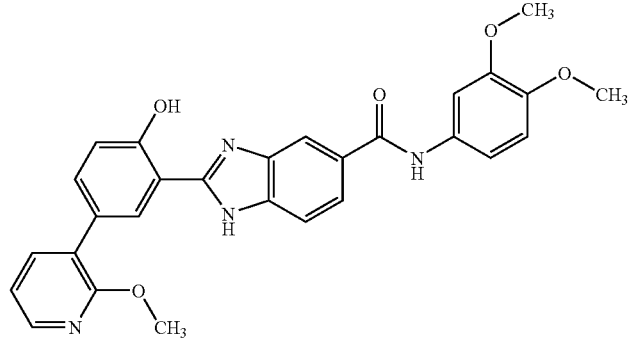 [SMILES: COc1ccc(NC(=O)c2ccc3[nH]c(-c4cc(-c5cccnc5OC)ccc4O)nc3c2)cc1OC] | 497.53 |
| 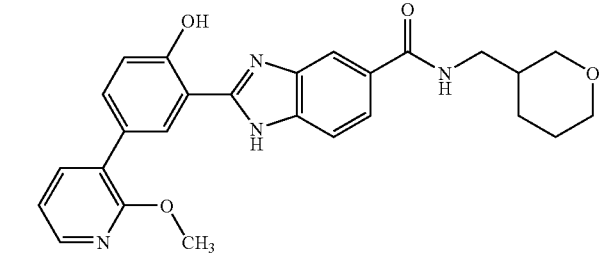 [SMILES: COc1ncccc1-c1ccc(O)c(-c2nc3cc(C(=O)NCC4CCCOC4)ccc3[nH]2)c1] | 459.52 |
| 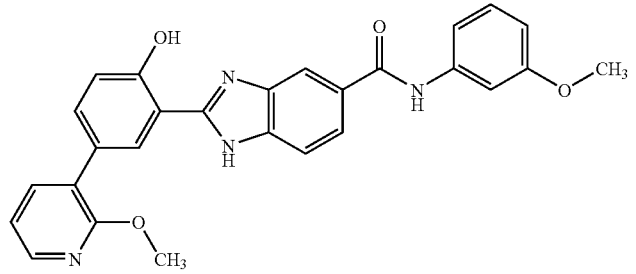 | 467.50 |
| 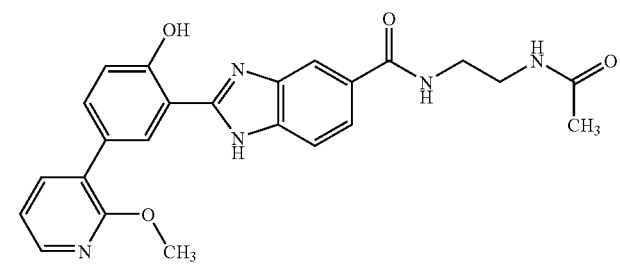 [SMILES: COc1ncccc1-c1ccc(O)c(-c2nc3cc(C(=O)NCCNC(C)=O)ccc3[nH]2)c1] | 446.48 |

| Structure | M + 1 |
|---|---|
| 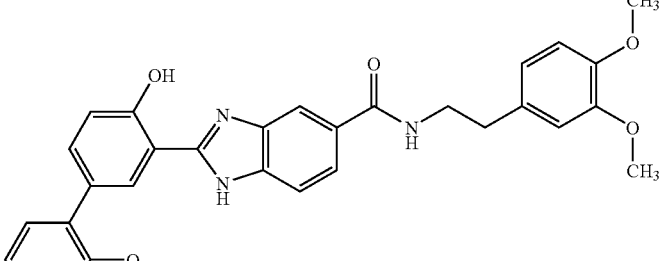 | 525.58 |
| 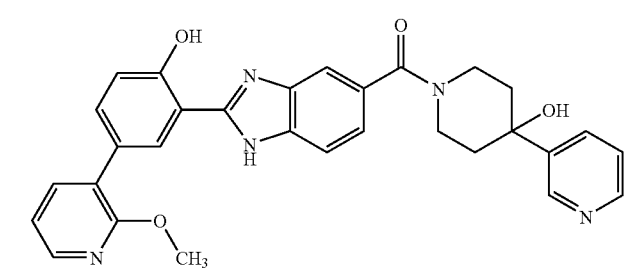 [SMILES: COc1ncccc1-c1ccc(O)c(-c2nc3cc(C(=O)N4CCC(O)(c5cccnc5)CC4)ccc3[nH]2)c1] | 522.58 |
| 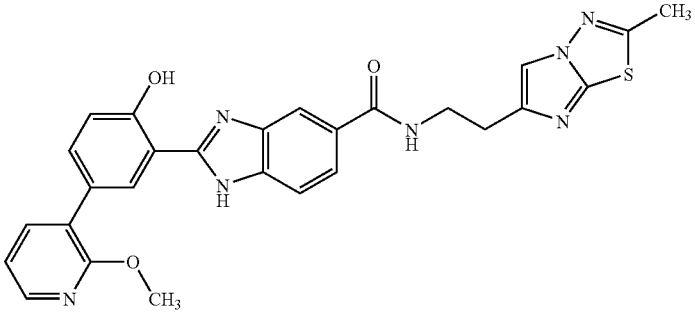 [SMILES: COc1ncccc1-c1ccc(O)c(-c2nc3cc(C(=O)NCCc4cn5nc(C)sc5n4)ccc3[nH]2)c1] | 526.59 |
| 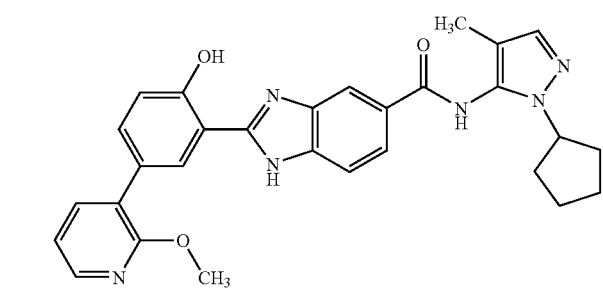 [SMILES: COc1ncccc1-c1ccc(O)c(-c2nc3cc(C(=O)Nc4c(C)cnn4C4CCCC4)ccc3[nH]2)c1] | 509.58 |
| 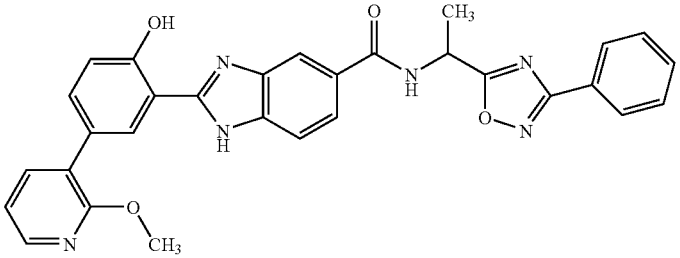 [SMILES: COc1ncccc1-c1ccc(O)c(-c2nc3cc(C(=O)NC(C)c4nc(-c5ccccc5)no4)ccc3[nH]2)c1] | 533.56 |

-continued
| Structure | M + 1 |
|---|---|
| 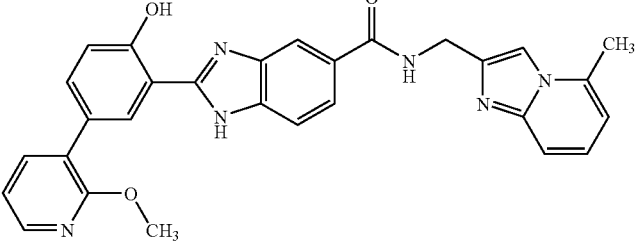 | 505.55 |
| 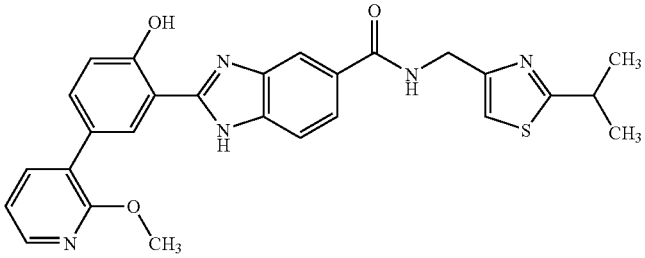 | 500.60 |
| 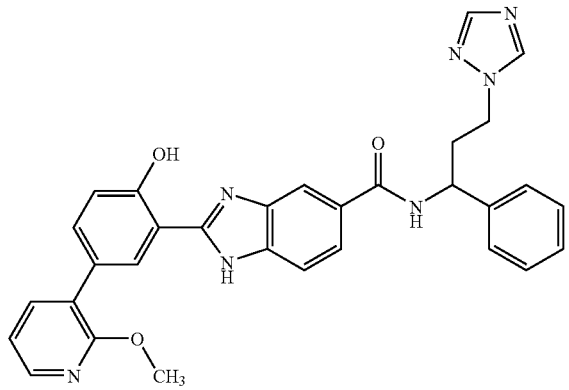 [SMILES: COc1ncccc1-c1ccc(O)c(-c2nc3cc(C(=O)NC(CCn4cncn4)c4ccccc4)ccc3[nH]2)c1] | 546.61 |
| 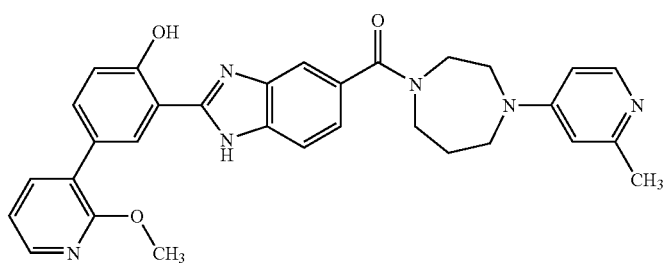 [SMILES: COc1ncccc1-c1ccc(O)c(-c2nc3cc(C(=O)N4CCCN(c5ccnc(C)c5)CC4)ccc3[nH]2)c1] | 535.62 |
| 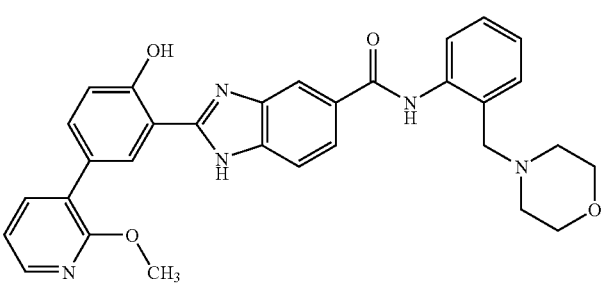 [SMILES: COc1ncccc1-c1ccc(O)c(-c2nc3cc(C(=O)Nc4ccccc4CN4CCOCC4)ccc3[nH]2)c1] | 536.61 |

| Structure | M + 1 |
| --- | --- |
| 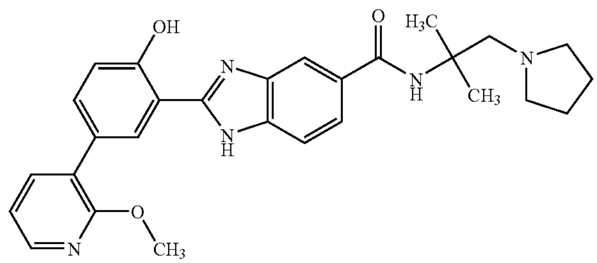 [SMILES: COc1ncccc1-c1ccc(O)c(-c2nc3cc(C(=O)NC(C)(C)CN4CCCC4)ccc3[nH]2)c1] | 486.59 |
| 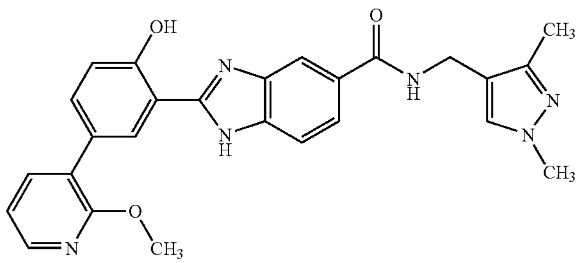 [SMILES: COc1ncccc1-c1ccc(O)c(-c2nc3cc(C(=O)NCc4cn(C)nc4C)ccc3[nH]2)c1] | 469.52 |
| 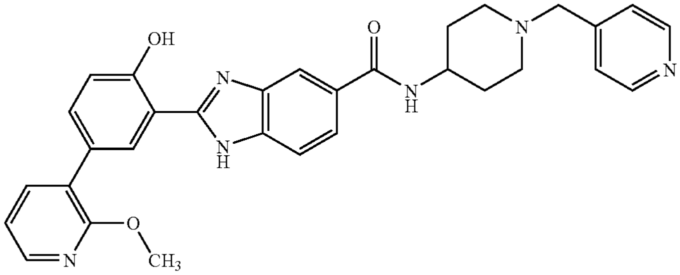 | 535.62 |
| 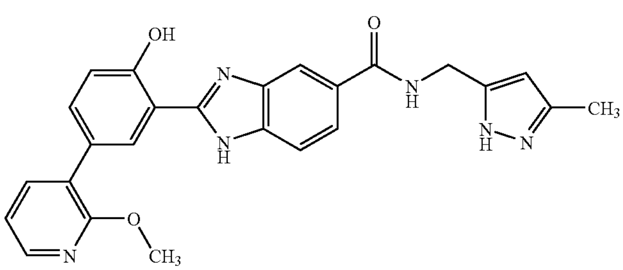 [SMILES: COc1ncccc1-c1ccc(O)c(-c2nc3cc(C(=O)NCc4cc(C)n[nH]4)ccc3[nH]2)c1] | 455.49 |
| 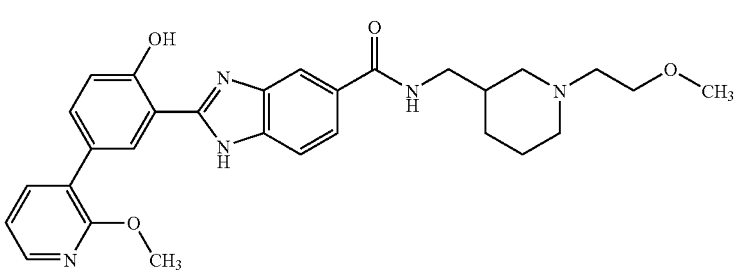 [SMILES: COCCN1CCCC(CNC(=O)c2ccc3[nH]c(-c4cc(-c5cccnc5OC)ccc4O)nc3c2)C1] | 516.62 |

| Structure | M + 1 |
|---|---|
| 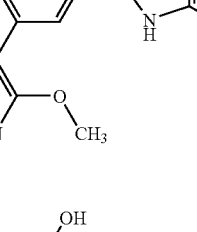 | 483.57 |
| 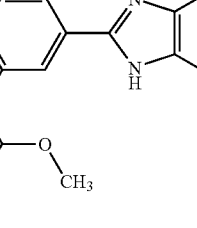 | 455.49 |
| 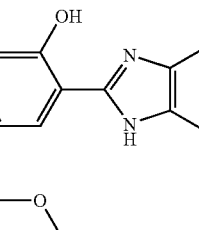 | 486.59 |
| 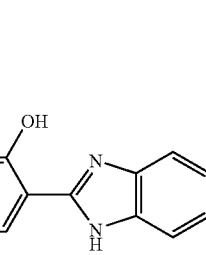 | 495.56 |
| 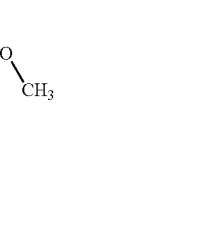 | 472.54 |

-continued

| Structure | M + 1 |
|---|---|
| (structure) | 473.55 |
| (structure) | 469.49 |
| (structure) | 456.48 |
| (structure) | 467.50 |
| (structure) | 501.58 |

-continued
| Structure | M + 1 |
|---|---|
| 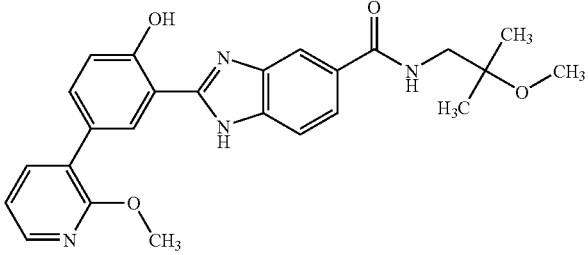 [SMILES: COc1ncccc1-c1ccc(O)c(-c2nc3cc(C(=O)NCC(C)(C)OC)ccc3[nH]2)c1] | 447.51 |
| 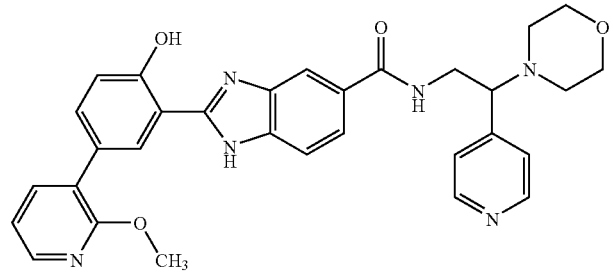 | 551.62 |
| 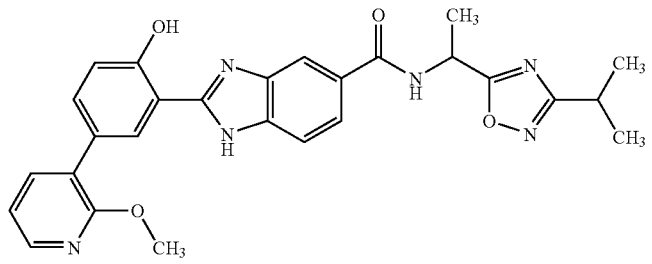 [SMILES: COc1ncccc1-c1ccc(O)c(-c2nc3cc(C(=O)NC(C)c4nc(C(C)C)no4)ccc3[nH]2)c1] | 499.55 |
| 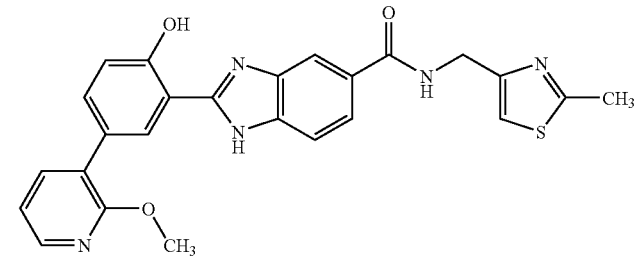 [SMILES: COc1ncccc1-c1ccc(O)c(-c2nc3cc(C(=O)NCc4csc(C)n4)ccc3[nH]2)c1] | 472.54 |
| 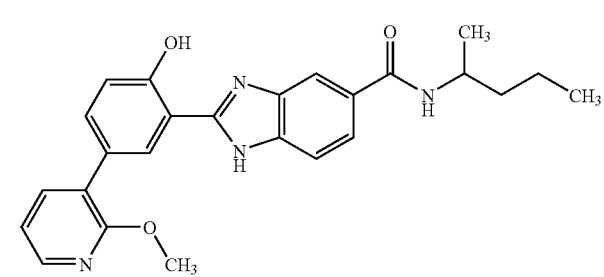 | 431.51 |

| Structure | M + 1 |
|---|---|
| 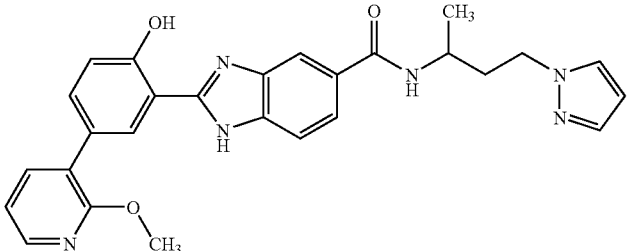 | 483.55 |
| 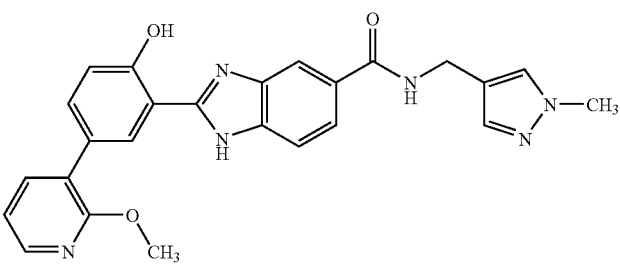 [SMILES: COc1ncccc1-c1ccc(O)c(-c2nc3cc(C(=O)NCc4cnn(C)c4)ccc3[nH]2)c1] | 455.49 |
| 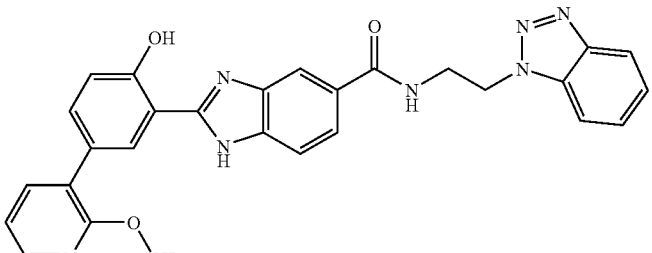 | 506.54 |
| 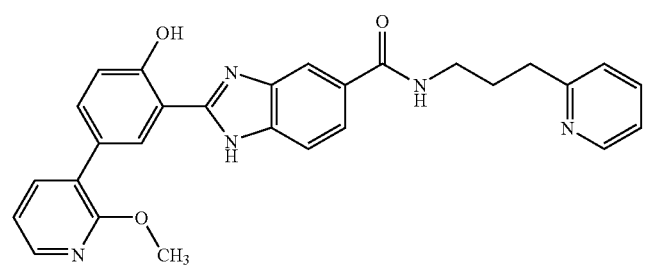 | 480.54 |
| 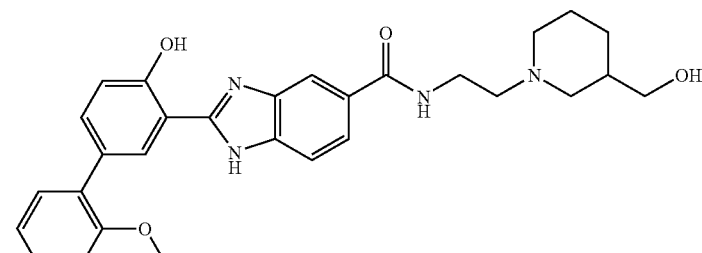 | 502.59 |

| Structure | M + 1 |
|---|---|
| (structure) | 533.65 |
| (structure) | 533.56 |
| (structure) | 529.62 |
| (structure) | 495.51 |
| (structure) | 496.54 |

-continued
| Structure | M + 1 |
|---|---|
| 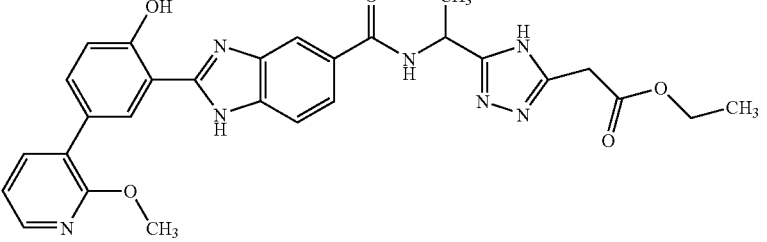 | 542.57 |
| 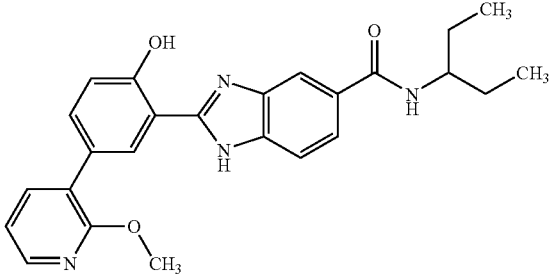 [SMILES: CCC(CC)NC(=O)c1ccc2[nH]c(-c3cc(-c4cccnc4OC)ccc3O)nc2c1] | 431.51 |
| 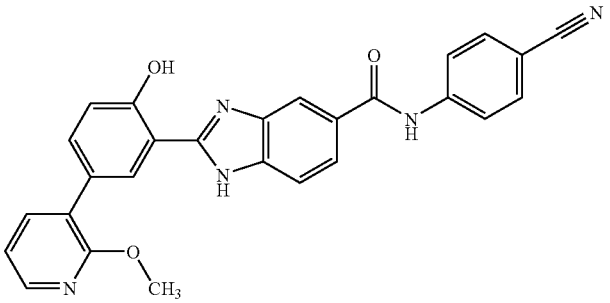 [SMILES: COc1ncccc1-c1ccc(O)c(-c2nc3cc(C(=O)Nc4ccc(C#N)cc4)ccc3[nH]2)c1] | 462.48 |
| 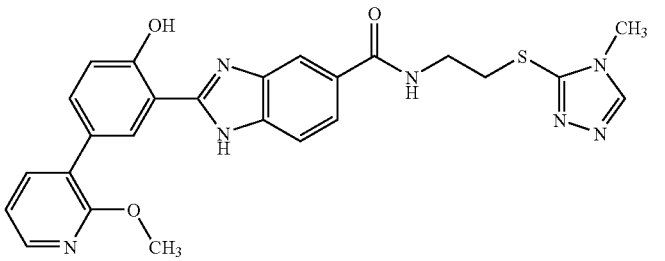 [SMILES: COc1ncccc1-c1ccc(O)c(-c2nc3cc(C(=O)NCCSc4nncn4C)ccc3[nH]2)c1] | 502.57 |
| 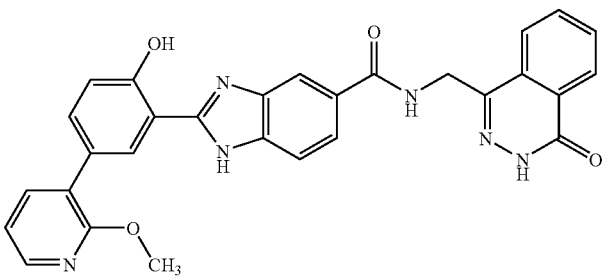 [SMILES: COc1ncccc1-c1ccc(O)c(-c2nc3cc(C(=O)NCc4n[nH]c(=O)c5ccccc45)ccc3[nH]2)c1] | 519.54 |

| Structure | M + 1 |
|---|---|
| (structure) | 540.64 |
| (structure) | 437.47 |
| (structure) | 522.54 |
| (structure) | 488.52 |
| (structure) | 502.57 |

-continued

| Structure | M + 1 |
|---|---|
| 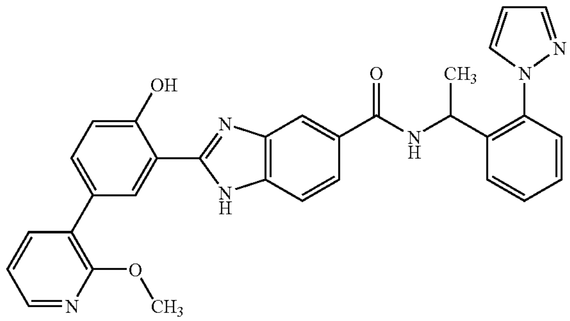 [SMILES: COc1ncccc1-c1ccc(O)c(-c2nc3cc(C(=O)NC(C)c4ccccc4-n4cccn4)ccc3[nH]2)c1] | 531.59 |
| 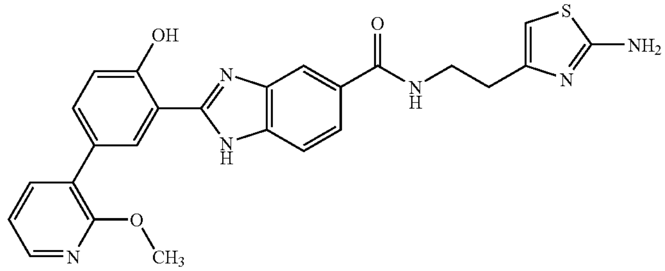 [SMILES: COc1ncccc1-c1ccc(O)c(-c2nc3cc(C(=O)NCCc4csc(N)n4)ccc3[nH]2)c1] | 487.56 |
| 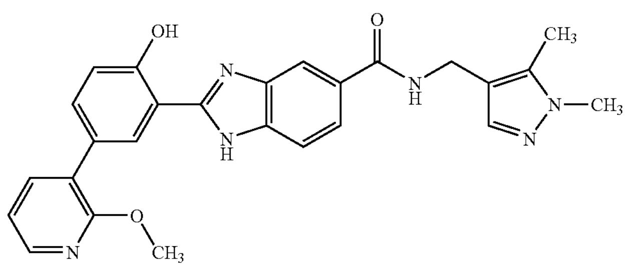 [SMILES: COc1ncccc1-c1ccc(O)c(-c2nc3cc(C(=O)NCc4cnn(C)c4C)ccc3[nH]2)c1] | 469.52 |
| 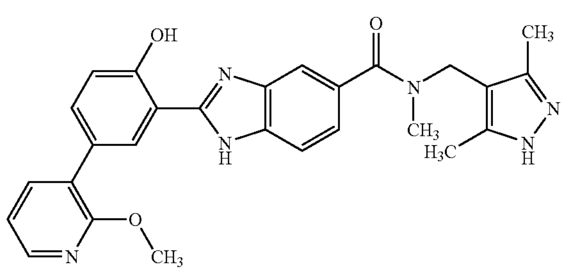 [SMILES: COc1ncccc1-c1ccc(O)c(-c2nc3cc(C(=O)N(C)Cc4c(C)n[nH]c4C)ccc3[nH]2)c1] | 483.55 |
| 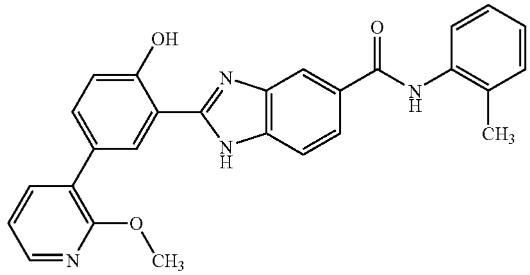 [SMILES: COc1ncccc1-c1ccc(O)c(-c2nc3cc(C(=O)Nc4ccccc4C)ccc3[nH]2)c1] | 451.50 |

-continued

| Structure | M + 1 |
|---|---|
| 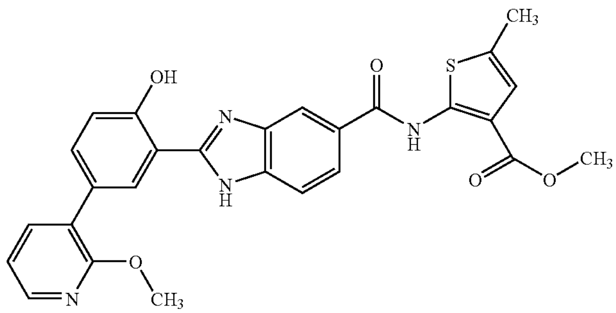 [SMILES: COC(=O)c1cc(C)sc1NC(=O)c1ccc2[nH]c(-c3cc(-c4cccnc4OC)ccc3O)nc2c1] | 515.56 |
| 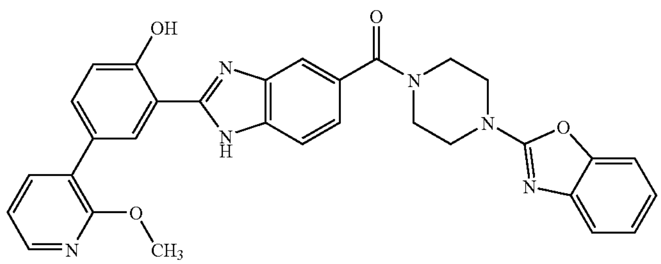 [SMILES: COc1ncccc1-c1ccc(O)c(-c2nc3cc(C(=O)N4CCN(c5nc6ccccc6o5)CC4)ccc3[nH]2)c1] | 547.59 |
| 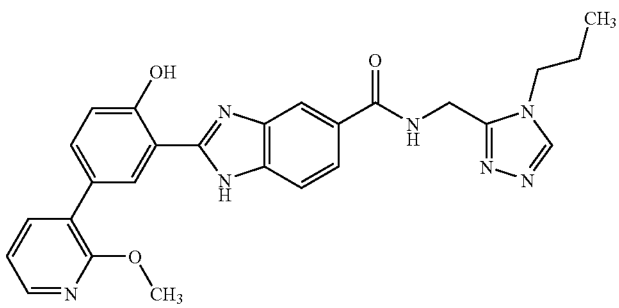 [SMILES: CCCn1cnnc1CNC(=O)c1ccc2[nH]c(-c3cc(-c4cccnc4OC)ccc3O)nc2c1] | 484.53 |
| 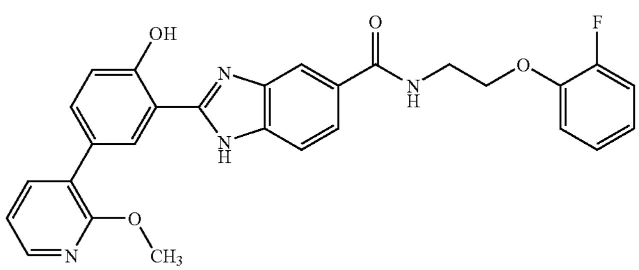 [SMILES: COc1ncccc1-c1ccc(O)c(-c2nc3cc(C(=O)NCCOc4ccccc4F)ccc3[nH]2)c1] | 499.52 |
| 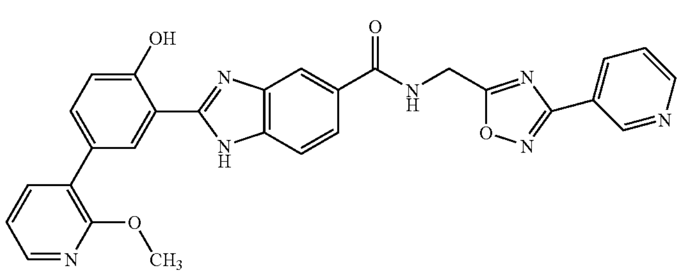 | 520.52 |

| Structure | M + 1 |
|---|---|
| 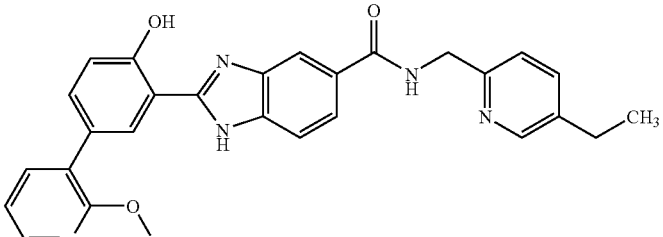 | 480.54 |
| 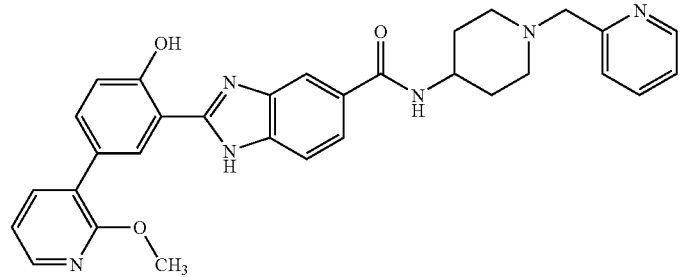 [SMILES: COc1ncccc1-c1ccc(O)c(-c2nc3cc(C(=O)NC4CCN(Cc5ccccn5)CC4)ccc3[nH]2)c1] | 535.62 |
| 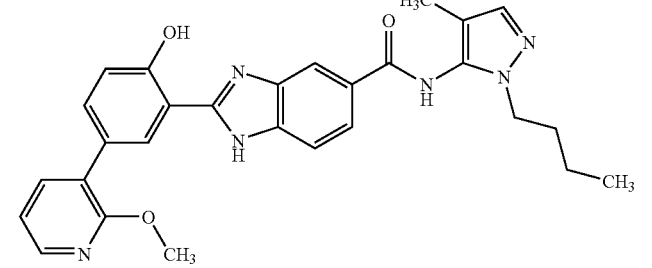 | 497.57 |
| 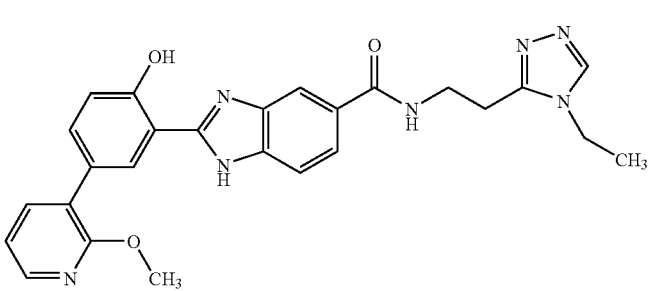 [SMILES: CCn1cnnc1CCNC(=O)c1ccc2[nH]c(-c3cc(-c4cccnc4OC)ccc3O)nc2c1] | 484.53 |
| 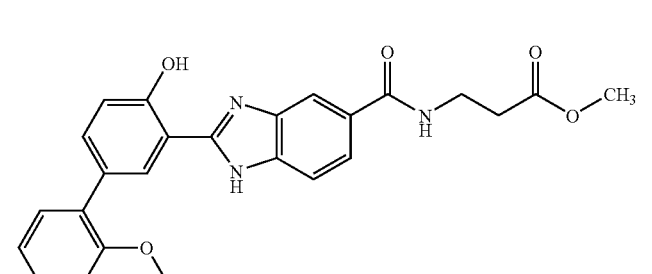 | 447.47 |

| Structure | M + 1 |
|---|---|
| 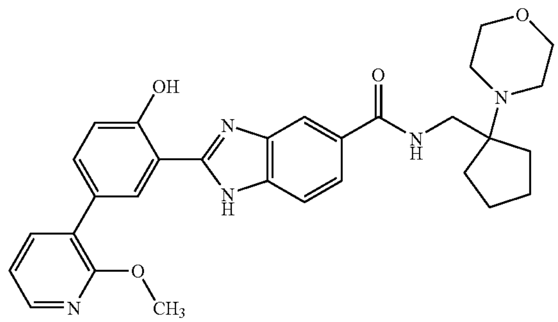 [SMILES: COc1ncccc1-c1ccc(O)c(-c2nc3cc(C(=O)NCC4(N5CCOCC5)CCCC4)ccc3[nH]2)c1] | 528.63 |
| 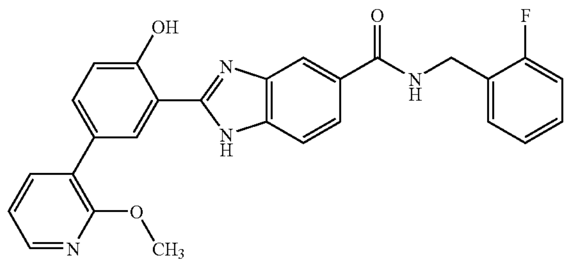 [SMILES: COc1ncccc1-c1ccc(O)c(-c2nc3cc(C(=O)NCc4ccccc4F)ccc3[nH]2)c1] | 469.49 |
| 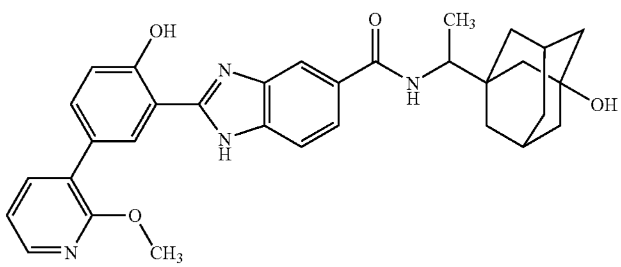 [SMILES: COc1ncccc1-c1ccc(O)c(-c2nc3cc(C(=O)NC(C)C45CC6CC(CC(O)(C6)C4)C5)ccc3[nH]2)c1] | 539.65 |
| 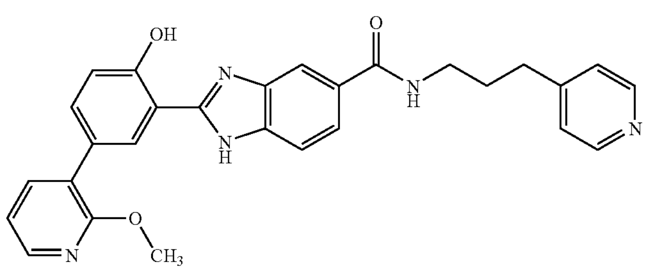 [SMILES: COc1ncccc1-c1ccc(O)c(-c2nc3cc(C(=O)NCCCc4ccncc4)ccc3[nH]2)c1] | 480.54 |
| 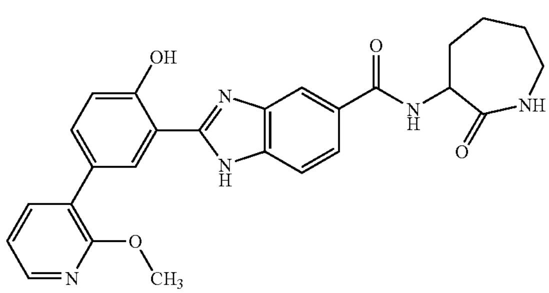 [SMILES: COc1ncccc1-c1ccc(O)c(-c2nc3cc(C(=O)NC4CCCCNC4=O)ccc3[nH]2)c1] | 472.52 |

| Structure | M + 1 |
|---|---|
| 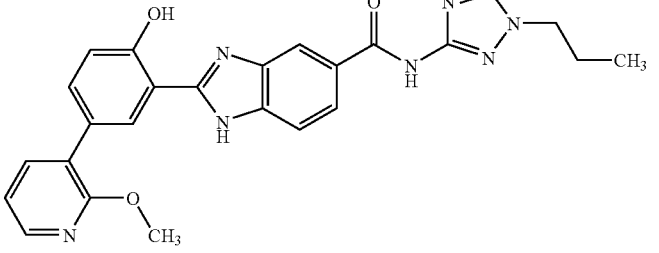 | 470.51 |
| 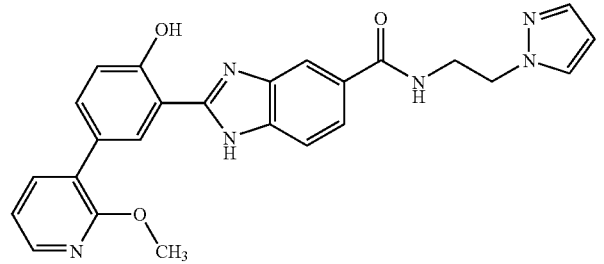 [SMILES: COc1ncccc1-c1ccc(O)c(-c2nc3cc(C(=O)NCCn4cccn4)ccc3[nH]2)c1] | 455.49 |
| 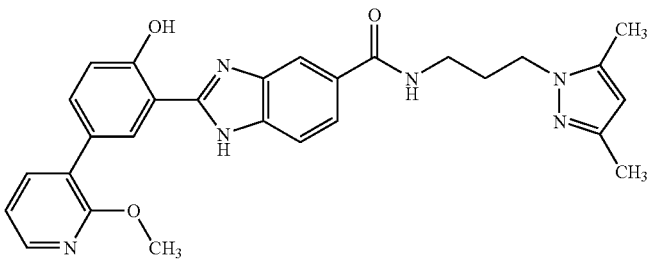 [SMILES: COc1ncccc1-c1ccc(O)c(-c2nc3cc(C(=O)NCCCn4nc(C)cc4C)ccc3[nH]2)c1] | 497.57 |
| 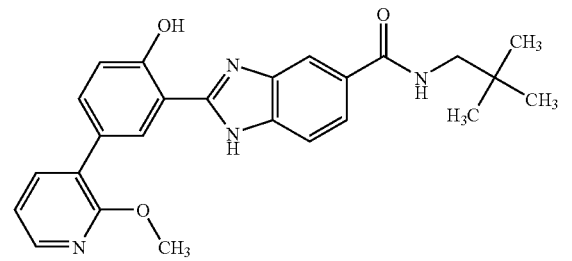 [SMILES: COc1ncccc1-c1ccc(O)c(-c2nc3cc(C(=O)NCC(C)(C)C)ccc3[nH]2)c1] | 431.51 |
| 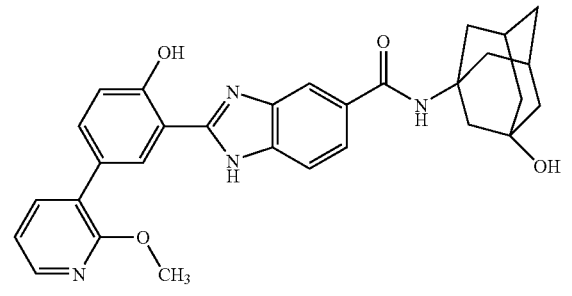 [SMILES: COc1ncccc1-c1ccc(O)c(-c2nc3cc(C(=O)NC45CC6CC(CC(O)(C6)C4)C5)ccc3[nH]2)c1] | 511.60 |

-continued
| Structure | M + 1 |
|---|---|
| 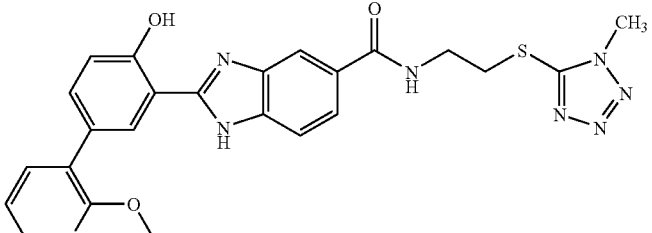 | 503.56 |
| 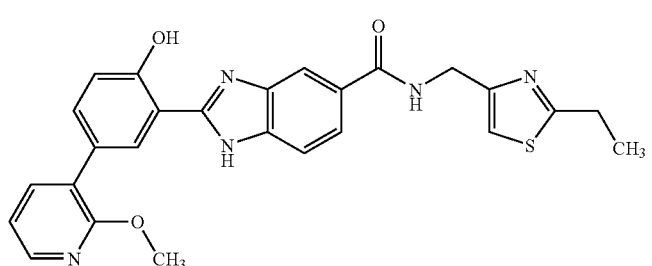 | 486.57 |
| 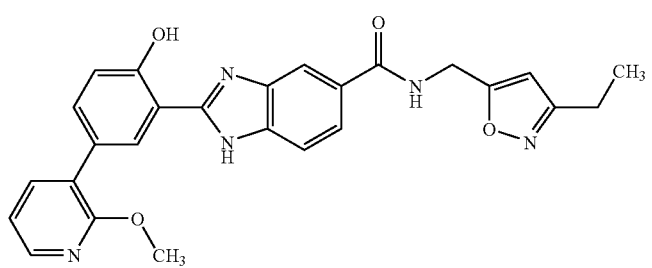 [SMILES: CCc1cc(CNC(=O)c2ccc3[nH]c(-c4cc(-c5cccnc5OC)ccc4O)nc3c2)on1] | 470.50 |
| 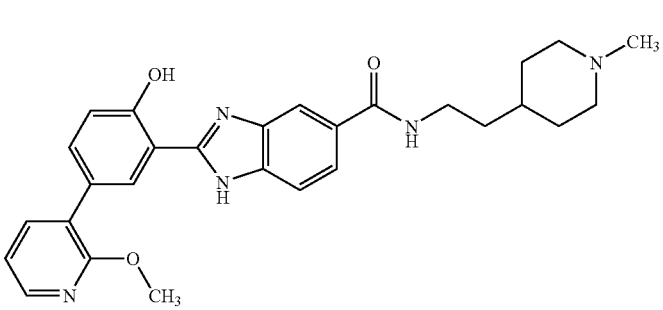 [SMILES: COc1ncccc1-c1ccc(O)c(-c2nc3cc(C(=O)NCCC4CCN(C)CC4)ccc3[nH]2)c1] | 486.59 |
| 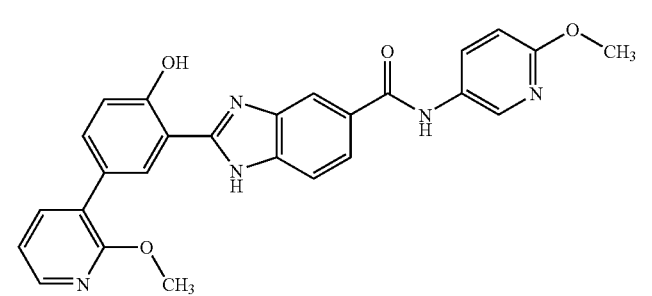 [SMILES: COc1ccc(NC(=O)c2ccc3[nH]c(-c4cc(-c5cccnc5OC)ccc4O)nc3c2)cn1] | 468.49 |

| Structure | M + 1 |
|---|---|
| 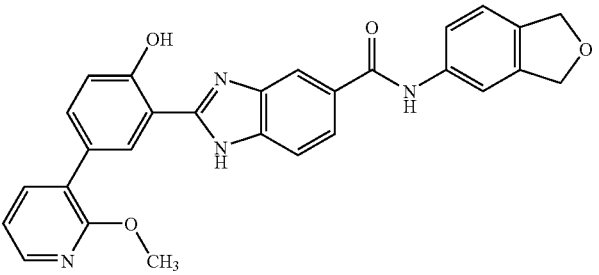 [SMILES: COc1ncccc1-c1ccc(O)c(-c2nc3cc(C(=O)Nc4ccc5c(c4)COC5)ccc3[nH]2)c1] | 479.51 |
| 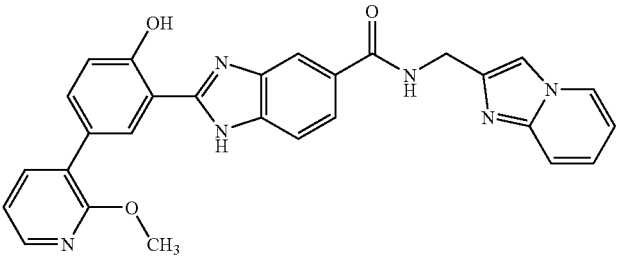 [SMILES: COc1ncccc1-c1ccc(O)c(-c2nc3cc(C(=O)NCc4cn5ccccc5n4)ccc3[nH]2)c1] | 491.53 |
| 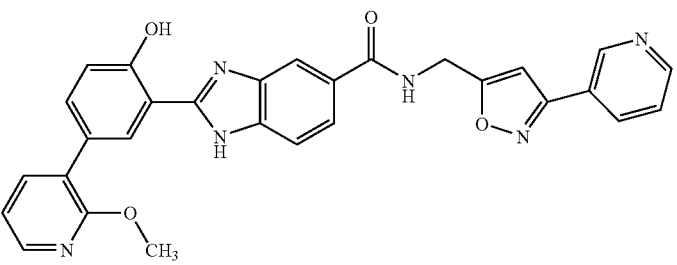 | 519.54 |
| 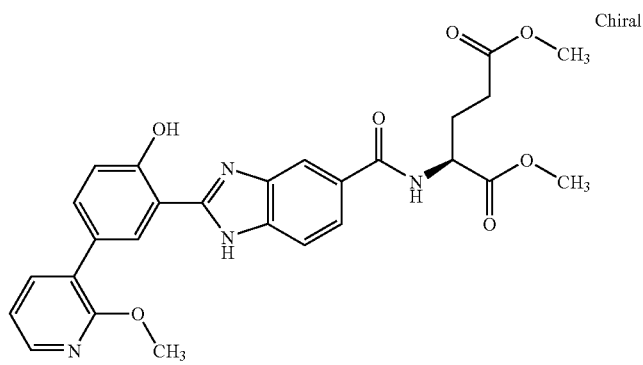 [SMILES: COC(=O)CC[C@H](NC(=O)c1ccc2[nH]c(-c3cc(-c4cccnc4OC)ccc3O)nc2c1)C(=O)OC] Chiral | 519.53 |
| 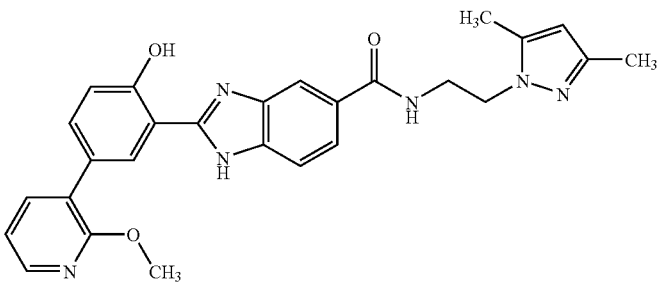 [SMILES: COc1ncccc1-c1ccc(O)c(-c2nc3cc(C(=O)NCCn4nc(C)cc4C)ccc3[nH]2)c1] | 483.55 |

-continued

| Structure | M + 1 |
|---|---|
| 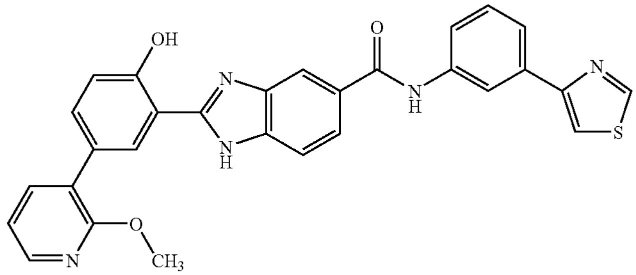 [SMILES: COc1ncccc1-c1ccc(O)c(-c2nc3cc(C(=O)Nc4cccc(-c5cscn5)c4)ccc3[nH]2)c1] | 520.59 |
| 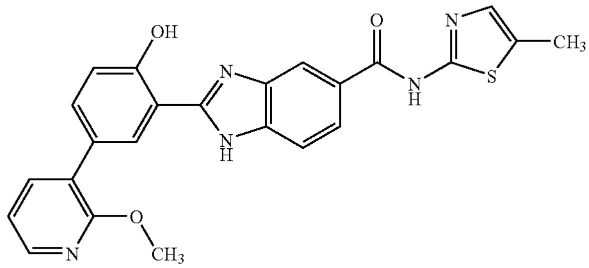 [SMILES: COc1ncccc1-c1ccc(O)c(-c2nc3cc(C(=O)Nc4ncc(C)s4)ccc3[nH]2)c1] | 458.51 |
| 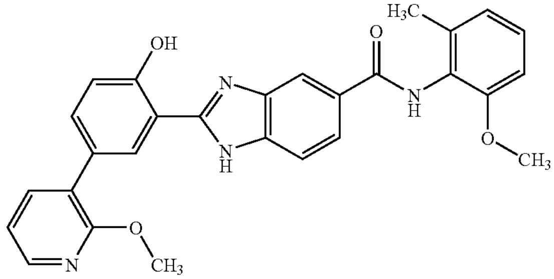 [SMILES: COc1cccc(C)c1NC(=O)c1ccc2[nH]c(-c3cc(-c4cccnc4OC)ccc3O)nc2c1] | 481.53 |
| 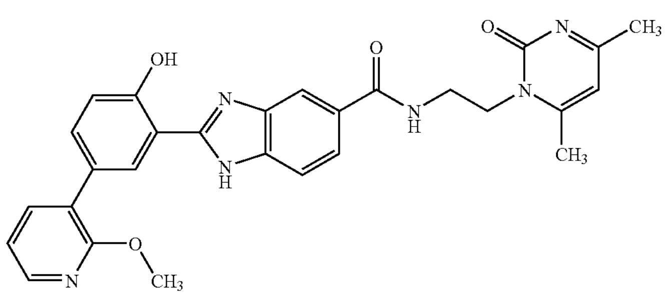 [SMILES: COc1ncccc1-c1ccc(O)c(-c2nc3cc(C(=O)NCCn4c(C)cc(C)nc4=O)ccc3[nH]2)c1] | 511.56 |
| 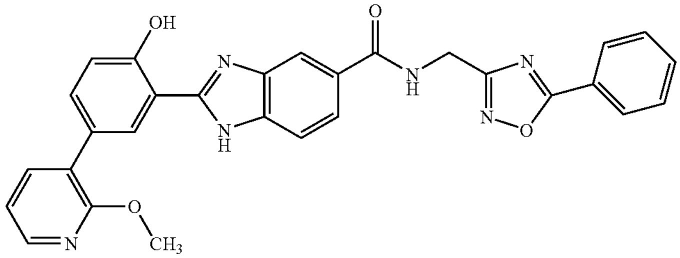 [SMILES: COc1ncccc1-c1ccc(O)c(-c2nc3cc(C(=O)NCc4noc(-c5ccccc5)n4)ccc3[nH]2)c1] | 519.54 |

| Structure | M + 1 |
| --- | --- |
| (structure) | 462.48 |
| (structure) | 517.56 |
| (structure) | 522.60 |
| (structure) | 466.52 |
| (structure) | 468.49 |

-continued

| Structure | M + 1 |
|---|---|
| (Chiral) | 419.46 |
| 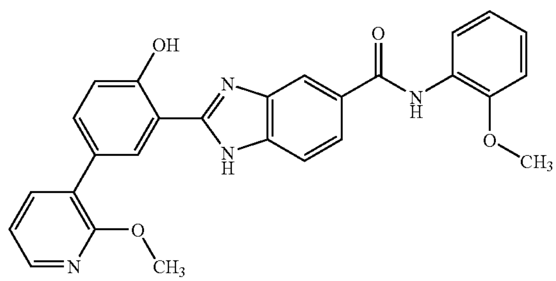 [SMILES: COc1ccccc1NC(=O)c1ccc2[nH]c(-c3cc(-c4cccnc4OC)ccc3O)nc2c1] | 467.50 |
| 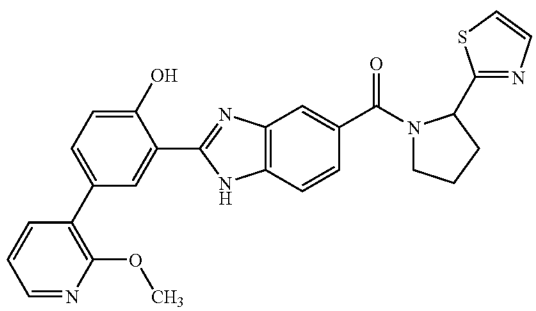 [SMILES: COc1ncccc1-c1ccc(O)c(-c2nc3cc(C(=O)N4CCCC4c4nccs4)ccc3[nH]2)c1] | 498.58 |
| 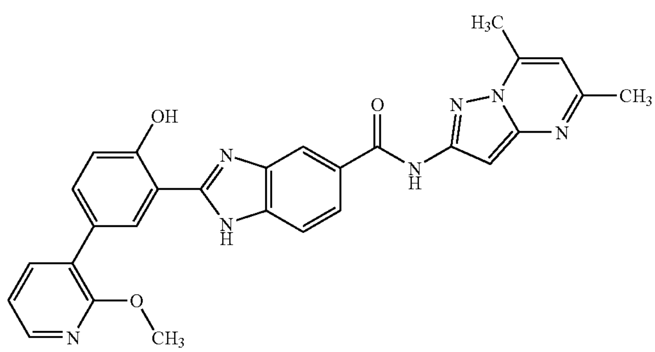 [SMILES: COc1ncccc1-c1ccc(O)c(-c2nc3cc(C(=O)Nc4cc5nc(C)cc(C)n5n4)ccc3[nH]2)c1] | 506.54 |
| 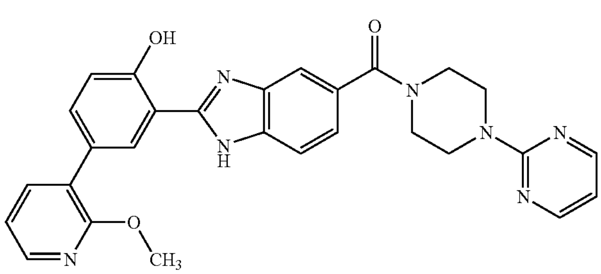 [SMILES: COc1ncccc1-c1ccc(O)c(-c2nc3cc(C(=O)N4CCN(c5ncccn5)CC4)ccc3[nH]2)c1] | 508.56 |

-continued

| Structure | M + 1 |
|---|---|
| 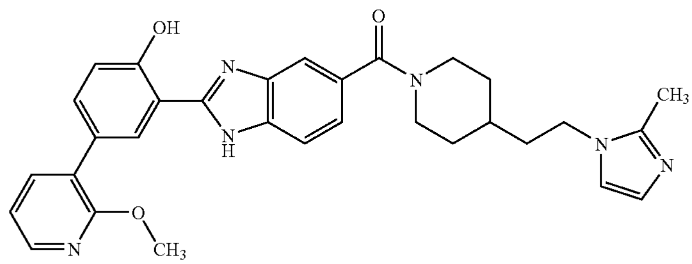 [SMILES: COc1ncccc1-c1ccc(O)c(-c2nc3cc(C(=O)N4CCC(CCn5ccnc5C)CC4)ccc3[nH]2)c1] | 537.64 |
| 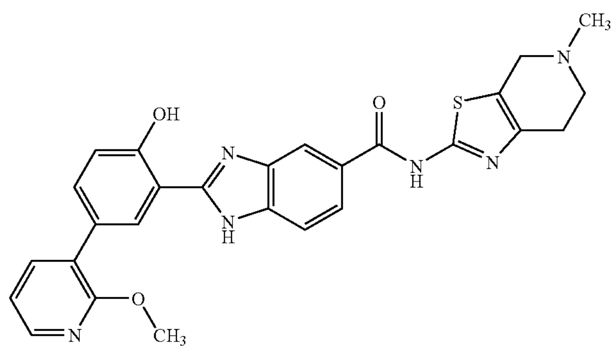 [SMILES: COc1ncccc1-c1ccc(O)c(-c2nc3cc(C(=O)Nc4nc5c(s4)CN(C)CC5)ccc3[nH]2)c1] | 513.59 |
| 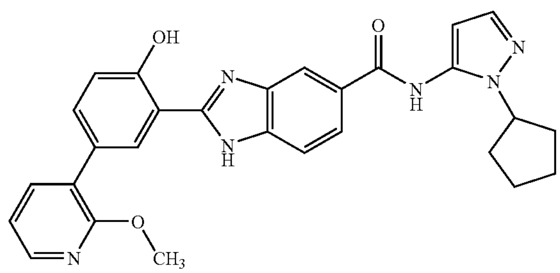 [SMILES: COc1ncccc1-c1ccc(O)c(-c2nc3cc(C(=O)Nc4ccnn4C4CCCC4)ccc3[nH]2)c1] | 495.56 |
| 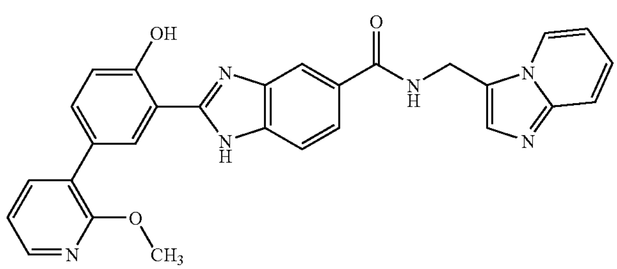 [SMILES: COc1ncccc1-c1ccc(O)c(-c2nc3cc(C(=O)NCc4cnc5ccccn45)ccc3[nH]2)c1] | 491.53 |
| 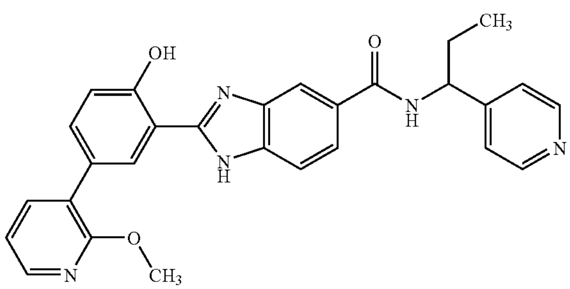 [SMILES: CCC(NC(=O)c1ccc2[nH]c(-c3cc(-c4cccnc4OC)ccc3O)nc2c1)c1ccncc1] | 480.54 |

-continued

| Structure | M + 1 |
|---|---|
| 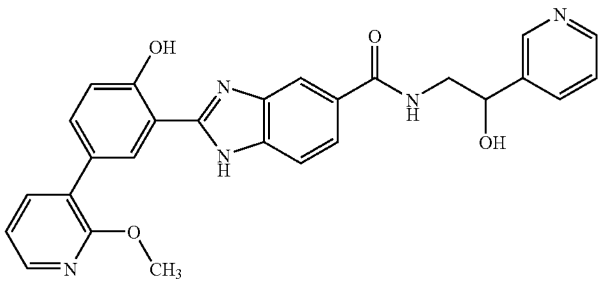 [SMILES: COc1ncccc1-c1ccc(O)c(-c2nc3cc(C(=O)NCC(O)c4cccnc4)ccc3[nH]2)c1] | 482.52 |
| 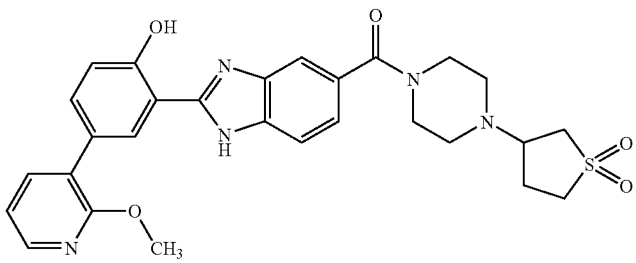 [SMILES: COc1ncccc1-c1ccc(O)c(-c2nc3cc(C(=O)N4CCN(C5CCS(=O)(=O)C5)CC4)ccc3[nH]2)c1] | 548.64 |
| 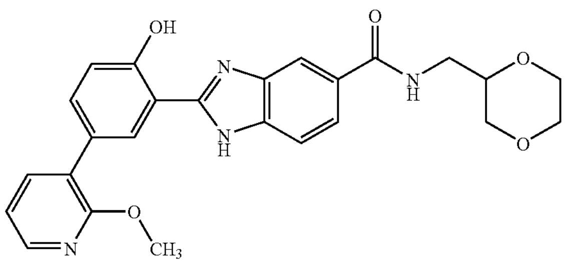 | 461.49 |
| 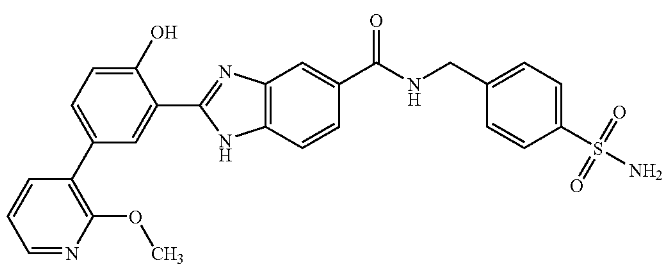 [SMILES: COc1ncccc1-c1ccc(O)c(-c2nc3cc(C(=O)NCc4ccc(S(N)(=O)=O)cc4)ccc3[nH]2)c1] | 530.58 |
| 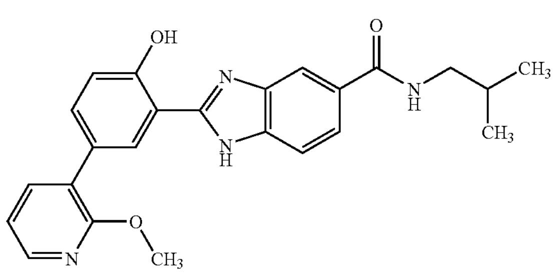 [SMILES: COc1ncccc1-c1ccc(O)c(-c2nc3cc(C(=O)NCC(C)C)ccc3[nH]2)c1] | 417.48 |

-continued
| Structure | M + 1 |
|---|---|
| 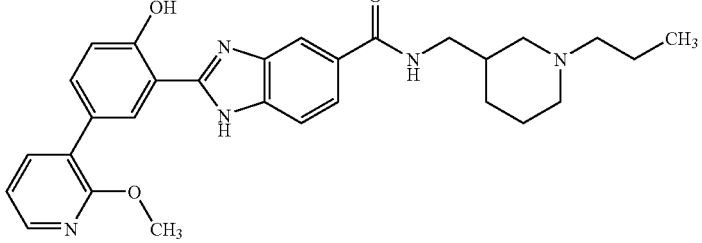 | 500.62 |
| 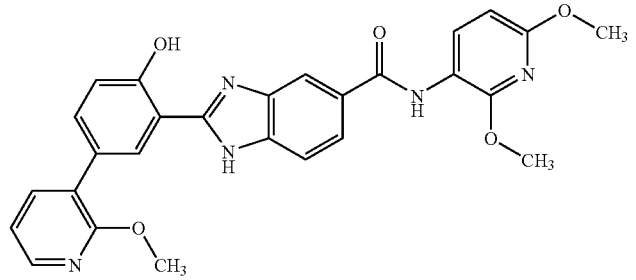 [SMILES: COc1ccc(NC(=O)c2ccc3[nH]c(-c4cc(-c5cccnc5OC)ccc4O)nc3c2)c(OC)n1] | 498.51 |
| 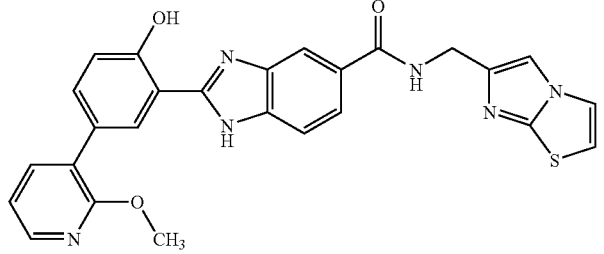 [SMILES: COc1ncccc1-c1ccc(O)c(-c2nc3cc(C(=O)NCc4cn5ccsc5n4)ccc3[nH]2)c1] | 497.55 |
| 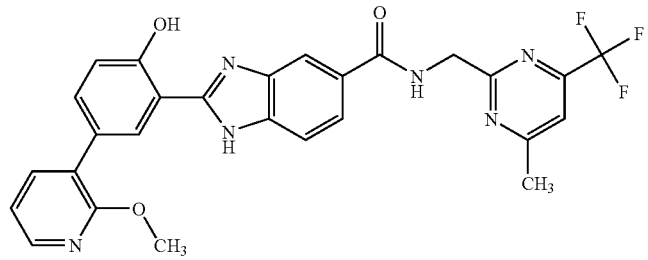 [SMILES: COc1ncccc1-c1ccc(O)c(-c2nc3cc(C(=O)NCc4nc(C)cc(C(F)(F)F)n4)ccc3[nH]2)c1] | 535.50 |
| 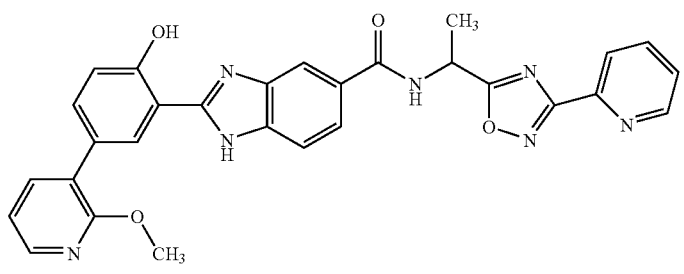 | 534.55 |

-continued

| Structure | M + 1 |
|---|---|
| 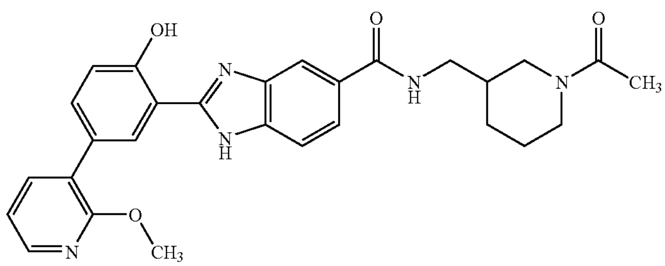 [SMILES: COc1ncccc1-c1ccc(O)c(-c2nc3cc(C(=O)NCC4CCCN(C(C)=O)C4)ccc3[nH]2)c1] | 500.57 |
| 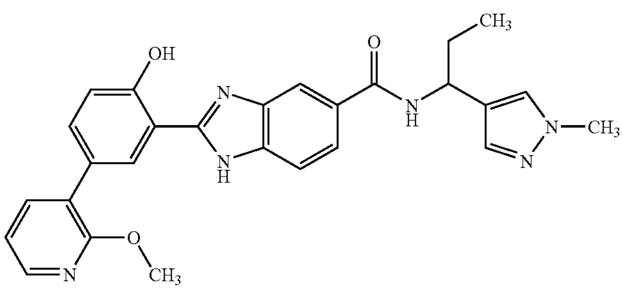 [SMILES: CCC(NC(=O)c1ccc2[nH]c(-c3cc(-c4cccnc4OC)ccc3O)nc2c1)c1cnn(C)c1] | 483.55 |
| 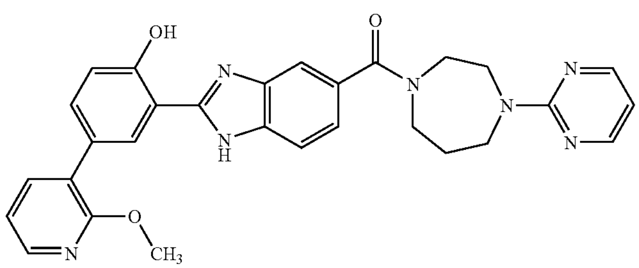 [SMILES: COc1ncccc1-c1ccc(O)c(-c2nc3cc(C(=O)N4CCCN(c5ncccn5)CC4)ccc3[nH]2)c1] | 522.58 |
| 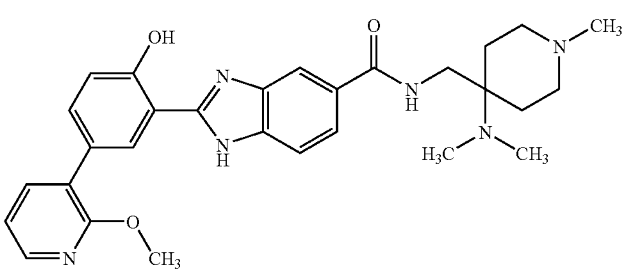 [SMILES: COc1ncccc1-c1ccc(O)c(-c2nc3cc(C(=O)NCC4(N(C)C)CCN(C)CC4)ccc3[nH]2)c1] | 515.63 |
| 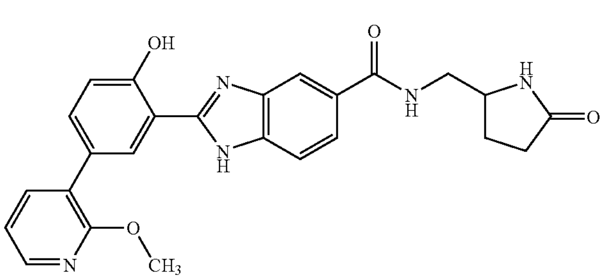 [SMILES: COc1ncccc1-c1ccc(O)c(-c2nc3cc(C(=O)NCC4CCC(=O)N4)ccc3[nH]2)c1] | 458.49 |

-continued
| Structure | M + 1 |
|---|---|
| 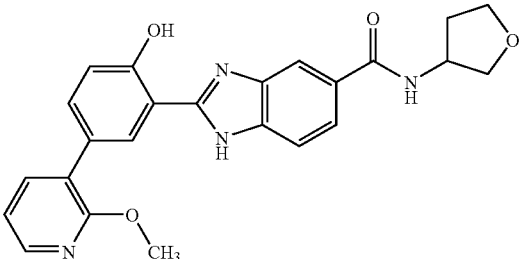 | 431.47 |
| 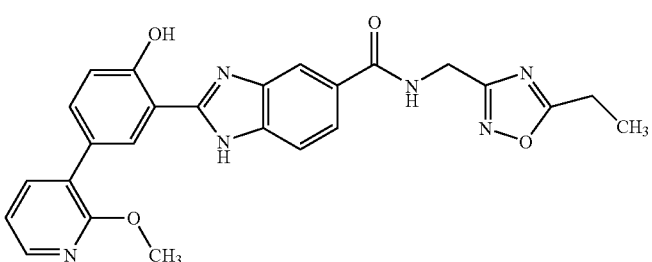 | 471.49 |
| 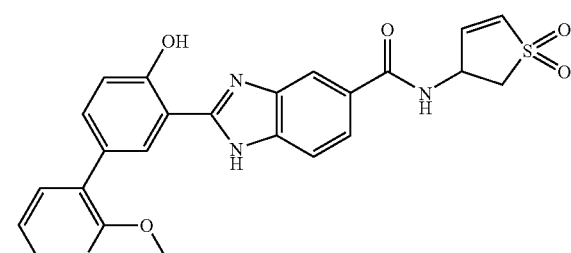 | 477.51 |
| 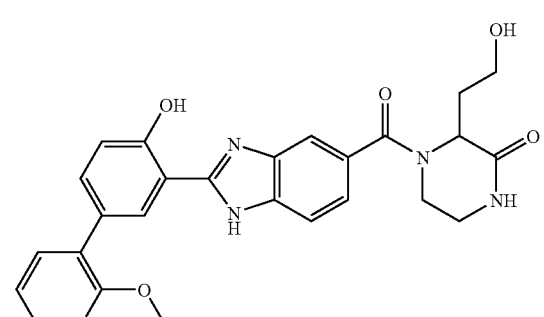 | 488.52 |
| 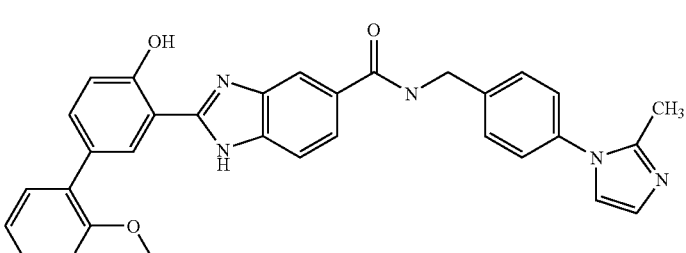 | 531.59 |

-continued

| Structure | M + 1 |
|---|---|
| 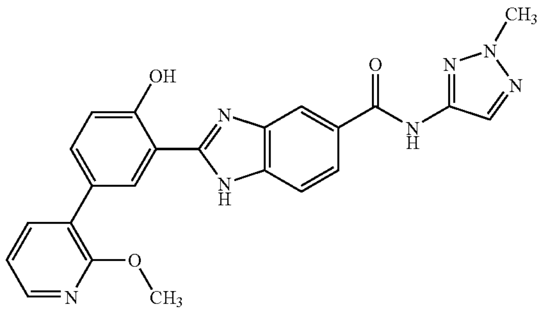 [SMILES: COc1ncccc1-c1ccc(O)c(-c2nc3cc(C(=O)Nc4cnn(C)n4)ccc3[nH]2)c1] | 442.45 |
| 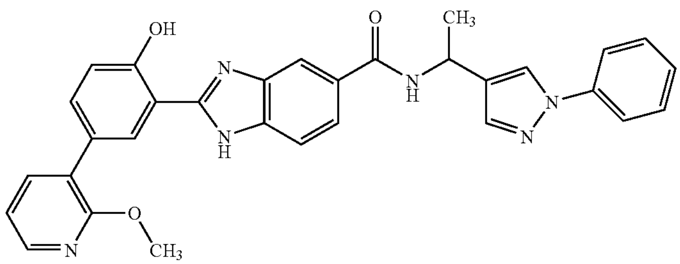 [SMILES: COc1ncccc1-c1ccc(O)c(-c2nc3cc(C(=O)NC(C)c4cnn(-c5ccccc5)c4)ccc3[nH]2)c1] | 531.59 |
| 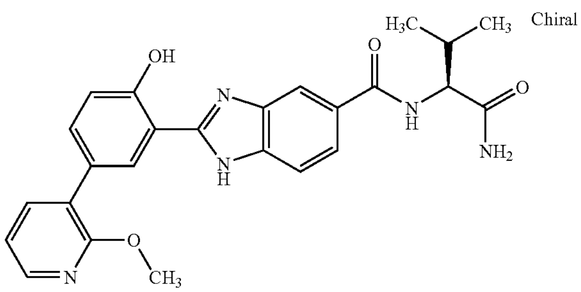 [SMILES: COc1ncccc1-c1ccc(O)c(-c2nc3cc(C(=O)N[C@H](C(N)=O)C(C)C)ccc3[nH]2)c1] | 460.51 |
| 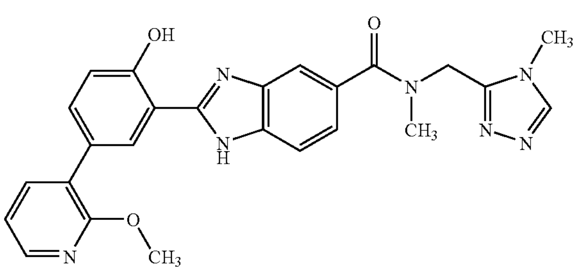 [SMILES: COc1ncccc1-c1ccc(O)c(-c2nc3cc(C(=O)N(C)Cc4nncn4C)ccc3[nH]2)c1] | 470.51 |
| 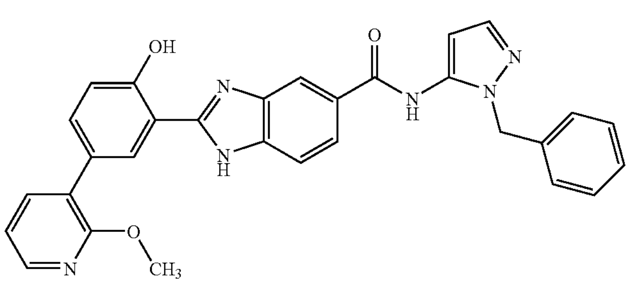 [SMILES: COc1ncccc1-c1ccc(O)c(-c2nc3cc(C(=O)Nc4ccnn4Cc4ccccc4)ccc3[nH]2)c1] | 517.56 |

-continued
| Structure | M + 1 |
|---|---|
| 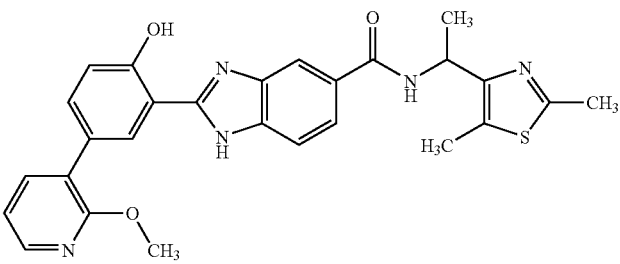 [SMILES: COc1ncccc1-c1ccc(O)c(-c2nc3cc(C(=O)NC(C)c4nc(C)sc4C)ccc3[nH]2)c1] | 500.60 |
| 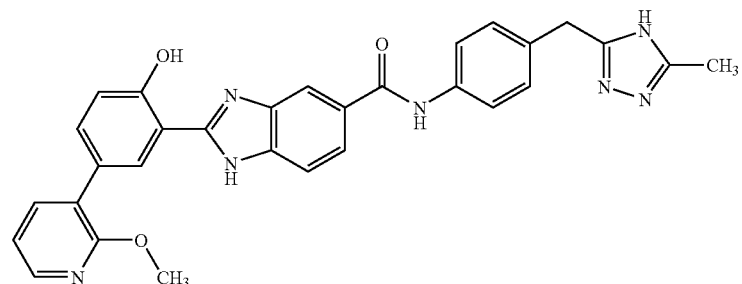 | 532.58 |
| 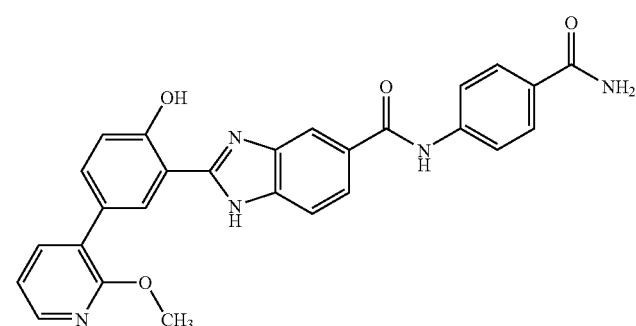 | 480.50 |
| 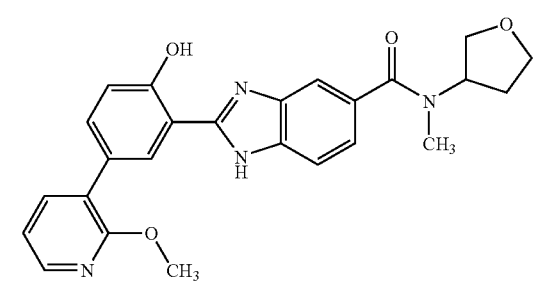 [SMILES: COc1ncccc1-c1ccc(O)c(-c2nc3cc(C(=O)N(C)C4CCOC4)ccc3[nH]2)c1] | 445.49 |
| 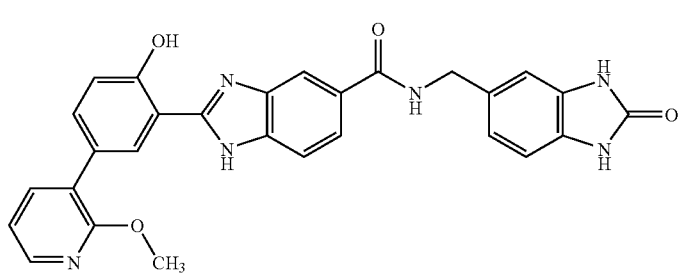 [SMILES: COc1ncccc1-c1ccc(O)c(-c2nc3cc(C(=O)NCc4ccc5[nH]c(=O)[nH]c5c4)ccc3[nH]2)c1] | 507.53 |

-continued

| Structure | M + 1 |
|---|---|
| 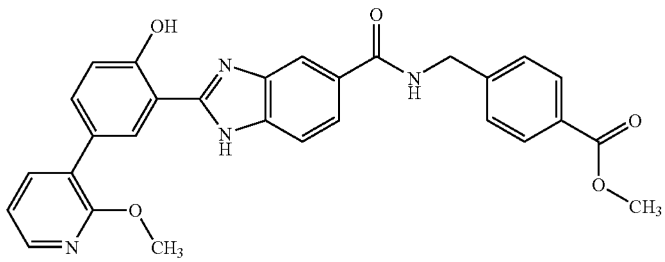 [SMILES: COC(=O)c1ccc(CNC(=O)c2ccc3[nH]c(-c4cc(-c5cccnc5OC)ccc4O)nc3c2)cc1] | 509.54 |
| 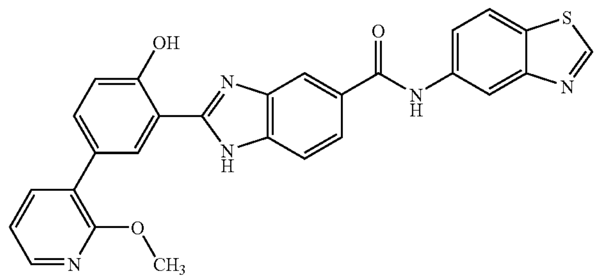 [SMILES: COc1ncccc1-c1ccc(O)c(-c2nc3cc(C(=O)Nc4ccc5scnc5c4)ccc3[nH]2)c1] | 494.55 |
| 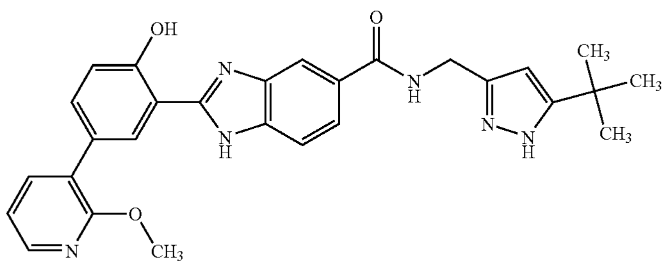 [SMILES: COc1ncccc1-c1ccc(O)c(-c2nc3cc(C(=O)NCc4cc(C(C)(C)C)[nH]n4)ccc3[nH]2)c1] | 497.57 |
| 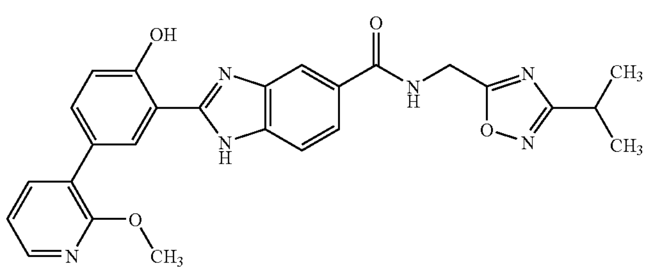 [SMILES: COc1ncccc1-c1ccc(O)c(-c2nc3cc(C(=O)NCc4nc(C(C)C)no4)ccc3[nH]2)c1] | 485.52 |
| 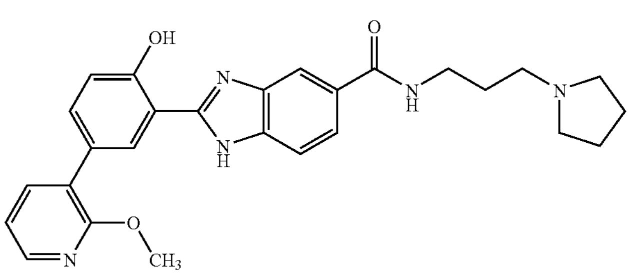 [SMILES: COc1ncccc1-c1ccc(O)c(-c2nc3cc(C(=O)NCCCN4CCCC4)ccc3[nH]2)c1] | 472.56 |

-continued
| Structure | M + 1 |
|---|---|
| 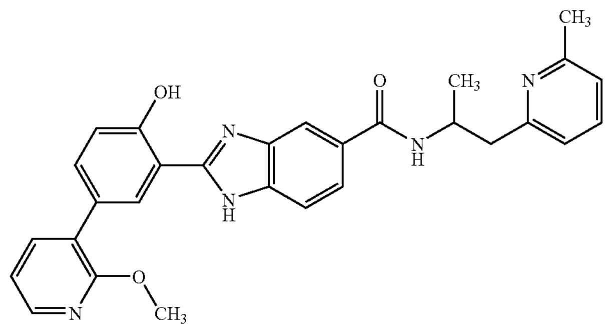 [SMILES: COc1ncccc1-c1ccc(O)c(-c2nc3cc(C(=O)NC(C)Cc4cccc(C)n4)ccc3[nH]2)c1] | 494.57 |
| 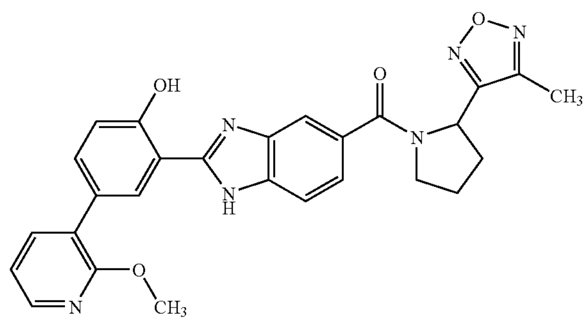 [SMILES: COc1ncccc1-c1ccc(O)c(-c2nc3cc(C(=O)N4CCCC4c4nonc4C)ccc3[nH]2)c1] | 497.53 |
| 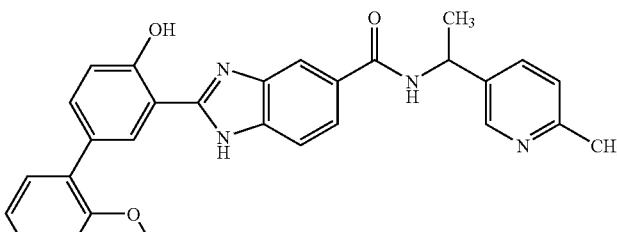 | 480.54 |
| 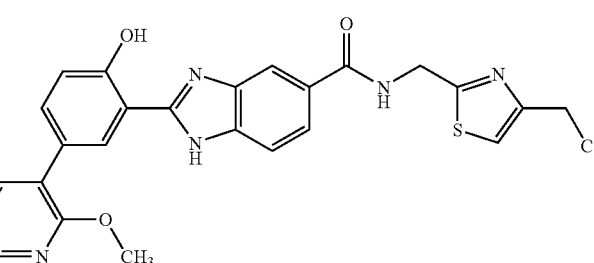 | 486.57 |
| 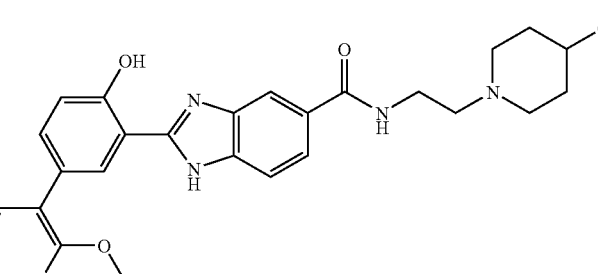 | 488.56 |

-continued

| Structure | M + 1 |
|---|---|
| 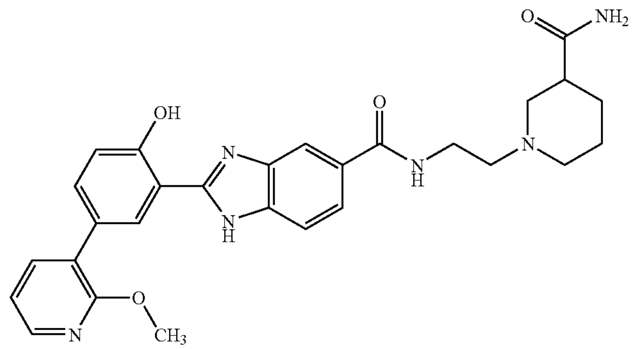 [SMILES: COc1ncccc1-c1ccc(O)c(-c2nc3cc(C(=O)NCCN4CCCC(C(N)=O)C4)ccc3[nH]2)c1] | 515.59 |
| 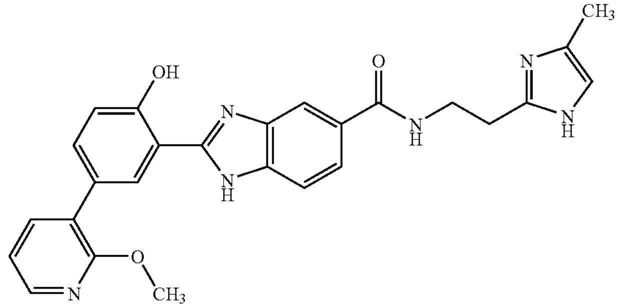 [SMILES: COc1ncccc1-c1ccc(O)c(-c2nc3cc(C(=O)NCCc4nc(C)c[nH]4)ccc3[nH]2)c1] | 469.52 |
| 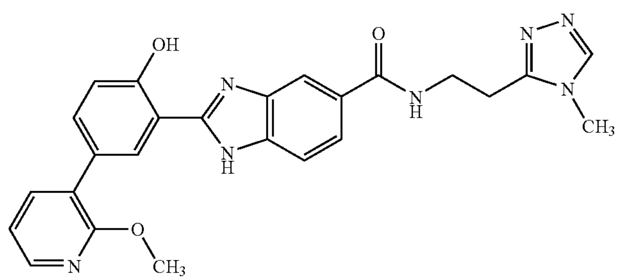 [SMILES: COc1ncccc1-c1ccc(O)c(-c2nc3cc(C(=O)NCCc4nncn4C)ccc3[nH]2)c1] | 470.51 |
| 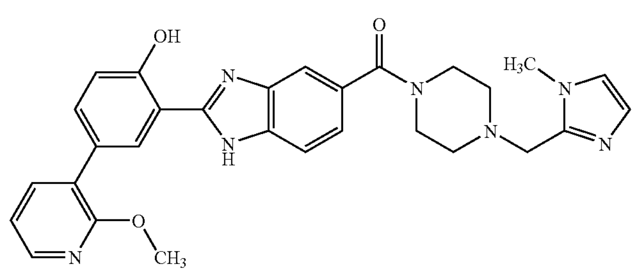 [SMILES: COc1ncccc1-c1ccc(O)c(-c2nc3cc(C(=O)N4CCN(Cc5nccn5C)CC4)ccc3[nH]2)c1] | 524.60 |
| 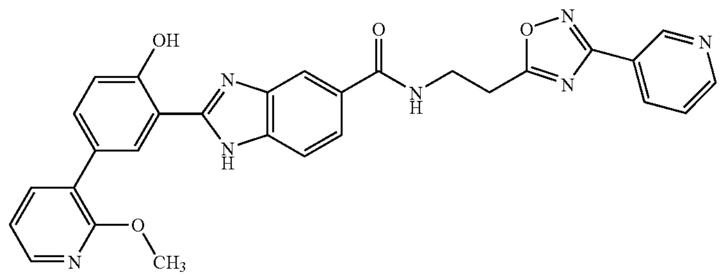 [SMILES: COc1ncccc1-c1ccc(O)c(-c2nc3cc(C(=O)NCCc4nc(-c5cccnc5)no4)ccc3[nH]2)c1] | 534.55 |

-continued
| Structure | M + 1 |
|---|---|
| 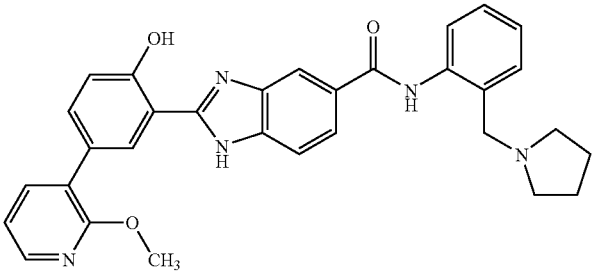 [SMILES: COc1ncccc1-c1ccc(O)c(-c2nc3cc(C(=O)Nc4ccccc4CN4CCCC4)ccc3[nH]2)c1] | 520.61 |
| 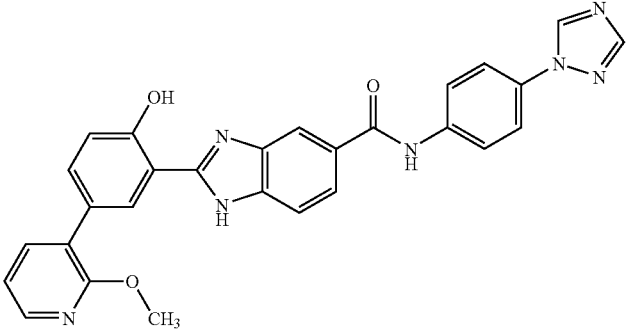 [SMILES: COc1ncccc1-c1ccc(O)c(-c2nc3cc(C(=O)Nc4ccc(-n5cncn5)cc4)ccc3[nH]2)c1] | 504.52 |
| 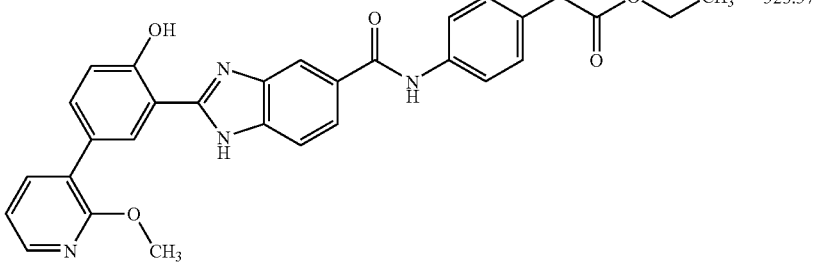 | 523.57 |
| 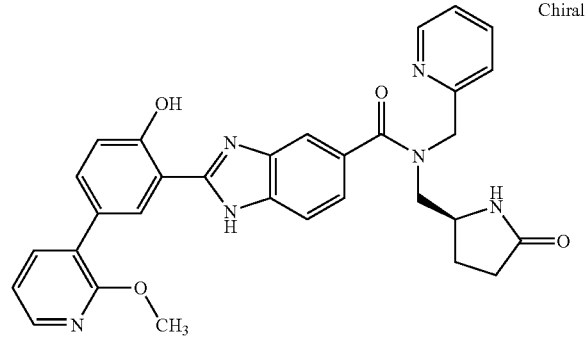 [SMILES: COc1ncccc1-c1ccc(O)c(-c2nc3cc(C(=O)N(Cc4ccccn4)C[C@@H]4CCC(=O)N4)ccc3[nH]2)c1] Chiral | 549.61 |
| 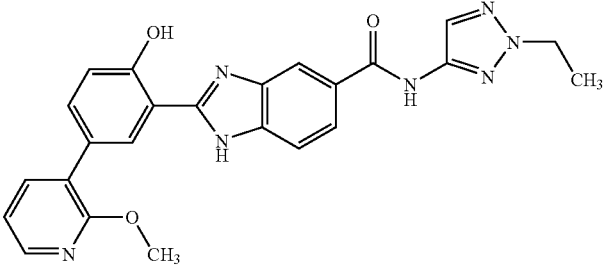 [SMILES: CCn1ncc(NC(=O)c2ccc3[nH]c(-c4cc(-c5cccnc5OC)ccc4O)nc3c2)n1] | 456.48 |

| Structure | M + 1 |
|---|---|
| 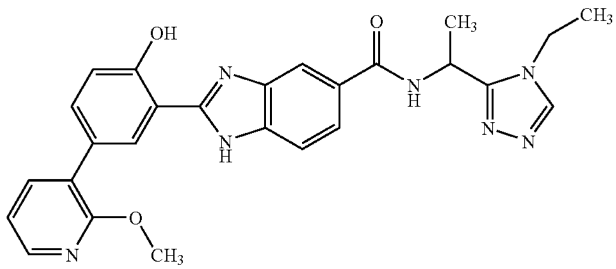 [SMILES: CCn1cnnc1C(C)NC(=O)c1ccc2[nH]c(-c3cc(-c4cccnc4OC)ccc3O)nc2c1] | 484.53 |
| 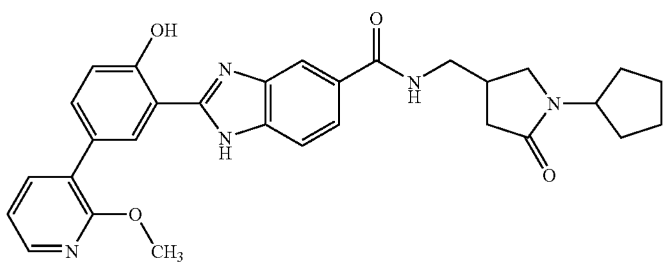 [SMILES: COc1ncccc1-c1ccc(O)c(-c2nc3cc(C(=O)NCC4CC(=O)N(C5CCCC5)C4)ccc3[nH]2)c1] | 526.61 |
| 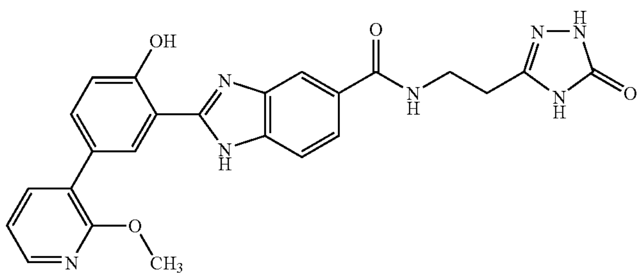 [SMILES: COc1ncccc1-c1ccc(O)c(-c2nc3cc(C(=O)NCCc4n[nH]c(=O)[nH]4)ccc3[nH]2)c1] | 472.48 |
| 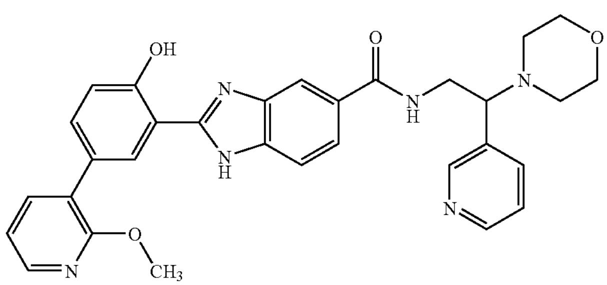 [SMILES: COc1ncccc1-c1ccc(O)c(-c2nc3cc(C(=O)NCC(c4cccnc4)N4CCOCC4)ccc3[nH]2)c1] | 551.62 |
| 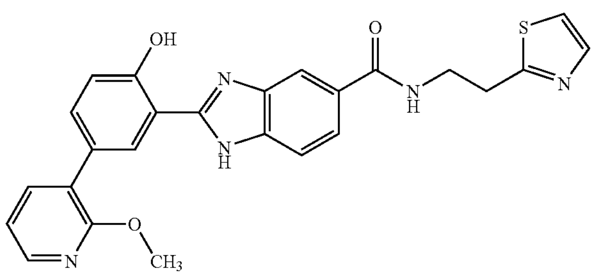 [SMILES: COc1ncccc1-c1ccc(O)c(-c2nc3cc(C(=O)NCCc4nccs4)ccc3[nH]2)c1] | 472.54 |

-continued

| Structure | M + 1 |
|---|---|
| 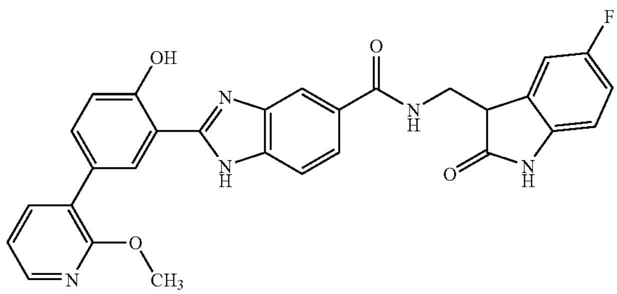 [SMILES: COc1ncccc1-c1ccc(O)c(-c2nc3cc(C(=O)NCC4C(=O)Nc5ccc(F)cc54)ccc3[nH]2)c1] | 524.53 |
| 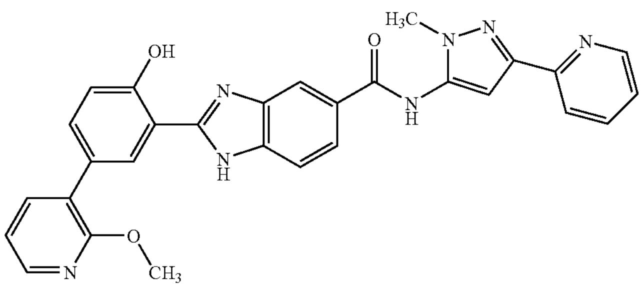 [SMILES: COc1ncccc1-c1ccc(O)c(-c2nc3cc(C(=O)Nc4cc(-c5ccccn5)nn4C)ccc3[nH]2)c1] | 518.55 |
| 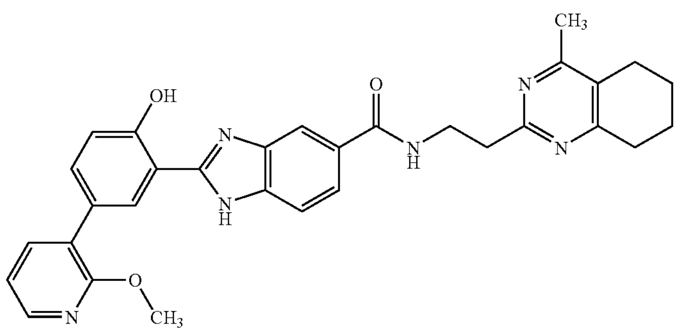 [SMILES: COc1ncccc1-c1ccc(O)c(-c2nc3cc(C(=O)NCCc4nc(C)c5c(n4)CCCC5)ccc3[nH]2)c1] | 535.62 |
| 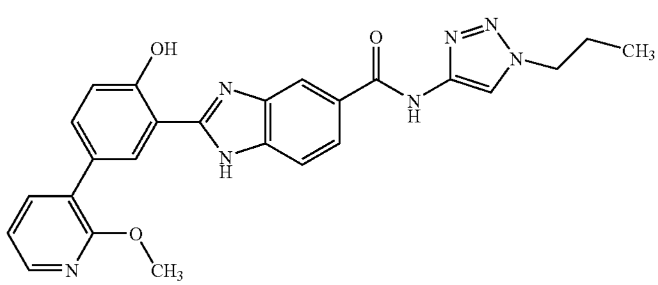 [SMILES: CCCn1cc(NC(=O)c2ccc3[nH]c(-c4cc(-c5cccnc5OC)ccc4O)nc3c2)nn1] | 470.51 |
| 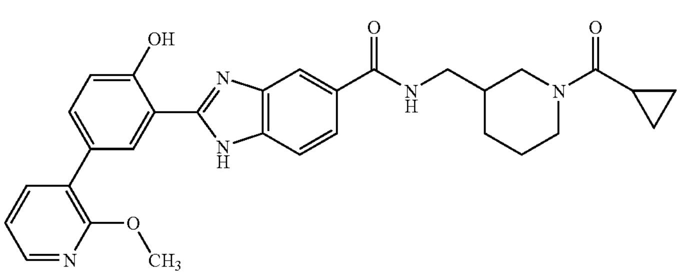 [SMILES: COc1ncccc1-c1ccc(O)c(-c2nc3cc(C(=O)NCC4CCCN(C(=O)C5CC5)C4)ccc3[nH]2)c1] | 526.61 |

-continued
| Structure | M + 1 |
|---|---|
| 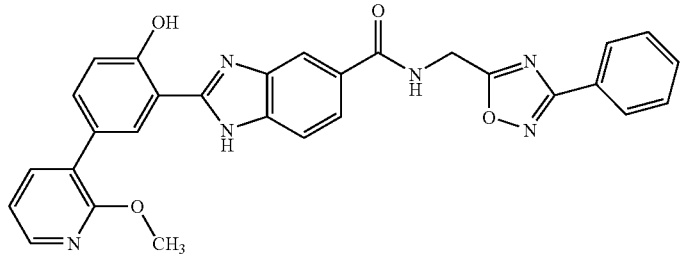 [SMILES: COc1ncccc1-c1ccc(O)c(-c2nc3cc(C(=O)NCc4nc(-c5ccccc5)no4)ccc3[nH]2)c1] | 519.54 |
| 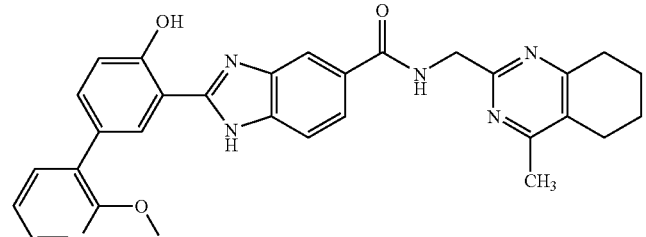 | 521.60 |
| 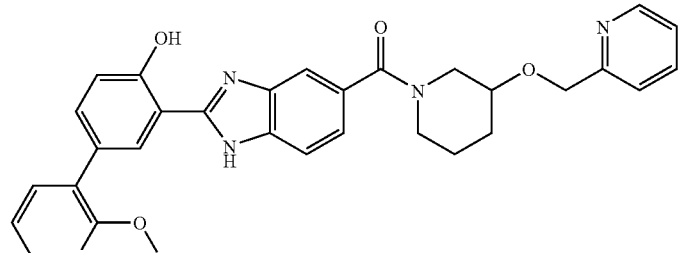 | 536.61 |
| 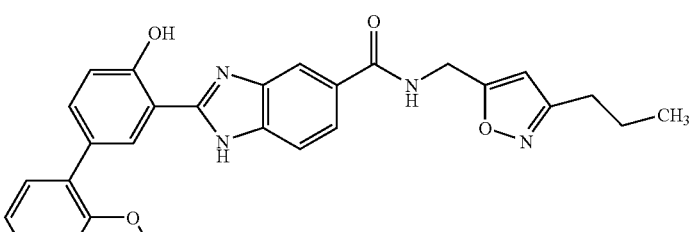 | 484.53 |
| 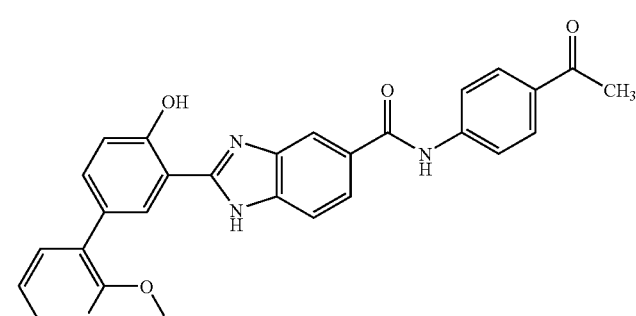 | 479.51 |

-continued
| Structure | M + 1 |
|---|---|
| 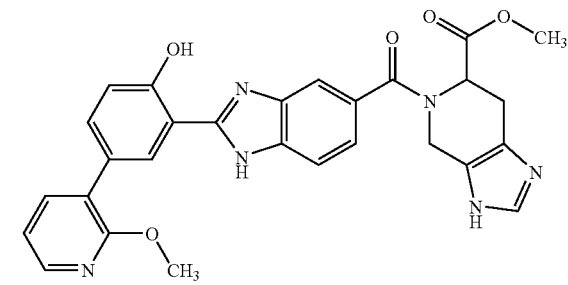 [SMILES: COC(=O)C1Cc2nc[nH]c2CN1C(=O)c1ccc2[nH]c(-c3cc(-c4cccnc4OC)ccc3O)nc2c1] | 525.54 |
| 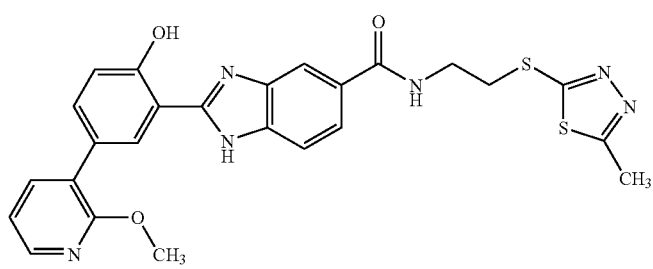 [SMILES: COc1ncccc1-c1ccc(O)c(-c2nc3cc(C(=O)NCCSc4nnc(C)s4)ccc3[nH]2)c1] | 519.62 |
| 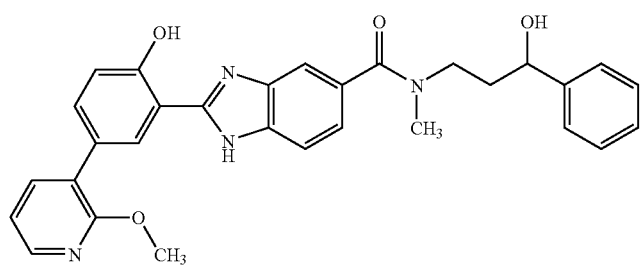 [SMILES: COc1ncccc1-c1ccc(O)c(-c2nc3cc(C(=O)N(C)CCC(O)c4ccccc4)ccc3[nH]2)c1] | 509.58 |
| 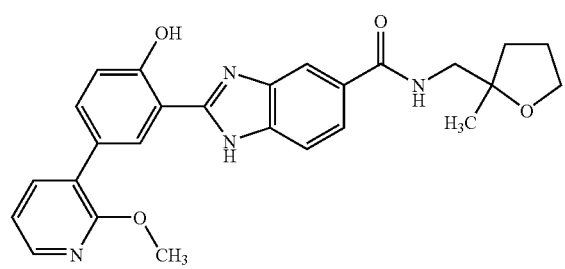 [SMILES: COc1ncccc1-c1ccc(O)c(-c2nc3cc(C(=O)NCC4(C)CCCO4)ccc3[nH]2)c1] | 459.52 |
| 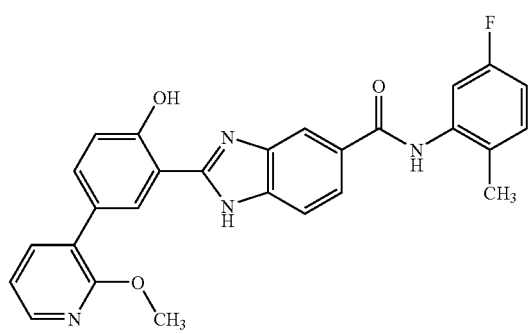 [SMILES: COc1ncccc1-c1ccc(O)c(-c2nc3cc(C(=O)Nc4cc(F)ccc4C)ccc3[nH]2)c1] | 469.49 |

-continued

| Structure | M + 1 |
|---|---|
| 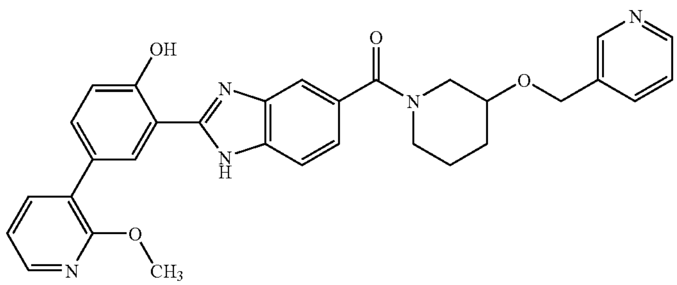 [SMILES: COc1ncccc1-c1ccc(O)c(-c2nc3cc(C(=O)N4CCCC(OCc5cccnc5)C4)ccc3[nH]2)c1] | 536.61 |
| 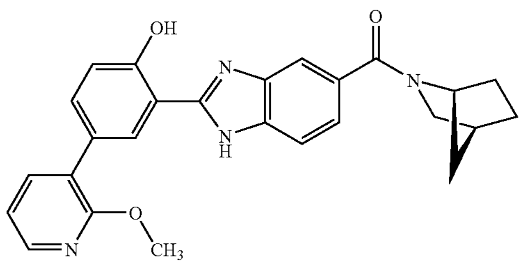 [SMILES: COc1ncccc1-c1ccc(O)c(-c2nc3cc(C(=O)N4C[C@H]5CC[C@H]4C5)ccc3[nH]2)c1] | 441.51 |
| 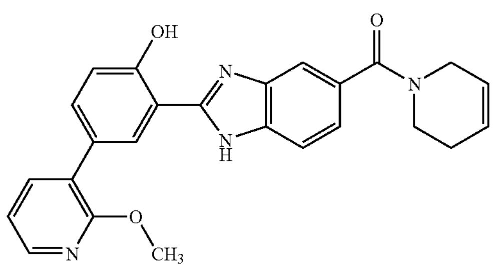 [SMILES: COc1ncccc1-c1ccc(O)c(-c2nc3cc(C(=O)N4CC=CCC4)ccc3[nH]2)c1] | 427.48 |
| 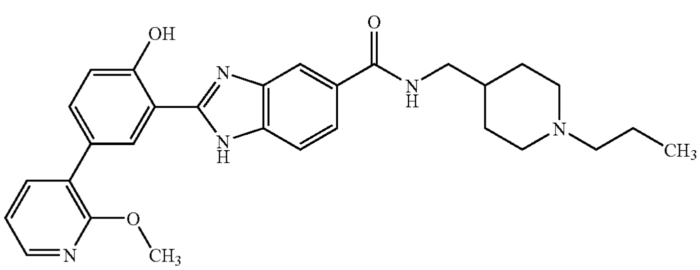 [SMILES: CCCN1CCC(CNC(=O)c2ccc3[nH]c(-c4cc(-c5cccnc5OC)ccc4O)nc3c2)CC1] | 500.62 |
| 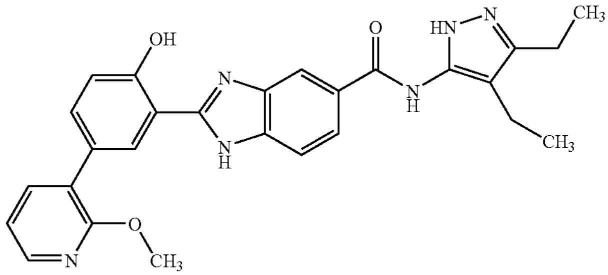 [SMILES: CCc1n[nH]c(NC(=O)c2ccc3[nH]c(-c4cc(-c5cccnc5OC)ccc4O)nc3c2)c1CC] | 483.55 |

-continued
| Structure | M + 1 |
|---|---|
| 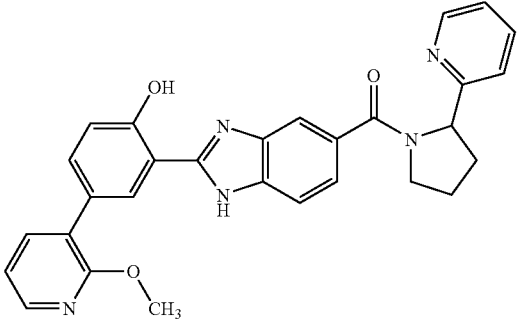 [SMILES: COc1ncccc1-c1ccc(O)c(-c2nc3cc(C(=O)N4CCCC4c4ccccn4)ccc3[nH]2)c1] | 492.55 |
| 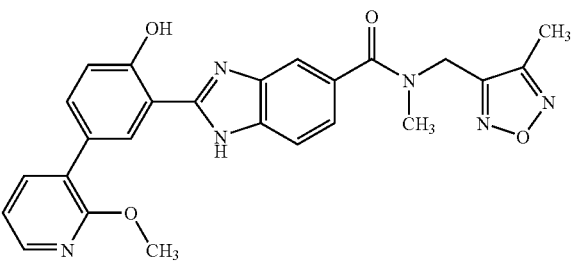 [SMILES: COc1ncccc1-c1ccc(O)c(-c2nc3cc(C(=O)N(C)Cc4nonc4C)ccc3[nH]2)c1] | 471.49 |
| 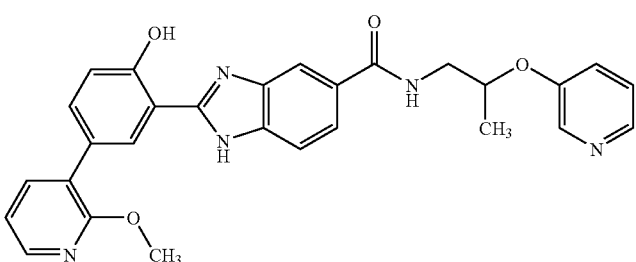 | 496.54 |
| 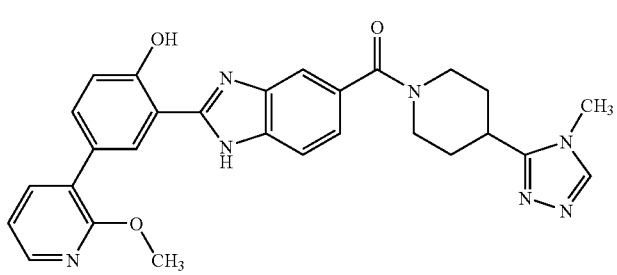 [SMILES: COc1ncccc1-c1ccc(O)c(-c2nc3cc(C(=O)N4CCC(c5nncn5C)CC4)ccc3[nH]2)c1] | 510.57 |
| 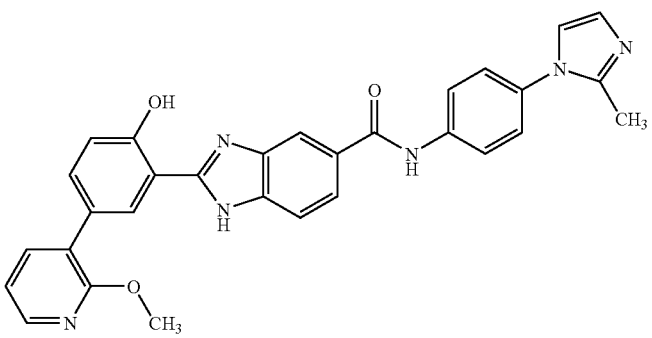 [SMILES: COc1ncccc1-c1ccc(O)c(-c2nc3cc(C(=O)Nc4ccc(-n5ccnc5C)cc4)ccc3[nH]2)c1] | 517.56 |

-continued
| Structure | M + 1 |
|---|---|
| 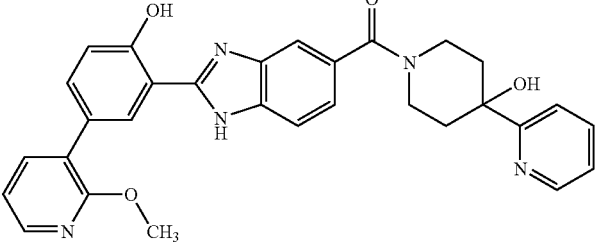 | 522.58 |
| 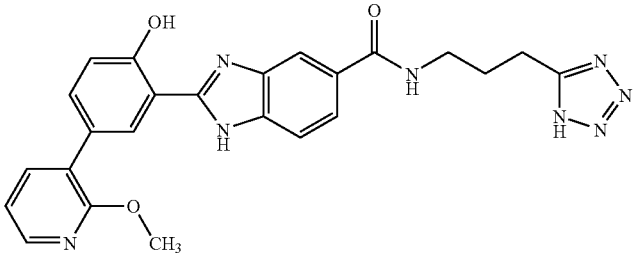 [SMILES: COc1ncccc1-c1ccc(O)c(-c2nc3cc(C(=O)NCCCc4nnn[nH]4)ccc3[nH]2)c1] | 471.49 |
| 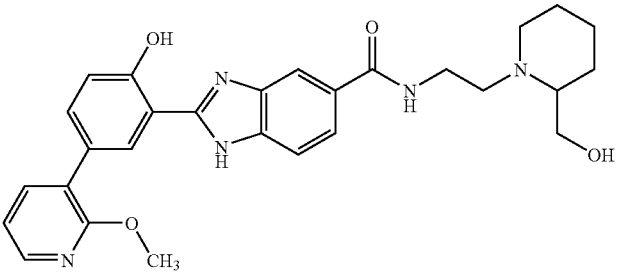 [SMILES: COc1ncccc1-c1ccc(O)c(-c2nc3cc(C(=O)NCCN4CCCCC4CO)ccc3[nH]2)c1] | 502.59 |
| 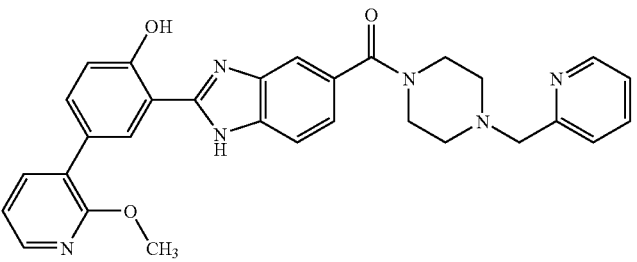 [SMILES: COc1ncccc1-c1ccc(O)c(-c2nc3cc(C(=O)N4CCN(Cc5ccccn5)CC4)ccc3[nH]2)c1] | 521.60 |
| 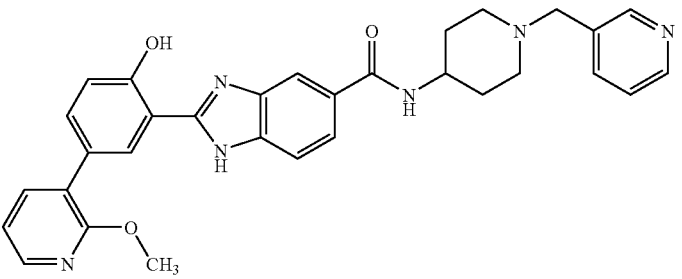 [SMILES: COc1ncccc1-c1ccc(O)c(-c2nc3cc(C(=O)NC4CCN(Cc5cccnc5)CC4)ccc3[nH]2)c1] | 535.62 |

-continued

| Structure | M + 1 |
|---|---|
| (structure) | 506.54 |
| (structure) | 525.59 |
| (structure) Chiral | 461.54 |
| (structure) Chiral | 472.52 |
| (structure) | 447.47 |

| Structure | M + 1 |
|---|---|
| 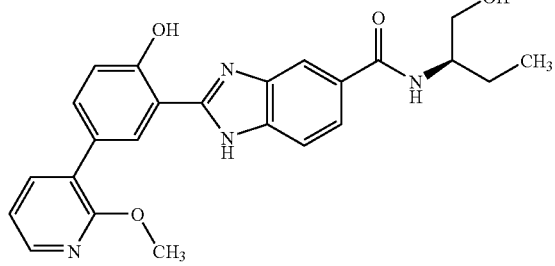 | 433.48 |
| 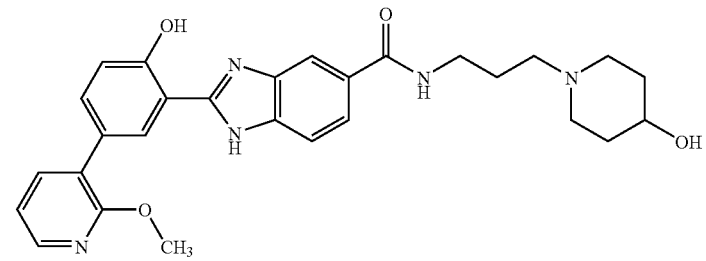 [SMILES: COc1ncccc1-c1ccc(O)c(-c2nc3cc(C(=O)NCCCN4CCC(O)CC4)ccc3[nH]2)c1] | 502.59 |
| 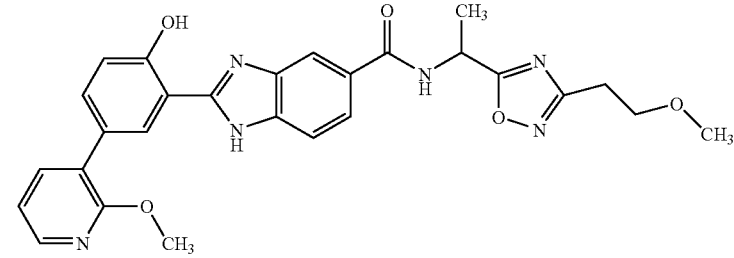 [SMILES: COCCc1noc(C(C)NC(=O)c2ccc3[nH]c(-c4cc(-c5cccnc5OC)ccc4O)nc3c2)n1] | 515.55 |
| 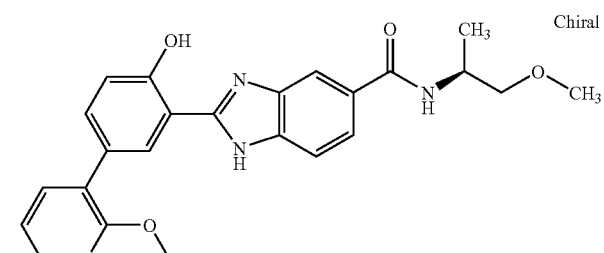 | 433.48 |
| 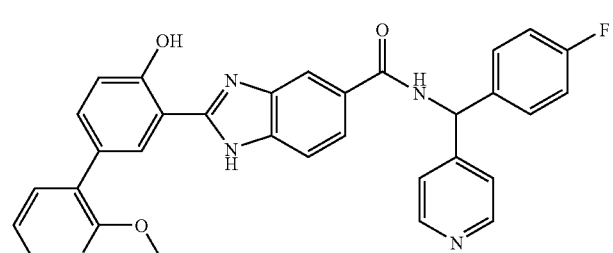 | 546.58 |

-continued

| Structure | M + 1 |
|---|---|
| (structure) | 477.49 |
| (structure) | 497.57 |
| (structure) | 509.54 |
| (structure) | 520.56 |
| (structure) | 531.59 |

| Structure | M + 1 |
|---|---|
| 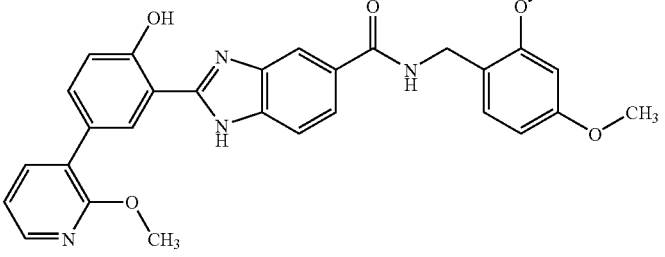 | 511.55 |
| 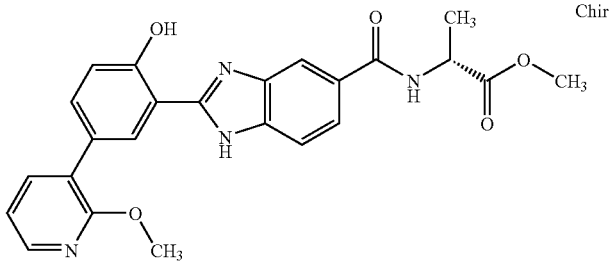 Chiral | 447.47 |
| 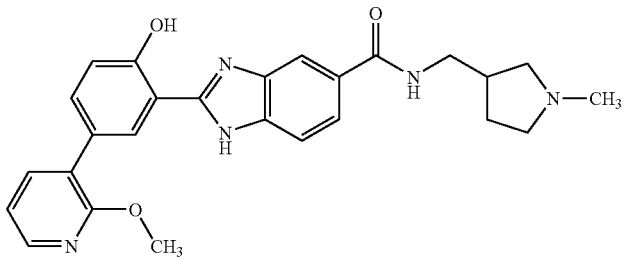 [SMILES: COc1ncccc1-c1ccc(O)c(-c2nc3cc(C(=O)NCC4CCN(C)C4)ccc3[nH]2)c1] | 458.54 |
| 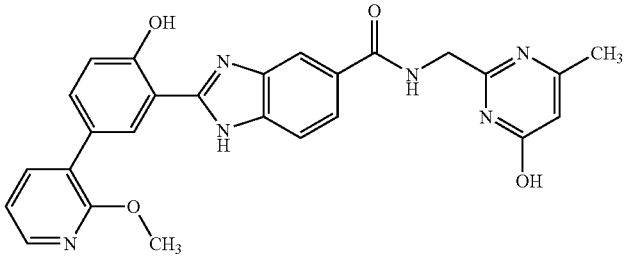 [SMILES: COc1ncccc1-c1ccc(O)c(-c2nc3cc(C(=O)NCc4nc(C)cc(O)n4)ccc3[nH]2)c1] | 483.50 |
| 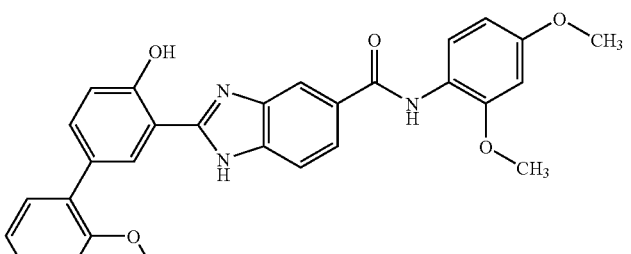 | 497.53 |

-continued

| Structure | M + 1 |
|---|---|
| (structure) | 389.43 |
| (structure) | 472.56 |
| (structure) | 481.53 |
| (structure) | 539.56 |
| (structure) | 485.58 |

-continued
| Structure | M + 1 |
|---|---|
| 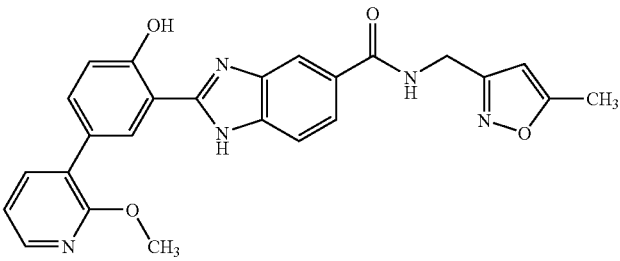 [SMILES: COc1ncccc1-c1ccc(O)c(-c2nc3cc(C(=O)NCc4cc(C)on4)ccc3[nH]2)c1] | 456.48 |
| 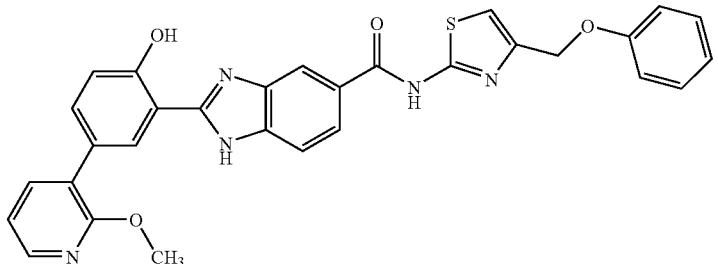 | 550.61 |
| 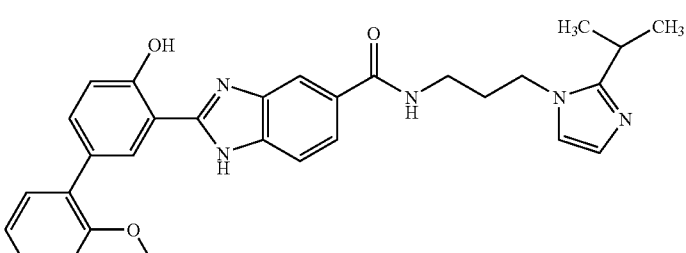 | 511.60 |
| 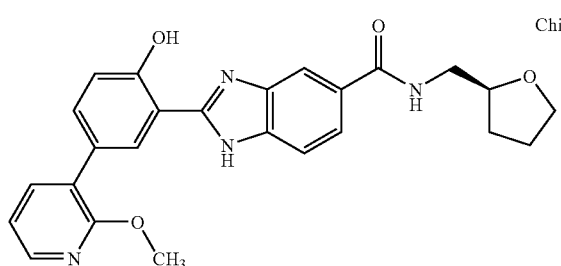 Chiral | 445.49 |
| 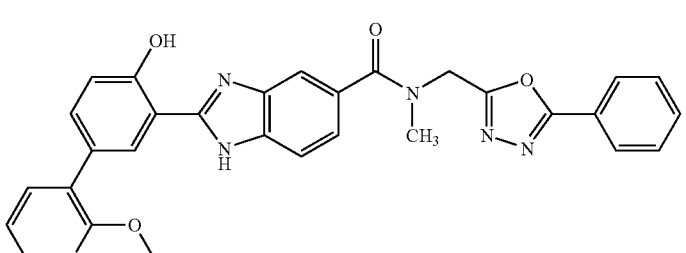 | 533.56 |

| Structure | M + 1 |
|---|---|
| 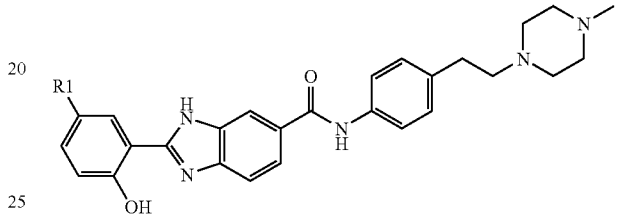 | 535.58 |

5.2.5.3 Preparation of Compounds According to Formula (5)

Compounds according to formula (5), (5a) and (5b) can be prepared according to any method apparent to those of skill in the art. The present invention provides the following exemplary methods for their preparation.

Compounds of formula (5) can be prepared according to the general scheme 5-A:

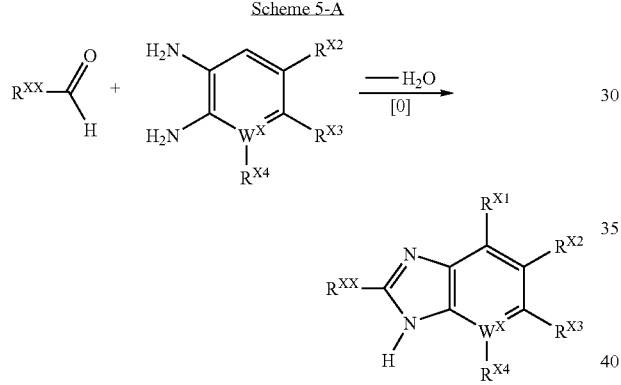

There are many references in the literature for this type of benzimidazole-forming reaction, such as Abdelkrim Ben Alloum et al., 2003, *Tetrahedron Letters* 44:5935-5937, the contents of which are hereby incorporated by reference in their entirety.

Further schemes for preparing compounds according to formula (5) include the following:

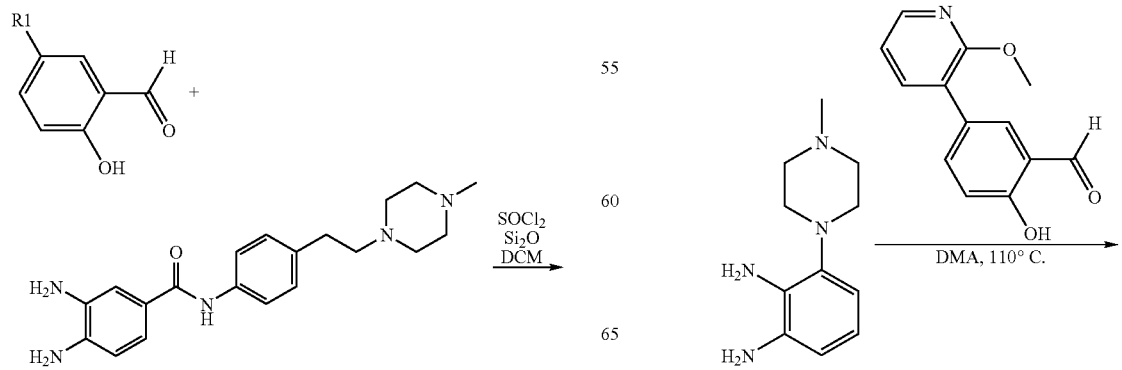

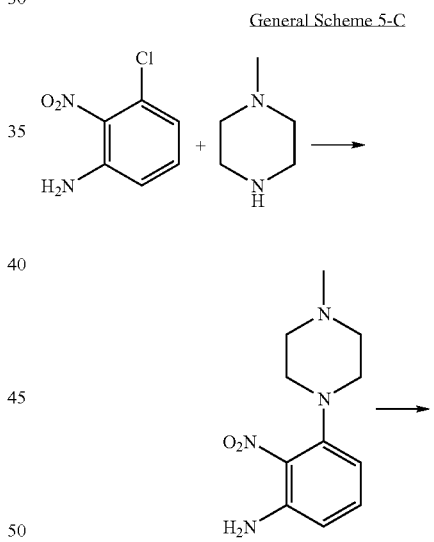

-continued

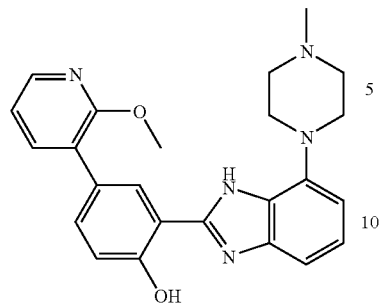

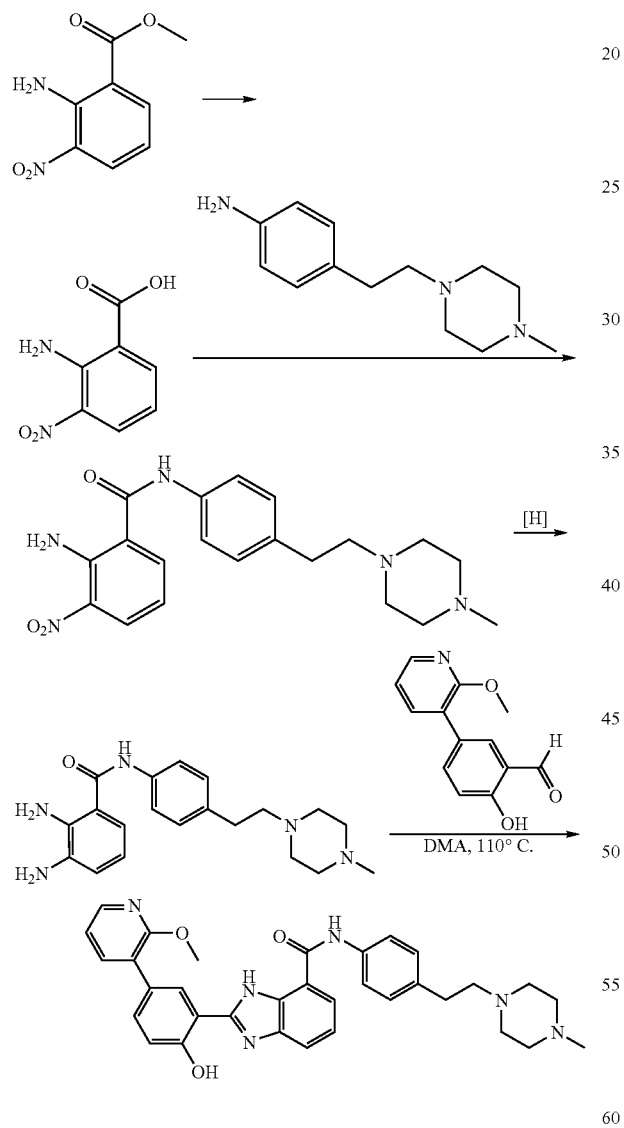

Detailed methods for preparation of compounds according to formula (5) are provided in the examples below.

5.2.6 Compounds According to Formula 6

In certain embodiments, the present invention provides compounds of formula (6) that are represented in formula (6a):

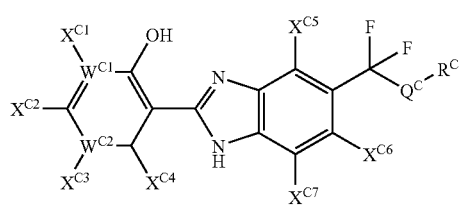

Formula (6a)

In formula (6a), $W^{C1}$, $W^{C2}$, $X^{C1}$ through $X^{C7}$, $Q^C$ and $R^C$ are as described for formula (6), above.

In certain embodiments, the present invention provides compounds of formula (6) that are represented in formula (6b):

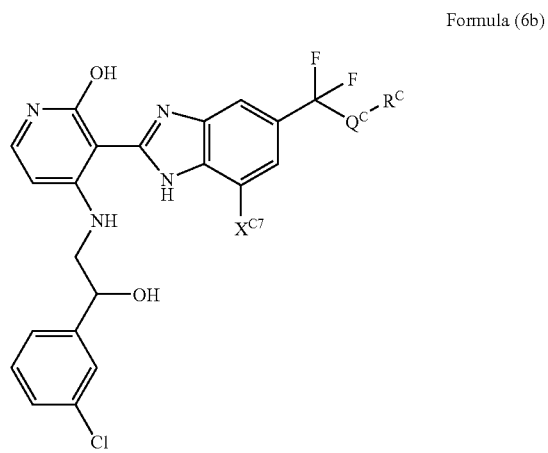

Formula (6b)

In formula (6b), $X^{C7}$ is hydrogen or methyl

In formula (6b), $Q^C$ is a carbonyl group or a methylene group.

In formula (6b), $R^C$ is as described for formula (6), above.

In certain embodiments, the present invention provides compounds of formula (6) that are represented in formula (6c):

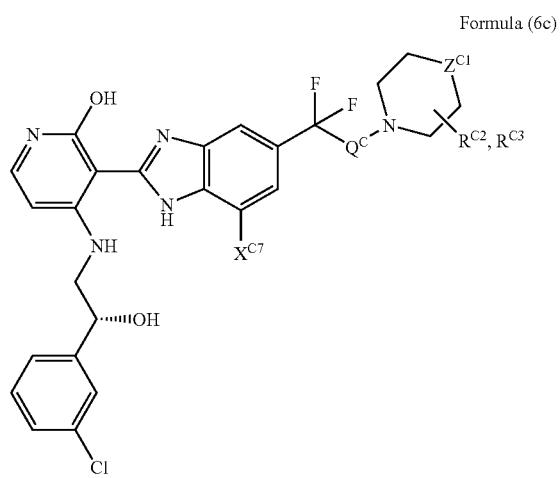

Formula (6c)

In formula (6c), $Z^{C1}$ is O, S, S=O, S(=O)$_2$ or N—RC1

In formula (6c), $X^{C7}$ is hydrogen or methyl.

In formula (6c), $Q^C$ is a carbonyl group or a methylene group.

In formula (6c), $R^{C1}$ is selected from lower alkyl, heteroalkyl, cycloalkyl, optionally substituted aryl or heteroaryl, optionally substituted arylalkyl or heteroarylalkyl.

In formula (6c), $R^{C2}$ and $R^{C3}$ are selected from hydrogen or lower alkyl, and $R^{C2}$ with $R^{C3}$ can form together a double bond to oxygen, thus forming an oxo-group (C=O).

The following are further non-limiting examples of specific embodiments of formula (6c):

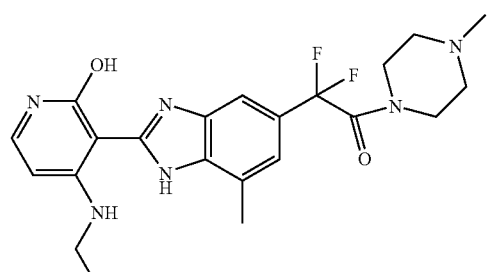

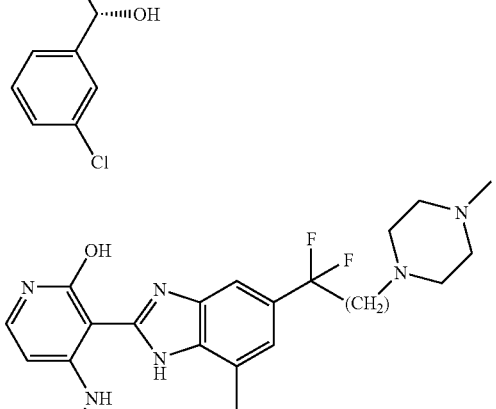

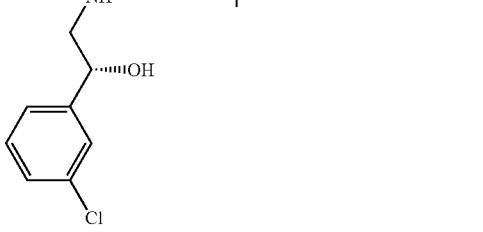

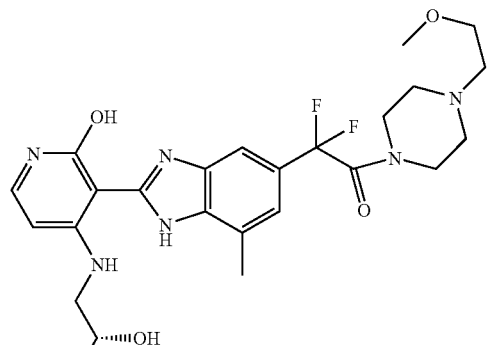

-continued

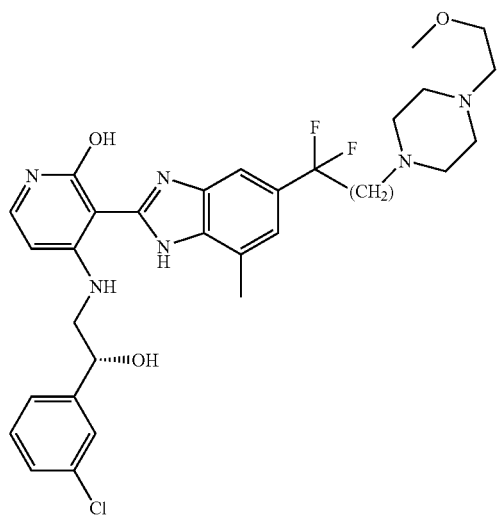

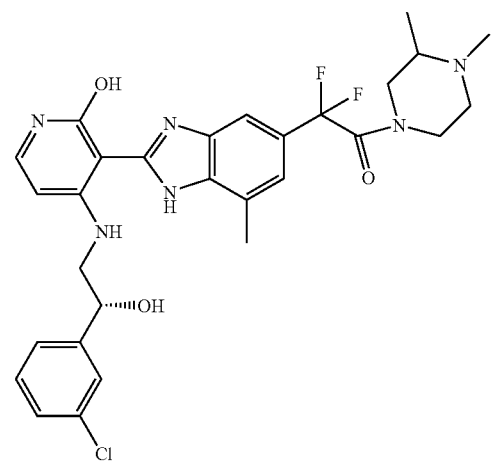

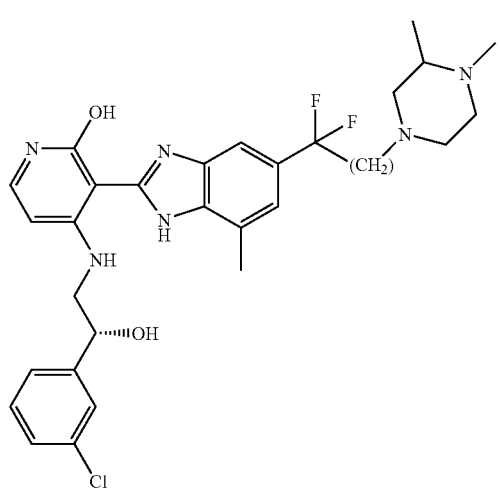

531
-continued
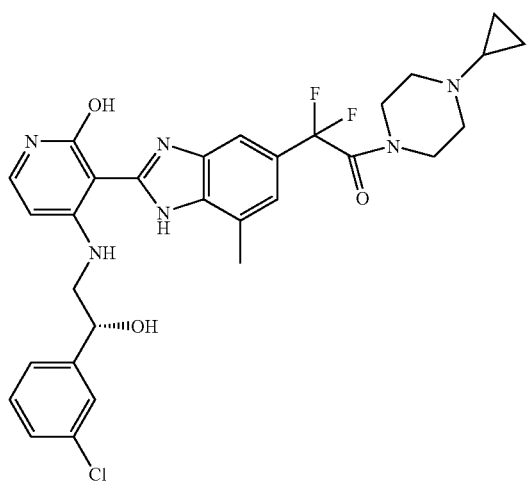
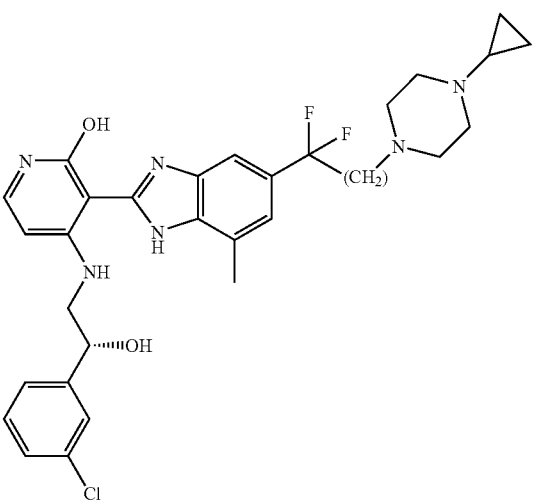
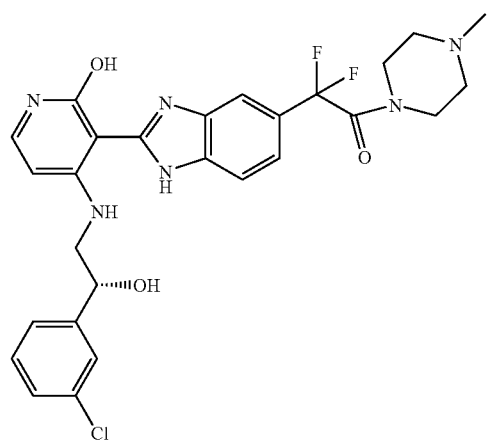
532
-continued
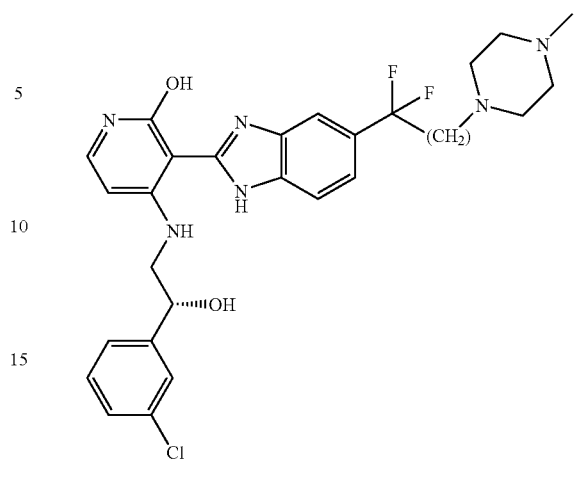
5.2.6.1 Preparation of Compounds According to Formula (6)
Compounds according to formula (6) can be prepared according to scheme 6-1:
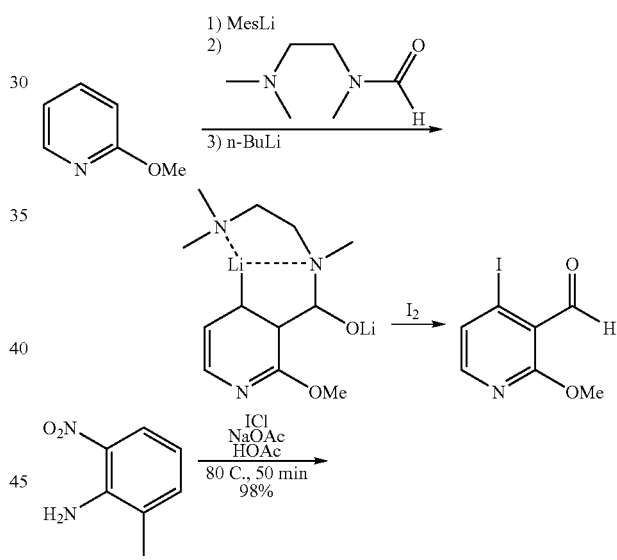
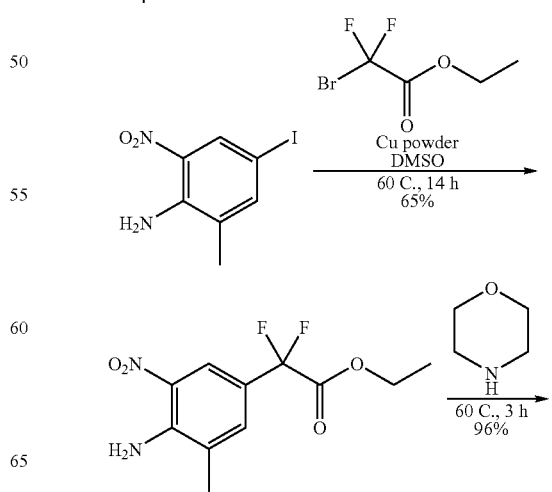

533
-continued

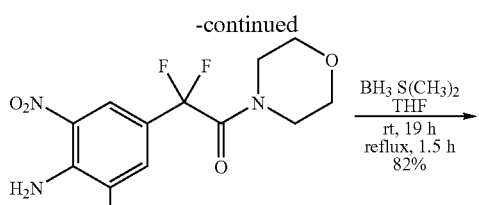

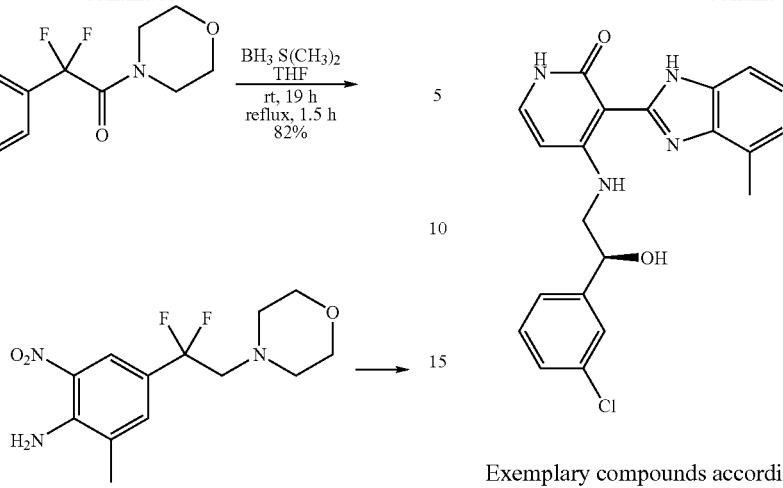

534
-continued

Exemplary compounds according to formula 6, and methods of their preparation, are described in detail in the examples below.

5.3 Methods of Use

In another aspect, this present invention provides methods for modulating the activity of a tyrosine kinase. In general, the methods comprise the step of contacting the tyrosine kinase with a compound of the invention. The contacting can be in any environ known to those of skill in the art, for instance, in vitro, in vivo, ex vivo or otherwise. In certain embodiments, the present invention provides methods of modulating the activity of a tyrosine kinase in a mammal in need thereof comprising contacting the tyrosine kinase with a compound of the invention.

As used herein, the term "modulation" or "modulating" refers to the alteration of the catalytic activity of a tyrosine kinase. In particular, modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

In certain embodiments, the receptor tyrosine kinase is selected from the group consisting of EGFR, HBER2, HER3, HER4, IR, IGF1R, IRR, PDGFRα, PDGFRβ, TrkA, TrkB, TrkC, HGFR, CSFIR, C-Kit, C-fms, Flk4, KDR/Flk-1, Flt-1, FGF1R, FGF2R, FGF3R and FGF4R.

In certain embodiments, the intracellular tyrosine kinase is selected from the group consisting of Alk, Src, Frk, Btk, Csk, Abl, ZAP70, Fes, Fps, Fak, Jak1, Jak2, Jak3, Jak4, Ack, Yes, Fyn, Lyn, Lck, Blk, Hck, Fgr and Yrk.

In another aspect, the present invention provides methods for treating or preventing a tyrosine kinase related disorder in a subject in need thereof. In general, the methods comprise administering to the subject an amount of a compound of the invention effective to treate or prevent the disorder. The compound can be in the form of a pharmaceutical composition or a unit dose as described below.

A tyrosine kinase related disorder can be any disorder known to those of skill in the art to be related to tyrosine kinase activity. Such disorders include those related to excessive tyrosine kinase active, those related to reduced tyrosine kinase activity and to those that can be treated or prevented by modulation of tyrosine kinase activity. Excessive tyrosine kinase activity can arise as the result of, for example: (1) tyrosine kinase expression in cells which normally do not express tyrosine kinases; (2) increased tyrosine kinase expression leading to unwanted cell proliferation, differentiation and/or growth; or, (3) decreased tyrosine kinase expression leading to unwanted reductions in cell proliferation, differentiation and/or growth.

The tyrosine kinase related disorder can be a cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma in a further aspect of this invention.

The above-referenced tyrosine kinase related disorder can be an IGFR-related disorder selected from diabetes, an autoimmune disorder, Alzheimer's and other cognitive disorders, a hyperproliferation disorder, aging, cancer, acromegaly, Crohn's disease, endometriosis, diabetic retinopathy, restenosis, fibrosis, psoriasis, osteoarthritis, rheumatoid arthritis, an inflammatory disorder and angiogenesis.

Other disorders which might be treated with compounds of this invention include, without limitation, immunological and cardiovascular disorders such as atherosclerosis.

5.4 Compositions and Method of Administration

In certain aspects, the present invention provides compostions comprising a compound of the present invention. The compositions can be used, for example, in the methods of use described above.

In certain embodiments, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients or diluents. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, New York, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are in certain embodiments anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are in certain embodiments packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent in certain embodiments in purified form, together with a suitable amount of carrier so as to provide the form for proper administration to the patient. The formulation should suit the mode of administration. In certain embodiments, the pharmaceutical compositions or single unit dosage forms are sterile and in suitable form for administration to a subject, in certain embodiments an animal subject, such as a mammalian subject, particularly a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day. Particular dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the compound.

5.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

5.4.2 Controlled Release Dosage Forms

Active ingredients such as the compounds of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

5.4.4 Transdermal, Topical & Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.4.5 Dosage & Frequency of Administration

The amount of the compound or composition of the invention which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of a compound include milligram or microgram amounts of the active peptide per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). In general, the recommended daily dose range of a compound of the invention for the conditions described herein lie within the range of from about 0.01 mg to about 1000 mg per day, given as a single once-a-day dose in certain embodiments as divided doses throughout a day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

6. EXAMPLES

6.1 Example 1

Compounds According to Formula (1)

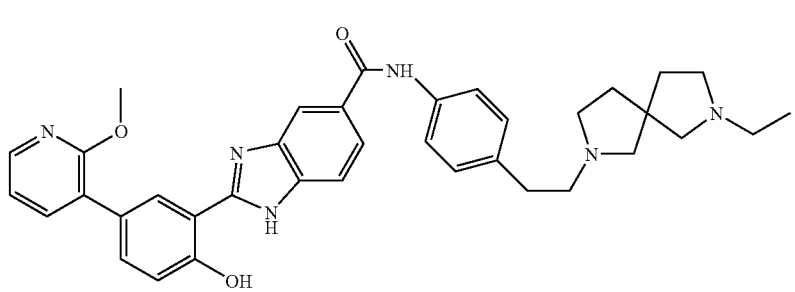

A

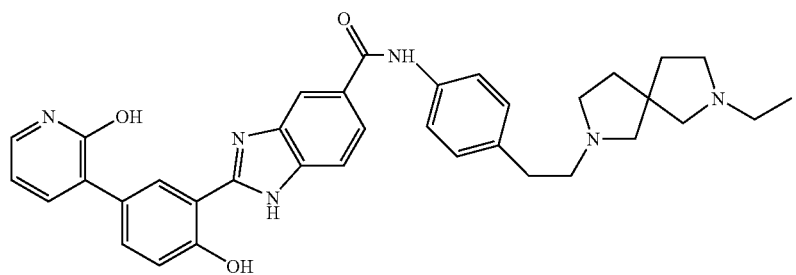

B

2-Ethyl-7-[2-(4-nitro-phenyl)-ethyl]-2,7-diaza-spiro[4.4]nonane

A mixture of 2-Ethyl-2,7-diaza-spiro[4.4]nonane (1.0 g, 6.49 mM), Diisopropylethylamine (3 ml), 4-nitrophenethyl bromide (1.49 g, 6.47 mM) in Dioxane was heated at 95° C. for 16 h. The cooled reaction mixture was partitioned between ethyl acetate (2×100 ml) and dilute 0.1 N KOH, the organic phase dried over sodium sulfate, filtered and evaporated to afford crude 2-Ethyl-7-[2-(4-nitro-phenyl)-ethyl]-2,7-diaza-spiro[4.4]nonane which was used as is in the next step.

4-[2-(7-Ethyl-2,7-diaza-spiro[4.4]non-2-yl)-ethyl]-phenylamine

2-Ethyl-7-[2-(4-nitro-phenyl)-ethyl]-2,7-diaza-spiro[4.4]nonane from above was dissolved in ethanol (60 ml) and 20% Pd(OH)2 (30 mg) was added and the reaction was stirred 16 h under an atmosphere of hydrogen gas by means of a balloon reservoir. The reaction was filtered thru Celite and the filtrate evaporated to afford 4-[2-(7-Ethyl-2,7-diaza-spiro[4.4]non-2-yl)-ethyl]-phenylamine and a crude oil (1.45 g) which was used as is in the next step.

N-{4-[2-(7-Ethyl-2,7-diaza-spiro[4.4]non-2-yl)-ethyl]-phenyl}-4-fluoro-3-nitro-benzamide 4-[2-(7-Ethyl-2,7-diaza-spiro[4.4]non-2-yl)-ethyl]-phenylamine from above was dissolved in dichloromethane to which was added diisopropylamine (1 ml) and the reaction was cooled in an ice bath. A solution of 4-Fluoro-3-nitro-benzoyl chloride (0.5 N, 8 ml) was added and the reaction stirred for 1 h then evaporated under reduced pressure to a yellow foam which was used as is in the next step.

4-Amino-N-{4-[2-(7-ethyl-2,7-diaza-spiro[4.4]non-2-yl)-ethyl]-phenyl}-3-nitro-benzamide N-{4-[2-(7-Ethyl-2,7-diaza-spiro[4.4]non-2-yl)-ethyl]-phenyl}-4-fluoro-3-nitro-benzamide from above was dissolved in DMF (15 ml) and the solution was cooled in an ice bath and saturated with ammonia gas for 10 min. The flask was sealed and left at room temperature overnight. The DMF was then evaporated under reduced pressure and the residue partitioned between dichloromethane and 0.1 N KOH. The organic phase was dried over sodium sulfate, filtered and evaporated under reduced pressure. The residue was purified on silica gel using 10% MeOH/CH$_2$Cl$_2$ 1% TEA to afford 4-Amino-N-{4-[2-(7-ethyl-2,7-diaza-spiro[4.4]non-2-yl)-ethyl]-phenyl}-3-nitro-benzamide (996 mg) as a yellow foam which was used as is in the next step. $^1$H NMR (300 MHz, d$^6$-DMSO) δ 10.2 (s, 1H), 8.70 (s, 1H), 7.96 (d, 1H), 7.82 (s, 2H), 7.63 (dd, 2H), 7.24 (dd, 2H), 7.10 (d, 1H), 2.65-2.35 (m, 14H), 1.96 (m, 4H), 1.23 (t, 3H).

3,4-Diamino-N-{4-[2-(7-ethyl-2,7-diaza-spiro[4.4]non-2-yl)-ethyl]-phenyl}-benzamide 4-Amino-N-{4-[2-(7-ethyl-2,7-diaza-spiro[4.4]non-2-yl)-ethyl]-phenyl}-3-nitro-benzamide from above was dissolved in ethanol (25 ml) and 1N HCl (6 ml) to which was added 20% Pd(OH)2 and the mixture hydrogenated overnight under an atmosphere of hydrogen gas. The reaction was then filtered thru Celite and the filtrate evaporated to afford crude 3,4-Diamino-N-{4-[2-(7-ethyl-2,7-diaza-spiro[4.4]non-2-yl)-ethyl]-phenyl}-benzamide (1.18 g, 4×HCl salt) as a tan foam which was used as is in the next step.

2-[2-Hydroxy-5-(2-methoxy-pyridin-3-yl)-phenyl]-1H-benzoimidazole-5-carboxylic acid {4-[2-(7-ethyl-2,7-diaza-spiro[4.4]non-2-yl)-ethyl]-phenyl}-amide A mixture of 2-Hydroxy-5-(2-methoxy-pyridin-3-yl)-benzaldehyde (20 mg) and 3,4-Diamino-N-{4-[2-(7-ethyl-2,7-diaza-spiro[4.4]non-2-yl)-ethyl]-phenyl}-benzamide HCl salt (60 mg) in dimethylacetamide (1.5 ml) was heated at 95° C. for 3 h then cooled and purified by RP-HPLC (0.1% TFA) to afford (A) 2-[2-Hydroxy-5-(2-methoxy-pyridin-3-yl)-phenyl]-1H-benzoimidazole-5-carboxylic acid {4-[2-(7-ethyl-2,7-diaza-spiro[4.4]non-2-yl)-ethyl]-phenyl}-amide (10 mg) LCMS MH+ 617.5 as well as (B) 2-[2-Hydroxy-5-(2-hydroxy-pyridin-3-yl)-phenyl]-1H-benzoimidazole-5-carboxylic acid {4-[2-(7-ethyl-2,7-diaza-spiro[4.4]non-2-yl)-ethyl]-phenyl}-amide (10 mg) LCMS MH+ 603.7.

Using procedures analogous to the above the following compounds were prepared.

Starting from 2-Methyl-2,8-diaza-spiro[5.5]undecane we obtained 2-[2-Hydroxy-5-(2-hydroxy-pyridin-3-yl)-phenyl]-1H-benzoimidazole-5-carboxylic acid {4-[2-(8-methyl-2,8-diaza-spiro[5.5]undec-2-yl)-ethyl]-phenyl}-amide. LCMS [MH+]631.5.

Starting with 3-Methyl-1,3,8-triaza-spiro[4.5]decane-2,4-dione we obtained 2-[2-Hydroxy-5-(2-methoxy-pyridin-3-yl)-phenyl]-1H-benzoimidazole-5-carboxylic acid {4-[2-(3-methyl-2,4-dioxo-1,3,8-triaza-spiro[4.5]dec-8-yl)-ethyl]-phenyl}-amide LCMS MH+ 646.5.

Starting with 1,3-Dimethyl-1,3,8-triaza-spiro[4.5]decane-2,4-dione we obtained 2-[2-Hydroxy-5-(2-methoxy-pyridin-3-yl)-phenyl]-1H-benzoimidazole-5-carboxylic acid {4-[2-(1,3-dimethyl-2,4-dioxo-1,3,8-triaza-spiro[4.5]dec-8-yl)-ethyl]-phenyl}-amide LCMS MH+ 660.5.

Further compounds prepared according to formula (1) include the following:

| MOLSTRUCTURE | MW (M + 1) |
|---|---|
| 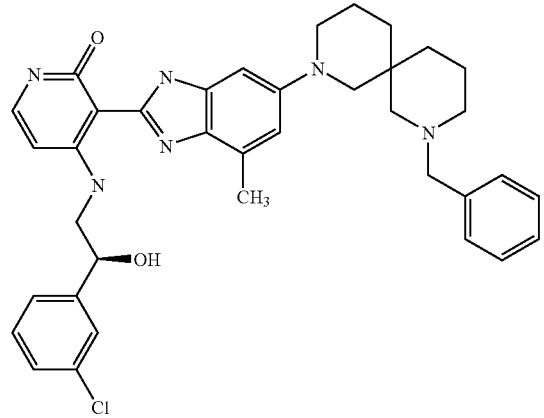 | 638.2 |
| 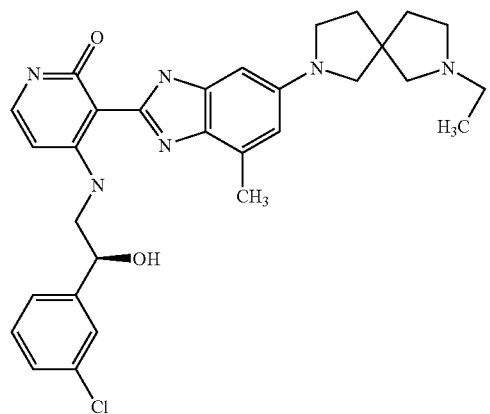 | 548.1 |
| 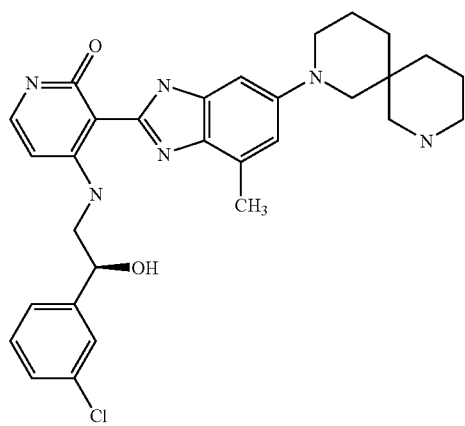 | 548.1 |
| 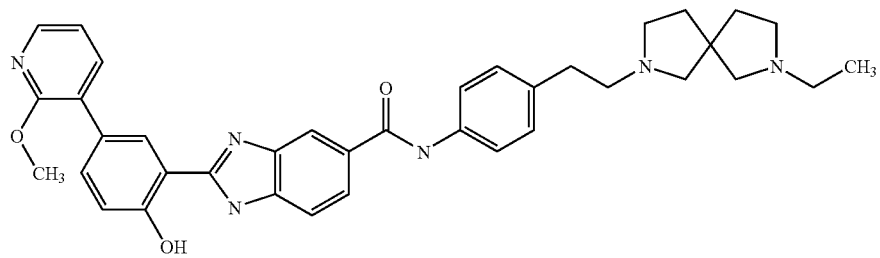 [SMILES: CCN1CCC2(CCN(CCc3ccc(NC(=O)c4ccc5[nH]c(-c6cc(-c7cccnc7OC)ccc6O)nc5c4)cc3)C2)C1] | 617.8 |

-continued
| MOLSTRUCTURE | MW (M + 1) |
|---|---|
| | 603.7 |
| | 631.8 |
| | 617.8 |
6.2 Example 2
General Synthesis of Compounds of Formula (I)
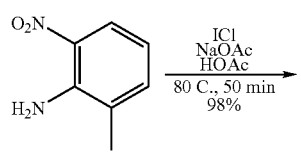
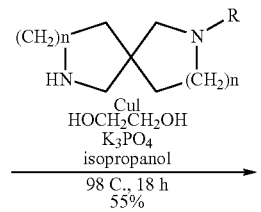
-continued
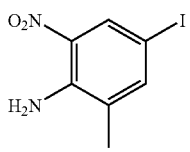

-continued

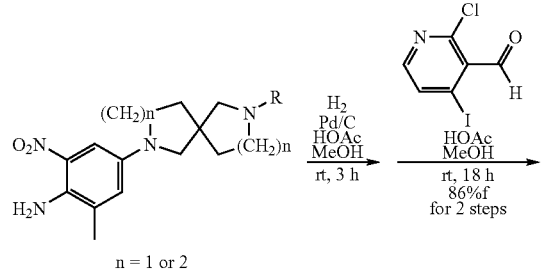

n = 1 or 2

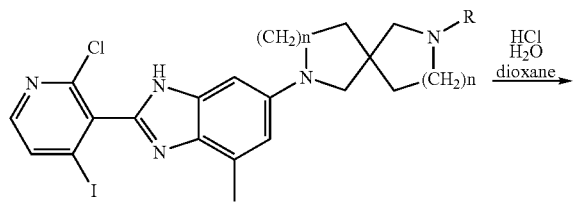

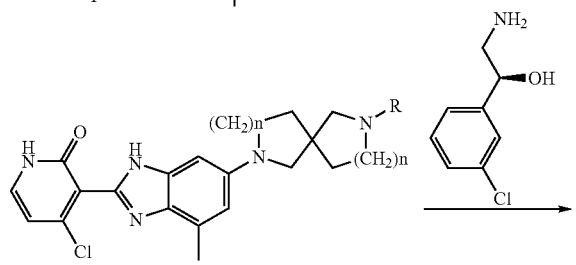

6.3 Example 3

Synthesis of Compounds of Formula (1)

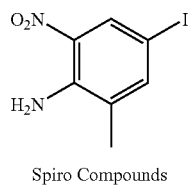

Spiro Compounds

4-Iodo-2-methyl-6-nitroaniline

To a mixture of 2-methyl-6-nitroaniline (106.5 g, 0.7 mol) and NaOAc (63.2 g, 0.77 mol) in acetic acid (525 mL) was added a solution of ICl (125 g, 0.77 mol) in acetic acid (350 mL). The mixture was heated at 80° C. for 50 min and poured into H$_2$O (2100 mL). After stayed at the room temperature for 16 h, the mixture was filtered to furnish yellow solid that was washed with H$_2$O (3×350 mL). Drying under reduced pressure at 40° C. for 48 h afforded the title compound (191 g, 98%). $^1$H NMR (CDCl$_3$) δ 2.22 (s, 3H), 6.20 (br s, 2H NH), 7.53 (s, 1H), 8.34 (s, 1H). ESI-MS m/z 279 (MH$^+$).

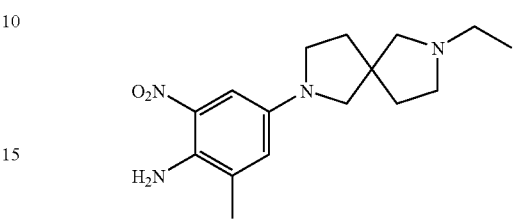

4-(7-Ethyl-2,7-diaza-spiro[4.4]non-2-yl)-2-methyl-6-nitro-phenylamine

A suspension of 4-iodo-2-methyl-6-nitroaniline (1.39 g, 5 mmol), 2-ethyl-2,7-diaza-spiro[4.4]nonane (770 mg, 5 mmol), CuI (190.5 mg, 1.0 mmol), ethylene glycol (931 mg, 15 mmol) and K$_3$PO$_4$ (3.2 g, 15 mmol) in isopropanol (40 mL) was sealed and heated at 90° C. for 19 h. After cooled down to room temperature, the reaction mixture was concentrated. The residue was purified by chromatography (16:1 CH$_2$Cl$_2$/MeOH) to afford the title compound (910 mg, 60%). $^1$H NMR (CDCl$_3$) δ 1.29 (t, J=8 Hz, 3H), 1.96-2.19 (4H), 2.24 (s, 3H), 2.77-3.01 (6H), 3.22-3.40 (4H), 5.78 (br s, 2H NH), 6.80 (s, 1H), 7.06 (s, 1H). ESI-MS m/z 305 (MH$^+$).

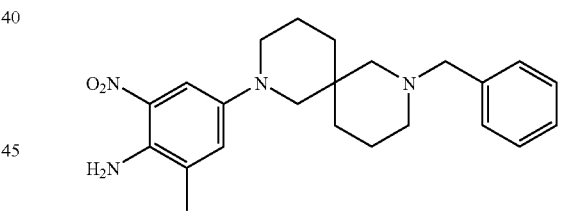

4-(8-Benzyl-2,8-diaza-spiro[5.5]undec-2-yl)-2-methyl-6-nitro-phenylamine

A suspension of 4-iodo-2-methyl-6-nitroaniline (1.39 g, 5 mmol), 2-benzyl-2,8-diaza-spiro[5.5]undecane (1.22 g, 5 mmol), CuI (190.5 mg, 1.0 mmol), ethylene glycol (931 mg, 15 mmol) and K$_3$PO$_4$ (3.2 g, 15 mmol) in isopropanol (40 mL) was sealed and heated at 90° C. for 19 h. After cooled down to room temperature, the reaction mixture was concentrated. The residue was purified by chromatography (99:1 CH$_2$Cl$_2$/MeOH) to afford the title compound (593 mg, 30%). $^1$H NMR (CDCl$_3$) δ 1.24 (m, 2H), 1.48-1.68 (6H), 2.01-2.24 (m, 2H), 2.24 (s, 3H), 2.57 (m, 2H), 2.73 (d, J=12 Hz, 1H), 2.82 (m, 1H), 3.03 (m, 1H), 3.14 (d, J=12 Hz, 1H), 3.47 (d, J=9 Hz, 2H), 5.30 (br s, 2H NH), 7.11 (s, 1H), 7.19-7.33 (5H), 7.44 (s, 1H). ESI-MS m/z 395 (MH$^+$).

551

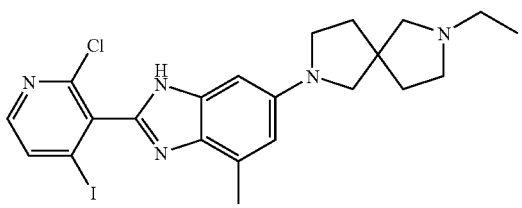 [SMILES: CCN1CCC2(CCN(c3cc(C)c4nc(-c5c(I)ccnc5Cl)[nH]c4c3)C2)C1]

2-(2-Chloro-4-iodo-pyridin-3-yl)-6-(7-ethyl-2,7-diaza-spiro[4.4]non-2-yl)-4-methyl-1H-benzoimidazole To a solution of 4-(7-ethyl-2,7-diaza-spiro[4.4]non-2-yl)-2-methyl-6-nitro-phenylamine (304 mg, 1.0 mmol) in MeOH (47.5 mL) were added Pd/C (10%, 40 mg) and acetic acid (2.5 mL). The mixture was stirred under atmospheric hydrogen (balloon) at the room temperature for 3 h and then filter over Celite. The filtrate was mixed with 2-chloro-3-formyl-4-iodopyridine (267.5 mg, 1.0 mmol), stirred at the room temperature for 18 h, and evaporated to dryness under reduced pressure. The residue was dissolved in MeOH (10 mL) and 28% aqueous NH$_4$OH solution (0.5 mL) was added. After it was stirred for 5 min, the mixture was concentrated and chromatographed (5:1, CH$_2$Cl$_2$/MeOH) to afford the title compound (450 mg, 86%). $^1$H NMR (MeOH-d$_4$) δ 1.38 (t, J=8 Hz, 3H), 2.10-2.21 (4H), 2.56 (s, 3H), 3.28-3.57 (10H), 6.55 (s, 1H), 6.57 (s, 1H), 8.03 (d, J=6 Hz, 1H), 8.13 (d, J=6 Hz, 1H). ESI-MS m/z 522 (MH$^+$).

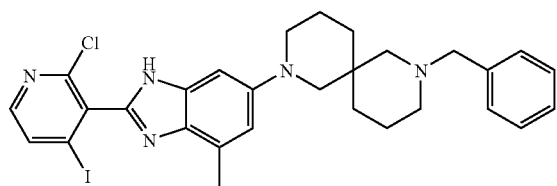 [SMILES: Cc1cc(N2CCCC3(CCCN(Cc4ccccc4)C3)C2)cc2[nH]c(-c3c(I)ccnc3Cl)nc12]

2-Benzyl-8-[2-(2-chloro-4-iodo-pyridin-3-yl)-7-methyl-3H-benzoimidazol-5-yl]-2,8-diaza-spiro[5.5]undecane To a solution of 4-(8-benzyl-2,8-diaza-spiro[5.5]undec-2-yl)-2-methyl-6-nitro-phenylamine (394 mg, 1.0 mmol) in MeOH (47.5 mL) were added Pd/C (10%, 40 mg) and acetic acid (2.5 mL). The mixture was stirred under atmospheric hydrogen (balloon) at the room temperature for 3 h and filter over Celite. The filtrate was mixed with 2-chloro-3-formyl-4-iodopyridine (267.5 mg, 1.0 mmol), stirred at the room temperature for 18 h, and evaporated to dryness under reduced pressure. The residue was dissolved in MeOH (10 mL) and 28% aqueous NH$_4$OH solution (0.5 mL) was added. After it was stirred for 5 min, the mixture was concentrated and chromatographed (330:10:1 CH$_2$Cl$_2$/MeOH/28% aqueous NH$_4$OH) to afford the title compound (55 mg, 9%). $^1$H NMR (CDCl$_3$) δ 1.22-1.36 (2H), 1.49-1.84 (6H), 1.95-2.59 (6H), 2.59 (s, 3H), 2.94-3.45 (6H), 6.82 (s, 1H), 6.87 (s, 1H), 7.16-7.33 (5H), 7.72 (d, J=6 Hz, 1H), 7.99 (d, J=6 Hz, 1H). ESI-MS m/z 612 (MH$^+$).

552

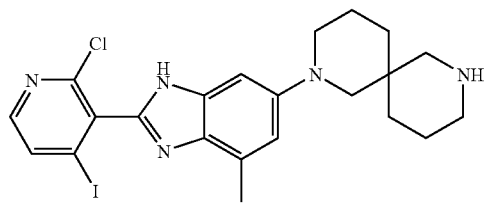 [SMILES: Cc1cc(N2CCCC3(CCCNC3)C2)cc2[nH]c(-c3c(I)ccnc3Cl)nc12]

2-[2-(2-Chloro-4-iodo-pyridin-3-yl)-7-methyl-3H-benzoimidazol-5-yl]-2,8-diaza-spiro[5.5]undecane To a solution of 4-(8-benzyl-2,8-diaza-spiro[5.5]undec-2-yl)-2-methyl-6-nitro-phenylamine (394 mg, 1.0 mmol) in MeOH (47.5 mL) were added Pd/C (10%, 40 mg) and acetic acid (2.5 mL). The mixture was stirred under atmospheric hydrogen (balloon) at the room temperature for 3 h and filter over Celite. The filtrate was mixed with 2-chloro-3-formyl-4-iodopyridine (267.5 mg, 1.0 mmol), stirred at the room temperature for 18 h, and evaporated to dryness under reduced pressure. The residue was dissolved in MeOH (10 mL) and 28% aqueous NH$_4$OH solution (0.5 mL) was added. After it was stirred for 5 min, the mixture was concentrated and chromatographed (100:9:1 CH$_2$Cl$_2$/MeOH/28% aqueous NH$_4$OH) to afford the title compound (288 mg, 55%). $^1$H NMR (CDCl$_3$) δ 1.28-1.72 (8H), 2.57 (s, 3H), 2.57-3.12 (8H), 6.82 (s, 1H), 6.92 (s, 1H), 6.73 (d, J=6 Hz, 1H), 7.98 (d, J=6 Hz, 1H). ESI-MS m/z 522 (MH$^+$).

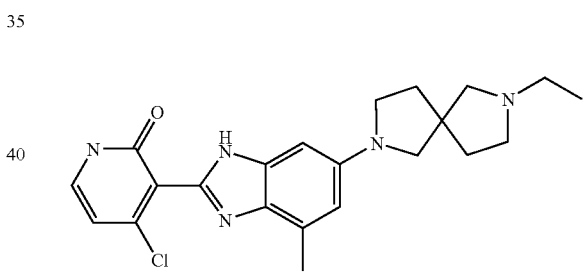

4-Chloro-3-[6-(7-ethyl-2,7-diaza-spiro[4.4]non-2-yl)-4-methyl-1H-benzoimidazol-2-yl]-1H-pyridin-2-one To a suspension of 2-(2-chloro-4-iodo-pyridin-3-yl)-6-(7-ethyl-2,7-diaza-spiro[4.4]non-2-yl)-4-methyl-1H-benzoimidazole (450 mg, 0.86 mmol) in H$_2$O (1.5 mL) was added a solution of HCl in dioxane (4 M, 20 mL, 80 mmol). After it was heated at 85° C. for 5 h, the reaction mixture was evaporated to dryness under reduced pressure. The residue was purified by chromatography (100:10:1 CH$_2$Cl$_2$/MeOH/28% aqueous NH$_4$OH) to afford the title compound (53 mg, 15%). $^1$H NMR (MeOH-d$_4$) δ 1.18 (t, J=8 Hz, 3H), 1.87-2.07 (4H), 2.54 (s, 3H), 2.60-2.91 (6H), 3.19-3.39 (4H), 6.46 (s, 1H), 6.50 (s, 1H), 6.57 (d, J=6 Hz, 1H), 7.51 (d, J=6 Hz, 1H). ESI-MS m/z 412 (MH$^+$).

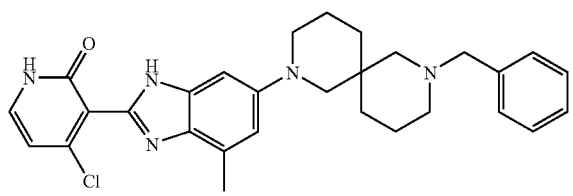 [SMILES: Cc1cc(N2CCCC3(CCCN(Cc4ccccc4)C3)C2)cc2[nH]c(-c3c(Cl)cc[nH]c3=O)nc12]

3-[6-(8-Benzyl-2,8-diaza-spiro[5.5]undec-2-yl)-4-methyl-1H-benzoimidazol-2-yl]-4-chloro-1H-pyridin-2-one To a suspension of 2-benzyl-8-[2-(2-chloro-4-iodo-pyridin-3-yl)-7-methyl-3H-benzoimidazol-5-yl]-2,8-diaza-spiro[5.5]undecane (55 mg, 0.09 mmol) in H$_2$O (0.75 mL) was added a solution of HCl in dioxane (4 M, 10 mL, 40 mmol). After it was heated at 85° C. for 18 h, the reaction mixture was evaporated to dryness under reduced pressure. The residue was purified by chromatography (170:10:1 CH$_2$Cl$_2$/MeOH/28% aqueous NH$_4$OH) to afford the title compound (17 mg, 38%). $^1$H NMR (MeOH-d$_4$) δ 1.23-1.35 (2H), 1.50-1.72 (6H), 2.09-2.31 (2H), 2.55 (s, 3H), 2.58-2.65 (2H), 2.88-3.72 (6H), 6.60 (d, J=6 Hz, 1H), 6.83 (s, 1H), 7.19-7.32 (6H), 7.52 (d, J=6 Hz, 1H). ESI-MS m/z 502 (MH$^+$).

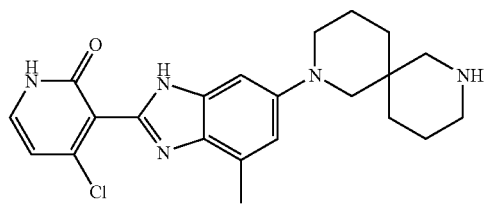 [SMILES: Cc1cc(N2CCCC3(CCCNC3)C2)cc2[nH]c(-c3c(Cl)cc[nH]c3=O)nc12]

4-Chloro-3-[6-(2,8-diaza-spiro[5.5]undec-2-yl)-4-methyl-1H-benzoimidazol-2-yl]-1H-pyridin-2-one To a suspension of 2-[2-(2-chloro-4-iodo-pyridin-3-yl)-7-methyl-3H-benzoimidazol-5-yl]-2,8-diaza-spiro[5.5]undecane (144 mg, 0.28 mmol) in H$_2$O (1.5 mL) was added a solution of HCl in dioxane (4 M, 20 mL, 80 mmol). After it was heated at 85° C. for 18 h, the reaction mixture was evaporated to dryness under reduced pressure. The residue was purified by chromatography (50:10:1 CH$_2$Cl$_2$/MeOH/28% aqueous NH$_4$OH) to afford the title compound (16 mg, 27%). $^1$H NMR (MeOH-d$_4$) δ 1.35-1.82 (8H), 2.54 (s, 3H), 2.90-3.19 (8H), 6.60 (d, J=7 Hz, 1H), 6.89 (s, 1H), 6.96 (s, 1H), 7.58 (d, J=7 Hz, 1H). ESI-MS m/z 412 (MH$^+$).

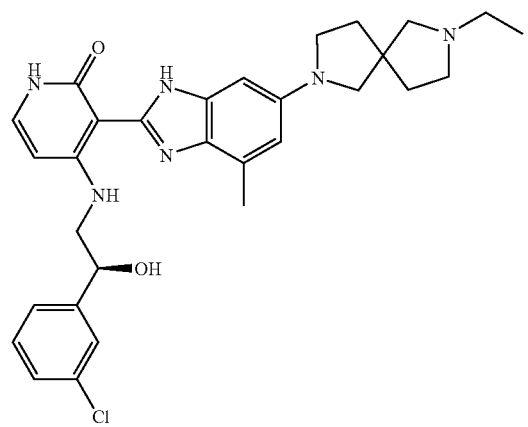 [SMILES: CCN1CCC2(CCN(c3cc(C)c4nc(-c5c(NC[C@@H](O)c6cccc(Cl)c6)cc[nH]c5=O)[nH]c4c3)C2)C1]

4-[(S)-2-(3-Chloro-phenyl)-2-hydroxy-ethylamino]-3-[6-(7-ethyl-2,7-diaza-spiro[4.4]non-2-yl)-4-methyl-1H-benzoimidazol-2-yl]-1H-pyridin-2-one A solution of 4-chloro-3-[6-(7-ethyl-2,7-diaza-spiro[4.4]non-2-yl)-4-methyl-1H-benzoimidazol-2-yl]-1H-pyridin-2-one (53 mg, 0.13 mmol), (S)-2-amino-1-(3-chlorophenyl)-ethanol (27 mg, 0.156 mmol) and Et$_3$N (26 mg, 0.26 mmol) in EtOH (0.5 mL) was heated at 80° C. for 18 h and then the reaction mixture was evaporated. The residue was purified by chromatography (150:8:1 CH$_2$Cl$_2$/MeOH/28% aqueous NH$_4$OH) to afford the title compound (25 mg, 35%). $^1$H NMR (MeOH-d$_4$) δ 1.16 (t, J=8 Hz, 3H), 1.80-2.02 (4H), 2.48-2.80 (4H), 2.50 (s, 3H), 3.19-3.39 (4H), 3.63 (m, 2H), 4.81 (m, 1H), 4.95 (m, 2H), 6.18 (d, J=6 Hz, 1H), 6.38 (s, 1H), 6.44 (s, 1H), 7.17-7.31 (3H), 7.38 (d, J=6 Hz, 1H), 7.55 (s, 1H). ESI-MS m/z 547 (MH$^+$).

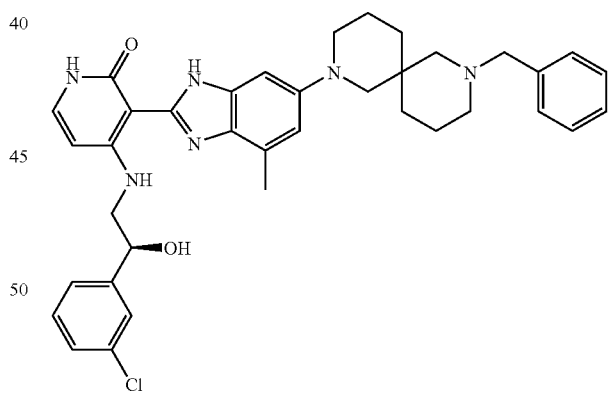

3-[6-(8-Benzyl-2,8-diaza-spiro[5.5]undec-2-yl)-4-methyl-1H-benzoimidazol-2-yl]-4-[(S)-2-(3-chlorophenyl)-2-hydroxy-ethylamino]-1H-pyridin-2-one A solution of 3-[6-(8-benzyl-2,8-diaza-spiro[5.5]undec-2-yl)-4-methyl-1H-benzoimidazol-2-yl]-4-chloro-1H-pyridin-2-one (17 mg, 0.034 mmol), (S)-2-amino-1-(3-chlorophenyl)-ethanol (29 mg, 0.17 mmol) and Et$_3$N (34 mg, 0.34 mmol) in EtOH (0.5 mL) was heated at 80° C. for 16 h and then the reaction mixture was evaporated. The residue was purified by chromatography (25:1 CH$_2$Cl$_2$/MeOH) to afford the title compound (8 mg, 64%). $^1$H NMR (MeOH-d$_4$) δ 1.28 (m, 2H), 1.50-1.83 (4H), 2.07-2.27 (2H), 2.48-2.61 (2H), 2.54 (s, 3H), 2.82-2.94 (2H), 3.041-3.23 (2H), 3.40-3.55 (2H), 3.59-3.73 (2H), 4.75 (m, 1H), 4.98 (m, 1H), 6.20 (d, J=6 Hz, 1H), 6.75 (s, 1H), 6.84 (s, 1H), 7.19-7.32 (8H), 7.35-7.42 (2H), 7.54 (s, 1H). ESI-MS m/z 637 (MH$^+$).

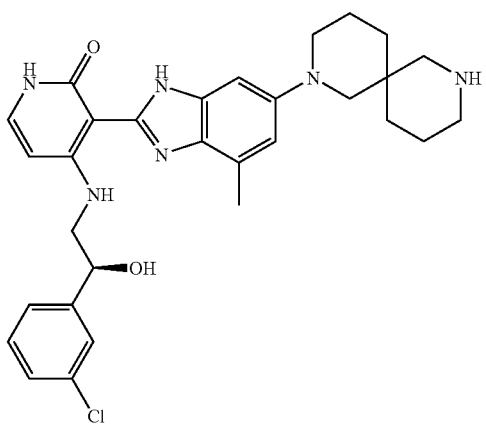 [SMILES: Cc1cc(N2CCCC3(CCCNC3)C2)cc2[nH]c(-c3c(NC[C@@H](O)c4cccc(Cl)c4)cc[nH]c3=O)nc12]

4-[(S)-2-(3-Chloro-phenyl)-2-hydroxy-ethylamino]-3-[6-(2,8-diaza-spiro[5.5]undec-2-yl)-4-methyl-1H-benzoimidazol-2-yl]-1H-pyridin-2-one A solution of 4-Chloro-3-[6-(2,8-diaza-spiro[5.5]undec-2-yl)-4-methyl-1H-benzoimidazol-2-yl]-1H-pyridin-2-one (16 mg, 0.039 mmol), (S)-2-amino-1-(3-chlorophenyl)-ethanol (20 mg, 0.117 mmol) and Et$_3$N (16 mg, 0.156 mmol) in EtOH (0.5 mL) was heated at 80° C. for 16 h. After it was cooled to room temperature, the reaction mixture was filtered to furnish yellow solid that was washed with MeOH (3×3 mL). The yellow solid then was mixed with 3 mL MeOH and the mixture was heated at 100° C. for 1 h. After it was cooled to room temperature, the mixture was filtered to furnish yellow solid that was washed with MeOH (3×2 mL) to afford the title compound (10 mg, 47%). ESI-MS m/z 547 (MH$^+$).

6.4 Example 4

Procedure for the Synthesis of Optically Active Aminoalcohol:
(S)-2-(3-chlorophenyl)-2-hydroxy-ethylamine

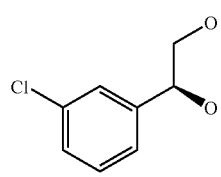 [SMILES: OC[C@@H](O)c1cccc(Cl)c1]

(S)-1-(3-Chlorophenyl)-ethane-1,2-diol

AD mix alpha (86.0 g) was added to a stirred mixture of tert-BuOH (300 ml) and H$_2$O (300 ml), mixture was stirred for 15 min at RT, than cooled to 0° C. 3-Chlorostyrene (8.51 g, 0.061 mol) was added over 15 min. The mixture was stirred at 0° C. for 48 h. The reaction was quenched by adding 10% aq. sodium sulfite (120 ml) followed by addition of EtOAc (200 ml). The layers were separated and the aqueous layer was extracted with EtOAc (200 ml). The combined organic layers were washed with 0.4 M H$_2$SO$_4$ in saturated Na$_2$SO$_4$ (100 ml), followed by drying over Na$_2$SO$_4$. The solvent was evaporated, the residue was separated on SiO$_2$ (70 g) (CHCl$_3$-MeOH 0 to 10%). Colorless oil, 9.83 g (0.057 mol, 93%). $^1$H NMR (300 MHz, DMSO) δ 7.20-7.40 (m, 4H), 5.39 (d, J=4.6 Hz, 1H), 4.76 (t, J=5.8 Hz, 1H), 4.54 (q, 4.9=Hz, 1H), 3.43 (m, 2H)

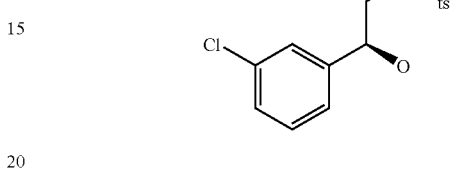

Toluene-4-sulfonic acid (S)-2-(3-chlorophenyl)-2-hydroxyethyl ester

To a mixture of (S)-1-(3-Chloro-phenyl)-ethane-1,2-diol (9.83 g, 0.057 mol) and triethylamine (11.8 ml, 0.086 mol) a solution of TsCl (10.87 g, 0.057 mol) in dichloromethane (50 ml) was added at 0° C. over 30 min. The mixture was stirred at 0° C. for 4 h. Precipitate formed was removed by filtration, the filtrate was washed with water (50 ml), dried over Na$_2$SO$_4$, evaporated. The residue vas dissolved in CH$_2$Cl$_2$ (200 ml), filtered through a SiO$_2$ pad, evaporated. Colorless oil, 16.34 g (0.050 mol, 88%). $^1$H NMR (300 MHz, DMSO) δ 7.67 (d, J=8.5 Hz, 2H), 7.42 (d, J=8.5 Hz, 2H), 7.20-7.35 (m, 4H), 5.90 (d, J=4.9 Hz, 1H), 4.79 (q, J=5.1 Hz, 1H), 4.03 (m, 2H), 2.41 (s, 3H)

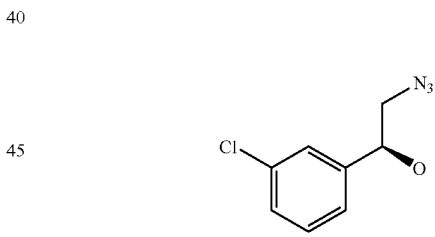

(S)-2-Azido-1-(3-chlorophenyl)-ethanol

A mixture of toluene-4-sulfonic acid (S)-2-(3-chlorophenyl)-2-hydroxyethyl ester (16.34 g, 0.050 mol), sodium azide (6.50 g, 0.10 mol) and DMSO (50 ml) was stirred for 2 h at 80° C. Water (100 ml) was added, extracted with hexane-ether (1:1) mixture (2×150 ml). Combined extract was dried over Na$_2$SO$_4$, evaporated. The residue was separated on SiO$_2$ (100 g), hexane-EtOAc, 0 to 20%. Colorless oil, 7.0 g, (0.035 mol, 71%). $^1$H NMR (300 MHz, DMSO) δ 7.46 (s, 1H), 7.36 (m, 3H), 5.95 (d, J=4.5 Hz, 1H), 4.82 (q, J=5.3 Hz, 1H), 3.35 (m, 2H).

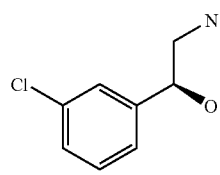 [SMILES: NC[C@@H](O)c1cccc(Cl)c1]

(S)-2-Amino-1-(3-chloro-phenyl)-ethanol

A mixture of (S)-2-Azido-1-(3-chlorophenyl)-ethanol (5.14 g, 0.026 mol), NaBH$_4$ (1.97 g, 0.052 mol) and isopropanol (100 ml) was stirred at 80° C. for 24 h. The solvent was evaporated, the residue was separated on SiO$_2$ (15 g) CHCl$_3$-MeOH (0 to 30%). Colorless oil, 3.70 g (0.021 mol, 83%). The material was reacted with Boc$_2$O in dichloromethane and NEt$_3$ and analyzed by chiral SFC using a CHIRALPAK AD-H column, 30% MeOH and determined to be 91% ee. LCMS [M+H]$^+$ 172.4. $^1$H NMR (300 MHz, DMSO) δ 7.24-7.39 (m, 4H), 4.46 (dd, J=4.3, 7.5 Hz, 1H), 2.68 (dd, J=4.3, 12.8 Hz, 1H), 2.57 (dd, J=7.5, 13.0 Hz, 1H).

The above procedure can be used for the synthesis of additional chiral aromatic and heteroaromatic alkanolamines and also their partially or fully hydrogenated derivatives.

6.5 Example 5

Synthesis of Compounds of Formula (2)

[4-(2-Chloro-pyrimidin-4-yl)-phenyl]-dimethylamine

A mixture of 4-dimethylaminophenyl boronic acid (10 g, 60.6 mM), 2,4-dichloropyrimidine (9 g, 60.4 mM), Na$_2$CO$_3$ (12 g, 114.2 mM), tetrakistriphenylphosphine palladium (2.5 g, 2.1 mM), dimethoxyethane (120 ml) and water (35 ml) was heated at 80° C. under a nitrogen atmosphere for 16 hr. The reaction was cooled in an ice bath and the resulting yellow suspension was filtered and the solid washed with water (3×50 ml) then ethyl acetate (2×50 ml). The solid was dried in vaccuo to afford [4-(2-Chloro-pyrimidin-4-yl)-phenyl]-dimethyl-amine (11.1 g, 78% yield) as an orange solid. ES-MS MH+234, 236, $^1$H NMR (300 MHz, ppm, DMSO-d$_6$): 8.57 (d, 1H), 8.05 (d, 2H), 7.92 (d, 1H), 6.80 (d, 1H), 3.03 (s, 6H)

3-Amino-1-[4-(4-dimethylamino-phenyl)-pyrimidin-2-yl]-1H-pyrazole-4-carboxylic acid ethyl ester A mixture of [4-(2-Chloro-pyrimidin-4-yl)-phenyl]-dimethyl-amine (2.0 g, 8.58 mM), 3-Amino-1H-pyrazole-4-carboxylic acid ethyl ester (1.32 g, 8.58 mM), Cs$_2$CO$_3$ (4.4 g, 13.58 mM) in DMF (15 ml) was heated 2 hr at 105° C. The reaction was then cooled to room temperature and diluted with water (100 mL) and the yellow precipitate collected via filtration and was washed with water (2×30 ml) then ethyl ether (2×30 ml). The solid was dried under vacuo and comprised a mixture of 3-Amino-1-[4-(4-dimethylamino-phenyl)-pyrimidin-2-yl]-1H-pyrazole-4-carboxylic acid ethyl ester and 5-Amino-1-[4-(4-dimethylamino-phenyl)-pyrimidin-2-yl]-1H-pyrazole-4-carboxylic acid ethyl ester in a ratio of approximately 6:4. The solid is flushed thru a pad of silica eluting with 5% MeOH/dichloromethane/1% TEA and the material is pooled and evaporated to a solid. Crystallization from dichloromethane/MeOH afforded the slower of the two isomers 3-Amino-1-[4-(4-dimethylamino-phenyl)-pyrimidin-2-yl]-1H-pyrazole-4-carboxylic acid ethyl ester (1.1 g, 36.4% yield) as a bright yellow solid. ES-MS MH+353, $^1$H NMR (300 MHz, ppm, DMSO-d$_6$): 8.84 (s, 1H), 8.63 (d, 1H), 8.15 (d, 2H), 7.77 (d, 1H), 6.93 (d, 2H), 5.85 (br s, 2H) 4.27 (q, 2H), 3.04 (s, 6H), 1.32 (t, 3H). Chromatography of the filtrate on silica eluting 1% TEA/EtOAc can provide the other faster isomer 5-Amino-1-[4-(4-dimethylamino-phenl)-pyrimidin-2-yl]-1H-pyrazole-4-carboxylic acid ethyl ester as an off-white solid. ES-MS MH+ 353, $^1$H NMR (300 MHz, ppm, DMSO-d$_6$): 8.7 (d, 1H), 8.12 (d, 2H), 7.83 (d, 1H), 7.79 (s, 1H), 7.64 (br S, 2H), 6.84 (d, 2H), 4.28 (q, 2H), 3.04 (s, 6H), 1.28 (t, 3H).

3-Amino-1-[4-(4-dimethylamino-phenyl)-pyrimidin-2-yl]-1H-pyrazole-4-carboxylic acid A suspension of 3-Amino-1-[4-(4-dimethylamino-phenyl)-pyrimidin-2-yl]-1H-pyrazole-4-carboxylic acid ethyl ester (250 mg, 0.71 mM) in 1 N KOH (3 ml) and MeOH (4 ml) was heated at 95° C. for 1 hr allowing some methanol to distil off. The reaction was cooled to room temperature and neutralized with 1 N HCl. The resulting precipitate was collected via filtration, washed with water (1×3 ml) and then dried in vacuo overnight to afford 3-Amino-1-[4-(4-dimethylamino-phenyl)-pyrimidin-2-yl]-1H-pyrazole-4-carboxylic acid (170 mg, 73% yield) as a yellow solid. ES-MS MH+325.4 $^1$H NMR (300 MHz, ppm, DMSO-d$_6$): 8.72 (s, 1H), 8.60 (d, 1H), 8.15 (d, 2H), 7.70 (d, 1H), 6.82 (d, 2H), 5.77 (br, 2H), 3.03 (s, 6H)

3-Amino-1-[4-(4-dimethylamino-phenyl)-pyrimidin-2-yl]-1H-pyrazole-4-carboxylic acid {4-[2-(4-methyl-piperazin-1-yl)-ethyl]-phenyl}-amide A mixture of 3-Amino-1-[4-(4-dimethylamino-phenyl)-pyrimidin-2-yl]-1H-pyrazole-4-carboxylic acid (35 mg, 0.108 mM) diisopropylethylamine (70 ul, 0.402 mM), 4-[2-(4-Methyl-piperazin-1-yl)-ethyl]-phenylamine (30 mg, 0.1369 mM) in DMF (1 ml) to which was added HBTU (60 mg, 0.1583 mM) and the stirred 16 hr at room temperature. The resulting suspension was filtered and the solid washed with water (1×1 ml) and dried in vacuo to afford 3-Amino-1-[4-(4-dimethylamino-phenyl)-pyrimidin-2-yl]-1H-pyrazole-4-carboxylic acid {4-[2-(4-methyl-piperazin-1-yl)-ethyl]-phenyl}-amide (13 mg, 21% yield). ES-MS MH+526.7. The filtrate may be purified via RP-HPLC 0.1% TFA to afford additional material.

By application of the above procedure the following compounds were prepared:

| MOLSTRUCTURE | MW (M + 1) |
|---|---|
| 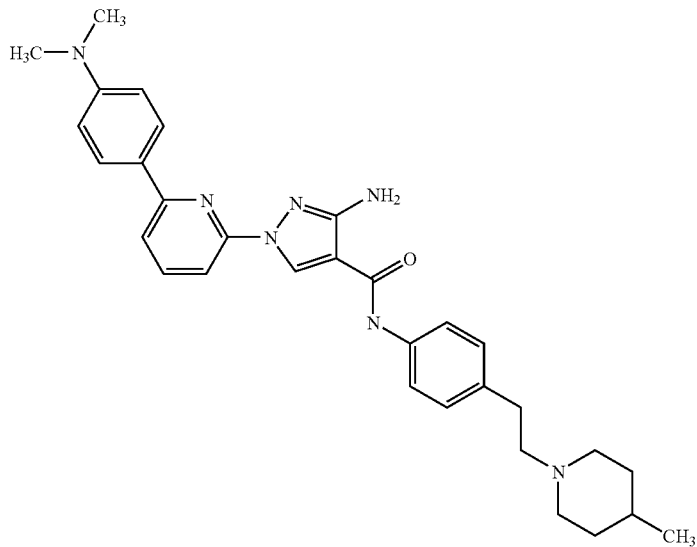 | 525.7 |
| 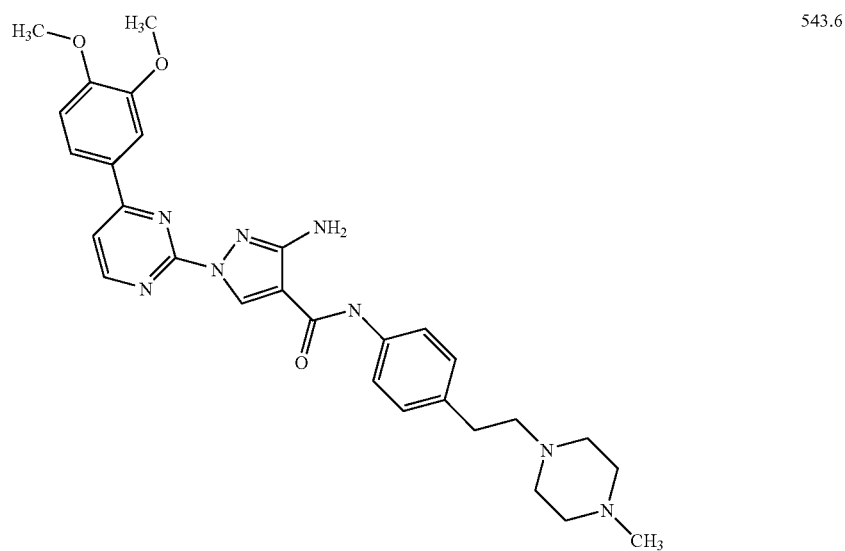 | 543.6 |

| MOLSTRUCTURE | MW (M + 1) |
|---|---|
| 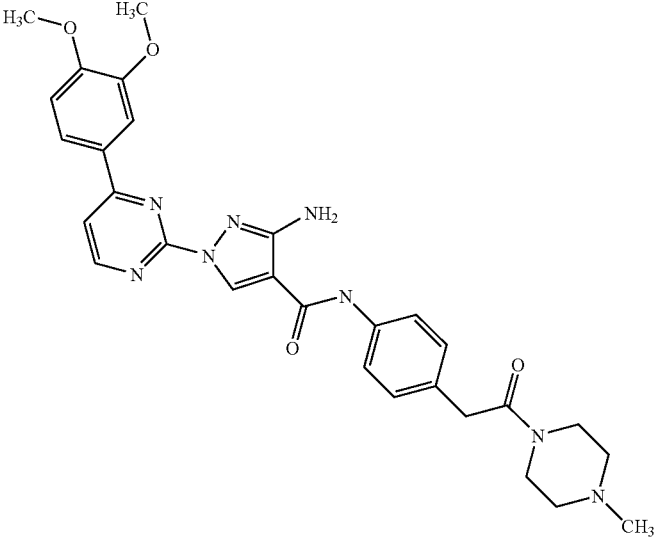 | 557.6 |
| 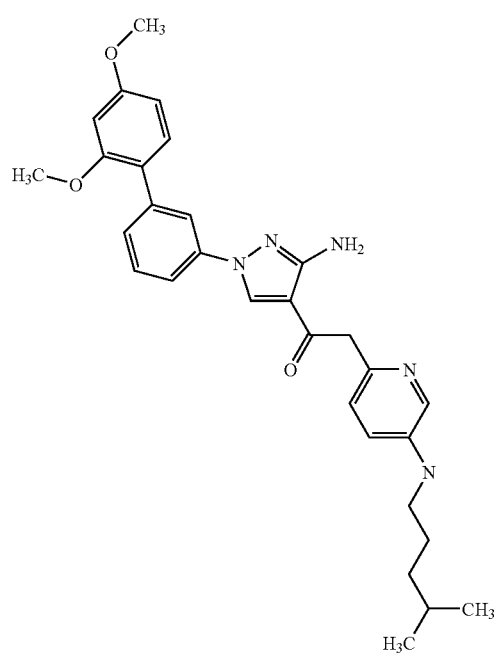 [SMILES: COc1ccc(-c2cccc(-n3cc(C(=O)Cc4ccc(NCCCC(C)C)cn4)c(N)n3)c2)c(OC)c1] | 518.6 |

| MOLSTRUCTURE | MW (M + 1) |
|---|---|
| 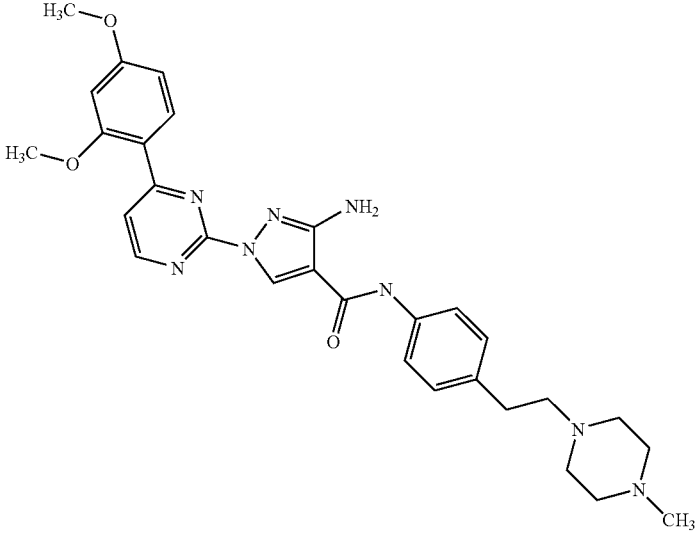 | 543.6 |
| 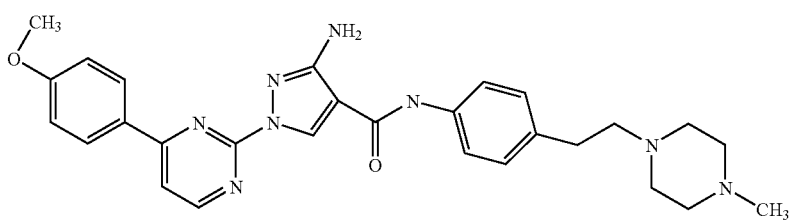 [SMILES: COc1ccc(-c2ccnc(-n3cc(C(=O)Nc4ccc(CCN5CCN(C)CC5)cc4)c(N)n3)n2)cc1] | 513.6 |
| 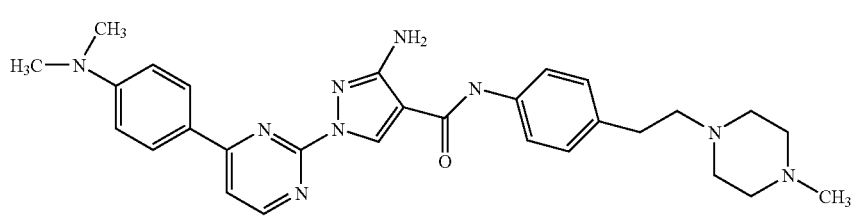 | 526.7 |
| 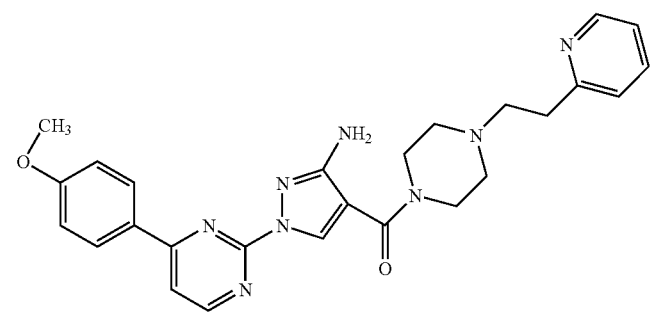 [SMILES: COc1ccc(-c2ccnc(-n3cc(C(=O)N4CCN(CCc5ccccn5)CC4)c(N)n3)n2)cc1] | 485.6 |
| 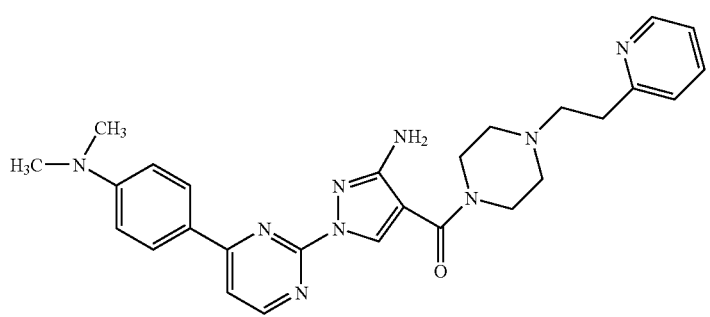 [SMILES: CN(C)c1ccc(-c2ccnc(-n3cc(C(=O)N4CCN(CCc5ccccn5)CC4)c(N)n3)n2)cc1] | 498.6 |

| MOLSTRUCTURE | MW (M + 1) |
|---|---|
| 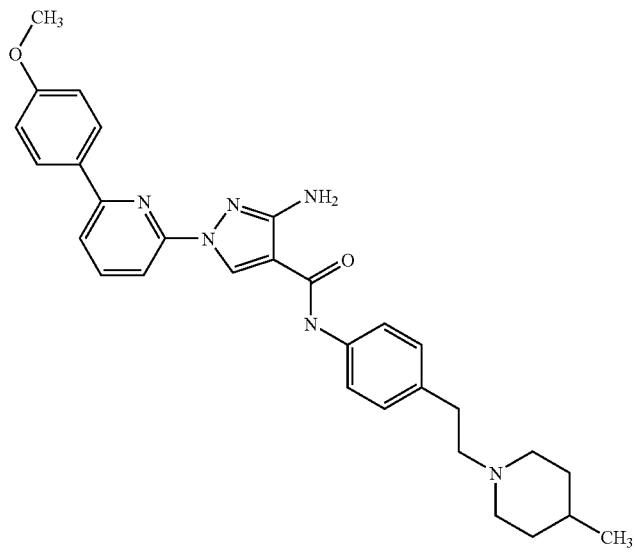 [SMILES: COc1ccc(-c2cccc(-n3cc(C(=O)Nc4ccc(CCN5CCC(C)CC5)cc4)c(N)n3)n2)cc1] | 512.6 |
| 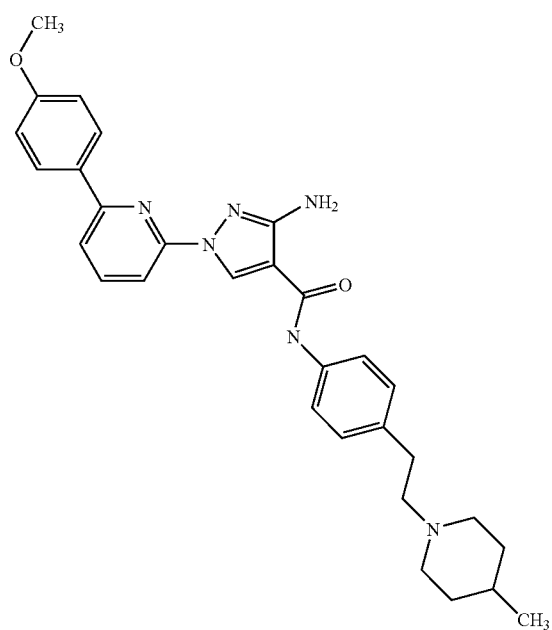 [SMILES: COc1ccc(-c2cccc(-n3cc(C(=O)Nc4ccc(CCN5CCC(C)CC5)cc4)c(N)n3)n2)cc1] | 512.6 |

| MOLSTRUCTURE | MW (M + 1) |
|---|---|
| 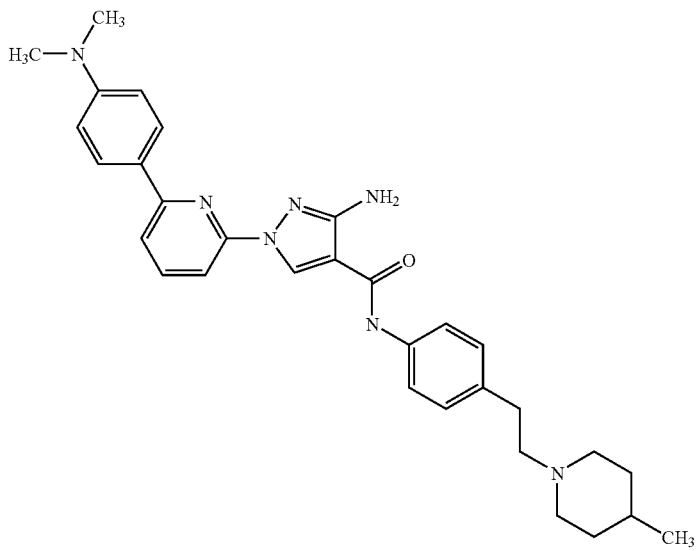 | 525.7 |
| 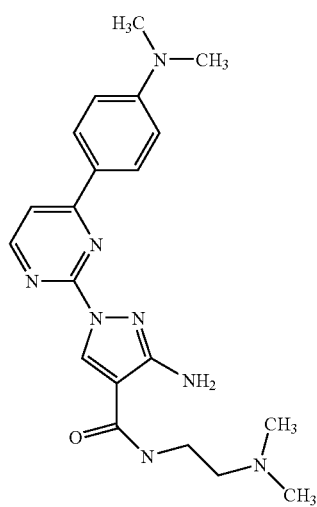 [SMILES: CN(C)CCNC(=O)c1cn(-c2nccc(-c3ccc(N(C)C)cc3)n2)nc1N] | 395.5 |
| 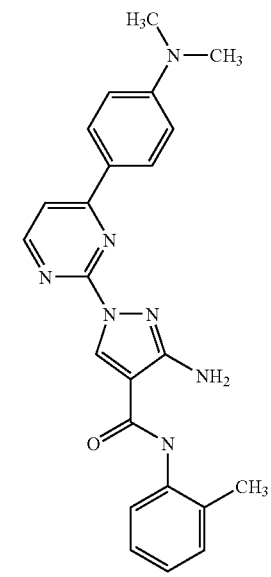 [SMILES: Cc1ccccc1NC(=O)c1cn(-c2nccc(-c3ccc(N(C)C)cc3)n2)nc1N] | 414.5 |

| MOLSTRUCTURE | MW (M + 1) |
|---|---|
| 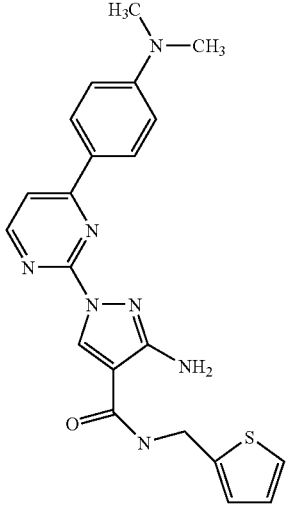 [SMILES: CN(C)c1ccc(-c2ccnc(-n3cc(C(=O)NCc4cccs4)c(N)n3)n2)cc1] | 404.4 |
| 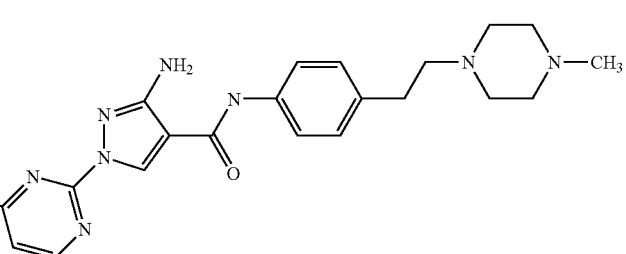 | 526.7 |
| 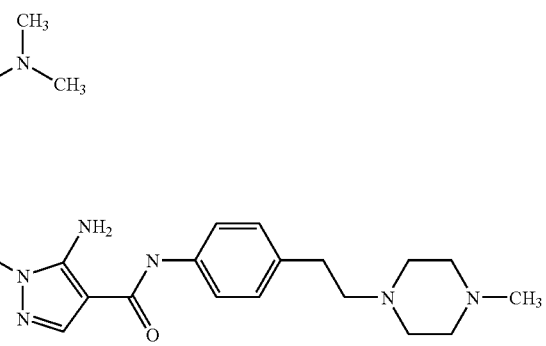 | 526.7 |
| 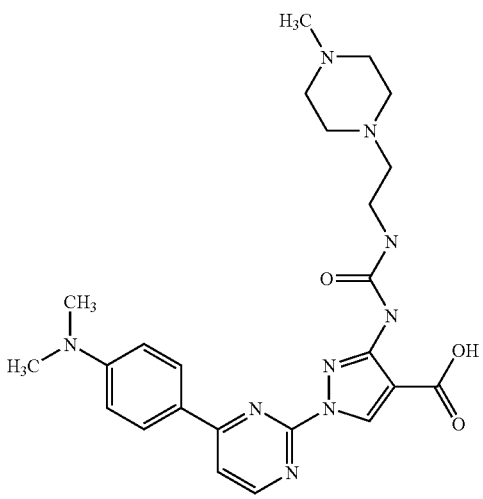 [SMILES: CN1CCN(CCNC(=O)Nc2nn(-c3nccc(-c4ccc(N(C)C)cc4)n3)cc2C(=O)O)CC1] | 494.6 |

| MOLSTRUCTURE | MW (M + 1) |
|---|---|
| 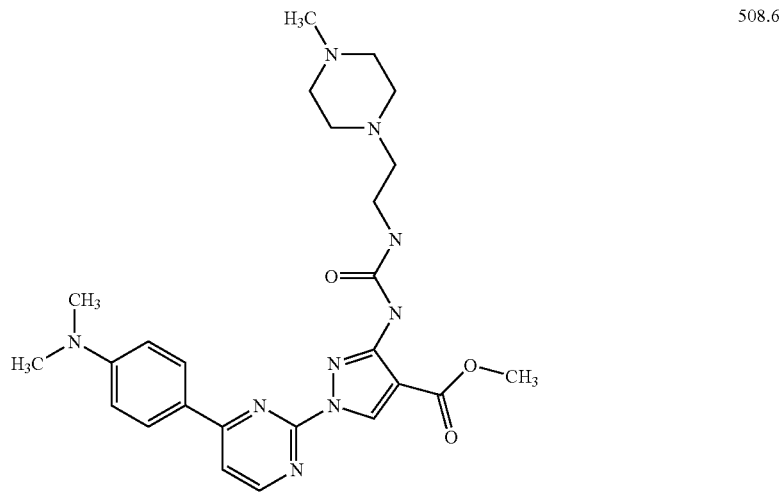 | 508.6 |
| 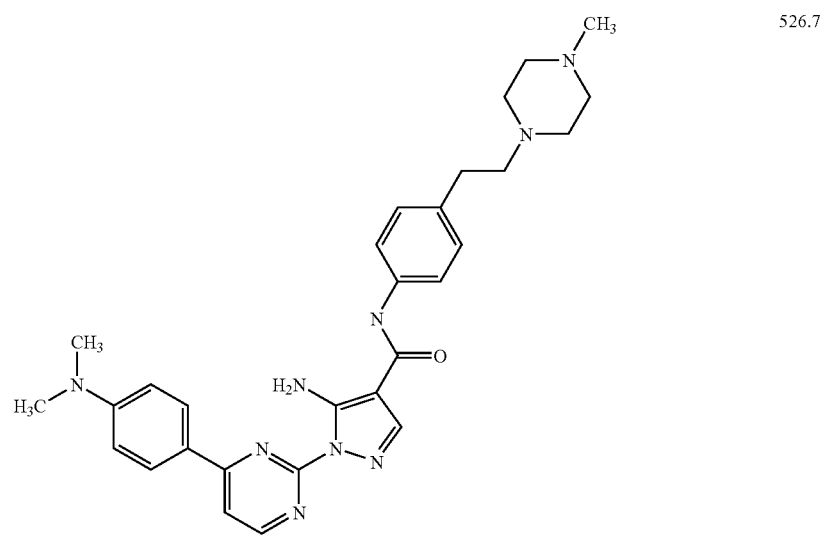 | 526.7 |
| 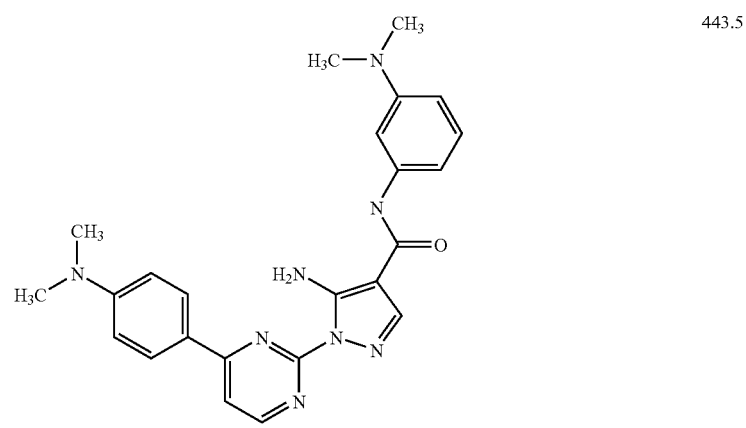 | 443.5 |

-continued
| MOLSTRUCTURE | MW (M + 1) |
|---|---|
| 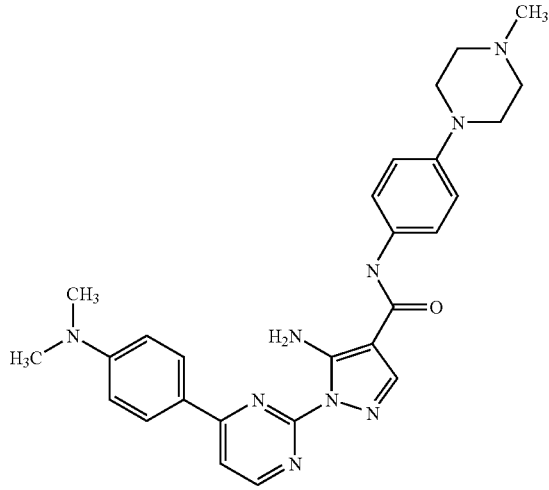 | 498.6 |
| 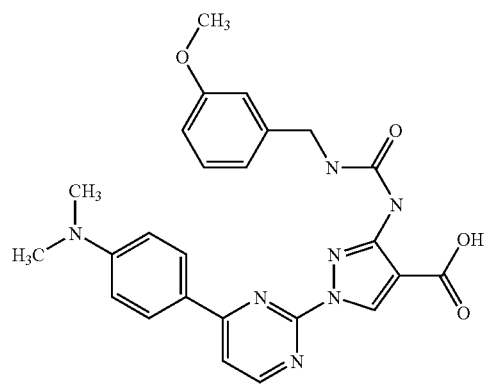 [SMILES: COc1cccc(CNC(=O)Nc2nn(-c3nccc(-c4ccc(N(C)C)cc4)n3)cc2C(=O)O)c1] | 488.5 |
| 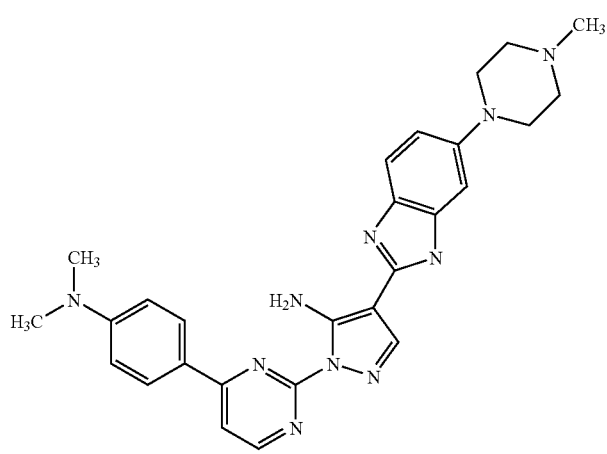 | 495.6 |

| MOLSTRUCTURE | MW (M + 1) |
|---|---|
|  | 495.6 |

6.6 Example 6

Synthesis of Compounds of Formula (3)

The compounds of formula 3 were prepared according to the following general scheme, Scheme 1.

Scheme 1.

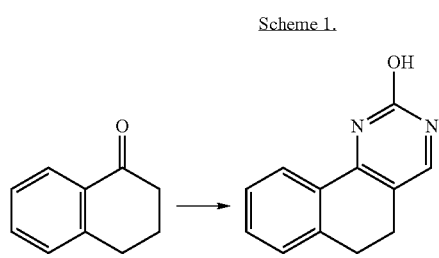 [SMILES: O=C1CCCc2ccccc21 ; Oc1ncc2c(n1)-c1ccccc1CC2]

Preparation 1: 5,6-Dihydro-benzo[h]quinazolin-2-ol (1)

A mixture of alpha-tetralone (60 g, 0.41 M), urea (27 g, 0.45 M), triethylorthoformate (68 ml, 0.41 M), in methanol (80 ml) to which was then added methanesulfonic acid (100 drops) was heated at 100° C. for 30 min. then at 130° C. for 1 hr while allowing some solvent to distill off. The resulting thick suspension was cooled slurried with acetone (100 ml) and the solids isolated via filtration washing with acetone (2×80 ml). The solid was dried under reduced pressure overnight to afford 1 as a yellow solid (42.1 g as a 1:1 urea complex, 35.6% yield).

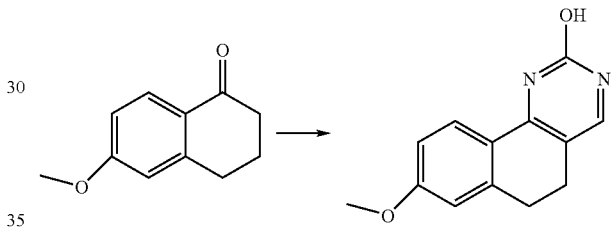

Preparation 2: 8-Methoxy-5,6-dihydro-benzo[h]quinazolin-2-ol

A mixture of 6-Methoxy-3,4-dihydro-2H-naphthalen-1-one (90 g, 0.511 M), urea (30.7 g, 0.511 M), triethylorthoformate (159 g, 1.07 M), ethanol (300 ml) and methane sulfonic acid (300 drops) was heated in the microwave at 90° C. for 1 hr. then cooled to room temperature. The solvent was removed under reduced pressure and the residue dried under vaccuo. The solid residue was then suspended in ethanol (250 ml) cooled to 0° C. and the precipitate was isolated via filtration and washed with ethanol (2×50 ml) and dried in vaccuo to give 8-Methoxy-5,6-dihydro-benzo[h]quinazolin-2-ol (43.95 g, 38% yield as a 1:1 urea complex) ES-MS MH+ 229.3 $^1$H NMR (300 MHz, ppm, DMSO-$d_6$): 11.45 (br S, 1H), 8.08 (d, 1H), 7.76 (br S, 1H), 6.95 (d, 1H), 6.91 (s, 1H), 5.4 (br S, 6H), 3.83 (s, 3H), 2.85 (m, 2H), 2.66 (m, 2H).

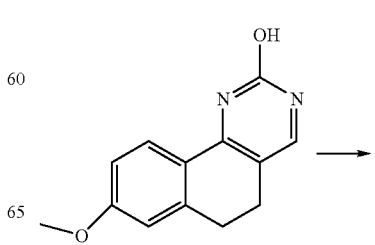

2

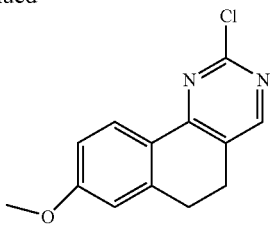

Preparation 3: 2-Chloro-8-methoxy-5,6-dihydro-benzo[h]quinazoline (2)

A suspension of 8-Methoxy-5,6-dihydro-benzo[h]quinazolin-2-ol as a 1:1 urea complex from preparation 1 (20 g, 69.0 mM) in POCl$_3$ (350 ml) was heated under nitrogen atmosphere at 100° C. for 20 hr. The POCl$_3$ was removed under reduced pressure and the residue was suspended in dichloromethane (300 ml) and cooled in an ice bath and then concentrated sodium bicarbonate (500 ml) was carefully added followed by 1 N NaOH (200 ml) and the phases separated. The aqueous phase was extracted with dichloromethane (3×500 ml) and the pooled organic phases were dried over Na$_2$SO$_4$, filtered and the filtrate evaporated under reduced pressure to give 2-Chloro-8-methoxy-5,6-dihydro-benzo[h]quinazoline (2, 14.46 g, 86% yield) as a yellow solid. ES-MS MH+ 247.1. $^1$H NMR (300 MHz, ppm, DMSO-d$_6$): 8.54 (s, 1H), 8.09 (d, 1H), 6.99 (m, 3H) 3.84 (s, 3H), 2.91 (m, 4H).

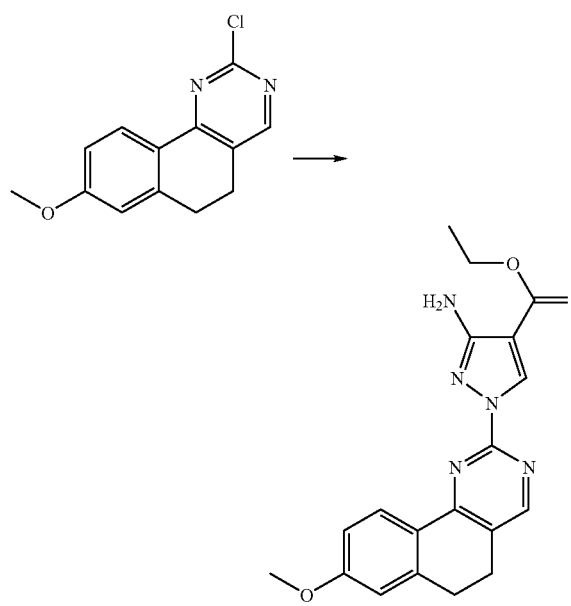

Preparation 4: 3-Amino-1-(8-methoxy-5,6-dihydro-benzo[h]quinazolin-2-yl)-1H-pyrazole-4-carboxylic acid ethyl ester(3)

A mixture of 2-Chloro-8-methoxy-5,6-dihydro-benzo[h]quinazoline (2, 5.0 g, 20.27 mM), 3-Amino-1H-pyrazole-4-carboxylic acid ethyl ester (3.14 g, 20.27 mM), Cs$_2$CO$_3$ (8.59 g, 26.35 mM) in DMF (40 ml) was stirred at 100° C. for 2.5 hr then cooled to room temperature and diluted with water (400 ml). The resulting precipitate was isolated via filtration and the solid washed with water (3×50 mL) then methanol (3×30 ml). The solid was dried under reduced pressure which was comprised of a 7:3 mixture of 3-Amino-1-(8-methoxy-5,6-dihydro-benzo[h]quinazolin-2-yl)-1H-pyrazole-4-carboxylic acid ethyl ester(3) and it's isomer 5-Amino-1-(5,6-dihydro-benzo[h]quinazolin-2-yl)-1H-pyrazole-4-carboxylic acid ethyl ester identical to the material prepared in preparation 6 below. The solid was then crystallized from dichloromethane (40 ml) to give the slower (TLC, EtOAc) of two isomers 3-Amino-1-(8-methoxy-5,6-dihydro-benzo[h]quinazolin-2-yl)-1H-pyrazole-4-carboxylic acid ethyl ester (3, 4.0 g, 2 crops, 54% yield). ES-MS MH+ 366. The mother liquors may be purified via chromatography on silica eluting with ethyl acetate to provide the faster isomer 5-Amino-1-(5,6-dihydro-benzo[h]quinazolin-2-yl)-1H-pyrazole-4-carboxylic acid ethyl ester.

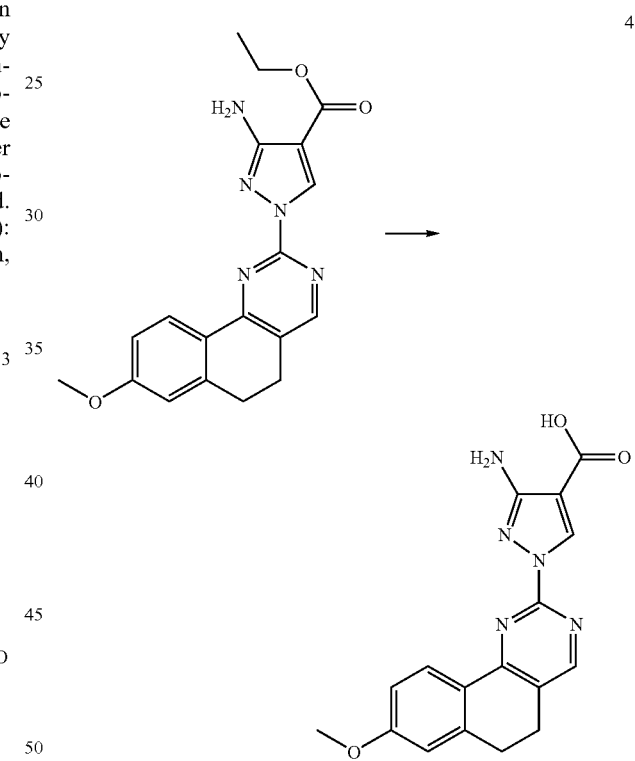

Preparation 5: 3-Amino-1-(8-methoxy-5,6-dihydro-benzo[h]quinazolin-2-yl)-1H-pyrazole-4-carboxylic acid (4)

A mixture of 3-Amino-1-(8-methoxy-5,6-dihydro-benzo[h]quinazolin-2-yl)-1H-pyrazole-4-carboxylic acid ethyl ester(3, 3.15 g, 8.63 mM), 1 N NaOH (15 mL), and methanol (20 mL) was heated at 100° C. for 3 hr then cooled to room temperature and diluted with water (100 mL). the pH was adjusted with 1 N HCl to approximately 3-4 and the resulting precipitate was isolated via filtration, washed with water (2×80 mL) and dried in vaccuo to give 3-Amino-1-(8-methoxy-5,6-dihydro-benzo[h]quinazolin-2-yl)-1H-pyrazole-4-carboxylic acid (4, 3.02 g, 100% yield). ES-MS MH+ 338.4

$^1$H NMR (300 MHz, ppm, DMSO-d$_6$): 8.81 (s, 1H), 8.57 (s, 1H), 8.2 (d, 1H), 7.0 (dd, 1H), 6.95 (s, 1H), 3.85 (s, 3H), 2.93 (m, 4H).

Preparation 6: 5-Amino-1-(5,6-dihydro-benzo[h]quinazolin-2-yl)-1H-pyrazole-4-carboxylic acid ethyl ester A mixture of (8-Methoxy-5,6-dihydro-benzo[h]quinazolin-2-yl)-hydrazine (100 mg, 0.41 mM), ethyl(ethoxymethylene)cyanoacetate (76 mg, 0.44 mM) in acetic acid (1 ml) was heated for 16 hr then evaporated. The residue was partitioned between dichloromethane and sodium bicarbonate (sat., 50 ml), the organic phase dried with sodium sulfate, filtered and evaporated to a solid. The solid was triturated with ethyl acetate and isolated via filtration and dried under reduced pressure to afford 5-Amino-1-(5,6-dihydro-benzo[h]quinazolin-2-yl)-1H-pyrazole-4-carboxylic acid ethyl ester (63 mg, 42% yield) as a tan solid. ES-MS MH+ 366.3. $^1$H NMR (300 MHz, ppm, DMSO-d$_6$): 8.65 (s, 1H), 8.17 (d, 1H), 7.78 (s, 1H), 7.55 (br s, 2H), 7.02 (d, 1H), 6.98 (s, 1H), 4.25 (q, 2H), 3.86 (s, 3H), 2.95 (m, 4H), 1.30 (t, 3H).

Preparation 7: 5-Amino-1-(7-methoxy-5,6-dihydro-benzol[h]quinazolin-2-yl)-1H-pyrazole-4-carboxylic acid {4-[2-(4-methyl-piperazin-1-yl)-ethyl]-phenyl}-amide A mixture of 3-Amino-1-(8-methoxy-5,6-dihydro-benzo[h]quinazolin-2-yl)-1H-pyrazole-4-carboxylic acid (40 mg, 0.118 mM), diisopropylethylamine (70 ul, 0.402 mM), 4-[2-(4-Methyl-piperazin-1-yl)-ethyl]-phenylamine (30 mg, 0.1369 mM) in DMF (1 ml) to which was added HBTU (60 mg, 0.1583 mM) and the stirred 16 hr at room temperature. The resulting suspension was filtered and the solid washed with water (1×1 ml) and dried in vacuo to afford 5-Amino-1-(7-methoxy-5,6-dihydro-benzo[h]quinazolin-2-yl)-1H-pyrazole-4-carboxylic acid {4-[2-(4-methyl-piperazin-1-yl)-ethyl]-phenyl}-amide (12 mg, 19% yield) as a white solid. ES-MS MH+ 539. The filtrate may be purified via RP-HPLC 0.1% TFA to afford additional material.

Using a procedure analogous to Preparation 5 the following was prepared: 5-Amino-1-(5,6-dihydro-benzo[h]quinazolin-2-yl)-1H-pyrazole-4-carboxylic acid. The title compound ( ) was prepared from 5-Amino-1-(5,6-dihydro-benzo[h]quinazolin-2-yl)-1H-pyrazole-4-carboxylic acid ethyl ester $^1$H NMR (300 MHz, ppm, DMSO-d$_6$):

Using methods analogous to Preparation 1 the following compounds were prepared 10H-9-Oxa-2,4-diaza-phenanthren-3-ol: The title compound (7.65 g) was prepared from chroman-4-one (20 g) ES-MS MH+ 201

10H-9-Thia-2,4-diaza-phenanthren-3-ol: The title compound (217 mg) was prepared from thiochroman-4-one (3.2 g) ES-MS MH+ 217.4

6,7-Dihydro-5H-benzo[6,7]cyclohepta[1,2-d]pyrimidin-2-ol: The title compound (700 mg) was obtained starting with 6,7,8,9-Tetrahydro-benzocyclohepten-5-one (2 g).

9-Methoxy-5,6-dihydro-benzo[h]quinazolin-2-ol: The title compound (420 mg) was prepared starting with 7-Methoxy-3,4-dihydro-2H-naphthalen-1-one (8.14 g).

Synthesis of Final Amide Compounds

General

Solvents were evaporated on a Savant SpeedVac Plus SC250DDA concentrator equipped with a Savant VLP80 pump and Refrigerated Vapor Trap RVT4104. Kieselgel 60 (0.04×0.063 mm) (Merck), silica gel 60 RP-18 (EM Science), and Celite 545 (Merck) were used. Dowex 50W×2H ion-exchange resin prior using was washed with methanol until pH 7. All final products were dried in vacuo at 40° C. for 24 h.

Preparation Of Amides 1N,5-Disubstituted-4-Pyrazinecarboxylic Acid+Amines

Intermediate acid (200 umol) was dissolved in DMF (400 uL) and treated with a solution of BOP (200 umol) in DMFA (400 uL). Solutions of building block amines, (either commercial, or prepared by literature or other methods, as outlined below), (250 umol) in dichloromethane (500 uL) and diisopropylethylamine (75 uL) were added, and the mixtures were left overnight at room temperature.

Isolation and purification depended on the basidity of the final products.

For basic amides the reaction mixtures were applied on a columns with Dowex 50W×2H (4 mL of suspension prepared from Dowex-10% water in dioxane, 1:1), washed with 10% water in dioxane (3×4 mL), and eluted with 30% diethylamine in methanol (6 mL). Solvent was evaporated, and the residues were dissolved in dichloromethane and passed through silica (50 uL) to give after evaporating and drying desired amides.

For neutral amides the reaction mixtures were quenched with water (100 uL) and evaporated to dryness on a Savant evaporator at 63° C. for 6 h. Residues were dissolved in dichloromethane (200 uL), applied onto columns with dry silica gel RP-18 (40-63 um, 0.8 g), and left overnight. Sorbent was consecutively washed with water (2×2 mL) and 10% acetonitrile in water (4×2 mL), and products were eluted with 70% acetonitrile in water (6 mL). Solvent was evaporated to dryness on a Savant evaporator at 63° C. for 6 h, and residues were dissolved in dichloromethane (1 mL) and treated with aqueous 4% KOH (200 uL). Mixtures were stirred on a Vortex stirrer, and organic layer was passed through Celite 545 (4 uL of suspension prepared from Dowex—methanol, 1:1). Eluates were evaporated to final volume 500 uL and passed through silica (50 uL) to give after evaporating and drying desired amides.

Average yield 42.69 umol.

The following is a general outline of methodologies useful in the preparation of compounds of formula 3.

Scheme 1

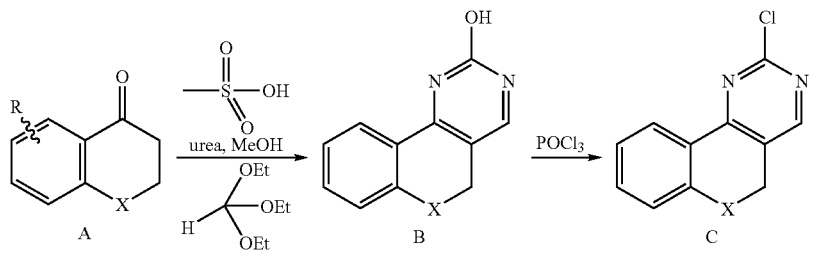

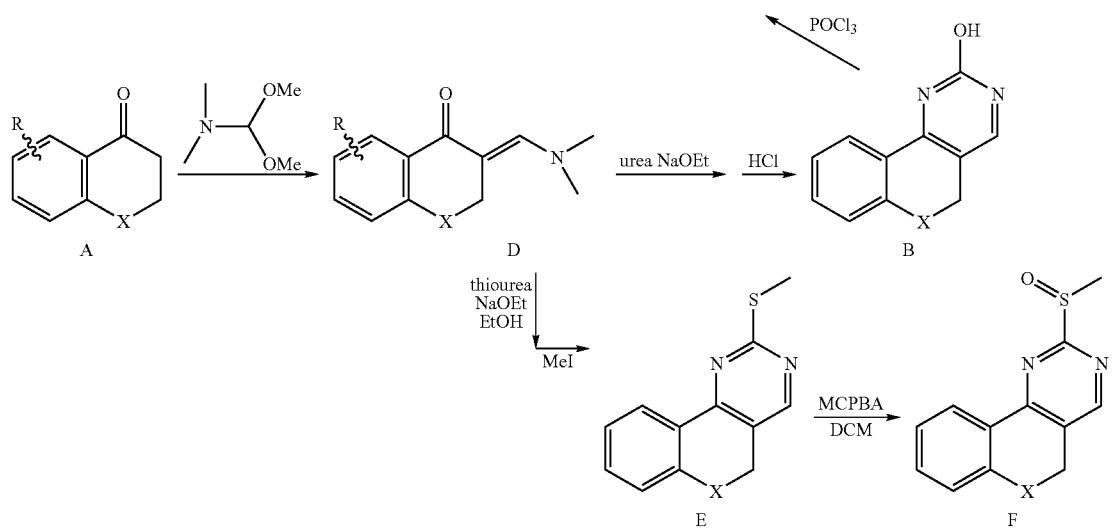

Compounds of the present invention can be prepared by any of the above methods. As shown in SCHEME 1 the respective ketones A can be reacted with urea, trialkylorthoformate such as trimethyl or triethylorthoformate for example to afford respective compound B. Reaction of compound B with POCl₃ either neat or with a cosolvent, for example toluene or dichlorobenzene, with or without the addition of PCl5 affords the respective compound C. Alternatively Compound A may be reacted with dimethylformrnamide dimethyl acetal for example to give intermediate D. Reaction of intermediate D with urea, sodium alkoxide for example NaOMe or NaOEt in a solvent such as ethanol affords respective compound B as the sodium salt which is neutralized with dilute acid to give B. Reaction of intermediate D with thiourea as above followed by reaction with methyl iodide affords intermediate E which is oxidized using an oxidant for example metachloro perbenzoic acid in a solvent such as dichloromethane give compound F.

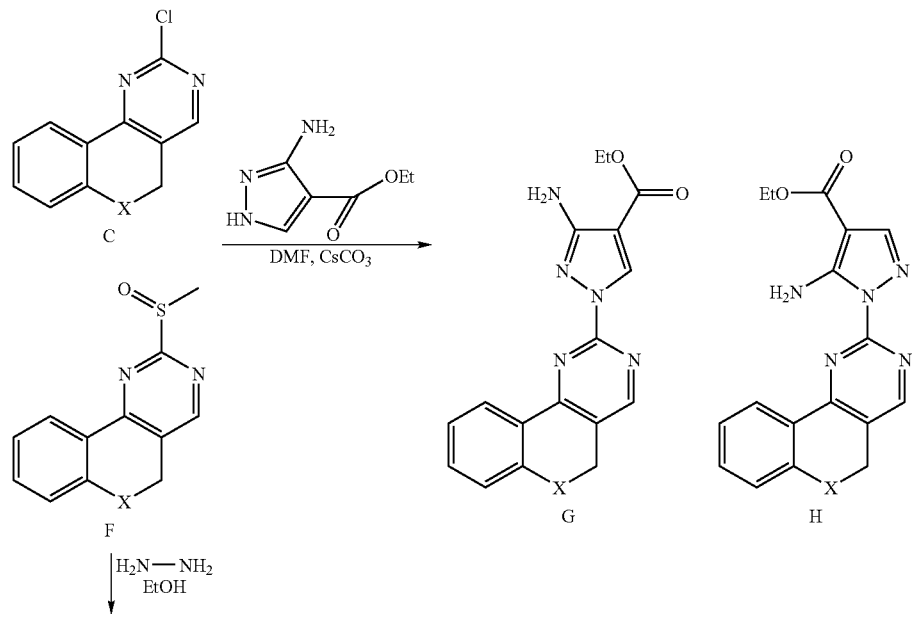

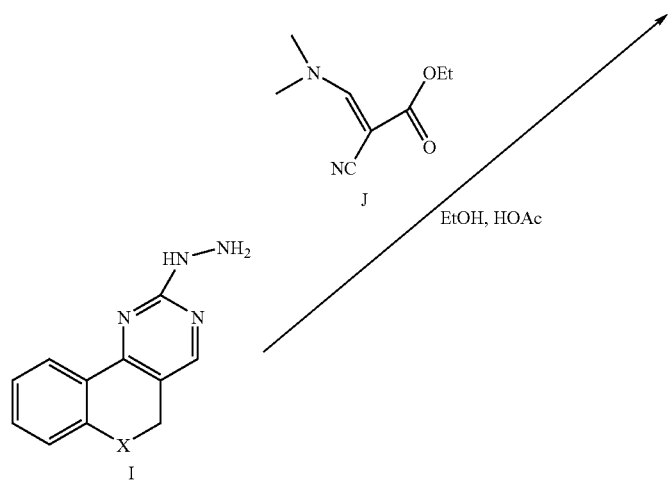

Compound C or D from SCHEME 1 may be reacted with an aminopyrazole in a solvent such as DMF with a base like cesium carbonate to afford an approximate 7:3 mixture of compounds G and H. These may be separately isolated via crystallization or chromatograpy or trituration with solvents such as ethyl acetate or ethanol. Alternatively compound H may be prepared by reaction of compound C or D with hydrazine in an alcohol to afford intermediate I which can then be reacted with compound J, prepared from reaction of the cyano acetate and DMFDMA, in a solvent like ethanol and an acid like acetic acid to give compound H.

SCHEME 3

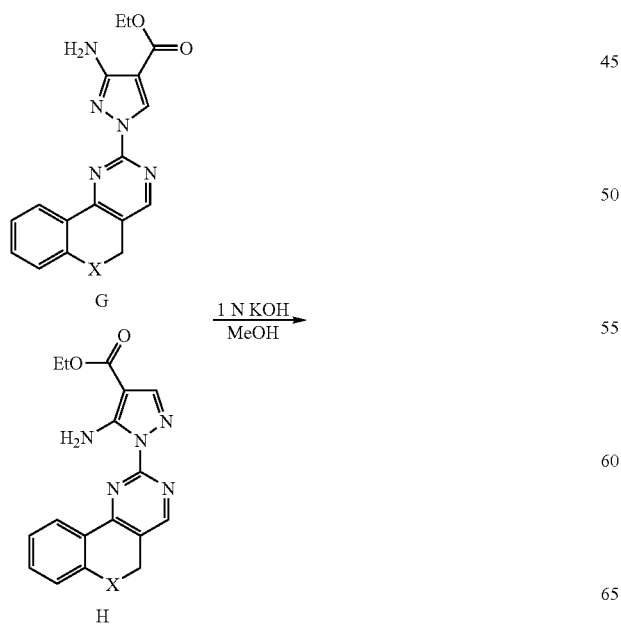

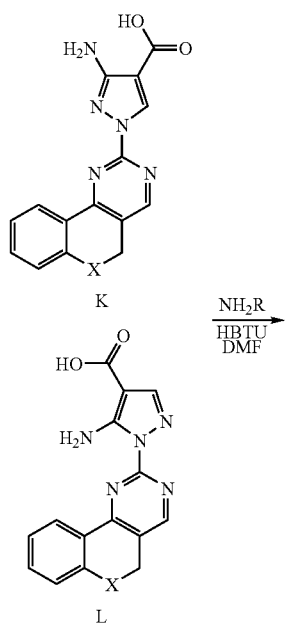

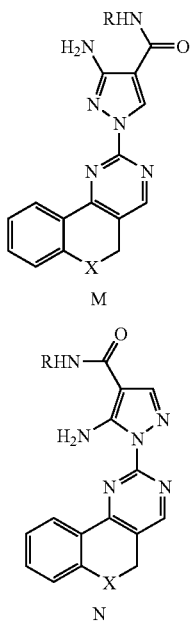

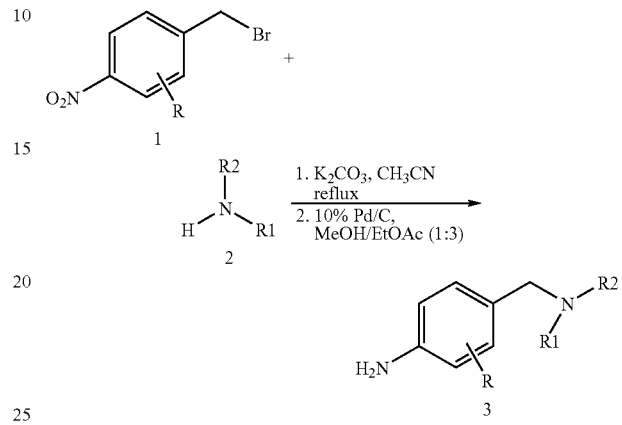

was evaporated to give 4-[2-substituted aminoethyl] aniline 3 which was used as such in the next step.

Reference: Cross, P. E.; Arrowsmith, J. E.; Thomas, G. N.; Gwilt, M.; Burges, R. A; Higgins, A. J.; J. Med. Chem. 1990, 33, 1151-1155.

2. Typical Procedure for the Synthesis of 4-[Substituted Aminomethyl] Aniline Compounds:

Compounds G and H may separately be treated with a hydroxide source such as aqueous potassium hydroxide and methanol to yield the respective acids K and L. Acids K and L may separately be treated in a solvent such as DMF and an organic base such as DIPEA with a coupling agent such as HBTU or BOP for example to yield amides M and N.

1. Typical Procedure for the Synthesis of 4-[2-Substituted Aminoethyl] Aniline Compounds:

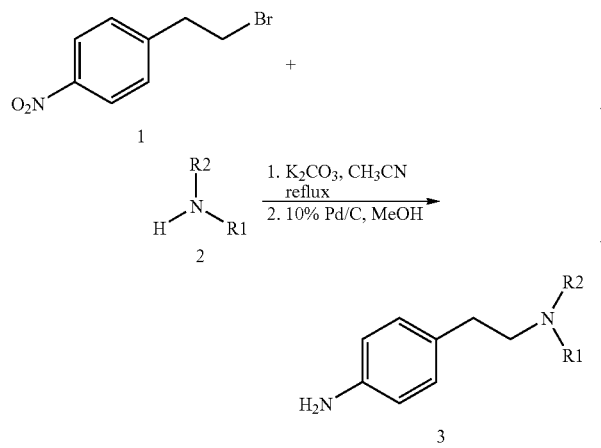

To a solution of 4-nitro phenethylbromide 1 (0.460 g, 2 mmol) and disubstituted amine 2 (2 mmol) in acetonitrile (6 mL) was added potassium carbonate (0.276 g, 2 mmol) and resulting reaction mixture was stirred under reflux. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave 4-[2-substituted aminoethyl] nitro benzene derivative. Then dissolved in methanol (10 mL), 10% Pd/C (0.050 g) was added and stirred under hydrogen atmosphere (hydrogen balloon). After completion of the reaction, palladium catalyst was filtered off and solvent was evaporated to give 4-[2-substituted aminoethyl] aniline 3 which was used as such in the next step.

To a solution of 4-nitro benzylbromide derivative 1 (0.460 g, 2 mmol) and disubstituted amine 2 (2 mmol) in acetonitrile (6 mL) was added potassium carbonate (0.276 g, 2 mmol) and resulting reaction mixture was stirred under reflux. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave 4-[substituted aminomethyl] nitro benzene derivative. Then dissolved in methanol/ethylacetate (1:3, 10 mL), 10% Pd/C (0.050 g) was added and stirred under hydrogen atmosphere (hydrogen balloon). After completion of the reaction, palladium catalyst was filtered off and solvent was evaporated to give 4-[2-substituted aminoethyl] aniline 3 which was used as such in the next step.

Reference: Cross, P. E.; Arrowsmith, J. E.; Thomas, G. N.; Gwilt, M.; Burges, R. A; Higgins, A. J.; J. Med. Chem. 1990, 33, 1151-1155.

3. Typical Procedure for the Synthesis of Alkoxy Substituted Aniline Compounds:

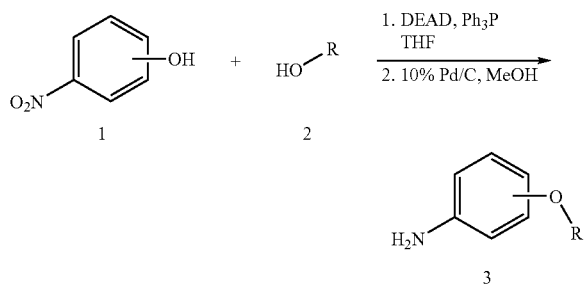

To a stirred solution of nitro phenol 1 (0.765 g, 5.5 mmol), alcohol 2 (5 mmol) and triphenylphosphine (1.442, 5.5 mmol) in THF (20 mL) cooled to 0° C. was added diethylazodicarboxylate dropwise under $N_2$ atmosphere. Resulting reaction mixture was stirred at room temperature. After completion of the reaction, solvent was removed on rotavap and residue was treated with 4M HCl (3 mL, 12 mmol) and washed thoroughly with ethyl acetate (2×10 mL). Then aquoes layer was basified with 4M NaOH to P$^H$ ~10, extracted with chloroform (2×10 mL) and dried over anhydrous sodium sulfate. Filtered and evaporation of solvent gave alkoxy nitro benzene derivative. Then dissolved in methanol (20 mL), 10% Pd/C (0.050 g) was added and stirred under hydrogen atmosphere (hydrogen balloon). After completion of the reaction, palladium catalyst was filtered off and solvent was evaporated to give 4-[2-substituted aminoethyl] aniline 3 which was used as such in the next step.

Reference: Defacqz, N.; Tran-Trieu, V.; Cordi, A.; Marchand-Brynaert, J.; Tetrahedron Lett. 2003, 44, 9111-9114.

4. Typical Procedure for the Synthesis of 3-fluoro-4-(Substituted Amino) Aniline Compounds:

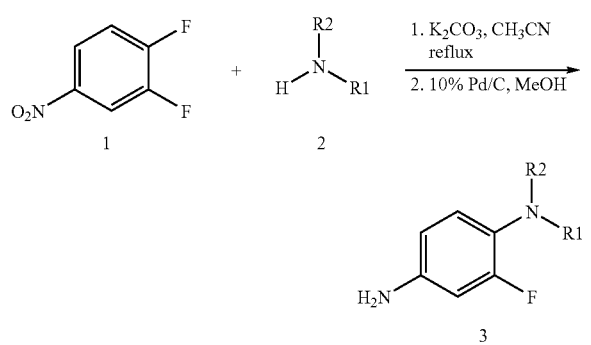

To a solution of 1,2-difluoro-4-nitro benzene 1 (0.320 g, 2 mmol) and disubstituted amine 2 (2 mmol) in acetonitrile (8 mL) was added potassium carbonate (0.276 g, 2 mmol) and resulting reaction mixture was stirred under reflux. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave 3-fluoro-4-(substituted amino) nitro benzene derivative. Then dissolved in methanol (10 mL), 10% Pd/C (0.050 g) was added and stirred under hydrogen atmosphere (hydrogen balloon). After completion of the reaction, palladium catalyst was filtered off and solvent was evaporated to give 3-fluoro-4-(substituted amino) aniline 3 which was used as such in the next step.

Reference: Bevan, C. W. L; Eur. J. Chem. Chem. 1968, 238-241.

5. Typical Procedure for the Synthesis of Pyridinyloxy Alkylamine Compounds:

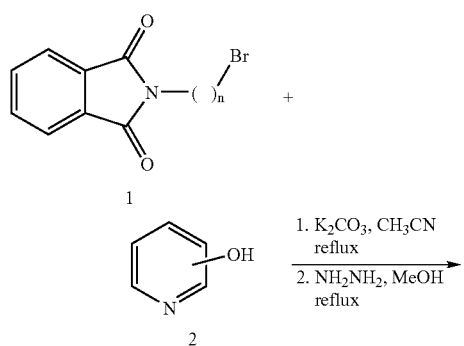

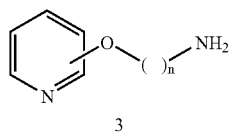

To a solution of bromoalkyl phthalimide 1 (5 mmol) and pyridinol 2 (5 mmol) in acetonitrile (10 mL) was added potassium carbonate (0.690 g, 5 mmol) and resulting reaction mixture was stirred under reflux. After completion of the reaction, solvent was removed on rotavap and residue was dissolved in chloroform (20 mL). Then washed with water (5 mL) and saturated sodium bicarbonate solution (5 mL), dried over anhydrous sodium sulfate. Filtered and evaporation of solvent gave pyridinyloxy alkyl-1H-isoindole-1,3(2H)-dione. Then dissolved in methanol (10 mL), hydrazine hydrate (0.48 mL, 15 mmol) was added and stirred under reflux to give a precipitate. Filtered, washed with methanol (5 mL) and evaporation of solvent gave pyridinyloxy alkylamine 3 which was used as such in the next step.

References: Giardina, G. A. M.; Raveglia, L. F.; Grugni, M.; Sarau, H. M.; Farina, C.; J. Med. Chem. 1999, 42, 1053-1065. Effland, R. M.; Helsley, G. C.; Tegeler, J. J.; J. Heterocycl. Chem. 1982, 19, 537-539.

6. Typical Procedure for the Synthesis of 2-(4-pyridin-2-ylpiperazin-1-yl)Ethanamine Compounds:

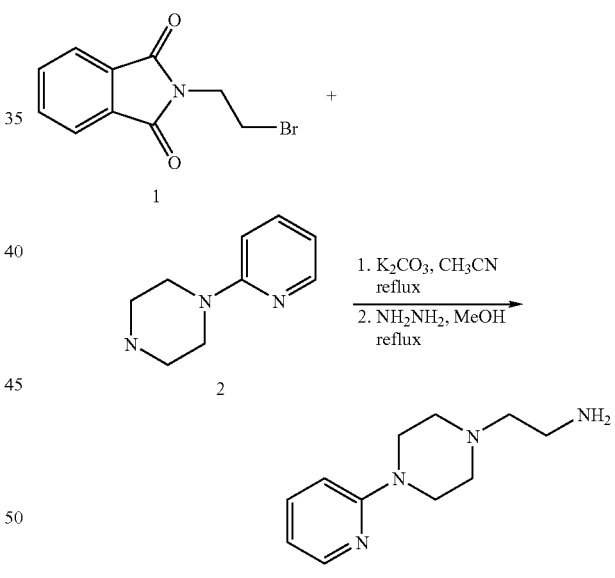

To a solution of bromoethyl phthalimide 1 (5 mmol) and 2-pyridyl piperazine 2 (5 mmol) in acetonitrile (10 mL) was added potassium carbonate (0.690 g, 5 mmol) and resulting reaction mixture was stirred under reflux. After completion of the reaction, solvent was removed on rotavap and residue was dissolved in chloroform (20 mL). Then washed with water (5 mL) and saturated sodium bicarbonate solution (5 mL), dried over anhydrous sodium sulfate. Filtered and evaporation of solvent gave pyridinylpiperazine ethyl-1H-isoindole-1,3(2H)-dione. Then dissolved in methanol (10 mL), hydrazine hydrate (0.48 mL, 15 mmol) was added and stirred under reflux to give a precipitate. Filtered, washed with methanol (5 mL) and evaporation of solvent gave 2-(4-pyridin-2-ylpiperazin-1-yl)ethanamine 3 which was used as such in the next step.

References: Giardina, G. A. M.; Raveglia, L. F.; Grugni, M.; Sarau, H. M.; Farina, C.; J. Med. Chem. 1999, 42, 1053-1065. Effland, R. M.; Helsley, G. C.; Tegeler, J. J.; J. Heterocycl. Chem. 1982, 19, 537-539.

7. Procedure for the Synthesis of 1-(3-pyridin-4-ylpropyl)piperazine:

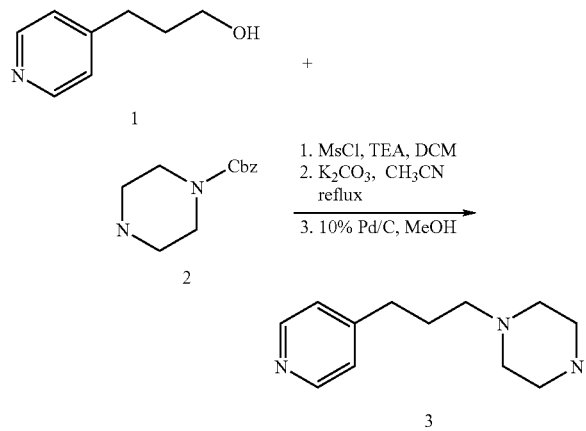

To a solution of 4-pyridyl propanol 1 (0.274 g, 2 mmol) and triethylamine (0.33 mL, 2.4 mmol) in DCM (6 mL) cooled to 0° C. was added methanesulfonyl chloride (0.15 mL, 2 mmol) dropwise. After completion of the reaction, diluted with DCM (10 mL), washed with saturated sodiumbicarbonate solution and dried over anhydrous sodium sulfate. Filtered and evaporation of solvent gave mesylate derivative. Dissolved in acetonitrile (6 mL), amine 2 (2 mmol) and potassium carbonate (0.276 g, 2 mmol) were added, and resulting reaction mixture was stirred under reflux. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave a residue. Then dissolved in methanol (10 mL), 10% Pd/C (0.050 g) was added and stirred under hydrogen atmosphere (hydrogen balloon). After completion of the reaction, palladium catalyst was filtered off and solvent was evaporated to give 1-(3-pyridin-4-ylpropyl)piperazine 3 which was used as such in the next step.

8. Procedure for the Synthesis of 1-(3-pyridin-4-ylpropyl)piperidin-4-amine:

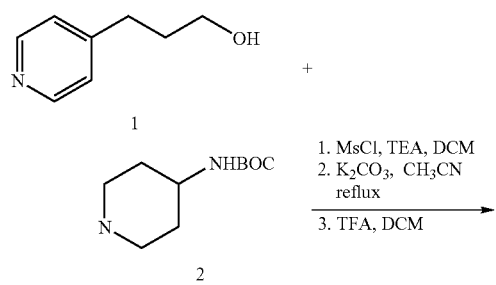

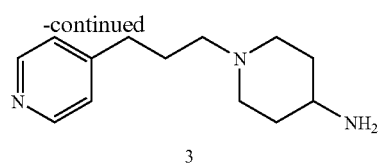

To a solution of 4-pyridyl propanol 1 (0.274 g, 2 mmol) and triethylamine (0.33 mL, 2.4 mmol) in DCM (6 mL) cooled to 0° C. was added methanesulfonyl chloride (0.15 mL, 2 mmol) dropwise. After completion of the reaction, diluted with DCM (10 mL), washed with saturated sodiumbicarbonate solution and dried over anhydrous sodium sulfate. Filtered and evaporation of solvent gave mesylate derivative. Dissolved in acetonitrile (6 mL), amine 2 (2 mmol) and potassium carbonate (0.276 g, 2 mmol) were added, and resulting reaction mixture was stirred under reflux. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave a residue. Then dissolved in DCM (4 mL), TFA (0.5 mL) was added and stirred at room temperature. After completion of the reaction, solvent was evaporated to give 1-(3-pyridin-4-ylpropyl)piperidin-4-amine-3 which was used as such in the next step.

9. Procedure for the Synthesis of 4-[3-(4-methylpiperazin-1-yl)propyl]aniline:

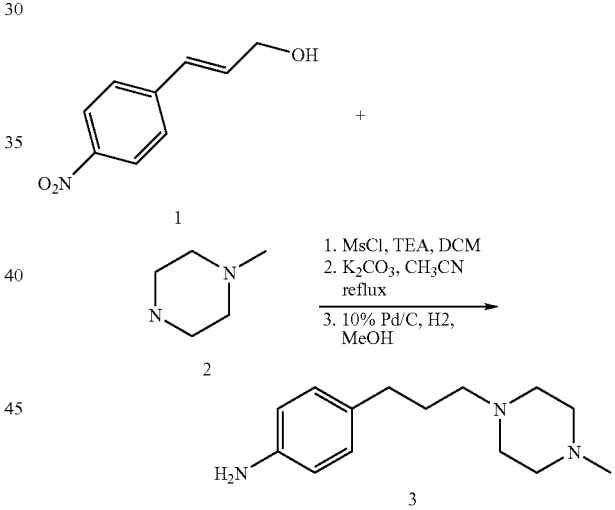

To a solution of 4-nitro cinnamyl alcohol 1 (0.274 g, 5 mmol) and triethylamine (0.83 mL, 6 mmol) in DCM (20 mL) cooled to 0° C. was added methanesulfonyl chloride (0.38 mL, 5 mmol) dropwise. After completion of the reaction, diluted with DCM (20 mL), washed with saturated sodiumbicarbonate solution and dried over anhydrous sodium sulfate. Filtered and evaporation of solvent gave chloro derivative. Dissolved in acetonitrile (20 mL), amine 2 (5 mmol) and potassium carbonate (0.690 g, 5 mmol) were added, and resulting reaction mixture was stirred under reflux. After completion of the reaction, solvent was removed on rotavap and residue was dissolved in chloroform (20 mL). Then washed with water (10 mL) and saturated sodium bicarbonate solution (10 mL), dried over anhydrous sodium sulfate. Filtered and evaporation of solvent gave a residue. Then dissolved in methanol (20 mL), 10% Pd/C (0.050 g) was added and stirred under hydrogen atmosphere (hydrogen balloon).

After completion of the reaction, palladium catalyst was filtered off and solvent was evaporated to 4-[3-(4-methylpiperazin-1-yl)propyl]aniline 3 which was used as such in the next step.

10. Procedure for the Synthesis of 4-[(1E)-3-(4-methylpiperazin-1-yl)prop-1-enyl]aniline:

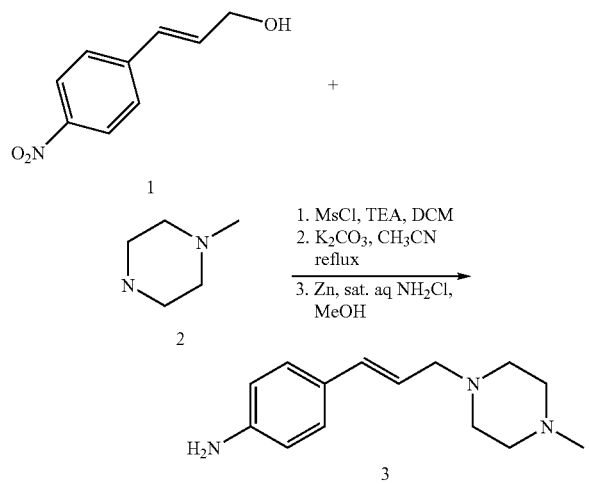

To a solution of 4-nitro cinnamyl alcohol 1 (0.274 g, 5 mmol) and triethylamine (0.83 mL, 6 mmol) in DCM (20 mL) cooled to 0° C. was added methanesulfonyl chloride (0.38 mL, 5 mmol) dropwise. After completion of the reaction, diluted with DCM (20 mL), washed with saturated sodiumbicarbonate solution and dried over anhydrous sodium sulfate. Filtered and evaporation of solvent gave chloro derivative. Dissolved in acetonitrile (20 mL), amine 2 (5 mmol) and potassium carbonate (0.690 g, 5 mmol) were added, and resulting reaction mixture was stirred under reflux. After completion of the reaction, solvent was removed on rotavap and residue was dissolved in chloroform (20 mL). Then washed with water (10 mL) and saturated sodium bicarbonate solution (10 mL), dried over anhydrous sodium sulfate. Filtered and evaporation of solvent gave 1-methyl-4-[(2E)-3-(4-nitrophenyl)prop-2-enyl]piperazine. Then 1-methyl-4-[(2E)-3-(4-nitrophenyl)prop-2-enyl]piperazine (0.100 g) dissolved in methanol (4 mL), Zn powder (0.300 g) and saturated aquoes ammonium chloride solution (1 mL) was added, and stirred under reflux. After completion of the reaction, diluted with methanol (4 mL), decanted and evaporated to give residue. Basified with saturated aquoes sodiumbicarbonate solution (2 mL) and extracted with ethyl acetate (2×4 mL). Evaporation of solvent gave 4-[(1E)-3-(4-methylpiperazin-1-yl)prop-1-enyl]aniline 3 which was used as such in the next step.

11. Procedure for the Synthesis of 1-[4-(dimethylamino)benzyl]piperidin-4-amine:

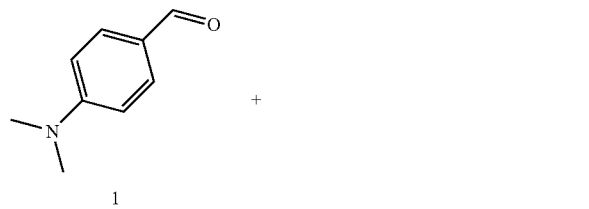

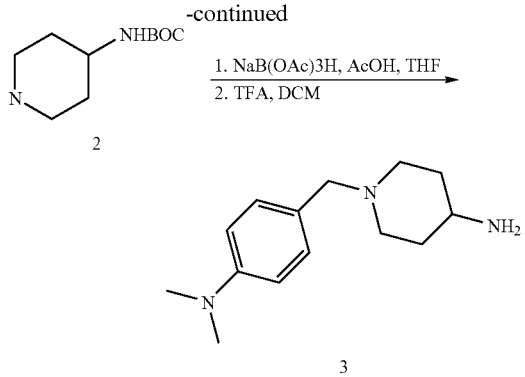

To a solution of 4-dimethylamino benzaldehyde 1 (0.300 g, 2 mmol) and amine 2 (2 mmol) in THF (6 mL) was added acetic acid (0.23 mL) followed by sodiumtriacetoxyborohydride. Resulting reaction mixture was stirred at room temperature for 18 h. After completion of the reaction, solvent was removed on rotavap and residue was dissolved in chloroform (10 mL). Then washed with water (5 mL) and saturated sodium bicarbonate solution (5 mL), dried over anhydrous sodium sulfate. Filtered and evaporation of solvent gave a residue. Then dissolved in DCM (4 mL), TFA (0.5 mL) was added and stirred at room temperature. After completion of the reaction, solvent was evaporated to give 1-[4-(dimethylamino)benzyl]piperidin-4-amine 3 which was used as such in the next step.

12. Procedure for the Synthesis of 4-[4-(pyridin-4-ylmethyl)piperazin-1-yl]aniline:

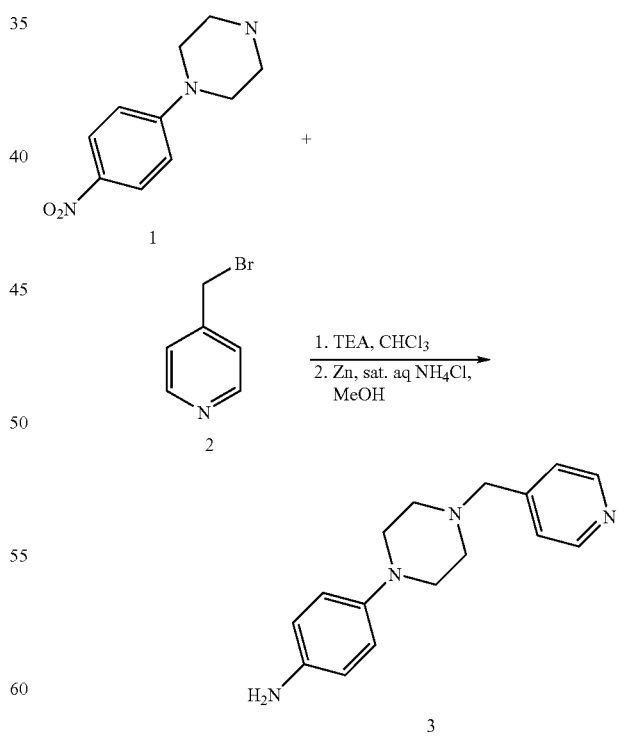

To a solution of 4-nitro phenyl piperazine 1 (0.414 g, 2 mmol) and 4-pyridylmethyl bromide hydrobromide 2 (0.506 g, 2 mmol) in chloroform (10 mL) cooled to 0° C. was added triethylamine (0.83 mL, 6 mmol) dropwise. Resulting reaction mixture was stirred at room temperature. After completion of the reaction, washed with water (10 mL) and saturated sodium bicarbonate solution (10 mL), dried over anhydrous sodium sulfate. Filtered and evaporation of solvent gave 1-(4-nitrophenyl)-4-(pyridin-4-ylmethyl)piperazine. Then 1-(4-nitrophenyl)-4-(pyridin-4-ylmethyl)piperazine (0.560 g) dissolved in methanol (20 mL), Zn powder (1.500 g) and saturated aquoes ammonium chloride solution (5 mL) was added, and stirred under reflux. After completion of the reaction, diluted with methanol (10 mL), decanted and evaporated to give residue. Basified with saturated aquoes sodiumbicarbonate solution (10 mL) and extracted with ethyl acetate (2×4 mL). Evaporation of solvent gave 4-[4-(pyridin-4-ylmethyl)piperazin-1-yl]aniline 3 which was used as such in the next step.

12. Typical Procedure for the Synthesis of 3-amino-1-(8-methoxy-5,6-dihydrobenzo[h]quinazolin-2-yl)-1H-pyrazole-4-carboxylic amide:

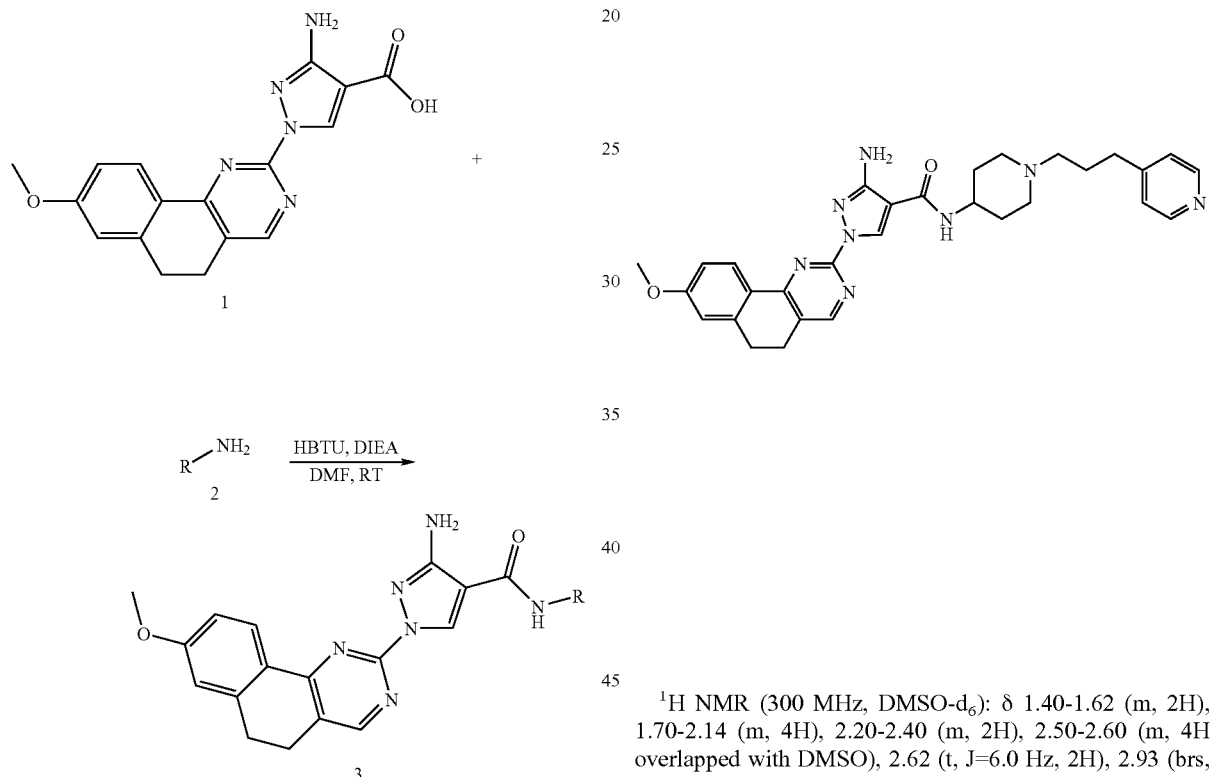

To a solution of 3-amino-1-(8-methoxy-5,6-dihydrobenzo[h]quinazolin-2-yl)-1H-pyrazole-4-carboxylic acid 1 (0.084 g, 0.25 mmol), HBTU (0.113 g, 0.3 mmol) and DIEA (0.18 mL, 1 mmol) in DMF (1 mL) was added amine 2 (0.3 mmol). Resulting reaction mixture was stirred at room temperature for 18 h. After completion of the reaction, solvent was removed on rotavap and residue was purified by preparative HPLC to give 3-amino-1-(8-methoxy-5,6-dihydrobenzo[h]quinazolin-2-yl)-1H-pyrazole-4-carboxylic amide 3.

Analytical Data:

$^1$H NMR (300 MHz, DMSO-d$_6$): δ 1.40-1.62 (m, 2H), 1.70-2.14 (m, 4H), 2.20-2.40 (m, 2H), 2.50-2.60 (m, 4H overlapped with DMSO), 2.62 (t, J=6.0 Hz, 2H), 2.93 (brs, 4H), 3.65-3.85 (m, 1H), 3.99 (s, 3H), 5.89 (s, 2H), 7.05 (d, J=9.0 Hz, 1H), 7.27 (d, J=6.0 Hz, 2H), 8.09 (brs, 1H), 8.27 (d, J=9.0 Hz, 1H), 8.47 (d, J=6.0 Hz, 2H), 8.56 (s, 1H), 9.21 (s, 1H); LCMS m/z 539 (M+H$^+$), ELSD 100%.

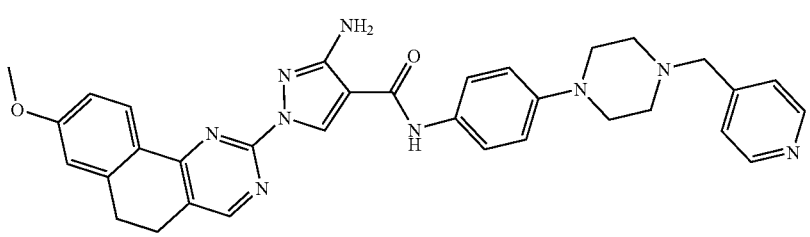 [SMILES: COc1ccc2c(c1)CCc1cnc(-n3cc(C(=O)Nc4ccc(N5CCN(Cc6ccncc6)CC5)cc4)c(N)n3)nc1-2]

$^1$H NMR (300 MHz, DMSO-d$_6$): δ 2.57 (brs, 4H), 2.89 (brs, 4H), 3.14 (brs, 4H), 3.61 (s, 2H), 3.86 (s, 3H), 5.97 (s, 2H), 6.92-7.05 (m, 3H), 7.39 (d, J=6.0 Hz, 1H), 7.59 (d, J=9.0 Hz, 1H), 8.30 (d, J=9.0 Hz, 1H), 8.59 (d, J=12.0 Hz, 2H), 9.41 (s, 1H), 9.84 (s, 1H); LCMS m/z 588 (M+H$^+$), ELSD 97.6%.

6.7 Example 7

Synthesis of Compounds According to Formula (4)

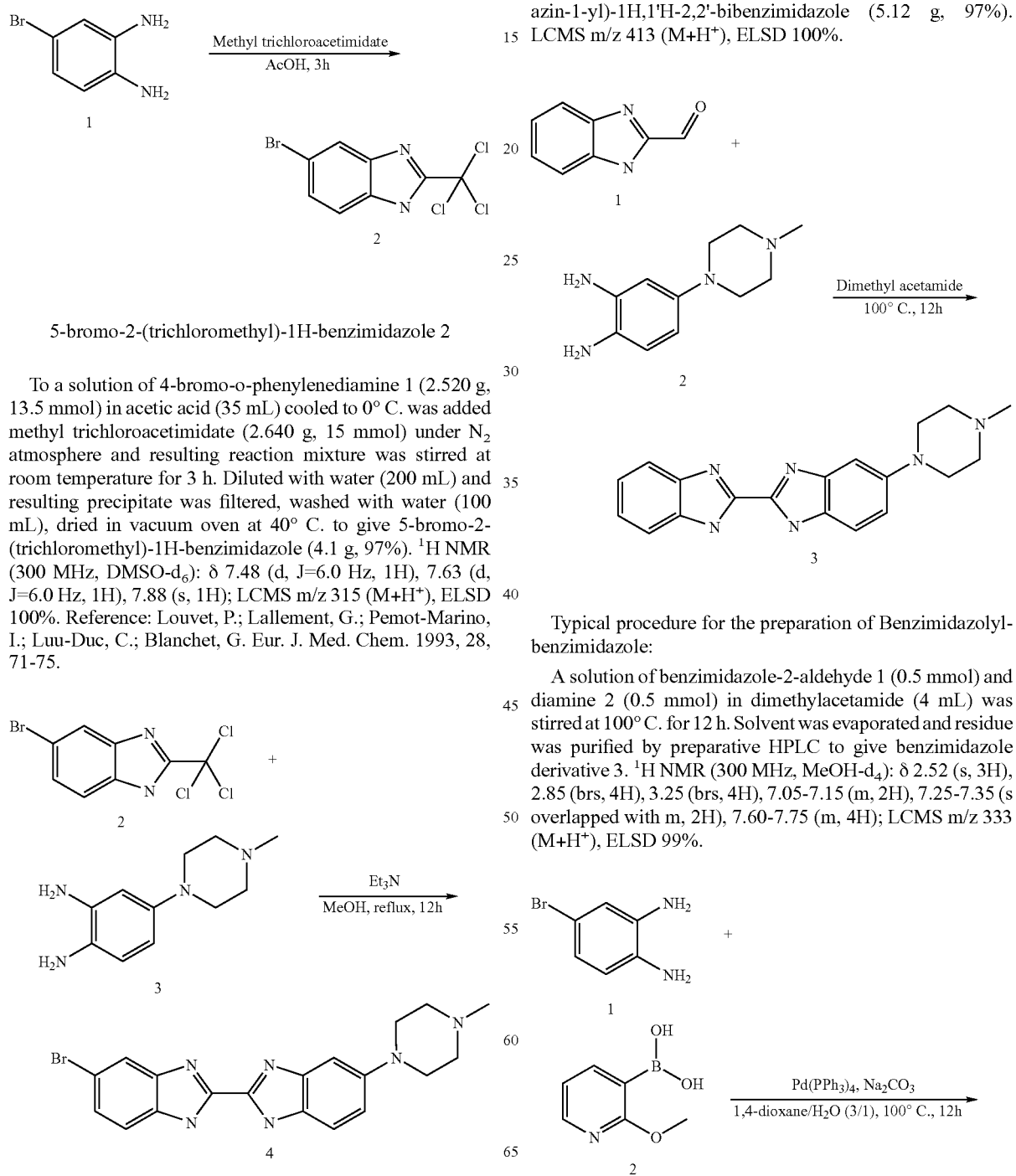

5-bromo-2-(trichloromethyl)-1H-benzimidazole 2

To a solution of 4-bromo-o-phenylenediamine 1 (2.520 g, 13.5 mmol) in acetic acid (35 mL) cooled to 0° C. was added methyl trichloroacetimidate (2.640 g, 15 mmol) under N$_2$ atmosphere and resulting reaction mixture was stirred at room temperature for 3 h. Diluted with water (200 mL) and resulting precipitate was filtered, washed with water (100 mL), dried in vacuum oven at 40° C. to give 5-bromo-2-(trichloromethyl)-1H-benzimidazole (4.1 g, 97%). $^1$H NMR (300 MHz, DMSO-d$_6$): δ 7.48 (d, J=6.0 Hz, 1H), 7.63 (d, J=6.0 Hz, 1H), 7.88 (s, 1H); LCMS m/z 315 (M+H$^+$), ELSD 100%. Reference: Louvet, P.; Lallement, G.; Pemot-Marino, I.; Luu-Duc, C.; Blanchet, G. Eur. J. Med. Chem. 1993, 28, 71-75.

5-bromo-5'-(4-methylpiperazin-1-yl)-1H,1'H-2,2'-bibenzimidazole 4

To a solution of 5-bromo-2-(trichloromethyl)-1H-benzimidazole 2 (4.020 g, 12.84 mmol) and 2-amino-4-(4-methylpiperazin-1-yl)phenylamine 3 (2.645 g, 12.84 mmol) in methanol (5 mL) was added triethyl amine (7.70 mL, 51.36 mmol) under N$_2$ atmosphere and resulting reaction mixture was refluxed for 12 h. Solvent was evaporated and saturated sodiumbicarbonate was added to the residue to give a precipitate. Filtered, washed with water (200 mL) and dried in vacuum oven at 40° C. to give 5-bromo-5'-(4-methylpiperazin-1-yl)-1H,1'H-2,2'-bibenzimidazole (5.12 g, 97%). LCMS m/z 413 (M+H$^+$), ELSD 100%.

Typical procedure for the preparation of Benzimidazolyl-benzimidazole:

A solution of benzimidazole-2-aldehyde 1 (0.5 mmol) and diamine 2 (0.5 mmol) in dimethylacetamide (4 mL) was stirred at 100° C. for 12 h. Solvent was evaporated and residue was purified by preparative HPLC to give benzimidazole derivative 3. $^1$H NMR (300 MHz, MeOH-d$_4$): δ 2.52 (s, 3H), 2.85 (brs, 4H), 3.25 (brs, 4H), 7.05-7.15 (m, 2H), 7.25-7.35 (s overlapped with m, 2H), 7.60-7.75 (m, 4H); LCMS m/z 333 (M+H$^+$), ELSD 99%.

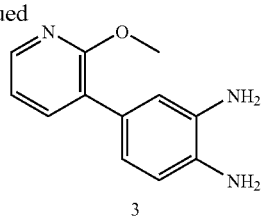

2-amino-4-(2-methoxypyridin-3-yl)phenylamine 3

To a solution of 4-bromo-o-phenylenediamine 1 (0.935 g, 5 mmol), 2-methoxy-3-pyridyl boronic acid 2 and $Na_2CO_3$ (1.060 g, 10 mmols) in 1,4-dioxane/H2O (3:1, 20 mL) flushed with $N_2$ was added $Pd(PPh_3)_4$ (0.575 g, 0.5 mmol) in one portion. Resulting reaction mixture was stirred under $N_2$ atmosphere at 100° C. for 12 h. Solvent was evaporated and residue was extracted with ethyl acetate (20 mL). Dried over anhydrous sodiumsulfate. Filtered, and evaporation of solvent gave a crude residue which was used as such in the following reaction. (0.850 g).

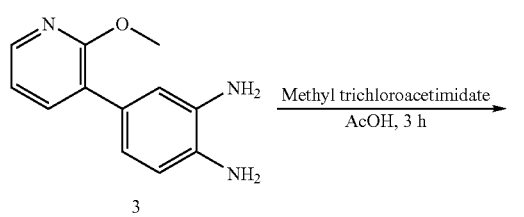

5-(2-methoxypyridin-3-yl)-2-(trichloromethyl)-1H-benzimidazole 4

To a solution of 2-amino-4-(2-methoxypyridin-3-yl)phenylamine 3 obtained from above reaction (0.215 g, 1 mmol) in acetic acid (2 mL) cooled to 0° C. was added methyl trichloroacetimidate (0.193 g, 1.1 mmol) under $N_2$ atmosphere and resulting reaction mixture was stirred at room temperature for 3 h. Acetic acid was evaporated to give crude 5-(2-methoxypyridin-3-yl)-2-(trichloromethyl)-1H-benzimidazole which was used as such in the following step (0.3 g). Reference: Louvet, P.; Lallement, G.; Pemot-Marino, I.; Luu-Duc, C.; Blanchet, G. Eur. J. Med. Chem. 1993, 28, 71-75.

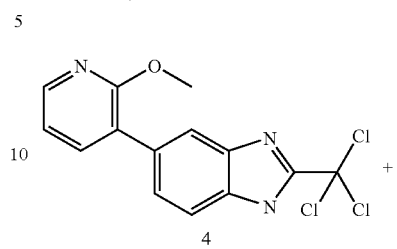

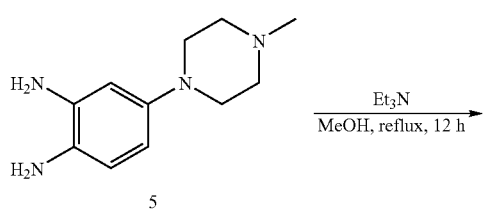

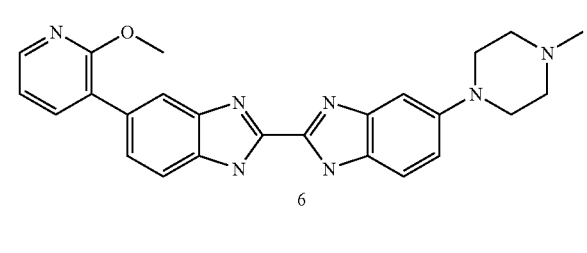

5-(2-methoxy-3-pyridyl)-5'-(4-methylpiperazin-1-yl)-1H,1'H-2,2'-bibenzimidazole 6

To a solution of 5-(2-methoxypyridin-3-yl)-2-(trichloromethyl)-1H-benzimidazole 4 obtained from above reaction (0.171 g, 0.5 mmol) and 2-amino-4-(4-methylpiperazin-1-yl)phenylamine 5 (0.103 g, 0.5 mmol) in methanol (2 mL) was added triethyl amine (0.6 mL, 4 mmol) under $N_2$ atmosphere and resulting reaction mixture was refluxed for 12 h. Solvent was evaporated and residue was purified by preparative HPLC to give 5-(2-methoxy-3-pyridyl)-5'-(4-methylpiperazin-1-yl)-1H,1'H-2,2'-bibenzimidazole (10 mg). LCMS m/z 440 (M+H$^+$), ELSD 100%.

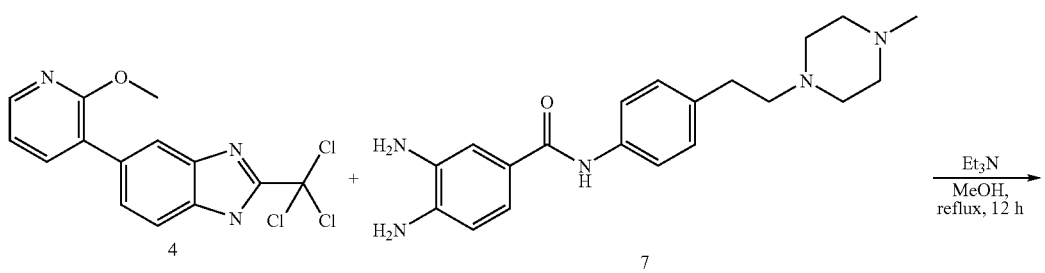

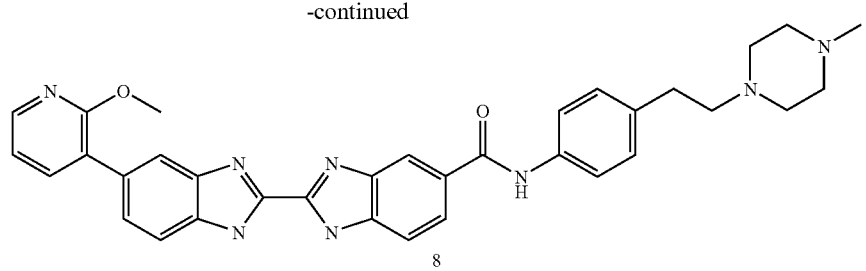

6'-(2-methoxy-3-pyridyl)-3H,1'H-[2,2']bibenzoimi-
dazolyl-5-carboxylic acid-{4-[2-(4-methylpiperazin-
1-yl)-ethyl]-phenyl}amide 8

To a solution of 5-(2-methoxypyridin-3-yl)-2-(trichlorom-
ethyl)-1H-benzimidazole 4 obtained from above reaction
(0.171 g, 0.5 mmol) and diamine derivative 7 (0.180 g, 0.5
mmol) in methanol (2 mL) was added triethyl amine (0.6 mL,
4 mmol) under $N_2$ atmosphere and resulting reaction mixture
was refluxed for 12 h. Solvent was evaporated and residue
was purified by preparative HPLC to give 6'-(2-methoxy-3-
pyridyl)-3H,1'H-[2,2']bibenzoimidazolyl-5-carboxylic acid-
{4-[2-(4-methylpiperazin-1-yl)-ethyl]-phenyl}amide (21
mg). LCMS m/z 587 (M+H$^+$), ELSD 100%.

6.8 Example 8

Synthesis of Compounds of Formula (5)

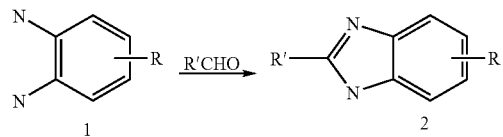

Method A: An array of 231 8-mL vials (3 diamines and 77
aldehydes) was prepared. Each vial was charged with the
appropriate aldehyde (125 μmole each). To each of the 8-mL
vials was added an aliquot of the appropriate stock solution of
diamine 1 in 5% (v/v) AcOH-abs. EtOH (125 μmole each).
The vials were capped and heated to 80° C. for 16 h in J-KEM
block. The solvent was removed from each vial using the
Genevac centrifical vacuum evaporator. The residue was dis-
solved in DMSO and filtered through a bed of celite (Thomp-
son Instrument Company, California, 35 mg of celite per
well). The filtered solutions of crude products were subjected
to purification by reverse phase HPLC and analyzed by
HPLC-MS.

The following compounds were prepared according to
method A:

| MOLSTRUCTURE | Calcd MS | M + H found |
|---|---|---|
| 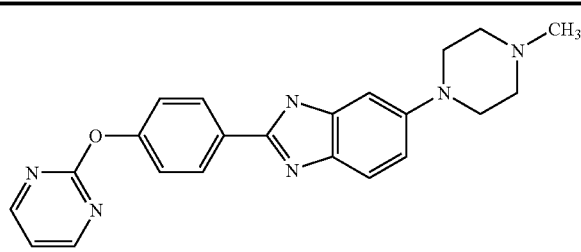 | 386.2 | 387.2 |
| 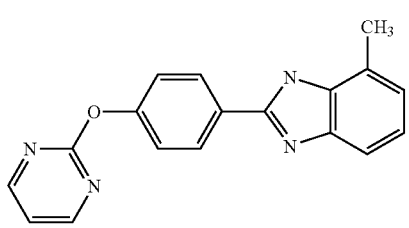 [SMILES: Cc1cccc2nc(-c3ccc(Oc4ncccn4)cc3)[nH]c12] | 302.1 | 303.1 |

-continued

| MOLSTRUCTURE | Calcd MS | M + H found |
|---|---|---|
| | 388.2 | 389.2 |
| | 373.2 | 374.2 |
| | 359.2 | 360.2 |
| | 275.1 | 276.1 |
| | 349.1 | 350.1 |
| | 334.2 | 335.2 |
| | 250.1 | 251.1 |
| | 407.1 | 408.1 |

-continued
| MOLSTRUCTURE | Calcd MS | M + H found |
|---|---|---|
| 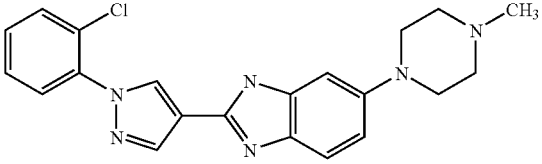 [SMILES: CN1CCN(c2ccc3nc(-c4cnn(-c5ccccc5Cl)c4)[nH]c3c2)CC1] | 392.2 | 393.2 |
| 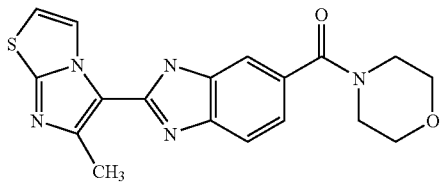 [SMILES: Cc1nc2sccn2c1-c1nc2ccc(C(=O)N3CCOCC3)cc2[nH]1] | 367.1 | 368.1 |
| 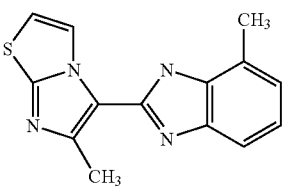 | 268.1 | 269.1 |
| 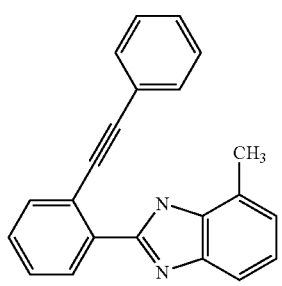 [SMILES: Cc1cccc2nc(-c3ccccc3C#Cc3ccccc3)[nH]c12] | 308.1 | 309.1 |
| 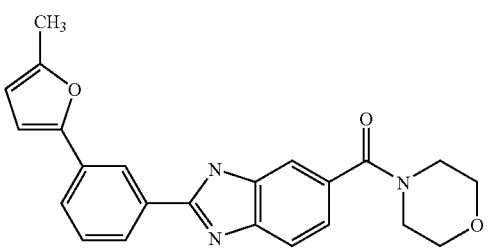 [SMILES: Cc1ccc(-c2cccc(-c3nc4ccc(C(=O)N5CCOCC5)cc4[nH]3)c2)o1] | 387.2 | 388.2 |
| 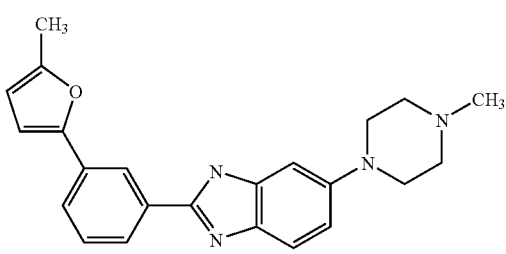 [SMILES: Cc1ccc(-c2cccc(-c3nc4ccc(N5CCN(C)CC5)cc4[nH]3)c2)o1] | 372.2 | 373.2 |
| 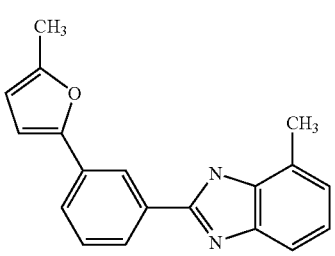 [SMILES: Cc1ccc(-c2cccc(-c3nc4cccc(C)c4[nH]3)c2)o1] | 288.1 | 289.1 |

-continued
| MOLSTRUCTURE | Calcd MS | M + H found |
|---|---|---|
| 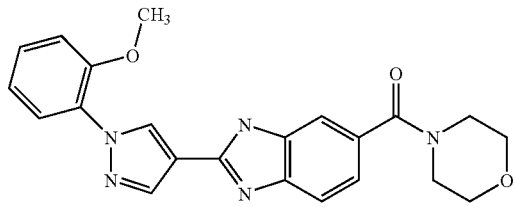 [SMILES: COc1ccccc1-n1cc(-c2nc3ccc(C(=O)N4CCOCC4)cc3[nH]2)cn1] | 403.2 | 404.2 |
| 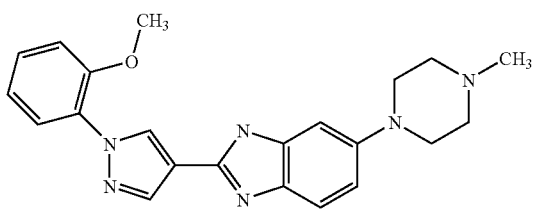 [SMILES: COc1ccccc1-n1cc(-c2nc3ccc(N4CCN(C)CC4)cc3[nH]2)cn1] | 388.2 | 389.2 |
| 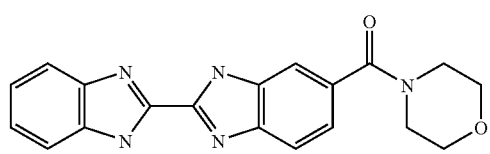 [SMILES: O=C(c1ccc2nc(-c3nc4ccccc4[nH]3)[nH]c2c1)N1CCOCC1] | 347.1 | 348.1 |
| 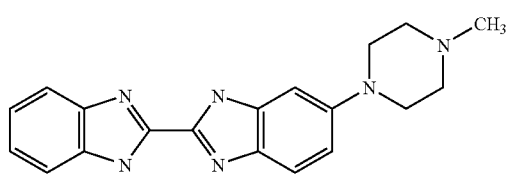 [SMILES: CN1CCN(c2ccc3nc(-c4nc5ccccc5[nH]4)[nH]c3c2)CC1] | 332.2 | 333.2 |
| 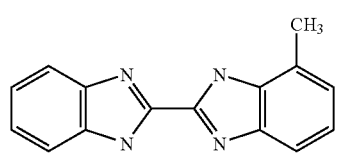 [SMILES: Cc1cccc2nc(-c3nc4ccccc4[nH]3)[nH]c12] | 248.1 | 249.1 |
| 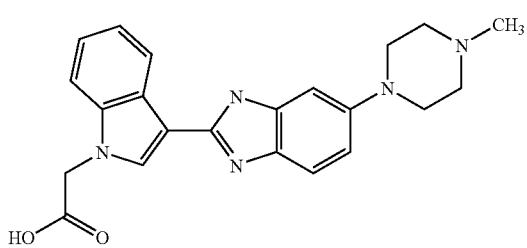 [SMILES: CN1CCN(c2ccc3nc(-c4cn(CC(=O)O)c5ccccc45)[nH]c3c2)CC1] | 389.2 | 390.2 |
| 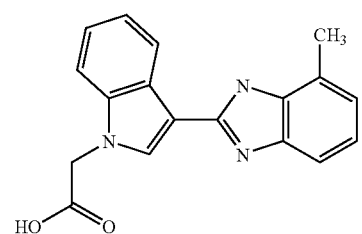 [SMILES: Cc1cccc2nc(-c3cn(CC(=O)O)c4ccccc34)[nH]c12] | 305.1 | 306.1 |

-continued

| MOLSTRUCTURE | Calcd MS | M + H found |
|---|---|---|
| | 376.2 | 377.2 |
| | 292.1 | 293.1 |
| | 403.2 | 404.2 |
| | 388.2 | 389.2 |
| | 390.1 | 391.1 |
| | 375.2 | 376.2 |

-continued
| MOLSTRUCTURE | Calcd MS | M + H found |
|---|---|---|
| 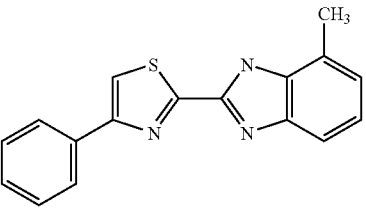 [SMILES: Cc1cccc2nc(-c3nc(-c4ccccc4)cs3)[nH]c12] | 291.1 | 292.1 |
| 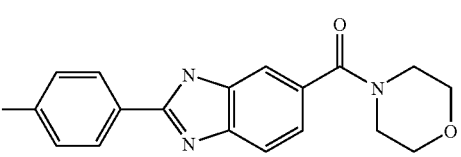 | 373.2 | 374.2 |
| 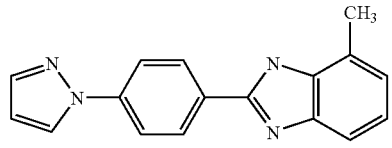 [SMILES: Cc1cccc2nc(-c3ccc(-n4cccn4)cc3)[nH]c12] | 274.1 | 275.1 |
| 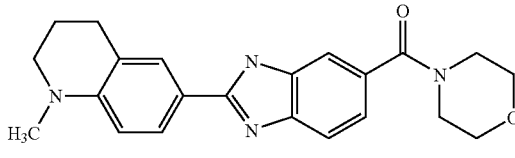 | 376.2 | 377.2 |
| 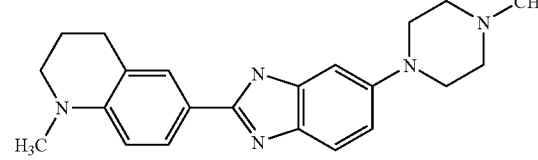 | 361.2 | 362.2 |
| 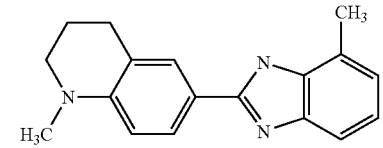 [SMILES: Cc1cccc2nc(-c3ccc4c(c3)CCCN4C)[nH]c12] | 277.2 | 278.2 |
| 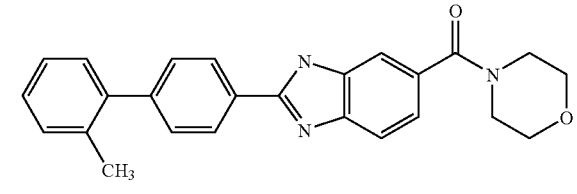 [SMILES: Cc1ccccc1-c1ccc(-c2nc3ccc(C(=O)N4CCOCC4)cc3[nH]2)cc1] | 397.2 | 398.2 |
| 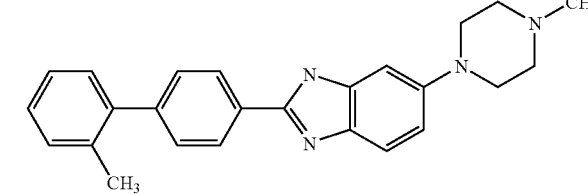 | 382.2 | 383.2 |

-continued
| MOLSTRUCTURE | Calcd MS | M + H found |
|---|---|---|
| 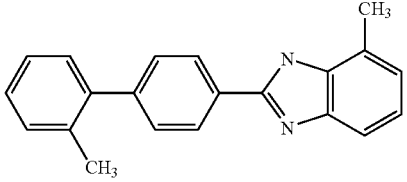 [SMILES: Cc1ccccc1-c1ccc(-c2nc3cccc(C)c3[nH]2)cc1] | 298.1 | 299.1 |
| 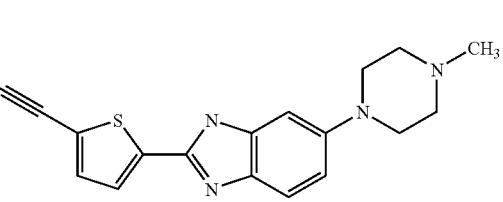 | 380.2 | 381.2 |
| 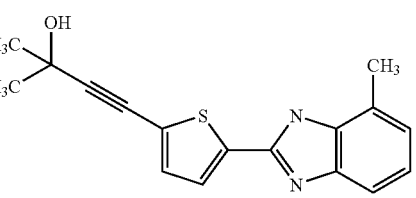 | 296.1 | 297.1 |
| 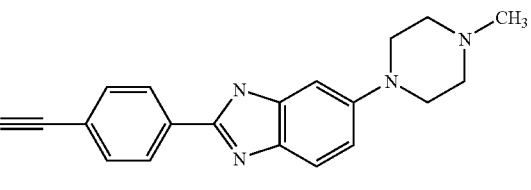 | 394.2 | 395.2 |
| 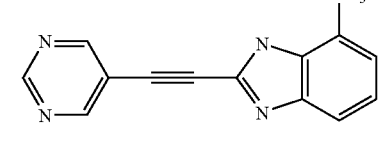 | 310.1 | 311.1 |
| 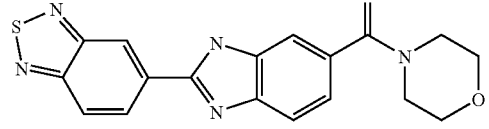 | 365.1 | 366.1 |
| 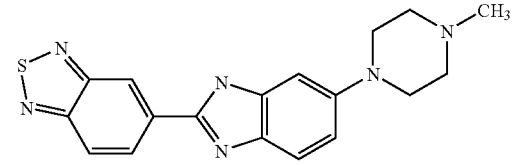 [SMILES: CN1CCN(c2ccc3nc(-c4ccc5nsnc5c4)[nH]c3c2)CC1] | 350.1 | 351.1 |
| 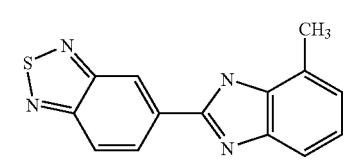 [SMILES: Cc1cccc2nc(-c3ccc4nsnc4c3)[nH]c12] | 266.1 | 267.1 |
| 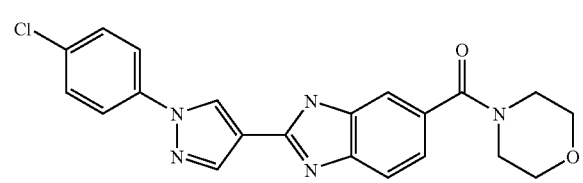 [SMILES: O=C(c1ccc2nc(-c3cnn(-c4ccc(Cl)cc4)c3)[nH]c2c1)N1CCOCC1] | 407.1 | 408.1 |

-continued

| MOLSTRUCTURE | Calcd MS | M + H found |
|---|---|---|
| | 392.2 | 393.2 |
| | 308.1 | 309.1 |
| | 408.1 | 409.1 |
| | 393.1 | 394.1 |
| | 309.1 | 310.1 |
| | 410.2 | 411.2 |
| | 395.2 | 396.2 |
| | 311.1 | 312.1 |

-continued
| MOLSTRUCTURE | Calcd MS | M + H found |
|---|---|---|
| 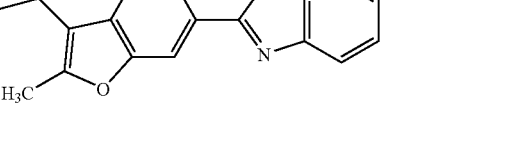 | 452.2 | 453.2 |
| 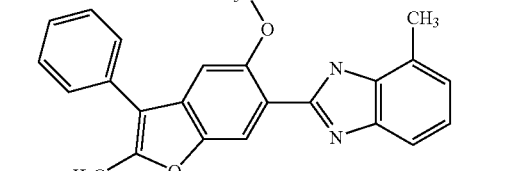 | 368.2 | 369.2 |
| 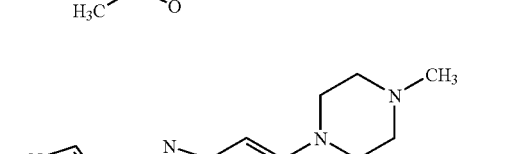 | 358.2 | 359.2 |
| 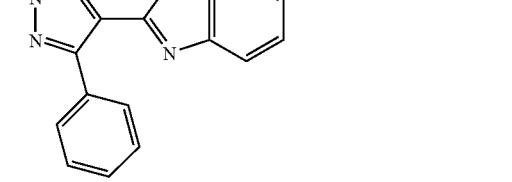 | 274.1 | 275.1 |
| 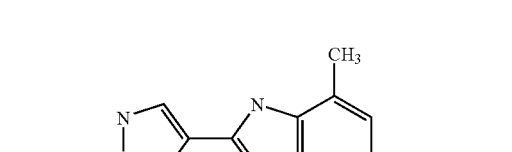 | 391.1 | 392.1 |
| 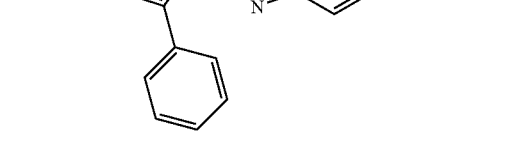 | 376.2 | 377.2 |

| MOLSTRUCTURE | Calcd MS | M + H found |
|---|---|---|
| 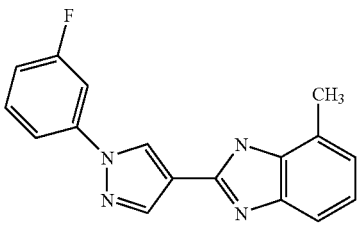 [SMILES: Cc1cccc2nc(-c3cnn(-c4cccc(F)c4)c3)[nH]c12] | 292.1 | 293.1 |
| 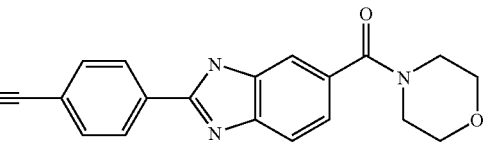 | 389.2 | 390.2 |
| 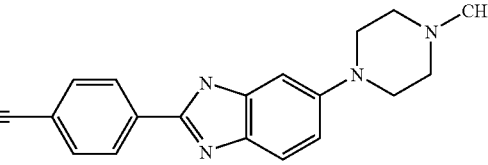 | 374.2 | 375.2 |
| 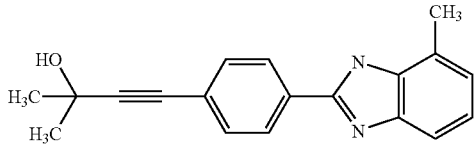 | 290.1 | 291.1 |
| 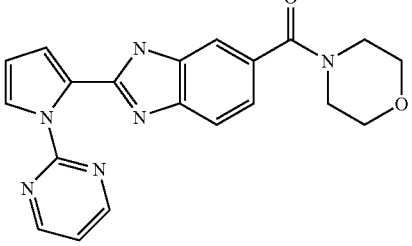 | 374.1 | 375.1 |
| 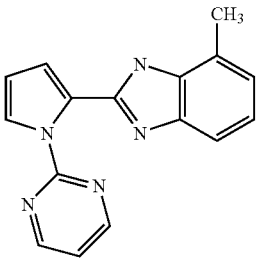 [SMILES: Cc1cccc2nc(-c3cccn3-c3ncccn3)[nH]c12] | 275.1 | 276.1 |
| 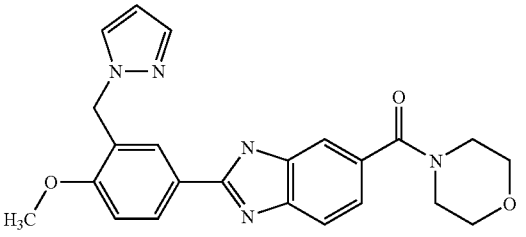 [SMILES: COc1ccc(-c2nc3ccc(C(=O)N4CCOCC4)cc3[nH]2)cc1Cn1cccn1] | 417.2 | 418.2 |

-continued
| MOLSTRUCTURE | Calcd MS | M + H found |
|---|---|---|
| 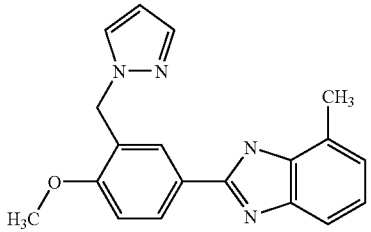 [SMILES: COc1ccc(-c2nc3cccc(C)c3[nH]2)cc1Cn1cccn1] | 318.1 | 319.1 |
| 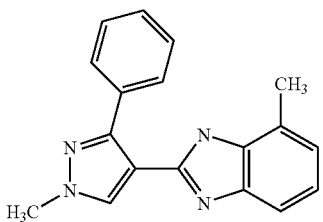 [SMILES: Cc1cccc2nc(-c3cn(C)nc3-c3ccccc3)[nH]c12] | 288.1 | 289.1 |
| 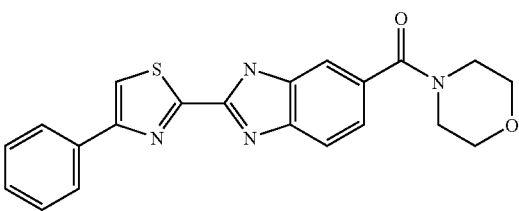 [SMILES: O=C(c1ccc2nc(-c3nc(-c4ccccc4)cs3)[nH]c2c1)N1CCOCC1] | 390.1 | 391.1 |
| 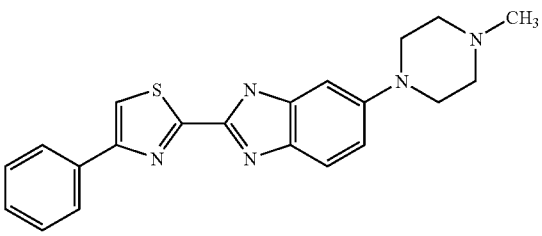 [SMILES: CN1CCN(c2ccc3nc(-c4nc(-c5ccccc5)cs4)[nH]c3c2)CC1] | 375.2 | 376.2 |
| 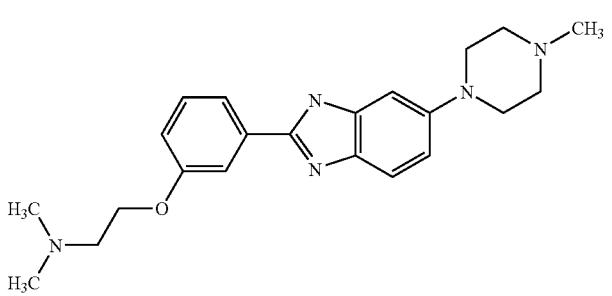 | 379.2 | 380.2 |
| 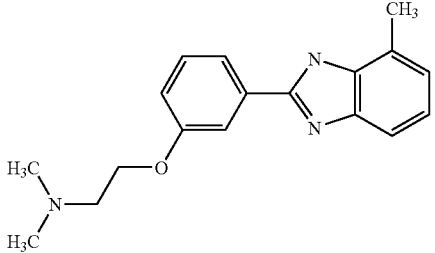 [SMILES: Cc1cccc2nc(-c3cccc(OCCN(C)C)c3)[nH]c12] | 295.2 | 296.2 |

-continued

| MOLSTRUCTURE | Calcd MS | M + H found |
|---|---|---|
| (structure) | 422.2 | 423.2 |
| (structure) | 407.3 | 408.3 |
| (structure) | 394.2 | 395.2 |
| (structure) | 427.2 | 428.2 |
| (structure) | 343.2 | 344.2 |
| (structure) | 301.1 | 302.1 |

-continued

| MOLSTRUCTURE | Calcd MS | M + H found |
|---|---|---|
| | 433.1 | 434.1 |
| | 415.2 | 416.2 |
| | 443.2 | 444.2 |
| | 428.2 | 429.2 |
| | 344.2 | 345.2 |
| | 434.1 | 435.1 |

-continued
| MOLSTRUCTURE | Calcd MS | M + H found |
|---|---|---|
| 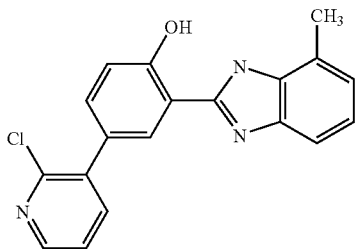 [SMILES: Cc1cccc2nc(-c3cc(-c4cccnc4Cl)ccc3O)[nH]c12] | 335.1 | 336.1 |
| 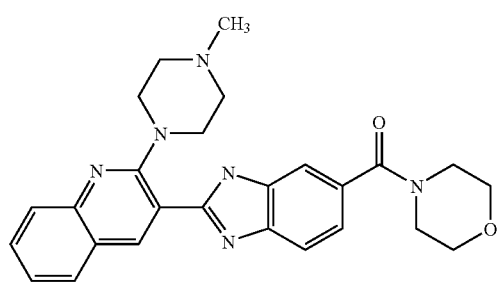 [SMILES: CN1CCN(c2nc3ccccc3cc2-c2nc3ccc(C(=O)N4CCOCC4)cc3[nH]2)CC1] | 456.2 | 457.2 |
| 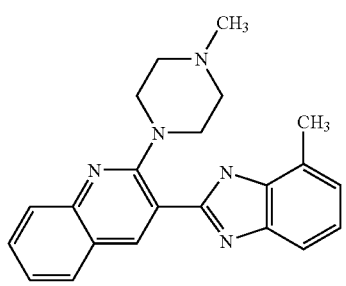 [SMILES: Cc1cccc2nc(-c3cc4ccccc4nc3N3CCN(C)CC3)[nH]c12] | 357.2 | 358.2 |
| 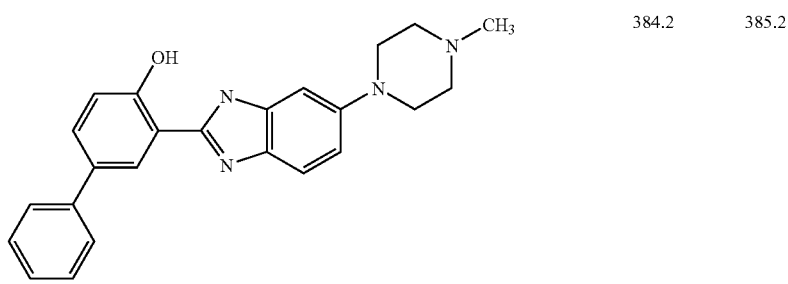 | 384.2 | 385.2 |
| 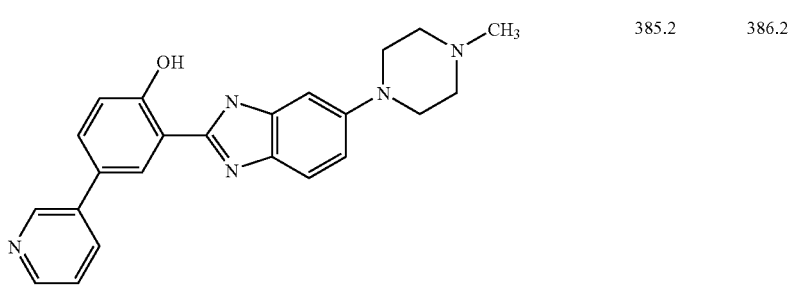 | 385.2 | 386.2 |

-continued

| MOLSTRUCTURE | Calcd MS | M + H found |
|---|---|---|
| (4-methylpiperazinyl benzimidazole with hydroxyphenyl-isopropylphenyl biphenyl) | 426.2 | 427.2 |
| 2-cyclohexyl-5-(4-methylpiperazin-1-yl)benzimidazole | 298.2 | 299.2 |
| 2-cyclohexyl-4-methylbenzimidazole | 214.1 | 215.1 |
| 2-(3,5-di-tert-butyl-2-hydroxyphenyl)-5-(morpholine-4-carbonyl)benzimidazole | 435.3 | 436.3 |
| 2-(3,5-di-tert-butyl-2-hydroxyphenyl)-5-(4-methylpiperazin-1-yl)benzimidazole | 420.3 | 421.3 |
| 2-(1H-indol-3-yl)-5-(morpholine-4-carbonyl)benzimidazole | 346.1 | 347.1 |
| 2-(1H-indol-3-yl)-5-(4-methylpiperazin-1-yl)benzimidazole | 331.2 | 332.2 |

-continued
| MOLSTRUCTURE | Calcd MS | M + H found |
|---|---|---|
| 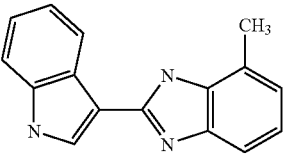 [SMILES: Cc1cccc2nc(-c3c[nH]c4ccccc34)[nH]c12] | 247.1 | 248.1 |
| 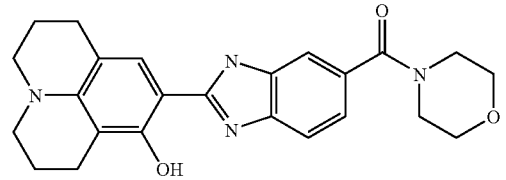 [SMILES: O=C(c1ccc2nc(-c3cc4c5c(c3O)CCCN5CCC4)[nH]c2c1)N1CCOCC1] | 418.2 | 419.2 |
| 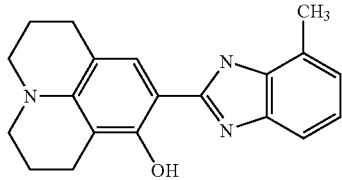 [SMILES: Cc1cccc2nc(-c3cc4c5c(c3O)CCCN5CCC4)[nH]c12] | 319.2 | 320.2 |
| 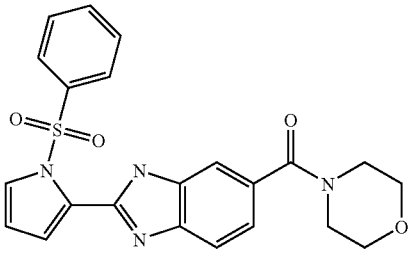 [SMILES: O=C(c1ccc2nc(-c3cccn3S(=O)(=O)c3ccccc3)[nH]c2c1)N1CCOCC1] | 436.1 | 437.1 |
| 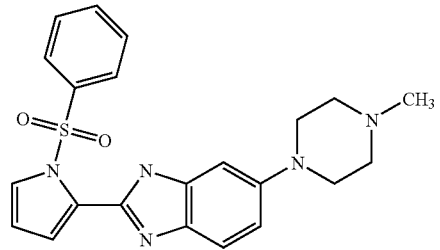 [SMILES: CN1CCN(c2ccc3nc(-c4cccn4S(=O)(=O)c4ccccc4)[nH]c3c2)CC1] | 421.2 | 422.2 |
| 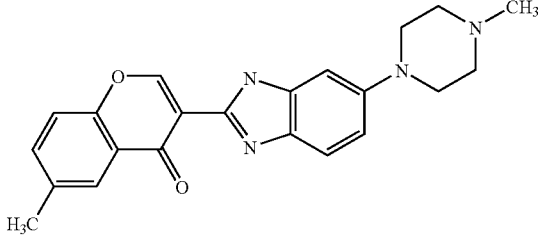 [SMILES: Cc1ccc2occ(-c3nc4ccc(N5CCN(C)CC5)cc4[nH]3)c(=O)c2c1] | 374.2 | 375.2 |
| 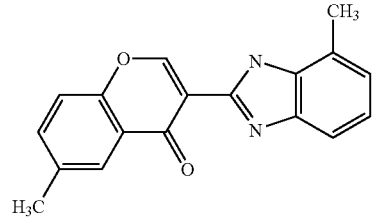 [SMILES: Cc1ccc2occ(-c3nc4cccc(C)c4[nH]3)c(=O)c2c1] | 290.1 | 291.1 |

-continued

| MOLSTRUCTURE | Calcd MS | M + H found |
|---|---|---|
| | 378.1 | 379.1 |
| | 294.1 | 295.1 |
| | 368.1 | 369.1 |
| | 353.2 | 354.2 |
| | 269.1 | 270.1 |
| | 408.1 | 409.1 |

| MOLSTRUCTURE | Calcd MS | M + H found |
|---|---|---|
| | 402.2 | 403.2 |
| | 318.1 | 319.1 |
| | 394.1 | 395.1 |
| | 394.2 | 395.2 |
| | 295.2 | 296.2 |
| | 364.2 | 365.2 |

-continued

| MOLSTRUCTURE | Calcd MS | M + H found |
|---|---|---|
| (structure) | 280.2 | 281.2 |
| (structure) | 379.2 | 380.2 |
| (structure) | 351.2 | 352.2 |
| (structure) | 336.2 | 337.2 |
| (structure) | 429.2 | 430.2 |
| (structure) | 414.2 | 415.2 |
| (structure) | 330.1 | 331.1 |

-continued

| MOLSTRUCTURE | Calcd MS | M + H found |
|---|---|---|
| | 355.1 | 356.1 |
| | 340.2 | 341.2 |
| | 256.1 | 257.1 |
| | 325.2 | 326.2 |
| | 310.2 | 311.2 |
| | 393.2 | 394.2 |
| | 378.2 | 379.2 |

| MOLSTRUCTURE | Calcd MS | M + H found |
|---|---|---|
| 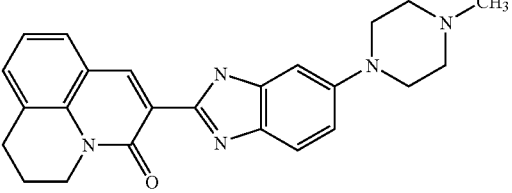 | 399.2 | 400.2 |
| 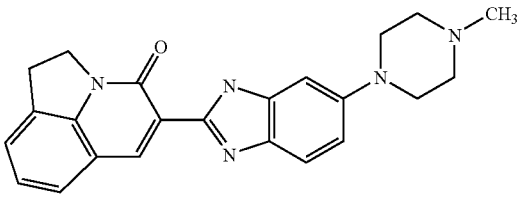 | 385.2 | 386.2 |
| 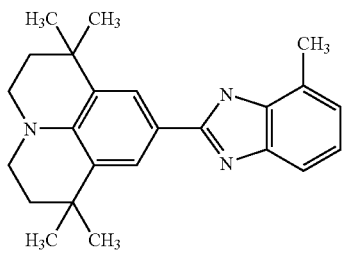 [SMILES: Cc1cccc2nc(-c3cc4c5c(c3)C(C)(C)CCN5CCC4(C)C)[nH]c12] | 375.2 | 376.2 |
| 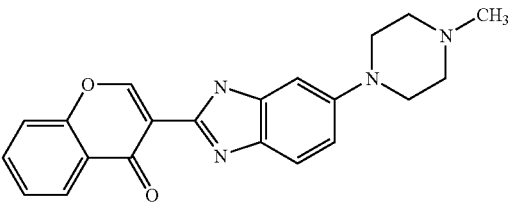 | 360.2 | 361.2 |
| 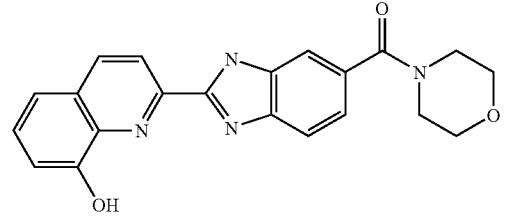 [SMILES: O=C(c1ccc2nc(-c3ccc4cccc(O)c4n3)[nH]c2c1)N1CCOCC1] | 374.1 | 375.1 |
| 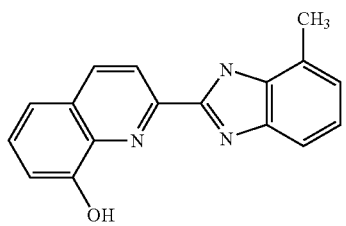 [SMILES: Cc1cccc2nc(-c3ccc4cccc(O)c4n3)[nH]c12] | 275.1 | 276.1 |
| 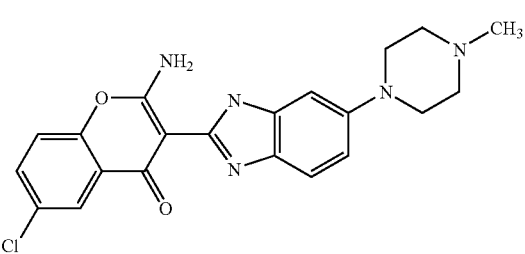 | 409.1 | 410.1 |

-continued

| MOLSTRUCTURE | Calcd MS | M + H found |
|---|---|---|
| | 358.2 | 359.2 |
| | 403.2 | 404.2 |
| | 304.2 | 305.2 |
| | 344.2 | 345.2 |
| | 260.1 | 261.1 |
| | 401.2 | 402.2 |

Method B: An array of 231 8-mL vials (3 diamines and 77 aldehydes) was prepared. After diamine 1 (3, 150 µmol each) in anhydrous DMF (1 mL each vial) was heated to 40° C. in J-KEM block, the appropriate aldehyde (125 µmol each) in absolute EtOH (5 mL each) was added in small portions to the diamine solution over a 1 h period. The reaction was stirred overnight at 78° C. in a sealed vial in J-KEM block. The temperature was reduced to 70° C. and the vessel uncapped to allow EtOH to evaporate. The residue was dissolved in DMSO and filtered through a bed of celite (Thompson Instrument Company, California, 35 mg of celite per well). The sample was then concentrated under reduced pressure to afford the crude product which was then directly purified by reverse phase HPLC.

The following compounds were prepared according to method B:

| MOLSTRUCTURE | Calcd MS | M + H found |
|---|---|---|
|  | 519.2 | 520.2 |
|  | 533.3 | 534.3 |
|  | 506.2 | 507.2 |
|  | 520.3 | 521.3 |
|  | 492.2 | 493.2 |
|  | 467.2 | 468.2 |

-continued
| MOLSTRUCTURE | Calcd MS | M + H found |
|---|---|---|
| 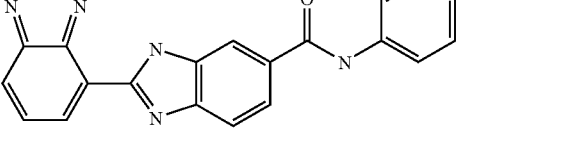 | 481.2 | 482.2 |
| 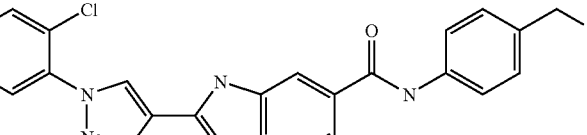 | 525.2 | 526.2 |
|  | 539.2 | 540.2 |
| 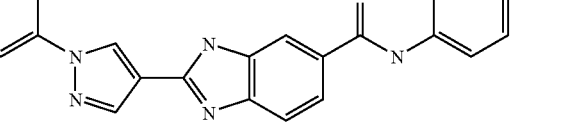 | 499.2 | 500.2 |
| 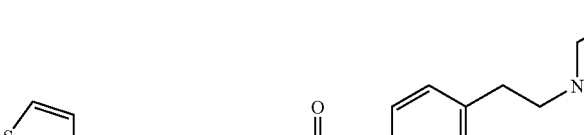 | 410.2 | 411.2 |
| 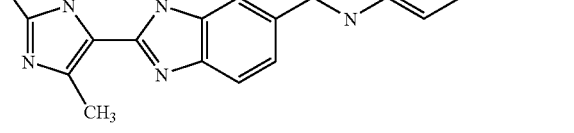 | 505.2 | 506.2 |

-continued

| MOLSTRUCTURE | Calcd MS | M + H found |
|---|---|---|
| | 519.3 | 520.3 |
| | 430.2 | 431.2 |
| | 521.3 | 522.3 |
| | 446.2 | 447.2 |
| | 479.2 | 480.2 |
| | 522.2 | 523.2 |

-continued

| MOLSTRUCTURE | Calcd MS | M + H found |
|---|---|---|
| | 536.3 | 537.3 |
| | 447.2 | 448.2 |
| | 521.3 | 522.3 |
| | 535.3 | 536.3 |
| | 508.2 | 509.2 |

-continued
| MOLSTRUCTURE | Calcd MS | M + H found |
|---|---|---|
| 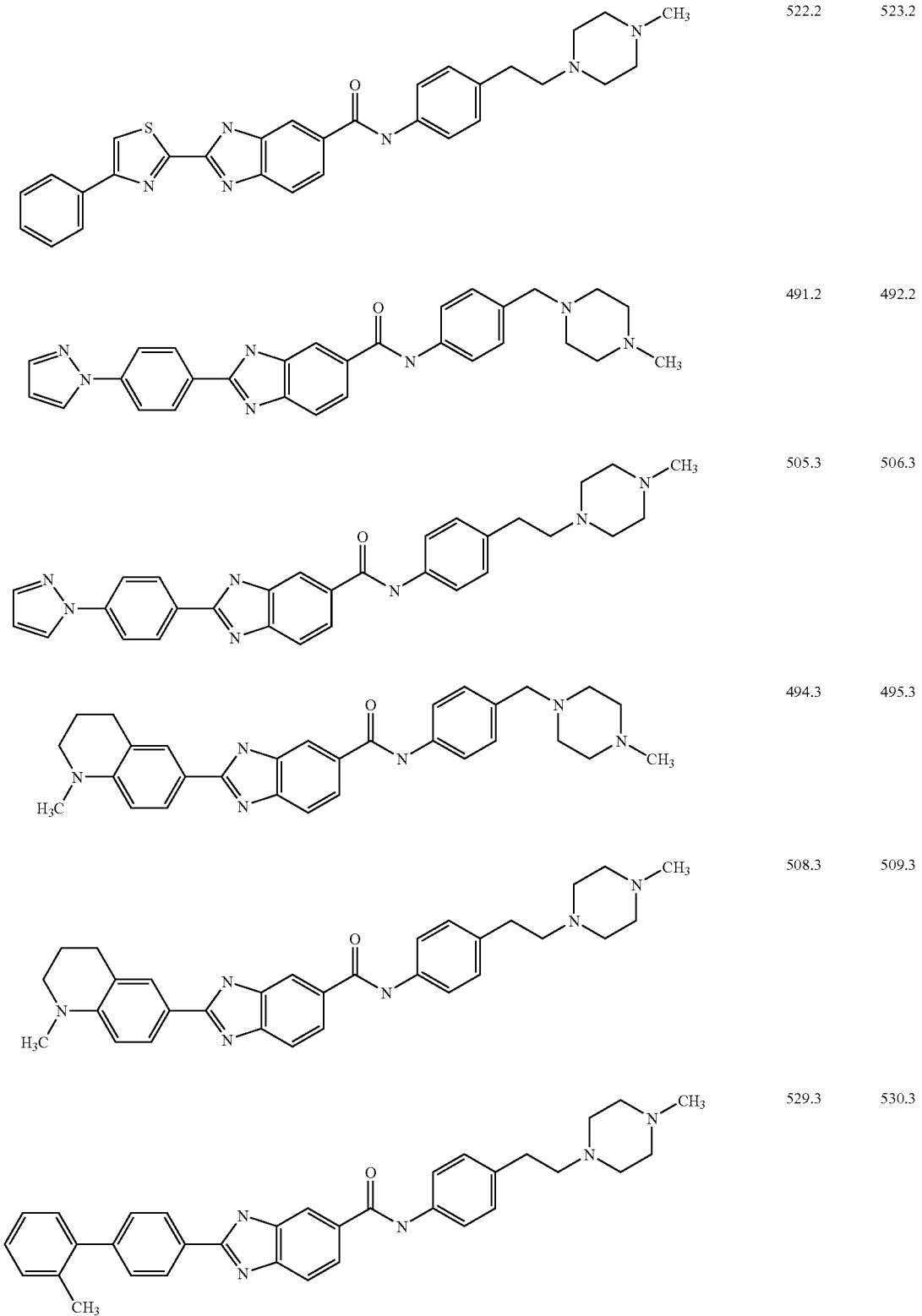 | 522.2 | 523.2 |
| | 491.2 | 492.2 |
| | 505.3 | 506.3 |
| | 494.3 | 495.3 |
| | 508.3 | 509.3 |
| | 529.3 | 530.3 |

-continued

| MOLSTRUCTURE | Calcd MS | M + H found |
|---|---|---|
| | 513.2 | 514.2 |
| | 527.2 | 528.2 |
| | 438.2 | 439.2 |
| | 541.3 | 542.3 |
| | 452.2 | 453.2 |
| | 483.2 | 484.2 |
| | 497.2 | 498.2 |

-continued
| MOLSTRUCTURE | Calcd MS | M + H found |
|---|---|---|
| 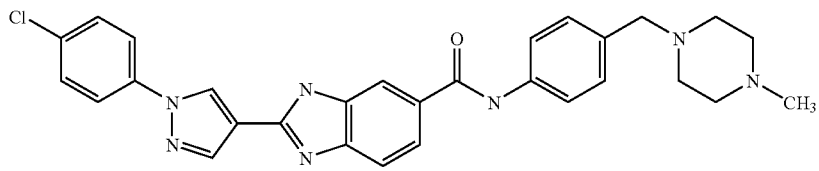 [SMILES: CN1CCN(Cc2ccc(NC(=O)c3ccc4nc(-c5cnn(-c6ccc(Cl)cc6)c5)[nH]c4c3)cc2)CC1] | 525.2 | 526.2 |
| 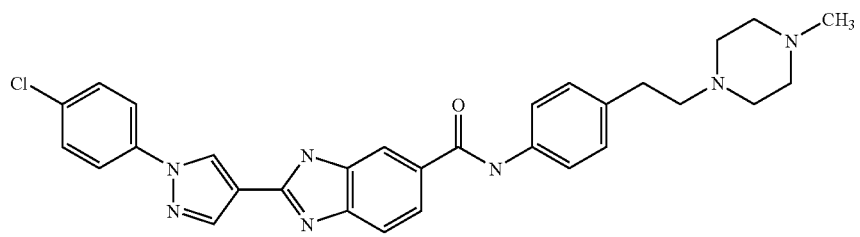 [SMILES: CN1CCN(CCc2ccc(NC(=O)c3ccc4nc(-c5cnn(-c6ccc(Cl)cc6)c5)[nH]c4c3)cc2)CC1] | 539.2 | 540.2 |
| 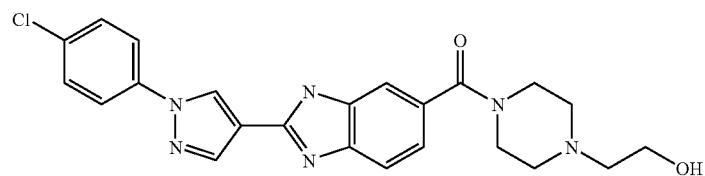 [SMILES: O=C(c1ccc2nc(-c3cnn(-c4ccc(Cl)cc4)c3)[nH]c2c1)N1CCN(CCO)CC1] | 450.2 | 451.2 |
| 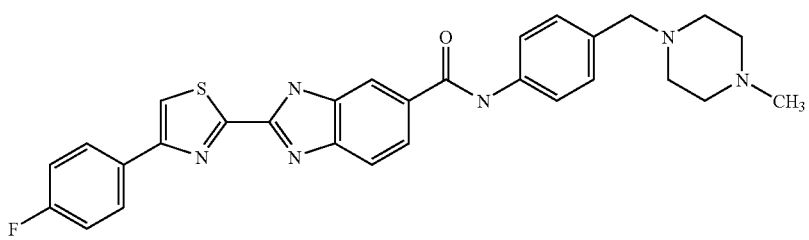 [SMILES: CN1CCN(Cc2ccc(NC(=O)c3ccc4nc(-c5nc(-c6ccc(F)cc6)cs5)[nH]c4c3)cc2)CC1] | 526.2 | 527.2 |
| 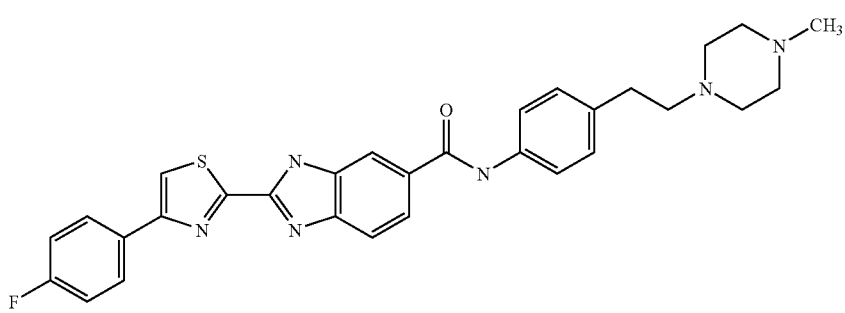 [SMILES: CN1CCN(CCc2ccc(NC(=O)c3ccc4nc(-c5nc(-c6ccc(F)cc6)cs5)[nH]c4c3)cc2)CC1] | 540.2 | 541.2 |
| 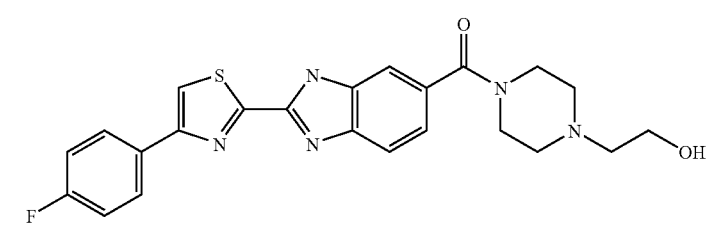 [SMILES: O=C(c1ccc2nc(-c3nc(-c4ccc(F)cc4)cs3)[nH]c2c1)N1CCN(CCO)CC1] | 451.1 | 452.1 |

| MOLSTRUCTURE | Calcd MS | M + H found |
|---|---|---|
| 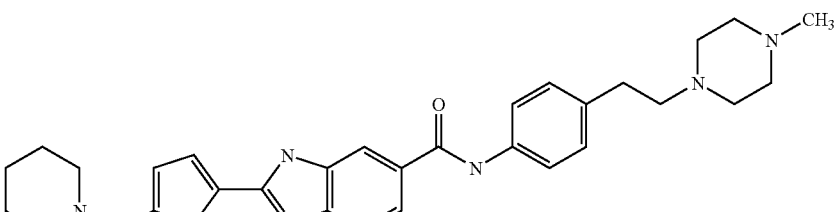 | 542.3 | 543.3 |
| 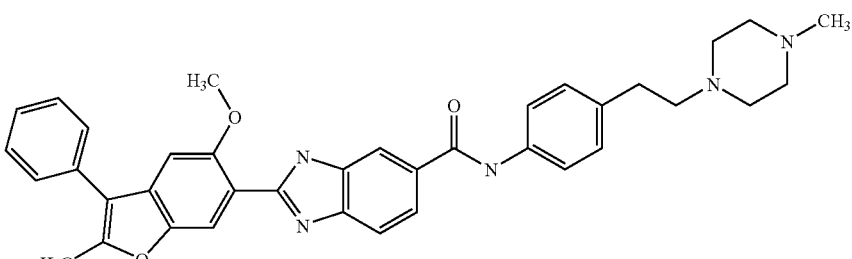 | 599.3 | 600.3 |
| 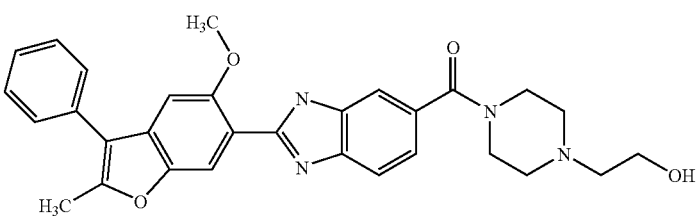 [SMILES: COc1cc2c(-c3ccccc3)c(C)oc2cc1-c1nc2ccc(C(=O)N3CCN(CCO)CC3)cc2[nH]1] | 510.2 | 511.2 |
| 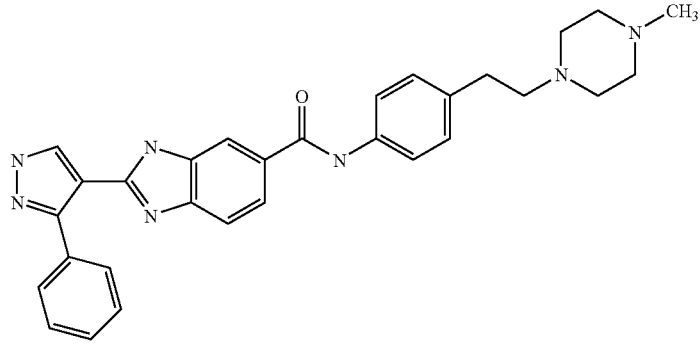 [SMILES: CN1CCN(CCc2ccc(NC(=O)c3ccc4nc(-c5c[nH]nc5-c5ccccc5)[nH]c4c3)cc2)CC1] | 505.3 | 506.3 |
| 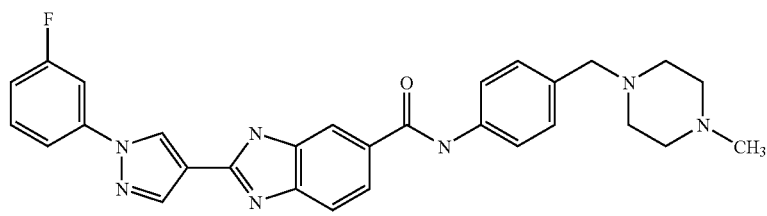 [SMILES: CN1CCN(Cc2ccc(NC(=O)c3ccc4nc(-c5cnn(-c6cccc(F)c6)c5)[nH]c4c3)cc2)CC1] | 509.2 | 510.2 |
| 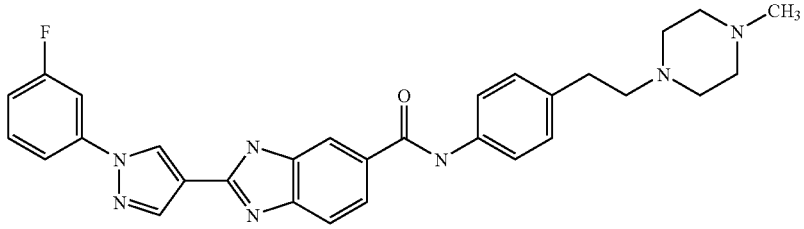 [SMILES: CN1CCN(CCc2ccc(NC(=O)c3ccc4nc(-c5cnn(-c6cccc(F)c6)c5)[nH]c4c3)cc2)CC1] | 523.2 | 524.2 |

| MOLSTRUCTURE | Calcd MS | M + H found |
|---|---|---|
| | 434.2 | 435.2 |
| | 507.3 | 508.3 |
| | 521.3 | 522.3 |
| | 432.2 | 433.2 |
| | 506.3 | 507.3 |
| | 417.2 | 418.2 |

-continued

| MOLSTRUCTURE | Calcd MS | M + H found |
|---|---|---|
| | 535.3 | 536.3 |
| | 460.2 | 461.2 |
| | 505.3 | 506.3 |
| | 508.2 | 509.2 |
| | 522.2 | 523.2 |
| | 433.2 | 434.2 |

-continued

| MOLSTRUCTURE | Calcd MS | M + H found |
|---|---|---|
| | 526.3 | 527.3 |
| | 554.3 | 555.3 |
| | 465.3 | 466.3 |
| | 560.3 | 561.3 |
| | 574.3 | 575.3 |

-continued
| MOLSTRUCTURE | Calcd MS | M + H found |
|---|---|---|
| 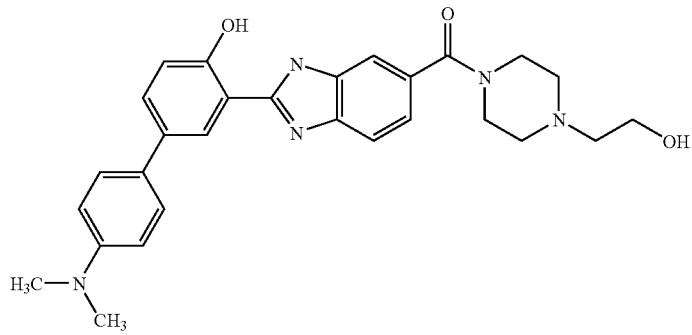 [SMILES: CN(C)c1ccc(-c2ccc(O)c(-c3nc4ccc(C(=O)N5CCN(CCO)CC5)cc4[nH]3)c2)cc1] | 485.2 | 486.2 |
| 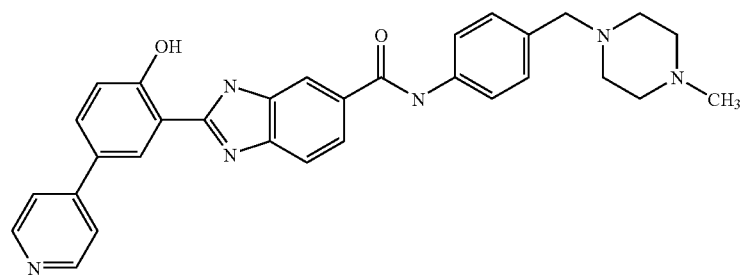 [SMILES: CN1CCN(Cc2ccc(NC(=O)c3ccc4nc(-c5cc(-c6ccncc6)ccc5O)[nH]c4c3)cc2)CC1] | 518.2 | 519.2 |
| 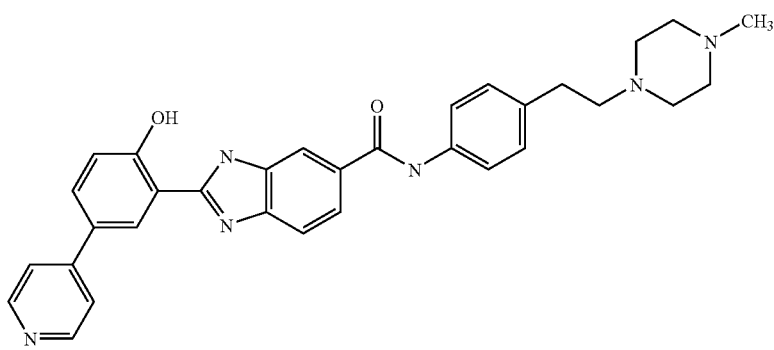 [SMILES: CN1CCN(CCc2ccc(NC(=O)c3ccc4nc(-c5cc(-c6ccncc6)ccc5O)[nH]c4c3)cc2)CC1] | 532.3 | 533.3 |
| 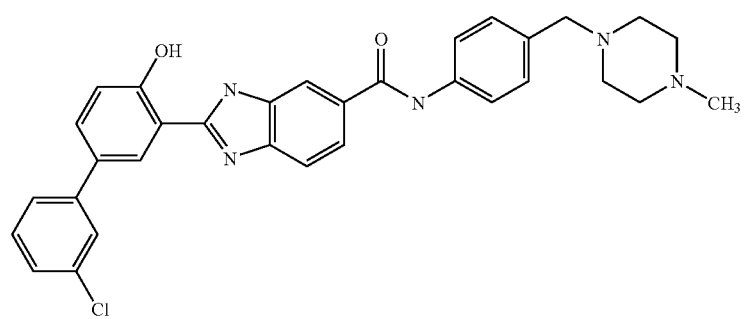 [SMILES: CN1CCN(Cc2ccc(NC(=O)c3ccc4nc(-c5cc(-c6cccc(Cl)c6)ccc5O)[nH]c4c3)cc2)CC1] | 551.2 | 552.2 |

-continued

| MOLSTRUCTURE | Calcd MS | M + H found |
| --- | --- | --- |
| | 565.2 | 566.2 |
| | 562.3 | 563.3 |
| | 473.2 | 474.2 |
| | 561.3 | 562.3 |
| | 575.3 | 576.3 |

-continued
| MOLSTRUCTURE | Calcd MS | M + H found |
|---|---|---|
| 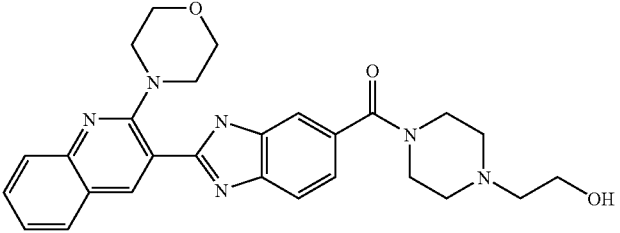 [SMILES: O=C(c1ccc2nc(-c3cc4ccccc4nc3N3CCOCC3)[nH]c2c1)N1CCN(CCO)CC1] | 486.2 | 487.2 |
| 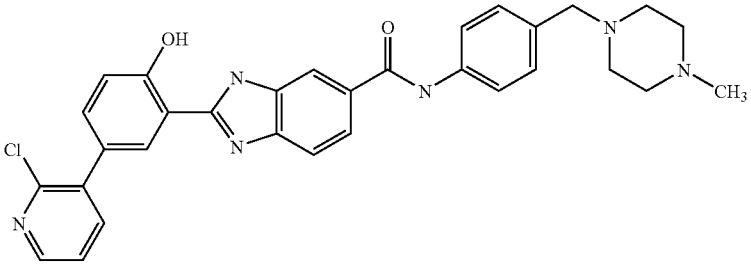 [SMILES: CN1CCN(Cc2ccc(NC(=O)c3ccc4nc(-c5cc(-c6cccnc6Cl)ccc5O)[nH]c4c3)cc2)CC1] | 552.2 | 553.2 |
| 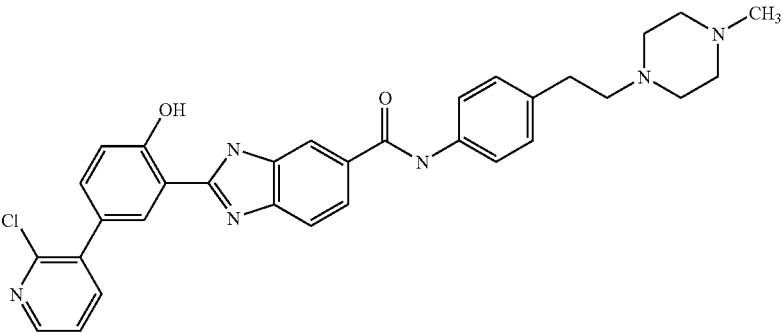 [SMILES: CN1CCN(CCc2ccc(NC(=O)c3ccc4nc(-c5cc(-c6cccnc6Cl)ccc5O)[nH]c4c3)cc2)CC1] | 566.2 | 567.2 |
| 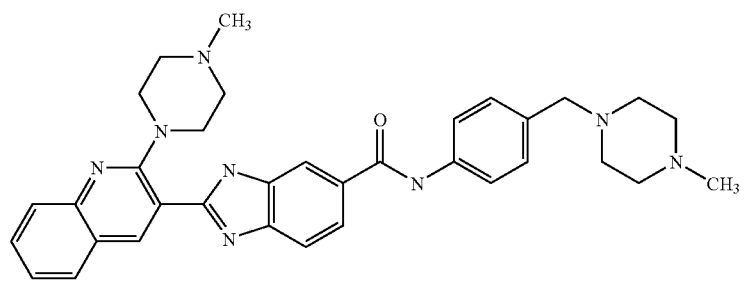 [SMILES: CN1CCN(Cc2ccc(NC(=O)c3ccc4nc(-c5cc6ccccc6nc5N5CCN(C)CC5)[nH]c4c3)cc2)CC1] | 574.3 | 575.3 |
| 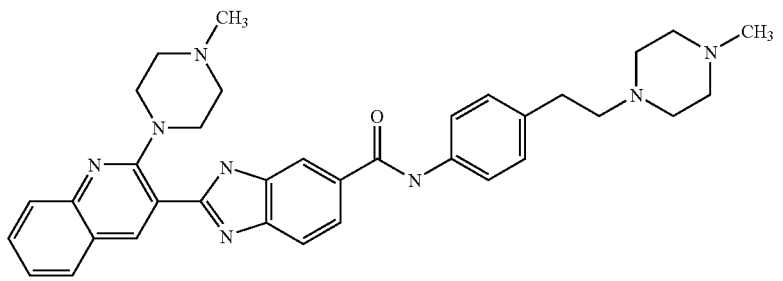 [SMILES: CN1CCN(CCc2ccc(NC(=O)c3ccc4nc(-c5cc6ccccc6nc5N5CCN(C)CC5)[nH]c4c3)cc2)CC1] | 588.3 | 589.3 |

-continued

| MOLSTRUCTURE | Calcd MS | M + H found |
|---|---|---|
| | 517.2 | 518.2 |
| | 531.3 | 532.3 |
| | 518.2 | 519.2 |
| | 532.3 | 533.3 |
| | 559.3 | 560.3 |

-continued
| MOLSTRUCTURE | Calcd MS | M + H found |
|---|---|---|
| 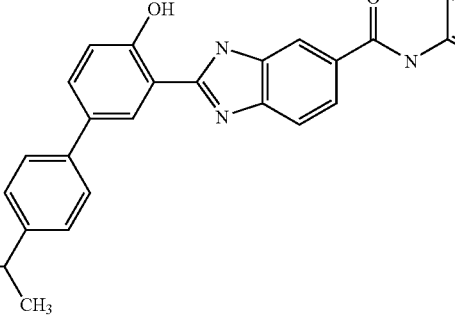 | 573.3 | 574.3 |
| 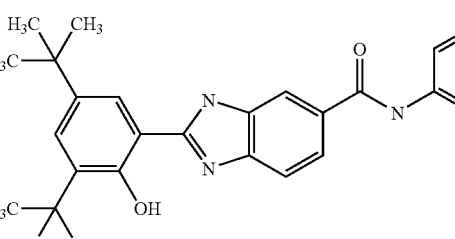 | 553.3 | 554.3 |
| 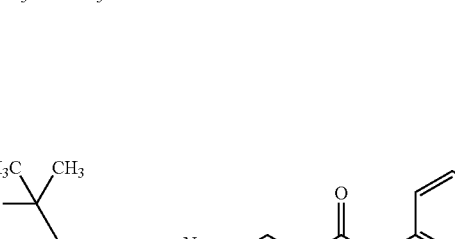 | 567.4 | 568.4 |
| 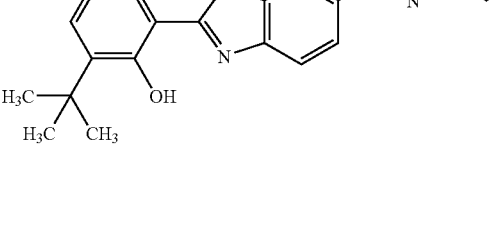 | 389.2 | 390.2 |
| 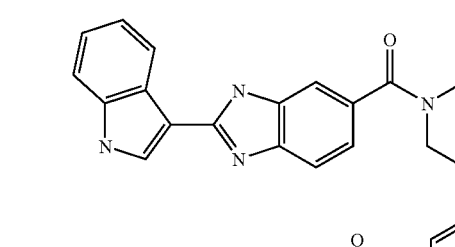 | 536.3 | 537.3 |

-continued
| MOLSTRUCTURE | Calcd MS | M + H found |
|---|---|---|
| 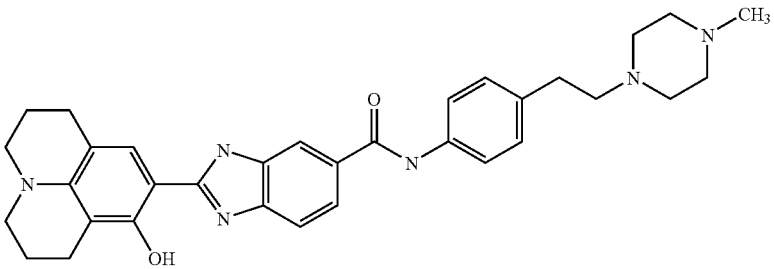 [SMILES: CN1CCN(CCc2ccc(NC(=O)c3ccc4nc(-c5cc6c7c(c5O)CCCN7CCC6)[nH]c4c3)cc2)CC1] | 550.3 | 551.3 |
| 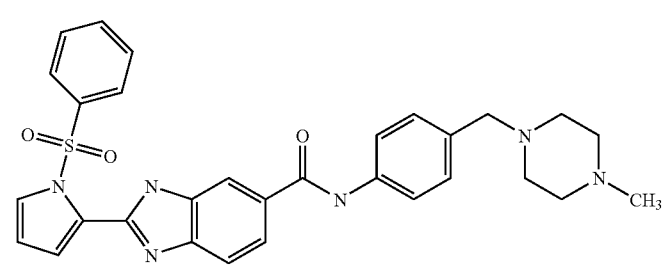 [SMILES: CN1CCN(Cc2ccc(NC(=O)c3ccc4nc(-c5cccn5S(=O)(=O)c5ccccc5)[nH]c4c3)cc2)CC1] | 554.2 | 555.2 |
| 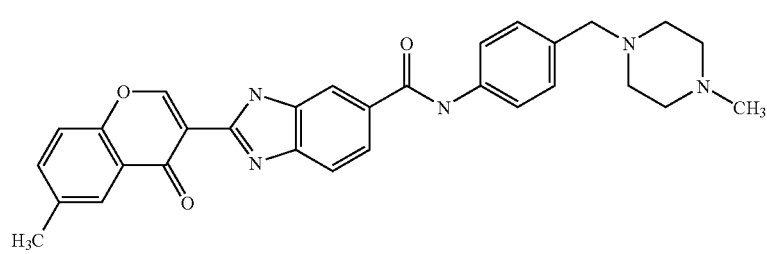 [SMILES: Cc1ccc2occ(-c3nc4ccc(C(=O)Nc5ccc(CN6CCN(C)CC6)cc5)cc4[nH]3)c(=O)c2c1] | 507.2 | 508.2 |
| 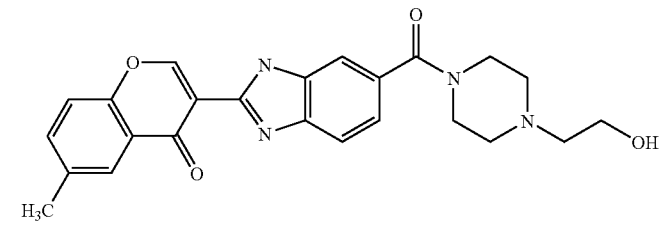 [SMILES: Cc1ccc2occ(-c3nc4ccc(C(=O)N5CCN(CCO)CC5)cc4[nH]3)c(=O)c2c1] | 432.2 | 433.2 |
| 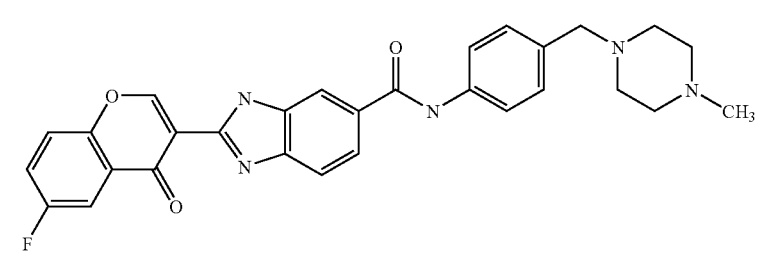 [SMILES: CN1CCN(Cc2ccc(NC(=O)c3ccc4nc(-c5coc6ccc(F)cc6c5=O)[nH]c4c3)cc2)CC1] | 511.2 | 512.2 |
| 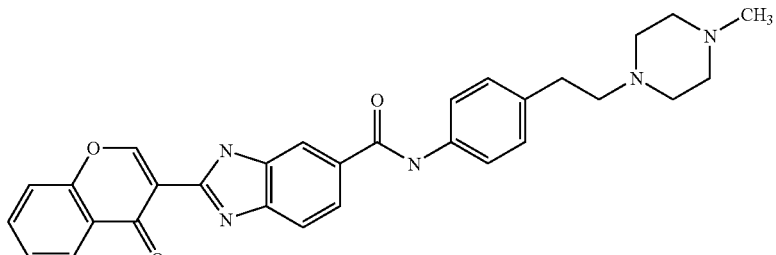 | 525.2 | 526.2 |

-continued

| MOLSTRUCTURE | Calcd MS | M + H found |
|---|---|---|
| | 500.3 | 501.3 |
| | 541.2 | 542.2 |
| | 535.3 | 536.3 |
| | 549.3 | 550.3 |
| | 527.2 | 528.2 |
| | 512.3 | 513.3 |

-continued
| MOLSTRUCTURE | Calcd MS | M + H found |
|---|---|---|
| 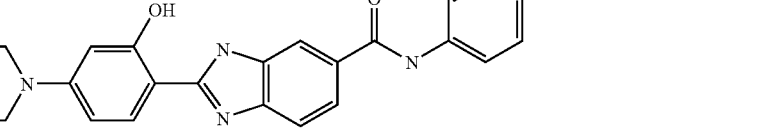 | 526.3 | 527.3 |
| 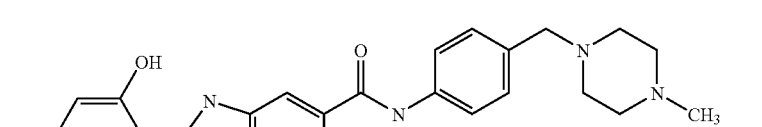 | 497.3 | 498.3 |
| 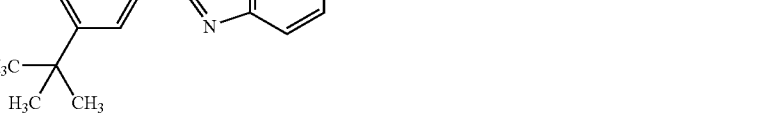 | 511.3 | 512.3 |
| 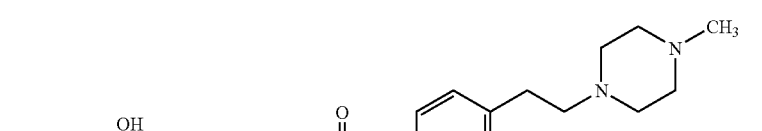 | 422.2 | 423.2 |
| 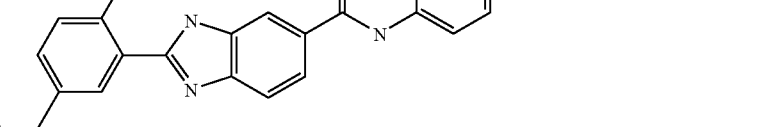 | 497.3 | 498.3 |
| 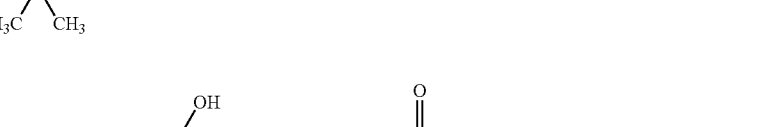 | 511.3 | 512.3 |

-continued

| MOLSTRUCTURE | Calcd MS | M + H found |
|---|---|---|
| (structure) | 422.2 | 423.2 |
| (structure) | 483.3 | 484.3 |
| (structure) | 394.2 | 395.2 |
| (structure) | 547.3 | 548.3 |
| (structure) | 561.3 | 562.3 |
| (structure) | 473.2 | 474.2 |

| MOLSTRUCTURE | Calcd MS | M + H found |
|---|---|---|
| | 443.2 | 444.2 |
| | 457.3 | 458.3 |
| | 368.2 | 369.2 |
| | 511.3 | 512.3 |
| | 525.3 | 526.3 |
| | 436.3 | 437.2 |
| | 532.3 | 533.3 |

-continued

| MOLSTRUCTURE | Calcd MS | M + H found |
|---|---|---|
| | 546.3 | 547.3 |
| | 457.2 | 458.2 |
| | 518.2 | 519.2 |
| | 492.2 | 493.2 |
| | 491.2 | 492.2 |
| | 505.2 | 506.2 |

| MOLSTRUCTURE | Calcd MS | M + H found |
|---|---|---|
| 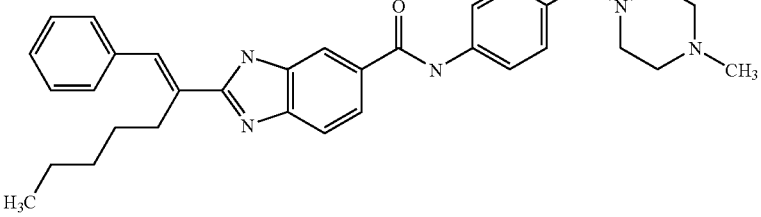 | 521.3 | 522.3 |
| 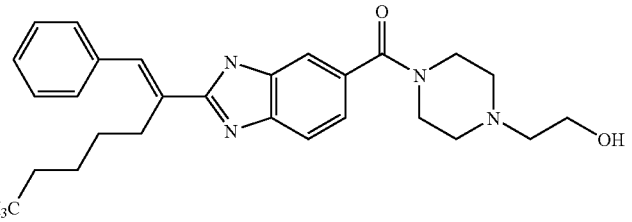 | 446.3 | 447.3 |
| 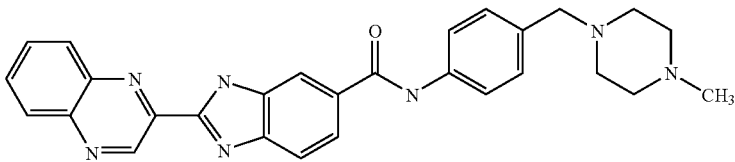 [SMILES: CN1CCN(Cc2ccc(NC(=O)c3ccc4nc(-c5cnc6ccccc6n5)[nH]c4c3)cc2)CC1] | 477.2 | 478.2 |
| 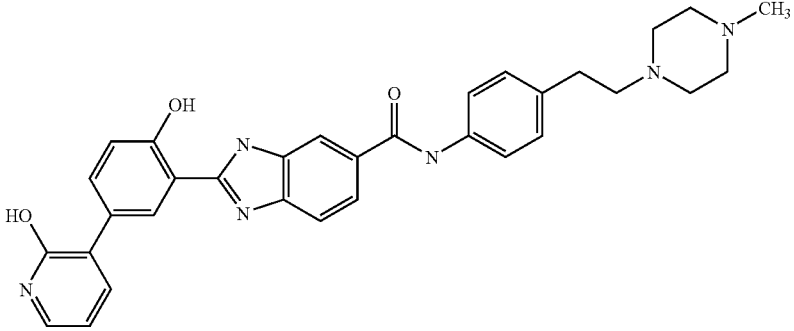 [SMILES: CN1CCN(CCc2ccc(NC(=O)c3ccc4nc(-c5cc(-c6cccnc6O)ccc5O)[nH]c4c3)cc2)CC1] | 548.3 | 549.3 |

Method C: An array of 2318-mL vials (3 diamines and 77 aldehydes) was prepared. To a solution of diamine 1 (125 μmole each) in absolute EtOH/HOAc (95/5, v/v, 1.25 mL) was added aldehyde (125 μmole each, 1.25 mL). The vial was capped and heated at 85° C. for 48 h on an orbital shaker. After the reaction cooled down to about 50° C., the cap was removed and the vial was heated at 85° C. for 1 h to evaporate solvents. The residue was dissolved in DMSO and filtered through a bed of celite (Thompson Instrument Company, California, 35 mg of celite per well). The sample was then concentrated under reduced pressure to afford the crude product which was then directly purified by reverse phase HPLC.

The following compounds were prepared according to method C:

| MOLSTRUCTURE | Calcd MS | M + H found |
|---|---|---|
| 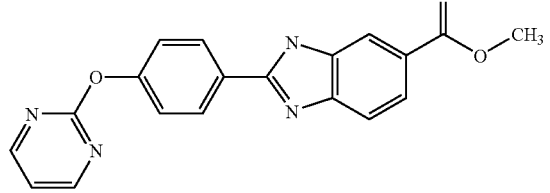 | 346.1 | 347.1 |

-continued

| MOLSTRUCTURE | Calcd MS | M + H found |
|---|---|---|
| | 328.1 | 329.1 |
| | 315.1 | 316.1 |
| | 319.1 | 320.1 |
| | 262.1 | 263.1 |
| | 301.1 | 302.1 |
| | 237.1 | 238.1 |
| | 276.1 | 277.1 |
| | 352.1 | 353.1 |

-continued

| MOLSTRUCTURE | Calcd MS | M + H found |
|---|---|---|
| | 295.1 | 296.1 |
| | 334.1 | 335.1 |
| | 312.1 | 313.1 |
| | 294.1 | 295.1 |
| | 295.1 | 296.1 |
| | 334.1 | 335.1 |
| | 332.1 | 333.1 |

-continued
| MOLSTRUCTURE | Calcd MS | M + H found |
|---|---|---|
| 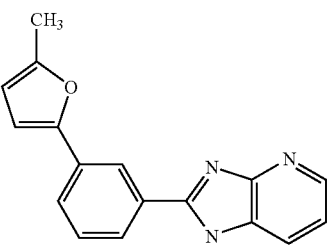 [SMILES: Cc1ccc(-c2cccc(-c3nc4ncccc4[nH]3)c2)o1] | 275.1 | 276.1 |
| 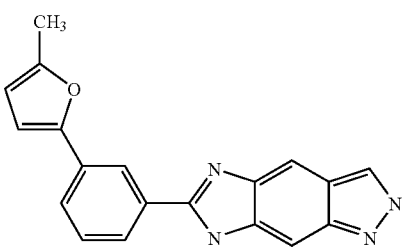 [SMILES: Cc1ccc(-c2cccc(-c3nc4cc5c[nH]nc5cc4[nH]3)c2)o1] | 314.1 | 315.1 |
| 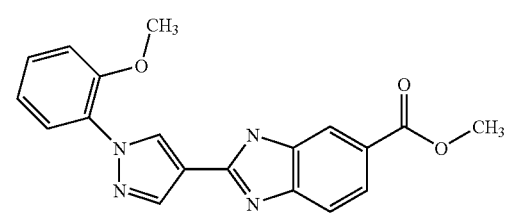 [SMILES: COC(=O)c1ccc2nc(-c3cnn(-c4ccccc4OC)c3)[nH]c2c1] | 348.1 | 349.1 |
| 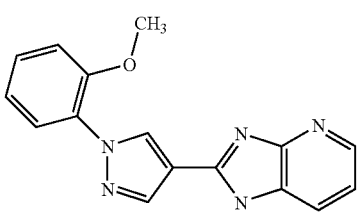 [SMILES: COc1ccccc1-n1cc(-c2nc3ncccc3[nH]2)cn1] | 291.1 | 292.1 |
| 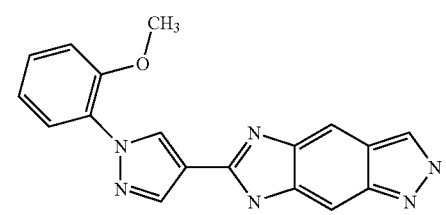 [SMILES: COc1ccccc1-n1cc(-c2nc3cc4c[nH]nc4cc3[nH]2)cn1] | 330.1 | 331.1 |
| 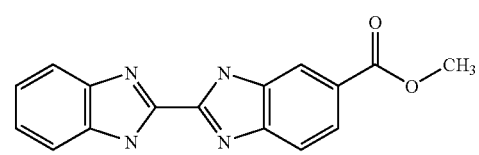 [SMILES: COC(=O)c1ccc2nc(-c3nc4ccccc4[nH]3)[nH]c2c1] | 292.1 | 293.1 |
| 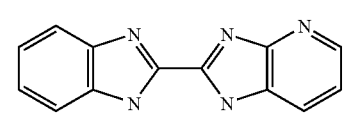 [SMILES: c1ccc2[nH]c(-c3nc4ncccc4[nH]3)nc2c1] | 235.1 | 236.1 |
| 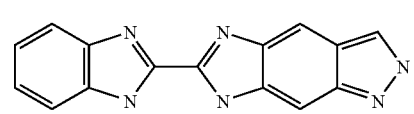 [SMILES: c1ccc2[nH]c(-c3nc4cc5c[nH]nc5cc4[nH]3)nc2c1] | 274.1 | 275.1 |

-continued
| MOLSTRUCTURE | Calcd MS | M + H found |
|---|---|---|
| 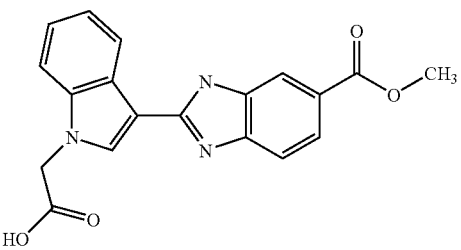 [SMILES: COC(=O)c1ccc2nc(-c3cn(CC(=O)O)c4ccccc34)[nH]c2c1] | 349.1 | 350.1 |
| 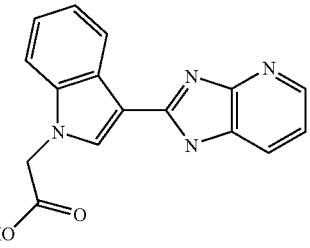 | 292.1 | 293.1 |
| 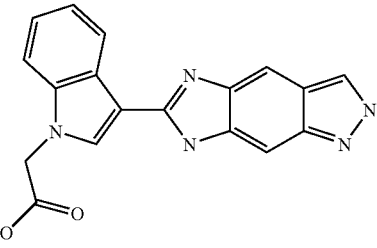 | 331.1 | 332.1 |
| 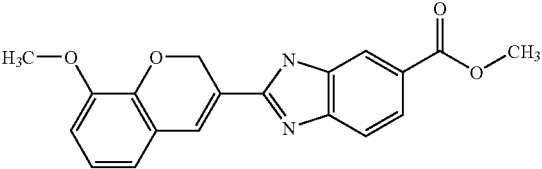 | 336.1 | 337.1 |
| 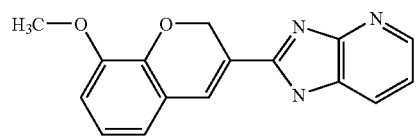 | 279.1 | 280.1 |
| 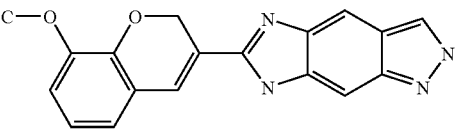 | 318.1 | 319.1 |
| 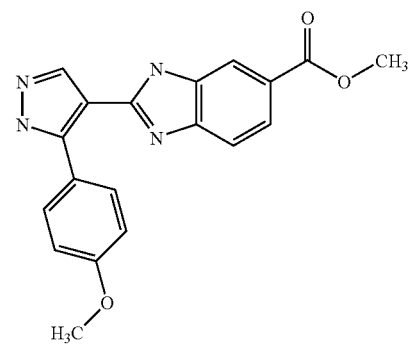 [SMILES: COC(=O)c1ccc2nc(-c3cn[nH]c3-c3ccc(OC)cc3)[nH]c2c1] | 348.1 | 349.1 |

-continued

| MOLSTRUCTURE | Calcd MS | M + H found |
|---|---|---|
| | 291.1 | 292.1 |
| | 330.1 | 331.1 |
| | 335.1 | 336.1 |
| | 278.1 | 279.1 |
| | 317.1 | 318.1 |
| | 318.1 | 319.1 |
| | 261.1 | 262.1 |
| | 300.1 | 301.1 |

-continued
| MOLSTRUCTURE | Calcd MS | M + H found |
|---|---|---|
| 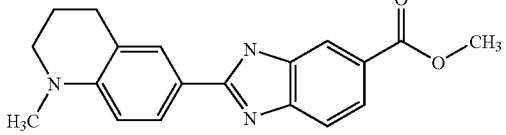 | 321.1 | 322.1 |
| 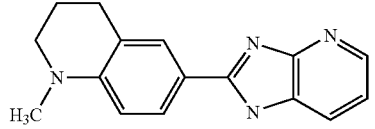 | 264.1 | 265.1 |
| 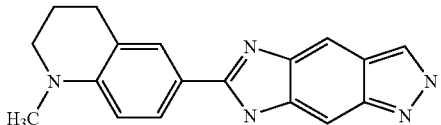 | 303.1 | 304.1 |
| 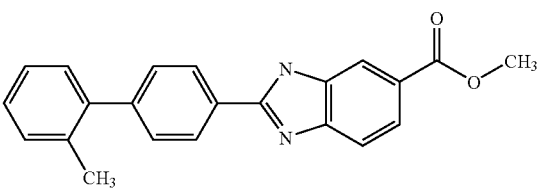 [SMILES: COC(=O)c1ccc2nc(-c3ccc(-c4ccccc4C)cc3)[nH]c2c1] | 342.1 | 343.1 |
| 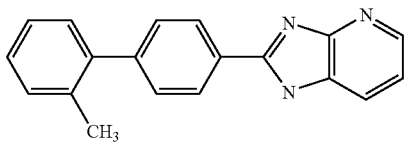 [SMILES: Cc1ccccc1-c1ccc(-c2nc3ncccc3[nH]2)cc1] | 285.1 | 286.1 |
| 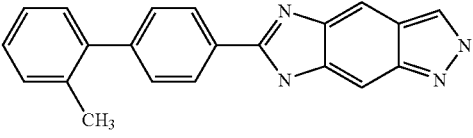 | 324.1 | 325.1 |
| 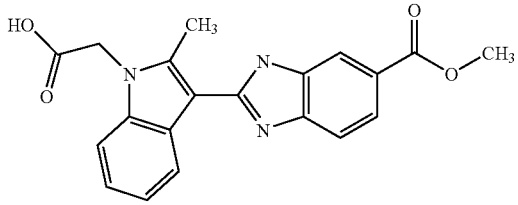 [SMILES: COC(=O)c1ccc2nc(-c3c(C)n(CC(=O)O)c4ccccc34)[nH]c2c1] | 363.1 | 364.1 |
| 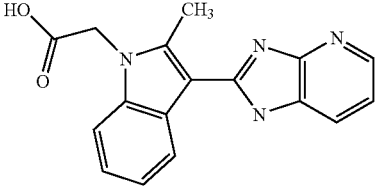 [SMILES: Cc1c(-c2nc3ncccc3[nH]2)c2ccccc2n1CC(=O)O] | 306.1 | 307.1 |
| 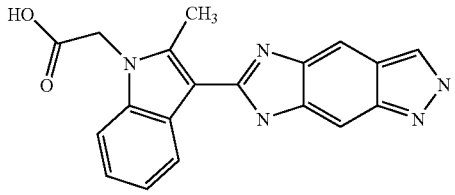 [SMILES: Cc1c(-c2nc3cc4c[nH]nc4cc3[nH]2)c2ccccc2n1CC(=O)O] | 345.1 | 346.1 |

-continued

| MOLSTRUCTURE | Calcd MS | M + H found |
|---|---|---|
| (methyl 2-(5-(3-hydroxy-3-methylbut-1-ynyl)thiophen-2-yl)-1H-benzimidazole-5-carboxylate) | 340.1 | 341.1 |
| (2-(5-(3-hydroxy-3-methylbut-1-ynyl)thiophen-2-yl)-3H-imidazo[4,5-b]pyridine) | 283.1 | 284.1 |
| (2-(5-(3-hydroxy-3-methylbut-1-ynyl)thiophen-2-yl)-imidazo-pyrazole fused) | 322.1 | 323.1 |
| (methyl 2-(4-(pyrimidin-5-ylethynyl)phenyl)-1H-benzimidazole-5-carboxylate) | 354.1 | 355.1 |
| (2-(4-(pyrimidin-5-ylethynyl)phenyl)-3H-imidazo[4,5-b]pyridine) | 297.1 | 298.1 |
| (methyl 2-(benzo[c][1,2,5]thiadiazol-5-yl)-1H-benzimidazole-5-carboxylate) | 310.1 | 311.1 |
| (2-(benzo[c][1,2,5]thiadiazol-5-yl)-imidazo-pyrazole fused) | 292.1 | 293.1 |
| (methyl 2-(1-(4-chlorophenyl)-1H-pyrazol-4-yl)-1H-benzimidazole-5-carboxylate) | 352.1 | 353.1 |

-continued

| MOLSTRUCTURE | Calcd MS | M + H found |
|---|---|---|
| | 295.1 | 296.1 |
| | 334.1 | 335.1 |
| | 353.1 | 354.1 |
| | 296.1 | 297.1 |
| | 335.1 | 336.1 |
| | 355.1 | 356.1 |
| | 298.1 | 299.1 |
| | 337.1 | 338.1 |

-continued
| MOLSTRUCTURE | Calcd MS | M + H found |
|---|---|---|
| 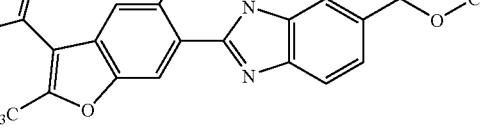 | 412.1 | 413.1 |
| 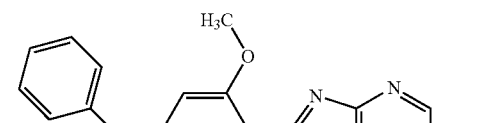 | 355.1 | 356.1 |
| 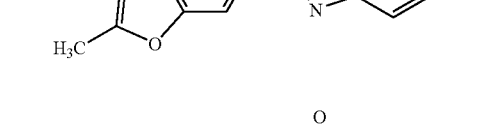 | 318.1 | 319.1 |
| 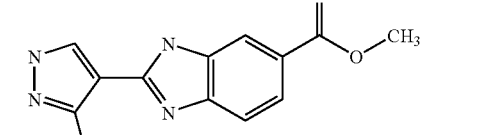 | 261.1 | 262.1 |
|  | 300.1 | 301.1 |
| 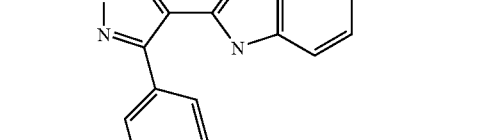 | 336.1 | 337.1 |

-continued
| MOLSTRUCTURE | Calcd MS | M + H found |
|---|---|---|
| 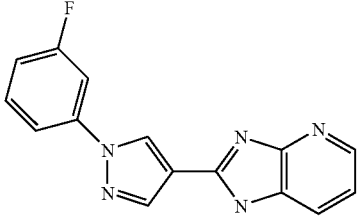 [SMILES: Fc1cccc(-n2cc(-c3nc4ncccc4[nH]3)cn2)c1] | 279.1 | 280.1 |
| 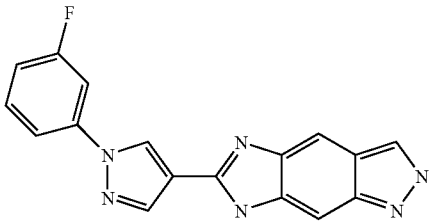 [SMILES: Fc1cccc(-n2cc(-c3nc4cc5c[nH]nc5cc4[nH]3)cn2)c1] | 318.1 | 319.1 |
| 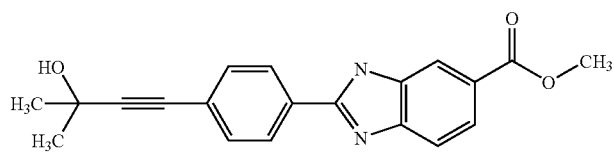 | 334.1 | 335.1 |
| 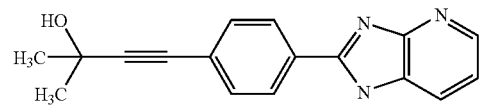 | 277.1 | 278.1 |
| 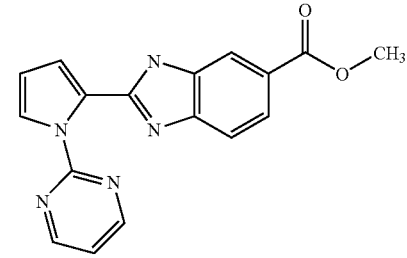 [SMILES: COC(=O)c1ccc2nc(-c3cccn3-c3ncccn3)[nH]c2c1] | 319.1 | 320.1 |
| 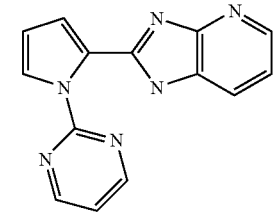 [SMILES: c1cnc(-n2cccc2-c2nc3ncccc3[nH]2)nc1] | 262.1 | 263.1 |
| 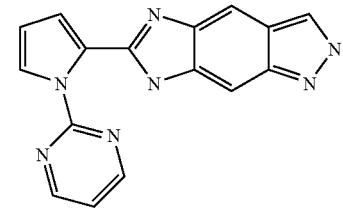 [SMILES: c1cnc(-n2cccc2-c2nc3cc4c[nH]nc4cc3[nH]2)nc1] | 301.1 | 302.1 |

-continued
| MOLSTRUCTURE | Calcd MS | M + H found |
|---|---|---|
| 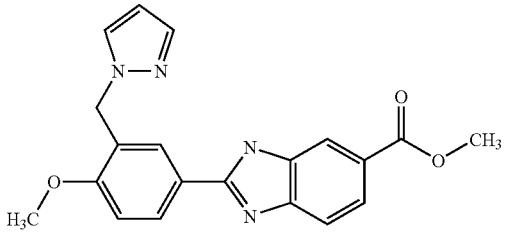 | 362.1 | 363.1 |
| 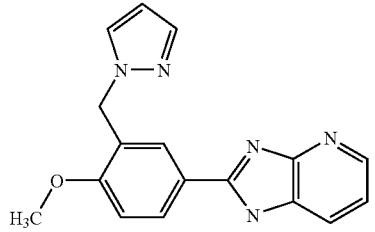 [SMILES: COc1ccc(-c2nc3ncccc3[nH]2)cc1Cn1cccn1] | 305.1 | 306.1 |
| 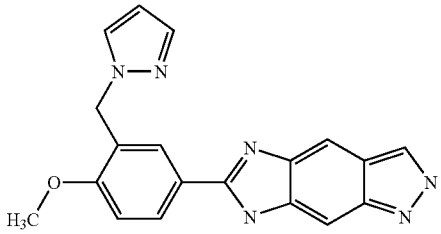 [SMILES: COc1ccc(-c2nc3cc4c[nH]nc4cc3[nH]2)cc1Cn1cccn1] | 344.1 | 345.1 |
| 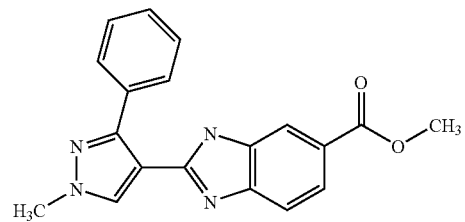 | 332.1 | 333.1 |
| 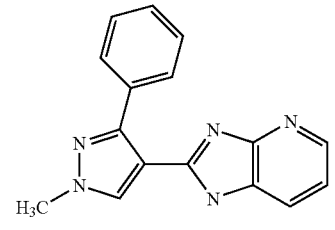 [SMILES: Cn1cc(-c2nc3ncccc3[nH]2)c(-c2ccccc2)n1] | 275.1 | 276.1 |
| 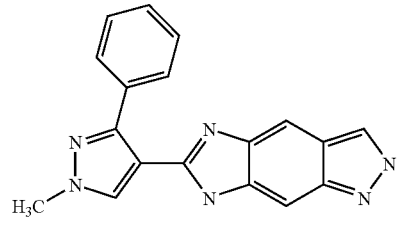 [SMILES: Cn1cc(-c2nc3cc4c[nH]nc4cc3[nH]2)c(-c2ccccc2)n1] | 314.1 | 315.1 |

-continued

| MOLSTRUCTURE | Calcd MS | M + H found |
|---|---|---|
| | 335.1 | 336.1 |
| | 278.1 | 279.1 |
| | 317.1 | 318.1 |
| | 282.1 | 283.1 |
| | 321.2 | 322.2 |
| | 367.2 | 368.2 |
| | 310.2 | 311.2 |

-continued
| MOLSTRUCTURE | Calcd MS | M + H found |
|---|---|---|
| 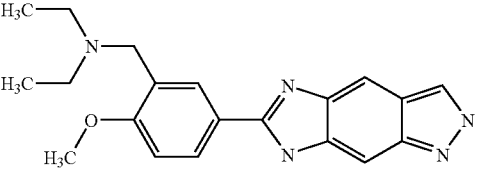 [SMILES: CCN(CC)Cc1cc(-c2nc3cc4c[nH]nc4cc3[nH]2)ccc1OC] | 349.2 | 350.2 |
| 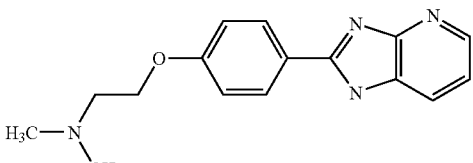 | 282.1 | 283.1 |
| 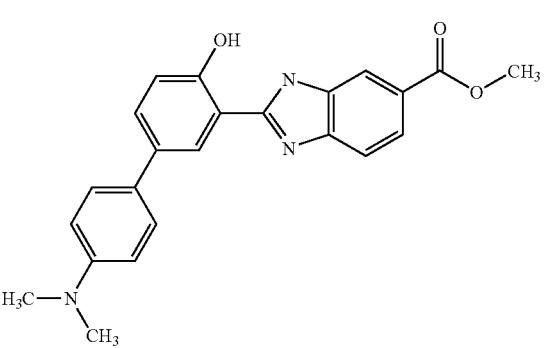 | 387.2 | 388.2 |
| 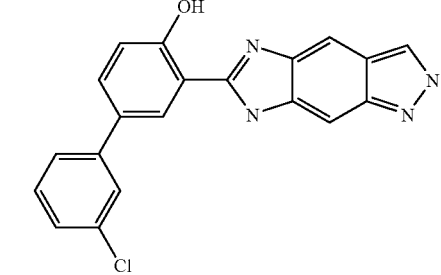 [SMILES: Oc1ccc(-c2cccc(Cl)c2)cc1-c1nc2cc3c[nH]nc3cc2[nH]1] | 360.1 | 361.1 |
| 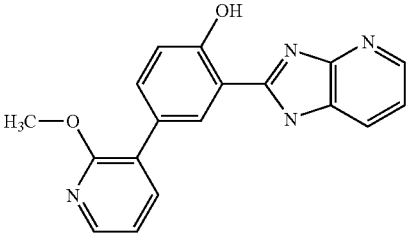 [SMILES: COc1ncccc1-c1ccc(O)c(-c2nc3ncccc3[nH]2)c1] | 318.1 | 319.1 |
| 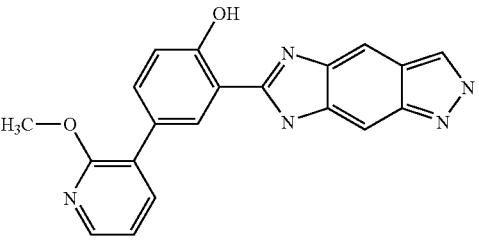 [SMILES: COc1ncccc1-c1ccc(O)c(-c2nc3cc4c[nH]nc4cc3[nH]2)c1] | 357.1 | 358.1 |

-continued

| MOLSTRUCTURE | Calcd MS | M + H found |
|---|---|---|
| | 388.2 | 389.2 |
| | 331.1 | 332.1 |
| | 379.1 | 380.1 |
| | 322.1 | 323.1 |
| | 361.1 | 362.1 |
| | 401.2 | 402.2 |

-continued
| MOLSTRUCTURE | Calcd MS | M + H found |
|---|---|---|
| 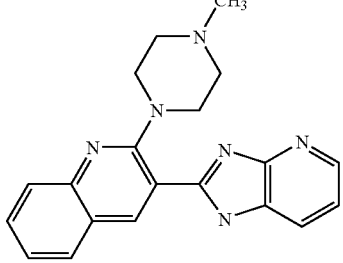 | 344.2 | 345.2 |
| 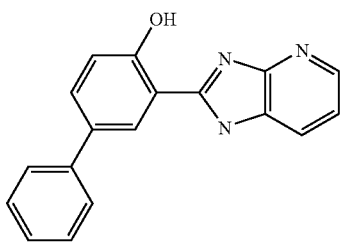 [SMILES: Oc1ccc(-c2ccccc2)cc1-c1nc2ncccc2[nH]1] | 287.1 | 288.1 |
| 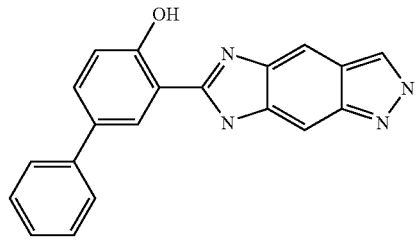 [SMILES: Oc1ccc(-c2ccccc2)cc1-c1nc2cc3c[nH]nc3cc2[nH]1] | 326.1 | 327.1 |
| 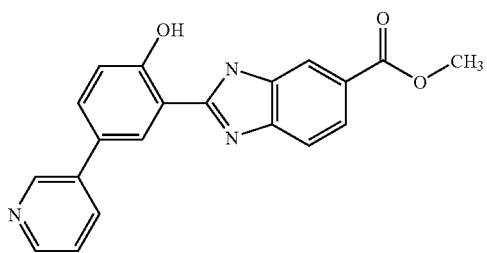 [SMILES: COC(=O)c1ccc2nc(-c3cc(-c4cccnc4)ccc3O)[nH]c2c1] | 345.1 | 346.1 |
| 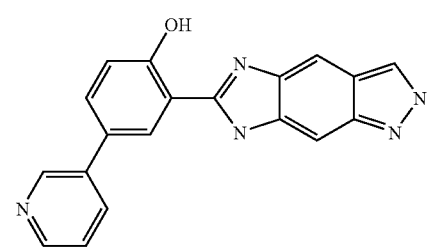 [SMILES: Oc1ccc(-c2cccnc2)cc1-c1nc2cc3c[nH]nc3cc2[nH]1] | 327.1 | 328.1 |

-continued
| MOLSTRUCTURE | Calcd MS | M + H found |
|---|---|---|
| 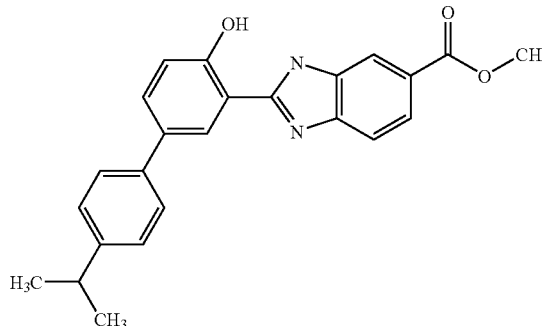 | 386.2 | 387.2 |
| 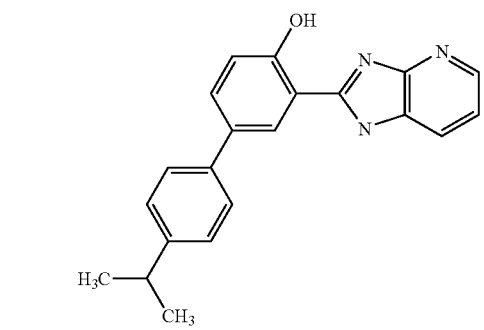 [SMILES: CC(C)c1ccc(-c2ccc(O)c(-c3nc4ncccc4[nH]3)c2)cc1] | 329.2 | 330.2 |
| 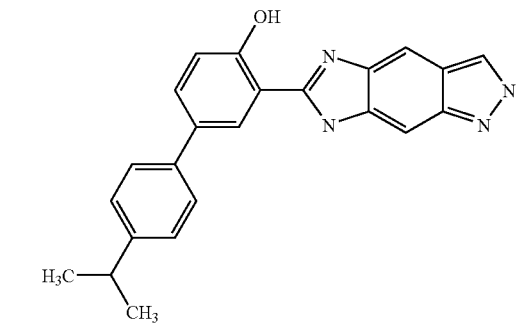 [SMILES: CC(C)c1ccc(-c2ccc(O)c(-c3nc4cc5c[nH]nc5cc4[nH]3)c2)cc1] | 368.2 | 369.2 |
| 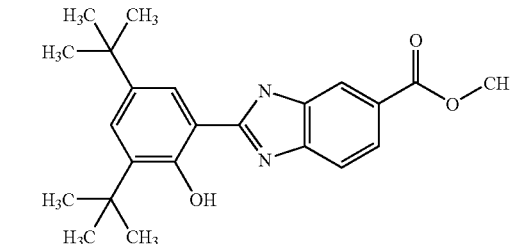 | 380.2 | 381.2 |
| 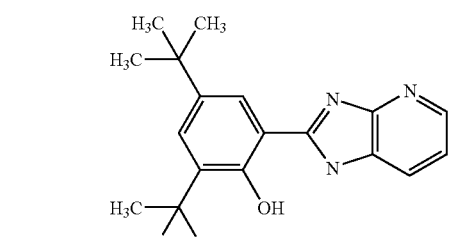 | 323.2 | 324.2 |

-continued
| MOLSTRUCTURE | Calcd MS | M + H found |
|---|---|---|
| 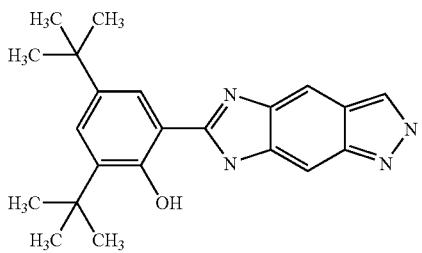 [SMILES: CC(C)(C)c1cc(-c2nc3cc4c[nH]nc4cc3[nH]2)c(O)c(C(C)(C)C)c1] | 362.2 | 363.2 |
| 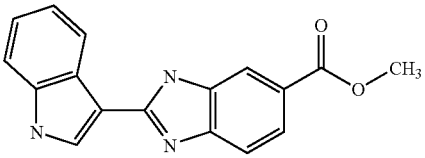 [SMILES: COC(=O)c1ccc2nc(-c3c[nH]c4ccccc34)[nH]c2c1] | 291.1 | 292.1 |
| 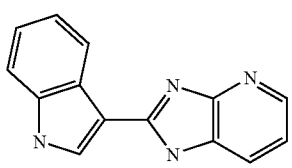 [SMILES: c1cnc2nc(-c3c[nH]c4ccccc34)[nH]c2c1] | 234.1 | 235.1 |
| 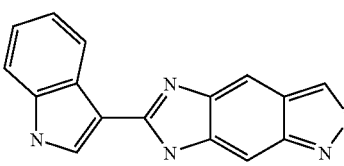 | 273.1 | 274.1 |
| 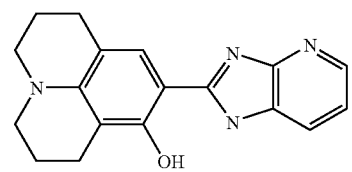 [SMILES: Oc1c(-c2nc3ncccc3[nH]2)cc2c3c1CCCN3CCC2] | 306.1 | 307.1 |
| 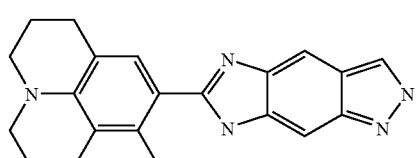 | 345.2 | 346.2 |
| 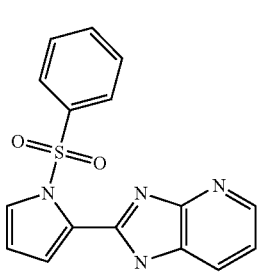 [SMILES: O=S(=O)(c1ccccc1)n1cccc1-c1nc2ncccc2[nH]1] | 324.1 | 325.1 |
| 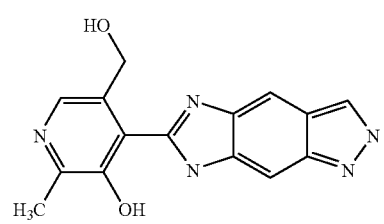 [SMILES: Cc1ncc(CO)c(-c2nc3cc4c[nH]nc4cc3[nH]2)c1O] | 295.1 | 296.1 |

-continued
| MOLSTRUCTURE | Calcd MS | M + H found |
|---|---|---|
| 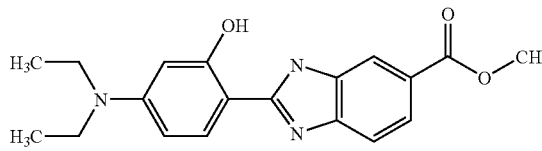 | 339.2 | 340.2 |
| 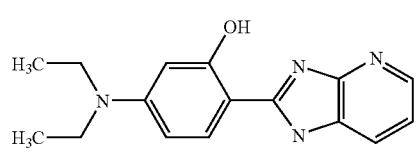 [SMILES: CCN(CC)c1ccc(-c2nc3ncccc3[nH]2)c(O)c1] | 282.1 | 283.1 |
| 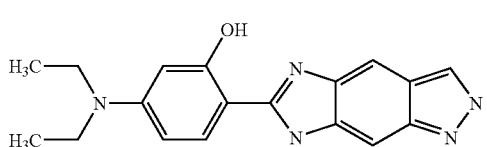 | 321.2 | 322.2 |
| 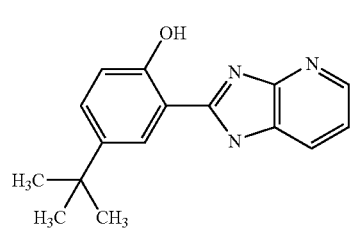 [SMILES: CC(C)(C)c1ccc(O)c(-c2nc3ncccc3[nH]2)c1] | 267.1 | 268.1 |
| 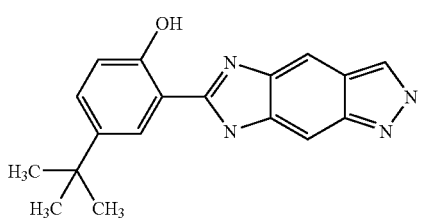 [SMILES: CC(C)(C)c1ccc(O)c(-c2nc3cc4c[nH]nc4cc3[nH]2)c1] | 306.1 | 307.1 |
| 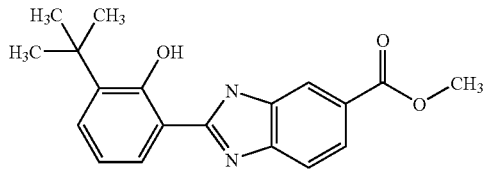 [SMILES: COC(=O)c1ccc2nc(-c3cccc(C(C)(C)C)c3O)[nH]c2c1] | 324.1 | 325.1 |
| 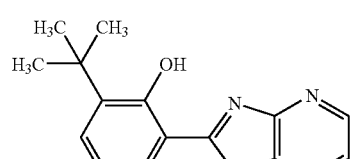 | 267.1 | 268.1 |
| 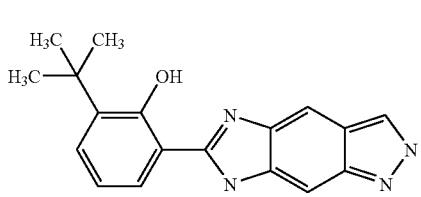 [SMILES: CC(C)(C)c1cccc(-c2nc3cc4c[nH]nc4cc3[nH]2)c1O] | 306.1 | 307.1 |

-continued

| MOLSTRUCTURE | Calcd MS | M + H found |
|---|---|---|
| | 296.1 | 297.1 |
| | 278.1 | 279.1 |
| | 374.1 | 375.1 |
| | 317.1 | 318.1 |
| | 356.1 | 357.1 |
| | 300.1 | 301.1 |
| | 243.1 | 244.1 |
| | 282.1 | 283.1 |

-continued
| MOLSTRUCTURE | Calcd MS | M + H found |
|---|---|---|
| 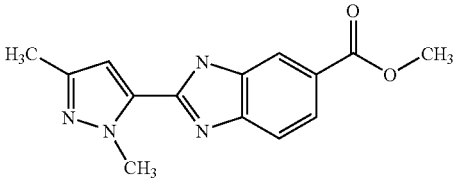 | 270.1 | 271.1 |
| 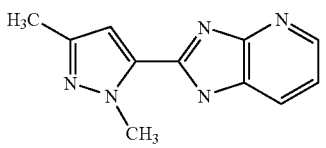 [SMILES: Cc1cc(-c2nc3ncccc3[nH]2)n(C)n1] | 213.1 | 214.1 |
| 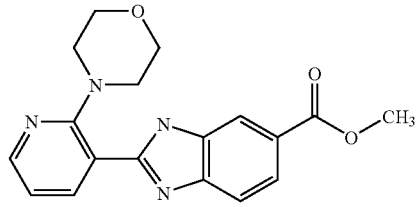 [SMILES: COC(=O)c1ccc2nc(-c3cccnc3N3CCOCC3)[nH]c2c1] | 338.1 | 339.1 |
| 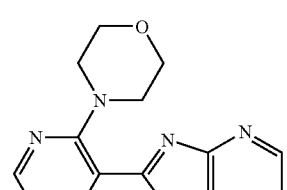 | 281.1 | 282.1 |
| 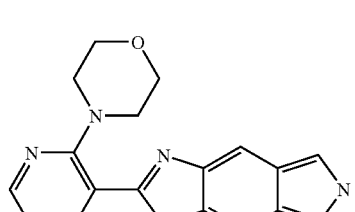 | 320.1 | 321.1 |
| 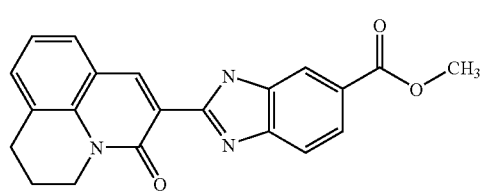 [SMILES: COC(=O)c1ccc2nc(-c3cc4cccc5c4n(c3=O)CCC5)[nH]c2c1] | 359.1 | 360.1 |
| 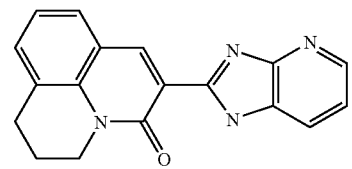 [SMILES: O=c1c(-c2nc3ncccc3[nH]2)cc2cccc3c2n1CCC3] | 302.1 | 303.1 |

-continued
| MOLSTRUCTURE | Calcd MS | M + H found |
|---|---|---|
| 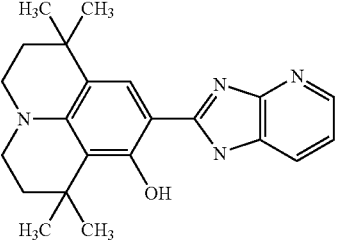 [SMILES: CC1(C)CCN2CCC(C)(C)c3c(O)c(-c4nc5ncccc5[nH]4)cc1c32] | 362.2 | 363.2 |
| 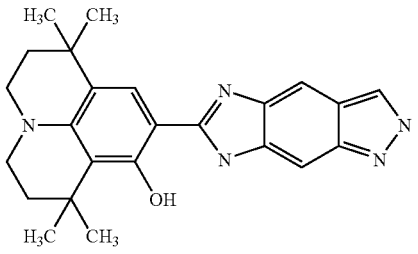 [SMILES: CC1(C)CCN2CCC(C)(C)c3c(O)c(-c4nc5cc6c[nH]nc6cc5[nH]4)cc1c32] | 401.2 | 402.2 |
| 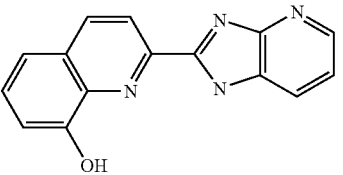 [SMILES: Oc1cccc2ccc(-c3nc4ncccc4[nH]3)nc12] | 262.1 | 263.1 |
| 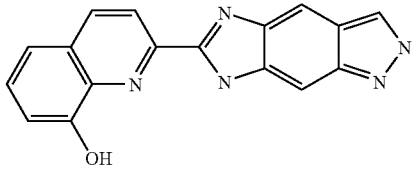 [SMILES: Oc1cccc2ccc(-c3nc4cc5c[nH]nc5cc4[nH]3)nc12] | 301.1 | 302.1 |
| 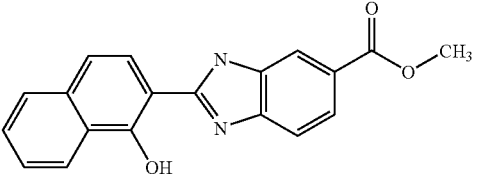 [SMILES: COC(=O)c1ccc2nc(-c3ccc4ccccc4c3O)[nH]c2c1] | 318.1 | 319.1 |
| 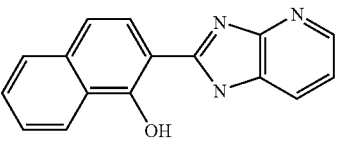 [SMILES: Oc1c(-c2nc3ncccc3[nH]2)ccc2ccccc12] | 261.1 | 262.1 |
| 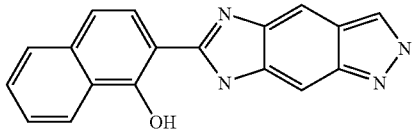 [SMILES: Oc1c(-c2nc3cc4c[nH]nc4cc3[nH]2)ccc2ccccc12] | 300.1 | 301.1 |

-continued
| MOLSTRUCTURE | Calcd MS | M + H found |
|---|---|---|
| 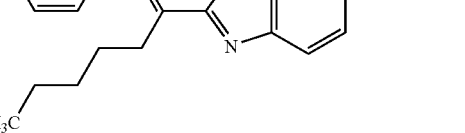 | 348.2 | 349.2 |
| 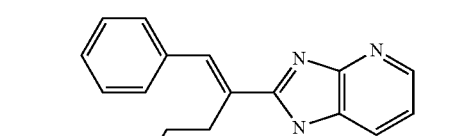 | 291.2 | 292.2 |
|  | 304.1 | 305.1 |
| 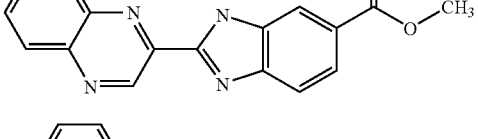 | 286.1 | 287.1 |
| 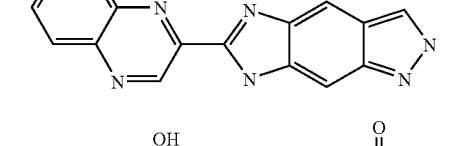 | 361.1 | 362.1 |
| 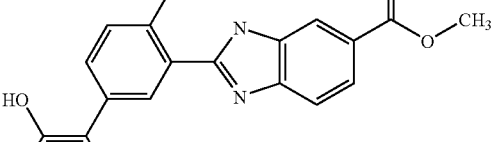 | 304.1 | 305.1 |
6.9 Example 9
Preparation of 2-Hydroxyaryl Benzimidazoles
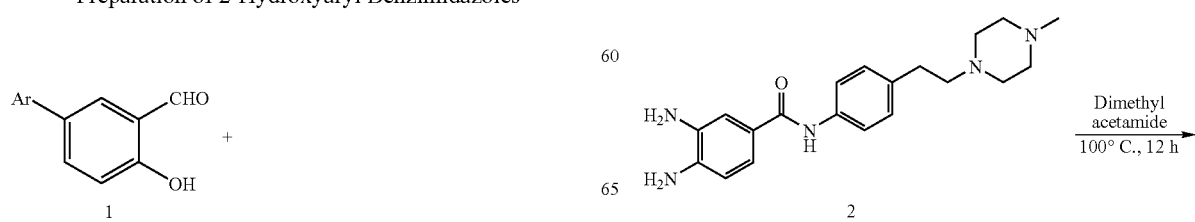
-continued -continued

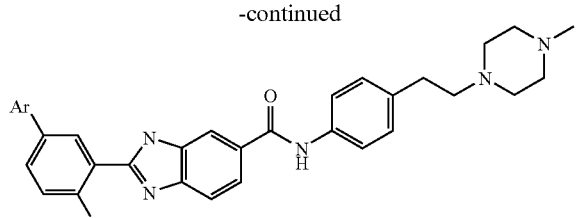

3

A solution of salicylaldehyde derivative 1 (0.5 mmol) and diamine 2 (0.176 g, 0.5 mmol) in dimethylacetamide (4 mL) was stirred at 100° C. for 12 h. Solvent was evaporated and the residue was purified by preparative HPLC to give benzimidazole derivative 3.

The aryl and heteroaryl salicylaldehyde derivatives (1) were prepared by reacting the appropriate arylboronic acid with 5-bromosalicylaldehyde, respectively its substituted derivative, or heteroanalog, either commercially available, or prepared according to general methodology. The reaction sequence is generally known as Suzuki reaction and is outlined in the following scheme:

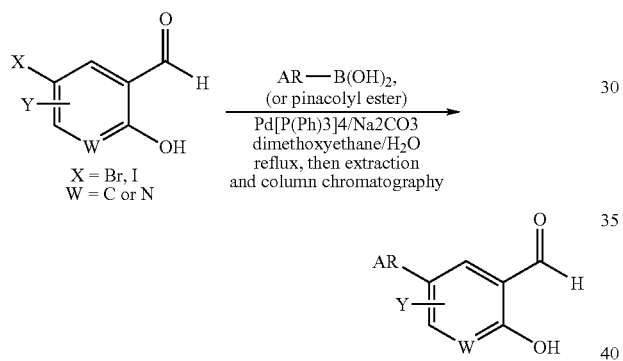

AR=optionally substituted aryl or heteroaryl

The reaction was also performed using the boronic acid derived from the salicylaldehyde portion, according to the following scheme:

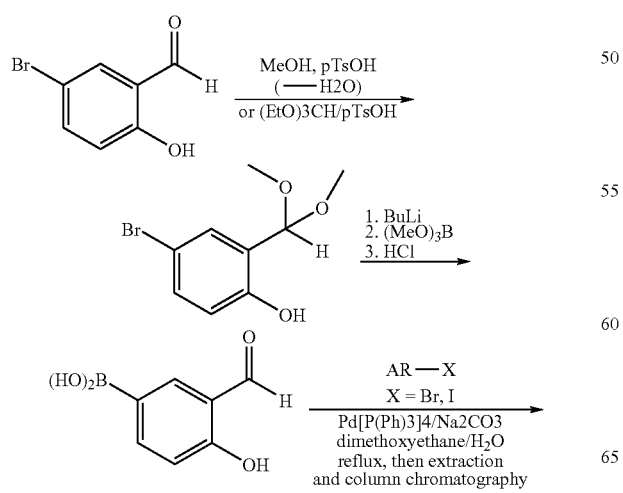

-continued

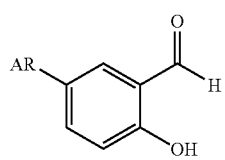

Preparation of Building Blocks—Substituted Aldehydes:

6.10 Example 10

General Procedure for Suzuki Reaction

A mixture of 5-bromosalicylaldehyde (2.01 g, 10.0 mmol), boronic acid (11.0 mmol), sodium carbonate (1.17 g, 11.0 mmol), Pd(PPh$_3$)$_4$ (0.58 g, 0.50 mmol), DME (18 ml) and water (6 ml) was degassed, stirred under N$_2$ at 100° C. for 5 h. After cooling to RT, water (10 ml) and DCM (20 ml) were added, mixture was shacked for 30 min, organic layer was separated, water layer was extracted with DCM (2*100 ml). Extracts were dried over Na$_2$SO$_4$, evaporated. The residue was dissolved in DCM (5 ml), purified ob SiO$_2$ (50 g) hexane-EtOAc (0 to 20%).

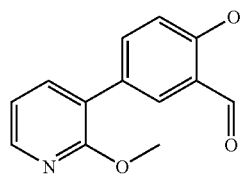 [SMILES: COc1ncccc1-c1ccc(O)c(C=O)c1]

2-Hydroxy-5-(2-methoxy-pyridin-3-yl)-benzaldehyde

A mixture of 5-bromosalicylaldehyde (2.88 g, 14.3 mmol), 2-methoxypyridyl-3-boronic acid (2.20 g, 15.7 mmol), sodium carbonate (1.68 g, 15.7 mmol), Pd(PPh$_3$)$_4$ (0.84 g, 0.73 mmol), DME (21 ml) and water (7 ml) was degassed, stirred under N$_2$ at 100° C. for 5 h. After cooling to RT, water (10 ml) and DCM (20 ml) were added, mixture was shacked for 30 min, organic layer was separated, water layer was extracted with DCM (2*100 ml). Extracts were dried over Na$_2$SO$_4$, evaporated. The residue was dissolved in DCM (5 ml), purified ob SiO$_2$ (100 g) hexane-EtOAc (0 to 20%). White solid 2.23 g (9.70 mmol, 68%). $^1$H NMR (300 MHz, DMSO) δ 10.88 (s, 1H), 10.31 (s, 1H), 8.16 (dd, J=1.9, 5.1 Hz, 1H), 7.84 (d, J=2.5 Hz, 1H), 7.74 (m, 2H), 7.08 (m, 2H), 3.88 (s, 3H).

This method is applicable to the synthesis of substituted derivatives and the following compounds were prepared by application of the above methodology:

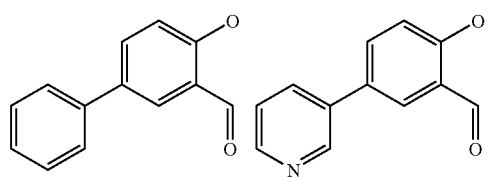

735
-continued
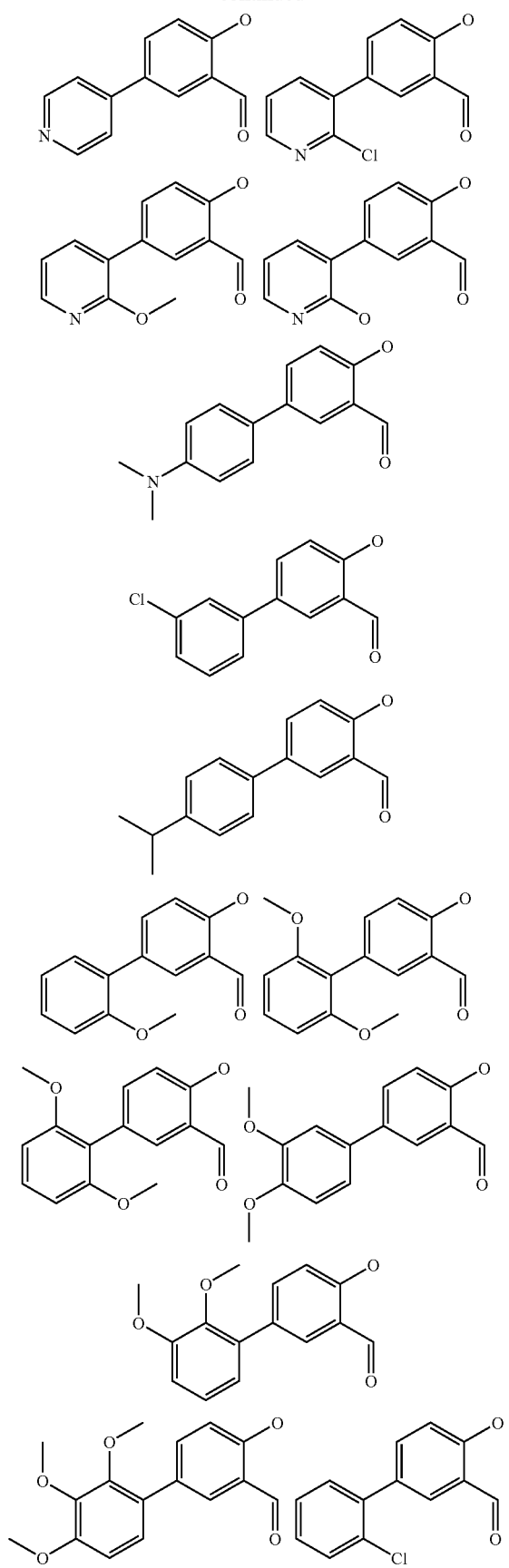
736
-continued
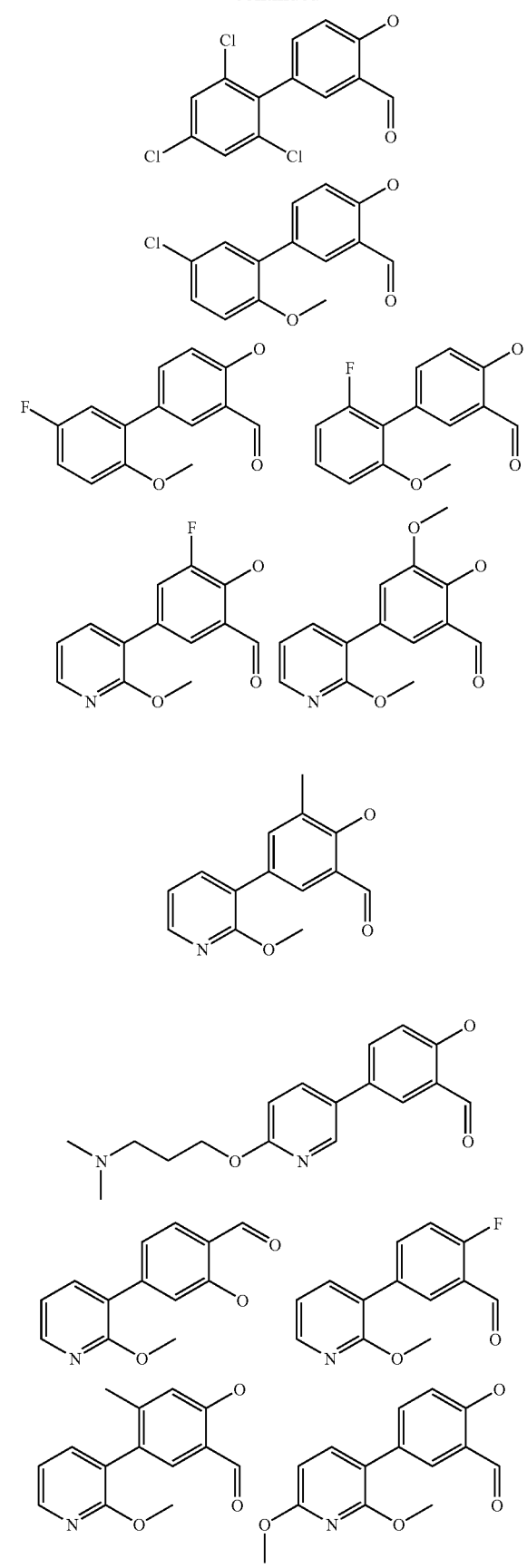

-continued

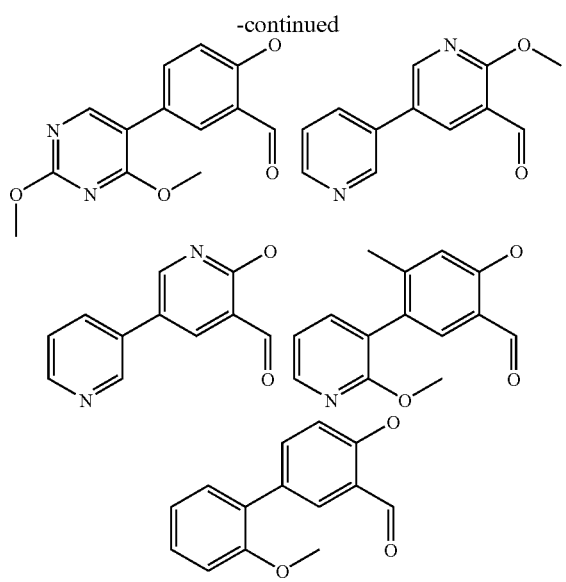

Additional aldehydes were prepared by application of the following two methodologies (Suzuki Reaction):

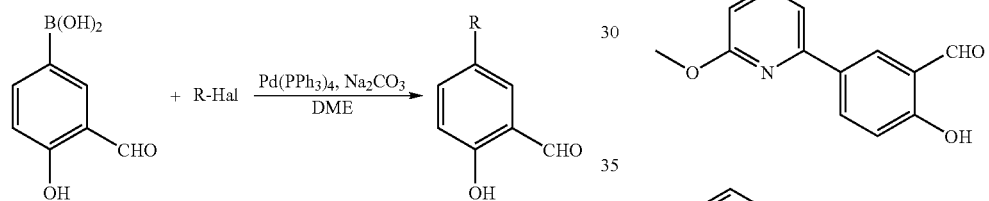

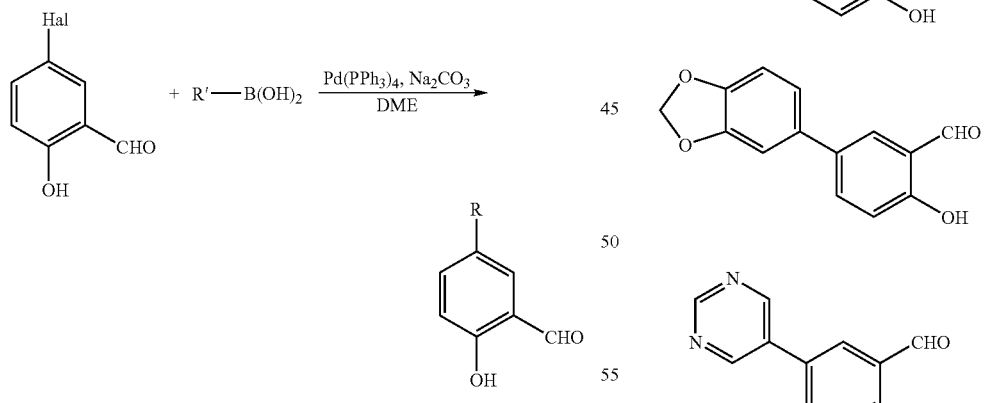

In a 250-mL three-necked flask, the halo-substituted compound R-Hal (18 mmol) was dissolved in redistilled dimethoxyethane (40 mL). The mixture was stirred for 5 min under argon atmosphere. Then tetrakis(triphenylphosphine) palladium (0.7 g, 0.6 mmol) was added. The reaction mixture was stirred for 45 min under argon atmosphere. Then a deaerated solution of boric acid R'—B(OH)$_2$ (1.1 eq.) in a minimal amount of redistilled methanol (~5 mL per 2 g of boric acid) was added dropwise. After 10 min of stirring, deaerated 2 M Na$_2$CO$_3$ (50 mL) was slowly added dropwise with vigorous stirring under argon atmosphere. The obtained suspension was refluxed for approx. 20 h. Then the reaction mixture was cooled to room temperature and evaporated to dryness in a rotary evaporator, not exceeding 40° C. The dry residue was dispersed in an ultrasonic bath and carefully acidified with 1 N HCl to pH ~2 with stirring. Then solid NaHCO$_3$ was added with vigorous stirring, adjusting pH to ~5. After that, the mixture was extracted with CHCl$_3$ (6×30 mL). The combined extracts were evaporated in a rotary evaporator. The dry residue was dissolved in a minimal amount of CHCl$_3$ and passed through a silica gel column (chloroform-hexane, 4:1, as eluent). The compounds obtained, the scheme of synthesis, and yields are listed in the table below:

| Compound | Scheme of Synthesis | Yield, % |
|---|---|---|
|  | A | 28 |
|  | A | 26 |
|  | A | 44 |
|  | B | 54 |
|  | A | 28 |
|  | B | 40 |

| Compound | Scheme of Synthesis | Yield, % |
|---|---|---|
| (biphenyl-CHO-OH) | B | 14 |
| (dimethoxy biphenyl-CHO-OH) | B | 33 |
| (pyridinyl-phenyl-CHO-OH) | A | 67 |
| (benzothiazolyl-phenyl-CHO-OH) | B | 42 |
| (pyridinyl-phenyl-CHO-OH) | A | 33 |
| (methylquinolinyl-phenyl-CHO-OH) | A | 24 |
| (dimethylpyrazinyl-phenyl-CHO-OH) | A | 70 |

| Compound | Scheme of Synthesis | Yield, % |
|---|---|---|
| (pyrazinyl-phenyl-CHO-OH) | A | 50 |

Preparation of 3-formyl-hydroxyphenyl Boronic Acid

4-Bromo-2-dimethoxymethylphenol

A mixture of 5-bromosalicylaldehyde (41.0 g, 0.200 mol), trimethyl orthoformate (205 ml, 1.83 mol) and dry p-toluenesulfonic acid (1.77 g, 0.010 mol) was refluxed for 24 h. After the reaction mixture was cooled to the RT, sodium bicarbonate (50 g) was carefully added, and the mixture was ultrasonicated for 5 min. The liquid was separated; the solid was washed with dry benzene (25 ml) and removed by filtration. Combined solutions were evaporated. The residue was triturated with dry hexane (30 ml) if necessary cooled to −18° C. Precipitate formed was collected by filtration, washed with dry hexane (20 ml). Slightly yellow crystals, 44.2 g (0.179 mol, 89%).

3-Formyl-hydroxyphenyl boronic acid

To a solution of 4-bromo-2-dimethoxymethylphenol (10.0 g, 0.36 mol) in abs. ether (200 ml) n-BuLi (68 ml of 1.6 M hexane solution, 0.109 mol) was added dropwise under argon keeping the reaction mixture temperature below 25° C. Than the reaction mixture was refluxed for 3 h, then cooled to −95° C., trimethyl borate (14.3 ml, 0.128 mol) was added dropwise keeping the temperature below −95° C. After the addition was completed the temperature was increased to the RT overnight. Aqueous 1 M HCl (200 ml) was added to the stirring reaction mixture to reach pH 1.0. Organic phase was separated; aqueous phase was extracted with ether (4×50 ml). Combined organic phases were evaporated; the residue was triturated with benzene (25 ml) using an ultrasonic bath. Tan precipitate formed was collected by filtration, washed with hexane (2×10 ml) dried. Yield 2.63 g (15.8 mmol, 43%).

6.11 Example 11

Benzoimidazole Amide Formed via Coupling with the Acid

2-[2-Hydroxy-5-(2-methoxy-pyridin-3-yl)-phenyl]-3H-benzoimidazole-5-carboxylic acid To an ice-cold flask with a rubber stopper were added 2-hydroxy-5-(2-methoxy-pyridin-3-yl)-benzaldehyde (22.35 g, 0.0975 mol) and 3,4-diamino-benzoic acid (17.2 g, 0.113 mol) and the solid mixture was stirred at 0° C. for 15 min. Then DMA (120 mL) was added into the mixture via a syringe and the resulting solution was stirred at 0° C. for 2 h, and at the room temperature for 3 h. The rubber stopper was removed and the reaction mixture was stirred at 110° C. for 14 h open to the air. The DMA was removed under reduced pressure and the residue was mixed with 200 mL EtOAc, and sonicated for 15 min. The mixture was filtered to get the solid precipitate, which was mixture with 150 mL EtOAc, and sonicated for 5 min. The resulting mixture was filtered to get the solid crude that was dried at 40° C. for 6 h under reduced pressure to afford a mixture of the title compound and DMA (ratio 1:1) (16.15 g, 38%). $^1$H NMR (DMSO-d$_4$) δ 3.92 (s, 3H), 7.14 (m, 1H), 7.15 (s, 1H), 7.64 (d, J=6 Hz, 1H), 7.74 (d, J=6 Hz, 1H), 7.84 (d, J=6 Hz, 1H), 7.91 (d, J=6 Hz, 1H), 8.19 (d, J=6 Hz, 1H), 8.21 (d, J=6 Hz, 1H), 8.29 (s, 1H). DMA also shows as 61.96 (s, 3H), 2.79 (s, 3H) and 2.94 (s, 3H). ESI-MS m/z 362.5 (MH$^+$).

2-[2-Hydroxy-5-(2-methoxy-pyridin-3-yl)-phenyl]-3H-benzoimidazole-5-carboxylic acid [2-methoxy-4-(4-methyl-piperazin-1-yl)-phenyl]-amide To a solution of 2-[2-hydroxy-5-(2-methoxy-pyridin-3-yl)-phenyl]-3H-benzoimidazole-5-carboxylic acid (containing 1 equivalent of DMA, 44 mg, 0.1 mmol), 2-methoxy-4-(4-methyl-piperazin-1-yl)-phenylamine di HCl salt (29.4 mg, 0.1 mmol) and HATU (38 mg, 0.1 mmol) in DMF (1.2 mL) was added DIEA (45 mg, 0.35 mmol). The reaction mixture was stirred at room temperature for 2 h and heated at 60° C. for 3 h, and then evaporated to dry under reduced pressure. The residue was diluted with DMSO (1.5 mL), filtered and then purified with using HPLC (TFA/H$_2$O/CH$_3$CN) to afford the title compound (26.4 mg, 39%). ESI-MS m/z 565.5 (MH$^+$).

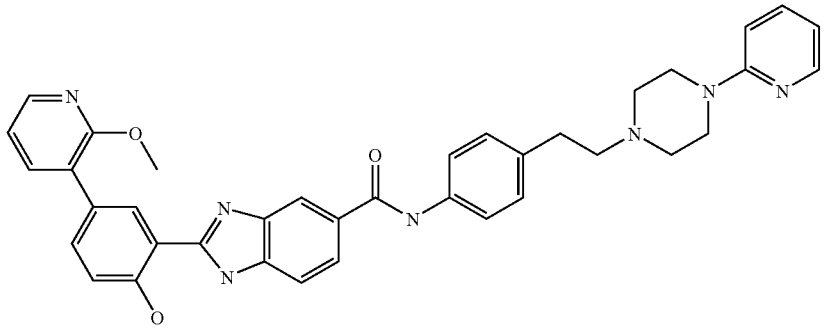 [SMILES: COc1ncccc1-c1ccc(O)c(-c2nc3cc(C(=O)Nc4ccc(CCN5CCN(c6ccccn6)CC5)cc4)ccc3[nH]2)c1]

2-[2-Hydroxy-5-(2-methoxy-pyridin-3-yl)-phenyl]-1H-benzoimidazole-5-carboxylic acid {4-[2-(4-pyridin-2-yl-piperazin-1-yl)-ethyl]-phenyl}-amide To a solution of 2-[2-hydroxy-5-(2-methoxy-pyridin-3-yl)-phenyl]-3H-benzoimidazole-5-carboxylic acid (containing 1 equivalent of DMA, 44 mg, 0.1 mmol), 4-[2-(4-pyridin-2-yl-piperazin-1-yl)-ethyl]-phenylamine (28.2 mg, 0.1 mmol) and HATU (38 mg, 0.1 mmol) in DMF (1.2 mL) was added DIEA (45 mg, 0.35 mmol). The reaction mixture was stirred at room temperature for 2 h and heated at 60° C. for 3 h, and then evaporated to dry under reduced pressure. The residue was diluted with DMSO (1.5 mL), filtered and then purified with using HPLC (TFA/H$_2$O/CH$_3$CN) to afford the title compound (26.6 mg, 39%). $^1$H NMR (MeOH-d$_4$) δ 3.10-4.01 (12H), 3.98 (s, 3H), 6.87 (m, 1H), 7.04-7.12 (2H), 7.21 (d, J=9 Hz, 1H), 7.36 (d, J=6 Hz, 2H), 7.72-7.83 (5H), 7.89 (d, J=6 Hz, 1H), 8.09 (d, J=6 Hz, 1H), 8.17 (t, J=3 Hz, 2H), 8.26 (s, 1H), 8.37 (s, 1H). ESI-MS m/z 626.5 (MH$^+$).

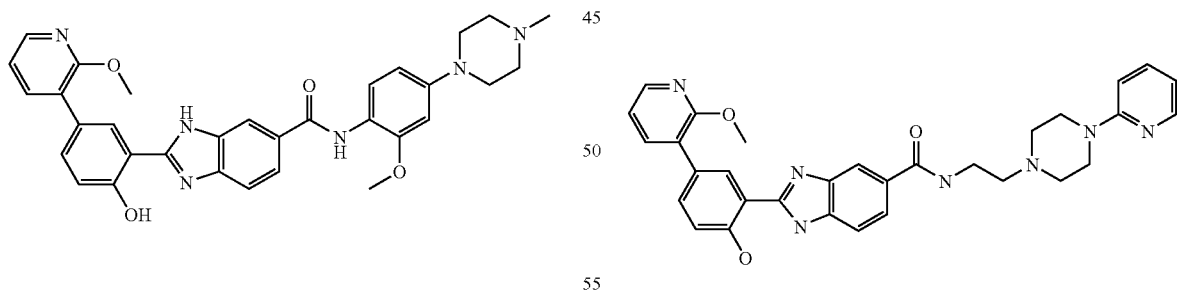

2-[2-Hydroxy-5-(2-methoxy-pyridin-3-yl)-phenyl]-1H-benzoimidazole-5-carboxylic acid [2-(4-pyridin-2-yl-piperazin-1-yl)-ethyl]-amide $^1$H NMR (MeOH-d$_4$) δ 3.49-4.01 (12H), 3.98 (s, 3H), 6.88 (m, 1H), 6.90-7.11 (2H), 7.20 (d, J=9 Hz, 1H), 7.74-7.87 (4H), 8.03 (d, J=9 Hz, 1H), 8.16 (m, 2H), 8.25 (s, 1H), 8.35 (s, 1H). ESI-MS m/z 550.7 (MH$^+$).

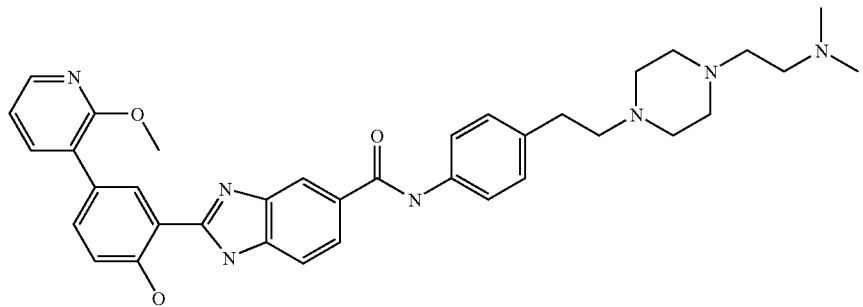 [SMILES: COc1ncccc1-c1ccc(O)c(-c2nc3cc(C(=O)Nc4ccc(CCN5CCN(CCN(C)C)CC5)cc4)ccc3[nH]2)c1]

2-[2-Hydroxy-5-(2-methoxy-pyridin-3-yl)-phenyl]-1H-benzoimidazole-5-carboxylic acid (4-{2-[4-(2-dimethylamino-ethyl)-piperazin-1-yl]-ethyl}-phenyl)-amide $^1$H NMR (MeOH-d$_4$) δ 2.56 (m, 2H), 2.83 (t, J=6 Hz, 2H), 2.96 (s, 6H), 3.06-3.68 (12H), 3.99 (s, 3H), 7.09 (m, 1H), 7.19 (d, J=9 Hz, 1H), 7.33 (d, J=9 Hz, 2H), 7.72-7.86 (5H), 8.03 (d, J=9 Hz, 1H), 8.15 (m, 1H), 8.25 (s, 1H), 8.34 (s, 1H). ESI-MS m/z 620.7 (MH$^+$).

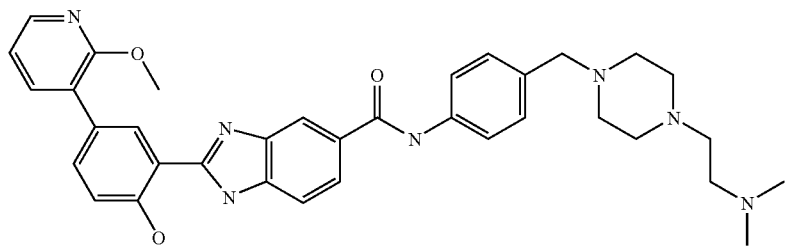 [SMILES: COc1ncccc1-c1ccc(O)c(-c2nc3cc(C(=O)Nc4ccc(CN5CCN(CCN(C)C)CC5)cc4)ccc3[nH]2)c1]

2-[2-Hydroxy-5-(2-methoxy-pyridin-3-yl)-phenyl]-1H-benzoimidazole-5-carboxylic acid {4-[4-(2-dimethylamino-ethyl)-piperazin-1-ylmethyl]-phenyl}-amide $^1$H NMR (MeOH-d$_4$) δ 2.52 (m, 2H), 2.82 (t, J=6 Hz, 2H), 2.93 (s, 6H), 3.12-3.56 (10H), 3.99 (s, 3H), 7.09 (m, 1H), 7.20 (d, J=9 Hz, 1H), 7.55 (d, J=9 Hz, 2H), 7.74-7.92 (5H), 8.07 (d, J=9 Hz, 1H), 8.15 (m, 1H), 8.25 (s, 1H), 8.33 (s, 1H). ESI-MS m/z 606.5 (MH$^+$).

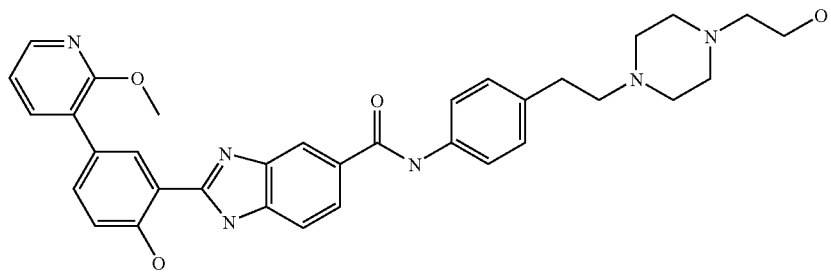 [SMILES: COc1ncccc1-c1ccc(O)c(-c2nc3cc(C(=O)Nc4ccc(CCN5CCN(CCO)CC5)cc4)ccc3[nH]2)c1]

2-[2-Hydroxy-5-(2-methoxy-pyridin-3-yl)-phenyl]-1H-benzoimidazole-5-carboxylic acid (4-{2-[4-(2-hydroxy-ethyl)-piperazin-1-yl]-ethyl}-phenyl)-amide $^1$H NMR (MeOH-$d_4$) δ 2.97-3.40 (14H), 3.85 (t, J=5 Hz, 2H), 4.00 (s, 3H), 7.10 (m, 1H), 7.22 (d, J=9 Hz, 1H), 7.32 (d, J=9 Hz, 2H), 7.69 (d, J=9 Hz, 2H), 7.79-7.84 (2H), 7.89 (d, J=9 Hz, 1H), 8.10 (d, J=9 Hz, 1H), 8.17 (m, 1H), 8.26 (s, 1H), 8.36 (s, 1H). ESI-MS m/z 593.5 (MH$^+$).

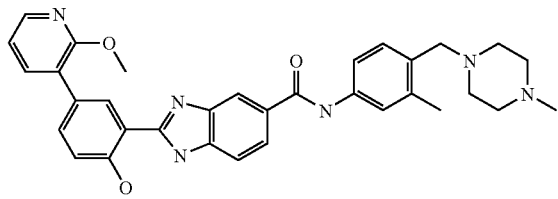 [SMILES: COc1ncccc1-c1ccc(O)c(-c2nc3cc(C(=O)Nc4ccc(CN5CCN(C)CC5)c(C)c4)ccc3[nH]2)c1]

2-[2-Hydroxy-5-(2-methoxy-pyridin-3-yl)-phenyl]-1H-benzoimidazole-5-carboxylic acid [3-methyl-4-(4-methyl-piperazin-1-ylmethyl)-phenyl]-amide $^1$H NMR (MeOH-$d_4$) δ 2.34 (s, 3H), 2.85-3.40 (8H), 2.87 (s, 3H), 3.78 (s, 2H), 3.99 (s, 3H), 7.10 (m, 1H), 7.21-7.39 (4H), 7.80-7.84 (2H), 7.90 (d, J=9 Hz, 1H), 8.15-8.18 (2H), 8.26 (s, 1H), 8.41 (s, 1H). ESI-MS m/z 563.5 (MH$^+$).

6.12 Example 12

Benzimidazole Amide Library via Coupling Reaction of the Acid with Amines

General Scheme

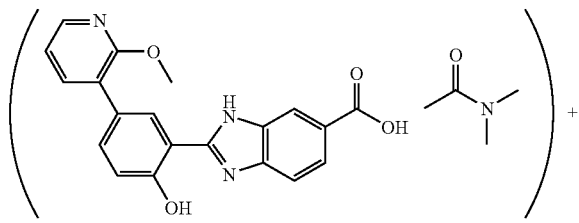

Library Protocol:
Prepare 0.25 M solutions of the carboxylic acids in anhydrous DMF;
Prepare 0.25 M solutions of the anilines in anhydrous DMF;
Prepare 0.5 M solutions of DIEA in anhydrous DMF;
Prepare 0.28 M solutions HATU in anhydrous DMF (freshly prepared);

Arrange 12×75 mm culture tubes in an 8×11 array in a block;
Place 500 uL (0.1 mmol, 1.0 eq) of the acid solution from Step A into the appropriate tubes;
Add 500 uL (0.1 mmol, 1.0 eq) of the aniline solution from Step B into the appropriate tubes;
Add 500 uL (0.2 mmol, 2.0 eq) of the DIEA solution from Step C into each tube;
Add 500 uL (0.11 mmol, 1.1 eq) of the HATU solution from Step D into each tube;
Seal each tube with a tube plug;
Place the tubes on a orbital shaker at 150 rpm for 18 h;
Uncap the tubes and remove the solvents in a GeneVac;
Purify the residue by HPLC (TFA/H$_2$O/CH$_3$CN).
By application of this methodology, certain amide compounds of the invention were prepared.

Benzoimidazole Amide Formed from Condensation of Aryldiamine with Aldehyde

General Scheme 1

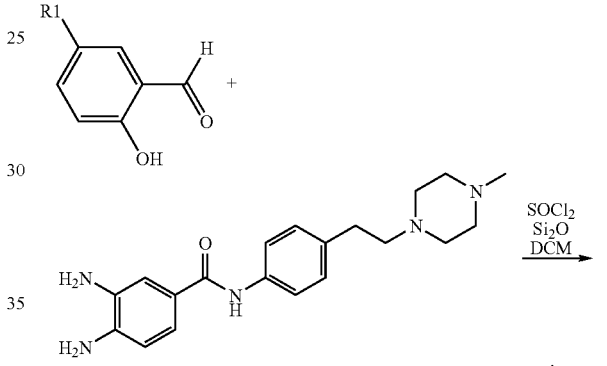

General Scheme 3

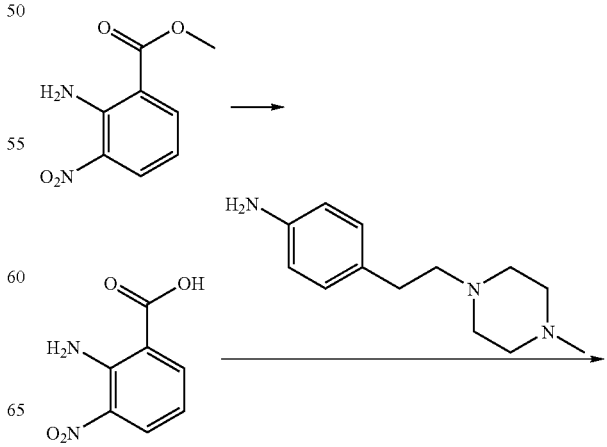

-continued

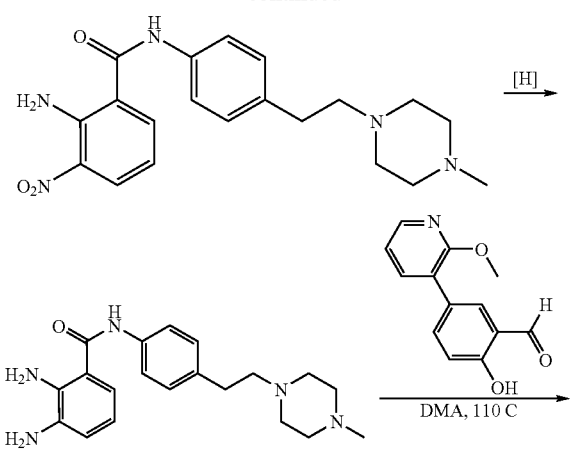

the room temperature for 1 h (gas was released from the reaction mixture). 3,4-Diamino-N-{4-[2-(4-methyl-piperazin-1-yl)-ethyl]-phenyl}-benzamide (707.0 mg, 2.0 mmol) and 2-hydroxy-5-(2-methoxy-pyridin-3-yl)-benzaldehyde (458.5 mg, 2.0 mmol) were added, and the resulting mixture was stirred at the room temperature for 4 h. After methanol (10 mL) was added, the reaction mixture was stirred at room temperature for another 1 h and was evaporated under reduced pressure. The residue on silica gel was purified by chromatography (250:10:1 CH$_2$Cl$_2$/MeOH/28% aqueous NH$_4$OH) to afford the title compound (528 mg, 47%). $^1$H NMR (MeOH-d$_4$) δ 2.25 (s, 3H), 2.35-2.71 (12H), 3.94 (s, 3H), 6.96 (m, 1H), 7.00 (d, J=9 Hz, 1H), 7.11 (d, J=9 Hz, 2H), 7.50-7.60 (4H), 7.66 (d, J=9 Hz, 1H), 7.79 (d, J=9 Hz, 1H), 8.06 (d, J=7 Hz, 1H), 8.10 (s, 1H), 8.14 (s, 1H). ESI-MS m/z 563 (MH$^+$).

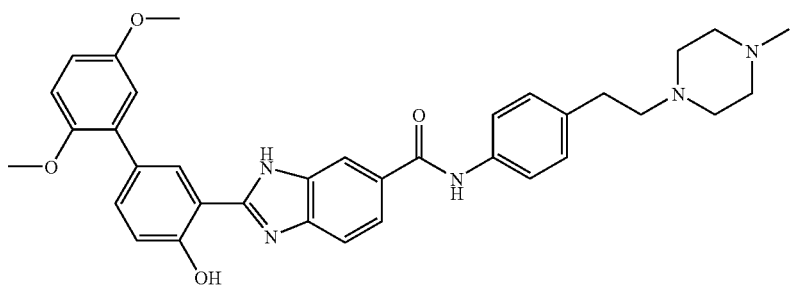

2-(4-Hydroxy-2',5'-dimethoxy-biphenyl-3-yl)-3H-benzoimidazole-5-carboxylic acid {4-[2-(4-methyl-piperazin-1-yl)-ethyl]-phenyl}-amide To a suspension of silica gel (0.8 g) in dichloromethane (3 mL) was added SOCl$_2$ (0.6 mL) and the mixture was stirred at the room temperature for 1 h (gas was released from the reaction mixture). 3,4-Diamino-N-{4-[2-(4-methyl-piperazin-1-yl)-ethyl]-phenyl}-benzamide (178.2 mg, 0.5 mmol), 4-hydroxy-2',5'-dimethoxy-biphenyl-3-carbaldehyde (129.1 mg, 0.5 mmol) and 2 mL dichloromethane were added, and the resulting reaction mixture was stirred at the room temperature for 4 h. After methanol (5 mL) was added, the reaction mixture was stirred at room temperature for another 1 h and was evaporated under reduced pressure. The residue on silica gel was purified by chromatography (250:10:1 CH$_2$Cl$_2$/MeOH/28% aqueous NH$_4$OH) to afford the title compound (217 mg, 84%). $^1$H NMR (MeOH-d$_4$) δ 2.26 (s, 3H), 2.37-2.72 (12H), 3.73 (s, 3H), 3.77 (s, 3H), 6.80 (m, 1H), 6.94 (s, 1H), 6.95 (m, 1H), 7.03 (d, J=9 Hz, 1H), 7.13 (d, J=9 Hz, 2H), 7.49-7.64 (4H), 7.80 (d, J=9 Hz, 1H), 8.10 (s, 1H), 8.17 (s, 1H). ESI-MS m/z 592 (MH$^+$).

-continued

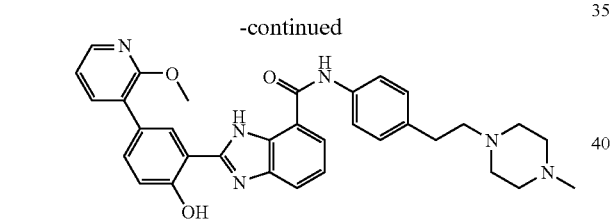

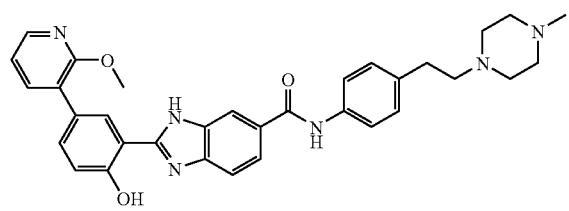

2-[2-Hydroxy-5-(2-methoxy-pyridin-3-yl)-phenyl]-3H-benzoimidazole-5-carboxylic acid {4-[2-(4-methyl-piperazin-1-yl)-ethyl]-phenyl}-amide To a suspension of silica gel (6.0 g) in dichloromethane (20 mL) was added SOCl$_2$ (1.5 mL) and the mixture was stirred at

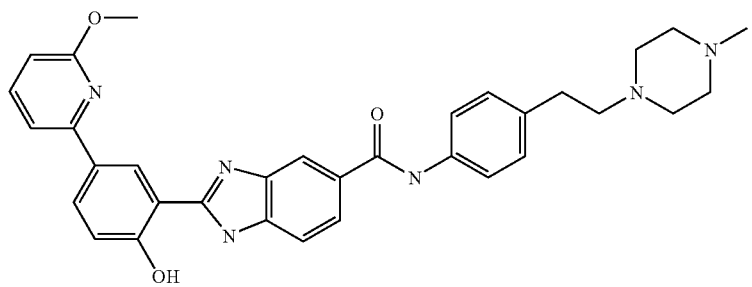 [SMILES: COc1cccc(-c2ccc(O)c(-c3nc4cc(C(=O)Nc5ccc(CCN6CCN(C)CC6)cc5)ccc4[nH]3)c2)n1]

2-[2-Hydroxy-5-(6-methoxy-pyridin-2-yl)-phenyl]-1H-benzoimidazole-5-carboxylic acid {4-[2-(4-methyl-piperazin-1-yl)-ethyl]-phenyl}-amide To a suspension of silica gel (0.8 g) in dichloromethane (5 mL) was added SOCl$_2$ (0.6 mL) and the mixture was stirred at the room temperature for 1 h (gas was released from the reaction mixture). 3,4-Diamino-N-{4-[2-(4-methyl-piperazin-1-yl)-ethyl]-phenyl}-benzamide (178.2 mg, 0.5 mmol), 2-hydroxy-5-(6-methoxy-pyridin-2-yl)-benzaldehyde (114.6 mg, 0.5 mmol) and 2 mL dichloromethane were added, and the resulting reaction mixture was stirred at the room temperature for 4 h. After methanol (5 mL) was added, the reaction mixture was stirred at room temperature for another 1 h and was evaporated under reduced pressure. The residue on silica gel was purified by chromatography (250:10:1 CH$_2$Cl$_2$/MeOH/28% aqueous NH$_4$OH) to afford the title compound (190 mg, 68%). $^1$H NMR (MeOH-d$_4$) δ 2.26 (s, 3H), 2.37-2.72 (12H), 4.01 (s, 3H), 6.62 (d, J=9 Hz, 1H), 7.04 (d, J=9 Hz, 1H), 7.12 (d, J=9 Hz, 2H), 7.37 (d, J=6 Hz, 1H), 7.55 (d, J=9 Hz, 1H), 7.54-7.63 (2H), 7.76 (d, J=6 Hz, 1H), 8.04 (d, J=6 Hz, 1H), 8.13 (s, 1H), 8.53 (s, 1H). ESI-MS m/z 563 (MH$^+$).

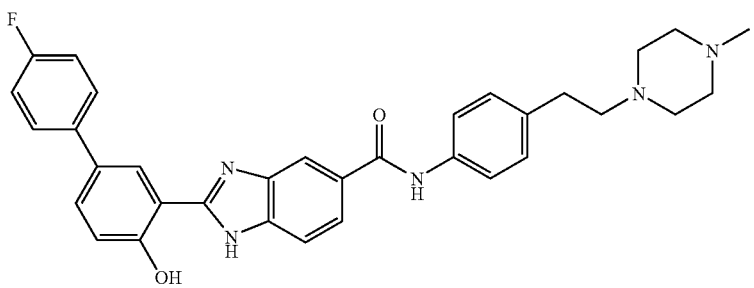 [SMILES: CN1CCN(CCc2ccc(NC(=O)c3ccc4[nH]c(-c5cc(-c6ccc(F)cc6)ccc5O)nc4c3)cc2)CC1]

2-(4'-Fluoro-4-hydroxy-biphenyl-3-yl)-1H-benzoimidazole-5-carboxylic acid {4-[2-(4-methyl-piperazin-1-yl)-ethyl]-phenyl}-amide $^1$H NMR (MeOH-d$_4$) δ 2.25 (s, 3H), 2.35-2.71 (12H), 7.00 (d, J=9 Hz, 1H), 7.04-7.12 (5H), 7.48-7.60 (6H), 7.73 (d, J=9 Hz, 1H), 8.11 (d, J=7 Hz, 1H). ESI-MS m/z 550 (MH$^+$).

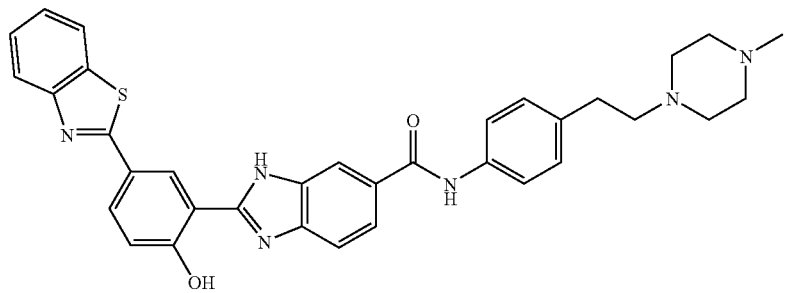 [SMILES: CN1CCN(CCc2ccc(NC(=O)c3ccc4nc(-c5cc(-c6nc7ccccc7s6)ccc5O)[nH]c4c3)cc2)CC1]

2-(5-Benzothiazol-2-yl-2-hydroxy-phenyl)-3H-benzoimidazole-5-carboxylic acid {4-[2-(4-methyl-piperazin-1-yl)-ethyl]-phenyl}-amide $^1$H NMR (MeOH-d$_4$) δ 2.31 (s, 3H), 2.48-2.79 (12H), 7.04 (d, J=9 Hz, 1H), 7.16 (d, J=9 Hz, 2H), 7.33 (m, 1H), 7.42 (m, 1H), 7.56 (d, J=9 Hz, 2H), 7.57 (m, 1H), 7.77 (d, J=9 Hz, 1H), 7.82-7.96 (3H), 8.12 (s, 1H), 8.52 (s, 1H). ESI-MS m/z 589 (MH$^+$).

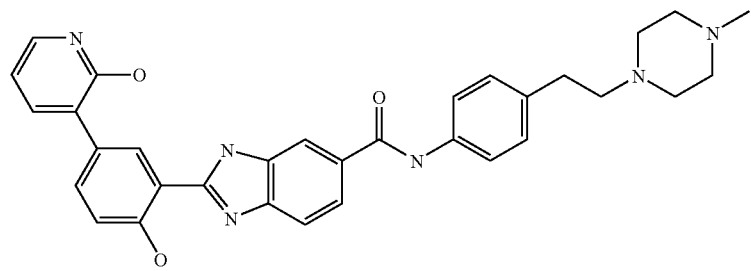 [SMILES: CN1CCN(CCc2ccc(NC(=O)c3ccc4nc(-c5cc(-c6cccnc6O)ccc5O)[nH]c4c3)cc2)CC1]

2-[2-Hydroxy-5-(2-hydroxy-pyridin-3-yl)-phenyl]-3H-benzoimidazole-5-carboxylic acid {4-[2-(4-methyl-piperazin-1-yl)-ethyl]-phenyl}-amide $^1$H NMR (MeOH-d$_4$) δ 2.32 (s, 3H), 2.45-2.85 (12H), 6.51 (m, 1H), 7.06 (d, J=9 Hz, 1H), 7.22 (d, J=9 Hz, 2H), 7.41 (d, J=6 Hz, 1H), 7.61-7.71 (3H), 7.77 (d, J=6 Hz, 1H), 7.86 (d, J=9 Hz, 1H), 8.22 (s, 1H), 8.30 (s, 1H). ESI-MS m/z 549.5 (MH$^+$).

General Scheme 2

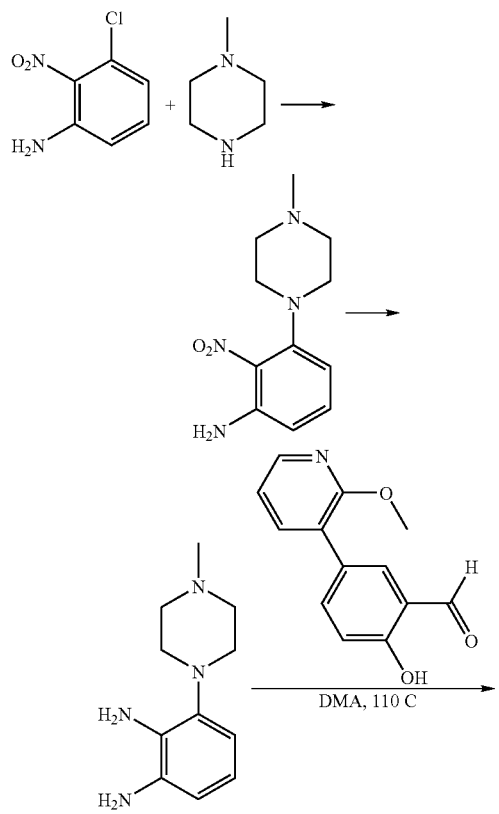

-continued

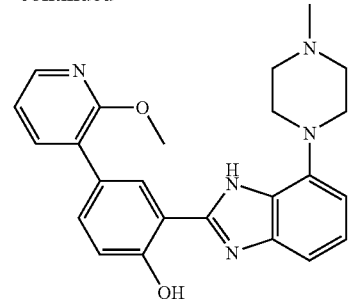

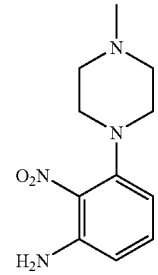

3-(4-Methyl-piperazin-1-yl)-2-nitro-phenylamine

A mixture of 3-chloro-2-nitro-phenylamine (172.6 mg, 1 mmol) and 1-methyl-piperazine (1.5 mL) was heated at 200° C. in a Biotage Initiator Sixty microwave reactor for 15 min, cooled to the room temperature, and concentrated under reduced pressure. The residue was purified by chromatography (500:10:1 CH$_2$Cl$_2$/MeOH/28% aqueous NH$_4$OH) to afford the title compound (139 mg, 59%). $^1$H NMR (MeOH-d$_4$) δ 2.32 (s, 3H), 2.55 (m, 4H), 2.99 (m, 4H), 6.45 (d, J=9 Hz, 1H), 6.57 (d, J=9 Hz, 1H), 7.15 (dd, J=9 Hz and 9 Hz, 1H). ESI-MS m/z 237.3 (MH$^+$).

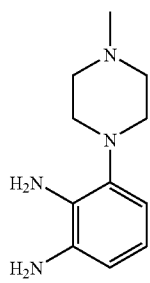

3-(4-Methyl-piperazin-1-yl)-benzene-1,2-diamine

To a solution of 3-(4-methyl-piperazin-1-yl)-2-nitro-phenylamine (139 mg, 0.59 mmol) in MeOH (20 mL) were added Pd/C (10%, 14 mg) and the mixture was stirred under atmospheric hydrogen (balloon) at the room temperature for 1 h. The reaction mixture was filter over Celite to afford the title compound (120 mg, 99%). $^1$H NMR (MeOH-d$_4$) δ 2.34 (s, 3H), 2.62 (br, 4H), 2.99 (m, 4H), 6.51-6.65 (3H). ESI-MS m/z 207.1 (MH$^+$).

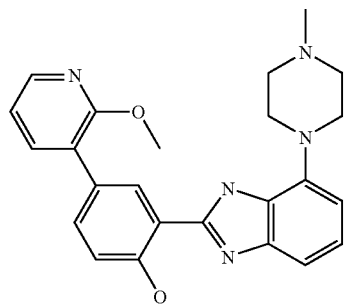 [SMILES: COc1ncccc1-c1ccc(O)c(-c2nc3cccc(N4CCN(C)CC4)c3[nH]2)c1]

4-(2-Methoxy-pyridin-3-yl)-2-[7-(4-methyl-piperazin-1-yl)-1H-benzoimidazol-2-yl]-phenol To mixture of 2-hydroxy-5-(2-methoxy-pyridin-3-yl)-benzaldehyde (57 mg, 0.25 mmol) and 3-(4-methyl-piperazin-1-yl)-benzene-1,2-diamine (51 mg, 0.25 mol) was added DMA (1 mL) and the resulting solution was stirred at the room temperature for 15 min, heated at 110° C. for 15 h open to the air, concentrated under reduced pressure. The residual crude was purified by chromatography (500:10:1 CH$_2$Cl$_2$/MeOH/28% aqueous NH$_4$OH) to afford the title compound (10.8 mg, 10.5%). $^1$H NMR (MeOH-d$_4$) δ 2.41 (s, 3H), 2.78 (m, 4H), 3.49 (m, 4H), 3.97 (s, 3H), 6.72 (m, 1H) 7.05-7.20 (4H), 7.56 (d, J=9 Hz, 1H), 7.78 (d, J=9 Hz, 1H), 8.10-8.13 (2H). ESI-MS m/z 416.5 (MH$^+$).

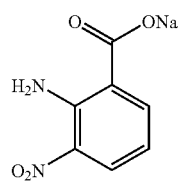

2-Amino-3-nitro-benzoic acid sodium salt

A suspension of 2-amino-3-nitro-benzoic acid methyl ester (785 mg, 4 mmol) and sodium hydroxide (194 mg, 4.4 mmol) in mixed solvent of EtOH (2 mL) and water (2 mL) was heated at 80° C. for 5 h. After it was cooled to the room temperature, the red colored precipitate was formed and dried at 40° C. under reduced pressure to afford the crude product.

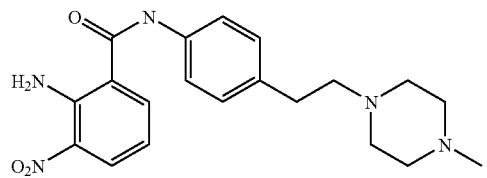

2-Amino-N-{4-[2-(4-methyl-piperazin-1-yl)-ethyl]-phenyl}-3-nitro-benzamide

To a mixture of 2-amino-3-nitro-benzoic acid sodium salt (205 mg, 1.0 mmol), 4-[2-(4-methyl-piperazin-1-yl)-ethyl]-phenylamine (219 mg, 1.0 mmol) and HATU (400 mg, 1.05 mmol) in DMF (2 mL) was added DIEA (0.52 mL, 388 mg, 3.0 mmol). The reaction mixture was stirred at room temperature for 1 h and heated at 70° C. for 1 h, and then evaporated under reduced pressure. The residue was purified by chromatography (50:10:1 CH$_2$Cl$_2$/MeOH/28% aqueous NH$_4$OH) to afford the title compound (300 mg, 78%). $^1$H NMR (MeOH-d$_4$) δ 2.44 (s, 3H), 2.50-2.85 (12H), 6.74 (dd, J=9 Hz and 9 Hz, 1H), 7.23 (d, J=9 Hz, 2H), 7.58 (d, J=9 Hz, 2H), 7.91 (d, J=9 Hz, 1H), 8.29 (d, J=9 Hz, 1H). ESI-MS m/z 384.5 (MH$^+$).

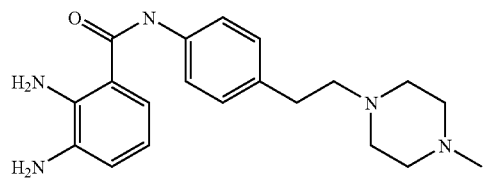 [SMILES: CN1CCN(CCc2ccc(NC(=O)c3cccc([N+](=O)[O-])c3N)cc2)CC1]

2,3-Diamino-N-{4-[2-(4-methyl-piperazin-1-yl)-ethyl]-phenyl}-benzamide

To a solution of 2-amino-N-{4-[2-(4-methyl-piperazin-1-yl)-ethyl]-phenyl}-3-nitro-benzamide (300 mg, 0.78 mmol) in MeOH (100 mL) were added Pd/C (10%, 30 mg) and the mixture was stirred under atmospheric hydrogen (balloon) at the room temperature for 1 h. The reaction mixture was filter over Celite to afford the title compound (261 mg, 94%). $^1$H NMR (MeOH-d$_4$) δ 2.39 (s, 3H), 2.55-2.83 (12H), 6.62 (dd, J=9 Hz and 9 Hz, 1H), 6.86 (d, J=9 Hz, 1H), 7.08 (d, J=9 Hz, 1H), 7.22 (d, J=9 Hz, 2H), 7.54 (d, J=9 Hz, 2H). ESI-MS m/z 354.3 (MH$^+$).

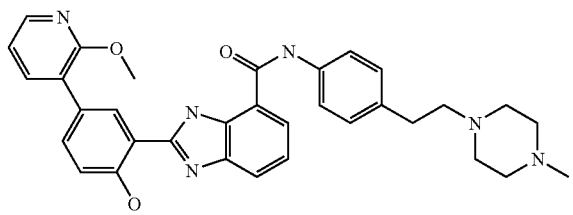 [SMILES: COc1ncccc1-c1ccc(O)c(-c2nc3cccc(C(=O)Nc4ccc(CCN5CCN(C)CC5)cc4)c3[nH]2)c1]

2-[2-Hydroxy-5-(2-methoxy-pyridin-3-yl)-phenyl]-3H-benzoimidazole-4-carboxylic acid 4-[2-(4-methyl-piperazin-1-yl)-ethyl]-phenyl}-amide To mixture of 2-hydroxy-5-(2-methoxy-pyridin-3-yl)-benzaldehyde (65 mg, 0.283 mmol) and 2,3-diamino-N-{4-[2-(4-methyl-piperazin-1-yl)-ethyl]-phenyl}-benzamide (100 mg, 0.283 mol) was added DMA (3 mL) and the resulting solution was stirred at the room temperature for 1 h, heated at 110° C. for 15 h open to the air, concentrated under reduced pressure. The residue was diluted with DMSO (1.5 mL), filtered and then purified with using HPLC (TFA/H$_2$O/CH$_3$CN) to afford the title compound (15.8 mg, 7%). $^1$H NMR (MeOH-d$_4$) δ 2.91 (s, 3H), 2.97-3.39 (12H), 3.98 (s, 3H), 7.07 (m, 1H), 7.20 (d, J=9 Hz, 1H), 7.31 (d, J=9 Hz, 2H), 7.60 (m, 1H), 7.72-7.85 (4H), 7.94 (d, J=9 Hz, 1H), 8.10-8.18 (2H), 8.40 (s, 1H). ESI-MS m/z 563.3 (MH$^+$).

Benzimidazole Amides Formed from Methyl Ester

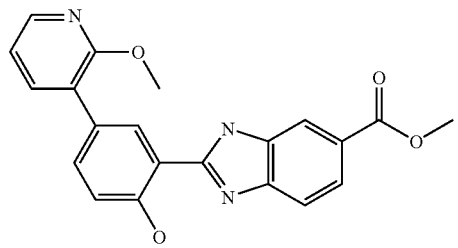 [SMILES: COC(=O)c1ccc2nc(-c3cc(-c4cccnc4OC)ccc3O)[nH]c2c1]

2-[2-Hydroxy-5-(2-methoxy-pyridin-3-yl)-phenyl]-3H-benzoimidazole-5-carboxylic acid methyl ester To an ice-cold flask with a rubber stopper were added 2-hydroxy-5-(2-methoxy-pyridin-3-yl)-benzaldehyde (2.29 g, 10 mol) and 3,4-diamino-benzoic acid methyl ester (1.83 g, 11 mmol) and the solid mixture was stirred at 0° C. for 15 min. Then DMA (10 mL) was added into the mixture via a syringe and the resulting solution was stirred at 0° C. for 1.5 h, and at the room temperature for 1.5 h. The rubber stopper was removed and the reaction mixture was stirred at 110° C. for 14 h open to the air. The DMA was removed under reduced pressure and the residue was mixed with 50 mL MeOH, and sonicated for 15 min. The mixture was filtered to get the solid precipitate, which was re-crystallized in 300 mL MeOH to afford the title compound (1.6 g, 42%). $^1$H NMR (DMSO-d$_6$) δ 3.90 (s, 3H), 3.93 (s, 3H), 7.12-7.17 (2H), 7.65 (d, J=9 Hz, 1H), 7.76 (d, J=9 Hz, 1H), 7.83 (d, J=9 Hz, 1H), 7.91 (d, J=9 Hz, 1H), 8.20 (d, J=6 Hz, 1H), 8.26 (s, 1H), 8.29 (s, 1H). ESI-MS m/z 376.3 (MH$^+$).

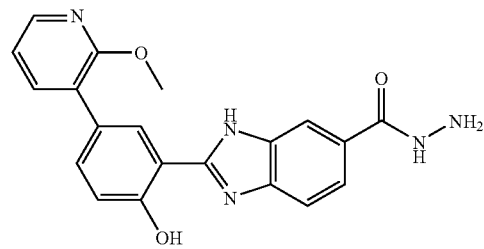 [SMILES: COc1ncccc1-c1ccc(O)c(-c2nc3ccc(C(=O)NN)cc3[nH]2)c1]

2-[2-Hydroxy-5-(2-methoxy-pyridin-3-yl)-phenyl]-3H-benzoimidazole-5-carboxylic acid hydrazide To a suspension of 2-[2-hydroxy-5-(2-methoxy-pyridin-3-yl)-phenyl]-3H-benzoimidazole-5-carboxylic acid methyl ester (37.5 mg, 0.1 mmol) in EtOH (1 mL) was added anhydrous hydrazine (32 mg, 1 mmol). The reaction mixture was heated at 90° C. for 18 h, cooled to the room temperature, filtered to get the solid precipitate that was dried under reduced pressure to afford the title compound (25 mg, 33%). $^1$H NMR (DMSO-d$_6$) δ 3.92 (s, 3H), 4.51 (br s, 2H, NH), 7.11-7.17 (2H), 7.63 (d, J=9 Hz, 1H), 7.71 (d, J=9 Hz, 1H), 7.79-7.85 (2H), 8.10-8.21 (2H), 8.29 (s, 1H), 9.87 (br, 1H, NH). ESI-MS m/z 376.3 (MH$^+$).

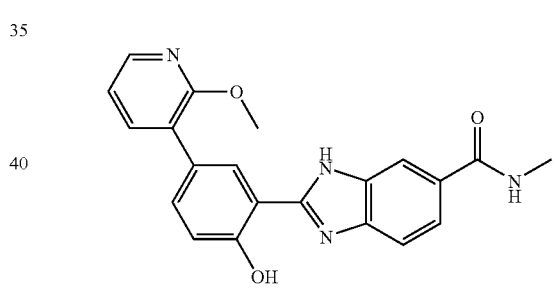

2-[2-Hydroxy-5-(2-methoxy-pyridin-3-yl)-phenyl]-3H-benzoimidazole-5-carboxylic acid methylamide A suspension of 2-[2-hydroxy-5-(2-methoxy-pyridin-3-yl)-phenyl]-3H-benzoimidazole-5-carboxylic acid methyl ester (37.5 mg, 0.1 mmol) in aqueous methylamine solution (40%, 2 mL) was heated at 140° C. in a Biotage Initiator Sixty microwave reactor for 15 min, cooled to the room temperature, and concentrated under reduced pressure. The residue was purified by chromatography (500:10:1 CH$_2$Cl$_2$/MeOH/28% aqueous NH$_4$OH) to afford the title compound (19 mg, 50%). $^1$H NMR (DMSO-d$_6$) δ 2.84 (s, 3H), 3.92 (s, 3H), 7.11-7.17 (2H), 7.62-7.83 (4H), 8.10-8.29 (3H), 8.50 (br, 1H, NH). ESI-MS m/z 375.3 (MH$^+$).

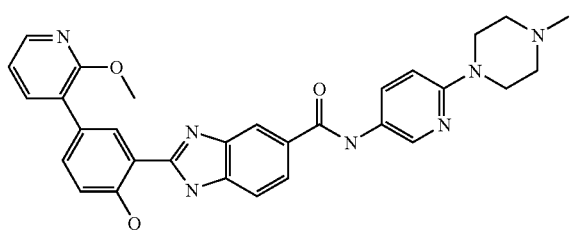 [SMILES: COc1ncccc1-c1ccc(O)c(-c2nc3cc(C(=O)Nc4ccc(N5CCN(C)CC5)nc4)ccc3[nH]2)c1]

2-[2-Hydroxy-5-(2-methoxy-pyridin-3-yl)-phenyl]-1H-benzoimidazole-5-carboxylic acid [6-(4-methyl-piperazin-1-yl)-pyridin-3-yl]-amide To a solution of 6-(4-methyl-piperazin-1-yl)-pyridin-3-ylamine (38.4 mg, 0.2 mmol) in dry DCE (1 mL) were added AlMe$_3$ in toluene solution (2.0 M, 160 µL, 0.32 mmol), and then 2-[2-hydroxy-5-(2-methoxy-pyridin-3-yl)-phenyl]-3H-benzoimidazole-5-carboxylic acid methyl ester (37.5 mg, 0.1 mmol). The reaction mixture was heated at 80° C. for 16.5 h, cooled to the room, loaded on silica gel, and chromatographyed (250:10:1 CH$_2$Cl$_2$/MeOH/28% aqueous NH$_4$OH) to afford the title compound (10.7 mg, 20%). $^1$H NMR (MeOH-d$_4$) δ 2.35 (s, 3H), 2.57 (m, 4H), 3.54 (m, 4H), 3.97 (s, 3H), 6.84 (d, J=9 Hz, 1H), 7.03-7.10 (2H), 7.58 (d, J=9 Hz, 1H), 7.68 (d, J=9 Hz, 1H), 7.78 (d, J=9 Hz, 1H), 7.86-7.93 (2H), 8.13 (m, 1H), 8.17 (s, 1H), 8.22 (s, 1H), 8.41 (s, 1H). ESI-MS m/z 536.3 (MH$^+$).

Benzimidazole Amides formed via Coupling of the Acid Derivatives

General Scheme

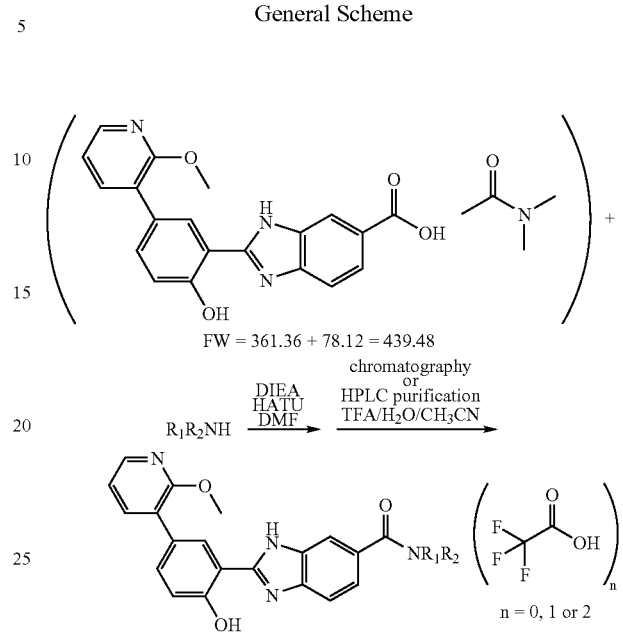

General Scheme 2

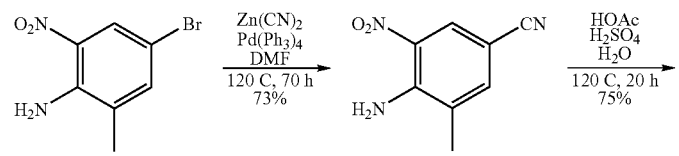

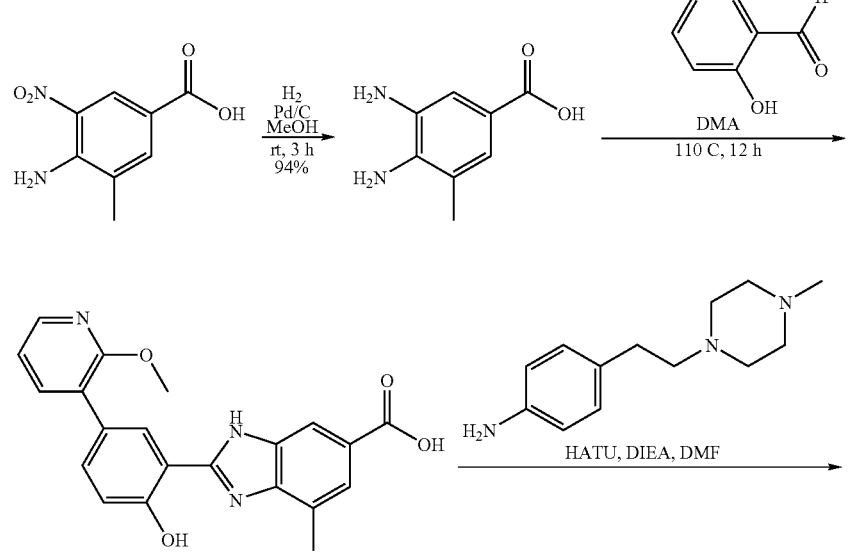

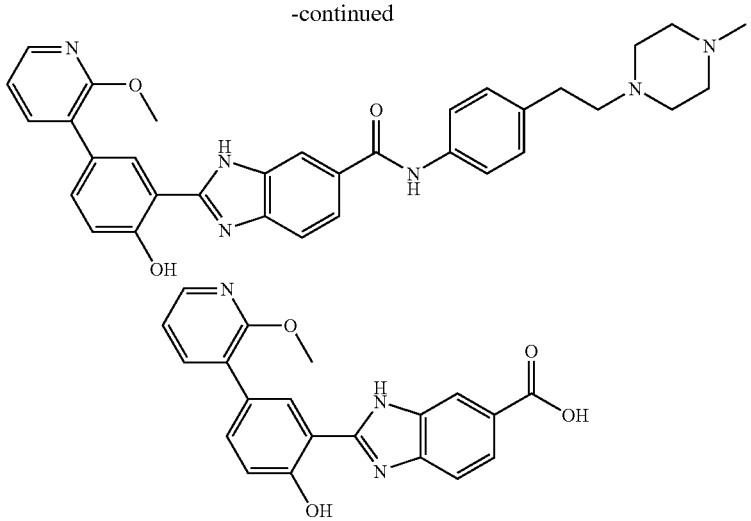

2-[2-Hydroxy-5-(2-methoxy-pyridin-3-yl)-phenyl]-3H-benzoimidazole-5-carboxylic acid To mixture of 2-hydroxy-5-(2-methoxy-pyridin-3-yl)-benzaldehyde (22.35 g, 0.0975 mol) and 3,4-diamino-benzoic acid (17.2 g, 0.113 mol) was added DMA (120 mL) via a syringe and the resulting solution was stirred at 0° C. for 2 h, and at the room temperature for 3 h. The robber stopper was removed and the reaction mixture was heated at 110° C. for 14 h open to the air. The DMA was removed under reduced pressure and the residue was mixed with 200 mL EtOAc, and sonicated for 15 min. The mixture was filtered to get the solid precipitate, which was mixture with 150 mL EtOAc, and sonicated for 5 min. The resulting mixture was filtered to get the solid crude that was dried at 40° C. for 6 h under reduced pressure to afford a mixture of the title compound and DMA (ratio 1:1) (16.15 g, 38%). $^1$H NMR (DMSO-d$_6$) δ 3.92 (s, 3H), 7.14 (m, 1H), 7.15 (s, 1H), 7.64 (d, J=6 Hz, 1H), 7.74 (d, J=6 Hz, 1H), 7.84 (d, J=6 Hz, 1H), 7.91 (d, J=6 Hz, 1H), 8.19 (d, J=6 Hz, 1H), 8.21 (d, J=6 Hz, 1H), 8.29 (s, 1H). DMA also shows as 61.96 (s, 3H), 2.79 (s, 3H) and 2.94 (s, 3H). ESI-MS m/z 362.5 (MH$^+$).

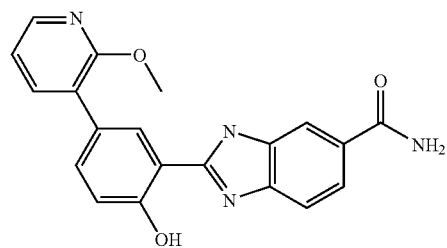 [SMILES: COc1ncccc1-c1ccc(O)c(-c2nc3ccc(C(N)=O)cc3[nH]2)c1]

2-[2-Hydroxy-5-(2-methoxy-pyridin-3-yl)-phenyl]-3H-benzoimidazole-5-carboxylic acid amide To a mixture of 2-[2-hydroxy-5-(2-methoxy-pyridin-3-yl)-phenyl]-3H-benzoimidazole-5-carboxylic acid (containing 1 equivalent of DMA, 145 mg, 0.33 mmol), NH$_4$Cl (160 mg, 3.0 mmol) and HATU (141 mg, 0.37 mmol) in DMF (2 mL) was added DIEA (0.52 mL, 388 mg, 3.0 mmol). The reaction mixture was stirred at room temperature for 3 h and heated at 60° C. for 15 h, and then evaporated under reduced pressure. The residue was purified by chromatography (333:10:1 CH$_2$Cl$_2$/MeOH/28% aqueous NH$_4$OH) to afford the title compound (29 mg, 24%). $^1$H NMR (DMSO-d$_6$) δ 3.94 (s, 3H), 7.11-7.17 (2H), 7.36 (br s, 1H), 7.64 (d, J=9 Hz, 1H), 7.67 (d, J=9 Hz, 1H), 7.83-7.88 (2H), 8.05 (br s, 1H), 8.19-8.21 (2H), 8.30 (s, 1H). ESI-MS m/z 361.3 (MH$^+$).

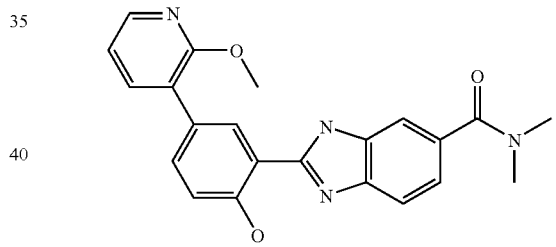

2-[2-Hydroxy-5-(2-methoxy-pyridin-3-yl)-phenyl]-3H-benzoimidazole-5-carboxylic acid dimethylamide To a solution of 2-[2-hydroxy-5-(2-methoxy-pyridin-3-yl)-phenyl]-3H-benzoimidazole-5-carboxylic acid (containing 1 equivalent of DMA, 44 mg, 0.1 mmol), dimethylamine in THF (0.5 mL, 2 M, 1 mmol) and HATU (38 mg, 0.1 mmol) in DMF (1.5 mL) was added DIEA (26 mg, 0.2 mmol). The reaction mixture was stirred at room temperature for 1 h and heated at 65° C. for 15 h, and then evaporated under reduced pressure. The residue was purified by chromatography (500:10:1 CH$_2$Cl$_2$/MeOH/28% aqueous NH$_4$OH) to afford the title compound (31 mg, 80%). $^1$H NMR (MeOH-d$_4$) δ 3.05 (s, 3H), 3.12 (s, 3H), 3.95 (s, 3H), 7.00-7.06 (2H), 7.31 (d, J=9 Hz, 1H), 7.52-7.75 (4H), 8.08-8.14 (2H). ESI-MS m/z 389.5 (MH$^+$).

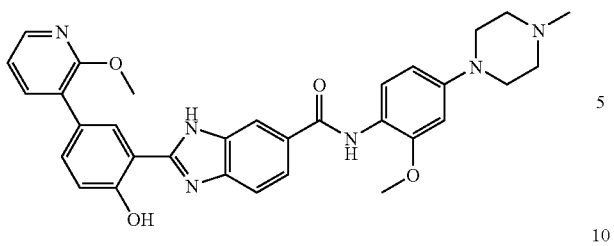

2-[2-Hydroxy-5-(2-methoxy-pyridin-3-yl)-phenyl]-3H-benzoimidazole-5-carboxylic acid [2-methoxy-4-(4-methyl-piperazin-1-yl)-phenyl]-amide To a solution of 2-[2-hydroxy-5-(2-methoxy-pyridin-3-yl)-phenyl]-3H-benzoimidazole-5-carboxylic acid (containing 1 equivalent of DMA, 44 mg, 0.1 mmol), 2-methoxy-4-(4-methyl-piperazin-1-yl)-phenylamine di HCl salt (29.4 mg, 0.1 mmol) and HATU (38 mg, 0.1 mmol) in DMF (1.2 mL) was added DIEA (45 mg, 0.35 mmol). The reaction mixture was stirred at room temperature for 2 h and heated at 60° C. for 3 h, and then evaporated under reduced pressure. The residue was diluted with DMSO (1.5 mL), filtered and then purified with using HPLC (TFA/H$_2$O/CH$_3$CN) to afford the title compound (26.4 mg, 39%). ESI-MS m/z 565.5 (MH$^+$).

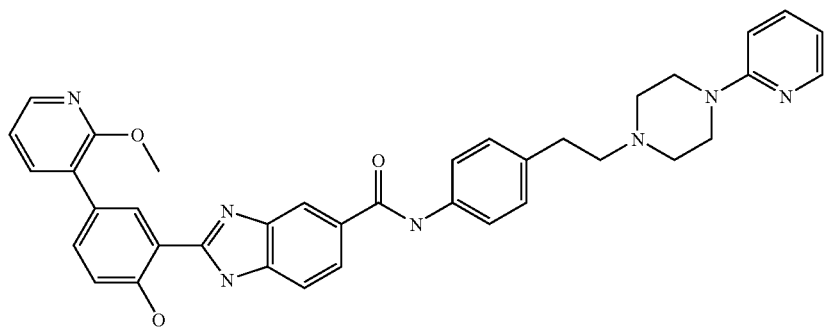 [SMILES: COc1ncccc1-c1ccc(O)c(-c2nc3cc(C(=O)Nc4ccc(CCN5CCN(c6ccccn6)CC5)cc4)ccc3[nH]2)c1]

2-[2-Hydroxy-5-(2-methoxy-pyridin-3-yl)-phenyl]-1H-benzoimidazole-5-carboxylic acid {4-[2-(4-pyridin-2-yl-piperazin-1-yl)-ethyl]-phenyl}-amide To a solution of 2-[2-hydroxy-5-(2-methoxy-pyridin-3-yl)-phenyl]-3H-benzoimidazole-5-carboxylic acid (containing 1 equivalent of DMA, 44 mg, 0.1 mmol), 4-[2-(4-pyridin-2-yl-piperazin-1-yl)-ethyl]-phenylamine (28.2 mg, 0.1 mmol) and HATU (38 mg, 0.1 mmol) in DMF (1.2 mL) was added DIEA (45 mg, 0.35 mmol). The reaction mixture was stirred at room temperature for 2 h and heated at 60° C. for 3 h, and then evaporated under reduced pressure. The residue was diluted with DMSO (1.5 mL), filtered and then purified with using HPLC (TFA/H$_2$O/CH$_3$CN) to afford the title compound (26.6 mg, 39%). $^1$H NMR (MeOH-d$_4$) δ 3.10-4.01 (12H), 3.98 (s, 3H), 6.87 (m, 1H), 7.04-7.12 (2H), 7.21 (d, J=9 Hz, 1H), 7.36 (d, J=6 Hz, 2H), 7.72-7.83 (5H), 7.89 (d, J=6 Hz, 1H), 8.09 (d, J=6 Hz, 1H), 8.17 (t, J=3 Hz, 2H), 8.26 (s, 1H), 8.37 (s, 1H). ESI-MS m/z 626.5 (MH$^+$).

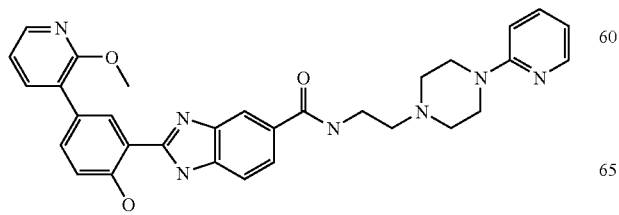

2-[2-Hydroxy-5-(2-methoxy-pyridin-3-yl)-phenyl]-1H-benzoimidazole-5-carboxylic acid [2-(4-pyridin-2-yl-piperazin-1-yl)-ethyl]-amide $^1$H NMR (MeOH-d$_4$) δ 3.49-4.01 (12H), 3.98 (s, 3H), 6.88 (m, 1H), 6.90-7.11 (2H), 7.20 (d, J=9 Hz, 1H), 7.74-7.87 (4H), 8.03 (d, J=9 Hz, 1H), 8.16 (m, 2H), 8.25 (s, if), 8.35 (s, 1H). ESI-MS m/z 550.7 (MH$^+$).

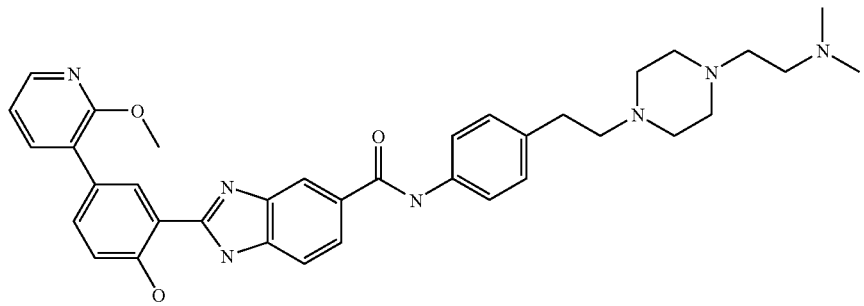 [SMILES: COc1ncccc1-c1ccc(O)c(-c2nc3cc(C(=O)Nc4ccc(CCN5CCN(CCN(C)C)CC5)cc4)ccc3[nH]2)c1]

2-[2-Hydroxy-5-(2-methoxy-pyridin-3-yl)-phenyl]-1H-benzoimidazole-5-carboxylic acid (4-{2-[4-(2-dimethylamino-ethyl)-piperazin-1-yl]-ethyl}-phenyl)-amide $^1$H NMR (MeOH-d$_4$) δ 2.56 (m, 2H), 2.83 (t, J=6 Hz, 2H), 2.96 (s, 6H), 3.06-3.68 (12H), 3.99 (s, 3H), 7.09 (m, 1H), 7.19 (d, J=9 Hz, 1H), 7.33 (d, J=9 Hz, 2H), 7.72-7.86 (5H), 8.03 (d, J=9 Hz, 1H), 8.15 (m, 1H), 8.25 (s, 1H), 8.34 (s, 1H). ESI-MS m/z 620.7 (MH$^+$).

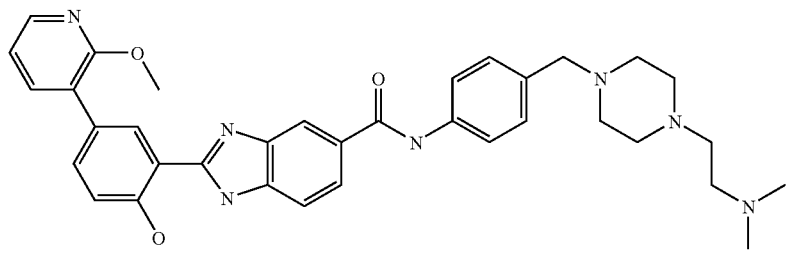 [SMILES: COc1ncccc1-c1ccc(O)c(-c2nc3cc(C(=O)Nc4ccc(CN5CCN(CCN(C)C)CC5)cc4)ccc3[nH]2)c1]

2-[2-Hydroxy-5-(2-methoxy-pyridin-3-yl)-phenyl]-1H-benzoimidazole-5-carboxylic acid {4-[4-(2-dimethylamino-ethyl)-piperazin-1-ylmethyl]-phenyl}-amide $^1$H NMR (MeOH-d$_4$) δ 2.52 (m, 2H), 2.82 (t, J=6 Hz, 2H), 2.93 (s, 6H), 3.12-3.56 (10H), 3.99 (s, 3H), 7.09 (m, 1H), 7.20 (d, J=9 Hz, 1H), 7.55 (d, J=9 Hz, 2H), 7.74-7.92 (5H), 8.07 (d, J=9 Hz, 1H), 8.15 (m, 1H), 8.25 (s, 1H), 8.33 (s, 1H). ESI-MS m/z 606.5 (MH$^+$).

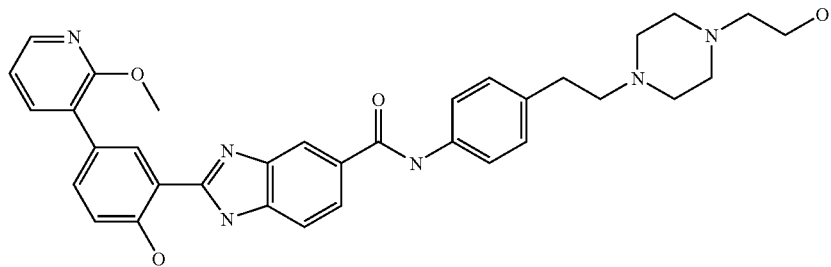 [SMILES: COc1ncccc1-c1ccc(O)c(-c2nc3cc(C(=O)Nc4ccc(CCN5CCN(CCO)CC5)cc4)ccc3[nH]2)c1]

2-[2-Hydroxy-5-(2-methoxy-pyridin-3-yl)-phenyl]-1H-benzoimidazole-5-carboxylic acid (4-{2-[4-(2-hydroxy-ethyl)-piperazin-1-yl]-ethyl}-phenyl)-amide $^1$H NMR (MeOH-d$_4$) δ 2.97-3.40 (14H), 3.85 (t, J=5 Hz, 2H), 4.00 (s, 3H), 7.10 (m, 1H), 7.22 (d, J=9 Hz, 1H), 7.32 (d, J=9 Hz, 2H), 7.69 (d, J=9 Hz, 2H), 7.79-7.84 (2H), 7.89 (d, J=9 Hz, 1H), 8.10 (d, J=9 Hz, 1H), 8.17 (m, 1H), 8.26 (s, 1H), 8.36 (s, 1H). ESI-MS m/z 593.5 (MH$^+$).

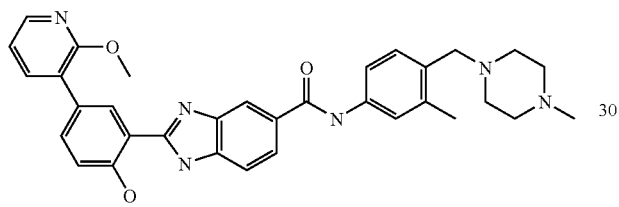

2-[2-Hydroxy-5-(2-methoxy-pyridin-3-yl)-phenyl]-1H-benzoimidazole-5-carboxylic acid [3-methyl-4-(4-methyl-piperazin-1-ylmethyl)-phenyl]-amide $^1$H NMR (MeOH-d$_4$) δ 2.34 (s, 3H), 2.85-3.40 (8H), 2.87 (s, 3H), 3.78 (s, 2H), 3.99 (s, 3H), 7.10 (m, 1H), 7.21-7.39 (4H), 7.80-7.84 (2H), 7.90 (d, J=9 Hz, 1H), 8.15-8.18 (2H), 8.26 (s, 1H), 8.41 (s, 1H). ESI-MS m/z 563.5 (MH$^+$).

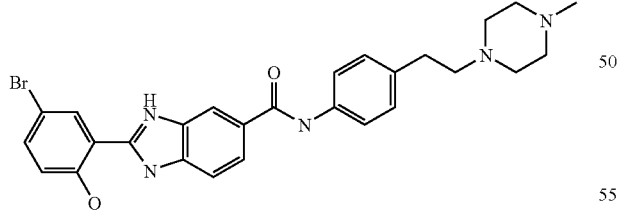

2-(5-Bromo-2-hydroxy-phenyl)-3H-benzoimidazole-5-carboxylic acid {4-[2-(4-methyl-piperazin-1-yl)-ethyl]-phenyl}-amide $^1$H NMR (MeOH-d$_4$) δ 2.34 (s, 3H), 2.50-2.85 (12H), 6.98 (d, J=9 Hz, 1H), 7.24 (d, J=9 Hz, 2H), 7.48 (d, J=9 Hz, 1H), 7.64 (d, J=9 Hz, 2H), 7.71 (d, J=9 Hz, 1H), 7.89 (d, J=9 Hz, 1H), 8.16 (s, 1H), 8.24 (s, 1H). ESI-MS m/z 534.3 (MH$^+$).

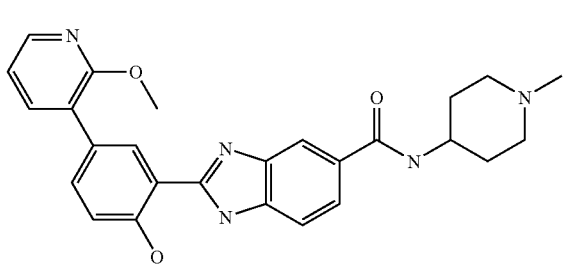 [SMILES: COc1ncccc1-c1ccc(O)c(-c2nc3cc(C(=O)NC4CCN(C)CC4)ccc3[nH]2)c1]

2-[2-Hydroxy-5-(2-methoxy-pyridin-3-yl)-phenyl]-1H-benzoimidazole-5-carboxylic acid (1-methyl-piperidin-4-yl)-amide $^1$H NMR (MeOH-d$_4$) δ 1.68-2.28 (6H), 2.32 (s, 3H), 2.95 (m, 2H), 3.91 (m, 1H), 3.96 (s, 3H), 7.00-7.06 (2H), 7.53-7.62 (2H), 7.71-7.76 (2H), 8.08-8.14 (3H) ESI-MS m/z 458.4 (MH$^+$).

General Scheme

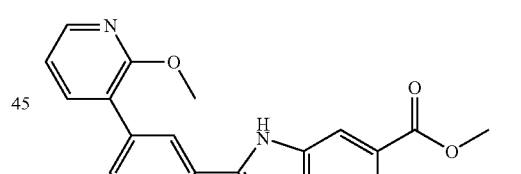

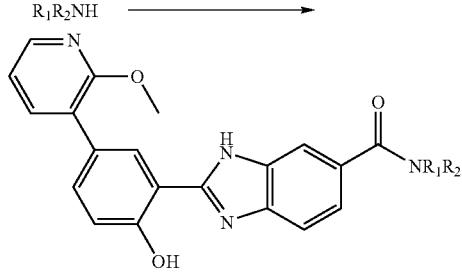

-continued

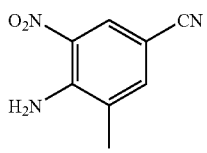

4-Amino-3-methyl-5-nitro-benzonitrile

A suspension of 4-bromo-2-methyl-6-nitroaniline (11.5 g, 50 mmol), Zn(CN)$_2$ (770 mg, 150 mmol), and Pd(PPh$_3$)$_4$ (2.32 g, 2.0 mmol) in DMF (100 mL) was sealed and heated at 120° C. for 70 h. After cooled down to room temperature, the reaction mixture was concentrated under reduced pressure. The residue was purified by chromatography with CH$_2$Cl$_2$ to afford the title compound (6.4 g, 73%). ESI-MS m/z 178 (MH$^+$).

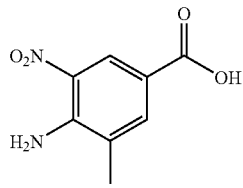

4-Amino-3-methyl-5-nitro-benzoic acid

To a suspension of 4-amino-3-methyl-5-nitro-benzonitrile (12.93 g, 0.073 mol) in mixed solvent of glacial acetic acid (50 mL) and water (100 mL) was added concentrated sulfuric acid (98%, 50 mL) slowly. The mixture was heated at 120° C. in sealed heavy wall flask for 20 h, cooled to room temperature and filtered to get the yellow precipitate which was dried at 40° C. under reduced pressure to afford the ½ H$_2$SO$_4$ salt of title compound (13.5 g, 75%). $^1$H NMR (DMSO-d$_6$) δ 2.25 (s, 3H), 7.81 (s, 1H) and 8.48 (s, 1H).

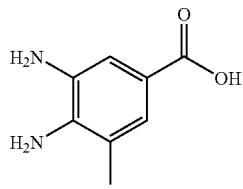

3,4-Diamino-5-methyl-benzoic acid

To a solution of the ½ H$_2$SO$_4$ salt 4-Amino-3-methyl-5-nitro-benzoic acid (116 mg, 0.47 mmol) in MeOH (40 mL) were added Pd/C (10%, 12 mg) and the mixture was stirred under atmospheric hydrogen (balloon) at the room temperature for 2.5 h. The reaction mixture was filter over Celite to afford the title compound (96 mg, 94%). $^1$H NMR (DMSO-d$_6$) δ 2.06 (s, 3H), 4.85-4.95 (4H, NH), 7.00 (s, 1H) and 7.04 (s, 1H). ESI-MS m/z 167.3 (MH$^+$).

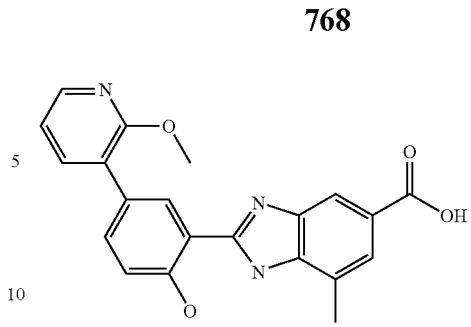

2-[2-Hydroxy-5-(2-methoxy-pyridin-3-yl)-phenyl]-7-methyl-3H-benzimidazole-5-carboxylic acid To mixture of 2-hydroxy-5-(2-methoxy-pyridin-3-yl)-benzaldehyde (144 mg, 0.4 mmol) and 3,4-diamino-5-methyl-benzoic acid (82 mg, 0.5 mol) was added DMA (0.8 mL) and the resulting solution was stirred at 0° C. for 0.5 h, and at the room temperature for 2.5 h. After it was heated open to the air at 110° C. for 15 h, the reaction mixture was concentrated under reduced pressure and the residual crude was used for the next step reaction without purification. ESI-MS m/z 376.3 (MH$^+$).

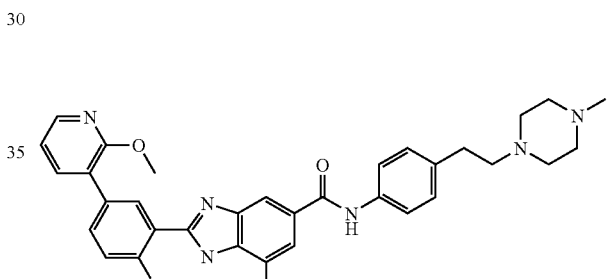

2-[2-Hydroxy-5-(2-methoxy-pyridin-3-yl)-phenyl]-7-methyl-3H-benzimidazole-5-carboxylic acid {4-[2-(4-methyl-piperazin-1-yl)-ethyl]-phenyl}-amide To a solution of the crude of 2-[2-hydroxy-5-(2-methoxy-pyridin-3-yl)-phenyl]-7-methyl-3H-benzoimidazole-5-carboxylic acid (estimated 0.4 mmol), 4-[2-(4-methyl-piperazin-1-yl)-ethyl]-phenylamine (88 mg, 0.4 mmol) and HATU (167 mg, 0.44 mmol) in DMF (5 mL) was added DIEA (0.5 mL, 371 mg, 2.87 mmol). The reaction mixture was stirred at room temperature for 2 h and heated at 60° C. for 15 h, and then evaporated to dry under reduced pressure. The residue was diluted with DMSO (1.5 mL), filtered and then purified with using HPLC (TFA/H$_2$O/CH$_3$CN) to afford the title compound (34.5 mg, 11% from two steps from 3,4-diamino-5-methyl-benzoic acid). $^1$H NMR (MeOH-d$_4$) δ 2.77 (s, 3H), 2.90 (s, 3H), 2.97-3.43 (12H), 3.97 (s, 3H), 7.09 (m, 1H), 7.22 (d, J=9 Hz, 1H), 7.31 (d, J=9 Hz, 2H), 7.70 (d, J=9 Hz, 2H), 7.82-7.84 (2H), 7.91 (s, 1H), 8.17 (m, 1H), 8.20 (s, 1H), 8.31 (s, 1H). ESI-MS m/z 577.5 (MH+).

Synthesis of the Fluorobenzimidazole Derivatives

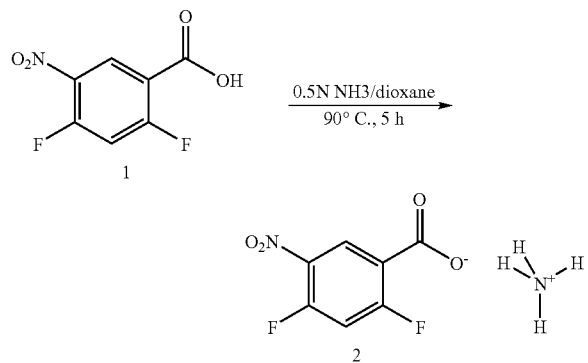

4-Amino-2-fluoro-5-nitrobenzoic acid ammoniate (2)

A suspension of 2,4-difluoro-5-nitrobenzoic acid (1.5 g, 24.6 mmol) was heated at 90° C. in a sealed vessel for 5 h and then cooled to room temperature. The yellow solid was collected by filtration and dried in vacuo at 40° C. for 20 h to afford the desired 4-amino-2-fluoro-5-nitrobenzoic acid ammoniate (2). An additional 6×5 g batches were synthesized for a total of 35 g (0.172 mmol) of 2,4-difluoro-5-nitrobenzoic acid (overall yield: 36.1 g, 0.166 mol, 97%). $^1$H NMR (MeOD): δ 8.60 (m, 1H), 6.62 (m, 1H)

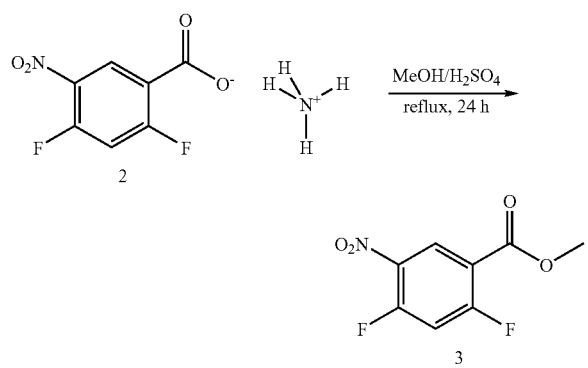

Methyl 4-amino-2-fluoro-5-nitrobenzoate (3)

Sulfuric acid (10 mL) was added to a solution of 4-amino-2-fluoro-5-nitrobenzoic acid ammoniate (10 g, 46 mmol) in methanol (100 mL) and refluxed for 30 h. The solution was cooled to ambient temperature and the solid thus obtained was collected by filtration, washed with hexanes, and dried in vacuo at 40° C. for 14 h to afford the desired methyl 4-amino-2-fluoro-5-nitrobenzoate as a yellow solid (6.84 g, 31.9 mmol, 69%). $^1$H NMR (MeOD) δ 8.62-8.58 (m, 1H), 6.63-6.59 (m, 1H).

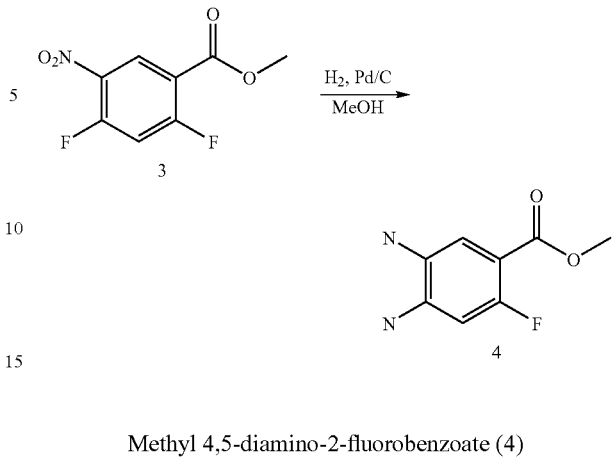

Methyl 4,5-diamino-2-fluorobenzoate (4)

A suspension of methyl 4-amino-2-fluoro-5-nitrobenzoate (6.84 g, 31.9 mmol) and 10% Pd/C (1.2 g) in methanol (200 mL) was hydrogenated under an atmosphere of hydrogen (balloon) for 20 h, filtered through Celite and the filtrate concentrated in vacuo to a residue. The residue was purified by flash chromatography (20% EtOAc/DCM) to afford the desired methyl 4,5-diamino-2-fluorobenzoate as a pink solid (2.36 g, 40%). $^1$H NMR (CDCl$_3$) δ 7.90 (s, 1H), 7.93 (s, 1H), 7.13 (d, J=8.7 Hz, 1H), 6.88 (s, 1H), 6.37 (d, J=13.5 Hz, 1H), 3.60 (t, J=6.9 Hz, 2H), 2.86 (t, J=6.9 Hz, 12H).

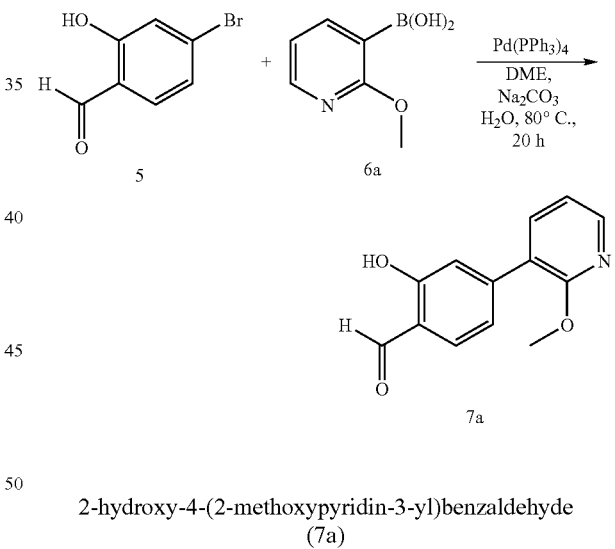

2-hydroxy-4-(2-methoxypyridin-3-yl)benzaldehyde (7a)

Pd(PPh$_3$)$_4$ (9 g, 0.008 mol) was added to a degassed suspension of 4-bromo-2-hydroxybenzaldehyde (5, 34.2 g, 0.17 mol), 2-methoxypyridine-3-boronic acid (6, 28.5 g, 0.186 mol) and sodium carbonate (18.5 g) in 1,2-dimethoxyethane (420 mL) and water (140 mL) and heated at 80° C. for 16 h. The reaction mixture was cooled to room temperature and filtered through Celite. Celite was washed with chloroform (2×200 mL) and water (200 mL). The organic layer was separated and concentrated in vacuo to a residue which was re-crystallized from EtOAc/hexanes to obtain the desired 2-hydroxy-4-(2-methoxypyridin-3-yl)benzaldehyde (7a) after isolation by filtration (16.25 g). The filtrate from the recrystallization process was evaporated to dryness and the residue purified by flash chromatography (15% EtOAc/hexanes) to obtain the desired 2-hydroxy-4-(2-methoxypyridin-3-yl)benzaldehyde (11.87 g) in an overall yield of 28.12 g (72%). $^1$H NMR (C$_6$D$_6$) δ 11.06 (s, 1H), 9.95 (s, 1H), 8.18 (dd, J=4.98 Hz, 1.83 Hz, 1H), 7.29-7.71 (m, 2H), 7.60 (dd, J=7.29 Hz, 1.83 Hz, 1H), 7.08-6.96 (m, 2H), 3.99 (s, 3H).

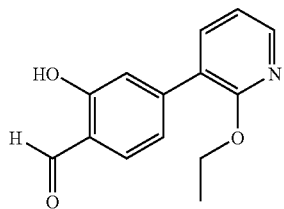

7b 4-(2-Ethoxypyridin-3-yl)-2-hydroxybenzaldehyde (7b) was synthesized as above by using 2-ethoxypyridine-3-boronic acid (6b) in the Suzuki coupling chemistry. $^1$H NMR δ 1.05 (s, 1H), 9.94 (s, 1H), 8.19-8.12 (m, 1H), 7.81-7.73 (m, 2H), 7.62-7.55 (m, 1H), 7.08-6.96 (m, 2H), 4.46-4.35 (m, 2H), 1.45-1.35 (m, 3H).

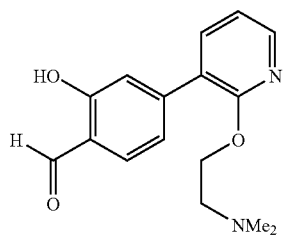

7c

4-{2-[2-(Dimethylamino)ethoxy]pyridin-3-yl}-2-hydroxybenzaldehyde (7c) was synthesized using {2-[2-(dimethylamino)ethoxy]pyridin-3-yl}boronic acid in the Suzuki coupling. $^1$H NMR δ11.05 (br s, 1H), 9.94 (s, 1H), 8.15 (dd, J=4.95 Hz, 1.86 Hz, 1H), 7.90 (d, J=2.28 Hz, 1H), 7.78 (dd, J=8.7 Hz, 2.34 Hz, 1H), 7.62 (dd, J=7.34 Hz, 1.89 Hz, 1H), 7.07-6.81 (m, 2H), 4.50 (t, J=5.85 Hz, 2H), 2.71 (t, J=5.82, 2H), 2.29 (s, 6H). ES-MS MH$^+$ 287.5.

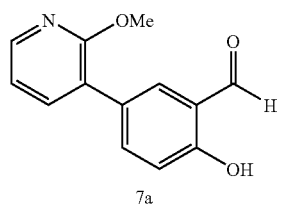

7a

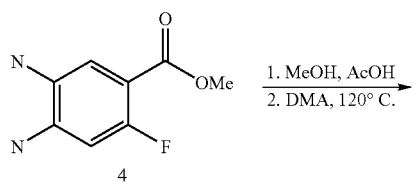

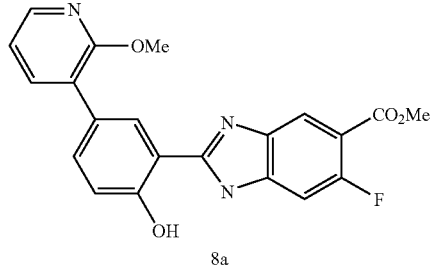

8a

Methyl 6-fluoro-2-[2-hydroxy-5-(2-methoxypyridin-3-yl)phenyl]-1H-benzimidazole-5-carboxylate (8a)

Aldehyde 7a (2.17 g, 9.46 mmol) and AcOH (2 mL) were successively added to a solution of ester 4 (2.3 g, 12.5 mmol) in methanol (250 mL) and mixture was stirred at room temperature for 16 h. The solvent was evaporated in vacuo and the residue was dissolved in N,N-dimethylacetamide (48 mL) and the brown solution was heated at 120° C. for 6 h. The solvent was removed in vacuo and the residue was purified by flash chromatpgraphy (20% EtOAc/hexanes) to afford the title compound, methyl 6-fluoro-2-[2-hydroxy-5-(2-methoxypyridin-3-yl)phenyl]-1H-benzimidazole-5-carboxylate as a colorless solid (8) (2.36 g, 63%). $^1$H NMR (CDCl$_3$) δ 11.07 (br s, 1H), 9.95 (br s, 1H), 8.17-8.20 (m, 1H), 7.79-7.71 (m, 2H), 7.63-7.58 (m, 1H), 7.08-7.96 (m, 2H), 3.99 (s, 3H).

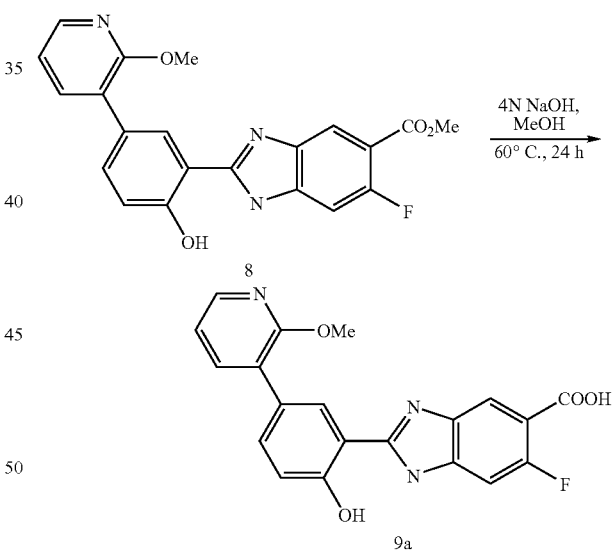

6-fluoro-2-[2-hydroxy-5-(2-methoxypyridin-3-yl) phenyl]-1H-benzimidazole-5-carboxylic acid (9a)

4M NaOH (17 mL) was added to a suspension of ester 8 (2.36 g, 6 mmol) in MeOH (45 mL) and heated at 60° C. for 20 h. The solvent was removed n vacuo and the residue was dissolved in water (35 mL). The solution was made acidic using 2N HCl (pH=2) and the solid collected by filtration, washed with water (2×20 mL) and dried in vacuo at 40° C. for 14 h to afford the title compound 9a as a colorless solid (2.3 g, 100%). ES-MS MH$^+$ 380.35.

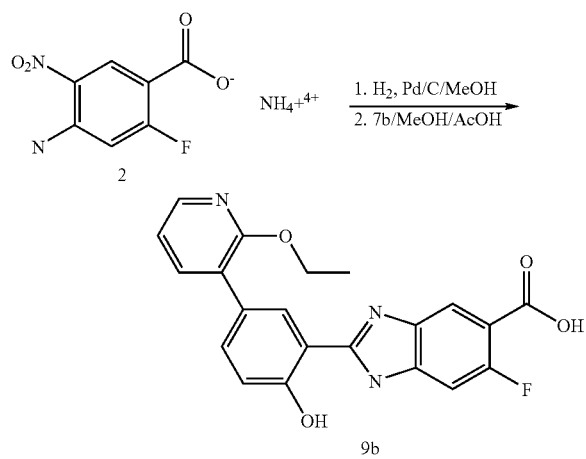

2-[5-(2-ethoxypyridin-3-yl)-2-hydroxyphenyl]-6-fluoro-1H-benzimidazole-5-carboxylic acid (9b)

A suspension of 10% Pd/C (10 mg) and ammonium salt 2 (100 mg, 0.45 mmol) was hydrogenated for 4 h under ambient conditions. The reaction mixture was filtered through Celite and the Celite was washed with MeOH. The filtrate was concentrated in vacuo and diluted with MeOH (15 mL). Then, aldehyde 7b (122 mg, 0.5 mmol) and AcOH (0.5 mL) were added and the purple reaction mixture was stirred open to air at ambient temperature for 15 h. The reaction mixture was concentrated in vacuo and the residue thus obtained was used as such in the next step. ES-MS MH+ 394.5.

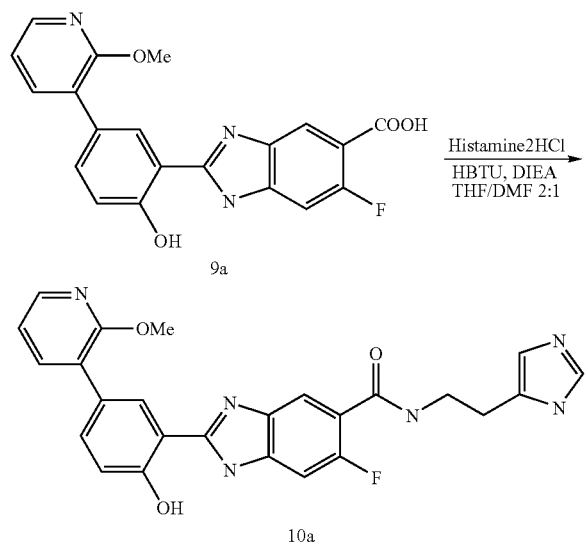

6-fluoro-N-[2-(1H-imidazol-4-yl)ethyl]-2-[2-hydroxy-5-(2-methoxypyridin-3-yl)phenyl]1H-benzimidazole-5-carboxamide (10a)

N,N-Diisopropylethylamine (4.6 mL, 26.4 mmol) and histamine·2HCl (1.16 g, 6.3 mmol) were successively added to a solution of acid 9a (2.3 g, 6 mmol) and HBTU (2.5 g, 6.6 mmol) in THF (70 mL) and DMF (35 mL). The reaction mixture was stirred at room temperature for 18 h and the solvent was evaporated in vacuo. Water (35 mL) was added to the residue and the fine precipitate was collected by filtration and suspended in methanol/water (1/1, 100 mL). The suspension was stirred at room temperature for 14 h and the solid was collected by filtration and dried in vacuo at 40° C. for 14 h to afford the desired 6-fluoro-N-[2-(1H-imidazol-4-yl)ethyl]-2-[2-hydroxy-5-(2-methoxypyridin-3-yl)phenyl] 1H-benzimidazole-5-carboxamide (10a) as a colorless solid. $^1$H NMR (DMSO-$d_6$) δ 13.79-11.28 (br s, 2H), 8.45-8.16 (m, 3H), 7.94-7.91 (m, 2H), 7.69-7.51 (m, 3H), 7.17-7.11 (m, 2H), 6.88 (s, 1H), 3.92 (s, 3H), 3.59-3.48 (m, 2H), 2.79 (t, J=6.6 Hz, 2H). ES-MS MH+ 473.48. EA was in agreement with the formula $C_{25}H_{21}FN_6O_3 \cdot 0.75H_2O$.

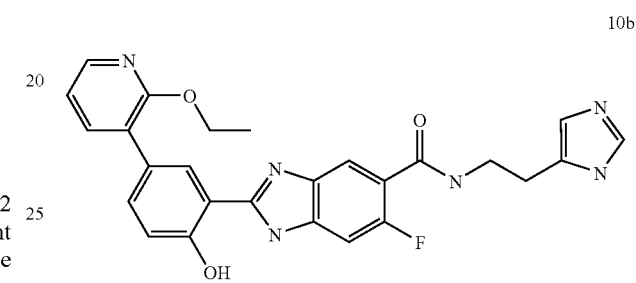

2-[5-(2-Ethoxypyridin-3-yl)-2-hydroxyphenyl]-6-fluoro-N-[2-(1H-imidazol-5-yl)ethyl]-1H-benzimidazole-5-carboxamide (10b)

was synthesized using aldehyde 9b in a similar manner as the methoxy derivative 10a in 16% overall yield. $^1$H NMR (MeOD) δ 8.45-8.16-8.06 (m, 2H), 7.96 (d, J=6.36 Hz, 1H), 7.91 (s, 1H), 7.76 (dd, J=7.32 Hz, 1.83 Hz 1H), 7.66-7.59 (m, 2H), 7.39 (d, J=11.31 Hz, 1H), 7.09-7.01 (m, 2H), 6.93 (br s, 1H), 4.45-4.36 (m, 2H), 3.68 (t, J=6.96 Hz, 2H), 2.93 (t, J=6.96 Hz, 2H) 2.93 (t, J=7.02 Hz, 3H). ES-MS MH+ 487.5.

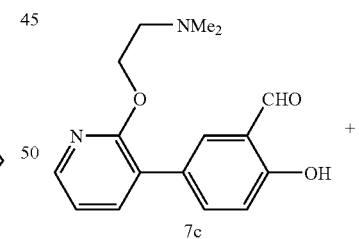

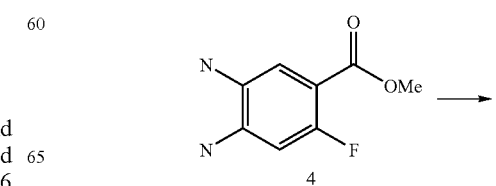

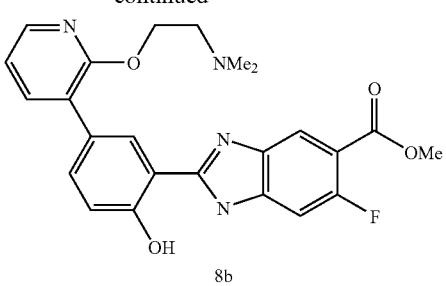

Methyl 2-(5-{2-[2-(dimethylamino)ethoxy]pyridin-3-yl}-2-hydroxyphenyl)-6-fluoro-1H-benzimidazole-5-carboxylate (8b)

Diamine (44 mg, 0.24 mmol, 1.3 eq.) was added to a solution of the aldehyde (50 mg, 0.18 mmol, 1.0 eq.) and AcOH (0.05 mL) in MeOH (5 mL) and stirred overnight at ambient temperature. The reaction mixture was evaporated in vacuo and the residue was dissolved in DMA (5 mL) and then heated at 120° C. for 5 h. The reaction mixture was concentrated in vacuo to a residual oil which was purified by flash chromatography [10% (5% aq. NH$_4$OH/MeOH)/DCM] (R$_f$=0.32) to afford the title compound as a yellow solid (31 mg, 39%). ES-MS MH$^+$ 451.47.

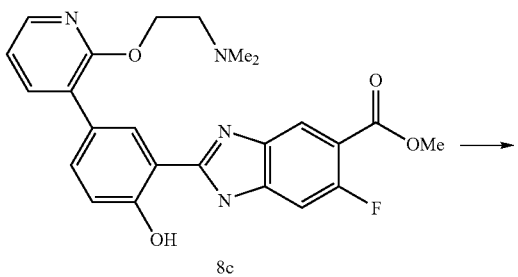

2-({3-[3-(5-Carboxy-6-fluoro-1H-benzimidazol-2-yl)-4-hydroxyphenyl]pyridin-2-yl}oxy)-N,N-dimethylethanaminium chloride (9c)

A solution of Ester 8c (31 mg, 0.071 mmol) in 10% aq. HCl (3 mL) was heated at 100° C. for 6 h. The reaction mixture was cooled to ambient temperature and concentrated in vacuo to a residue and azeotroped with toluene (3×10 mL) to afford the title compound which was used as such in the next step. ES-MS MH$^+$ 437.47.

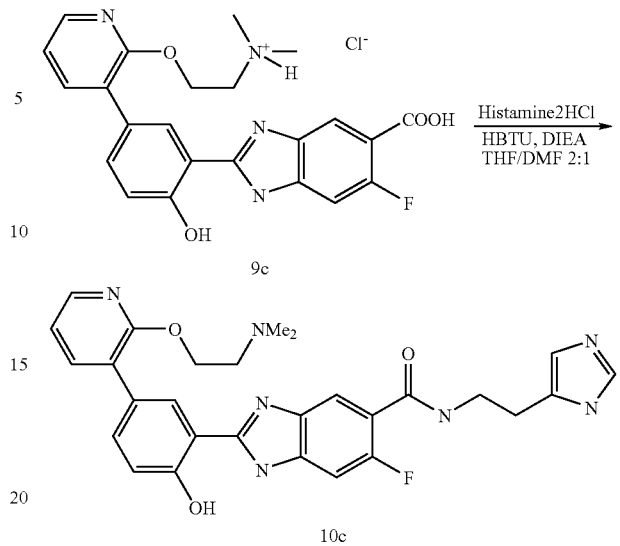

2-(5-{2-[2-(Dimethylamino)ethoxy]pyridin-3-yl}-2-hydroxyphenyl)-6-fluoro-N-[2-(1H-imidazol-5-yl)ethyl]-1H-benzimidazole-5-carboxamide (10c)

Et$_3$N (0.079 mL, 0.568 mmol, 8.0 eq.) was added to a mixture containing the crude carboxylic acid salt 9c (0.071 mmol, 1.0 eq.), histamine.2HCl (16 mg, 0.085 mmol, 1.2 eq.), EDC (15 mg, 0.078 mmol, 1.1 eq.) and HOBt (11 mg, 0.078 mmol, 1.1 eq.) in dry DMF (2 mL) and stirred for 16 h. The reaction mixture was concentrated in vacuo and the residue was purified by flash chromatography [10% (5% aq NH$_4$OH/MeOH)/DCM] to afford the title compound (R$_f$=0.40) as a light yellow powder (20.1 mg, 53%). ES-MS MH$^+$ 530.30.

6.13 Example 13

Synthesis of Compounds According to Formula (6)

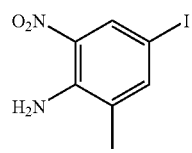

4-Iodo-2-methyl-6-nitroaniline

To a mixture of 2-methyl-6-nitroaniline (106.5 g, 0.7 mol) and NaOAc (63.2 g, 0.77 mol) in acetic acid (525 mL) was added a solution of ICl (125 g, 0.77 mol) in acetic acid (350 mL). The mixture was heated at 80° C. for 50 min and poured into H$_2$O (2100 mL). After stayed at the room temperature for 16 h, the mixture was filtered to furnish yellow solid that was washed with H$_2$O (3×350 mL). Drying under reduced pressure at 40° C. for 48 h afforded the title compound (191 g, 98%). $^1$H NMR (CDCl$_3$) δ 2.22 (s, 3H), 6.20 (br s, 2H NH), 7.53 (s, 1H), 8.34 (s, 1H). ESI-MS m/z 279 (MH$^+$).

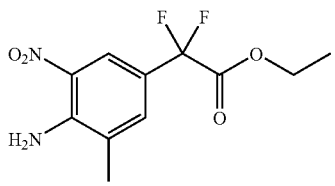 [SMILES: CCOC(=O)C(F)(F)c1cc(C)c(N)c([N+](=O)[O-])c1]

(4-Amino-3-methyl-5-nitro-phenyl)-difluoro-acetic acid ethyl ester

To a solution of 4-iodo-2-methyl-6-nitroaniline (2.78 g, 10 mmol) and 2-bromo-2,2-difluoroacetic acid ethyl ester (2.03 g, 10 mmol) in anhydrous DMSO (20 mL) was added copper powder (1.28 g, 20 mmol). The mixture was purged with $N_2$ and heated at 60° C. in a sealed vial for 14 h. After being cooled to the room temperature, the reaction mixture was poured into 20% aqueous $NH_4Cl$ solution (300 mL). The resulting mixture was basified to pHY=8.5 with saturated aqueous $Na_2CO_3$ solution and was extracted with EtOAc (3×100 mL). The organic extract was washed with brine (2×30 mL), dried over $Na_2SO_4$ and concentrated. The residue was purified by chromatography (40:1 hexanes/EtOAc) to afford the title compound (1.79 g, 65%). $^1H$ NMR ($CDCl_3$) δ 1.36 (t, 3H), 2.30 (s, 3H), 4.36 (q, 2H), 6.41 (br s, 2H NH), 7.51 (s, 1H), 8.33 (s, 1H). ESI-MS m/z 275 (MH$^+$), 255 (M-F)$^+$, 297 (M+Na)$^+$, 549 (2M+1)$^+$ and 571 (2M+Na)$^+$.

2-(4-Amino-3-methyl-5-nitro-phenyl)-2,2-difluoro-1-morpholin-4-yl-ethanone

A mixture of (4-amino-3-methyl-5-nitro-phenyl)-difluoro-acetic acid ethyl ester (3.5 g, 12.76 mmol) and morphine (20 mL, 20.0 g, 0.23 mol) was heated at 60° C. in a sealed vial for 3 h and was poured into 20% aqueous $NH_4Cl$ solution (300 mL), resulting an aqueous mixture that was extracted with EtOAc (3×100 mL). The organic extract was washed with brine (2×30 mL) and dried over $Na_2SO_4$. Removing solvent under reduced pressure afforded the title compound (3.88 g, 96%). $^1H$ NMR ($CDCl_3$) δ 2.29 (s, 3H), 3.60-3.68 (4H), 3.68-3.81 (4H), 6.43 (br s, 2H NH), 7.48 (s, 1H), 8.25 (s, 1H). ESI-MS m/z 316 (MH$^+$), 296 (M-F)$^+$, 338 (M+Na)$^+$, 631 (2M+1)$^+$ and 653 (2M+Na)$^+$.

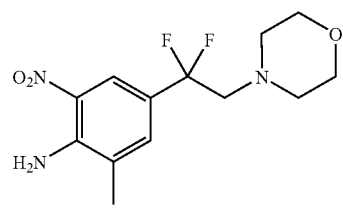 [SMILES: Cc1cc(C(F)(F)CN2CCOCC2)cc([N+](=O)[O-])c1N]

4-(1,1-Difluoro-2-morpholin-4-yl-ethyl)-2-methyl-6-nitro-phenylamine

To a solution of 2-(4-amino-3-methyl-5-nitro-phenyl)-2,2-difluoro-1-morpholin-4-yl-ethanone (945 mg, 3 mmol) in anhydrous THF (15 mL) was added $BH_3\cdot S(CH_3)_2$ (1 mL, 790 mg, 10.4 mmol) dropwise and slowly under $N_2$ at 0° C. The mixture was stirred under $N_2$ at the room temperature for 19 h and then refluxed under $N_2$ for 1.5 h. After being cooled to 0° C., MeOH (2 mL) was added dropwise and slowly. The reaction mixture was poured into 20% aqueous $NaHCO_3$ solution (150 mL) and extracted with EtOAc (3×50 mL). The organic extract was washed with brine (2×10 mL), dried over $Na_2SO_4$ and concentrated. The residue was purified by chromatography (2:3 hexanes/EtOAc) to afford the title compound (740 mg, 82%). $^1H$ NMR ($CDCl_3$) δ 2.29 (s, 3H), 2.56-2.61 (4H), 2.93 (t, J=12 Hz, 2H, $CH_2CF_2$), 3.62-3.63 (4H), 6.34 (br s, 2H NH), 7.44 (s, 1H), 8.25 (s, 1H). (s, 1H). ESI-MS m/z 302 (MH$^+$).

Synthesis of Difluoro Compound

General Scheme

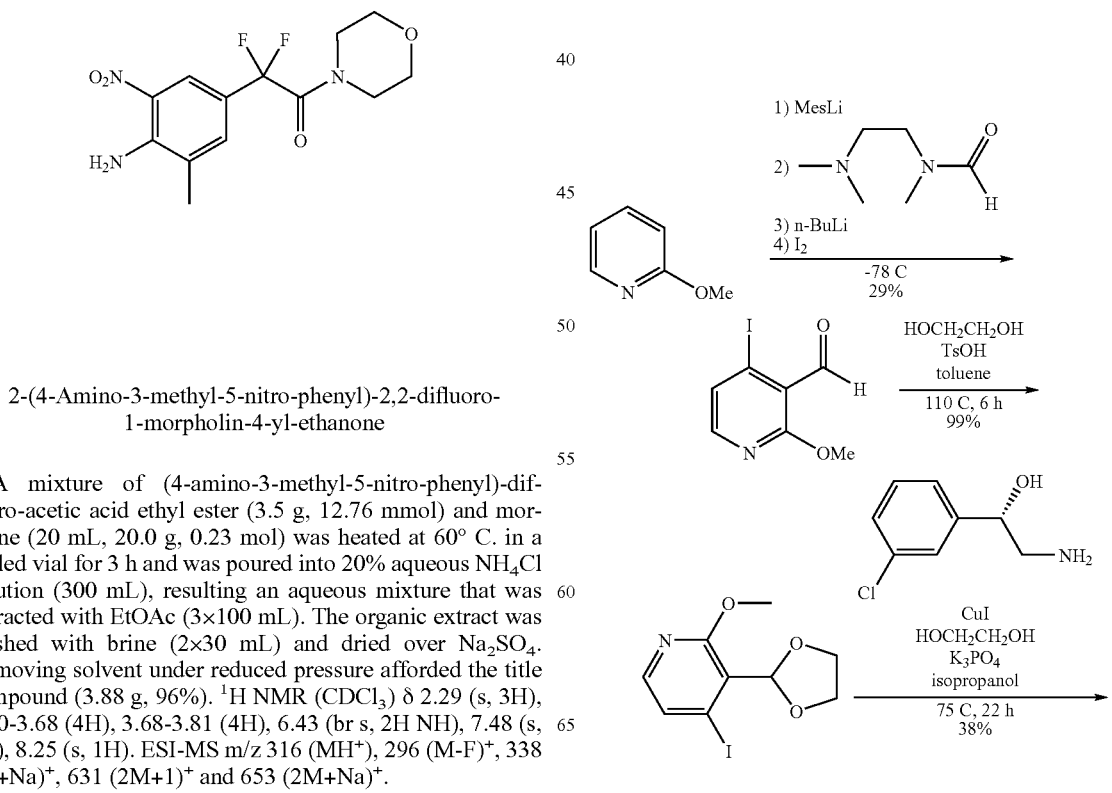

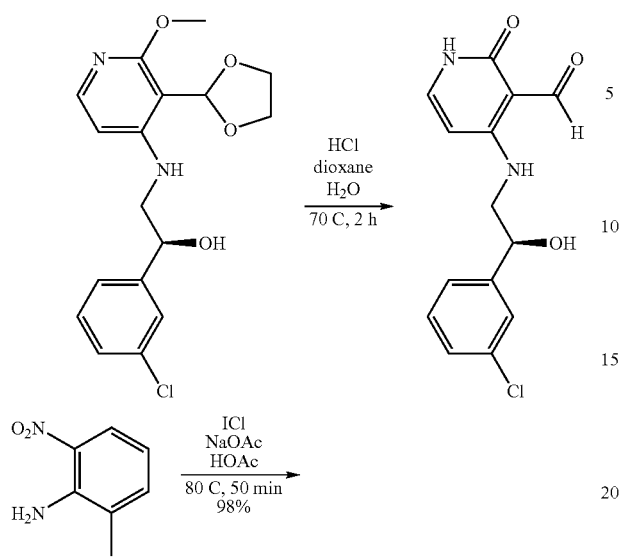

4-Iodo-2-methoxynicotinic aldehyde

To a solution of t-BuLi (1.7 M, 7.36 mL, 12.51 mmol) in 20 mL THF at −78° C. was added dropwise 2-bromomesitylene (0.91 mL, 5.95 mmol). After stirred for 1 h, 2-methoxypyridine (0.48 mL, 4.58 mmol) was added dropwise, and the mixture was warmed to 0° C. and stirred for 2 h. The solution was cooled to −78° C. and N-formyl-N,N',N-trimethylethylenediamine (0.7 mL, 5.06 mmol) was added. The mixture was stirred at −78° C. for 30 min and then warmed to −23° C. A hexane solution of n-BuLi (2.5 M, 2.75 mL, 6.87 mmol) was added dropwise, and the resulting yellow mixture was stirred for 3 h. The mixture was cooled to −78° C. and transferred via a double-tipped needle to a solution of iodine (2.17 g, 8.23 mmol) in 30 mL of THF at −78° C. After stirred at −78° C. for 30 min, the cooling bath was removed and the reaction mixture was allowed to warm to the room temperature. After the reaction mixture was cooled to −5° C., aqueous solution of $NH_4Cl$ (20 mL) was added dropwise and stirred for 15 min. The reaction mixture was poured into brine (300 mL) and extracted with EtOAc (5×100 mL). The combined extracts were washed with brine (2×50 mL), dried over $Na_2SO_4$ and concentrated. The residue was purified by chromatography (25:1 hexanes/EtOAc) to afford the title compound (350 mg, 29%). $^1$H NMR (CDCl$_3$) δ 4.05 (s, 3H, CH$_3$), 7.53 (d, J=6 Hz, 1H, ArH), 7.85 (d, J=6 Hz, 1H, ArH), 10.20 (s, 1H, CHO).

3-[1,3]Dioxolan-2-yl-4-iodo-2-methoxy-pyridine

To a solution of 4-iodo-2-methoxynicotinic aldehyde (5.26 g, 20.0 mmol) and ethylene glycol (2.48 g, 40 mmol) in toluene (400 mL) was added p-toluenesulfonic acid monohydrate (95 mg, 0.5 mmol). After it was refluxed under N₂ for 6 h, the reaction mixture was concentrated and the residue was diluted with 300 mL EtOAc and washed with 2×100 mL 10% Na₂CO₃ solution. The aqueous solution was extracted with EtOAc (3×50 mL) and the combined EtOAc extracts were washed with brine and dried over Na₂SO₄. Evaporation of solvent afforded the title product (6.07 g, 99%). ¹H NMR (CDCl₃) δ 3.95 (s, 3H), 4.07 (m, 2H), 4.33 (m, 2H), 6.25 (s, 1H), 7.40 (d, J=6 Hz, 1H), 7.70 (d, J=6 Hz, 1H). ESI-MS m/z 308.4 (MH⁺).

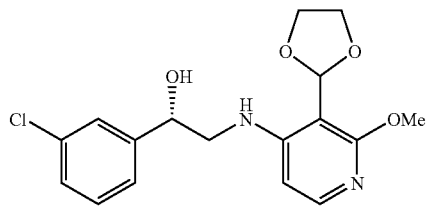 [SMILES: COc1nccc(NC[C@@H](O)c2cccc(Cl)c2)c1C1OCCO1]

(S)-1-(3-Chloro-phenyl)-2-(3-[1,3]dioxolan-2-yl-2-methoxy-pyridin-4-ylamino)-ethanol A suspension of 3-[1,3]dioxolan-2-yl-4-iodo-2-methoxy-pyridine (3.07 g, 10.0 mmol), (S)-2-amino-1-(3-chloro-phenyl)-ethanol (1.71 g, 10 mmol), CuI (190 mg, 1.0 mmol), ethylene glycol (1.86 g, 30 mmol) and K₃PO₄ (6.3 g, 30 mmol) in 2-propanol (200 mL) was sealed and heated at 75° C. for 22 h (CuI and K₃PO₄ were crushed into powders before added). After cooled down to room temperature, the reaction mixture was loaded on silica gel. The chromatography with eluant CH₂Cl₂: MeOH=100:1 afforded the title product (1.27 g, 38%). ¹H NMR (CDCl₃) δ 3.30 (m, 1H) 3.45 (m, 1H), 3.87 (s, 3H), 3.96-4.05 (4H), 4.85 n (m, 1H), 6.09 (s, 1H), 6.15-6.30 (2H), 7.21-7.35 (2H), 7.41 (s, 1H), 7.82 (d, J=6 Hz, 1H). ESI-MS m/z 351.4 (MH⁺).

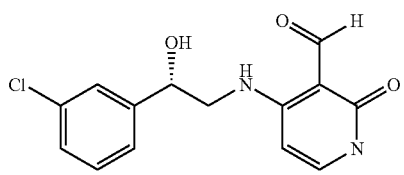 [SMILES: O=Cc1c(NC[C@@H](O)c2cccc(Cl)c2)cc[nH]c1=O]

4-[(S)-2-(3-Chloro-phenyl)-2-hydroxy-ethylamino]-2-oxo-1,2-dihydro-pyridine-3-carbaldehyde To a mixture of (S)-1-(3-chloro-phenyl)-2-(3-[1,3]dioxolan-2-yl-2-methoxy-pyridin-4-ylamino)-ethanol (223 mg, 0.64 mmol) and H₂O (0.75 mL) was added HCl solution in dioxane (4 M, 10 mL). After it was heated at 70° C. for 4 h, the reaction mixture was evaporated to dryness. HPLC purification of the residue afforded the title compound (20.1 mg, 11%). ¹H NMR (DMSO-d₆) δ3.37 (m, 1H) 3.58 (m, 1H), 4.58 (m, 1H), 5.95 (d, J=6 Hz, 1H), 7.30-7.40 (3H), 7.49 (s, 1H), 9.94 (s, 1H, CHO), 10.30 (m, 1H, NH), 10.95 (m, 1H, 1H). ESI-MS m/z 293.3 (MH⁺).

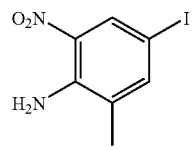

4-Iodo-2-methyl-6-nitroaniline

To a mixture of 2-methyl-6-nitroaniline (106.5 g, 0.7 mol) and NaOAc (63.2 g, 0.77 mol) in acetic acid (525 mL) was added a solution of ICl (125 g, 0.77 mol) in acetic acid (350 mL). The mixture was heated at 80° C. for 50 min and poured into H₂O (2100 mL). After stayed at the room temperature for 16 h, the mixture was filtered to furnish yellow solid that was washed with H₂O (3×350 mL). Drying under reduced pressure at 40° C. for 48 h afforded the title compound (191 g, 98%). ¹H NMR (CDCl₃) δ 2.22 (s, 3H), 6.20 (br s, 2H NH), 7.53 (s, 1H), 8.34 (s, 1H). ESI-MS m/z 279 (MH⁺).

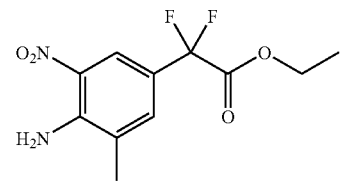 [SMILES: CCOC(=O)C(F)(F)c1cc(C)c(N)c([N+](=O)[O-])c1]

(4-Amino-3-methyl-5-nitro-phenyl)-difluoro-acetic acid ethyl ester

To a solution of 4-iodo-2-methyl-6-nitroaniline (2.78 g, 10 mmol) and 2-bromo-2,2-difluoroacetic acid ethyl ester (2.03 g, 10 mmol) in anhydrous DMSO (20 mL) was added copper powder (1.28 g, 20 mmol). The mixture was purged with N₂ and heated at 60° C. in a sealed vial for 14 h. After being cooled to the room temperature, the reaction mixture was poured into 20% aqueous NH₄Cl solution (300 mL). The resulting mixture was basified to pH=8.5 with saturated aqueous Na₂CO₃ solution and was extracted with EtOAc (3×100 mL). The organic extract was washed with brine (2×30 mL), dried over Na₂SO₄ and concentrated. The residue was purified by chromatography (40:1 hexanes/EtOAc) to afford the title compound (1.79 g, 65%). ¹H NMR (CDCl₃) δ 1.36 (t, 3H), 2.30 (s, 3H), 4.36 (q, 2H), 6.41 (br s, 2H NH), 7.51 (s, 1H), 8.33 (s, 1H). ESI-MS m/z 275 (MH⁺), 255 (M-F)⁺, 297 (M+Na)⁺, 549 (2M+1)⁺ and 571 (2M+Na)⁺.

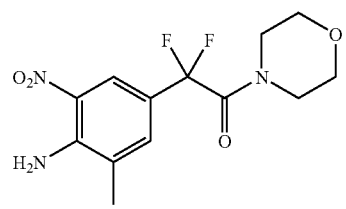 [SMILES: Cc1cc(C(F)(F)C(=O)N2CCOCC2)cc([N+](=O)[O-])c1N]

2-(4-Amino-3-methyl-5-nitro-phenyl)-2,2-difluoro-1-morpholin-4-yl-ethanone

A mixture of (4-amino-3-methyl-5-nitro-phenyl)-difluoro-acetic acid ethyl ester (3.5 g, 12.76 mmol) and morphine (20 mL, 20.0 g, 0.23 mol) was heated at 60° C. in a sealed vial for 3 h and was poured into 20% aqueous NH₄Cl solution (300 mL), resulting an aqueous mixture that was extracted with EtOAc (3×100 mL). The organic extract was washed with brine (2×30 mL) and dried over $Na_2SO_4$. Removing solvent under reduced pressure afforded the title compound (3.88 g, 96%). ¹H NMR (CDCl₃) δ 2.29 (s, 3H), 3.60-3.68 (4H), 3.68-3.81 (4H), 6.43 (br s, 2H NH), 7.48 (s, 1H), 8.25 (s, 1H). ESI-MS m/z 316 (MH⁺), 296 (M-F)⁺, 338 (M+Na)⁺, 631 (2M+1)⁺ and 653 (2M+Na)⁺.

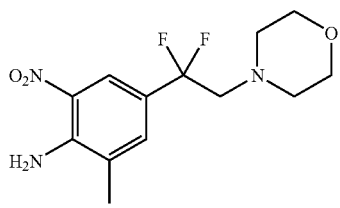 [SMILES: Cc1cc(C(F)(F)CN2CCOCC2)cc([N+](=O)[O-])c1N]

4-(1,1-Difluoro-2-morpholin-4-yl-ethyl)-2-methyl-6-nitro-phenylamine

To a solution of 2-(4-amino-3-methyl-5-nitro-phenyl)-2,2-difluoro-1-morpholin-4-yl-ethanone (945 mg, 3 mmol) in anhydrous THF (15 mL) was added BH₃.S(CH₃)₂ (1 mL, 790 mg, 10.4 mmol) dropwise and slowly under N₂ at 0° C. The mixture was stirred under N₂ at the room temperature for 19 h and then refluxed under N₂ for 1.5 h. After being cooled to 0° C., MeOH (2 mL) was added dropwise and slowly. The reaction mixture was poured into 20% aqueous NaHCO₃ solution (150 mL) and extracted with EtOAc (3×50 mL). The organic extract was washed with brine (2×10 mL), dried over Na₂SO₄ and concentrated. The residue was purified by chromatography (2:3 hexanes/EtOAc) to afford the title compound (740 mg, 82%). ¹H NMR (CDCl₃) δ2.29 (s, 3H), 2.56-2.61 (4H), 2.93 (t, J=12 Hz, 2H, CH₂CF₂), 3.62-3.63 (4H), 6.34 (br s, 2H NH), 7.44 (s, 1H), 8.25 (s, 1H). (s, 1H). ESI-MS m/z 302 (MH⁺).

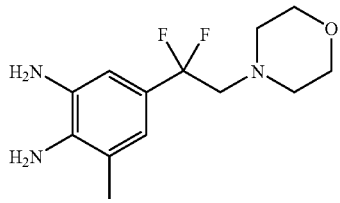

5-(1,1-Difluoro-2-morpholin-4-yl-ethyl)-3-methyl-benzene-1,2-diamine

To a solution of 4-(1,1-difluoro-2-morpholin-4-yl-ethyl)-2-methyl-6-nitro-phenylamine (60 mg, 0.2 mmol) in THF (5 mL) was added Raney nickel (100 mg) and cyclohexadiene (0.5 mL). TLC indicated the formation of the product after the reaction mixture was stirred for 3.5 h). The reaction mixture was filtered over Celite and evaporated to afforded crude title product that was used for the next step reaction without purification.

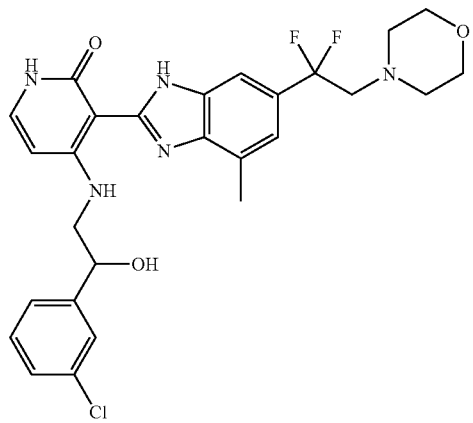 [SMILES: Cc1cc(C(F)(F)CN2CCOCC2)cc2[nH]c(-c3c(NCC(O)c4cccc(Cl)c4)cc[nH]c3=O)nc12]

4-[(S)-2-(3-Chloro-phenyl)-2-hydroxy-ethylamino]-3-[6-(1,1-difluoro-2-morpholin-4-yl-ethyl)-4-methyl-1H-benzoimidazol-2-yl]-1H-pyridin-2-one To a solution of 5-(1,1-difluoro-2-morpholin-4-yl-ethyl)-3-methyl-benzene-1,2-diamine (54 mg, 0.2 mmol), 4-[(S)-2-(3-chloro-phenyl)-2-hydroxy-ethylamino]-2-oxo-1,2-dihydro-pyridine-3-carbaldehyde (20.1 mg, 0.069 mmol) in EtOH (9.5 mL) was added HOAc (0.5 mL). After it was heated at 40° C. for 72 h, the reaction mixture was concentrated. HPLC purification of the residue afforded TFA salt of the title compound (0.56 mg, 0.4%). ¹H NMR (DMSO-d₆) δ 2.57 (s, 3H), 2.75-2.82 (4H), 2.93 (m, 2H), 3.37 (m, 1H) 3.48 (m, 1H), 3.56-3.72 (4H), 4.98 (m, 1H), 6.17 (d, J=6 Hz, 1H), 7.02-7.51 (7H). ESI-MS m/z 544.3 (MH⁺).

6.14 Example 14

IGF1R Activity of Compounds of the Invention

The present example demonstrates the tyrosine kinase activity of certain compounds of the invention.

Inhibition of IGF1R tyrosine phosphorylation was measured in the Alphascreen phosphotyrosine PT66 assay kit (Perkin Elmer Life sciences, Catalog number 6760602) according to the manufacturer's instructions. As a source of enzymatically active IGF1r kinase for this assay, SF9 insect cells were infected with recombinant baculovirus (Bac-to-Bac System, Invitrogen, Carlsbad, Calif.) encoding 6×His-tagged kinase domain portion of human IGF1R precursor protein corresponding to the amino acids positions 974 through 1293 (Abbott et al., 1992, *J. Biol. Chem.* 267:10759-10763) and recombinant kinase protein was purified to homogeneity using two-step chromatography on immobilized Ni²⁺ resin (Ni-NTA) and ion-exchange Q-Sepharose column. Biotinylated poly glu-tyr 4:1 (CIS bio-international, catalog number 61GT0BLA) was used for the kinase substrate. Compounds were serially diluted to give a concentration range from 20 to 0.1 µM and co-incubated with IGF1r kinase, biotinylated peptide substrate and alphascreen components for 1 hour and then read in a Perkin-Elmer alphafusion plate reader. A plot of counts per minute versus log concentration of compounds was fitted to a sigmoidal dose response curve using Graphpad Prism software to generate $IC_{50}$ values (see FIG. 1 for an example).

Cell viability of either MCF7 human breast tumor cells (American Type Culture Collection catalog #HTB 22) or NCI-H929 human plasmacytoma cells (ATCC catalog

CRL-9068) was assessed using the Promega CellTiter-Glo luminescent cell viability assay according to manufacturer's instructions. In brief, cells were plated at 10,000 cells per well in a clear bottom white 96 well microtiter plate (Costar catalog #3604) in 100 μL of cell growth medium. Compounds were then added to the cells to give final concentrations of compound ranging from 20 to 0.1 μM. Cells were incubated 48 hours after which 100 μL per well of celltiter-glo reagent was added and luminescence was measured in a BMG polarstar plate luminometer. A plot of counts per minute versus log concentration of compounds was fitted to a sigmoidal dose response curve using Graphpad Prism software to generate $IC_{50}$ values.

In the following table, the following symbols have the following meanings: A≤5 μM; 5 μM<B≤10 μM; 10 μM<C≤15 μM; 25 μM<D.

IGF1R Activity of Compounds of the Invention

| MOLSTRUCTURE | IGF1R IC50 (uM) | MCF7 IC50 (uM) | H929 IC50 (uM) |
|---|---|---|---|
| | A | B | B |
| | A | C | C |
| | A | 0 | D |

-continued

| MOLSTRUCTURE | IGF1R IC50 (uM) | MCF7 IC50 (uM) | H929 IC50 (uM) |
|---|---|---|---|
| | C | C | C |
| | A | C | B |
| | A | B | D |
| | A | B | B |
| | A | C | B |

-continued

| MOLSTRUCTURE | IGF1R IC50 (uM) | MCF7 IC50 (uM) | H929 IC50 (uM) |
|---|---|---|---|
| | A | B | A |
| | A | C | B |
| | A | D | 0 |
| | A | C | B |
| | A | C | 0 |

| MOLSTRUCTURE | IGF1R IC50 (uM) | MCF7 IC50 (uM) | H929 IC50 (uM) |
|---|---|---|---|
| 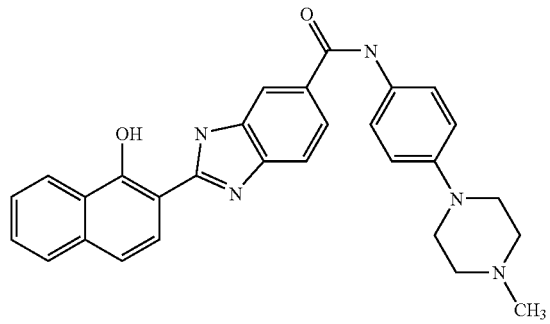 [SMILES: CN1CCN(c2ccc(NC(=O)c3ccc4nc(-c5ccc6ccccc6c5O)[nH]c4c3)cc2)CC1] | A | C | B |
| 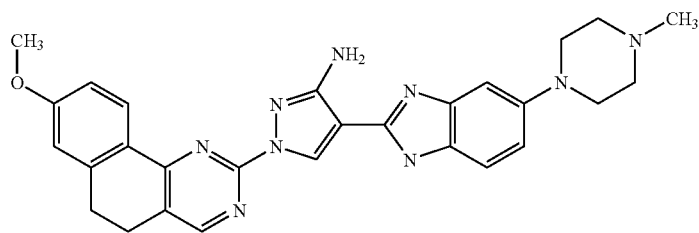 [SMILES: COc1ccc2c(c1)CCc1cnc(-n3cc(-c4nc5cc(N6CCN(C)CC6)ccc5[nH]4)c(N)n3)nc1-2] | A | C | B |
| 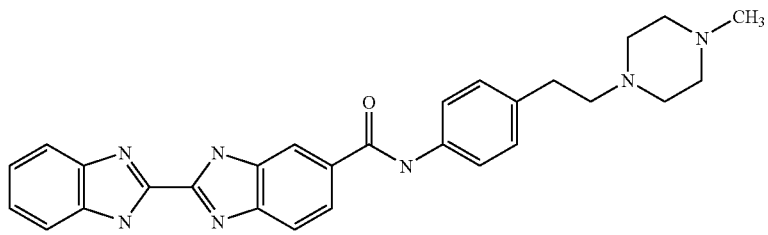 [SMILES: CN1CCN(CCc2ccc(NC(=O)c3ccc4nc(-c5nc6ccccc6[nH]5)[nH]c4c3)cc2)CC1] | A | D | B |
| 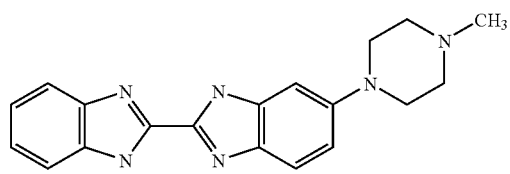 [SMILES: CN1CCN(c2ccc3nc(-c4nc5ccccc5[nH]4)[nH]c3c2)CC1] | A | C | C |
| 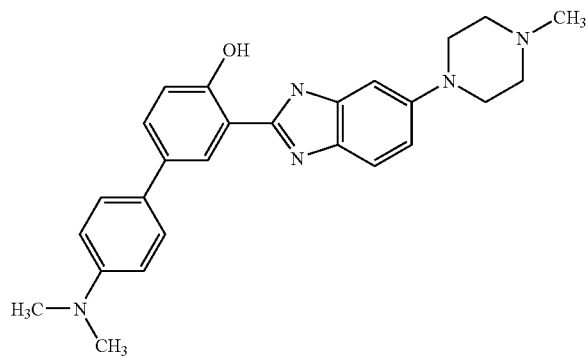 | A | C | B |

-continued

| MOLSTRUCTURE | IGF1R IC50 (uM) | MCF7 IC50 (uM) | H929 IC50 (uM) |
|---|---|---|---|
| | A | B | A |
| | A | D | C |
| | A | C | C |
| | A | C | D |
| | A | C | C |

-continued

| MOLSTRUCTURE | IGF1R IC50 (uM) | MCF7 IC50 (uM) | H929 IC50 (uM) |
|---|---|---|---|
| | A | B | A |
| | A | D | C |
| | A | C | A |
| | A | B | A |

| MOLSTRUCTURE | IGF1R IC50 (uM) | MCF7 IC50 (uM) | H929 IC50 (uM) |
|---|---|---|---|
| (structure) | A | B | A |
| (structure) | A | C | A |
| (structure) | A | C | A |
| (structure) | A | C | A |

6.15 Example 15

TrkA Activity of Compounds of the Invention

The present example demonstrates the tyrosine kinase activity of certain compounds of the invention.

Inhibition of TrkA tyrosine kinase activity was measured using the Alphascreen phosphotyrosine PT66 assay kit (Perkin Elmer Life Sciences, Catalog Number 6760602) according to the manufacturer's instructions. As a source of enzymatically active TrkA kinase for this assay, the commercial preparation of recombinant TrkA kinase domain (Upstate Cell Signaling, Catalog Number 14-571) was used. Biotinylated poly Glu-Tyr 4:1 (CIS bio-international, catalog number 61GT0BLA) was used for the kinase substrate. Compounds were serially diluted to give a concentration range from 10 to 0.005 μM and co-incubated with TrkA kinase, biotinylated peptide substrate and Alphascreen kit components for 1 hour and then read in a Perkin-Elmer Alpha Fusion plate reader. A plot of counts per minute versus log concentration of compounds was fitted to a sigmoidal dose response curve using Graphpad Prism software to generate $IC_{50}$ values.

In the following table, the following symbols have the following IC$_{50}$ values: XXX<20 nM; 20 nM<XX<200 nM; X>200 nM.
| Structure | IC50 TrkA |
|---|---|
| 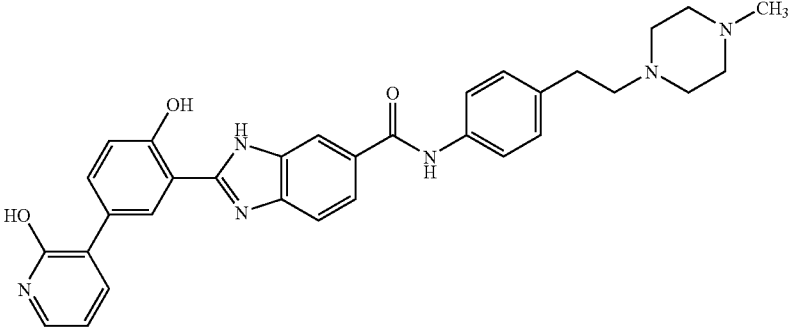 [SMILES: CN1CCN(CCc2ccc(NC(=O)c3ccc4nc(-c5cc(-c6cccnc6O)ccc5O)[nH]c4c3)cc2)CC1] | XX |
| 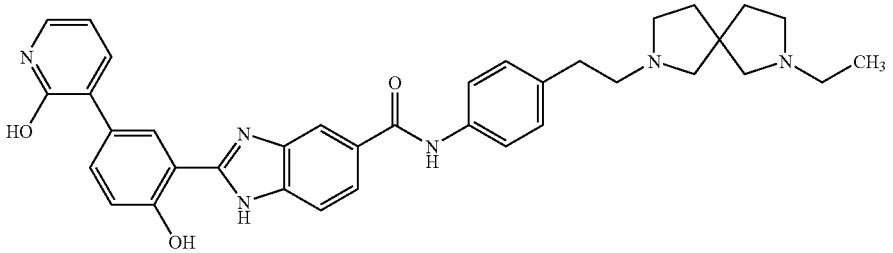 [SMILES: CCN1CCC2(CCN(CCc3ccc(NC(=O)c4ccc5[nH]c(-c6cc(-c7cccnc7O)ccc6O)nc5c4)cc3)C2)C1] | XXX |
| 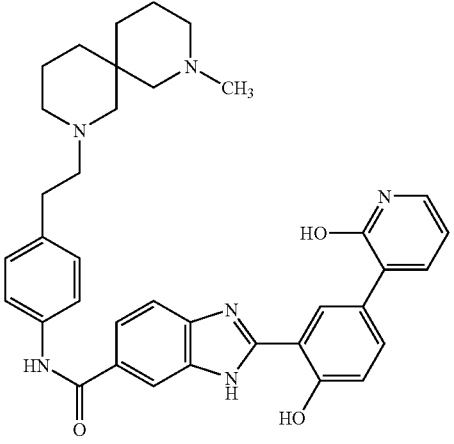 [SMILES: CN1CCCC2(CCCN(CCc3ccc(NC(=O)c4ccc5nc(-c6cc(-c7cccnc7O)ccc6O)[nH]c5c4)cc3)C2)C1] | X |
| 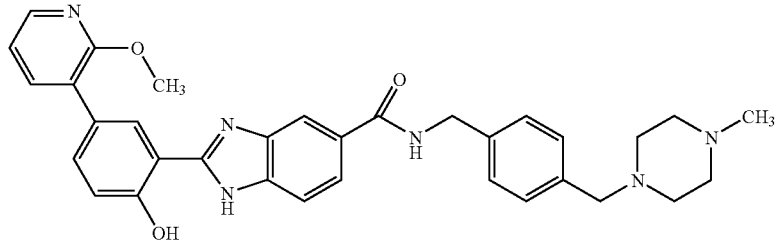 [SMILES: COc1ncccc1-c1ccc(O)c(-c2nc3cc(C(=O)NCc4ccc(CN5CCN(C)CC5)cc4)ccc3[nH]2)c1] | X |

| Structure | IC50 TrkA |
|---|---|
| 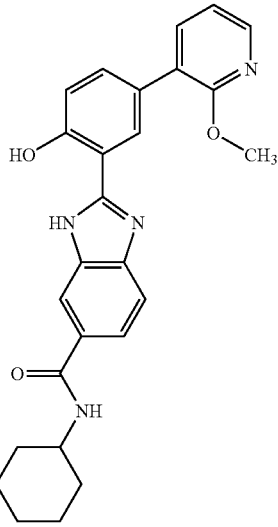 | X |
| 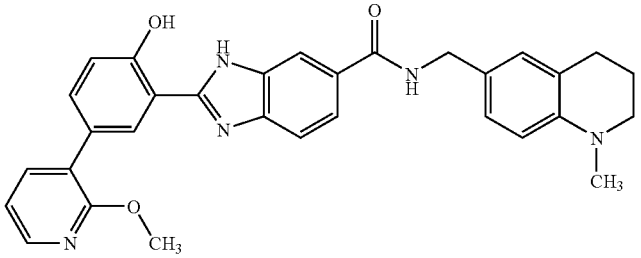 [SMILES: COc1ncccc1-c1ccc(O)c(-c2nc3ccc(C(=O)NCc4ccc5c(c4)CCCN5C)cc3[nH]2)c1] | X |
| 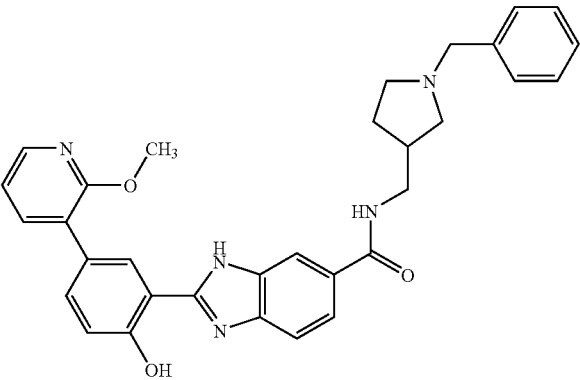 [SMILES: COc1ncccc1-c1ccc(O)c(-c2nc3ccc(C(=O)NCC4CCN(Cc5ccccc5)C4)cc3[nH]2)c1] | XX |
| 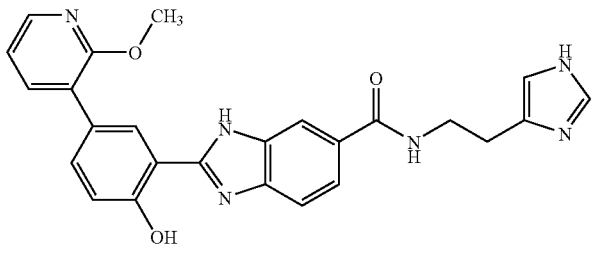 [SMILES: COc1ncccc1-c1ccc(O)c(-c2nc3ccc(C(=O)NCCc4c[nH]cn4)cc3[nH]2)c1] | XX |

-continued

| Structure | IC50 TrkA |
|---|---|
| | xx |
| | xxx |
| | xxx |
| | xx |
| | xxx |

-continued

| Structure | IC50 TrkA |
|---|---|
| 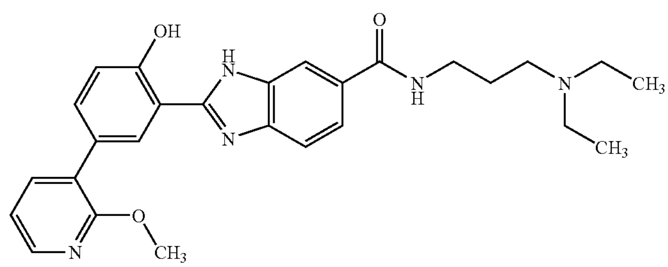 [SMILES: CCN(CC)CCCNC(=O)c1ccc2nc(-c3cc(-c4cccnc4OC)ccc3O)[nH]c2c1] | XXX |
| | X |
| | X |
| | X |
| | X |

| Structure | IC50 TrkA |
|---|---|
| 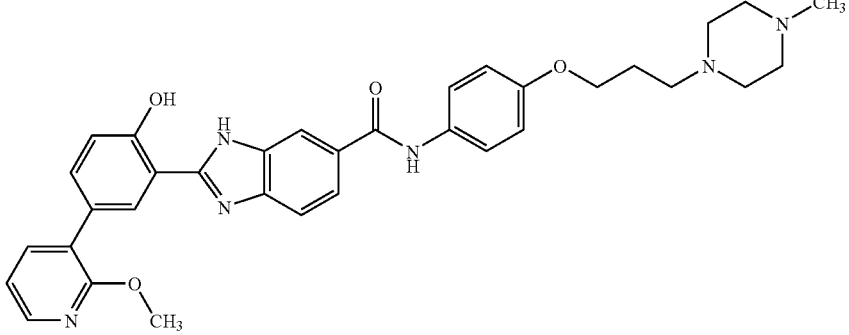 [SMILES: COc1ncccc1-c1ccc(O)c(-c2nc3ccc(C(=O)Nc4ccc(OCCCN5CCN(C)CC5)cc4)cc3[nH]2)c1] | X |
| 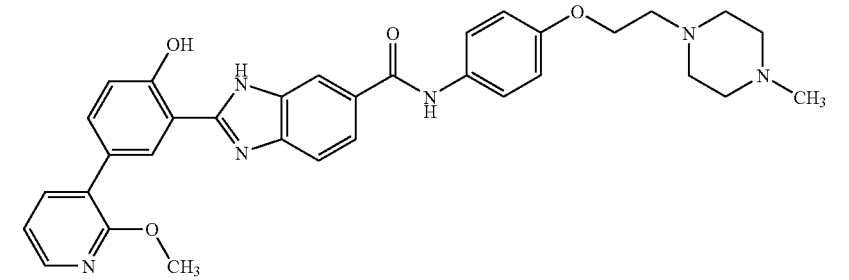 [SMILES: COc1ncccc1-c1ccc(O)c(-c2nc3ccc(C(=O)Nc4ccc(OCCN5CCN(C)CC5)cc4)cc3[nH]2)c1] | X |
| 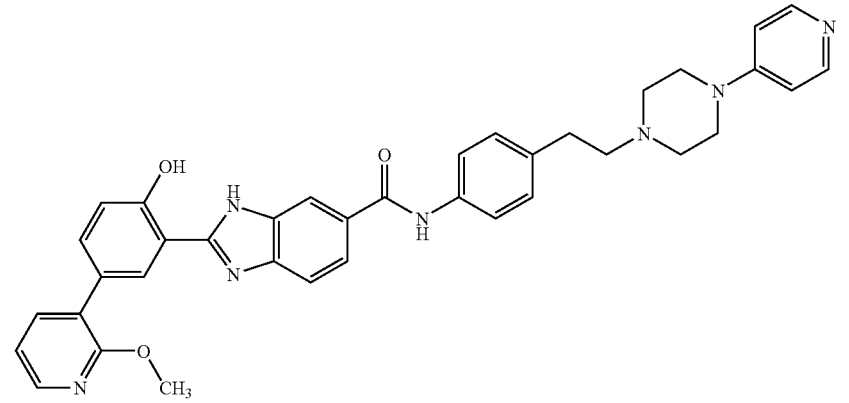 [SMILES: COc1ncccc1-c1ccc(O)c(-c2nc3ccc(C(=O)Nc4ccc(CCN5CCN(c6ccncc6)CC5)cc4)cc3[nH]2)c1] | XX |
| 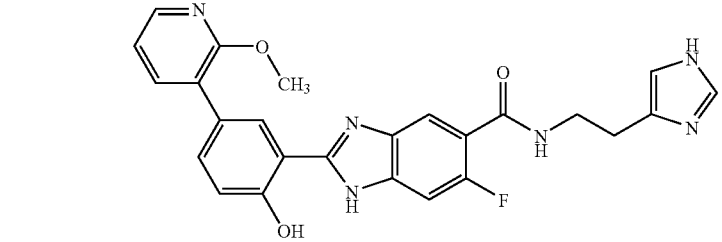 [SMILES: COc1ncccc1-c1ccc(O)c(-c2nc3cc(C(=O)NCCc4c[nH]cn4)c(F)cc3[nH]2)c1] | XXX |
| 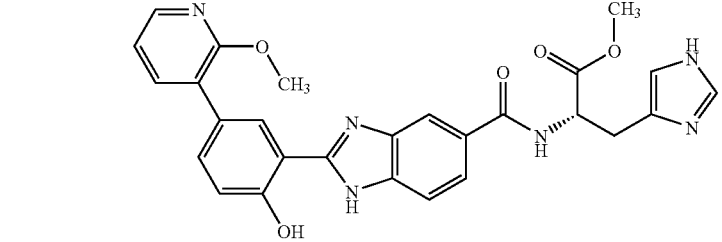 [SMILES: COC(=O)[C@H](Cc1c[nH]cn1)NC(=O)c1ccc2[nH]c(-c3cc(-c4cccnc4OC)ccc3O)nc2c1] | XX |

-continued
| Structure | IC50 TrkA |
|---|---|
| 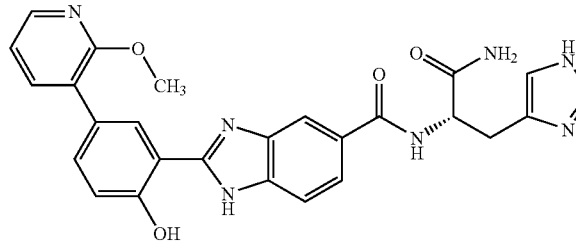 | XXX |
| 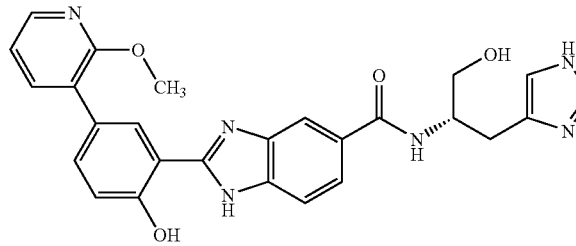 | XXX |
| 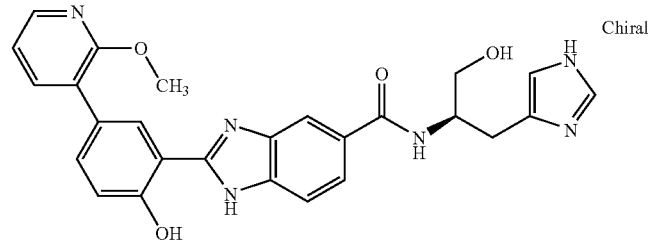 [SMILES: COc1ncccc1-c1ccc(O)c(-c2nc3cc(C(=O)N[C@@H](CO)Cc4c[nH]cn4)ccc3[nH]2)c1] | XXX |
| 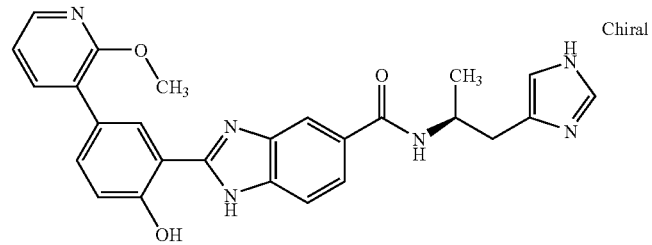 [SMILES: COc1ncccc1-c1ccc(O)c(-c2nc3cc(C(=O)N[C@@H](C)Cc4c[nH]cn4)ccc3[nH]2)c1] | X |
| 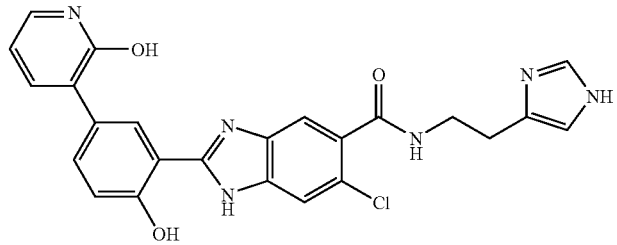 [SMILES: O=C(NCCc1c[nH]cn1)c1cc2nc(-c3cc(-c4cccnc4O)ccc3O)[nH]c2cc1Cl] | XXX |
| 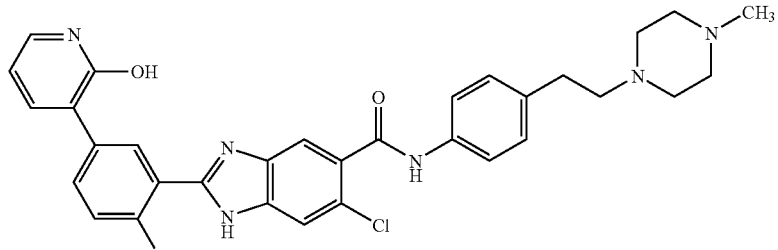 | XX |

| Structure | IC50 TrkA |
|---|---|
| 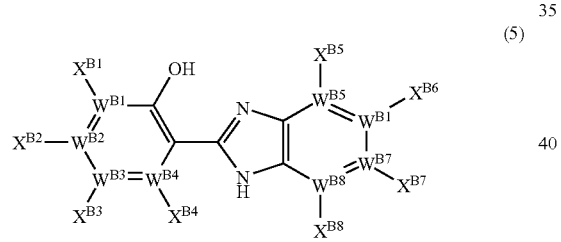 | XX |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound according to formula (5), or a stereoisomer, tautomer or salt thereof:

(5)

[formula image]

wherein:
each $W^{B1}$ through $W^{B4}$ is independently a carbon atom;
each $W^{B5}$ through $W^{B8}$ is independently a carbon atom or a nitrogen atom, wherein $W^{B5}$ through $W^{B8}$ is at most one nitrogen;
each $X^{B1}$ through $X^{B4}$ is absent or is independently selected from hydrogen, halogen, optionally substituted lower alkoxy, optionally substituted sulfonamido, optionally substituted ureido, trifluoromethyl, trifluoromethoxy, nitro, cyano, optionally substituted aryl or heteroaryl, aryloxy or heteroaryloxy, arylamino or heteroarylamino, nitrogen-heterocyclyl, connected either by its nitrogen, or a carbon atom, nitrogen-heterocyclyl-alkyl, connected either by its nitrogen or a carbon atom;
each $X^{B5}$ through $X^{B8}$ is independently selected from hydrogen, halogen, lower alkyl, lower alkoxy, trifluoromethyl, trifluoromethoxy, nitro, cyano, optionally substituted;
one of the substituents $X_{B5}$ through $X^{B8}$ is selected from the following:

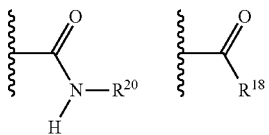

when any of $W^{B5}$ through $W^{B8}$ is nitrogen, then the corresponding substituent(s) $X^{B5}$ through $X^{B8}$ is absent;
each $R^{18}$ is —N—$(X^{42})_2$;
each $X^{42}$ is independently selected from hydrogen, lower alkyl, optionally substituted aryl, optionally substituted heteroaryl, and two $X^{42}$ can be combined to form an optionally substituted alkyl or optionally substituted heteroalkyl ring with 4 to 8 members;
$R^{20}$ is selected from:

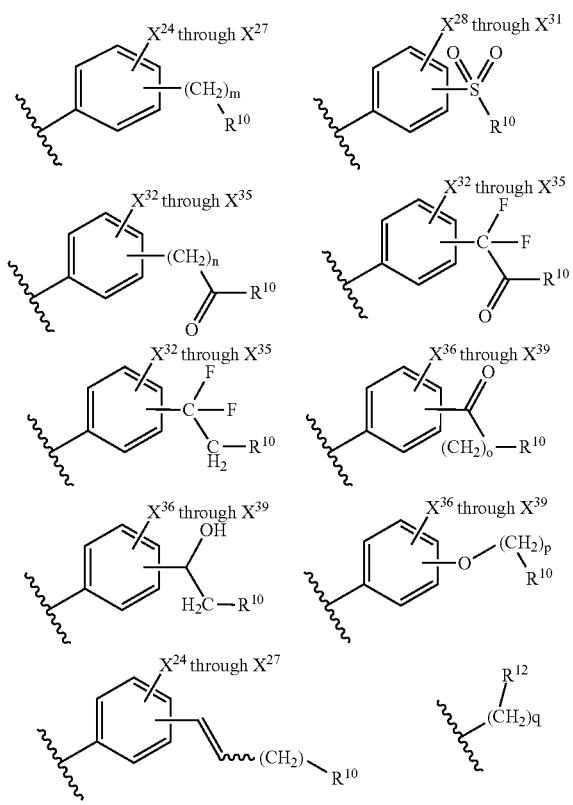

-continued

each m, n, o, p, or q is an integer from 0 to 6;
each $R^{12}$ is heteroaryl or heteroarylalkyl;
each $X^{24}$ through $X^{39}$ is independently hydrogen, halogen, trifluoromethyl, trifluoromethoxy, lower alkyl, lower alkoxy, di-lower alkylamino, hydroxy, or amido; and
each $R^{10}$ is selected from, heterocyclyl, heterocycloalkyl, heterocycloalkylaminoalkyl, heterocycloalkoxyalkyl, di-lower alkylaminocycloalkyl, lower alkylaminocycloalkyl, heterocyclo-cycloalkyl, heterocyclo-heterocycloalkyl, heteroaryl and heteroarylalkyl.

2. A compound selected from the group consisting of:

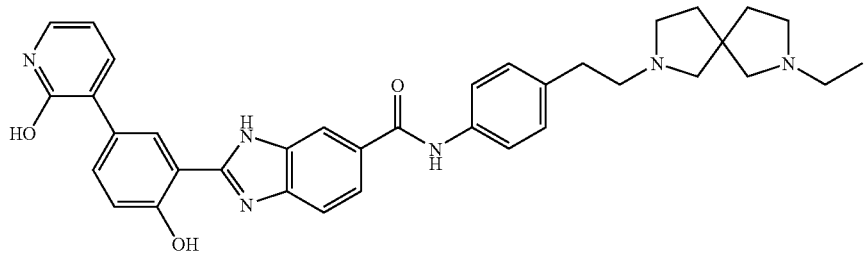 [SMILES: CCN1CCC2(CCN(CCc3ccc(NC(=O)c4ccc5nc(-c6cc(-c7cccnc7O)ccc6O)[nH]c5c4)cc3)C2)C1]

N-{4-[2-(7-ethyl-2,7-diazaspiro[4.4]non-2-yl)ethyl]phenyl}-2-[2-hydroxy-5-(2-hydroxypyridin-3-yl)phenyl]-1H-benzimidazole-6-carboxamide;

2-[2-hydroxy-5-(2-methoxypyridin-3-yl)phenyl]-N-[2-(1H-imidazol-4-yl)ethyl]-1H-benzimidazole-6-carboxamide;

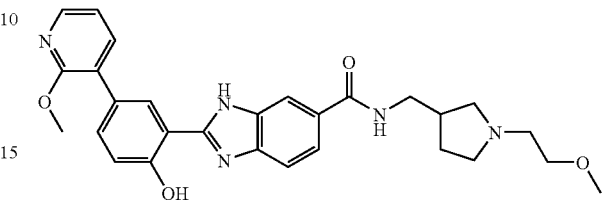

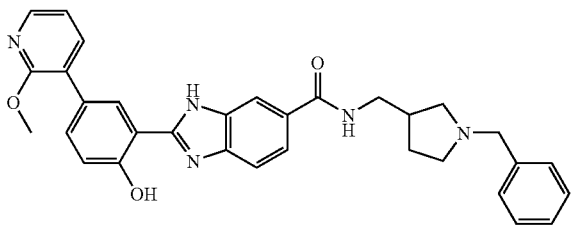 [SMILES: COc1ncccc1-c1ccc(O)c(-c2nc3ccc(C(=O)NCC4CCN(Cc5ccccc5)C4)cc3[nH]2)c1]

N-[(1-benzylpyrrolidin-3-yl)methyl]-2-[2-hydroxy-5-(2-methoxypyridin-3-yl)phenyl]-1H-benzimidazole-6-carboxamide;

2-[2-hydroxy-5-(2-methoxypyridin-3-yl)phenyl]-N-{[1-(2-methoxyethyl)pyrrolidin-3-yl]methyl}-1H-benzimidazole-6-carboxamide;

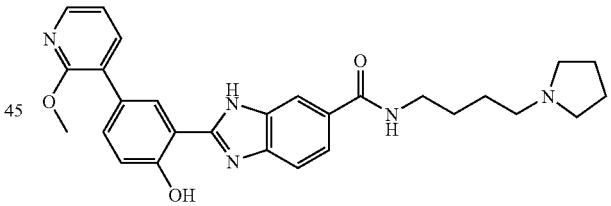

2-[2-hydroxy-5-(2-methoxypyridin-3-yl)phenyl]-N-(4-pyrrolidin-1-ylbutyl)-1H-benzimidazole-6-carboxamide;

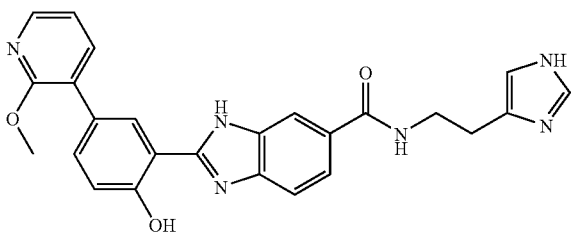 [SMILES: COc1ncccc1-c1ccc(O)c(-c2nc3ccc(C(=O)NCCc4c[nH]cn4)cc3[nH]2)c1]

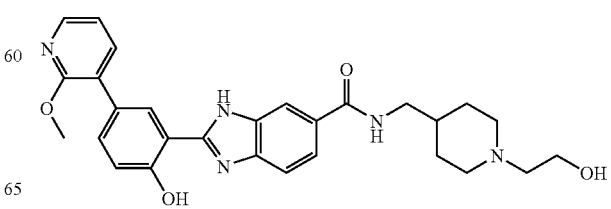

815

N-{[1-(2-hydroxyethyl)piperidin-4-yl]methyl}-2-[2-hydroxy-5-(2-methoxypyridin-3-yl)phenyl]-1H-benzimidazole-6-carboxamide;

816

2-[2-hydroxy-5-(2-methoxypyridin-3-yl)phenyl]-N-{4-[2-(4-pyridin-4-ylpiperazin-1-yl)ethyl]phenyl}-1H-benzimidazole-6-carboxamide;

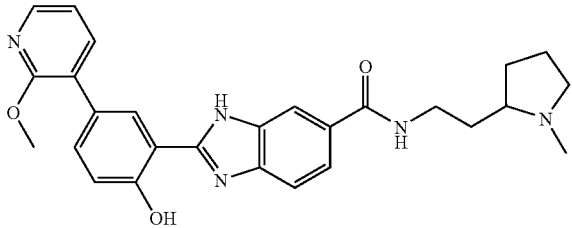 [SMILES: COc1ncccc1-c1ccc(O)c(-c2nc3ccc(C(=O)NCCC4CCCN4C)cc3[nH]2)c1]

2-[2-hydroxy-5-(2-methoxypyridin-3-yl)phenyl]-N-[2-(1-methylpyrrolidin-2-yl)ethyl]-1H-benzimidazole-6-carboxamide;

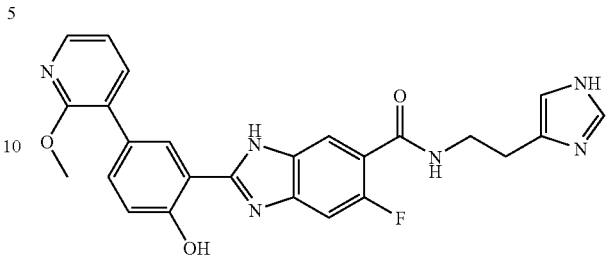

5-fluoro-2-[2-hydroxy-5-(2-methoxypyridin-3-yl)phenyl]-N-[2-(1H-imidazol-4-yl)ethyl]-1H-benzimidazole-6-carboxamide;

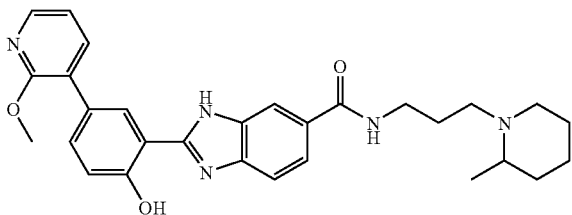 [SMILES: COc1ncccc1-c1ccc(O)c(-c2nc3ccc(C(=O)NCCCN4CCCCC4C)cc3[nH]2)c1]

2-[2-hydroxy-5-(2-methoxypyridin-3-yl)phenyl]-N-[3-(2-methylpiperidin-1-yl)propyl]-1H-benzimidazole-6-carboxamide;

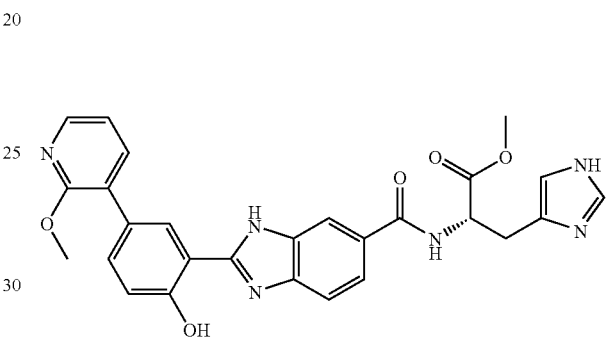

methyl N-({2-[2-hydroxy-5-(2-methoxypyridin-3-yl)phenyl]-1H-benzimidazol-6-yl}carbonyl)-L-histidinate;

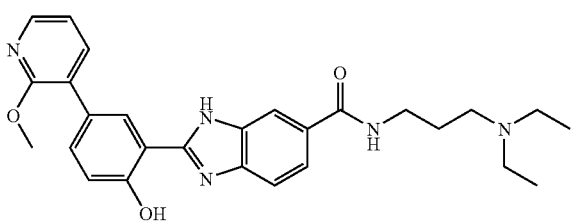 [SMILES: CCN(CC)CCCNC(=O)c1ccc2nc(-c3cc(-c4cccnc4OC)ccc3O)[nH]c2c1]

N-[3-(diethylamino)propyl]-2-[2-hydroxy-5-(2-methoxypyridin-3-yl)phenyl]-1H-benzimidazole-6-carboxamide;

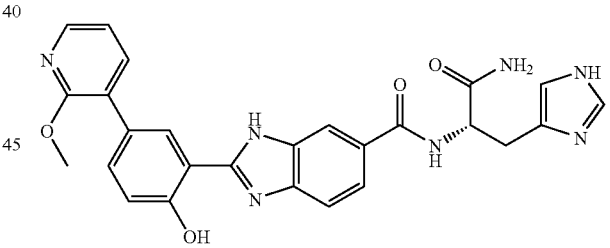

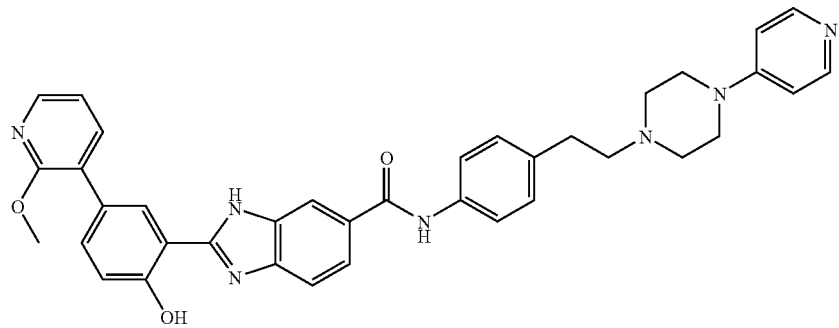 [SMILES: COc1ncccc1-c1ccc(O)c(-c2nc3ccc(C(=O)Nc4ccc(CCN5CCN(c6ccncc6)CC5)cc4)cc3[nH]2)c1]

817

N-[(1S)-2-amino-1-(1H-imidazol-4-ylmethyl)-2-oxoethyl]-2-[2-hydroxy-5-(2-methoxypyridin-3-yl)phenyl]-1H-benzimidazole-6-carboxamide;

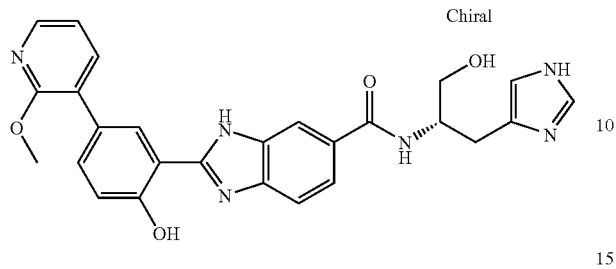

N-[(1S)-2-hydroxy-1-(1H-imidazol-4-ylmethyl)ethyl]-2-[2-hydroxy-5-(2-methoxypyridin-3-yl)phenyl]-1H-benzimidazole-6-carboxamide;

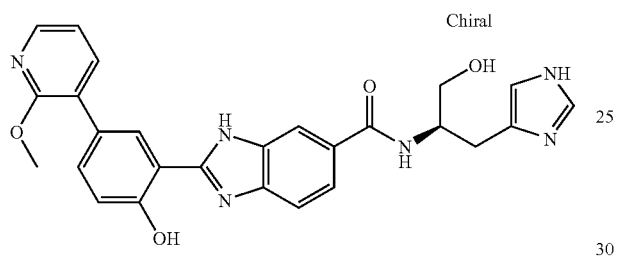

N-[(1R)-2-hydroxy-1-(1H-imidazol-4-ylmethyl)ethyl]-2-[2-hydroxy-5-(2-methoxypyridin-3-yl)phenyl]-1H-benzimidazole-6-carboxamide;

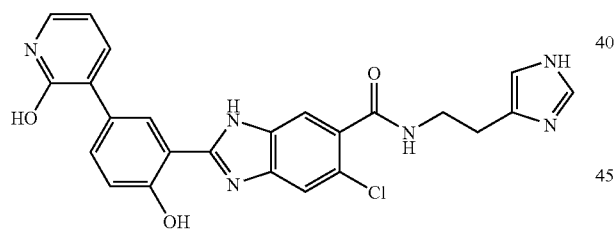

5-chloro-2-[2-hydroxy-5-(2-hydroxypyridin-3-yl)phenyl]-N-[2-(1H-imidazol-4-yl)ethyl]-1H-benzimidazole-6-carboxamide; and

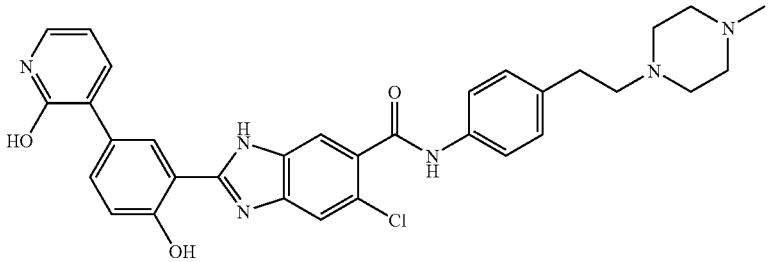 [SMILES: CN1CCN(CCc2ccc(NC(=O)c3cc4[nH]c(-c5cc(-c6cccnc6O)ccc5O)nc4cc3Cl)cc2)CC1]

818

5-chloro-2-[2-hydroxy-5-(2-hydroxypyridin-3-yl)phenyl]-N-{4-[2-(4-methylpiperazin-1-yl)ethyl]phenyl}-1H-benzimidazole-6-carboxamide.

3. A pharmaceutical composition comprising a compound having the following formula:

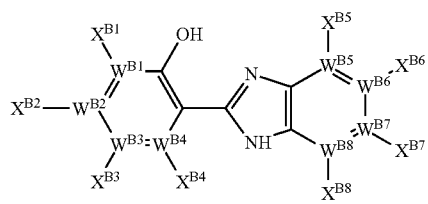

wherein:
each $W^{B1}$ through $W^{B4}$ is independently a carbon atom; each $W^{B5}$ through $W^{B8}$ is independently a carbon atom or a nitrogen atom, wherein $W^{B5}$ through $W^{B8}$ is at most one nitrogen;
each $X^{B1}$ through $X^{B4}$ is absent or is independently selected from hydrogen, halogen, optionally substituted lower alkoxy, optionally substituted sulfonamido, optionally substituted ureido, trifluoromethyl, trifluoromethoxy, nitro, cyano, optionally substituted aryl or heteroaryl, aryloxy or heteroaryloxy, arylamino or heteroarylamino, nitrogen-heterocyclyl, connected either by its nitrogen, or a carbon atom, nitrogen-heterocyclyl-alkyl, connected either by its nitrogen or a carbon atom;
each $X^{B5}$ through $X^{B8}$ is independently selected from hydrogen, halogen, lower alkyl, lower alkoxy, trifluoromethyl, trifluoromethoxy, nitro, cyano, optionally substituted;
one of the substituents $X^{B5}$ through $X^{B8}$ is selected from the following:

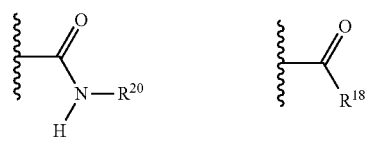

when any of $W^{B5}$ through $W^{B8}$ is nitrogen, then the corresponding substituent(s) $X^{B5}$ through $X^{B8}$ is absent;
each $R^{18}$ is —N—$(X^{42})_2$;
each $X^{42}$ is independently selected from hydrogen, lower alkyl, optionally substituted aryl, optionally substituted heteroaryl, and two $X^{42}$ can be combined to form an optionally substituted alkyl or optionally substituted heteroalkyl ring with 4 to 8 members;
$R^{20}$ is selected from:

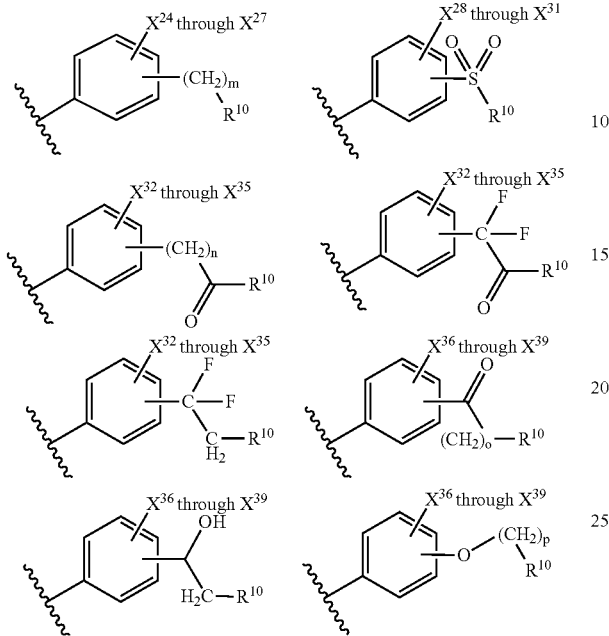
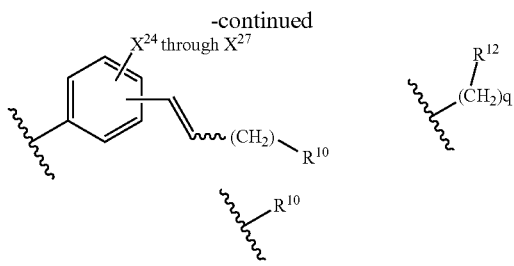

each m, n, o, p, or q is an integer from 0 to 6;

each $R^{12}$ is heteroaryl or heteroarylalkyl;

each $X^{24}$ through $X^{39}$ is independently hydrogen, halogen, trifluoromethyl, trifluoromethoxy, lower alkyl, lower alkoxy, di-lower alkylamino, hydroxy, or amido; and each $R^{10}$ is selected from, heterocyclyl, heterocycloalkyl, heterocycloalkylaminoalkyl, heterocycloalkoxyalkyl, di-lower alkylaminocycloalkyl, lower alkylaminocycloalkyl, heterocyclo-cycloalkyl, heterocyclo-heterocycloalkyl, heteroaryl, heteroarylalkyl; and one or more pharmaceutically acceptable diluents, excipients or carriers.

* * * * *

UNITED STATES PATENT AND TRADEMARK OFFICE
CERTIFICATE OF CORRECTION

PATENT NO. : 8,629,147 B2
APPLICATION NO. : 11/593191
DATED : January 14, 2014
INVENTOR(S) : Alexey Vyacheslavovich Anikin et al.

It is certified that error appears in the above-identified patent and that said Letters Patent is hereby corrected as shown below:

In the Claims:

(a) At column 811, lines 35-45, formula (5) of claim 1 should be:

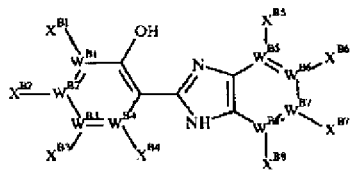

(b) At column 811, lines 66 and 67, should read:

one of the substituents $X^{B5}$ through $X^{B8}$ is selected from the following:

(c) At column 812, lines 60-65, the formula on the right should be:

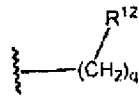

(d) At column 820, lines 5, the formula on the right should be:

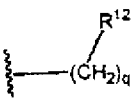

Signed and Sealed this
First Day of July, 2014

Michelle K. Lee
*Deputy Director of the United States Patent and Trademark Office*